United States Patent
Gibbons et al.

(10) Patent No.: US 8,999,998 B2
(45) Date of Patent: Apr. 7, 2015

(54) PYRAZOLOPYRIMIDINE JAK INHIBITOR COMPOUNDS AND METHODS

(75) Inventors: Paul Gibbons, San Francisco, CA (US); Emily Hanan, Redwood City, CA (US); Wendy Liu, Foster City, CA (US); Joseph P. Lyssikatos, Piedmont, CA (US); Steven R. Magnuson, Dublin, CA (US); Rohan Mendonca, Pleasanton, CA (US); Richard Pastor, San Francisco, CA (US); Thomas E. Rawson, Mountain View, CA (US); Michael Siu, Burlingame, CA (US); Mark Zak, San Mateo, CA (US); Aihe Zhou, San Jose, CA (US); Bing-Yan Zhu, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 331 days.

(21) Appl. No.: 13/382,145

(22) PCT Filed: Jul. 2, 2010

(86) PCT No.: PCT/US2010/040906
§ 371 (c)(1),
(2), (4) Date: Apr. 10, 2012

(87) PCT Pub. No.: WO2011/003065
PCT Pub. Date: Jan. 6, 2011

(65) Prior Publication Data
US 2012/0190665 A1 Jul. 26, 2012

Related U.S. Application Data

(60) Provisional application No. 61/222,918, filed on Jul. 2, 2009.

(51) Int. Cl.
*C07D 487/04* (2006.01)
*A61K 31/519* (2006.01)

(52) U.S. Cl.
CPC .................................. *C07D 487/04* (2013.01)

(58) Field of Classification Search
CPC ............................ C07D 487/04; A61K 31/519
USPC ....................................... 544/281; 514/259.3
See application file for complete search history.

(56) References Cited

U.S. PATENT DOCUMENTS

| | | | |
|---|---|---|---|
| 4,603,139 A | 7/1986 | King | |
| 4,847,256 A | 7/1989 | Tseng et al. | |
| 5,705,625 A | 1/1998 | Civin et al. | |
| 6,136,595 A | 10/2000 | Ihle et al. | |
| 6,210,654 B1 | 4/2001 | Ihle et al. | |
| 6,235,741 B1 | 5/2001 | Bilodeau et al. | |
| 7,070,972 B1 | 7/2006 | O'Shea et al. | |
| 7,161,003 B1 | 1/2007 | Guzi et al. | |
| 7,306,631 B2 | 12/2007 | Glenn et al. | |
| 2004/0097485 A1 | 5/2004 | Burkitt et al. | |
| 2005/0245546 A1 | 11/2005 | Cristalli | |
| 2005/0288502 A1 | 12/2005 | Andersen et al. | |
| 2006/0089362 A1 | 4/2006 | Seno et al. | |
| 2006/0142612 A1 | 6/2006 | Anthony et al. | |
| 2006/0153852 A1 | 7/2006 | Coleman et al. | |
| 2007/0082902 A1 | 4/2007 | Paruch et al. | |
| 2007/0270408 A1 | 11/2007 | Anderson et al. | |
| 2007/0281951 A1 | 12/2007 | Guzi et al. | |

(Continued)

FOREIGN PATENT DOCUMENTS

EP 1 040 817 A1 10/2000
EP 1 221 444 A1 7/2002

(Continued)

OTHER PUBLICATIONS

STN Structure Search, Supplier Ambinter, Downloaded Jan. 24, 2014, p. 1.*
Wilks et al., "The JAK kinases: Not just another kinase drug discovery target" Seminars in Cell & Development Biology 19(4):319-328 (Aug. 1, 2008).
(Applicant's Response in U.S. Appl. No. 13/099,179 dated Nov. 13, 2012).
(International Preliminary Report on Patentability for International Patent Application No. PCT/US2009/063014), (May 3, 2011).
(Non-Final Rejection of U.S. Appl. No. 13/099,179 dated Mar. 22, 2012).
(Notice of Allowance in U.S. Appl. No. 13/099,179 dated Feb. 5, 2013).
(Notice of Allowance in U.S. Appl. No. 13/099,179 dated Jun. 14, 2013).

(Continued)

*Primary Examiner* — Susanna Moore
(74) *Attorney, Agent, or Firm* — Tamara Kale; Genentech, Inc.

(57) ABSTRACT

A compound of Formula I, enantiomers, diasteriomers, tautomers or pharmaceutically acceptable salts thereof, wherein $R^1$, $R^2$ and $R^3$ are defined herein, are useful as inhibitors of one or more Janus kinases. A pharmaceutical composition that includes a compound of Formula I and a pharmaceutically acceptable carrier, adjuvant or vehicle, and methods of treating or lessening the severity of a disease or condition responsive to the inhibition of a Janus kinase activity in a patient are disclosed.

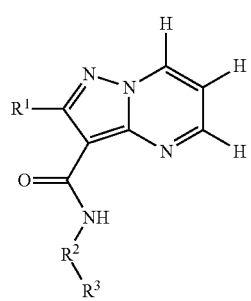

1 Claim, No Drawings

(56) References Cited

U.S. PATENT DOCUMENTS

| | | |
|---|---|---|
| 2009/0054410 A1 | 2/2009 | Griffioen et al. |
| 2009/0163545 A1 | 6/2009 | Goldfarb |

FOREIGN PATENT DOCUMENTS

| | | |
|---|---|---|
| WO | 98/14451 A1 | 4/1998 |
| WO | 01/42246 | 6/2001 |
| WO | 2004/037823 A1 | 5/2004 |
| WO | 2004/052315 | 6/2004 |
| WO | 2004/089471 | 10/2004 |
| WO | 2005/002552 A2 | 1/2005 |
| WO | 2005/058837 A1 | 6/2005 |
| WO | 2005/110477 A2 | 11/2005 |
| WO | 2006/052913 | 5/2006 |
| WO | 2007/013673 | 2/2007 |
| WO | 2007/039797 A1 | 4/2007 |
| WO | 2007/048066 A2 | 4/2007 |
| WO | 2007/065664 A2 | 6/2007 |
| WO | 2007/108750 A1 | 9/2007 |
| WO | 2008/004698 A2 | 1/2008 |
| WO | 2008/008539 A2 | 1/2008 |
| WO | 2008/052734 A1 | 5/2008 |
| WO | 2008/063671 A2 | 5/2008 |
| WO | 2009/017954 A1 | 2/2009 |
| WO | 2009/047359 A1 | 4/2009 |
| WO | 2009/073153 A2 | 6/2009 |
| WO | 2009/073153 A3 | 6/2009 |
| WO | 2010/019762 A1 | 2/2010 |
| WO | 2010/063487 A1 | 6/2010 |
| WO | 2010/089292 A1 | 8/2010 |
| WO | 2010/094647 A1 | 8/2010 |
| WO | 2011/003065 A2 | 1/2011 |
| WO | 2011/006074 A1 | 1/2011 |
| WO | 2011/048082 A1 | 4/2011 |
| WO | 2011/113802 A2 | 9/2011 |
| WO | 2011/134831 A1 | 11/2011 |

OTHER PUBLICATIONS

Dameshek, "Editorial: Some Speculations on the Myeloproliferative Syndromes" Blood 6(4):372-375 ( 1951).
Firmbach-Kraft et al., "tyk2, prototype of a novel class of non-receptor tyrosine kinase genes" Oncogene 5:1329-36 ( 1990).
Gausterer et al., "In Vivo Target Validation: Methodology and Case Studies on the Janus Kinase Tyk2" Anti-Inflammatory & Anti-Allergy Agents in Medicinal Chemistry (Cited in Office Action U.S. Appl. No. 13/099,179), 6:29-45 ( 2007).
Gavrin et al., "Synthesis of Pyrazolo [1,5-a] Pyrimidinone Regioisomers" Journal of Organic Chemistry (Cited in Office Action U.S. Appl. No. 13/099,179), 72(3):1043-1046 ( 2007).
Morgan et al., "A Role for JAK2 Mutations in Myeloproliferative Diseases" Annu Rev Med 59:213-222 ( 2008).
Wilks et al., "Two novel protein-tyrosine kinases, each with a second phosphotransferase-related catalytic domain, define a new class of protein kinase" Mol Cell Biol 11:2057-2065 ( 1991).
Yang et al., "Use ofN-(thiofuran-2) pyrazolo [1, 5-a] pyrimidine-3-methanamide compound for preparing the antineoplastic medicine" (Abstract Patent/Publication: CN101537007A), (Oct. 12, 2011).
(Notice of Allowance in U.S. Appl. No. 13/099,179 dated Sep. 18, 2013).
U.S. Appl. No. 61/224,196, filed Jul. 9, 2009.
(Rule 114(2) Communication from EPO dated Nov. 14, 2013).
Anderson et al., "Chemistry of the adenosine monophosphate site of rabbit muscle glycogen phosphorylase. I. Hydrophobic nature of and affinity labeling of the allosteric site" Biochemistry 12(10):1895-900 ( 1973).
Barraclough et al., "Inotropic 'A' ring substituted sulmazole and isomazole analogues" J Med Chem. 33(8):2231-9 ( 1990).
Baslund et al., "Targeting interleukin-15 in patients with rheumatoid arthritis: a proof-of-concept study" Arthritis Rheum 52(9):2686-92 (Sep. 2005).

Borrmann et al., "Structure-activity relationships of adenine and deazaadenine derivatives as ligands for adenine receptors, a new purinergic receptor family" J Med Chem. 52:5974-89 ( 2009).
Cartwright et al., "Imidazopyridine and pyrimidinopyridine systems from perfluorinated pyridine derivatives" Tetrahedron 63(30) (Jun. 13, 2007).
Changelian et al., "Prevention of organ allograft rejection by a specific Janus kinase 3 inhibitor" Science 302:875-8 (Oct. 2003).
Database Registry [Online] Chemical Abstracts Service, Columbus, Ohio, US; Jun. 10, 2008, 'Not yet assigned', Database accession No. 1026925-65-4 the whole document.
Database Registry [Online] Chemical Abstracts Service, Columbus, Ohio, US; Aug. 29, 2004, '9H-Purine, 9-(4-cholorphenyl)-8-(2-fluorophenyl)-6-(1 -pyrrolidinyl)-', Database accession No. 734532-63-9 the whole document.
Database Registry [Online] Chemical Abstracts Service, Columbus, Ohio, US; Jun. 8, 2008, 'Not yet assigned', Database accession No. 1026421-43-1 the whole document.
Database Registry [Online] Chemical Abstracts Service, Columbus, Ohio, US; Nov. 10, 2004, '3-Azabicyclo[3.1.0]hexan-6-amine, 3-[9-(4-chlorophenyl)-8-(2,3-dichloropheny l)-9H-purin-6-yl]-N,N-dimethyl-, (1.alpha.-5.alpha.,6.beta.)-', Database accession No. 777853-55-1 the whole document.
Database Registry [Online] Chemical Abstracts Service, Columbus, Ohio, US; Sep. 8, 2004, 3-Azabicyclo[3.1.0]hexan-6-amine, 3-[9-(4-chlorophenyl)-8-(2,3-dichlorophenyl)-9H-purin-6-yl]-N,N-dimethyl-, ( 1. alpha.-5. alpha. , 6. beta. )-, Database accession No. 741249-27-4 the whole document.
Database Registry [Online] Chemical Abstracts Service, Columbus, Ohio, US; Apr. 4, 2003 (2004-84-84), '9H-Purin-6-amine, 8-(2,4-dichlorophenyl)-', Database accession No. 501657-71-2 the whole document.
Database Registry [Online] Chemical Abstracts Service, Columbus, Ohio, US; Jun. 10, 2008, 'Not yet assigned', Database accession No. 1027012-36-7 the whole document.
Database Registry [Online] Chemical Abstracts Service, Columbus, Ohio, US; Jun. 13, 2008, 'Not yet assigned', Database accession No. 1027914-11-9 the whole document.
Database Registry [Online] Chemical Abstracts Service, Columbus, Ohio, US; Sep. 14, 2010, '1H-Imidazo[4,5-c]pyridin-4-amine, 2-(2-clorophenyl)-N-[3-methoxy-4-(3-methyl-1H-1,2,4-triazol-1-yl]phenyl]-1-(methylethyl=-', Database accession No. 1240783-28-1 the whole document.
Geldenhuys et al., "Virtual screening to identify novel antagonists for the G protein-coupled NK3 receptor" J Med Chem. 53:8080-8 (Nov. 2010).
Griffith et al., "Discovery of 1-[9-(4-chlorophenyl)-8-(2-chlorophenyl)-9H-purin-6-y11-4-ethylaminopiperidine-4-carboxylic acid amide hydrochloride (CP-945,598), a novel, potent, and selective cannabinoid type 1 receptor antagonist" J Med Chem. 52(2):234-7 (Jan. 22, 2009).
Hasnik et al., "Cross-Coupling reactions of Halopurines with Aryl- and alkyltrifluoroborates; The Scope and Limitations in the Synthesis of Modified Purines" Synthesis 9:1309-17 (Mar. 25, 2009).
IUPAC Ed—MacNaught Alan D et al. Compendium of Chemical Terminology: IUPAC Recommendations; [IUPAC Chemical Data Series], [ISBN: 978-0-86542-684-9] "cycloalkyl groups, [retrieved on Apr. 20, 2012; http://goldbook.iupac.org/about.html/]" Oxford [U.A.]:Blackwell Science, Oxford [U.A.].
IUPAC Ed—MacNaught Alan D et al. Compendium of Chemical Terminology: IUPAC Recommendations; [IUPAC Chemical Data Series], [ISBN: 978-0-86542-684-9] "alkyl groups, [retrieved on Apr. 20, 2012; http://goldbook.iupac.org/about.html/]"Blackwell Science, Oxford [U.A.].
Jacob, "Resolution of (+/−)-5-Bromonornicitine. Synthesis of (R)- and (S)-Nornicotine of High Enantiomeric Purity" J Org Chem 47:4165-67 ( 1982).
Kisseleva et al., "Signaling through the JAK/STAT pathway, recent advances and future challenges" Gene 285:1-24 (Feb. 2002).
Krueger et al., "A human interleukin-12/23 monoclonal antibody for the treatment of psoriasis" New Engl J Med 356(6):580-92 (Feb. 2007).

(56) References Cited

OTHER PUBLICATIONS

Levy et al., "Stats: transcriptional control and biological impact" Nat Rev Mol Cell Biol. 3(9):651-62 ( 2002).

Mannon et al., "Anti-interleukin-12 antibody for active Crohn's disease" New Engl J Med 351(20):2069-79 (Nov. 2004).

McCloskey et al., "New insights into the design of inhibitors of human S-adenosylmethionine decarboxylase: studies of adenine C8 substitution in structural analogues of S-adenosylmethionine" J Med Chem. 52(5):1388-407 ( 2009).

Medebielle et al., "Electrochemically induced SRNI substitution of fluorinated aryl halides. Application to the synthesis of fluorinated-aryl heterocycles" Electrochimica Acta 42(13):2049-55 ( 1997).

O'Shea et al., "Cytokine Signaling in 2002: New Surprises in the Jak/Stat Pathway" Cell 109:S121-S131 (Apr. 2002).

Ragan et al., "Development of a practical and Efficient Synthesis of CP-945,598-02,a CB1 Antagonist for the Treatment of Obesity" Organic Process Research and Development 13(2):192 (Dec. 22, 2008).

Reich et al., "Ustekinumab" Nat Rev Drug Discov 8(5):355-6 (May 2009).

Sahnoun et al., "A site selective C—H arylation of free-(NH2) adenines with aryl chlorides: application to the synthesis of 6,8-disubstituted adenines" Org Biomol Chem. 7(20):4271-8 (Oct. 21, 2009).

Sahnoun et al., "Microwave-assisted Pd(OH)2-catalyzed direct C—H arylation of free-(NH2) adenines with aryl halides" Tetrahedron Letters 49(51):7279-83 (Dec. 15, 2008).

Saltzman et al. et al., "Cloning and characterization of human Jak-2 kinase: high mRNA expression in immune cells and muscle tissue" Biochem Bioph Res Co 246:627-33 (May 1998).

Scheinecker et al., "Tocilizumab" Nat Rev Drug Discov 8(4):273-4 (Apr. 2009).

Schindler et al., "JAK-STAT signaling: from interferons to cytokines" J Biol Chem 282(28):20059-63 (Jul. 2007).

Storr et al., "Pd(0)/Cu(I)-mediated direct arylation of 2'-deoxyadenosines: mechanistic role of Cu(I) and reactivity comparisons with related purine nucleosides" J Org Chem 74(16):5810-21 (2009).

Tadashi et al., "Syntheses of Fused Heterocycles via cycloaddition of Hetaryne Studies on Heteroaromaticity, Part XLVII" Bulletin of the Chemical Society of Japan 44(3) (Jan. 1, 1971).

Watford et al., "Human tyk2 kinase deficiency: another primary immunodeficiency syndrome" Immunity 25:695-7 (Nov. 2006).

Wilks, "Two putative protein-tyrosine kinases identified by application of the polymerase chain reaction" P Natl Acad Sci USA 86:1603-1607 ( 1989).

Young et al., "Purine derivatives as competitive inhibitors of human erythrocyte membrane phosphatidylinositol 4-kinase" J Med Chem. 33(8):2073-80 (Aug. 1990).

(EP Office Action dated Aug. 13, 2013).

(File Registry RN 1252132-61-8 Entered STN: Nov. 9, 2010).

(File Registry RN 1316553-50-0 Entered STN: Aug. 12, 2011).

(File Registry RN 139894-27-3, Entered STN: Aug. 19, 2011).

(PCT ISR and the Written Opinion for PCT/2011/070313, mailed on Jan. 30, 2012.

(PCT ISR and Written Opinion for PCT/EP2011/053826, mailed on Apr. 2, 2012).

CAS Registry Database, 1089652-06-1, Downloaded Jun. 30, 2010, Publication Date Feb. 8, 2010.

CAS Registry Database, 1147525-55-0, Downloaded Jun. 30, 2010, Publication Date Feb. 8, 2010.

CAS Registry Database, 1214490-10-4, Downloaded Jun. 30, 2010, Publication Date Feb. 16, 2010.

CAS Registry Database, 1223183-38-7, Downloaded Jun. 30, 2010, Publication Date May 7, 2010.

Database Registry [Online] Chemical Abstracts Service, Columbus, Ohio, US: Jul. 12, 2010, '9H-Purine, 8-(2-chlorophenyl)-6-(4-methyl-1-piperazin yl)-9-[(tetrahydro-2H-piran-4-yl)methyl]-' Database accession No. 1231299-64-1 the whole document.

* cited by examiner

PYRAZOLOPYRIMIDINE JAK INHIBITOR COMPOUNDS AND METHODS

CROSS-REFERENCE TO RELATED APPLICATIONS

This application is made under 35 U.S.C. §371 based on International Application PCT/US2010/040906 filed on Jul. 2, 2010 which claims the benefit of priority under 35 USC 119(e) of U.S. Provisional Application No. 61/222,918, filed Jul. 2, 2009, the contents of both of which are incorporated herein by reference in their entirety.

FIELD OF THE INVENTION

Pyrazolopyrimidine compounds of Formula I, which are inhibitors of one or more Janus kinases, as well as compositions containing these compounds and methods of use including, but not limited to, in vitro, in situ and in vivo diagnosis or treatment of mammalian cells.

BACKGROUND OF INVENTION

Cytokine pathways mediate a broad range of biological functions, including many aspects of inflammation and immunity Janus kinases (JAK), including JAK1, JAK2, JAK3 and TYK2 are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFN-gamma), IL-2 and IL-6 cytokine receptor complexes (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). JAK1 knockout mice die perinatally due to defects in LIF receptor signaling (Kisseleva et al., 2002, gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4, and IL-6 pathways. A humanized monoclonal antibody targeting the IL-6 pathway (Tocilizumab) was recently approved by the European Commission for the treatment of moderate-to-severe rheumatoid arthritis (Scheinecker et al., 2009, Nat. Rev. Drug Discov. 8:273-274).

Biochemical and genetic studies have shown an association between JAK2 and single-chain (e.g., EPO), IL-3 and interferon gamma cytokine receptor families (Kisseleva et al., 2002, gene 285:1-24; Levy et al., 2005, Nat. Rev. Mol. Cell. Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders (MPDs) in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and 11-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

SUMMARY OF INVENTION

One embodiment includes a compound of Formula I:

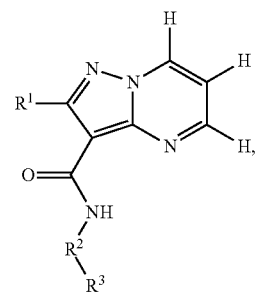

enantiomers, diasteriomers, tautomers or pharmaceutically acceptable salts thereof; wherein $R^1$, $R^2$ and $R^3$ are defined herein.

Another embodiment includes a pharmaceutical composition that includes a compound of Formula I and a pharmaceutically acceptable carrier, adjuvant or vehicle.

Another embodiment includes a method of treating or lessening the severity of a disease or condition responsive to the inhibition of one or more Janus kinase activity, selected from JAK1, JAK2, JAK3 and TYK2, in a patient. The method includes administering to the patient a therapeutically effective amount of a compound of Formula I.

Another embodiment includes the use of a compound of Formula I for therapy.

Another embodiment includes the use of a compound of Formula I for preventing, treating or lessening the severity of a disease. In one embodiment, the disease is an autoimmune disease.

Another embodiment includes the use of a compound of Formula I in the manufacture of a medicament for preventing, treating or lessening the severity of a disease. In one embodiment, the disease is an autoimmune disease.

Another embodiment includes a kit for treating a disease or disorder responsive to the inhibition of a Janus kinase. The kit includes a first pharmaceutical composition comprising a compound of Formula I and instructions for use.

DETAILED DESCRIPTION OF THE INVENTION

Reference will now be made in detail to certain embodiments, examples of which are illustrated in the accompanying structures and formulas. While the invention will be described in conjunction with the enumerated embodiments, the invention is intended to cover all alternatives, modifications, and equivalents, which may be included within the scope of the present invention as defined by the claims. One skilled in the art will recognize methods and materials similar or equivalent to those described herein, which could be used in the practice of the present invention.

DEFINITIONS

The term "alkyl" refers to a saturated linear or branched-chain monovalent hydrocarbon radical, wherein the alkyl radical may be optionally substituted independently with one or more substituents described herein. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (t-Bu, i-butyl, —$CH_2CH(CH_3)_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$), 1-heptyl and 1-octyl.

Groups of the type ($C_0$-$C_n$ alkyl)R, includes alkyl groups substituted by the R group at any of the atoms in the group available for substitution (in an exemplary embodiment, n is a number from 1-6 and R is —OH, —$OCH_3$, —$NH_2$, —N($CH_3$)$_2$, —CN, halogen, $C_3$-$C_6$ cycloalkyl, phenyl or 3- to 9-membered heterocyclyl), For example, the group ($C_0$-$C_3$ alkyl)CN includes the groups —CN, —$CH_2$CN, —$CH_2CH_2$CN, —CH(CN)$CH_3$, —$CH_2CH_2CH_2$CN, —CH(CN)$CH_2CH_3$, —$CH_2$CH(CN)$CH_3$, —C($CH_3$)$_2$CN, —C($CH_2$CN)$CH_3$. For example, the group ($C_0$-$C_2$ alkyl)$C_3$ cycloalkyl includes the groups:

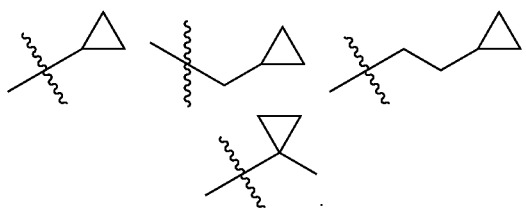

The term "alkenyl" refers to linear or branched-chain monovalent hydrocarbon radical with at least one site of unsaturation, i.e., a carbon-carbon double bond, wherein the alkenyl radical may be optionally substituted independently with one or more substituents described herein, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH═$CH_2$), prop-1-enyl (—CH═$CHCH_3$), prop-2-enyl (—$CH_2$CH═$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl" refers to a linear or branched monovalent hydrocarbon radical with at least one site of unsaturation, i.e., a carbon-carbon, triple bond, wherein the alkynyl radical may be optionally substituted independently with one or more substituents described herein. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane.

"Aryl" refers to a cyclic aromatic hydrocarbon group optionally substituted independently with one or more substituents described herein. In one example, the aryl group is 6-20 carbon atoms ($C_6$-$C_{20}$). In another example, the aryl group is $C_6$-$C_9$. In another example, the aryl group is a $C_6$ aryl group. Aryl includes bicyclic groups comprising an aromatic ring with a fused non-aromatic or partially saturated ring. Example aryl groups include, but are not limited to, phenyl, naphthalenyl, anthracenyl, indenyl, indanyl, 1,2-dihydronapthalenyl and 1,2,3,4-tetrahydronapthyl. In one example, aryl includes phenyl.

"Halogen" or "halogen" refer to F, Cl, Br or I.

The terms "heterocycle," "heterocyclyl" and "heterocyclic ring" are used interchangeably herein and refer to: (i) a saturated or partially unsaturated cyclic group (i.e., having one or more double and/or triple bonds within the ring) ("heterocycloalkyl"), or (ii) an aromatic cyclic group ("heteroaryl"), and in each case, which at least one ring atom is a heteroatom independently selected from nitrogen, oxygen, phosphorus and sulfur, the remaining ring atoms being carbon. The heterocyclyl group may be optionally substituted with one or more substituents described below. In one embodiment, heterocyclyl includes monocycles or bicycles having 1 to 9 carbon ring members ($C_1$-$C_9$) with the remaining ring atoms being heteroatoms selected from N, O, S and P. In other examples, heterocyclyl includes monocycles or bicycles having $C_1$-$C_5$, $C_3$-$C_5$ or $C_4$-$C_5$, with the remaining ring atoms being heteroatoms selected from N, O, S and P. In another embodiment, heterocyclyl includes 3-7-membered rings or 3-6 membered rings, containing one or more heteroatoms independently selected from N, O, S and P. In other examples, heterocyclyl includes monocyclic 3-, 4-, 5-, 6- or 7-membered rings, containing one or more heteroatoms independently selected from N, O, S and P. In another embodiment, heterocyclyl includes bi- or polycyclic or bridged 4-, 5-, 6-, 7-, 8- and 9-membered ring systems, containing one or more heteroatoms independently selected from N, O, S and P. Examples of bicycle systems include, but are not limited to, [3,5], [4,5], [5,5], [3,6], [4,6], [5,6], or [6,6]systems. Examples of bridged ring systems include, but are not limited to [2.2.1], [2.2.2], [3.2.2] and [4.1.0] arrangements, and having 1 to 3 heteroatoms selected from N, O, S and P. In another embodiment, heterocyclyl includes Spiro groups having 1 to 4 heteroatoms selected from N, O, S and P. The heterocyclyl group may be a carbon-linked group or heteroatom-linked group. "Heterocyclyl" includes a heterocyclyl group fused to a cycloalkyl group.

Exemplary heterocyclyl groups include, but are not limited to, oxiranyl, aziridinyl, thiiranyl, azetidinyl, oxetanyl, thietanyl, 1,2-dithietanyl, 1,3-dithietanyl, pyrrolidinyl, piperidinyl, morpholinyl, thiomorpholinyl, thioxanyl, piperazinyl, homopiperazinyl, homopiperidinyl, oxepanyl, thiepanyl, oxazepinyl, oxazepanyl, diazepanyl, 1,4-diazepanyl, diazepinyl, thiazepinyl, thiazepanyl, dihydrothienyl, dihydropyranyl, dihydrofuranyl, tetrahydropyranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, dioxanyl, 1,3-dioxolanyl, pyrazolinyl, pyrazolidinyl, dithianyl, dithiolanyl, pyrazolidinylimidazolinyl, imidazolidinyl, 3-azabicyclo[3.1.0]hexanyl, 3,6-diazabicyclo[3.1.1] heptanyl, 6-azabicyclo[3.1.1]heptanyl, 3-azabicyclo[3.1.1] heptanyl, 3-azabicyclo[4.1.0]heptanyl and azabicyclo[2.2.2] hexanyl. Examples of a heterocyclyl group wherein a ring atom is substituted with oxo (=O) are dihydropyridinonyl, pyridinonyl, piperidinonyl, pyrrolidinonyl, pyrimidinonyl, dihydropyrimidinonyl, piperazinonyl, pyrazinonyl, pyridazinonyl, dihydropyridazinonyl, dihydropyrrolonyl, pyrrolonyl, oxazolidinonyl, thiazolidinonyl, imidazolidinonyl, 1-oxothienyl, 1,1-dioxothienyl, 1-oxotetrahydrothienyl, 1,1-dioxotetrahydrothienyl and 1,1-dioxo-thiomorpholinyl. The heterocyclyl groups herein are optionally substituted independently with one or more substituents described herein. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

The term "heteroaryl" refers to an aromatic carbocyclic radical in which at least one ring atom is a heteroatom independently selected from nitrogen, oxygen and sulfur, the remaining ring atoms being carbon. Heteroaryl groups may be optionally substituted with one or more substituents described herein. In one example, the heteroaryl group contains 1 to 9 carbon ring atoms ($C_1$-$C_9$). In other examples, the heteroaryl group is $C_1$-$C_5$, $C_3$-$C_5$ or $C_4$-$C_5$. In one embodiment, exemplary heteroaryl groups include monocyclic aromatic 5-, 6- and 7-membered rings containing one or more heteroatoms independently selected from nitrogen, oxygen, and sulfur. In another embodiment, exemplary heteroaryl groups include fused ring systems of up to 9 carbon atoms wherein at least one aromatic ring contains one or more heteroatoms independently selected from nitrogen, oxygen, and sulfur. Fused systems can be fused at one or more points on the rings. "Heteroaryl" includes heteroaryl groups fused with an aryl, cycloalkyl or other heterocyclyl group. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl and furopyridinyl.

In certain embodiments, the heterocyclyl or heteroaryl group is C-attached. By way of example and not limitation, carbon bonded heterocyclyls include bonding arrangements at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. (2-pyridyl, 3-pyridyl, 4-pyridyl, 5-pyridyl, 6-pyridyl).

In certain embodiments, the heterocyclyl or heteroaryl group is N-attached. By way of example and not limitation, the nitrogen bonded heterocyclyl or heteroaryl group include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Treat" and "treatment" includes both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder, (for example, through a genetic mutation) or those in which the condition or disorder is to be prevented.

The phrase "therapeutically effective amount" means an amount of a compound of the present invention that (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase A2). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include Erlotinib (TARCEVA®, Genentech, Inc./OSI Pharm.), Trastuzumab (HERCEPTIN®, Genentech, Inc.); bevacizumab (AVASTIN®, Genentech, Inc.); Rituximab (RITUXAN®, Genentech, Inc./Biogen Idec, Inc.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIANIYCIN® (doxorubicin), morpholinodoxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASINO (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF inhibitors (e.g., ANGIOZYME®) and (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents; and (x) pharmaceutically acceptable salts, acids and derivatives of any of the above.

Humanized monoclonal antibodies with therapeutic potential as agents in combination with the Janus kinase inhibitors of the invention include: adalimumab, etanercept, infliximab, alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

The term "prodrug" as used in this application refers to a precursor or derivative form of a pharmaceutically active substance that is less efficacious to the patient or cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

"Liposome" refers to a vesicle composed of one or more lipids, phospholipids and/or surfactants, which is useful for delivery of a drug (such as a compound of Formula I and, optionally, a chemotherapeutic agent) to a mammal. The components of the liposome can be in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of a compound of Formula I. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

A "solvate" refers to an association or complex of one or more solvent molecules and a compound of Formula I. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, phthalimido, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include acetyl, trialkylsilyl, dialkylphenylsilyl, benzoyl, benzyl, benzyloxymethyl, methyl, methoxymethyl, triarylmethyl, and tetrahydropyranyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see T. W. Greene and P. Wuts, Protective Groups in Organic Synthesis, Third Ed., John Wiley & Sons, New York, 1999; and P. Kocienski, Protecting Groups, Third Ed., Verlag, 2003.

The term "patient" includes human patients and animal patients. The term "animal" includes companion animals (e.g., dogs, cats and horses), food-source animals, zoo animals, marine animals, birds and other similar animal species.

The phrase "pharmaceutically acceptable" indicates that the substance or composition must be compatible chemically and/or toxicologically, with the other ingredients comprising a formulation, and/or the mammal being treated therewith.

The terms "JAK kinase," and "Janus kinase" refer to the JAK1, JAK2, JAK3 and TYK2 protein kinases.

The terms "compound of this invention," and "compounds of the present invention", and "compounds of Formula I", unless otherwise indicated, include compounds of Formula I, formulas 1a-1n and stereoisomers, tautomers, solvates, metabolites, salts (e.g., pharmaceutically acceptable salts) and prodrugs thereof. Unless otherwise stated, structures depicted herein are also meant to include compounds that differ only in the presence of one or more isotopically enriched atoms. For example, compounds of Formula I and formulas 1a-1n, wherein one or more hydrogen atoms are replaced deuterium or tritium, or one or more carbon atoms are replaced by a $^{13}C$- or $^{14}C$-enriched carbon are within the scope of this invention.

Pyrazolopyrimidine Janus Kinase Inhibitor Compounds

In one embodiment, a compound of Formula I, and pharmaceutical formulations thereof, are provided that are useful in the treatment of diseases, conditions and/or disorders responsive to the inhibition of one or more Janus kinases.

Another embodiment includes compounds of Formula I:

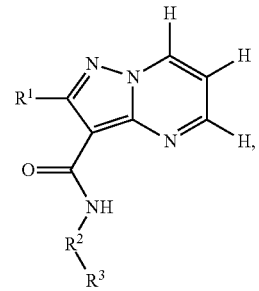

I enantiomers, diastereomers or pharmaceutically acceptable salts thereof, wherein:

$R^1$ is hydrogen, $C_1$-$C_6$ alkyl, —$OR^6$, —$NR^6R^7$ or halogen;

$R^2$ is 5- or 6-membered heteroaryl, wherein $R^2$ is optionally substituted with 1-3 $R^4$;

$R^3$ is phenyl, 5-6 membered heteroaryl, $C_3$-$C_6$ cycloalkyl or 3-10 membered heterocyclyl, wherein $R^3$ is optionally substituted by 1-5 $R^5$;

$R^4$ is independently $C_1$-$C_6$ alkyl, $C_2$-$C_6$ alkenyl, $C_2$-$C_6$ alkynyl, halogen, —($C_0$-$C_6$ alkyl)CN, —($C_0$-$C_6$ alkyl)$OR^6$, —($C_0$-$C_6$ alkyl)$SR^6$, —($C_0$-$C_6$ alkyl)$NR^6R^7$, —($C_0$-$C_6$ alkyl)$CF_3$, —($C_0$-$C_6$ alkyl)$C(O)R^6$, —($C_0$-$C_6$ alkyl)$C(O)OR^6$, —($C_0$-$C_6$ alkyl)$C(O)NR^6R^7$, —($C_0$-$C_6$ alkyl)$NR^6C(O)R^7$, —($C_0$-$C_6$ alkyl)C(O)3-6 membered heterocyclyl, —($C_0$-$C_6$ alkyl)($C_3$-$C_6$ cycloalkyl), —($C_0$-$C_6$ alkyl)phenyl, —($C_0$-$C_6$ alkyl)5-6 membered heteroaryl or —($C_0$-$C_6$ alkyl)(3-6-membered heterocyclyl), wherein $R^4$ is independently optionally substituted by $R^{15}$;

$R^5$ is independently $C_1$-$C_6$ alkyl, $C_2$-$C_6$ alkenyl, $C_2$-$C_6$ alkynyl, oxo, halogen, —($C_0$-$C_3$ alkyl)CN, —($C_0$-$C_3$ alkyl)$OR^{11}$, —($C_0$-$C_3$ alkyl)$SR^{11}$, —($C_0$-$C_3$ alkyl)$NR^{11}R^{12}$, —($C_0$-$C_3$ alkyl)$OCF_3$, —($C_0$-$C_3$ alkyl)$CF_3$, —($C_0$-$C_3$ alkyl)$NO_2$, —($C_0$-$C_3$ alkyl)$C(O)R^{11}$, —($C_0$-$C_3$ alkyl)$C(O)OR^{11}$, —($C_0$-$C_3$ alkyl)$C(O)NR^{11}R^{12}$, —($C_0$-$C_3$ alkyl)$NR^{11}C(O)R^{12}$, —($C_0$-$C_3$ alkyl)$S(O)_{1-2}R^{11}$, —($C_0$-$C_3$ alkyl)$NR^{11}S(O)_{1-2}R^{12}$, —($C_0$-$C_3$ alkyl)$S(O)_{1-2}NR^{11}R^{12}$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)C(O)(3-6-membered heterocyclyl), —($C_0$-$C_3$ alkyl)(5-6-membered heteroaryl) or —($C_0$-$C_3$ alkyl)phenyl, wherein $R^5$ is independently optionally substituted by halogen, $C_1$-$C_3$ alkyl, oxo, —$CF_3$, —($C_0$-$C_3$ alkyl)$OR^{13}$ or —($C_0$-$C_3$ alkyl)$NR^{13}R^{14}$; or two $R^5$ are taken together to form —$O(CH_2)_{1-3}O$—;

$R^6$ and $R^7$ are independently hydrogen, $C_1$-$C_6$ alkyl, $C_2$-$C_6$ alkenyl, $C_2$-$C_6$ alkynyl, —CN, —$OR^8$, —$NR^8R^9$, —$C(O)R^8$, —$C(O)OR^8$, —$C(O)NR^8R^9$, —$NR^8C(O)R^9$, —$NR^8C(O)OR^9$, —$OC(O)NR^8$, —$S(O)_{1-2}R^8$, —$NR^8S(O)_{1-2}R^9$, —$S(O)_{1-2}NR^8R^9$, $C_3$-$C_6$ cycloalkyl, phenyl, 3-6 membered heterocyclyl or 5-6 membered heteroaryl, wherein said $R^6$ and $R^7$ are independently optionally substituted by $R^{20}$, or $R^6$ and $R^7$ are taken together with the atom to which they are attached to form a 3-6-membered heterocyclyl, optionally substituted by halogen, oxo, —$CF_3$ or $C_1$-$C_3$ alkyl;

$R^8$ and $R^9$ are independently hydrogen or $C_1$-$C_3$ alkyl; or $R^8$ and $R^9$ are taken together with the atom to which they are attached to form a 3-6-membered heterocyclyl, optionally substituted by halogen, oxo, —$CF_3$ or $C_1$-$C_3$ alkyl;

$R^{11}$ is independently hydrogen, $C_1$-$C_6$ alkyl, $C_3$-$C_6$ cycloalkyl, 3-6 membered heterocyclyl, —$C(O)R^{13}$, —$C(O)OR^{13}$, —$C(O)NR^{13}R^{14}$, —$NR^{13}C(O)R^{14}$, —$S(O)_{1-2}R^{13}$, —$NR^{13}S(O)_{1-2}R^{14}$ or —$S(O)_{1-2}NR^{13}R^{14}$, wherein said alkyl, cycloalkyl and heterocyclyl are independently optionally substituted by oxo, $C_1$-$C_3$ alkyl, $OR^{13}$, $NR^{13}R^{14}$ or halogen;

$R^{12}$ is independently hydrogen or $C_1$-$C_3$ alkyl, wherein said alkyl is independently optionally substituted by halogen or oxo; or $R^{11}$ and $R^{12}$ are taken together with the atom to which they are attached to form a 3-6-membered heterocyclyl, optionally substituted by halogen, oxo, —$CF_3$ or $C_1$-$C_3$ alkyl;

$R^{13}$ and $R^{14}$ are independently hydrogen or $C_1$-$C_3$ alkyl optionally substituted by halogen or oxo; or $R^{13}$ and $R^{14}$ are taken together with the atom to which they are attached to form a 3-6-membered heterocyclyl, optionally substituted by halogen, oxo, —$CF_3$ or $C_1$-$C_3$ alkyl;

$R^{15}$ is $C_1$-$C_6$ alkyl, $C_2$-$C_6$ alkenyl, $C_2$-$C_6$ alkynyl, oxo, halogen, —CN, —$OR^{16}$, —$SR^{16}$, —$NR^{16}R^{17}$, —$OCF_3$, —$CF_3$, —$C(O)R^{16}$, —$C(O)OR^{16}$, —$C(O)NR^{16}R^{17}$, —$NR^{16}C(O)R^{17}$, —$NR^{16}C(O)OR^{17}$, —$OC(O)NR^{16}$, $C_3$-$C_6$ cycloalkyl, 3-6-membered heterocyclyl, —C(O)(3-6-membered heterocyclyl, 5-6-membered heteroaryl or phenyl, wherein $R^{15}$ is independently optionally substituted by halogen, $C_1$-$C_3$ alkyl, oxo, —CN, —$CF_3$, —$OR^{18}$, —$NR^{18}R^{19}$;

$R^{16}$ and $R^{17}$ are independently hydrogen or $C_1$-$C_6$ alkyl optionally substituted by oxo or halogen; or $R^{16}$ and $R^{17}$ are taken together with the atom to which they are attached to form a 3-6 membered heterocyclyl optionally substituted by oxo, halogen or $C_1$-$C_3$ alkyl;

$R^{18}$ and $R^{19}$ are independently hydrogen or $C_1$-$C_6$ alkyl optionally substituted by oxo or halogen; or $R^{18}$ and $R^{19}$ are taken together with the atom to which they are attached to form a 3-6 membered heterocyclyl optionally substituted by oxo, halogen or $C_1$-$C_3$ alkyl;

$R^{20}$ is $C_1$-$C_6$ alkyl, oxo, halogen, —$OR^{21}$, —$NR^{21}R^{22}$—CN, $C_3$-$C_6$ cycloalkyl, phenyl, 3-6 membered heterocyclyl or 5-6 membered heteroaryl, wherein $R^{20}$ is optionally substituted by oxo, halogen or $C_1$-$C_3$ alkyl; and $R^{20}$ and $R^{21}$ are independently hydrogen or $C_1$-$C_6$ alkyl optionally substituted by oxo or halogen; or $R^{20}$ and $R^{21}$ are taken together with the atom to which they are attached to form a 3-6 membered heterocyclyl optionally substituted by oxo, halogen or $C_1$-$C_3$ alkyl.

Another embodiment includes compounds of Formula I:

I enantiomers, diastereomers or pharmaceutically acceptable salts thereof, wherein:

$R^1$ is hydrogen, $C_1$-$C_6$ alkyl, —$OR^6$, —$NR^6R^7$ or halogen;
$R^2$ is 5- or 6-membered heteroaryl, wherein $R^2$ is optionally substituted with 1-3 $R^4$;
$R^3$ is phenyl, 5- or 6-membered heteroaryl, wherein $R^3$ is optionally substituted by 1-5 $R^5$;
$R^4$ is independently $C_1$-$C_6$ alkyl, $C_2$-$C_6$ alkenyl, $C_2$-$C_6$ alkynyl, halogen, —($C_0$-$C_6$ alkyl)$OR^6$, —($C_0$-$C_6$ alkyl)$SR^6$, —($C_0$-$C_6$ alkyl)$NR^6R^7$, —($C_0$-$C_6$ alkyl)$CF_3$, —($C_0$-$C_6$ alkyl)C(O)$R^6$, —($C_0$-$C_6$ alkyl)C(O)$OR^6$, —($C_0$-$C_6$ alkyl)C(O)$NR^6R^7$, —($C_0$-$C_6$ alkyl)($C_3$-$C_6$ cycloalkyl) or —($C_0$-$C_6$ alkyl)(3-6-membered heterocyclyl), wherein $R^4$ is independently optionally substituted by $C_1$-$C_3$ alkyl, oxo, halogen, —$CF_3$, —$OR^8$ or —$NR^8R^9$;

$R^5$ is independently $C_1$-$C_6$ alkyl, $C_2$-$C_6$ alkenyl, $C_2$-$C_6$ alkynyl, halogen, —($C_0$-$C_3$ alkyl)CN, —($C_0$-$C_3$ alkyl)$OR^{11}$, —($C_0$-$C_3$ alkyl)$SR^{11}$, —($C_0$-$C_3$ alkyl)$NR^{11}R^{12}$, —($C_0$-$C_3$ alkyl)$OCF_3$, —($C_0$-$C_3$ alkyl)$CF_3$, —($C_0$-$C_3$ alkyl)$NO_2$, —($C_0$-$C_3$ alkyl)C(O)$R^{11}$, —($C_0$-$C_3$ alkyl)C(O)$OR^{11}$, —($C_0$-$C_3$ alkyl)C(O)$NR^{11}R^{12}$, —($C_0$-$C_3$ alkyl)$NR^{11}C(O)R^{12}$, —($C_0$-$C_3$ alkyl)$S(O)_{1-2}R^{11}$, —($C_0$-$C_3$ alkyl)$NR^{11}S(O)_{1-2}R^{12}$, —($C_0$-$C_3$ alkyl)$S(O)_{1-2}NR^{11}R^{12}$, —($C_0$-$C_3$ alkyl)($C_3$-$C_6$ cycloalkyl), —($C_0$-$C_3$ alkyl)(3-6-membered heterocyclyl), —($C_0$-$C_3$ alkyl)C(O)(3-6-membered heterocyclyl), —($C_0$-$C_3$ alkyl)(5-6-membered heteroaryl) or —($C_0$-$C_3$ alkyl)phenyl, wherein $R^5$ is independently optionally substituted by halogen, $C_1$-$C_3$ alkyl, oxo, —$CF_3$, —($C_0$-$C_3$ alkyl)$OR^{13}$ or —($C_0$-$C_3$ alkyl)$NR^{13}R^{14}$; or two $R^5$ are taken together to form —$O(CH_2)_{1-3}O$—;

$R^6$ is independently hydrogen, $C_1$-$C_3$ alkyl, —$C(O)R^8$, —$C(O)OR^8$, —$C(O)NR^8R^9$, —$NR^8C(O)R^9$, —$S(O)_{1-2}R^8$, —$NR^8S(O)_{1-2}R^9$ or —$S(O)_{1-2}NR^8R^9$, wherein said alkyl is independently optionally substituted by oxo, OH or halogen;

$R^7$ is independently hydrogen or $C_1$-$C_3$ alkyl, wherein said alkyl is independently optionally substituted by halogen; or $R^6$ and $R^7$ are taken together with the atom to which they are attached to form a 5- or 6-membered heterocyclyl, optionally substituted by halogen, oxo, —$CF_3$ or $C_1$-$C_3$ alkyl;

$R^8$ and $R^9$ are independently hydrogen or $C_1$-$C_3$ alkyl; or $R^8$ and $R^9$ are taken together with the atom to which they are attached to form a 5- or 6-membered heterocyclyl, optionally substituted by halogen, oxo, —$CF_3$ or $C_1$-$C_3$ alkyl;

$R^{11}$ is independently hydrogen, $C_1$-$C_3$ alkyl, —$C(O)R^{13}$, —$C(O)OR^{13}$, —$C(O)NR^{13}R^{14}$, —$NR^{13}C(O)R^{14}$, —$S(O)_{1-2}R^{13}$, —$NR^{13}S(O)_{1-2}R^{14}$ or —$S(O)_{1-2}NR^{13}R^{14}$, wherein said alkyl is independently optionally substituted by oxo, OH or halogen;

$R^{12}$ is independently hydrogen or $C_1$-$C_3$ alkyl, wherein said alkyl is independently optionally substituted by halogen; or $R^{11}$ and $R^{12}$ are taken together with the atom to which they are attached to form a 5- or 6-membered heterocyclyl, optionally substituted by halogen, oxo, —$CF_3$ or $C_1$-$C_3$ alkyl; and $R^{13}$ and $R^{14}$ are independently hydrogen or $C_1$-$C_3$ alkyl; or $R^{13}$ and $R^{14}$ are taken together with the atom to which they are attached to form a 5- or 6-membered heterocyclyl, optionally substituted by halogen, oxo, —$CF_3$ or $C_1$-$C_3$ alkyl.

Another embodiment includes compounds of Formula I other than:

N-(5-methyl-4-(4-propylphenyl)thiazol-2-yl)pyrazolo[1,5-a]pyrimidine-3-carboxamide;

N-(4-(4-chlorophenyl)thiazol-2-yl)pyrazolo[1,5-a]pyrimidine-3-carboxamide; or

N-(3-methyl-1-phenyl-1H-pyrazol-5-yl)pyrazolo[1,5-a]pyrimidine-3-carboxamide.

In certain embodiments, $R^2$ is selected from pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, triazolyl, thiadiazolyl or furazanyl, and wherein $R^2$ is optionally substituted with 1-3 $R^4$. In one embodiment, $R^2$ is selected from pyridinyl or pyrazolyl, optionally substituted with 1-3 $R^4$.

In certain embodiments, $R^2$ is selected from thiazolyl, pyridinyl or pyrazolyl, optionally substituted with 1-3 $R^4$.

In certain embodiments, $R^4$ is independently $C_1$-$C_6$ alkyl, —($C_0$-$C_6$ alkyl)$OR^6$, —($C_0$-$C_6$ alkyl)$SR^6$, —($C_0$-$C_6$ alkyl)$NR^6R^7$, —($C_0$-$C_6$ alkyl)$CF_3$, —($C_0$-$C_6$ alkyl)C(O)$R^6$, —($C_0$-

$C_6$ alkyl)C(O)$OR^6$, —($C_0$-$C_6$ alkyl)C(O)$NR^6R^7$, —($C_0$-$C_6$ alkyl)($C_3$-$C_6$ cycloalkyl) or —($C_0$-$C_6$ alkyl)(3-6-membered heterocyclyl), wherein $R^4$ is independently optionally substituted by $C_1$-$C_3$ alkyl, oxo, halogen, —$CF_3$, —$OR^8$ or —$NR^8R^9$.

In certain embodiments, $R^4$ is $C_1$-$C_6$ alkyl, halogen, —($C_0$-$C_6$ alkyl)CN, —($C_0$-$C_6$ alkyl)$OR^6$, —($C_0$-$C_6$ alkyl)$NR^6R^7$, —($C_0$-$C_6$ alkyl)$CF_3$, —($C_0$-$C_6$ alkyl)C(O)$R^6$, —($C_0$-$C_6$ alkyl)C(O)$OR^6$, —($C_0$-$C_6$ alkyl)C(O)$NR^6R^7$, —($C_0$-$C_6$ alkyl)$NR^6$C(O)$R^7$, —($C_0$-$C_6$ alkyl)C(O)$_{3-6}$ membered heterocyclyl, —($C_0$-$C_6$ alkyl)($C_3$-$C_6$ cycloalkyl), —($C_0$-$C_6$ alkyl)phenyl, —($C_0$-$C_6$ alkyl)$_{5-6}$ membered heteroaryl or —($C_0$-$C_6$ alkyl)(3-6-membered heterocyclyl), wherein $R^4$ is independently optionally substituted by $R^{15}$.

In certain embodiments, $R^3$ is phenyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, triazolyl, thiadiazolyl or furazanyl, and wherein $R^3$ is optionally substituted by 1-5 $R^5$. In one embodiment, $R^3$ is phenyl, optionally substituted by 1-3 $R^5$.

In certain embodiments, $R^3$ is phenyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, triazolyl, thiadiazolyl, cyclohexenyl, dihydrobenzofuranyl, piperidinyl, pyridinonyl, pyrrolidinyl or furazanyl, and wherein $R^3$ is optionally substituted by 1-5 $R^5$.

In certain embodiments, $R^5$ is independently $C_1$-$C_6$ alkyl, halogen, —CN, —($C_0$-$C_3$ alkyl)$OR^{11}$, —($C_0$-$C_3$ alkyl)$SR^{11}$, —($C_0$-$C_3$ alkyl)$NR^{11}R^{12}$, —($C_0$-$C_3$ alkyl)$OCF_3$ or —$CF_3$, wherein said alkyl is independently optionally substituted by halogen, $C_1$-$C_3$ alkyl, oxo, —$CF_3$, —($C_0$-$C_3$ alkyl)$OR^{13}$ or —($C_0$-$C_3$ alkyl)$NR^{13}R^{14}$.

In certain embodiments, $R^3$ is phenyl, optionally substituted by 1-3 $R^5$; and $R^5$ is independently $C_1$-$C_6$ alkyl, halogen, —CN, —($C_0$-$C_3$ alkyl)$OR^{11}$, —($C_0$-$C_3$ alkyl)$SR^{11}$, —($C_0$-$C_3$ alkyl)$NR^{11}R^{12}$, —($C_0$-$C_3$ alkyl)$OCF_3$ or —$CF_3$, wherein said alkyl is independently optionally substituted by halogen, $C_1$-$C_3$ alkyl, oxo, —$CF_3$, —($C_0$-$C_3$ alkyl)$OR^{13}$ or —($C_0$-$C_3$ alkyl)$NR^{13}R^{14}$.

In certain embodiments, $R^3$ is phenyl, pyridinyl, dihydrobenzofuranyl, piperidinyl, pyrrolidinyl, pyridinonyl, imidazolyl or isoxazolyl, wherein $R^3$ is optionally substituted by 1-3 $R^5$; and $R^5$ is independently oxo, $C_1$-$C_6$ alkyl, $C_2$-$C_6$ alkenyl, $C_2$-$C_6$ alkynyl, $C_3$-$C_6$ cycloalkyl, halogen, —CN, —O($C_1$-$C_6$ alkyl), —S($C_1$-$C_6$ alkyl), —O($C_3$-$C_6$ cycloalkyl), —S($C_3$-$C_6$ cycloalkyl), —($C_0$-$C_3$ alkyl)$NR^{11}R^{12}$, —$OCF_3$, —$OCHF_2$, or —$CF_3$, wherein said alkyl, alkenyl, alkynyl and cycloalkyl are independently optionally substituted by halogen, $C_1$-$C_3$ alkyl, OH, $OCH_3$, $NH_2$, $NMe_2$, oxo or —$CF_3$.

In certain embodiments, $R^1$ is hydrogen, $OR^8$ or —$NR^6R^7$. In one embodiment, $R^1$ is hydrogen. In one embodiment, $R^1$ is —$NH_2$.

In certain embodiments, $R^2$ is pyrazolyl, optionally substituted by $R^4$, wherein $R^4$ is —($C_0$-$C_6$ alkyl)$OR^6$ or —($C_0$-$C_6$ alkyl)$SR^6$, and wherein $R^4$ is independently optionally substituted by $C_1$-$C_3$ alkyl, —$OR^8$ or —$NR^8R^9$. In one embodiment, $R^2$ is pyrazolyl, optionally substituted by $R^4$, wherein $R^4$ is —($C_0$-$C_6$ alkyl)$OR^6$ or —($C_0$-$C_3$ alkyl)$SR^6$, and wherein $R^4$ is independently optionally substituted by $C_1$-$C_3$ alkyl, —$OR^8$ or —$NR^8R^9$, $R^3$ is phenyl, optionally substituted by 1-3 $R^5$, and $R^5$ is independently $C_1$-$C_6$ alkyl, halogen, —CN, —$OR^{11}$, —$SR^{11}$ or —$CF_3$, wherein said alkyl is independently optionally substituted by halogen, —$CF_3$, —$OR^{13}$ or —$NR^{13}R^{14}$.

In certain embodiments, $R^2$ is pyrazolyl, optionally substituted by $R^4$, wherein $R^4$ is —($C_0$-$C_6$ alkyl)$CF_3$, and wherein $R^4$ is independently optionally substituted by $C_1$-$C_3$ alkyl, —$OR^8$ or —$NR^8R^9$. In one embodiment, $R^2$ is pyrazolyl, optionally substituted by $R^4$, wherein $R^4$ is —($C_0$-$C_6$ alkyl)$CF_3$, and wherein $R^4$ is independently optionally substituted by $C_1$-$C_3$ alkyl, —$OR^8$ or —$NR^8R^9$, $R^3$ is phenyl, optionally substituted by 1-3 $R^5$, and $R^5$ is independently $C_1$-$C_6$ alkyl, halogen, —CN, —$OR^{11}$, —$SR^{11}$ or —$CF_3$, wherein said alkyl is independently optionally substituted by halogen, $CF_3$, —$OR^{13}$ or —$NR^{13}R^{14}$.

In certain embodiments, $R^2$ is pyrazolyl, optionally substituted by $R^4$, wherein $R^4$ is —($C_0$-$C_6$ alkyl)$NR^6R^7$ or —($C_0$-$C_6$ alkyl)(3-6-membered heterocyclyl), and wherein $R^4$ is independently optionally substituted by $C_1$-$C_3$ alkyl, —$OR^8$ or —$NR^8R^9$. In one embodiment, $R^2$ is pyrazolyl, optionally substituted by $R^4$, wherein $R^4$ is —($C_0$-$C_6$ alkyl)$NR^6R^7$ or —($C_0$-$C_6$ alkyl)(3-6-membered heterocyclyl), and wherein $R^4$ is independently optionally substituted by $C_1$-$C_3$ alkyl, —$OR^8$ or —$NR^8R^9$, $R^3$ is phenyl, optionally substituted by 1-3 $R^5$, and $R^5$ is independently $C_1$-$C_6$ alkyl, halogen, —CN, —$OR^{11}$, —$SR^{11}$ or —$CF_3$, wherein said alkyl is independently optionally substituted by halogen, —$CF_3$, —$OR^{13}$ or —$NR^{13}R^{14}$.

In certain embodiments, $R^2$ is pyrazolyl, optionally substituted by $R^4$, wherein $R^4$ is —($C_0$-$C_6$ alkyl)($C_3$-$C_6$ cycloalkyl), and wherein $R^4$ is independently optionally substituted by $C_1$-$C_3$ alkyl, —$OR^8$ or —$NR^8R^9$. In one embodiment, $R^2$ is pyrazolyl, optionally substituted by $R^4$, wherein $R^4$ is —($C_0$-$C_6$ alkyl)($C_3$-$C_6$ cycloalkyl), and wherein $R^4$ is independently optionally substituted by $C_1$-$C_3$ alkyl, —$OR^8$ or —$NR^8R^9$, $R^3$ is phenyl, optionally substituted by 1-3 $R^5$, and $R^5$ is independently $C_1$-$C_6$ alkyl, halogen, —CN, —$OR^{11}$, —$SR^{11}$ or —$CF_3$, wherein said alkyl is independently optionally substituted by halogen, —$CF_3$, —$OR^{13}$ or —$NR^{13}R^{14}$.

In certain embodiments, $R^2$ is pyrazolyl, optionally substituted by $R^4$, wherein $R^4$ is —($C_0$-$C_6$ alkyl)C(O)$OR^6$ or —($C_0$-$C_6$ alkyl)C(O)$NR^6NR^7$, and wherein $R^4$ is independently optionally substituted by $C_1$-$C_3$ alkyl, —$OR^8$ or —$NR^8R^9$. In one embodiment, $R^2$ is pyrazolyl, optionally substituted by $R^4$, wherein $R^4$ is —($C_0$-$C_6$ alkyl)C(O)$OR^6$, and wherein $R^4$ is independently optionally substituted by $C_1$-$C_3$ alkyl, —$OR^8$ or —$NR^8R^9$, $R^3$ is phenyl, optionally substituted by 1-3 $R^5$, and $R^5$ is independently $C_1$-$C_6$ alkyl, halogen, —CN, —$OR^{11}$, —$SR^{11}$ or —$CF_3$, wherein said alkyl is independently optionally substituted by halogen, —$CF_3$, —$OR^{13}$ or —$NR^{13}R^{14}$.

In certain embodiments, $R^2$ is pyrazolyl, optionally substituted by $R^4$, wherein $R^4$ is $C_0$-$C_6$ alkyl, and wherein $R^4$ is independently optionally substituted by —$OR^8$ or —$NR^8R^9$. In one embodiment, $R^2$ is pyrazolyl, optionally substituted by $R^4$, wherein $R^4$ is $C_0$-$C_6$ alkyl, and wherein $R^4$ is independently optionally substituted by halogen, —$OR^8$ or —$NR^8R^9$, $R^3$ is phenyl, optionally substituted by 1-3 $R^5$, and $R^5$ is independently $C_1$-$C_6$ alkyl, halogen, —CN, —$OR^{11}$, —$SR^{11}$ or —$CF_3$, wherein said alkyl is independently optionally substituted by halogen, —$CF_3$, —$OR^{13}$ or —$NR^{13}R^{14}$.

In certain embodiments, $R^2$ is pyrazolyl, optionally substituted by $R^4$, wherein $R^4$ is —($C_0$-$C_6$ alkyl)CN, and wherein $R^4$ is independently optionally substituted by halogen, —$OR^8$ or —$NR^8R^9$. In one embodiment, $R^2$ is pyrazolyl, optionally substituted by $R^4$, wherein $R^4$ is —($C_0$-$C_6$ alkyl)CN, and wherein $R^4$ is independently optionally substituted by halogen, —$OR^8$ or —$NR^8R^9$, $R^3$ is phenyl, optionally substituted by 1-3 $R^5$, and $R^5$ is independently $C_1$-$C_6$ alkyl, halogen, —CN, —OR$^{11}$, —SR$^{11}$ or —CF$_3$, wherein said alkyl is independently optionally substituted by halogen, —CF$_3$, —OR$^{13}$ or —NR$^{13}$R$^{14}$.

In certain embodiments, R$^2$ is pyrazolyl, optionally substituted by R$^4$, wherein R$^4$ is C$_1$-C$_6$ alkyl optionally substituted by oxo, —OR$^8$, —NR$^8$R$^9$, —CN, halogen, C$_3$-C$_6$ cycloalkyl, or 5-6 membered heterocyclyl, 5-6 membered heterocyclyl optionally substituted by —OR$^8$, —NR$^8$R$^9$, —CN, halogen or oxo, —CH$_2$C(O)NR$^6$NR$^7$ optionally substituted by —OR$^8$, —NR$^8$R$^9$, —CN, halogen or C$_3$-C$_6$ cycloalkyl, or —CH$_2$(5-6 membered heterocyclyl optionally substituted by oxo, —OR$^8$, —NR$^8$R$^9$, —CN, halogen or C$_1$-C$_3$ alkyl, and R$^3$ is phenyl optionally substituted by 1-3 R$^5$.

In certain embodiments, R$^2$ is pyrazolyl, optionally substituted by R$^4$, wherein R$^4$ is —CH$_2$C(OH)(C$_1$-C$_3$ alkyl optionally substituted by halogen), —CH$_2$C(O)NR$^6$NR$^7$ or —CH$_2$C(O)(4-6 membered heterocyclyl), wherein R$^4$ is optionally substituted by oxo, —OR$^8$, —NR$^8$R$^9$, —CN, halogen, C$_1$-C$_6$ alkyl or C$_3$-C$_6$ cycloalkyl, and R$^3$ is phenyl optionally substituted by 1-3 R$^5$.

In certain embodiments, R$^2$ is pyridinyl, optionally substituted by C$_1$-C$_6$ alkyl and said alkyl is optionally substituted by halogen. In one embodiment, R$^2$ is pyridinyl, optionally substituted by C$_1$-C$_6$ alkyl and said alkyl is optionally substituted by halogen, R$^3$ is phenyl, optionally substituted by 1-3 R$^5$, and R$^5$ is independently C$_1$-C$_6$ alkyl, halogen, —CN, —OR$^{11}$, —SR$^{11}$ or —CF$_3$, wherein said alkyl is independently optionally substituted by halogen, —CF$_3$, —OR$^{13}$ or —NR$^{13}$R$^{14}$.

In certain embodiments, R$^4$ is —(C$_0$-C$_6$ alkyl)OR$^6$ or —(C$_0$-C$_6$ alkyl)SR$^6$, wherein said alkyl is independently optionally substituted by halogen, C$_1$-C$_3$ alkyl, oxo, —OR$^8$ or —NR$^8$R$^9$. In one embodiment, R$^4$ is selected from:

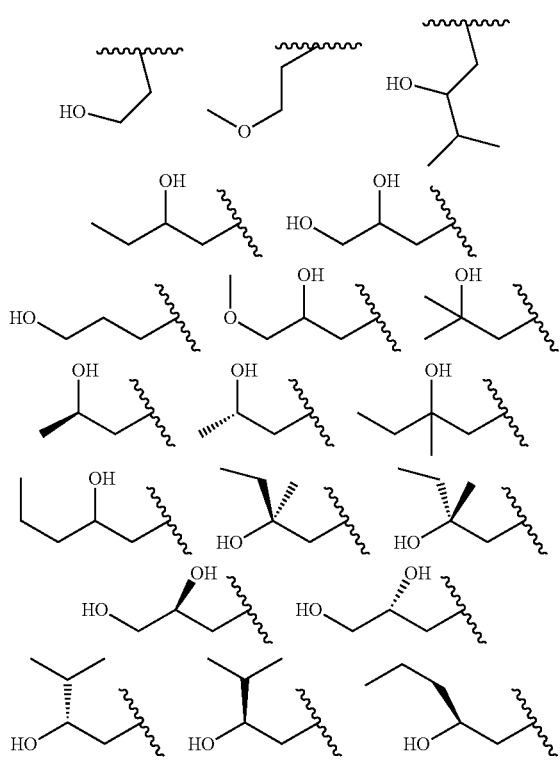
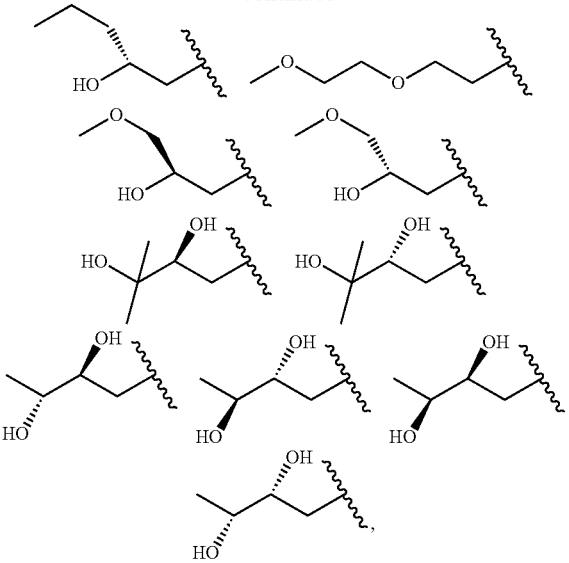

wherein the wavy line represents the point of attachment to R$^2$.

In certain embodiments, R$^4$ is —(C$_0$-C$_6$ alkyl)CF$_3$, wherein said alkyl is independently optionally substituted by halogen, C$_1$-C$_3$ alkyl, oxo, —OR$^8$ or —NR$^8$R$^9$. In one embodiment, R$^4$ is selected from:

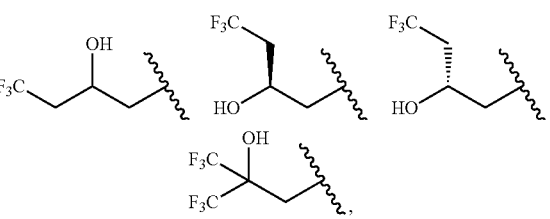

wherein the wavy line represents the point of attachment to R$^2$.

In certain embodiments, R$^4$ is —(C$_0$-C$_6$ alkyl)NR$^6$R$^7$, wherein said alkyl is independently optionally substituted by halogen, C$_1$-C$_3$ alkyl, oxo, —OR$^8$ or —NR$^8$R$^9$. In one embodiment, R$^4$ is selected from:

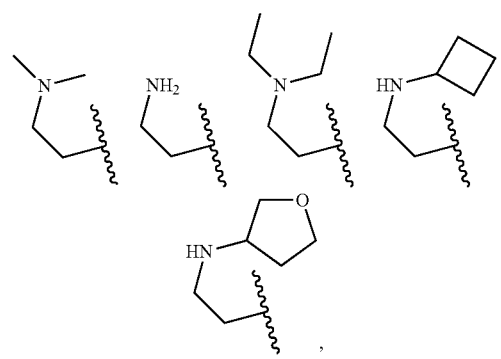

wherein the wavy line represents the point of attachment to R$^2$.

In certain embodiments, R$^4$ is —(C$_0$-C$_6$ alkyl)(3-6-membered heterocyclyl), wherein said alkyl and heterocyclyl are independently optionally substituted by halogen, $C_1$-$C_3$ alkyl, oxo, —$OR^8$ or —$NR^8R^9$. In one embodiment, said 3-6-membered heterocyclyl is oxetanyl, morpholinyl, piperidinyl, piperazinyl, pyrrolidinyl, pyrrolidinonyl, tetrahydrofuranyl, oxazolyl, isoxazolyl and tetrahydropyranyl, optionally substituted by halogen, $C_1$-$C_3$ alkyl, oxo, —$OR^8$ or —$NR^8R^9$. In one embodiment, $R^4$ is selected from:

alkyl, oxo, —$OR^8$ or —$NR^8R^9$. In one embodiment, 3-6-membered heterocyclyl is oxetanyl, morpholinyl, piperidinyl, piperazinyl, pyrrolidinyl, tetrahydrofuranyl, oxazolyl, isoxazolyl, dihydropyrrolyl and tetrahydropyranyl, optionally substituted by halogen, $C_1$-$C_3$ alkyl, oxo, —$OR^8$ or —$NR^8R^9$. In one embodiment, $R^4$ is selected from:

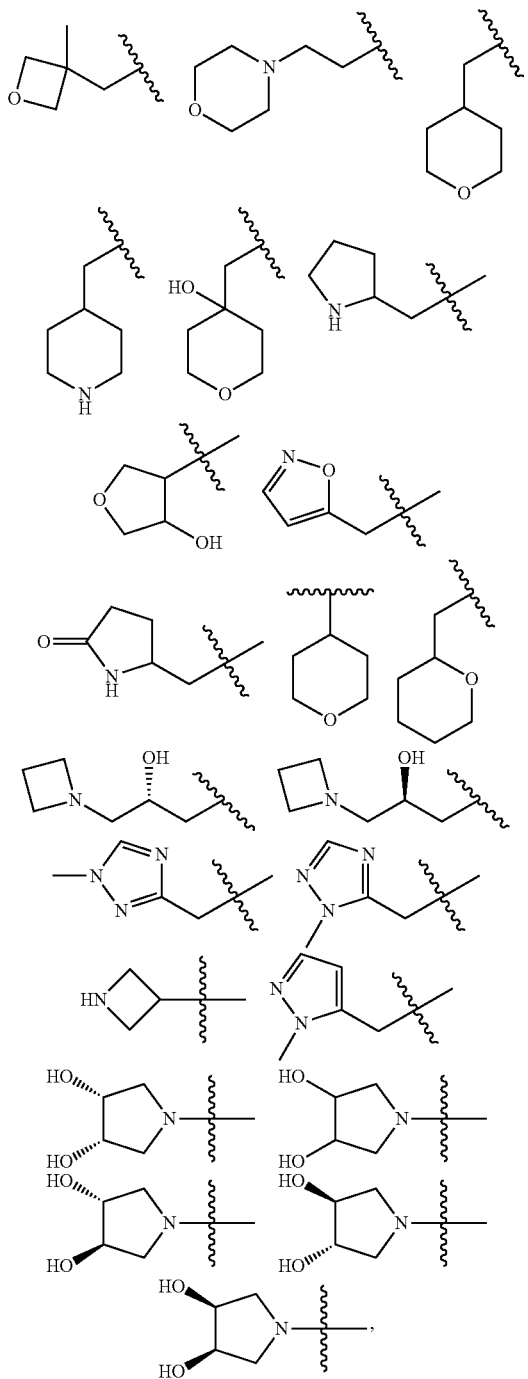

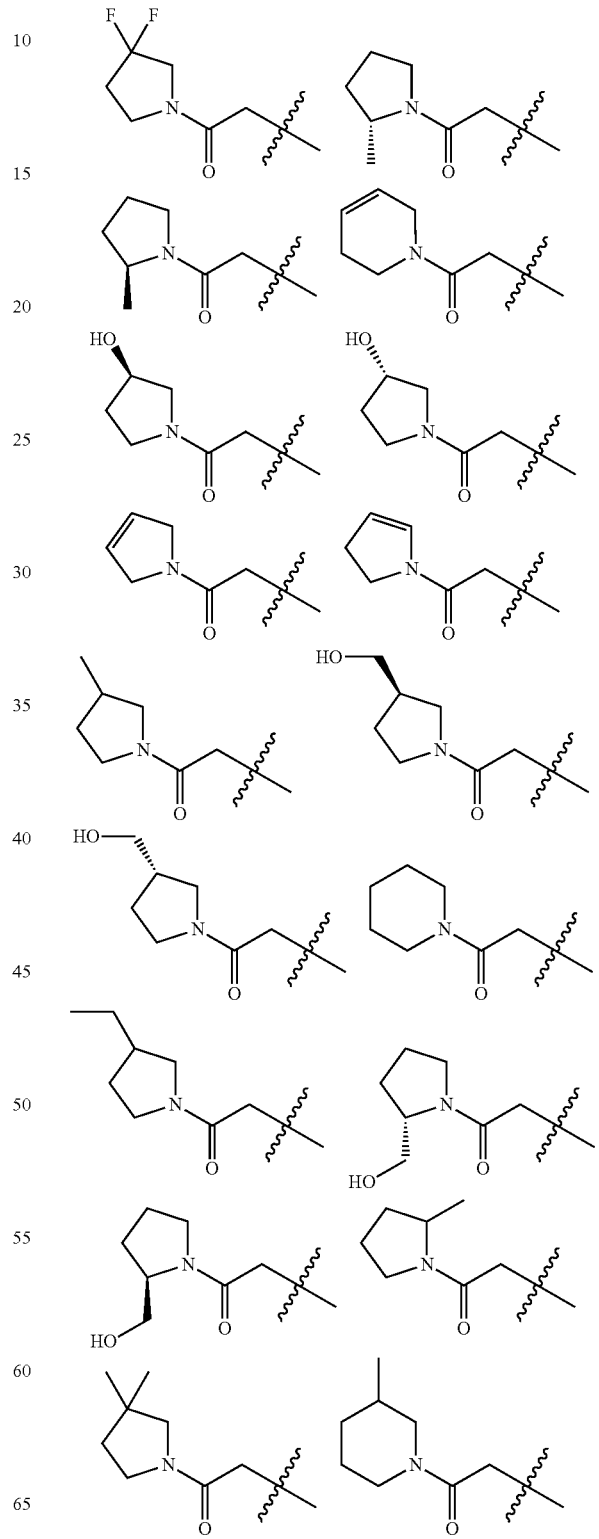

wherein the wavy line represents the point of attachment to $R^2$.

In certain embodiments, $R^4$ is —($C_0$-$C_6$ alkyl)C(O)(3-6-membered heterocyclyl), wherein said alkyl and heterocyclyl are independently optionally substituted by halogen, $C_1$-$C_3$

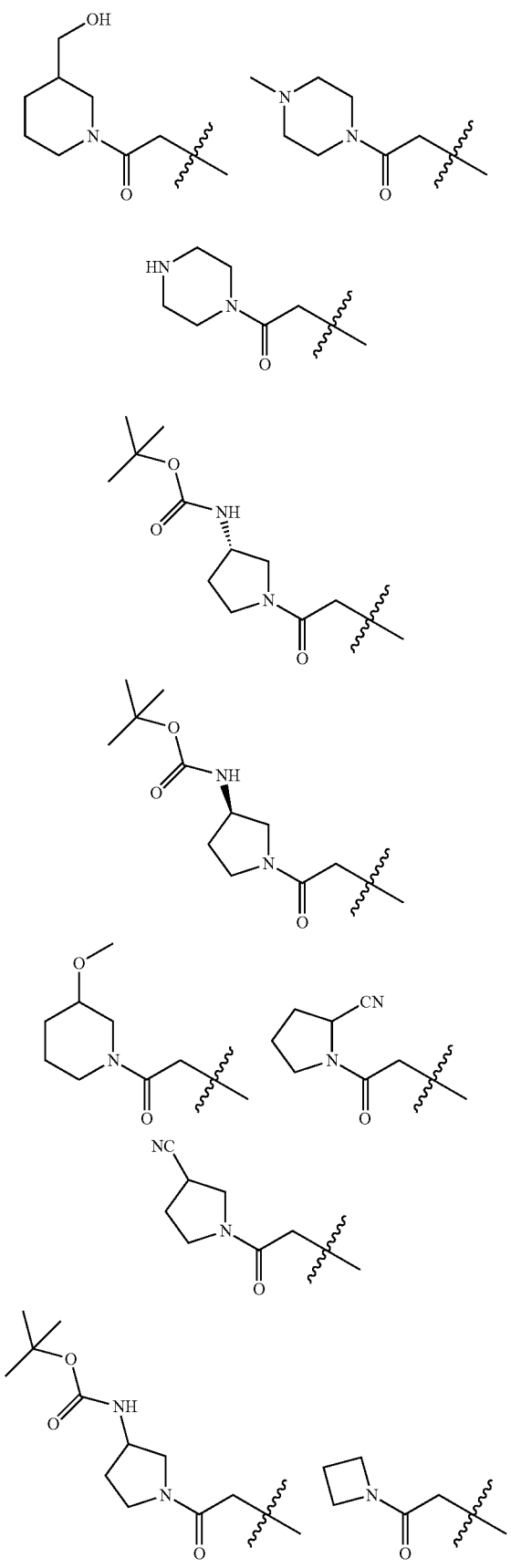
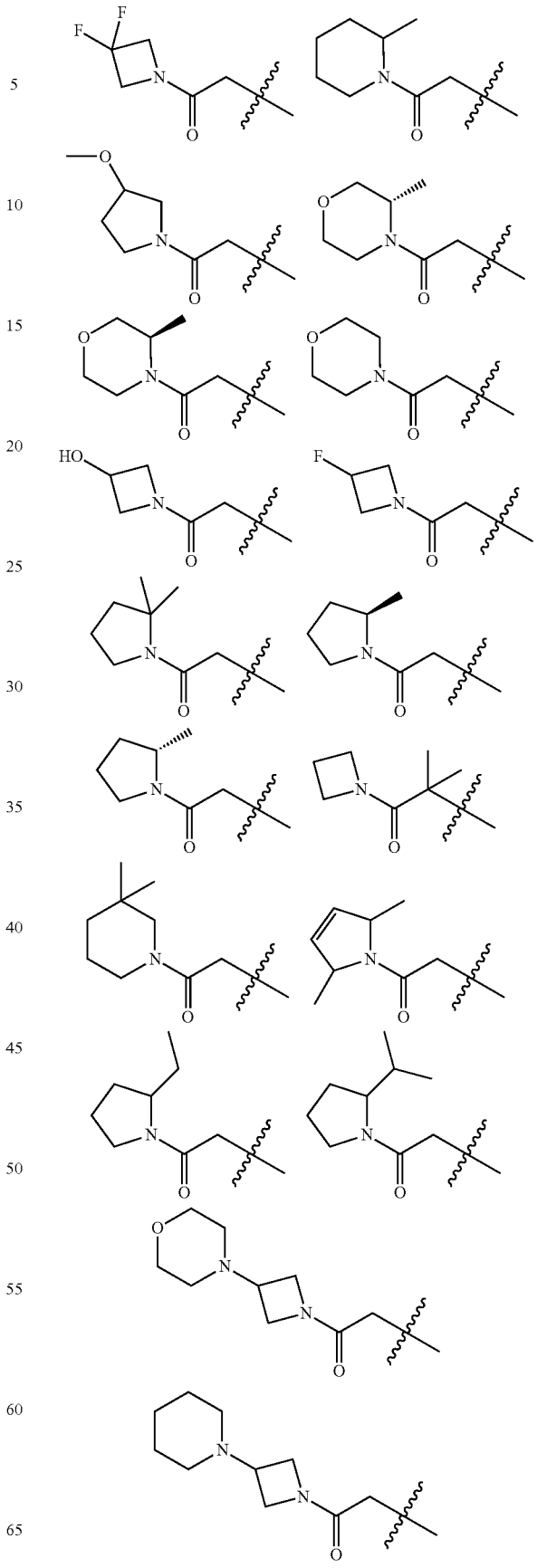

-continued

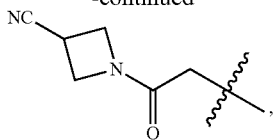

wherein the wavy line represents the point of attachment to R².

In certain embodiments, R⁴ is —(C₀-C₆ alkyl)(C₃-C₆ cycloalkyl), wherein said alkyl and cycloalkyl are independently optionally substituted by halogen, C₁-C₃ alkyl, oxo, —OR⁸ or —NR⁸R⁹. In certain embodiments, R⁴ is —(C₀-C₆ alkyl)(C₃-C₆ cycloalkyl), wherein said cycloalkyl is cyclopentyl or cyclohexyl optionally substituted by C₁-C₃ alkyl, —OR⁸ or —NR⁸R⁹. In one embodiment, R⁴ is selected from:

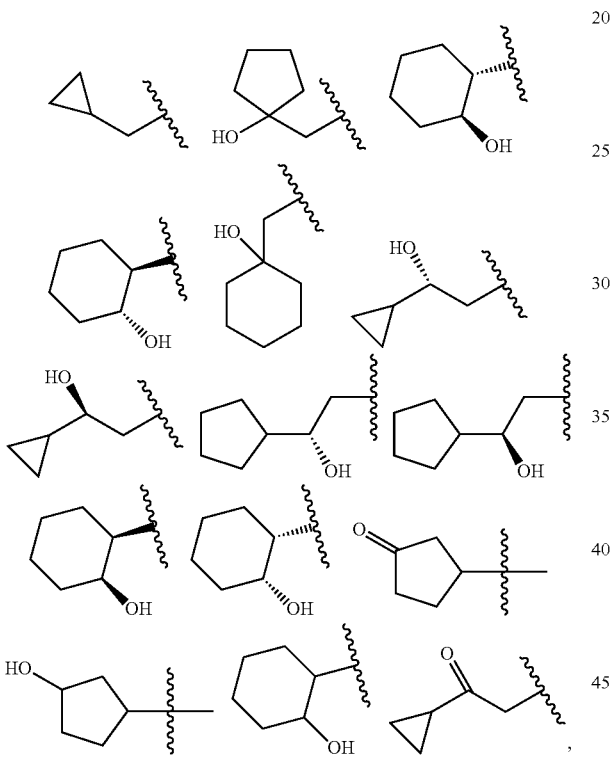

wherein the wavy line represents the point of attachment to R².

In certain embodiments, R⁴ is —(C₀-C₆ alkyl)C(O)OR⁶, —(C₀-C₆ alkyl)C(O)NR⁶NR⁷, —(C₀-C₆ alkyl)OC(O)NR⁶, —(C₀-C₆ alkyl)NR⁶C(O)OR⁷, —(C₀-C₆ alkyl)NR⁶C(O)NR⁷ or —(C₀-C₆ alkyl)NR⁶C(O)R⁷, wherein said alkyl is independently optionally substituted by halogen, C₁-C₃ alkyl, oxo, —OR⁸ or —NR⁸R⁹. In one embodiment, R⁴ is selected from:

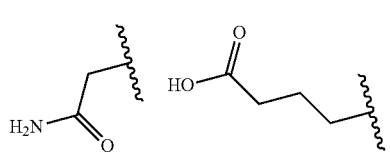

-continued

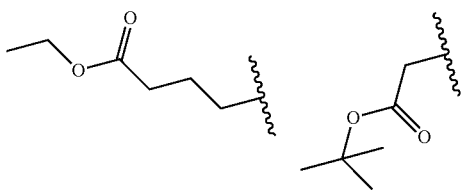
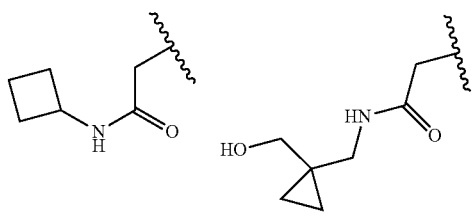
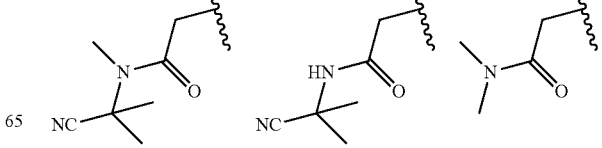

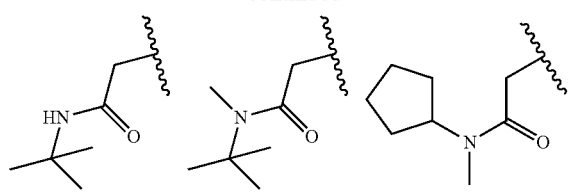
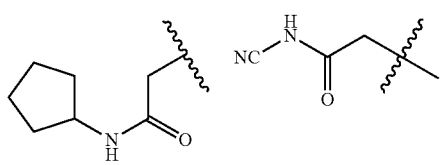
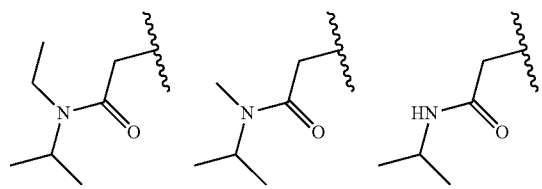
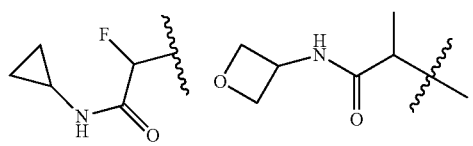
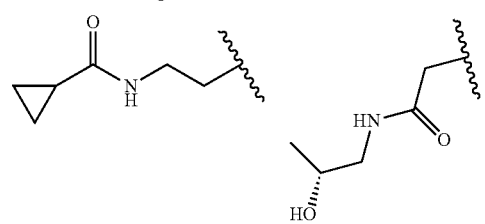
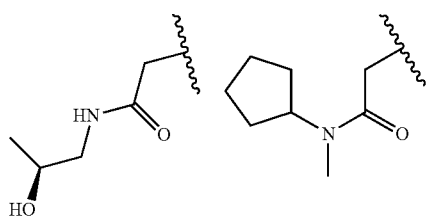
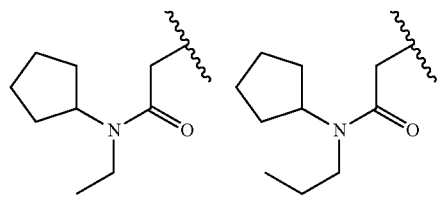
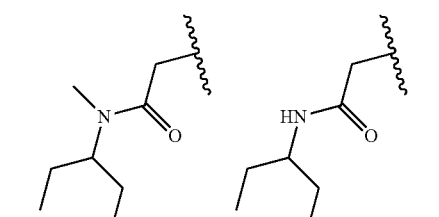
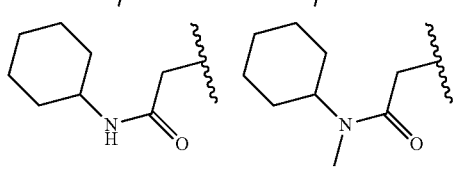
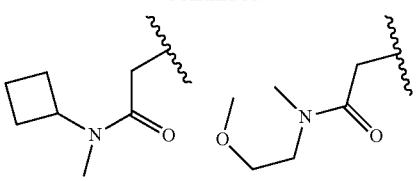
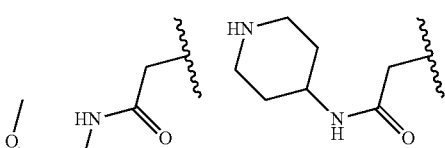
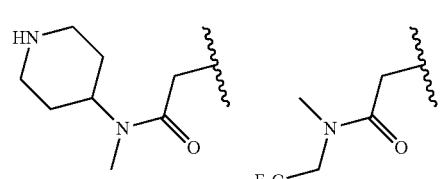
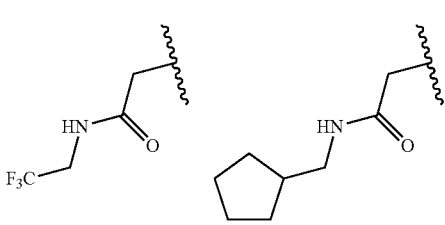
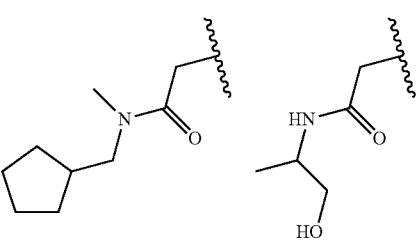
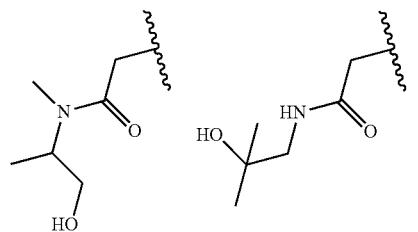
wherein the wavy line represents the point of attachment to $R^2$.
In certain embodiments, $R^4$ is $C_1$-$C_6$ alkyl, $C_2$-$C_6$ alkenyl or $C_2$-$C_6$ alkynyl optionally substituted by halogen, oxo, —$OR^8$ or —$NR^8R^9$. In one embodiment, $R^4$ is selected from:

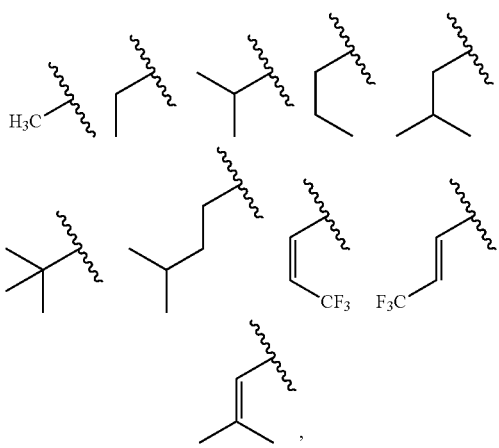

wherein the wavy line represents the point of attachment to $R^2$.

In certain embodiments, $R^4$ is —($C_0$-$C_6$ alkyl)CN, wherein said alkyl is optionally substituted by halogen, oxo, —$OR^8$ or —$NR^8R^9$. In one embodiment, $R^4$ is —$CH_2$CN, —$CH_2CH_2$CN or —CH($CH_3$)CN.

In certain embodiments, $R^4$ is halogen. In one embodiment, $R^4$ is F, Cl, Br or I. In one embodiment, $R^4$ is F or Cl.

In certain embodiments, $R^3$ is:

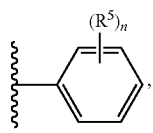

wherein n is 0, 1, 2 or 3 and the wavy line represents the point of attachment to $R^2$.

In one embodiment, n is 2. In one embodiment, $R^3$ is selected from:

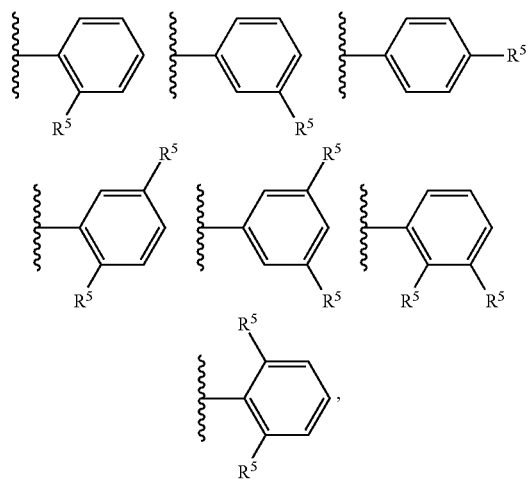

wherein the wavy line represents the point of attachment to $R^2$.

In certain embodiments, $R^3$ is phenyl or pyridinyl, optionally substituted by $C_1$-$C_6$ alkyl, halogen, —CN, —($C_0$-$C_3$ alkyl)$OR^6$, —($C_0$-$C_3$ alkyl)$SR^6$, —($C_0$-$C_3$ alkyl)$NR^6R^7$, —($C_0$-$C_3$ alkyl)$OCF_3$ or —$CF_3$, wherein said alkyl is independently optionally substituted by halogen, $C_1$-$C_3$ alkyl, oxo, —$CF_3$, —($C_0$-$C_3$ alkyl)$OR^8$ or —($C_0$-$C_3$ alkyl)$NR^8R^9$. In one embodiment, $R^3$ is selected from:

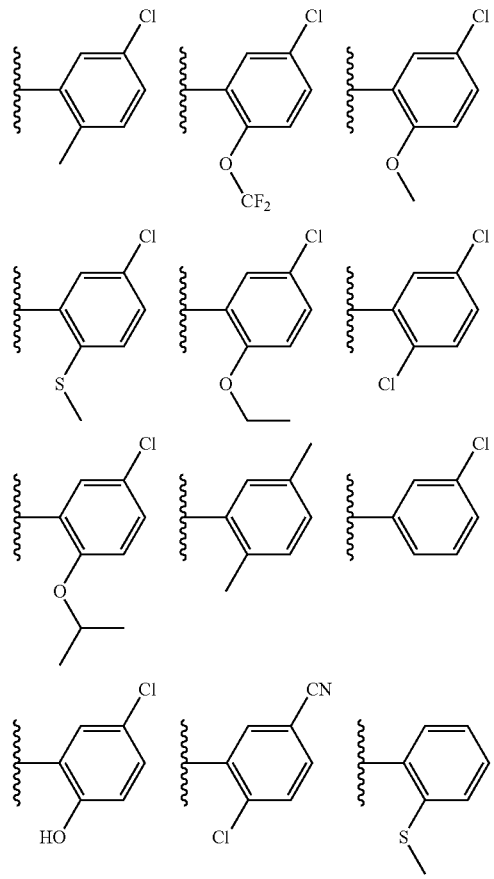

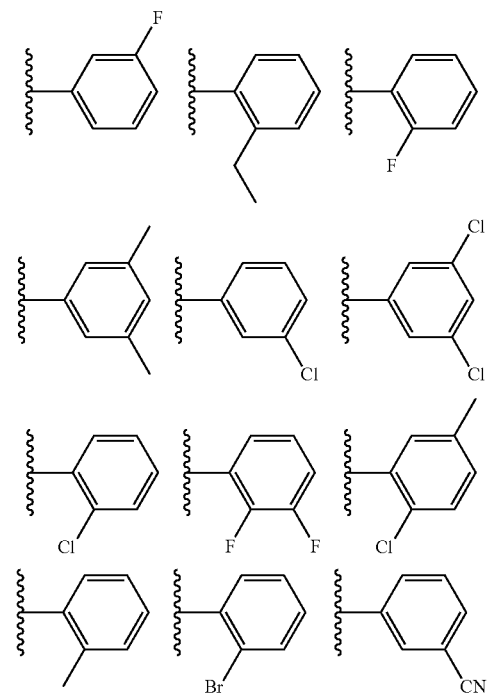

-continued

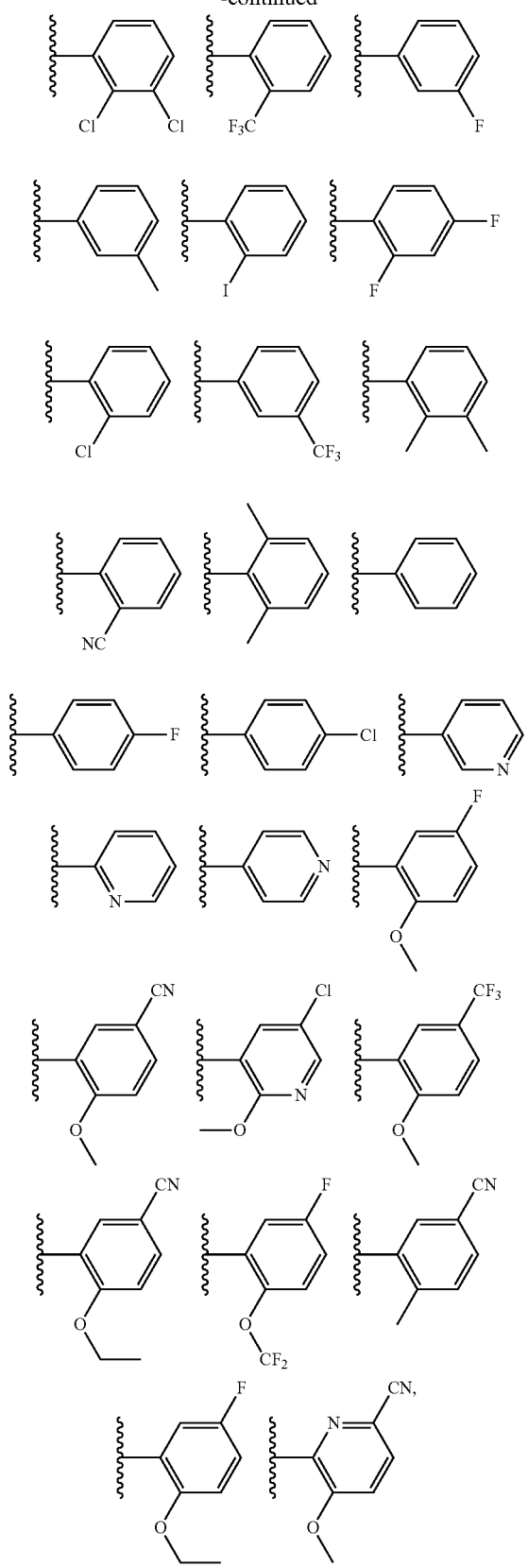

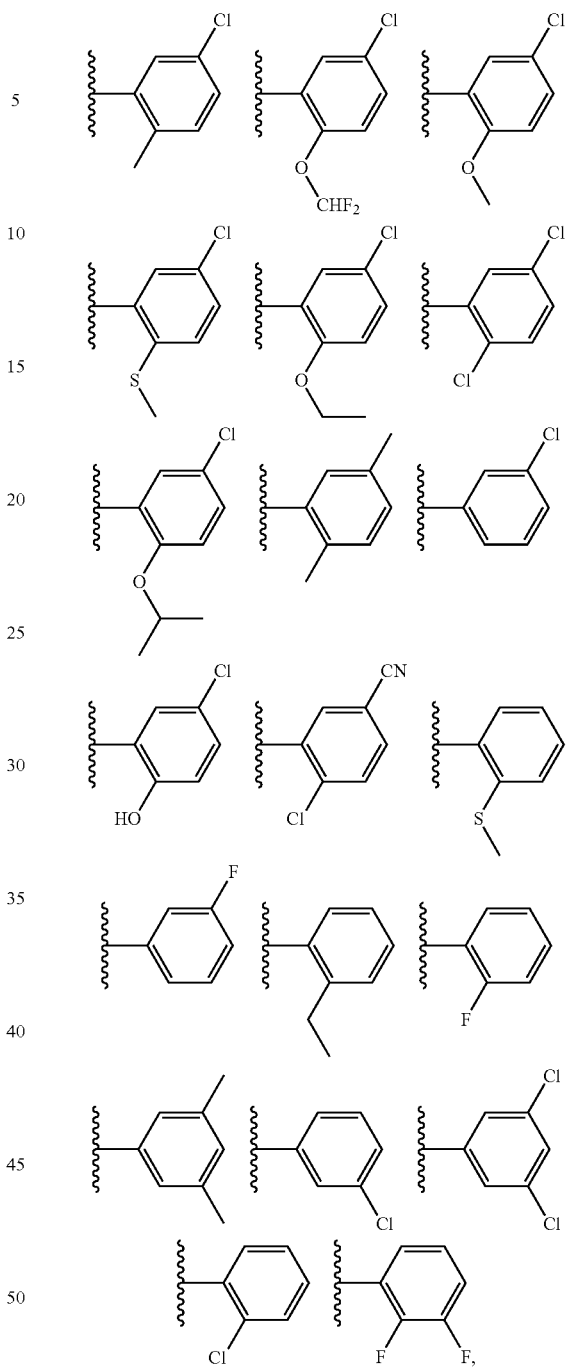

wherein the wavy line represents the point of attachment to $R^2$. In one embodiment, $R^3$ is selected from:

wherein the wavy line represents the point of attachment to $R^2$.

In certain embodiments, $R^3$ is 4-6 membered heterocyclyl optionally substituted by $C_1$-$C_6$ alkyl, halogen, —CN, —($C_0$-$C_3$ alkyl)$OR^6$, —($C_0$-$C_3$ alkyl)$SR^6$, —($C_0$-$C_3$ alkyl)$NR^6R^7$, —($C_0$-$C_3$ alkyl)$OCF_3$ or —$CF_3$, wherein said alkyl is independently optionally substituted by halogen, $C_1$-$C_3$ alkyl, oxo, —$CF_3$, —($C_0$-$C_3$ alkyl)$OR^8$ or —($C_0$-$C_3$ alkyl)$NR^8R^9$. In certain embodiments, said heterocyclyl is selected from azetidinyl, pyrrolidinyl, piperidinyl, piperazinyl, morpholinyl, tetrahydropyridinyl, and pyridinonyl. In certain embodiments, $R^3$ is selected from:

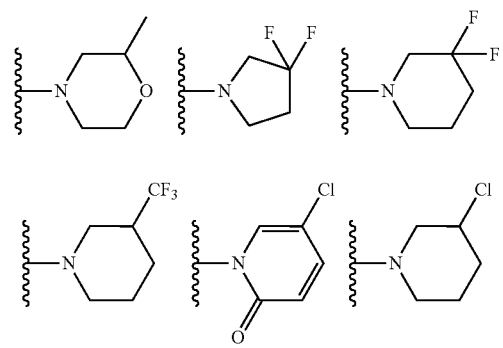

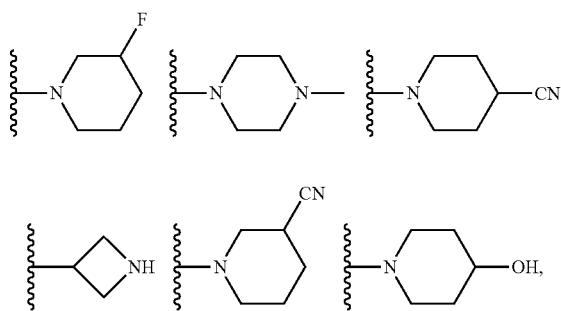

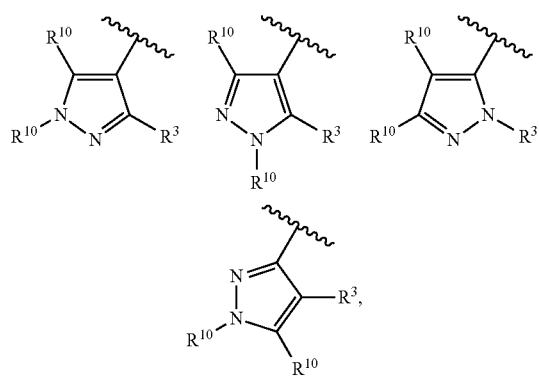

wherein the wavy line represents the point of attachment to $R^2$.

In certain embodiments, $R^2$ is selected from:

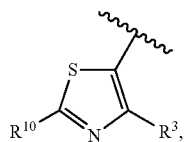

wherein $R^{10}$ is independently selected from hydrogen or $R^4$, and the wavy line represents the point of attachment to Formula I.

In certain embodiments, $R^2$ is selected from:

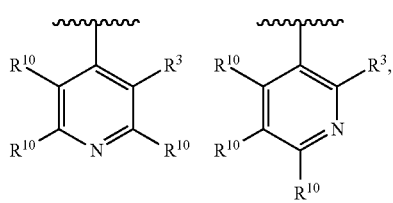

wherein $R^{10}$ is independently selected from hydrogen or $R^4$, and the wavy line represents the point of attachment to Formula I.

In certain embodiments, $R^2$ is selected from:

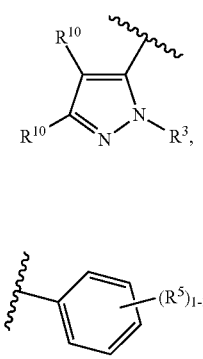

$R^3$ is

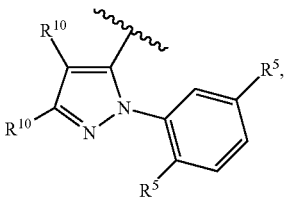

or pyridinyl, $R^{10}$ is hydrogen or $R^4$, and the wavy line represents the point of attachment to Formula I and $R^2$, respectively.

In certain embodiments, —$R^2$—$R^3$ in Formula I is

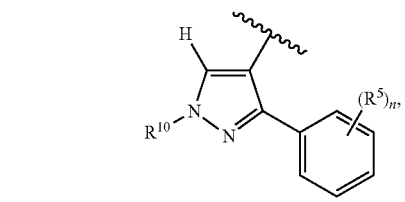

wherein, $R^{10}$ is hydrogen or $R^4$, and the wavy line represents the point of attachment to Formula I.

In certain embodiments, —$R^2$—$R^3$ in Formula I is wherein n is 0, 1, 2 or 3, $R^{10}$ is hydrogen or $R^4$, and the wavy line represents the point of attachment of $R^2$ to Formula I.

Another embodiment includes a compound of Formula I that has $K_i$ and/or $EC_{50}$ that is at least 15 fold, alternatively 10 fold, or 5 fold or more selective in inhibiting one Janus kinase activity over inhibiting one or more of the other Janus kinase activities.

The compounds of Formula I may contain asymmetric or chiral centers, and, therefore, exist in different stereoisomeric forms. It is intended that all stereoisomeric forms of the compounds of Formula I, including but not limited to: diastereomers, enantiomers, and atropisomers as well as mixtures thereof such as racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Both the single positional isomers and mixture of positional isomers, e.g., resulting from the N-oxidation of the pyrimidinyl and pyrrozolyl rings, or the E and Z forms of compounds of Formula I (for example oxime moieties), are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention, as defined by the claims, embrace both solvated and unsolvated forms.

In an embodiment, compounds of Formula I may exist in different tautomeric forms, and all such forms are embraced within the scope of the invention, as defined by the claims. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of Formula I, which are identical to those recited herein, but for the fact that one or more atoms are replaced by an atom having an atomic mass or mass number different from the atomic mass or mass number usually found in nature. All isotopes of any particular atom or element as specified are contemplated within the scope of the invention. Exemplary isotopes that can be incorporated into compounds of Formula I include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of Formula I can generally be prepared by following procedures analogous to those disclosed in the Schemes and/or in the Examples herein below, by substituting an isotopically labeled reagent for a non-isotopically labeled reagent.

Synthesis of Pyrazolopyrimidine JAK Inhibitor Compounds

Compounds of Formula I may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or *Comprehensive Heterocyclic Chemistry*, Editors Katrizky and Rees, Pergamon Press, 1984.

Compounds of Formula I may be prepared singly or as compound libraries comprising at least 2, for example 5 to 1,000 compounds, or 10 to 100 compounds of Formula I. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, enantiomers, diasteriomers, tautomers or pharmaceutically acceptable salts thereof.

For illustrative purposes, reaction Schemes 1-13 depicted below provide routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Compounds of the invention may be prepared from readily available starting materials using the general methods illustrated in Reaction Schemes 1-21 below.

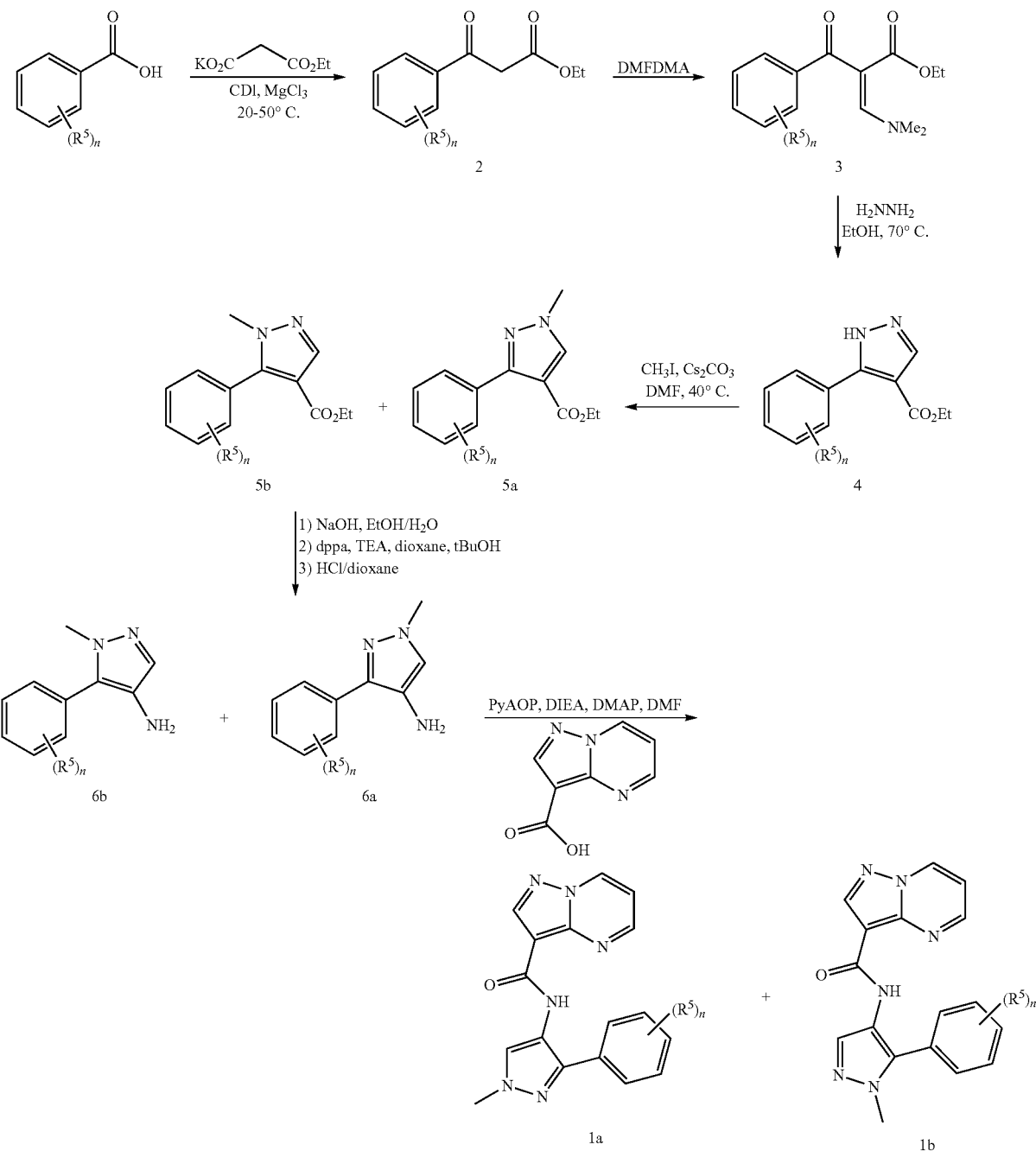

Reaction Scheme 1

Compounds of Formula I can be synthesized as shown in Reaction Scheme 1. For example, commercially available benzoic acids can be reacted with potassium 3-ethoxy-3-oxopropanoate in the presence of carbonyldiimidazole (CDI) and magnesium chloride to give β-keto-ester 2. Compound 2 can be heated with 1,1-dimethoxy-N,N-dimethylmethanamine (DMFDMA) to give compound 3. Cyclization of compound 3 with hydrazine in ethanol provides pyrazole compound 4. Methylation of compound 4 with iodomethane in the presence of a base such as cesium carbonate affords a mixture of the regioisomers 5a and 5b. Hydrolysis of the ethyl ester, followed by curtius rearrangement utilizing diphenylphosphonic azide (dppa) and t-butanol provides the t-butylcarbamate protected amino-pyrazole, which is unmasked with HCl to give amino-pyrazole compounds 6a and 6b. The regioisomers 6a and 6b can be separated at this stage using silica chromatography. Coupling of each regioisomer separately with commercially available pyrazolo[1,5-a]pyrimidine-3-carboxylic acid in the presence of 7-azabenzotriazol-1-yloxy-tris-(pyrrolidino)phosphonium hexafluorophosphate (PyAOP), diisopropylethylamine (DIEA), and 4-dimethylaminopyridine (DMAP) provides compounds of Formula 1a and 1b.

Reaction Scheme 2

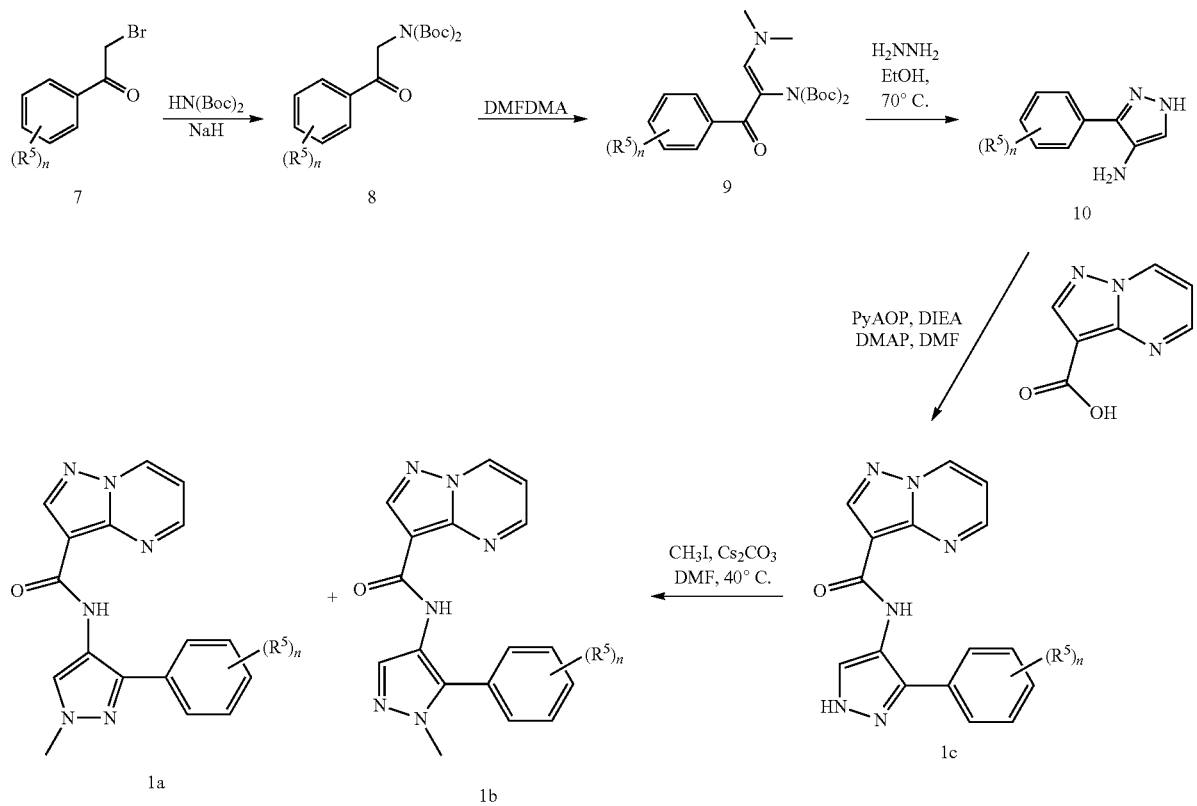

An alternative method for the synthesis of compounds of Formula I is illustrated in Reaction Scheme 2. Alkylation of di-tert-butyl iminodicarbonate with sodium hydride and various α-bromoketones 7 generates compound 8. Compound 8 can be heated with DMFDMA to give compound 9. Cyclization of compound 9 with hydrazine in ethanol provides pyrazole compound 10. Coupling of compound 10 with pyrazolo[1,5-a]pyrimidine-3-carboxylic acid in the presence of PyAOP, DIEA, and DMAP provides compounds of Formula 1c. Compounds of Formula 1c can be subjected to alkylation with iodomethane in the presence of cesium carbonate to yield compounds of Formula 1a and 1b.

Reaction Scheme 3

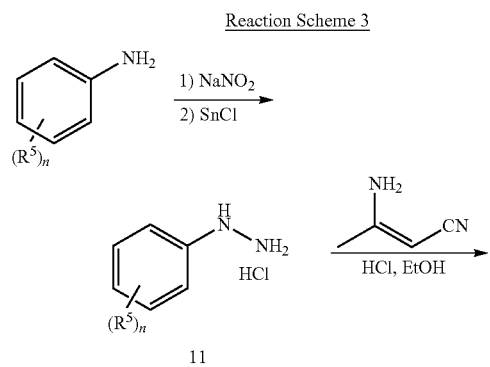

-continued

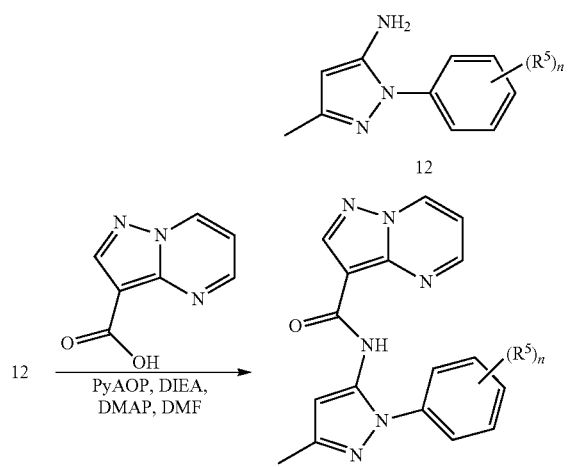

Reaction Scheme 3 illustrates the synthesis of compounds of Formula 1d. Subjection of commercially available anilines to diazotization and tin chloride mediated reduction provides compound 11. Condensation of compound 11 with 3-aminocrotonitrile in ethanolic hydrochloric acid generates aminopyrazole compound 12. Coupling of compound 12 with pyrazolo[1,5-a]pyrimidine-3-carboxylic acid in the presence of PyAOP, DIEA, and DMAP provides compounds of Formula 1d.

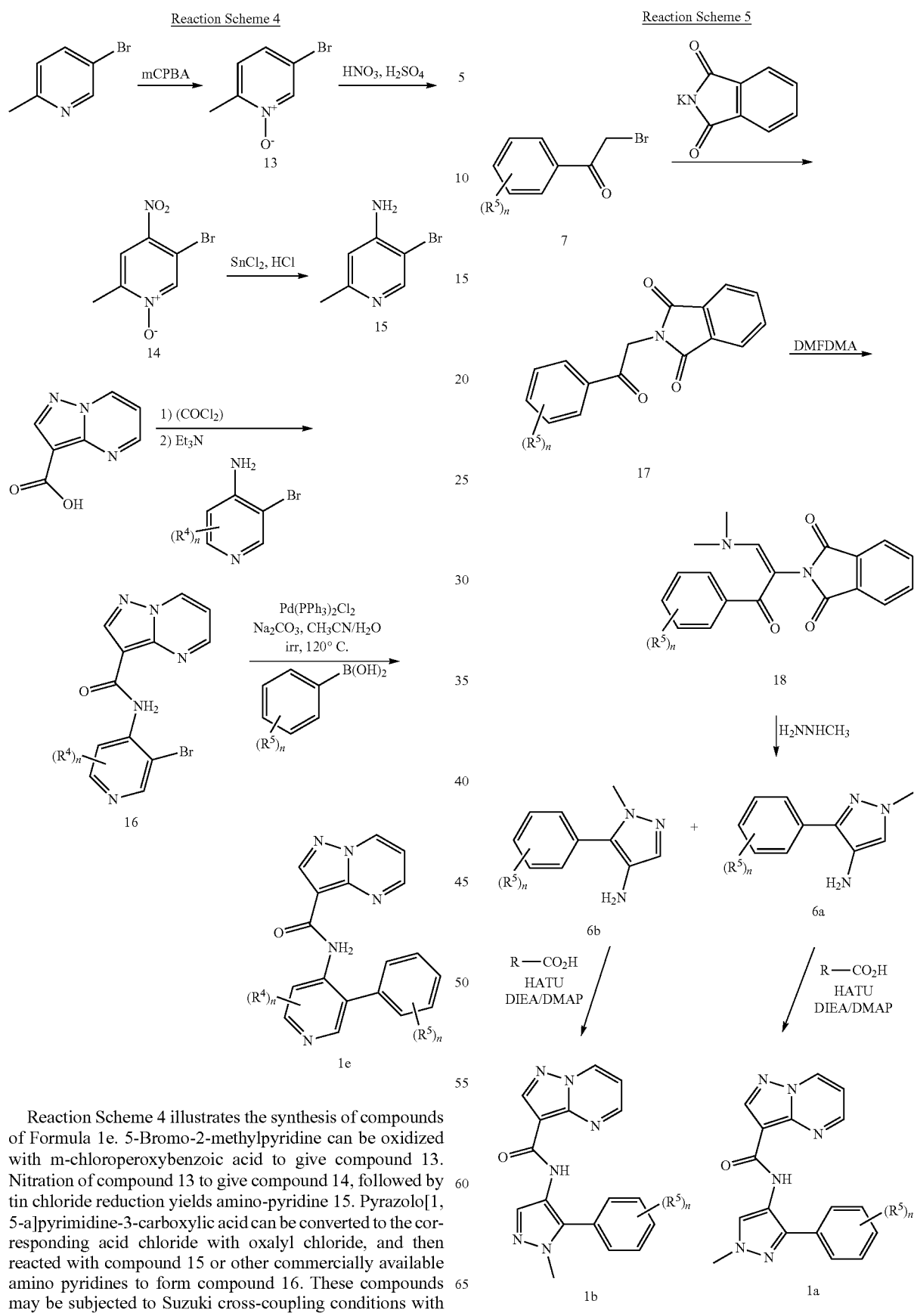

Reaction Scheme 4 illustrates the synthesis of compounds of Formula 1e. 5-Bromo-2-methylpyridine can be oxidized with m-chloroperoxybenzoic acid to give compound 13. Nitration of compound 13 to give compound 14, followed by tin chloride reduction yields amino-pyridine 15. Pyrazolo[1,5-a]pyrimidine-3-carboxylic acid can be converted to the corresponding acid chloride with oxalyl chloride, and then reacted with compound 15 or other commercially available amino pyridines to form compound 16. These compounds may be subjected to Suzuki cross-coupling conditions with aryl boronic acids to provide compounds of Formula 1e.

An alternative method for the synthesis of compounds of Formula 1 is described in Reaction Scheme 5. Alkylation of potassium phthalimide with α-bromoketones 7 generates compound 17. Condensation with DMFDMA yields compounds 18. Compounds of Formula 18 may be cyclized with N-methylhydrazine to provide a separable mixture of the regioisomers 6a and 6b. Coupling of each regioisomer separately under amide formation methods using hexafluorophosphate o-(7-azabenzo-triazol-1-yl)-1,1,3,3-tetramethyluronium (HATU) with commercially available pyrazolo[1,5-a]pyrimidine-3-carboxylic acid provides compounds of Formula 1a and 1b.

Reaction Scheme 7

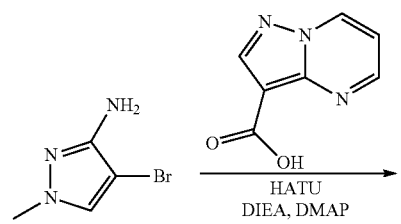

Reaction Scheme 6

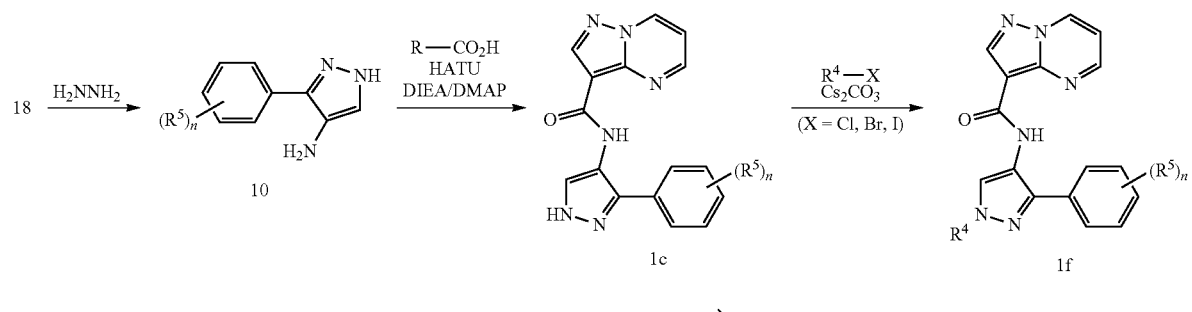

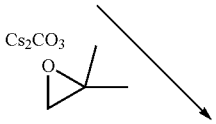

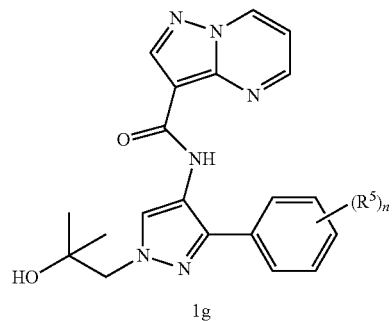

Reaction Scheme 6 illustrates a method for the synthesis of compounds of Formula 1g and 1f. Compound 18 may be cyclized with hydrazine to yield compound 10, which may then be coupled with pyrazolo[1,5-a]pyrimidine-3-carboxylic acid under amide formation conditions using HATU to provide compounds of Formula 1c. Alkylation of compound 1c with alkyl halides in the presence of cesium carbonate gives compounds of Formula 1f. Reaction of compound 1c with 2,2-dimethyloxirane in the presence of cesium carbonate provides compounds of Formula 1g.

-continued

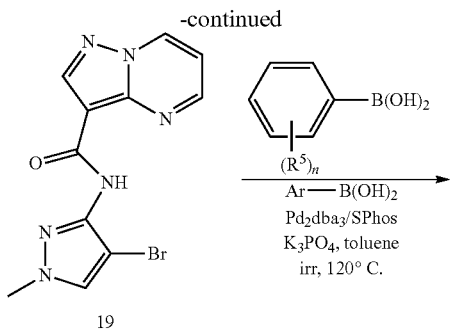

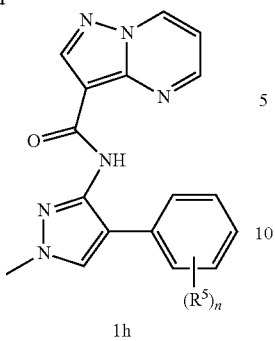

1h

Reaction Scheme 7 illustrates the synthesis of compounds of Formula 1h. Amide formation using HATU with 4-bromo-1-methyl-1H-pyrazol-3-amine and pyrazolo[1,5-a]pyrimidine-3-carboxylic acid provides compound 19. Palladium catalyzed Suzuki coupling of compound 19 with various boronic acids provides compounds of Formula 1h.

Reaction Scheme 8

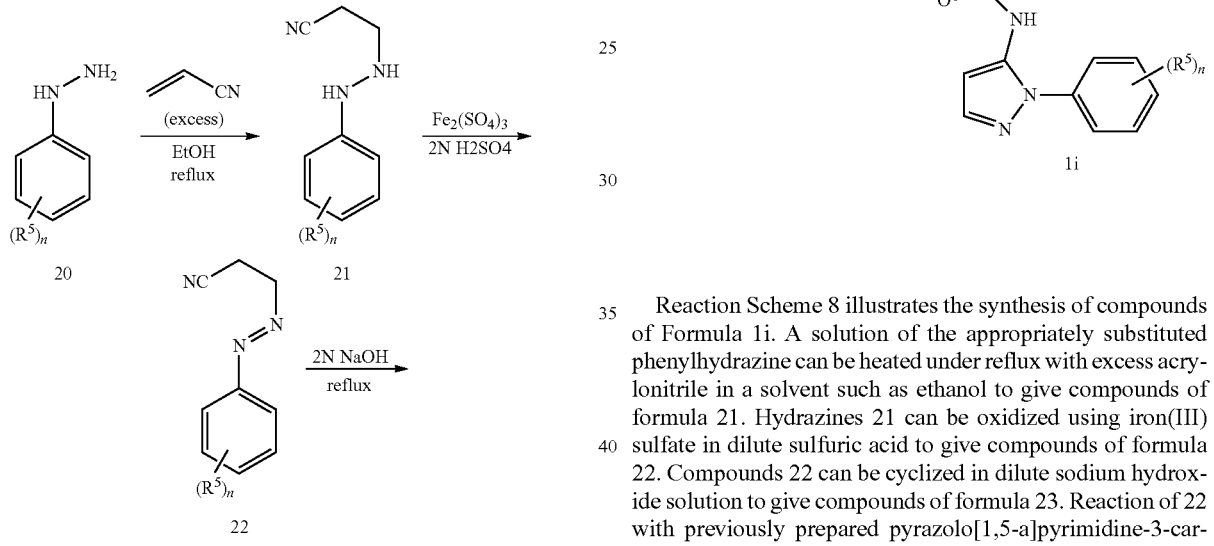

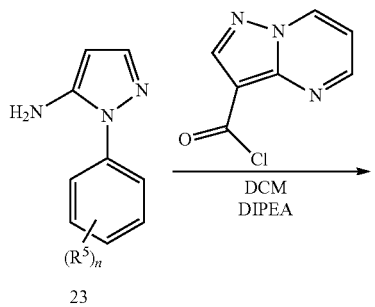

Reaction Scheme 8 illustrates the synthesis of compounds of Formula 1i. A solution of the appropriately substituted phenylhydrazine can be heated under reflux with excess acrylonitrile in a solvent such as ethanol to give compounds of formula 21. Hydrazines 21 can be oxidized using iron(III) sulfate in dilute sulfuric acid to give compounds of formula 22. Compounds 22 can be cyclized in dilute sodium hydroxide solution to give compounds of formula 23. Reaction of 22 with previously prepared pyrazolo[1,5-a]pyrimidine-3-carbonyl chloride gives the final compounds of formula 1i.

Reaction Scheme 9

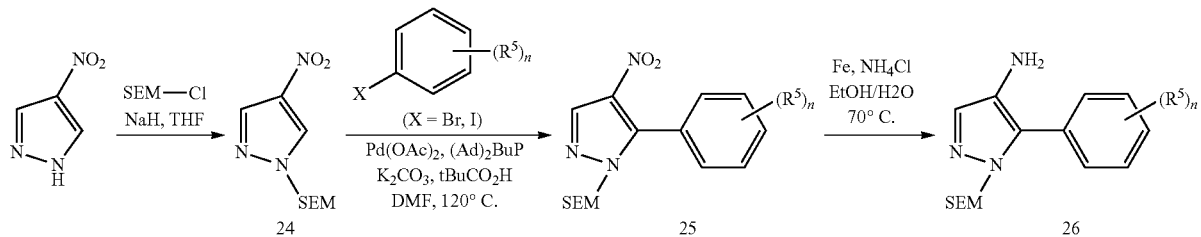

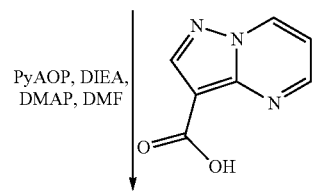

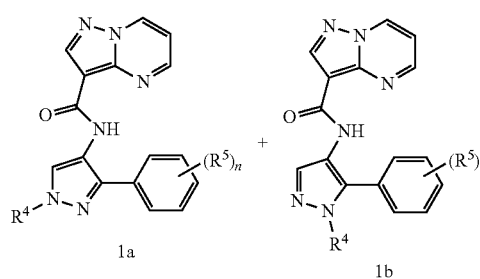 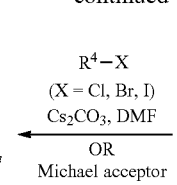 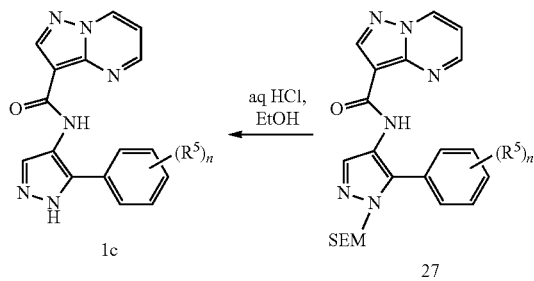

An alternate method for the synthesis of compounds of Formula 1a and 1b is shown in Reaction Scheme 9. Commercially available 4-nitro-1H-pyrazole may be protected with a [(3-(trimethylsilyl)ethoxy]methyl (SEM) group by treatment with sodium hydride and (2-(chloromethoxy)ethyl)trimethylsilane. The resulting compound 24 can be arylated with aryl bromides or iodides under palladium catalyzed conditions to generated 4-nitro-5-aryl-pyrazoles of formula 25. The nitro group of compounds 25 can be reduced in the presence of iron and ammonium chloride to generate amino pyrazoles 26. Amide bond coupling with commercially available pyrazolo[1,5-a]pyrimidine-3-carboxylic acid in the presence of PyAOP, DIEA, and DMAP provides compounds 27. Removal of the SEM protecting group by aqueous HCl in ethanol generates compounds 1c, which may be alkylated with alkyl halides in the presence of a suitable base such as cesium carbonate or with Michael acceptors to provide compounds of Formula 1a and 1b.

Reaction Scheme 10

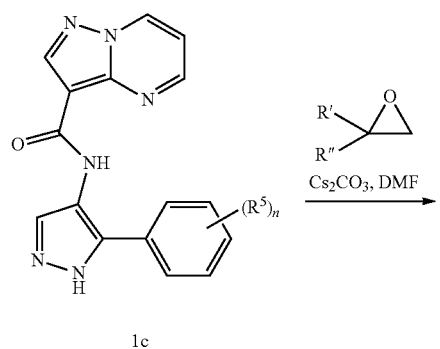

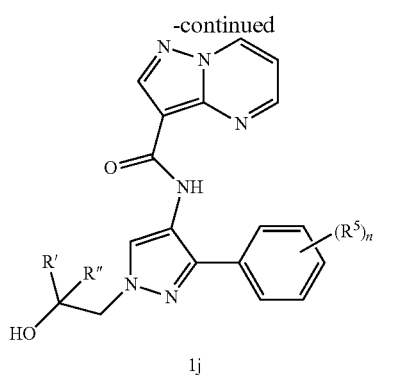

Reaction Scheme 10 illustrates the synthesis of compounds of Formula 1j and 1k. Pyrazole compounds 1c (prepared as described in either Reaction Scheme 2 or Reaction Scheme 9) may be alkylated with substituted epoxides in the presence of cesium carbonate to give the regioisomeric compounds of Formula 1j and 1k.

Reaction Scheme 11

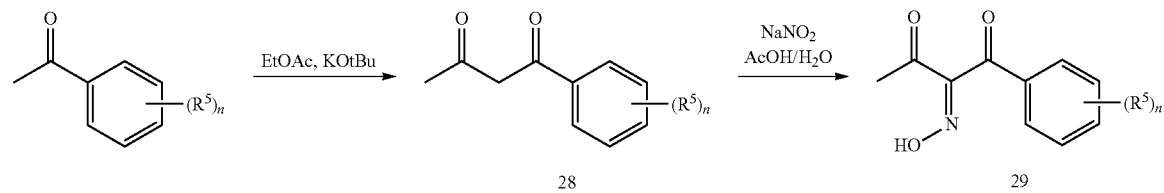

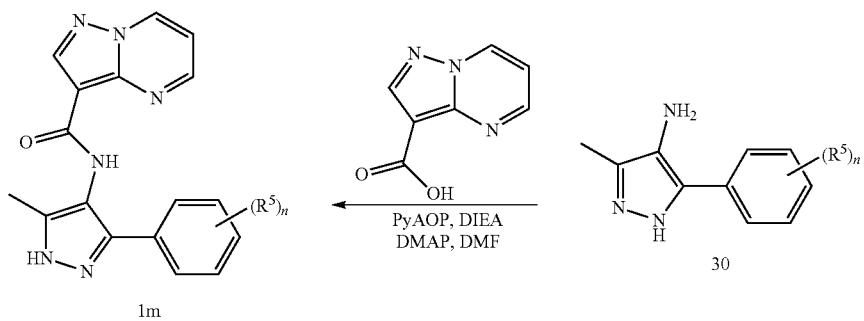

Compounds of Formula 1m can be synthesized as shown in Reaction Scheme 11. Commercially available acetophenones can be acylated with potassium tert-butoxide and ethyl acetate to generate di-ketone compounds of formula 28. Compounds 28 can be treated with sodium nitrite in the presence of acetic acid and water to provide hydroxyimino compounds 29, which may be subsequently cyclized with hydrazine to yield amino-pyrazole compounds 30. Amide bond coupling with commercially available pyrazolo[1,5-a]pyrimidine-3-carboxylic acid in the presence of PyAOP, DIEA, and DMAP provides compounds of Formula 1m.

alkyl bromides in the presence of cesium carbonate at 55° C. for 12 hours to give compound 31. Compound 31 can be reacted with aryl bromides in N,N-Dimethylacetamide in the presence of Palladium (II) acetate, Di(1-adamntyl)-n-butylphosphine, potassium carbonate and trimethylacetic acid to give compounds 32a and 32b. The ratio of products 32a: 32b varies depending on the substituent R1, but the reaction generally favors formation of product 32b. Compounds 32a and 32b can be reduced to compounds 33a and 33b in the presence of iron and ammonium chloride in ethanol and water. Coupling of compounds 33a and 33b with pyrazolo[1,

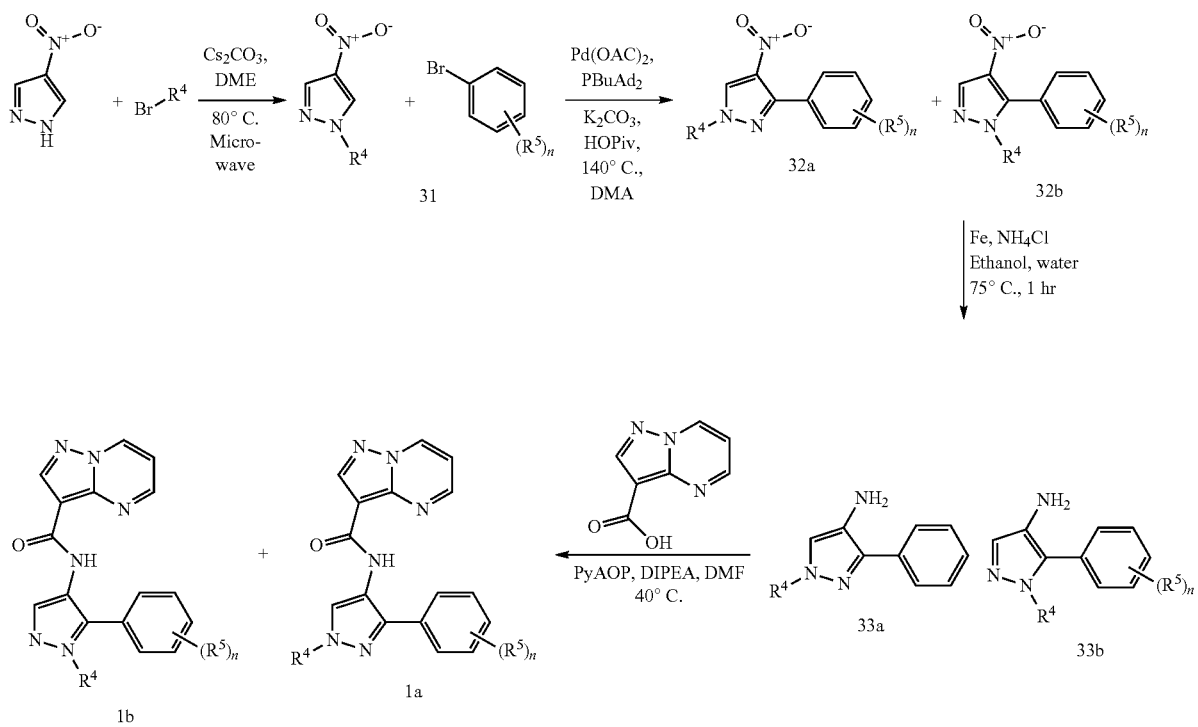

An alternate method for the synthesis of compounds of Formula 1a and 1b is shown in Reaction Scheme 12. Commercially available 4-Nitro-1H-pyrazole can be reacted with 5-a]pyrimidine-3-carboxylic acid in the presence of PyAOP, DIEA, and DMAP can provide compounds of Formula 1a and 1b.

Reaction Scheme 13

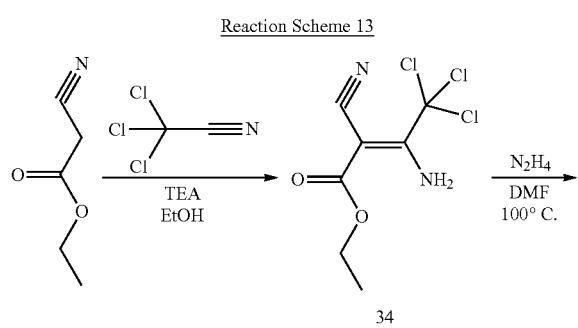

34

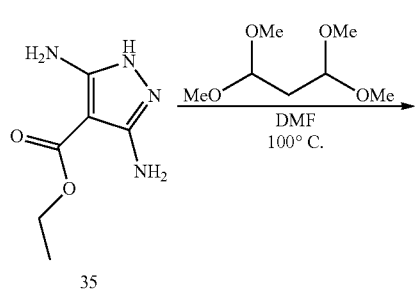

35

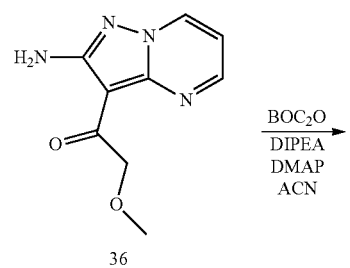

36

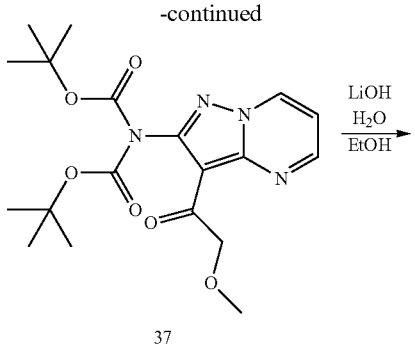

37

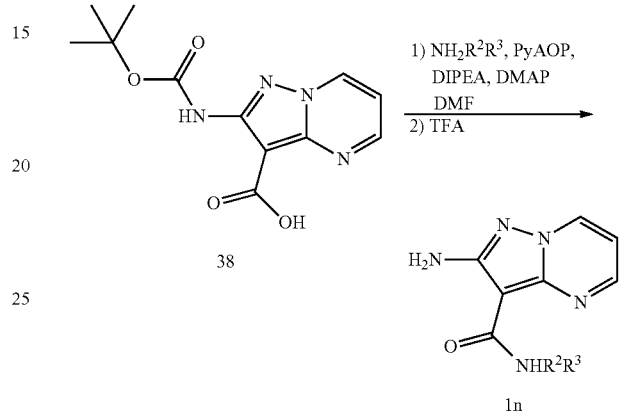

38

1n

Compounds of formula 1n can be synthesized as shown in reaction scheme 13. Trichloroacetonitrile can be reacted with cyanoacetic acid ethyl ester to give compound 34. Compound 34 can be condensed with hydrazine to give compound 35, which can then be condensed with 1,1,3,3-tetramethoxypropane to give compound 36. Amine 36 can be doubly Boc-protected to give compound 37, which can then be hydrolyzed with lithium hydroxide to give carboxylic acid 38. Carboxylic acid 38 can then be coupled to various amines in the presence of PyAOP, DIEA, and DMAP to give compounds of formula 1n.

Reaction Scheme 14

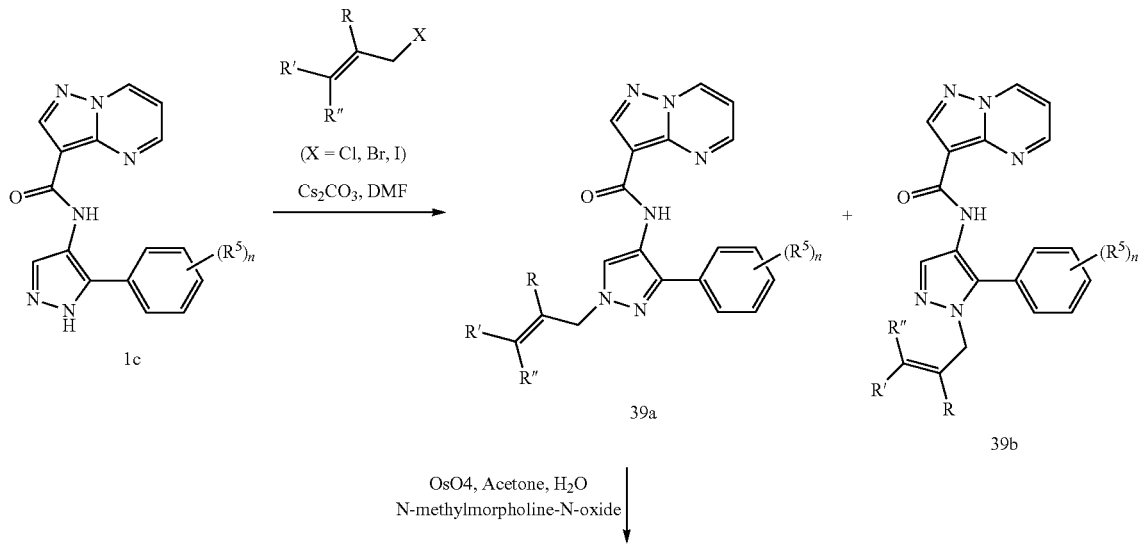

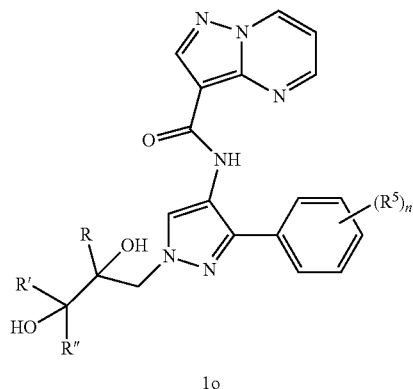

1o

Compounds of formula 1o can be synthesized as shown in reaction scheme 14. Pyrazole compounds 1c (prepared as described in either Reaction Scheme 2 or Reaction Scheme 9) may be alkylated with allyl halides in the presence of cesium carbonate to give the regioisomeric compounds of Formula 39a and 39b. The regioisomeric compounds may be separated by silica gel chromatography and the appropriate isomer reacted with osmium tetroxide in the presence of N-methyl-morpholine-N-oxide to give compounds of Formula 1o.

Reaction Scheme 15

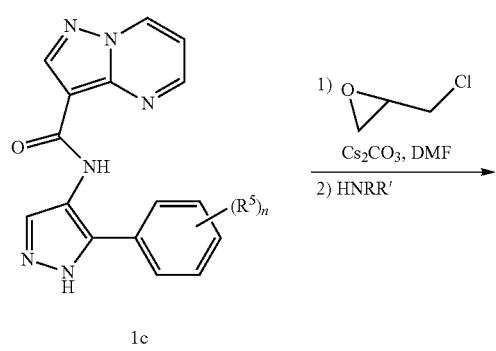

1c

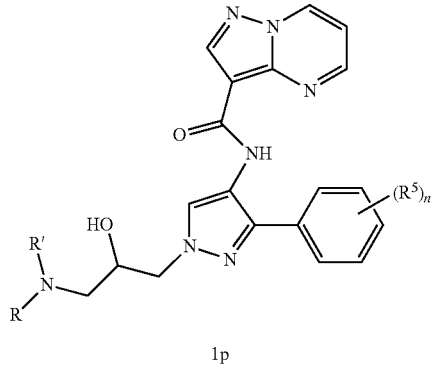

1p

+

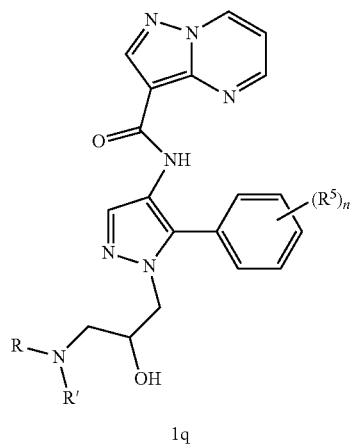

1q

Compounds of formula 1p and 1q can be synthesized as shown in reaction scheme 15. Pyrazole compounds 1c (prepared as described in either Reaction Scheme 2 or Reaction Scheme 9) may be alkylated with 2-(chloromethyl)oxirane in the presence of cesium carbonate and then treated with amines to give regioisomeric compounds of Formula 1p and 1q.

Reaction Scheme 16

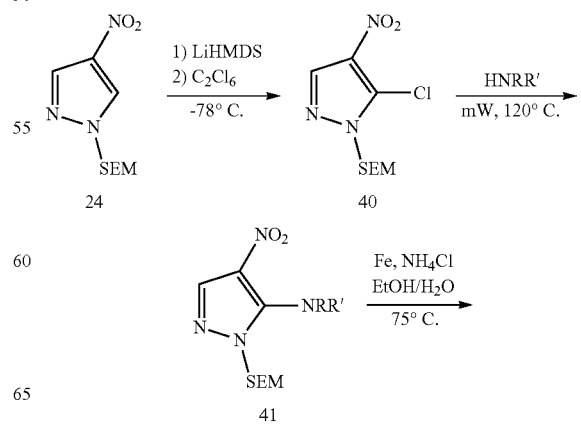

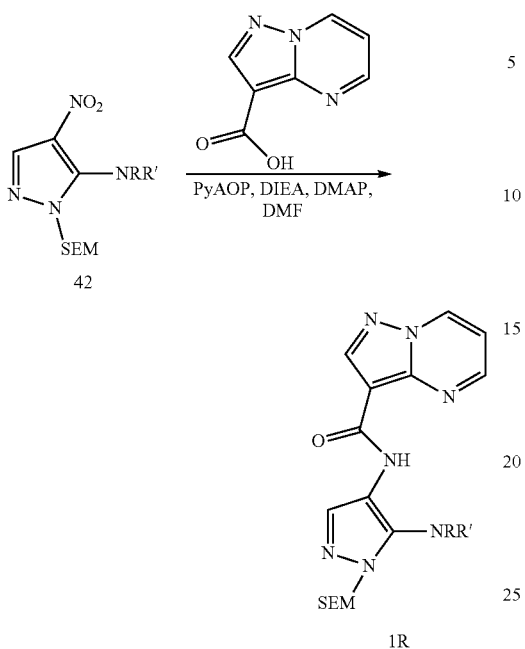

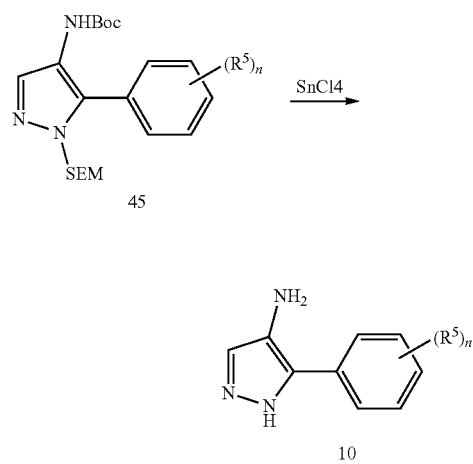

Reaction Scheme 16 illustrates the synthesis of compounds of formula 1R. Nitro-SEM pyrazole compound 24, prepared as in Reaction Scheme 9, may be regioselectively deprotonated with lithium hexamethyldisilazide at low temperature and quenched with hexachloroethane to yield 40. Upon heating in the microwave with an amine HNRR', wherein RR' are taken together with the nitrogen to which they are attached to form $R^3$ (for example, a 3-10 membered heterocyclyl group), this compound may be converted to 41. The nitro group of intermediate 41 can be reduced in the presence of iron and ammonium chloride to generate amino pyrazoles 42. Amide bond coupling with commercially available pyrazolo[1,5-a]pyrimidine-3-carboxylic acid in the presence of PyAOP, DIEA, and DMAP provides 1R. 1R may be further elaborated by removal of the SEM group and functionalizing as in Reaction Schemes 9, 10 14, 15, 18, or 19.

Reaction Scheme 17 illustrates an alternate synthesis for compounds of formula 10. Nitro-SEM pyrazole compound 24, prepared as in Reaction Scheme 9, may be regioselectively deprotonated with lithium hexamethyldisilazide at low temperature and quenched with iodine to yield 43. The nitro group of compound 43 can be reduced in the presence of iron and ammonium chloride, followed by Boc protection to generate compound 44. Compound 44 may be coupled under Suzuki conditions with aryl boronic acids or aryl boronates to yield compounds 45. After cleavage of the Boc group with tin tetrachloride, compounds of formula 10 are obtained.

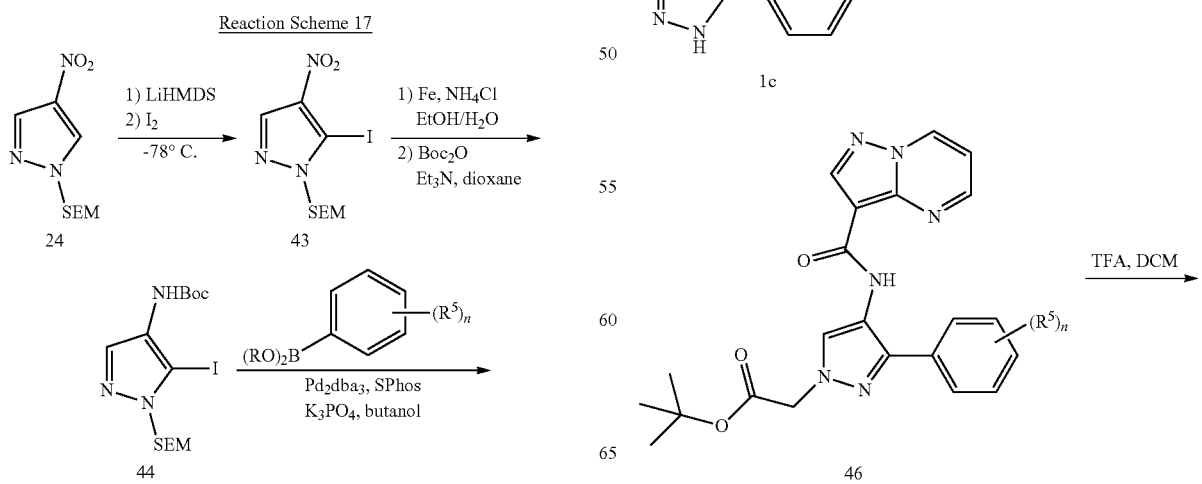

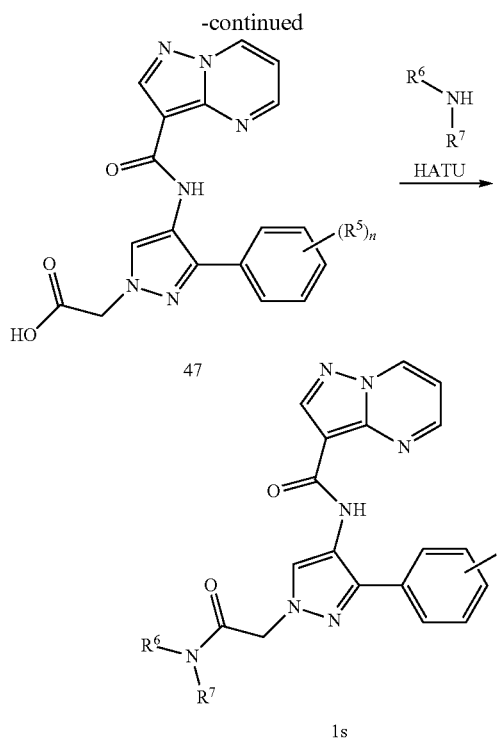

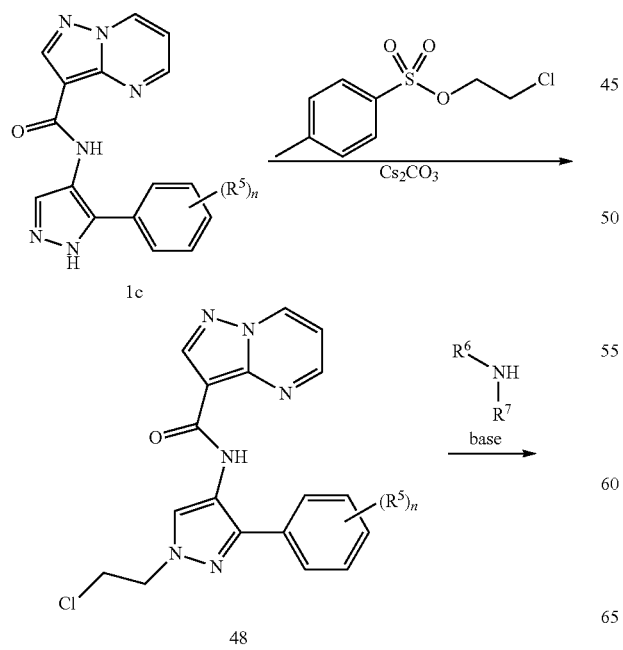

Compounds of formula 1s can be synthesized as shown in reaction scheme 18. Pyrazole compounds 1c (prepared as described in either Reaction Scheme 2 or Reaction Scheme 9) may be alkylated with t-butyl-bromoacetate in the presence of cesium carbonate to give intermediate 46. 46 may be treated with trifluoroacetic acid to give acids 47, which may then be reacted with primary or secondary amines in the presence of a coupling reagent such as N,N,N',N'-tetramethyl-O-(7-azabenzotriazol-1-yl)uronium hexafluorophosphate (HATU) to give compounds of formula 1s.

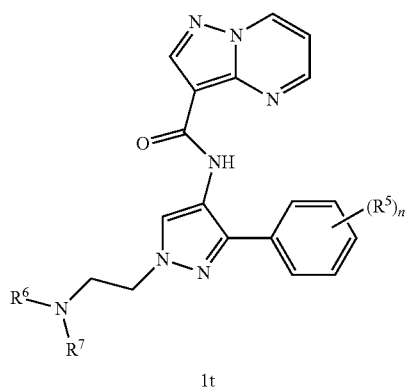

Compounds of formula 1t can be synthesized as shown in reaction scheme 19. Pyrazole compounds 1c (prepared as described in either Reaction Scheme 2 or Reaction Scheme 9) may be alkylated with 2-chloroethyl para-toluenesulfonate in the presence of cesium carbonate to give alkyl chlorides 48. 48 may then be reacted with primary or secondary amines in the presence of an appropriate base such as N,N-diisopropylethylamine to give compounds of formula 1t.

Reaction Scheme 20

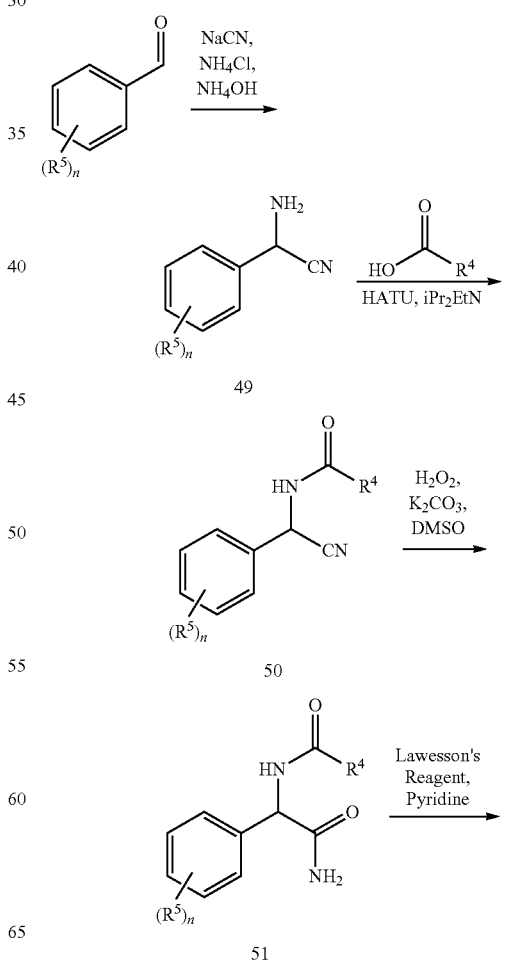

-continued

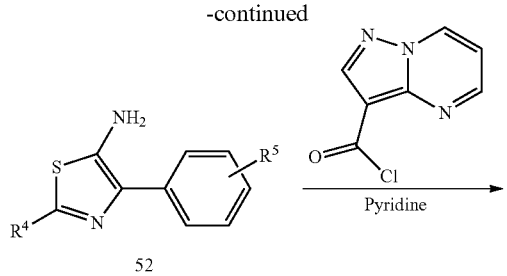

52

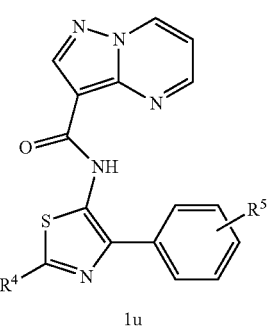

1u

Compounds of Formula 1u can be synthesized as shown in Reaction Scheme 20. For example, commercially available substituted benzaldehydes can be converted to compounds 49 by treatment with a cyanide source such as sodium cyanide in the presence of ammonium chloride and ammonium hydroxide. Compounds 49 can be coupled to carboxylic acids to provide compounds 50 using an amide coupling reagent such as HATU and base such as diisopropylethylamine. Compounds 50 can be treated with hydrogen peroxide and potassium carbonate to provide compounds 51. Cyclization of diamido compounds 51 using Lawesson's reagent and pyridine provides amino thiazolo compounds 52. Compounds of formula 1u can prepared by treatment of compounds 52 with previously prepared pyrazolo[1,5-a]pyrimidine-3-carbonyl chloride in pyridine.

Reaction Scheme 21

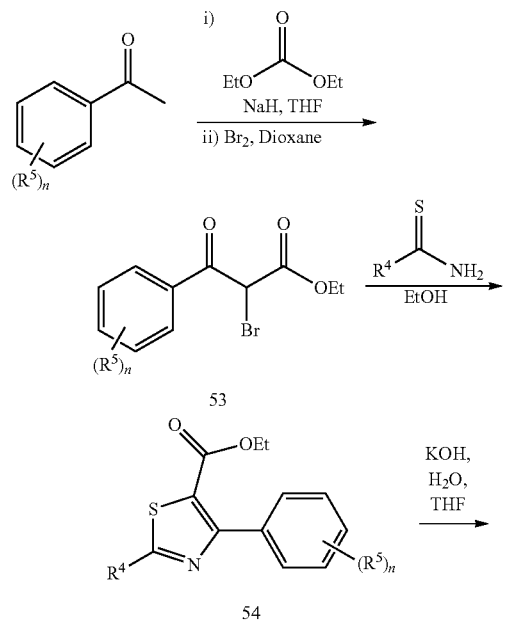

-continued

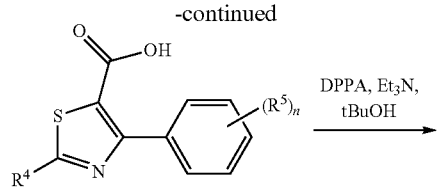

55

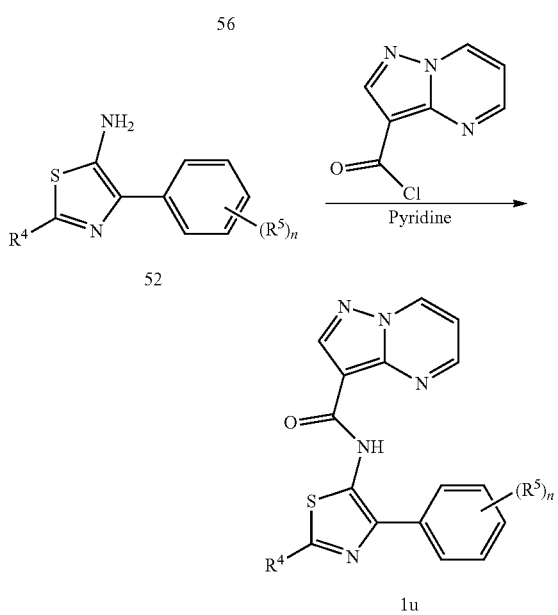

Alternatively compounds of Formula 1u can be synthesized as shown in Reaction Scheme 21. For example, compounds 53 can be prepared by treatment of commercially available substituted acetophenones with diethyl carbonate and subsequent bromination using for example bromine in dioxane. Treatment of compounds 53 with a suitably substituted thioamide or thiourea provides thiazole compounds 54. Compounds 54 can be hydrolysed using an aqueous base such as potassium hydroxide in a compatible solvent such as THF to afford acid compounds 55. Compounds 56 can be prepared by treatment of compounds 55 with diphenylphosphoryl azide (DPPA) in tert-butanol. Deprotection of compounds 56 under acidic conditions provides amino compounds 52. Compounds of formula 1u can prepared by treatment of compounds 52 with previously prepared pyrazolo[1,5-a]pyrimidine-3-carbonyl chloride in pyridine.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such as HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—NHSO$_2$R' or —NR"SO$_2$R') groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at an appropriate temperature, for example from about −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—CO$_2$R') may be converted into the corresponding acid group (—CO$_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —CO$_2$H to —CH$_2$CO$_2$H) by conversion to the corresponding acid chloride (—COCl) followed by Arndt-Eistert synthesis.

In a further example, —OH groups may be generated from the corresponding ester (e.g. —CO$_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—CO$_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column A single stereoisomer, e.g. an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513:375-378 (1990)). Enriched or purified enantiomers can be distinguished by methods used to distinguish other chiral molecules with asymmetric carbon atoms, such as optical rotation and circular dichroism.

Positional isomers, for example E and Z forms, of compounds of Formula I, and intermediates for their synthesis, may be observed by characterization methods such as NMR and analytical HPLC. For certain compounds where the energy barrier for interconversion is sufficiently high, the E and Z isomers may be separated, for example by preparatory HPLC.

Biological Evaluation

Previous studies have shown that the isolated kinase domains of human JAK1, JAK2, JAK3 or TYK2 phosphorylate peptide substrates in in vitro kinase assays (Saltzman et al., Biochem. Biophys. Res. Commun. 246:627-633 (2004)). The catalytically active kinase domain of human JAK1, JAK2, JAK3 or TYK2 was purified from extracts of SF9 insect cells infected with a recombinant baculovirus expression vector encoding the human JAK1, JAK2, JAK3 or TYK2 kinase domains (JAK1 amino acid residues N852-D1154 according to the numbering of GenBank sequence accession number P23458, JAK2 amino acid residues D812-G1132 according to the numbering of GenBank sequence accession number NP_004963.1; JAK3 amino acid residues S783-S1124 according to the numbering of GenBank sequence accession number P52333, and TYK2 amino acid residues N873-C1187 according to the numbering of GenBank sequence accession number P29597). The activity of the JAK1, JAK2, JAK3 or TYK2 kinase domains can be measured by a number of direct and indirect methods, including quantification of phosphorylation of peptide substrates derived from the human JAK3 protein (Saltzman et al., Biochem. Biophys. Res. Commun. 246:627-633 (2004)). The activity of the JAK1, JAK2, JAK3 or TYK2 kinase domains was measured in vitro by monitoring phosphorylation of JAK3 derived peptides using the Caliper LabChip technology (see Examples).

The compounds of the present invention are tested for their capacity to inhibit a Janus kinase activity and activation (primary assays) and for their biological effects on growing cells (secondary assays) as described herein. The compounds having Ki of less than 10 µM (preferably less than 5 µM, more preferably less than 1 µM, most preferably less than 0.5 µM) in the appropriate Janus kinase activity and activation assay (see Examples A and B), and EC50 of less than 20 µM (preferably less than 10 µM, more preferably less than 5 µM, most preferably less than 1 µM) in the appropriate cellular assays (see Example C) are useful as Janus kinase inhibitors.

Administration of Janus Kinase Inhibitor Compounds

Another embodiment includes a method of treating or lessening the severity of a disease or condition responsive to the inhibition of a Janus kinase activity in a patient. The method includes the step of administering to a patient a therapeutically effective amount of a compound of Formula I. In one embodiment, the disease is an autoimmune disease.

Another embodiment includes the use of a compound of Formula I for therapy.

Another embodiment includes the use of a compound of Formula I for preventing, treating or lessening the severity of a disease. In one embodiment, the disease is an autoimmune disease.

Another embodiment includes the use of a compound of Formula I in the manufacture of a medicament for preventing, treating or lessening the severity of a disease. In one embodiment, the disease is an autoimmune disease.

In one embodiment, a compound of Formula I is administered to a patient in a therapeutically effective amount to treat or lessen the severity of a disease or condition responsive to the inhibition of a Janus kinase activity, and said compound is at least 15 fold, alternatively 10 fold, alternatively 5 fold or more selective in inhibiting one Janus kinase activity over inhibiting one or more of the other Janus kinase activities.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the disease or condition is cancer.

In one embodiment, the disease is a myeloproliferative disorder.

In one embodiment, the myeloproliferative disorder is polycythemia vera, essential thrombocytosis, myelofibrosis or chronic myelogenous leukemia (CML).

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the cardiovascular disease is restenosis, cardiomegaly, atherosclerosis, myocardial infarction or congestive heart failure.

In one embodiment, the neurodegenerative disease is Alzheimer's disease, Parkinson's disease, amyotrophic lateral sclerosis, Huntington's disease, and cerebral ischemia, and neurodegenerative disease caused by traumatic injury, glutamate neurotoxicity or hypoxia.

In one embodiment, the inflammatory disease is inflammatory bowel disease, rheumatoid arthritis, psoriasis, contact dermatitis or delayed hypersensitivity reactions.

In one embodiment, the autoimmune disease is lupus or multiple sclerosis.

In one embodiment, the autoimmune disease is Crohn's disease, ulcerative colitis, Collagenous colitis, Lymphocytic colitis, Ischaemic colitis, Diversion colitis, Behçet's syndrome, Infective colitis and Indeterminate colitis.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. Methods in Immunotoxicology, Vol. 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through one or more of the Janus kinase pathways in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study using an autoimmune mechanism to mimic human arthritis; rat and mouse models (Example 68). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNF) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 69) determines the ability of compounds to inhibit the production of CD69 by B lymphocytes in human whole blood activated by crosslinking surface IgM with goat F(ab')2 anti-human IgM.

The T-cell Dependent Antibody Response (TDAR) is a predictive assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, Modern Methods in Immunotoxicology, Volume 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

A compound of Formula I may be administered by any route appropriate to the disease or condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary, and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound of Formula I is administered orally, it may be formulated as a pill, capsule, tablet, etc. with a pharmaceutically acceptable carrier or excipient. Where the compound of Formula I is administered parenterally, it may be formulated with a pharmaceutically acceptable parenteral vehicle and in a unit dosage injectable form, as detailed below.

A dose to treat human patients may range from about 10 mg to about 1000 mg of a compound of Formula I. A typical dose may be about 100 mg to about 300 mg of a compound of Formula I. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Pharmaceutical Formulations of Janus Kinase Inhibitor Compounds

Another embodiment includes a pharmaceutical composition that includes a compound of Formula I and a pharmaceutically acceptable carrier, adjuvant or vehicle.

In one embodiment, the pharmaceutical composition also includes an additional therapeutic agent selected from an anti-proliferative agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

In one embodiment, a compound of Formula I is present in a pharmaceutical formulation in an amount to detectably inhibit Janus kinase activity and a pharmaceutically acceptable carrier, adjuvant or vehicle.

In one embodiment, a compound of Formula I is present in a pharmaceutical formulation in an amount to detectably inhibit a Janus kinase activity and is at least 15 fold, alternatively 10 fold, or 5 fold or more selective in inhibiting one Janus kinase activity over inhibiting one or more of the other JAK1, JAK2, JAK3 and/or Tyk-2 activity.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound, such as a complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical, formulations of a compound of Formula I may be prepared for various routes and types of administration. A compound of Formula I having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

In an embodiment, the compound of Formula I for use in a pharmaceutical composition is substantially sterile. The compound ordinarily will be stored as a solid composition, although lyophilized formulations or aqueous solutions are acceptable.

The pharmaceutical compositions of the invention will be formulated, dosed, and administered in a fashion, i.e. amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the disorder. Such amount is preferably below the amount that is toxic to the host.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalogense or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of the compound of Formula I.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs may be prepared for oral use. Formulations of a compound of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For infections of the eye or other external tissues e.g. mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkyl oxide (e.g. ethylene oxide, propylene oxide) with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The pharmaceutical composition of a compound of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as an immunologic disorder (e.g. psoriasis or inflammation) or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be a NSAID or other anti-inflammatory agent. The second therapeutic agent may be a chemotherapeutic agent. The second therapeutic agent of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, geometric isomer, tautomer, solvate, metabolite, or pharmaceutically acceptable salt or prodrug thereof, in combination with a therapeutic agent such as an NSAID.

Another embodiment, therefore, includes a method of treating or lessening the severity of a disease or condition responsive to the inhibition of a Janus kinase in a patient, comprising administering to said patient a therapeutically effective amount of a compound of Formula I, and further comprising, administering a second therapeutic agent.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

In a particular embodiment of therapy, a compound of Formula I, or a stereoisomer, geometric isomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, geometric isomer, tautomer, solvate, metabolite, or pharmaceutically acceptable salt or prodrug thereof, and the use of at least one other cancer treatment method, or immunological disorder method. The amounts of the compound(s) of Formula I and the other pharmaceutically active immunologic or chemotherapeutic agent(s) and the relative timings of administration will be selected in order to achieve the desired combined therapeutic effect.

Metabolites of the Janus Kinase Inhibitor Compounds

Another embodiment includes in vivo metabolic products of an administered compound of Formula I. Such products may result for example from the oxidation, reduction, hydrolysis, amidation, deamidation, esterification, deesterification, enzymatic cleavage, and the like, of the administered compound.

Metabolite products typically are identified by preparing a radiolabelled (e.g. $^{14}C$ or $^{3}H$) isotope of a compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of a compound of Formula I.

Articles of Manufacture

Another embodiment includes a method of manufacturing a compound of Formula I. The method includes reacting a compound of formula (i):

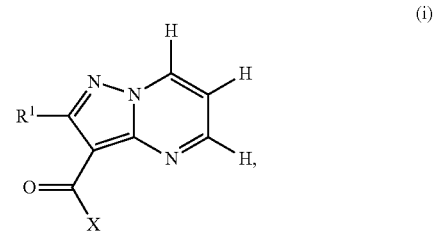

wherein $R^1$ is defined in Formula I, and X is a leaving group, for example, halogen, —OH, —O($C_1$-$C_{12}$ alkyl); with a compound of formulae (iia-c):

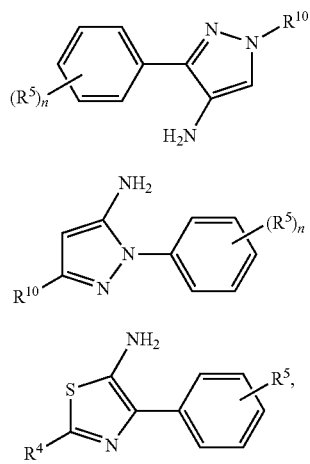

wherein R⁵ is defined in Formula I, and R¹⁰ is hydrogen or R⁴, and R⁴ is defined in Formula I; under conditions sufficient to form a compound of Formula I.

In an embodiment, said conditions include basic conditions, for example, carrying out the reaction in the presence of a base, such as an amine base, for example pyridine or an alikylated amine, such as dialkyl or trialkyl amine (e.g. trimethylamine, triethylamine, diisoproplyamine or diethylamine).

In an embodiment, said conditions include coupling conditions, for example, carrying out the reaction in the presence of PyAOP, DMAP and an alkylated amine, for example, diisopropylamine Another embodiment includes a kit for treating a disease or disorder responsive to the inhibition of a Janus kinase. The kit includes:
 a first pharmaceutical composition comprising a compound of Formula I; and
 instructions for use.

In another embodiment, the kit further includes:
 a second pharmaceutical composition, which includes a chemotherapeutic agent.

In one embodiment, the instructions include instructions for the simultaneous, sequential or separate administration of said first and second pharmaceutical compositions to a patient in need thereof.

In one embodiment, the first and second compositions are contained in separate containers.

In one embodiment, the first and second compositions are contained in the same container.

Containers for use include, for example, bottles, vials, syringes, blister pack, etc. The containers may be formed from a variety of materials such as glass or plastic. The container includes a compound of Formula I or formulation thereof which is effective for treating the condition and may have a sterile access port (for example the container may be an intravenous solution bag or a vial having a stopper pierceable by a hypodermic injection needle). The container includes a composition comprising at least one compound of Formula I. The label or package insert indicates that the composition is used for treating the condition of choice, such as cancer. In one embodiment, the label or package inserts indicates that the composition comprising the compound of Formula I can be used to treat a disorder. In addition, the label or package insert may indicate that the patient to be treated is one having a disorder characterized by overactive or irregular kinase activity. The label or package insert may also indicate that the composition can be used to treat other disorders.

The article of manufacture may comprise (a) a first container with a compound of Formula I contained therein; and (b) a second container with a second pharmaceutical formulation contained therein, wherein the second pharmaceutical formulation comprises a chemotherapeutic agent. The article of manufacture in this embodiment of the invention may further comprise a package insert indicating that the first and second compounds can be used to treat patients at risk of stroke, thrombus or thrombosis disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of Formula I, and alternative methods for preparing the compounds of Formula I are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

BIOLOGICAL EXAMPLES

Compounds of Formula I may be assayed for the ability to modulate the activity of Janus protein kinases, tyrosine kinases, additional serine/threonine kinases, and/or dual specificity kinases in vitro and in vivo. In vitro assays include biochemical and cell-based assays that determine inhibition of the kinase activity. Alternate in vitro assays quantify the ability of the compound of Formula I to bind to kinases and may be measured either by radiolabelling the compound of Formula I prior to binding, isolating the compound of Formula I/kinase complex and determining the amount of radiolabel bound, or by running a competition experiment where a compound of Formula I is incubated with known radiolabeled ligands. These and other useful in vitro assays are well known to those of skill in the art.

In an embodiment, the compounds of Formula I can be used to control, modulate or inhibit tyrosine kinase activity, for example Janus protein kinase activity, additional serine/threonine kinases, and/or dual specificity kinases. Thus, they are useful as pharmacological standards for use in the development of new biological tests, assays and in the search for new pharmacological agents.

Example A

JAK1, JAK2 and TYK2 Inhibition Assay Protocol

The activity of the isolated JAK1, JAK2 or TYK2 kinase domain was measured by monitoring phosphorylation of a peptide derived from JAK3 (Val-Ala-Leu-Val-Asp-Gly-Tyr-Phe-Arg-Leu-Thr-Thr) fluorescently labeled on the N-terminus with 5-carboxyfluorescein using the Caliper LabChip technology (Caliper Life Sciences, Hopkinton, Mass.). To determine the inhibition constants (Ki) of Examples 1-508, compounds were diluted serially in DMSO and added to 50 uL kinase reactions containing 1.5 nM JAK1, 0.2 nM purified JAK2 or 1 nM purified TYK2 enzyme, 100 mM Hepes pH7.2, 0.015% Brij-35, 1.5 uM peptide substrate, 25 uM ATP, 10 mM MgCl2, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., Biochim. Biophys. Acta. 185:269-296 (1969); William, J. W. and Morrison, J. F., Meth. Enzymol., 63:437-467 (1979).

Example B

JAK3 Inhibition Assay Protocol

The activity of the isolated JAK3 kinase domain was measured by monitoring phosphorylation of a peptide derived from JAK3 (Leu-Pro-Leu-Asp-Lys-Asp-Tyr-Tyr-Val-Val-Arg) fluorescently labeled on the N-terminus with 5-carboxy-fluorescein using the Caliper LabChip technology (Caliper Life Sciences, Hopkinton, Mass.). To determine the inhibition constants (Ki) of Examples 1-508, compounds were diluted serially in DMSO and added to 50 uL kinase reactions containing 5 nM purified JAK3 enzyme, 100 mM Hepes pH7.2, 0.015% Brij-35, 1.5 uM peptide substrate, 5 uM ATP, 10 mM MgCl$_2$, 4 mM DTT at a final DMSO concentration of 2%. Reactions were incubated at 22° C. in 384-well polypropylene microtiter plates for 30 minutes and then stopped by addition of 25 uL of an EDTA containing solution (100 mM Hepes pH 7.2, 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip 3000 according to the manufacturer's specifications. Ki values were then determined using the Morrison tight binding model. Morrison, J. F., *Biochim. Biophys. Acta.* 185:269-296 (1969); William, J. W. and Morrison, J. F., *Meth. Enzymol.,* 63:437-467 (1979).

Example C

Cell-Based Pharmacology Assays

The activities of Examples 1-508 were determined in cell-based assays that are designed to measure Janus kinase dependent signaling. Compounds were serially diluted in DMSO and incubated with Set-2 cells (German Collection of Microorganisms and Cell Cultures (DSMZ); Braunschweig, Germany), which express the JAK2V617F mutant protein, in 96-well microtiter plates for 1 hr at 37° C. in RPMI medium at a final cell density of $10^5$ cells per well and a final DMSO concentration of 0.57%. Compound-mediated effects on STAT5 phosphorylation were then measured in the lysates of incubated cells using the Meso Scale Discovery (MSD) technology (Gaithersburg, Md.) according to the manufacturer's protocol and EC$_{50}$ values were determined. Alternatively, serially diluted compounds were added to NK92 cells (American Type Culture Collection (ATCC); Manassas, Va.) in 96-well microtiter plates in RPMI medium at a final cell density of $10^5$ cells per well and a final DMSO concentration of 0.57%. Human recombinant IL-2 or IL-12 (R&D systems; Minneapolis, Minn.) was then added at a final concentration of 1.0 ng/mL or 30 ng/mL, respectively, to the microtiter plates containing the NK92 cells and compound and the plates were incubated for 1 hr at 37° C. Compound-mediated effects on STAT5 (IL-2-mediated) or STAT4 (IL-12-mediated) phosphorylation were then measured in the lysates of incubated cells using the Meso Scale Discovery (MSD) technology (Gaithersburg, Md.) according to the manufacturer's protocol and EC$_{50}$ values were determined.

PREPARATIVE EXAMPLES

Abbreviations

CD$_3$OD Deuterated Methanol
CDCl$_3$ Deuterated Chloroform
DAST Diethylaminosulfur trifluoride
DCM Dichloromethane
DIPEA Diisopropylethylamine
DMAP 4-Dimethylaminopyridine
DMF Dimethylformamide
DMF-DMA N,N-Dimethylformamide Dimethylacetal
DMSO Dimethylsulfoxide
DMSO-d6 Deuterated DMSO
DME 1,2-Dimethoxyethane
DMF Dimethylformamide
DPPA Diphenylphosphoryl azide
EtOAc Ethyl Acetate
EtOH Ethanol
HOAc Acetic acid
g gram
HATU (O-(7-azabenzotriazol-1-yl)-N,N,N',N'-tetramethyluronium hexafluorophosphate)
HCl Hydrochloric acid
Hex Hexane
HM-N Isolute® HM-N is a modified form of diatomaceous earth
IMS industrial methylated spirits
L liter
MeOH Methanol
mg milligram
mL milliliter
POCl$_3$ Phosphorus oxychloride
NaH Sodium Hydride
Na$_2$SO$_4$ Sodium Sulfate
NaHCO$_3$ Sodium bicarbonate
NaOH Sodium hydroxide
Pd(PPh$_3$)$_4$ Tetrakis(triphenylphosphine)palladium(0)
PyAOP (7-Azabenzotriazol-1-yloxy)tripyrrolidinophosphonium hexafluorophosphate
Lawesson's Reagent 2,4-Bis(4-methoxyphenyl)-1,3-dithia-2,4-diphosphetane 2,4-disulphide
NEt$_3$ Triethylamine
Pd$_2$dba$_3$ Tris-(dibenzylideneacetone)dipalladium(0)
Si-SPE Pre-packed Isolute® silica flash chromatography cartridge
Si-ISCO Pre-packed ISCO® silica flash chromatography cartridge
THF Tetrahydrofuran
SEM 2-(trimethylsilyl)ethoxymethyl
SEMCl 2-(trimethylsilyl)ethoxymethyl chloride
TEA Triethylamine
TFA Trifluoroacetic acid
General Experimental Conditions $^1$H NMR spectra were recorded at ambient temperature using a Varian Unity Inova (400 MHz) spectrometer with a triple resonance 5 mm probe, a Bruker AVIII spectrometer (400 MHz) using a BBI Broad Band Inverse 5 mm probe, a Bruker Avance DRX400 (400 MHz) spectrometer with a triple resonance 5 mm probe, or a Bruker AVIII spectrometer (500 MHz) using a QNP (Quad Nucleus detect) 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times (RT) and associated mass ions were performed using one of the following methods.

Method A: Experiments performed on a Waters Micromass ZQ quadrupole mass spectrometer linked to a Hewlett Packard HP1100 LC system with diode array detector. This system uses a Higgins Clipeus 5 micron C18 100×3.0 mm column and a 1 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Preparative High Pressure Liquid Chromatography (HPLC) was used to purify certain compounds. The system used was a Varian LC equipped with an automated UV-triggered fraction collector and a Gemini NX column (3×10 cm). The mobile phase was a gradient of 5-85% acetonitrile in water, containing 0.1% formic acid or ammonium hydroxide, over 10 minutes.

Chiral Supercritical Fluid Chromatography (SFC) was used to separate some racemic compounds into their component enantiomers. The system used was a Berger Pronto SFC equipped with an automated UV-triggered fraction collector. Chiral Technologies AD, OD, OJ, or AS (21.2×250 mm) are examples of the columns used. Run lengths varied from 5-10 minutes, and an isocratic mobile phase consisting of 5-50% MeOH:carbon dioxide was used.

Microwave experiments were carried out using a Biotage Initiator 60™ which uses a single-mode resonator and dynamic field tuning Temperature from 40-250° C. can be achieved, and pressures of up to 30 bar can be reached.

Example 1

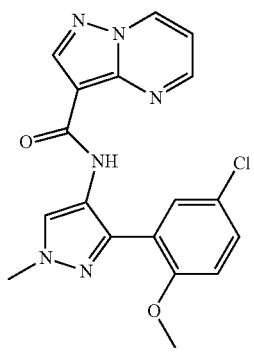 [SMILES: COc1ccc(Cl)cc1-c1nn(C)cc1NC(=O)c1cnn2cccnc12]

N-(3-(5-chloro-2-methoxyphenyl)-1-methyl-1H-pyrazol-4-yl)pyrazolo[1,5-a]pyrimidine-3-carboxamide

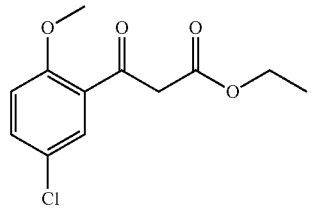 [SMILES: CCOC(=O)CC(=O)c1cc(Cl)ccc1OC]

ethyl 3-(5-chloro-2-methoxyphenyl)-3-oxopropanoate

To a stirring solution of 5-chloro-2-methoxybenzoic acid (1.87 g, 10.0 mmol, 1 eq) in 20 mL tetrahydrofuran was added N,N-carbonyldiimidazole (1.64 g, 10.1 mmol, 1.01 eq), and stirring was continued for twenty minutes to generate the acyl-imidazole. Separately, potassium ethyl malonate (4.08 g, 24.0 mmol, 2.39 eq) and magnesium chloride (1.15 g, 12.1 mmol, 1.20 eq) were suspended in 20 mL tetrahydrofuran. To the magnesium chloride mixture was added the acyl-imidazole solution. Stirring was continued at 50° C. for 1.5 hours. The reaction mixture was partitioned between ethyl acetate and water, and the organic portion dried over magnesium sulfate, filtered through a pad of celite, and concentrated to provide ethyl 3-(5-chloro-2-methoxyphenyl)-3-oxopropanoate, which was used without further purification. LCMS (ESI) m+H=257.2

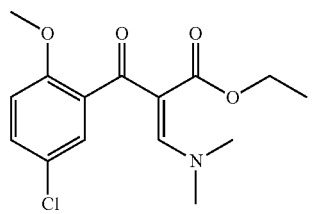 [SMILES: CCOC(=O)/C(=C\N(C)C)C(=O)c1cc(Cl)ccc1OC]

ethyl 2-(5-chloro-2-methoxybenzoyl)-3-(dimethylamino)acrylate

A stirred mixture of ethyl 3-(5-chloro-2-methoxyphenyl)-3-oxopropanoate (10.02 mmol, 1 eq) and 1,1-dimethoxy-N,N-dimethylmethanamine (3.0 mL, 22 mmol, 2.2 eq) was heated at 90° C. for 2 hours. After evaporation of excess 1,1-dimethoxy-N,N-dimethylmethanamine, the crude product was purified by flash chromatography on silica gel (0 to 80% ethyl acetate in dichloromethane) to yield 2.493 g (80%) of ethyl 2-(5-chloro-2-methoxybenzoyl)-3-(dimethylamino)acrylate. LCMS (ESI) m+H=312.2.

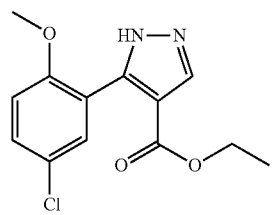 [SMILES: CCOC(=O)c1cn[nH]c1-c1cc(Cl)ccc1OC]

ethyl 5-(5-chloro-2-methoxyphenyl)-1H-pyrazole-4-carboxylate

A solution of ethyl 2-(5-chloro-2-methoxybenzoyl)-3-(dimethylamino)acrylate (2.49 g, 8.00 mmol, 1 eq) and hydrazine (0.40 mL, 13 mmol, 1.6 eq) in 20 mL ethanol was heated at 70° C. for 2 hours. Solvent and excess hydrazine were then evaporated to provide ethyl 5-(5-chloro-2-methoxyphenyl)-1H-pyrazole-4-carboxylate, which was used without further purification. LCMS (ESI) m+H=281.3.

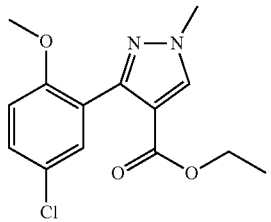 [SMILES: CCOC(=O)c1cn(C)nc1-c1cc(Cl)ccc1OC]

ethyl 3-(5-chloro-2-methoxyphenyl)-1-methyl-1H-pyrazole-4-carboxylate

To a solution of ethyl 5-(5-chloro-2-methoxyphenyl)-1H-pyrazole-4-carboxylate (2.24 g, 8.00 mmol, 1 eq) in 20 mL N,N-dimethylformamide was added cesium carbonate (3.417 g, 10.49 mmol, 1.3 eq) and iodomethane (0.60 mL, 9.6 mmol, 1.2 eq). The reaction mixture was stirred at 40° C. for 4 hours, then additional iodomethane was added (0.20 mL, 3.2 mmol, 0.4 eq). After a further 2.5 hours, the reaction mixture was partitioned between ethyl acetate and water. The organic portion was dried over magnesium sulfate and concentrated. The crude product was purified by flash chromatography on silica gel (0 to 35% ethyl acetate in dichloromethane) to yield 2.18 g (92%) of a 1:1 mixture of regioisomeric products, ethyl 3-(5-chloro-2-methoxyphenyl)-1-methyl-1H-pyrazole-4-carboxylate and ethyl 5-(5-chloro-2-methoxyphenyl)-1-methyl-1H-pyrazole-4-carboxylate. LCMS (ESI) m+H=295.1.

tert-butyl 3-(5-chloro-2-methoxyphenyl)-1-methyl-1H-pyrazol-4-ylcarbamate

A solution of ethyl 3-(5-chloro-2-methoxyphenyl)-1-methyl-1H-pyrazole-4-carboxylate and ethyl 5-(5-chloro-2-methoxyphenyl)-1-methyl-1H-pyrazole-4-carboxylate (1:1 mixture of regioisomers, 2.18 g, 7.40 mmol, 1 eq) in 15 mL ethanol was treated with 1.0 M aqueous sodium hydroxide (12 mL, 0.020 mmol, 4.0 eq). The reaction mixture was heated at 50° C. for 14 hours. After evaporation of the ethanol, the residue was diluted into water and adjusted to pH 2 with 1.0 M aqueous phosphoric acid. This solution was extracted twice with dichloromethane. The combined extracts were dried over MgSO$_4$ and concentrated to yield 1.79 g (91%) of the corresponding carboxylic acids which were carried forward immediately. LCMS (ESI) m+H=267.2. To a solution of this material in 15 mL dioxane was added triethylamine (2.0 mL, 14 mmol, 4.3 eq) and diphenylphosphonic azide (1.6 mL, 7.4 mmol, 2.2 eq). The reaction mixture was stirred at room temperature for 1 hour, at which time the reaction was heated to 90° C. and 15 mL t-butyl alcohol was added. After stirring at 90° C. for 2.5 hours, the solvent was evaporated and the residue partitioned between ethyl acetate and water. The organic portion was washed with brine, dried over magnesium sulfate, and concentrated. The crude product was purified by flash chromatography on silica gel (0 to 50% ethyl acetate in dichloromethane), separating the two regioisomers to obtain: 543.2 mg (48%) of tert-butyl 3-(5-chloro-2-methoxyphenyl)-1-methyl-1H-pyrazol-4-ylcarbamate. LCMS (ESI) m+H=338.3; $^1$H NMR (400 MHz, CDCl$_3$) δ: 7.84 (s, 1H), 7.39 (d, 1H), 7.23 (s, 1H), 6.96 (d, 1H), 5.92 (s, 1H), 3.89 (overlapping s and s, 6H), 1.48 (s, 9H), and 773.7 mg (68%) of tert-butyl 5-(5-chloro-2-methoxyphenyl)-1-methyl-1H-pyrazol-4-ylcarbamate. LCMS (ESI) m+H=338.3; $^1$H NMR (400 MHz, CDCl$_3$) δ: 7.84 (s, 1H), 7.59 (s, 1H), 7.29 (d, 1H), 6.93 (d, 1H), 3.89 (overlapping s and s, 6H), 1.48 (s, 9H).

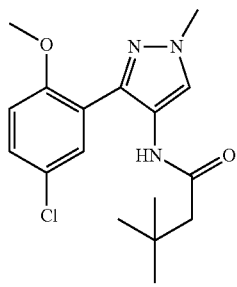 [SMILES: COc1ccc(Cl)cc1-c1nn(C)cc1NC(=O)CC(C)(C)C]

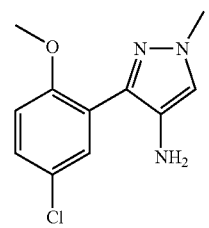 [SMILES: COc1ccc(Cl)cc1-c1nn(C)cc1N]

3-(5-chloro-2-methoxyphenyl)-1-methyl-1H-pyrazol-4-amine

To a stirring solution of tert-butyl 3-(5-chloro-2-methoxyphenyl)-1-methyl-1H-pyrazol-4-ylcarbamate (543.2 mg, 1.608 mmol, 1 eq) was added hydrogen chloride (5.0 mL of a 4.0 M solution in 1,4-dioxane, 0.020 mol, 12 eq). The reaction mixture was stirred at room temperature for 9 hours and then evaporated to dryness. The solid residue was partitioned between dichloromethane and a saturated aqueous solution of sodium bicarbonate. The aqueous portion was extracted once more with dichloromethane, and the combined organic extracts dried over magnesium sulfate and concentrated to give 3-(5-chloro-2-methoxyphenyl)-1-methyl-1H-pyrazol-4-amine, which was carried forward without purification. LCMS (ESI) m+H=238.2; $^1$H NMR (400 MHz, CDCl$_3$) δ: 7.53 (s, 1H), 7.28 (d, 1H), 7.02 (s, 1H), 6.91 (d, 1H), 3.91 (d, 2H), 3.87 (s, 3H), 3.84 (s, 3H).

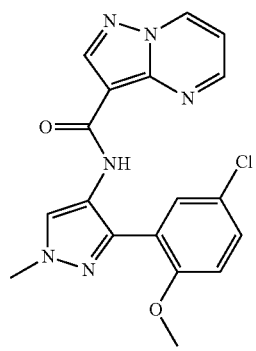 [SMILES: COc1ccc(Cl)cc1-c1nn(C)cc1NC(=O)c1cnn2cccnc12]

N-(3-(5-chloro-2-methoxyphenyl)-1-methyl-1H-pyrazol-4-yl)pyrazolo[1,5-a]pyrimidine-3-carboxamide A mixture of 3-(5-chloro-2-methoxyphenyl)-1-methyl-1H-pyrazol-4-amine (258 mg, 0.869 mmol, 1.00 eq), pyrazolo[1,5-a]pyrimidine-3-carboxylic acid (157 mg, 0.961 mmol, 1.11 eq), 7-azabenzotriazol-1-yloxy-tris-(pyrrolidino)phosphonium hexafluorophosphate (541 mg, 1.04 mmol, 1.20 eq), N,N-diisopropylethylamine (0.40 mL, 2.3 mmol, 2.6 eq), and 4-dimethylaminopyridine (30.7 mg, 0.251 mmol, 0.29 eq) in 8.0 mL N,N-dimethylformamide was stirred at 50° C. for 3 hours. The reaction mixture was partitioned between ethyl acetate and water, and the organic portion washed with brine, dried over magnesium sulfate, and concentrated to yield 232.3 mg (70%) of the crude product. The crude product was purified by reverse phase HPLC and lyophilized to give N-(3-(5-chloro-2-methoxyphenyl)-1-methyl-1H-pyrazol-4-yl)pyrazolo[1,5-a]pyrimidine-3-carboxamide. LCMS (ESI) m+H=383.0; $^1$H NMR (400 MHz, DMSO-$d_6$) δ: 9.66 (s, 1H), 9.32 (d, 1H), 8.76 (d, 1H), 8.65 (s, 1H), 8.26 (s, 1H), 7.48 (d, 1H), 7.40 (s, 1H), 7.28 (m, 2H), 3.91 (s, 3H), 3.84 (s, 3H).

Example 2

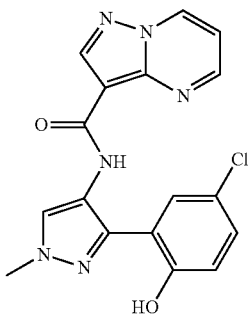 [SMILES: Cn1cc(NC(=O)c2cnn3cccnc23)c(-c2cc(Cl)ccc2O)n1]

N-(3-(5-chloro-2-hydroxyphenyl)-1-methyl-1H-pyrazol-4-yl)pyrazolo[1,5-a]pyrimidine-3-carboxamide To a solution of N-(3-(5-chloro-2-methoxyphenyl)-1-methyl-1H-pyrazol-4-yl)pyrazolo[1,5-a]pyrimidine-3-carboxamide (145 mg, 0.379 mmol, 1 eq) in 3.0 mL dichloromethane was added boron tribromide (1.1 mL of a 1.0 M solution in dichloromethane, 1.1 mmol, 2.9 eq). The reaction was stirred at room temperature for 16 hours. The reaction mixture was then quenched with methanol, diluted into ethyl acetate, and washed with saturated aqueous sodium bicarbonate and brine, dried over magnesium sulfate and concentrated. The resulting solid material was triturated with 2 mL DMSO, and the solids collected and dried under vacuum to yield 47.8 mg (34%) of N-(3-(5-chloro-2-hydroxyphenyl)-1-methyl-1H-pyrazol-4-yl)pyrazolo[1,5-a]pyrimidine-3-carboxamide. LCMS (ESI) m+H=369.0; $^1$H NMR (400 MHz, DMSO-$d_6$) δ: 10.45 (s, 1H), 9.99 (s, 1H), 9.33 (d, 1H), 8.76 (d, 1H), 8.65 (s, 1H), 8.27 (s, 1H), 7.45 (s, 1H), 7.30 (m, 2H), 7.08 (d, 1H), 3.92 (s, 3H).

Example 3

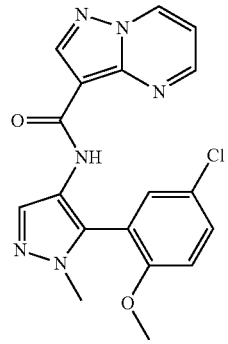 [SMILES: COc1ccc(Cl)cc1-c1c(NC(=O)c2cnn3cccnc23)cnn1C]

N-(5-(5-chloro-2-methoxyphenyl)-1-methyl-1H-pyrazol-4-yl)pyrazolo[1,5-a]pyrimidine-3-carboxamide

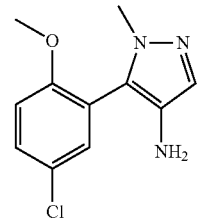 [SMILES: COc1ccc(Cl)cc1-c1c(N)cnn1C]

5-(5-chloro-2-methoxyphenyl)-1-methyl-1H-pyrazol-4-amine

To a solution of tert-butyl 5-(5-chloro-2-methoxyphenyl)-1-methyl-1H-pyrazol-4-ylcarbamate (774 mg, 2.29 mmol, 1 eq) was added hydrogen chloride (6.0 mL of a 4.0M solution in 1,4-dioxane, 24 mmol, 10 eq). The reaction mixture was stirred at room temperature for 4 hours and then evaporated to dryness. The solid residue was partitioned between dichloromethane and a saturated aqueous solution of sodium bicarbonate. The aqueous portion was extracted once more with dichloromethane, and the combined organic extracts dried over magnesium sulfate and concentrated to give 5-(5-chloro-2-methoxyphenyl)-1-methyl-1H-pyrazol-4-amine, which was carried forward without purification. LCMS (ESI) m+H=238.3; $^1$H NMR (400 MHz, CDCl$_3$) δ: 7.35 (d, 1H), 7.22 (overlapping s and s, 2H), 6.94 (d, 1H), 3.83 (s, 3H), 3.70 (d, 2H), 3.66 (s, 3H).

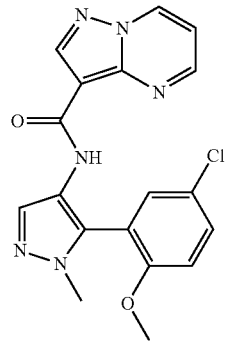 [SMILES: COc1ccc(Cl)cc1-c1c(NC(=O)c2cnn3cccnc23)cnn1C]

N-(5-(5-chloro-2-methoxyphenyl)-1-methyl-1H-pyrazol-4-yl)pyrazolo[1,5-a]pyrimidine-3-carboxamide A mixture of 5-(5-chloro-2-methoxyphenyl)-1-methyl-1H-pyrazol-4-amine (0.100 g, 0.421 mmol, 1 eq), pyrazolo[1,5-a]pyrimidine-3-carboxylic acid (77.2 mg, 0.473 mmol, 1.12 eq), 7-azabenzotriazol-1-yloxy-tris-(pyrrolidino)phosphonium hexafluorophosphate (269 mg, 0.519 mmol, 1.23 eq), N,N-diisopropylethylamine (0.15 mL, 0.86 mmol, 2.0 eq), and 4-dimethylaminopyridine (20.1 mg, 0.164 mmol, 0.39 eq) in 5.0 mL N,N-dimethylformamide was stirred at 50° C. for 2 hours. The reaction mixture was partitioned between ethyl acetate and water, and the organic portion washed with brine, dried over magnesium sulfate, and concentrated. The crude product was purified by reverse phase HPLC and lyophilized to give 82.2 mg (51%) of N-(5-(5-chloro-2-methoxyphenyl)-1-methyl-1H-pyrazol-4-yl)pyrazolo[1,5-a]pyrimidine-3-carboxamide. LCMS (ESI) m+H=383.0; $^1$H NMR (400 MHz, DMSO-$d_6$) δ: 9.51 (s, 1H), 9.31 (d, 1H), 8.67 (d, 1H), 8.63 (s, 1H), 7.98 (s, 1H), 7.58 (d, 1H), 7.54 (s, 1H), 7.31 (d, 1H), 7.28 (d of d, 1H), 3.85 (s, 3H), 3.70 (s, 3H).

Example 4 and Example 5

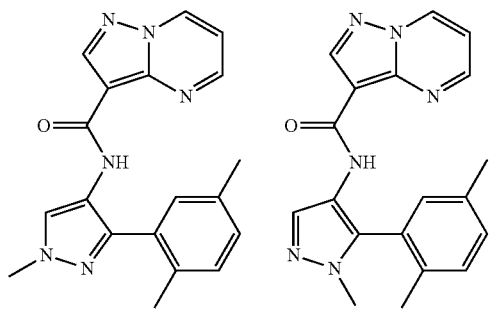

N-(3-(2,5-dimethylphenyl)-1-methyl-1H-pyrazol-4-yl)pyrazolo[1,5-a]pyrimidine-3-carboxamide N-(5-(2,5-dimethylphenyl)-1-methyl-1H-pyrazol-4-yl)pyrazolo[1,5-a]pyrimidine-3-carboxamide

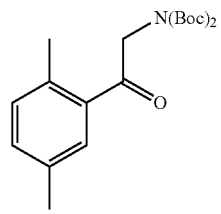

di-tert-butyl 2-(2,5-dimethylphenyl)-2-oxoethyliminodicarbonate

In an oven-dried flask, di-tert-butyl iminodicarboxylate (2.566 g, 11.81 mmol, 1.10 eq) was combined with sodium hydride (60% on mineral oil, 0.586 g, 14.6 mmol, 1.37 eq) and 30 mL N,N-dimethylformamide. The reaction mixture was stirred at room temperature for 1.5 hours, and then 2-bromo-1-(2,5-dimethylphenyl)ethanone (2.432 g, 10.71 mmol, 1 eq) was added. The reaction was stirred at room temperature for an additional 1.5 hours, and then partitioned between ethyl acetate and water. The organic portion was washed with water and brine, dried over magnesium sulfate, and concentrated. The crude product was purified by flash chromatography on silica gel (0 to 40% ethyl acetate in heptanes) to obtain 3.008 g (77%) of di-tert-butyl 2-(2,5-dimethylphenyl)-2-oxoethyl-iminodicarbonate. LCMS (ESI) m+Na=386.2.

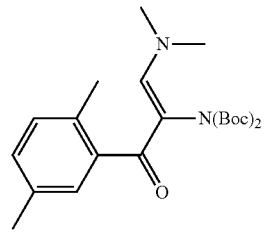

di-tert-butyl 1-(dimethylamino)-3-(2,5-dimethylphenyl)-3-oxoprop-1-en-2-yliminodicarbonate A stirred mixture of di-tert-butyl 2-(2,5-dimethylphenyl)-2-oxoethyliminodicarbonate (3.008 g, 8.275 mmol, 1 eq) and 1,1-dimethoxy-N,N-dimethylmethanamine (6.0 mL, 45 mmol, 5.4 eq) was heated at 70° C. for 17 hours and then 100° C. for 24 hours. After evaporation of excess 1,1-dimethoxy-N,N-dimethylmethanamine, the crude product was purified by flash chromatography on silica gel (0 to 50% ethyl acetate in heptanes) to yield 1.305 g (38%) of di-tert-butyl 1-(dimethylamino)-3-(2,5-dimethylphenyl)-3-oxoprop-1-en-2-yliminodicarbonate. LCMS (ESI) m+H=419.3.

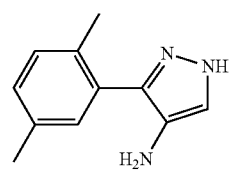

3-(2,5-dimethylphenyl)-1H-pyrazol-4-amine

Di-tert-butyl 1-(dimethylamino)-3-(2,5-dimethylphenyl)-3-oxoprop-1-en-2-yliminodicarbonate (1.305 g, 3.118 mmol, 1 eq) and hydrazine (0.20 mL, 6.4 mmol, 2.0 eq) were dissolved together in 15 mL ethanol. The reaction mixture was stirred at 70° C. for 1 hour and then evaporated to dryness under vacuum. The solid residue was dissolved in 8 mL dichloromethane and hydrogen chloride (8.0 mL of a 4.0 M solution in 1,4-dioxane, 0.10 mol, 40 eq) and stirred at room temperature for 3.5 hours. The solvent and excess hydrogen chloride were evaporated and the crude product partitioned between saturated aqueous sodium bicarbonate and dichloromethane. The aqueous layer was extracted once more with dichloromethane, and the combined organic extracts dried over magnesium sulfate and concentrated to give 3-(2,5-dimethylphenyl)-1H-pyrazol-4-amine, which was carried forward without purification. LCMS (ESI) m+H=188.3.

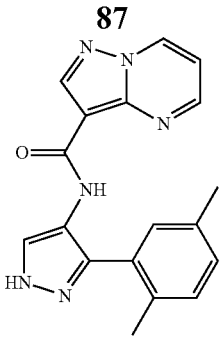

N-(3-(2,5-dimethylphenyl)-1H-pyrazol-4-yl)pyrazolo[1,5-a]pyrimidine-3-carboxamide A mixture of 3-(2,5-dimethylphenyl)-1H-pyrazol-4-amine (0.300 g, 1.60 mmol, 1 eq), pyrazolo[1,5-a]pyrimidine-3-carboxylic acid (289.2 mg, 1.773 mmol, 1.11 eq), 7-azabenzotriazol-1-yloxy-tris-(pyrrolidino)phosphonium hexafluorophosphate (1.087 g, 2.096 mmol, 1.31 eq), N,N-diisopropylethylamine (1.0 mL, 5.7 mmol, 3.6 eq), and 4-dimethylaminopyridine (42.3 mg, 0.346 mmol, 0.22 eq) in 8.0 mL N,N-dimethylformamide was stirred at 50° C. for 3 hours. The reaction mixture was partitioned between ethyl acetate and water, and the organic portion washed with brine, dried over magnesium sulfate, and concentrated. The crude product was purified by flash chromatography on silica gel (40 to 100% ethyl acetate in dichloromethane) to yield 299.8 mg (56%) of N-(3-(2,5-dimethylphenyl)-1H-pyrazol-4-yl)pyrazolo[1,5-a]pyrimidine-3-carboxamide. LCMS (ESI) m+H=333.3; $^1$H NMR (400 MHz, DMSO-d$_6$) δ: 9.67 (s, 0.7H), 9.55 (s, 0.3H), 9.32 (d, 1H), 8.64 (s, 1H), 8.49 (d, 1H), 8.27 (s, 1H), 7.29 (d, 1H), 7.22 (m, 3H), 2.34 (s, 3H), 2.24 (s, 3H).

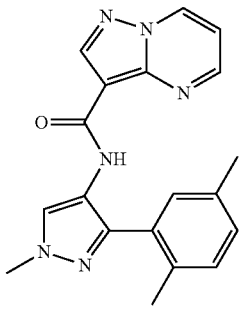

N-(3-(2,5-dimethylphenyl)-1-methyl-1H-pyrazol-4-yl)pyrazolo[1,5-a]pyrimidine-3-carboxamide

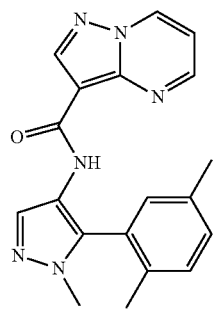 [SMILES: Cc1ccc(C)c(-c2c(NC(=O)c3cnn4cccnc34)cnn2C)c1]

N-(5-(2,5-dimethylphenyl)-1-methyl-1H-pyrazol-4-yl)pyrazolo[1,5-a]pyrimidine-3-carboxamide To a solution of N-(3-(2,5-dimethylphenyl)-1H-pyrazol-4-yl)pyrazolo[1,5-a]pyrimidine-3-carboxamide (0.255 g, 0.767 mmol, 1 eq) in 10 mL N,N-dimethylformamide is added iodomethane (60.0 µL, 0.964 mmol, 1.26 eq) and cesium carbonate (0.562 g, 1.72 mmol, 2.25 eq). The reaction mixture is stirred at 40° C. for 2.5 hours. The reaction mixture was partitioned between ethyl acetate and water, and the organic portion washed with brine, dried over magnesium sulfate, and concentrated. The mixture of regioisomeric products was separated and purified by flash chromatography on silica gel (20 to 90% ethyl acetate in dichloromethane) to yield: 84.3 mg (32%) of N-(3-(2,5-dimethylphenyl)-1-methyl-1H-pyrazol-4-yl)pyrazolo[1,5-a]pyrimidine-3-carboxamide. LCMS (ESI) m+H=347.1; $^1$H NMR (400 MHz, DMSO-d$_6$) δ: 9.65 (s, 1H), 9.30 (d, 1H), 8.65 (s, 1H), 8.47 (d, 1H), 8.27 (s, 1H), 7.27 (d, 1H), 7.23-7.19 (m, 3H), 3.91 (s, 3H), 2.33 (s, 3H), 2.25 (s, 3H), and 81.8 mg (31%) of N-(5-(2,5-dimethylphenyl)-1-methyl-1H-pyrazol-4-yl)pyrazolo[1,5-a]pyrimidine-3-carboxamide. LCMS (ESI) m+H=347.1; $^1$H NMR (400 MHz, DMSO-d$_6$) δ: 9.42 (s, 1H), 9.30 (d, 1H), 8.61 (s, 1H), 8.43 (d, 1H), 8.01 (s, 1H), 7.36 (d, 1H), 7.30 (d, 1H) 7.20 (m, 2H), 3.62 (s, 3H), 2.35 (s, 3H), 2.12 (s, 3H).

Example 6

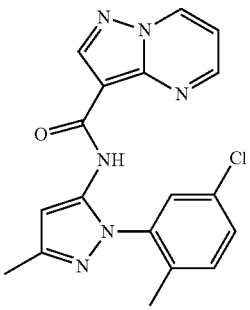 [SMILES: Cc1cc(NC(=O)c2cnn3cccnc23)n(-c2cc(Cl)ccc2C)n1]

N-(1-(5-chloro-2-methylphenyl)-3-methyl-1H-pyrazol-5-yl)pyrazolo[1,5-a]pyrimidine-3-carboxamide

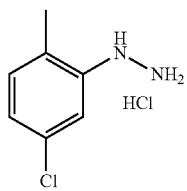

(5-chloro-2-methylphenyl)hydrazine hydrochloride

To a stirred suspension of 5-chloro-2-methylaniline (1.436 g, 10.14 mmol, 1. eq) in 10 mL water at 0° C. was added 10 mL concentrated hydrochloric acid. To this reaction mixture was added dropwise a solution of sodium nitrite (0.791 g, 11.5 mmol, 1.13 eq) in 5 mL water. The reaction mixture was stirred at 0° C. for 2 hours while tin chloride dihydrate (5.8826 g, 25.839 mmol, 2.55 eq), dissolved in 8 mL concentrated hydrochloric acid, was slowly added. Water was added as needed to maintain the stirring while solids formed. The reaction was kept at 0° C. for 45 minutes. The white solids were filtered and rinsed with two 50 mL portions of diethyl ether, then dried under vacuum to provide 1.49 g (76%) of (5-chloro-2-methylphenyl)hydrazine hydrochloride. $^1$H NMR (400 MHz, DMSO-d$_6$) δ: 10.08 (s, 3H), 7.98 (s, 1H), 7.13 (d, 1H), 6.97 (s, 1H), 6.91 (d, 1H), 2.14 (s, 3H).

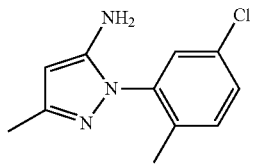

1-(5-chloro-2-methylphenyl)-3-methyl-1H-pyrazol-5-amine

To a solution of (5-chloro-2-methylphenyl)hydrazine hydrochloride (1.49 g, 7.72 mmol, 1 eq) in 8 mL ethanol was added hydrogen chloride (4.0 mL of a 5 M aqueous solution, 20 mmol, 2 eq) and 3-aminocrotonitrile (0.664 g, 8.09 mmol, 1.05 eq). The reaction mixture was stirred at 80° C. for 16 hours and then brought to neutral pH with saturated aqueous sodium bicarbonate. The resulting solution was extracted twice with dichloromethane, and the combined extracts were dried over magnesium sulfate and concentrated to give 1-(5-chloro-2-methylphenyl)-3-methyl-1H-pyrazol-5-amine, which was carried forward without further purification. LCMS (ESI) m+H=222.2; $^1$H NMR (400 MHz, DMSO-d$_6$) δ: 7.39 (d, 1H), 7.37 (d, 1H), 7.25 (s, 1H), 5.22 (s, 1H), 5.00 (s, 2H), 2.04 (overlapping s and s, 6H).

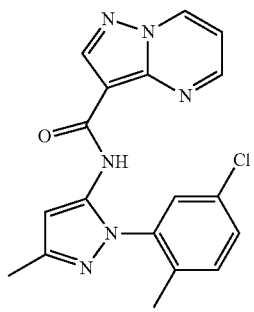 [SMILES: Cc1cc(NC(=O)c2cnn3cccnc23)n(-c2cc(Cl)ccc2C)n1]

N-(1-(5-chloro-2-methylphenyl)-3-methyl-1H-pyrazol-5-yl)pyrazolo pyrimidine-3-carboxamide A mixture of 1-(5-chloro-2-methylphenyl)-3-methyl-1H-pyrazol-5-amine (95.3 mg, 0.430 mmol, 1 eq), pyrazolo[1,5-a]pyrimidine-3-carboxylic acid (79.5 mg, 0.487 mmol, 1.13 eq), 7-azabenzotriazol-1-yloxy-tris-(pyrrolidino)phosphonium hexafluorophosphate (0.290 g, 0.558 mmol, 1.30 eq), N,N-diisopropylethylamine (0.2 mL, 1.1 mmol, 2.7 eq), and 4-dimethylaminopyridine (11.0 mg, 0.09 mmol, 0.21 eq) in 4.0 mL N,N-dimethylformamide was stirred at 75° C. for 3 days. The reaction mixture was partitioned between ethyl acetate and water, and the organic portion washed with brine, dried over magnesium sulfate, filtered through a silica gel plug, and concentrated. The crude product was purified by reverse phase HPLC and lyophilized to give 50.0 mg (30%) of N-(1-(5-chloro-2-methylphenyl)-3-methyl-1H-pyrazol-5-yl)pyrazolo[1,5-a]pyrimidine-3-carboxamide. LCMS (ESI) m+H=367.0; $^1$H NMR (400 MHz, DMSO-d$_6$) δ: 10.03 (s, 1H), 9.32 (d, 1H), 8.68 (s, 1H), 8.36 (d, 1H), 7.60 (d, 1H), 7.58 (s, 1H), 7.55 (d, 1H), 7.27 (d of d, 1H), 6.53 (s, 1H), 2.24 (s, 3H), 2.05 (s, 3H).

Example 7

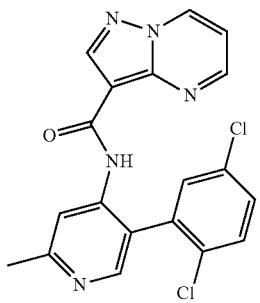 [SMILES: Cc1cc(NC(=O)c2cnn3cccnc23)c(-c2cc(Cl)ccc2Cl)cn1]

N-(5-(2,5-dichlorophenyl)-2-methylpyridin-4-yl)pyrazolo[1,5-a]pyrimidine-3-carboxamide

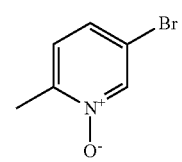

5-bromo-2-methylpyridine 1-oxide

A solution of 5-bromo-2-methylpyridine (2.0 g, 12 mmol, 1.0 eq) and m-chloroperoxybenzoic acid (70%, 2.89 g, 12.9 mmol, 1.1 eq) in 30 mL chloroform was stirred at room temperature for 4 hours. The reaction mixture was then partitioned between dichloromethane and 2 M aqueous sodium carbonate. The aqueous layer was extracted once more with dichloromethane, and the combined organic portions dried over magnesium sulfate and concentrated to give 5-bromo-2-methylpyridine 1-oxide. LCMS (ESI) m+H=189.0; $^1$H NMR (400 MHz, DMSO-d$_6$) δ: 8.57 (s, 1H), 7.50 (d, 1H), 7.45 (d, 1H), 2.30 (s, 3H).

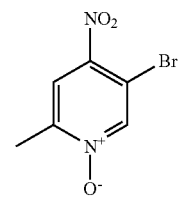

5-bromo-2-methyl-4-nitropyridine 1-oxide 5-bromo-2-methylpyridine 1-oxide (2.269 g, 12.07 mmol, 1 eq) was dissolved in sulfuric acid (4 mL, 80 mmol, 6 eq) and cooled at 0° C. Fuming nitric acid (3 mL, 60 mmol, 5 eq) was added dropwise. After addition of the nitric acid was complete, the reaction mixture was first warmed to room temperature and then heated to 90° C. After 2 hours the reaction was cooled in an ice bath and slowly adjusted to pH 10 with 2 M aqueous sodium carbonate. This solution was extracted twice with dichloromethane. The combined organic extracts were dried over magnesium sulfate and concentrated to yield 2.54 g (90%) of 5-bromo-2-methyl-4-nitropyridine 1-oxide. LMCS (ESI) m+H=233.0.

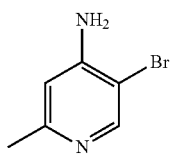

5-bromo-2-methylpyridin-4-amine

To a solution of 5-bromo-2-methyl-4-nitropyridine 1-oxide (2.54 g, 10.9 mmol, 1 eq) in 10 mL concentrated hydrochloric acid was added tin chloride dihydrate (9.96 g, 43.8 mmol, 4.01 eq). The reaction mixture was stirred at 90° C. for 24 hours, and then additional tin chloride dihydrate (3.15 g, 13.8 mmol, 1.27 eq) and 5 mL concentrated hydrochloric acid was added. The reaction mixture was kept at 90° C. for an additional 24 hours, and then cooled to room temperature and adjusted to neutral pH with 2 M aqueous sodium carbonate. The solution was extract three times with dichloromethane, and the combined organic extracts dried over magnesium sulfate and concentrated to give 5-bromo-2-methylpyridin-4-amine LCMS (ESI) m+H=187.2; $^1$H NMR (400 MHz, DMSO-$d_6$) δ: 8.07 (s, 1H), 6.51 (s, 1H), 6.13 (s, 2H), 2.22 (s, 3H).

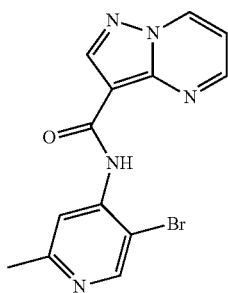 [SMILES: Cc1cc(NC(=O)c2cnn3cccnc23)c(Br)cn1]

N-(5-bromo-2-methylpyridin-4-yl)pyrazolo[1,5-a]pyrimidine-3-carboxamide

To a suspension of pyrazolo[1,5-a]pyrimidine-3-carboxylic acid (165.0 mg, 1.011 mmol, 1.2 eq) in 6 mL dichloromethane was added oxalyl chloride (0.90 mL of a 2.0 M solution in dichloromethane, 1.8 mmol, 2.1 eq) and three drops of N,N-dimethylformamide. After stirring at room temperature for 1 hour, the reaction mixture was concentrated and dried under vacuum to yield the acyl chloride. The solid residue was re-dissolved in 6 mL dichloromethane, and to this solution was added 5-bromo-2-methylpyridin-4-amine (157.6 mg, 0.8426 mmol, 1.0 eq) and triethylamine (0.50 mL, 3.6 mmol, 4.2 eq). The reaction was stirred at room temperature for one hour and then concentrated onto silica. The crude product was purified by flash chromatography on silica gel (0 to 100% ethyl acetate in dichloromethane) to yield 197.5 mg (71%) of N-(5-bromo-2-methylpyridin-4-yl)pyrazolo[1,5-a]pyrimidine-3-carboxamide. LCMS (ESI) m+H=332.2.

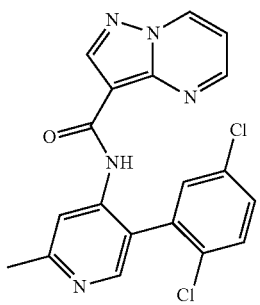 [SMILES: Cc1cc(NC(=O)c2cnn3cccnc23)c(-c2cc(Cl)ccc2Cl)cn1]

N-(5-(2,5-dichlorophenyl)-2-methylpyridin-4-yl)pyrazolo[1,5-a]pyrimidine-3-carboxamide N-(5-bromo-2-methylpyridin-4-yl)pyrazolo[1,5-a]pyrimidine-3-carboxamide (82.2 mg, 0.247 mmol, 1 eq), 2,5-dichlorophenylboronic acid (122.1 mg, 0.6399 mmol, 2.59 eq), and bis(triphenylphosphine)palladium(II) chloride (15.4 mg, 0.0219 mmol, 0.09 eq) were combined in a microwave vial. To these solids were added sodium carbonate (1.0 mL of a 1.0 M aqueous solution, 1.0 mmol, 4.0 eq) and 3.0 mL acetonitrile. The vial was sealed and subjected to microwave irradiation (120° C., 30 W) for 30 minutes. The reaction was partitioned between ethyl acetate and water, and the organic layer dried over magnesium sulfate and concentrated. The crude product was purified by reverse phase HPLC and lyophilized to give 45.3 mg (46%) of N-(5-(2,5-dichlorophenyl)-2-methylpyridin-4-yl)pyrazolo[1,5-a]pyrimidine-3-carboxamide. LCMS (ESI) m+H=398.0; $^1$H NMR (400 MHz, DMSO-$d_6$) δ: 9.75 (s, 1H), 9.32 (d, 1H), 8.71 (s, 1H), 8.48 (s, 1H), 8.26 (s, 1H), 8.21 (d, 1H), 7.78 (d, 1H), 7.75 (d, 1H), 7.69 (s, 1H), 7.26 (d of d, 1H), 2.55 (s, 3H).

Example 8

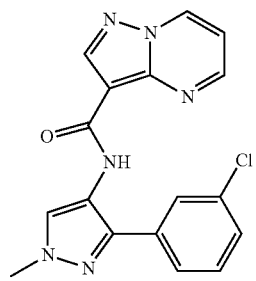 [SMILES: Cn1cc(NC(=O)c2cnn3cccnc23)c(-c2cccc(Cl)c2)n1]

N-(3-(3-chlorophenyl)-1-methyl-1H-pyrazol-4-yl)
pyrazolo[1,5-a]pyrimidine-3-carboxamide

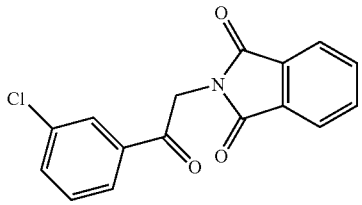 [SMILES: O=C(CN1C(=O)c2ccccc2C1=O)c1cccc(Cl)c1]

2-(2-(3-chlorophenyl)-2-oxoethyl)isoindoline-1,3-dione

A mixture of 2-bromo-3'-chloroacetophenone (0.927 g, 3.97 mmol, 1 eq) and potassium phthalimide (0.813 g, 4.39 mmol, 1.1 eq) in 15 mL N,N-dimethylformamide was stirred at 50° C. for one hour. The solvent was removed under vacuum. The resulting solids were triturated with ethyl acetate and filtered. The collected solids were dried under vacuum to give 24243-chlorophenyl)-2-oxoethyl)isoindoline-1,3-dione, which was carried forward without purification. ¹H NMR (400 MHz, DMSO-d₆) δ: 8.13 (s, 1H), 8.05 (d, 1H), 7.96 (m, 2H), 7.93 (m, 2H), 7.83 (d, 1H), 7.65 (t, 1H), 5.29 (s, 2H).

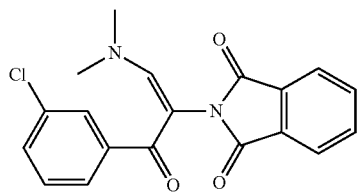 [SMILES: CN(C)/C=C(\C(=O)c1cccc(Cl)c1)N1C(=O)c2ccccc2C1=O]

2-(3-(3-chlorophenyl)-1-(dimethylamino)-3-oxo-prop-1-en-2-yl)isoindoline-1,3-dione A stirred mixture of 2-(2-(3-chlorophenyl)-2-oxoethyl)isoindoline-1,3-dione (782.2 mg, 2.610 mmol, 1 eq) and 1,1-dimethoxy-N,N-dimethylmethanamine (1.5 mL, 11 mmol, 4.3 eq) was heated at 100° C. for 18 hours. Excess 1,1-dimethoxy-N,N-dimethylmethanamine was removed under vacuum. The crude product was purified by flash chromatography on silica gel (50 to 100% ethyl acetate in heptanes) to yield 740 mg (80%) of 2-(3-(3-chlorophenyl)-1-(dimethylamino)-3-oxoprop-1-en-2-yl)isoindoline-1,3-dione LCMS (ESI) m+H=355.2; ¹H NMR (400 MHz, CDCl₃) δ: 7.90 (d of d, 2H), 7.77 (d of d, 2H), 7.57 (s, 1H), 7.44 (d, 1H), 7.37 (overlapping d and s, 2H), 7.31 (t, 1H), 3.00 (s, 6H).

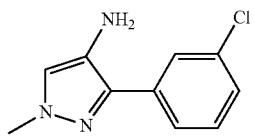

3-(3-chlorophenyl)-1-methyl-1H-pyrazol-4-amine

To a solution of 2-(3-(3-chlorophenyl)-1-(dimethylamino)-3-oxoprop-1-en-2-yl)isoindoline-1,3-dione (2.30 g, 6.48 mmol, 1 eq) in 50 mL ethanol was added N-methylhydrazine (1.4 mL, 26 mmol, 4.0 eq). The reaction mixture was stirred at 80° C. for 2 hours and then concentrated onto silica gel. The crude mixture of regioisomers was separated and purified by flash chromatography on silica gel (0 to 80% ethyl acetate in dichloromethane) to yield: 715 mg (53%) of 3-(3-chlorophenyl)-1-methyl-1H-pyrazol-4-amine LCMS (ESI) m+H=208.2; ¹H NMR (400 MHz, CDCl₃) δ: 7.78 (s, 1H), 7.63 (d, 1H), 7.33 (t, 1H), 7.25 (overlapping with CDCl₃, 1H), 7.04 (s, 1H), 3.84 (s, 3H), and 274.6 mg (20%) of 5-(3-chlorophenyl)-1-methyl-1H-pyrazol-4-amine. LCMS (ESI) m+H=208.2; ¹H NMR (400 MHz, CDCl₃) δ: 7.43 (t, 1H), 7.38 (overlapping d and s, 2H), 7.27 (d, 1H), 7.23 (s, 1H), 3.76 (s, 3H).

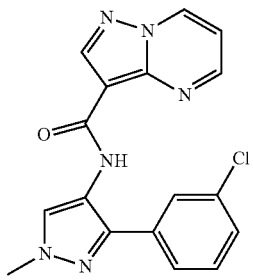 [SMILES: Cn1cc(NC(=O)c2cnn3cccnc23)c(-c2cccc(Cl)c2)n1]

N-(3-(3-chlorophenyl)-1-methyl-1H-pyrazol-4-yl)
pyrazolo[1,5-a]pyrimidine-3-carboxamide A mixture of 3-(2,5-dimethylphenyl)-1H-pyrazol-4-amine (400.0 mg, 1.926 mmol, 1 eq), pyrazolo[1,5-a]pyrimidine-3-carboxylic acid (342.9 mg, 2.102 mmol, 1.09 eq), 7-azabenzotriazol-1-yloxy-tris-(pyrrolidino)phosphonium hexafluorophosphate (1.205 g, 2.324 mmol, 1.21 eq), N,N-diisopropylethylamine (0.80 mL, 4.6 mmol, 2.4 eq), and 4-dimethylaminopyridine (43.4 mg, 0.355 mmol, 0.18 eq) in 15.0 mL N,N-dimethylformamide was stirred at 50° C. for 15 hours. The reaction mixture was partitioned between dichloromethane and water, and the aqueous layer extracted once more with dichloromethane. The combined organic portions were dried over magnesium sulfate and concentrated onto silica gel. The crude product was separated by flash chromatography on silica gel (0 to 70% ethyl acetate (containing 2% methanol) in dichloromethane). The resulting solid material was triturated with ethyl acetate. After sonication the solids were collected by filtration and dried under vacuum to yield 0.502 g (74%) of N-(3-(3-chlorophenyl)-1-methyl-1H-pyrazol-4-yl)pyrazolo[1,5-a]pyrimidine-3-carboxamide. LCMS (ESI) m+H=353.0; ¹H NMR (400 MHz, CDCl₃) δ: 10.00 (s, 1H), 9.38 (d, 1H), 8.85 (d, 1H), 8.70 (s, 1H), 8.33 (s, 1H), 7.84 (s, 1H), 7.76 (d, 1H), 7.57 (t, 1H), 7.49 (d, 1H), 7.34 (d of d, 1H), 3.93 (s, 3H).

Example 9

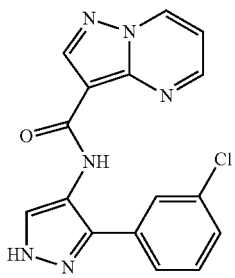 [SMILES: O=C(Nc1c[nH]nc1-c1cccc(Cl)c1)c1cnn2cccnc12]

N-(3-(3-chlorophenyl)-1H-pyrazol-4-yl)pyrazolo[1,5-a]pyrimidine-3-carboxamide

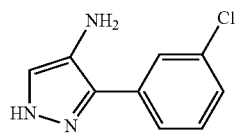

3-(3-chlorophenyl)-1H-pyrazol-4-amine

A mixture of 2-(3-(3-chlorophenyl)-1-(dimethylamino)-3-oxoprop-1-en-2-yl)isoindoline-1,3-dione (255 mg, 0.719 mmol, 1 eq) and hydrazine (0.15 mL, 4.8 mmol, 6.6 eq) in 10 mL ethanol was stirred under reflux for 2 hours. The ethanol and excess hydrazine were removed under vacuum. The crude product was purified by flash chromatography on silica gel (50 to 100% ethyl acetate in heptanes) to yield 111.4 mg (80%) of 3-(3-chlorophenyl)-1H-pyrazol-4-amine LCMS (ESI) m+H=194.0; $^1$H NMR (400 MHz, CD$_3$OD) δ: 7.75 (broad, 1H), 7.65 (broad, 1H), 7.41 (t, 1H), 7.32 and 7.30 (overlapping s and s, 2H).

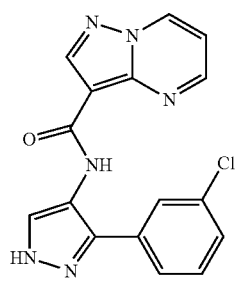 [SMILES: O=C(Nc1c[nH]nc1-c1cccc(Cl)c1)c1cnn2cccnc12]

N-(3-(3-chlorophenyl)-1H-pyrazol-4-yl)pyrazolo[1,5-a]pyrimidine-3-carboxamide

A mixture of 3-(3-chlorophenyl)-1H-pyrazol-4-amine (95.3 mg, 0.492 mmol, 1 eq), pyrazolo[1,5-a]pyrimidine-3-carboxylic acid (90.6 mg, 0.555 mmol, 1.13 eq), N,N,N',N'-tetramethyl-O-(7-azabenzotriazol-1-yl)uranium hexafluorophosphate (247.3 mg, 0.6504 mmol, 1.32 eq), N,N-diisopropylethylamine (0.20 mL, 1.1 mmol, 2.3 eq), and 4-dimethylaminopyridine (24.1 mg, 0.197 mmol, 0.40 eq) in 5.0 mL N,N-dimethylformamide was stirred at 50° C. for 3 hours. The reaction mixture was partitioned between ethyl acetate and water, and the organic portion washed with brine, dried over magnesium sulfate and concentrated. The crude product was purified by reverse phase HPLC and lyophilized to give 33.8 mg (20%) of N-(3-(3-chlorophenyl)-1H-pyrazol-4-yl)pyrazolo[1,5-a]pyrimidine-3-carboxamide. LCMS (ESI) m+H=339.0; $^1$H NMR (400 MHz, DMSO-d$_6$) δ: 13.05 (s, 1H), 9.99 (s, 1H), 9.38 (d, 1H), 8.84 (d, 1H), 8.70 (s, 1H), 8.31 (s, 1H), 7.86 (s, 1H), 7.78 (d, 1H), 7.58 (t, 1H), 7.50 (d, 1H), 7.34 (d of d, 1H).

Example 10

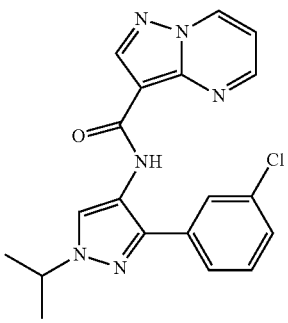 [SMILES: CC(C)n1cc(NC(=O)c2cnn3cccnc23)c(-c2cccc(Cl)c2)n1]

N-(3-(3-chlorophenyl)-1-isopropyl-1H-pyrazol-4-yl)pyrazolo[1,5-a]pyrimidine-3-carboxamide N-(3-(3-chlorophenyl)-1H-pyrazol-4-yl)pyrazolo[1,5-a]pyrimidine-3-carboxamide (68.9 mg, 0.203 mmol, 1 eq) was dissolved in 4 mL N,N-dimethylformamide. To this solution was added cesium carbonate (148 mg, 0.454 mmol, 2.23 eq) and isopropyl iodide (23.0 μL, 0.230 mmol, 1.13 eq). The reaction mixture was stirred at 50° C. for 2 hours. The reaction mixture was partitioned between ethyl acetate and water, and the organic portion washed with brine, dried over magnesium sulfate and concentrated. The crude product was purified by reverse phase HPLC and lyophilized to give 47.2 mg (61%) of N-(3-(3-chlorophenyl)-1-isopropyl-1H-pyrazol-4-yl)pyrazolo[1,5-a]pyrimidine-3-carboxamide. LCMS (ESI) m+H=381.1; $^1$H NMR (400 MHz, DMSO-d$_6$) δ: 9.99 (s, 1H), 9.37 (d, 1H), 8.85 (d, 1H), 8.70 (s, 1H), 8.36 (s, 1H), 7.85 (s, 1H), 7.77 (d, 1H), 7.57 (t, 1H), 7.48 (d, 1H), 7.34 (d of d, 1H), 4.59 (d of q, 1H), 1.48 (d, 6H).

Example 11

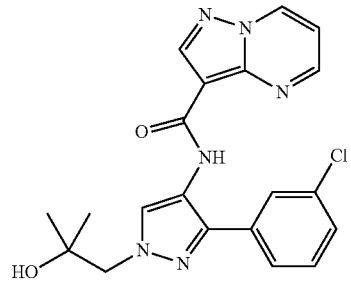 [SMILES: CC(C)(O)Cn1cc(NC(=O)c2cnn3cccnc23)c(-c2cccc(Cl)c2)n1]

N-(3-(3-chlorophenyl)-1-(2-hydroxy-2-methylpropyl)-1H-pyrazol-4-yl)pyrazolo[1,5-a]pyrimidine-3-carboxamide N-(3-(3-chlorophenyl)-1H-pyrazol-4-yl)pyrazolo[1,5-a]pyrimidine-carboxamide (58.9 mg, 0.174 mmol, 1 eq) was dissolved in 5 mL N,N-dimethylformamide. To this solution was added isobutylene oxide (0.5 mL, 6 mmol, 30 eq) and cesium carbonate (56.4 mg, 0.173 mmol, 1.0 eq). The reaction mixture was stirred at 50° C. for 7.5 hours. The reaction mixture was partitioned between ethyl acetate and water, and the organic portion washed with brine, dried over magnesium sulfate and concentrated. The crude product was purified by reverse phase HPLC and lyophilized to give 33.1 mg (46%) of N-(3-(3-chlorophenyl)-1-(2-hydroxy-2-methylpropyl)-1H-pyrazol-4-yl)pyrazolo[1,5-a]pyrimidine-3-carboxamide. LCMS (ESI) m+H=411.1; $^1$H NMR (400 MHz, DMSO-d$_6$) δ: 10.02 (s, 1H), 9.36 (d, 1H), 8.83 (d, 1H), 8.69 (s, 1H), 8.35 (s, 1H), 7.84 (s, 1H), 7.76 (d, 1H), 7.58 (t, 1H), 7.49 (d, 1H), 7.33 (d of d, 1H), 4.73 (s, 1H), 4.09 (s, 2H), 1.13 (s, 6H).

Example 12

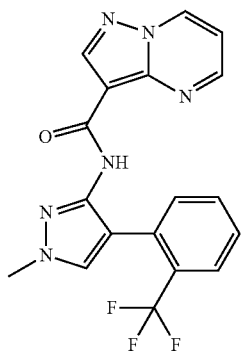 [SMILES: Cn1cc(-c2ccccc2C(F)(F)F)c(NC(=O)c2cnn3cccnc23)n1]

N-(1-methyl-4-(2-(trifluoromethyl)phenyl)-1H-pyrazol-3-yl)pyrazolo[1,5-a]pyrimidine-3-carboxamide

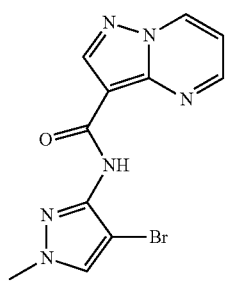 [SMILES: Cn1cc(Br)c(NC(=O)c2cnn3cccnc23)n1]

N-(4-bromo-1-methyl-1H-pyrazol-3-yl)pyrazolo[1,5-a]pyrimidine-3-carboxamide

A solution of pyrazolo[1,5-a]pyrimidine-3-carboxylic acid (165.5 mg, 1.014 mmol, 1.01 eq), 4-bromo-1-methyl-1H-pyrazol-3-amine (177.4 mg, 1.008 mmol, 1.0 eq), N,N,N',N'-tetramethyl-O-(7-azabenzotriazol-1-yl)uranium hexafluorophosphate (497 mg, 1.31 mmol, 1.30 eq), N,N-diisopropylethylamine (0.25 mL, 1.4 mmol, 1.4 eq), and 4-dimethylaminopyridine (33.8 mg, 0.277 mmol, 0.27 eq) in 5 mL N,N-dimethylformamide was heated at 50° C. for 4 days. The reaction mixture was partitioned between ethyl acetate and water, and the organic portion washed with brine, dried over magnesium sulfate and concentrated. The crude product was purified by flash chromatography on silica gel (20 to 80% ethyl acetate in dichloromethane (containing 5% methanol)) to yield 203.6 mg (63%) of N-(4-bromo-1-methyl-1H-pyrazol-3-yl)pyrazolo[1,5-a]pyrimidine-3-carboxamide. LCMS (ESI) m+H=321.1; $^1$H NMR (400 MHz, CD$_3$OD) δ: 9.16 (d, 1H), 8.84 (d, 1H), 8.68 (s, 1H), 7.76 (s, 1H), 7.28 (d of d, 1H), 3.88 (s, 3H).

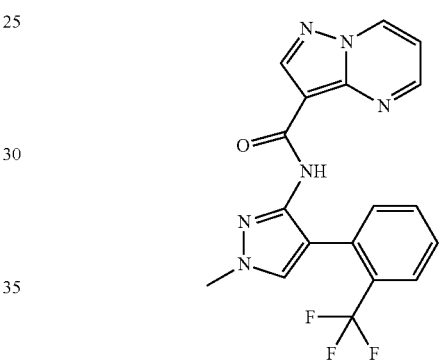

N-(1-methyl-4-(2-(trifluoromethyl)phenyl)-1H-pyrazol-3-yl)pyrazolo[1,5-a]pyrimidine-3-carboxamide To a stir-bar equipped microwave vial was added: N-(4-bromo-1-methyl-1H-pyrazol-3-yl)pyrazolo[1,5-a]pyrimidine-3-carboxamide (101 mg, 0.313 mmol, 1 eq), 2-trifluoromethylphenyl boronic acid (126.6 mg, 0.6666 mmol, 2.13 eq), bis(triphenylphosphine)palladium(II) chloride (26.8 mg, 0.0382 mmol, 0.12 eq), sodium carbonate (1.0 mL of a 2.0 M aqueous solution, 2 mmol, 6 eq), and 3 mL acetonitrile. The reaction mixture was subjected to microwave irradiation at 130° C. for 30 minutes. The reaction mixture was partitioned between ethyl acetate and water, and the organic portion washed with brine, dried over magnesium sulfate and concentrated. The crude product was purified by reverse phase HPLC and lyophilized to give 4.7 mg (4%) of N-(1-methyl-4-(2-(trifluoromethyl)phenyl)-1H-pyrazol-3-yl)pyrazolo[1,5-a]pyrimidine-3-carboxamide. LCMS (ESI) m+H=387.1; $^1$H NMR (400 MHz, DMSO-d$_6$) δ: 9.58 (s, 1H), 9.32 (d, 1H), 8.74 (d, 1H), 8.57 (s, 1H), 7.78 (s, 1H), 7.74 (d, 1H), 7.60 (t, 1H), 7.49 (m, 2H), 7.28 (d of d, 1H), 3.87 (s, 3H).

Example 13

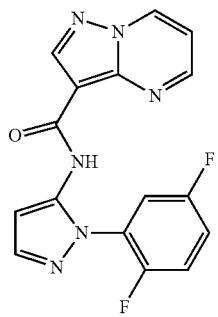 [SMILES: O=C(Nc1ccnn1-c1cc(F)ccc1F)c1cnn2cccnc12]

N-(1-(2,5-difluorophenyl)-1H-pyrazol-5-yl)pyrazolo[1,5-a]pyrimidine-3-carboxamide

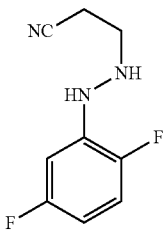

3-(2-(2,5-difluorophenyl)hydrazinyl)propanenitrile

A solution of acrylonitrile (10 mL), ethanol (20 mL) and 2,5-difluorophenylhydrazine (790 mg) was heated to reflux for 2 days. The reaction was concentrated under vacuum and the product purified by flash chromatography on silica gel with methylene chloride to give 790 mg (73%) 3-(2-(2,5-difluorophenyl)hydrazinyl)propanenitrile. LCMS (ESI) m+H=198.2; $^1$H NMR (400 MHz, CDCl$_3$) δ 6.99 (ddd, 1H), 6.89 (ddd, 1H), 6.38 (tt, 1H), 5.45 (s, 1H), 3.91 (s, 1H), 3.19 (td, 2H), 2.61 (t, 2H).

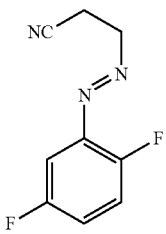 [SMILES: N#CCC/N=N/c1cc(F)ccc1F]

(E)-3-((2,5-difluorophenyl)diazenyl)propanenitrile

To a solution of 3-(2-(2,5-difluorophenyl)hydrazinyl)propanenitrile (790 mg) in 15 mL of 2N sulfuric acid was added 2.0 g of iron(III) sulfate hydrate. The reaction mixture was stirred at ambient temperature for 30 min as the iron sulfate slowly dissolved and a yellow oil precipitated. The reaction mixture was extracted with ether, and the extracts were washed with water, brine, dried over sodium sulfate, filtered through a plug of silica gel and concentrated to give 710 mg (91%) of (E)-3-((2,5-difluorophenyl)diazenyl)propanenitrile. LCMS (ESI) m+H=196.2. $^1$H NMR (400 MHz, CDCl$_3$) δ 7.34-7.08 (m, 3H), 4.54-4.31 (m, 2H), 2.99 (t, 2H).

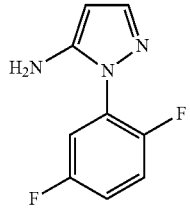 [SMILES: Nc1ccnn1-c1cc(F)ccc1F]

1-(2,5-difluorophenyl)-1H-pyrazol-5-amine

A mixture of (E)-3-((2,5-difluorophenyl)diazenyl)propanenitrile (710 mg) and 20 mL of 1N NaOH was heated to reflux with stirring for 30 min. The reaction mixture was cooled to ambient temperature and extracted with ether. The ether phase was washed with water, brine, dried over sodium sulfate and filtered through a plug of silica gel. Concentration under vacuum gave 630 mg (88%) of 1-(2,5-difluorophenyl)-1H-pyrazol-5-amine. LCMS (ESI) m+H=196.0; $^1$H NMR (400 MHz, CDCl$_3$) δ 7.54-7.43 (m, 1H), 7.35-7.00 (m, 3H), 5.63 (d, 1H), 3.96-3.71 (m, 2H).

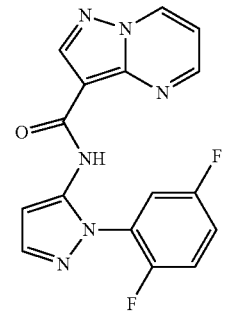 [SMILES: O=C(Nc1ccnn1-c1cc(F)ccc1F)c1cnn2cccnc12]

N-(1-(2,5-difluorophenyl)-1H-pyrazol-5-yl)pyrazolo[1,5-a]pyrimidine-3-carboxamide Pyrazolo[1,5-a]pyrimidine-3-carboxylic acid (0.020 g, 0.12 mmol), 3 mL of phosphoryl chloride and 32 μL of N,N-diisopropylethylamine were heated to 120° C. for 2 hr and evaporated to dryness. The residue was taken up in dichloromethane and added to a mixture of 1-(2,5-difluorophenyl)-1H-pyrazol-5-amine (18 mg), N,N-diisoproplyethylamine (32 μL) and dichloromethane (1 mL) and stirred overnight. The reaction mixture was concentrated and the product purified by flash chromatography on silica gel (95/5 dichloromethane/7M NH$_3$ in MeOH) to give 8.0 mg (20%) of N-(1-(2,5-difluorophenyl)-1H-pyrazol-5-yl)pyrazolo[1,5-a]pyrimidine-3-carboxamide. LCMS (ESI) m+H=341.2; $^1$H NMR (500 MHz, CDCl$_3$) δ 10.14 (s, 1H), 8.80 (dd, 1H), 8.72 (d, 1H), 8.38 (dd, 1H), 7.72 (t, 1H), 7.38 (ddd, 1H), 7.33-7.27 (m, 1H), 7.22 (ddd, 1H), 7.03-6.99 (m, 1H), 6.88 (d, 1H).

Example 14 and Example 15

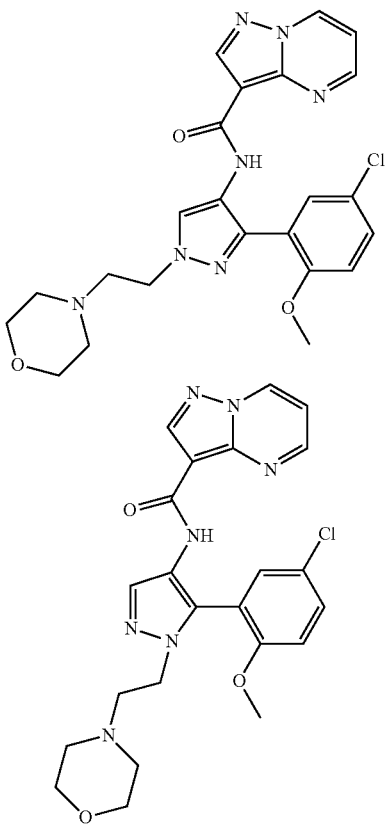

N-(3-(5-chloro-2-methoxyphenyl)-1-(2-morpholinoethyl)-1H-pyrazol-4-yl)pyrazolo[1,5-a]pyrimidine-3-carboxamide N-(5-(5-chloro-2-methoxyphenyl)-1-(2-morpholinoethyl)-1H-pyrazol-4-yl)pyrazolo[1,5-a]pyrimidine-3-carboxamide

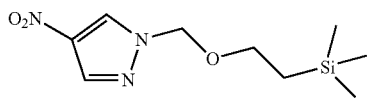 [SMILES: C[Si](C)(C)CCOCn1cc([N+](=O)[O-])cn1]

4-nitro-1-((2-(trimethylsilyl)ethoxy)methyl)-1H-pyrazole

In an oven-dried flask equipped with stir bar, 4-nitro-1H-pyrazole (6.598 g, 58.35 mmol) was dissolved in 50 mL THF. Sodium hydride (4.83 g of a 60% dispersion with mineral oil, 121 mmol) was added while cooling in an ice bath, and the reaction then stirred at room temperature for 10 minutes. [β-(trimethylsilyl)ethoxy]methyl chloride (12.0 mL, 67.8 mmol) was then added, and the reaction stirred at room temperature for 1.5 hours. The reaction was quenched with 50 mL water, and extracted with ethyl acetate. The organic extract was dried over magnesium sulfate and concentrated. The resulting crude material was purified by flash chromatography on silica gel (0 to 30% ethyl acetate in heptanes) to obtain 14.1 g (99%) of 4-nitro-1-((2-(trimethylsilyl)ethoxy)methyl)-1H-pyrazole. LCMS (ESI) m+H=244.2; $^1$H NMR (400 MHz, CDCl$_3$) δ: 8.28 (s, 1H), 8.08 (s, 1H), 5.43 (s, 2H), 3.61 (t, 2H), 0.92 (t, 2H).

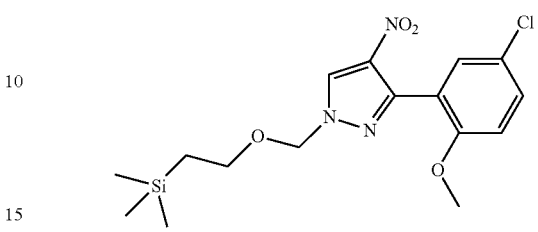

3-(5-chloro-2-methoxyphenyl)-4-nitro-1-((2-(trimethylsilyl)ethoxy)methyl)-1H-pyrazole To a solution of 4-nitro-1-((2-(trimethylsilyl)ethoxy)methyl)-1H-pyrazole (4.26 g, 17.5 mmol) in 40 mL N,N-dimethylacetamide was added 2-bromo-4-chloroanisole (3.35 mL, 24.6 mmol), palladium (II) acetate (197.2 mg, 0.878 mmol), di(1-adamantyl)-n-butylphosphine (469.5 mg, 1.309 mmol), potassium carbonate (7.27 g, 52.6 mmol), and trimethylacetic acid (0.452 g, 4.43 mmol). While stirring at room temperature, nitrogen gas was bubbled through the reaction mixture for 10 minutes, and the reaction then heated at 120° C. for 6 hours. The reaction was then cooled to room temperature, diluted into ethyl acetate, and washed with water and brine, dried over magnesium sulfate and concentrated. The crude material was purified by flash chromatography on silica gel (0 to 25% ethyl acetate in heptanes) to obtain 6.719 g (89%) of 3-(5-chloro-2-methoxyphenyl)-4-nitro-1-((2-(trimethylsilyl)ethoxy)methyl)-1H-pyrazole. LCMS (ESI) m+H=384.2; $^1$H NMR (400 MHz, CDCl$_3$) δ: 8.22 (s, 1H), 7.46 (d of d, 1H), 7.36 (d, 1H), 6.95 (d, 1H), 5.23 (m, 2H), 3.56 (m, 2H), 0.87 (m, 2H).

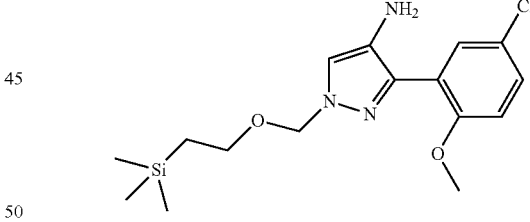

3-(5-chloro-2-methoxyphenyl)-1-((2-(trimethylsilyl)ethoxy)methyl)-1H-pyrazol-4-amine To a solution of 3-(5-chloro-2-methoxyphenyl)-4-nitro-1-((2-(trimethylsilyl)ethoxy)methyl)-1H-pyrazole (5.97 g, 15.6 mmol) in 25 mL ethanol was added 50 mL water, ammonium chloride (3.37 g, 62.9 mmol), and iron powder (4.367 g, 78.2 mmol). The reaction mixture was stirred at 75° C. for 1.5 hours. After cooling to room temperature, the reaction was diluted with dichloromethane and filtered through a celite pad, rinsing with more dichloromethane. The filtrate was added to 150 mL saturated aqueous sodium bicarbonate and extracted twice with dichloromethane. The combined organic extracts were dried over magnesium sulfate and concentrated to yield 5.50 g (100%) of 3-(5-chloro-2-methoxyphenyl)-1-

((2-(trimethylsilyl)ethoxy)methyl)-1H-pyrazol-4-amine, which was carried forward without purification. LCMS (ESI) m+H=354.3; ¹H NMR (400 MHz, CDCl₃) δ: 7.44 (d, 1H), 7.34 (d of d, 1H), 7.28 (s, 1H), 6.92 (d, 1H), 5.24 (s, 2H), 3.52 (t, 2H), 0.85 (t, 2H), −0.04 (s, 9H).

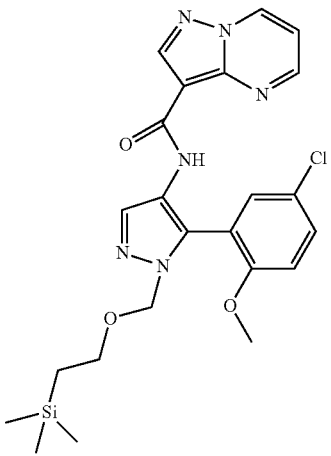 [SMILES: COc1ccc(Cl)cc1-c1c(NC(=O)c2cnn3cccnc23)cnn1COCC[Si](C)(C)C]

N-(5-(5-chloro-2-methoxyphenyl)-1-((2-(trimethylsilyl)ethoxy)methyl)-1H-pyrazol-4-yl)pyrazolo[1,5-a]pyrimidine-3-carboxamide A mixture of 3-(5-chloro-2-methoxyphenyl)-1-((2-(trimethylsilyl)ethoxy)methyl)-1H-pyrazol-4-amine (179.6 mg, 0.5075 mmol), pyrazolo[1,5-a]pyrimidine-3-carboxylic acid (91 mg, 0.560 mmol), 7-azabenzotriazol-1-yloxy-tris-(pyrrolidino)phosphonium hexafluorophosphate (326 mg, 0.630 mmol), N,N-diisopropylethylamine (0.25 mL, 1.4 mmol), and 4-dimethylaminopyridine (11.5 mg, 0.094 mmol) in 5.0 mL N,N-dimethylformamide was stirred at 40° C. for 1.5 hours. The reaction mixture was partitioned between ethyl acetate and water, and the organic portion washed with brine, dried over magnesium sulfate, filtered through a pad of silica gel, and concentrated to give 0.212 g (84%) of N-(5-(5-chloro-2-methoxyphenyl)-1-((2-(trimethylsilyl)ethoxy)methyl)-1H-pyrazol-4-yl)pyrazolo[1,5-a]pyrimidine-3-carboxamide, which was carried forward without purification. LCMS (ESI) m+H=499.2; ¹H NMR (400 MHz, CDCl₃) δ: 9.56 (s, 1H), 8.76 (d, J=7.0, 1H), 8.72 (s, 1H), 8.50 (d, J=4.1, 1H), 8.39 (s, 1H), 7.54 (d, J=2.6, 1H), 7.44 (dd, J=8.8, 2.6, 1H), 7.04-6.92 (m, 2H), 5.35 (d, 2H), 3.82 (s, 3H), 3.57 (m, 2H), 0.86 (m, 2H), −0.04 (s, 9H).

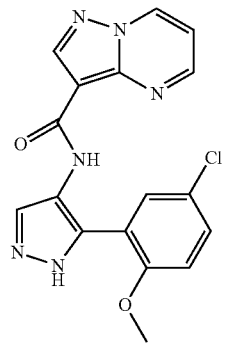 [SMILES: COc1ccc(Cl)cc1-c1[nH]ncc1NC(=O)c1cnn2cccnc12]

N-(5-(5-chloro-2-methoxyphenyl)-1H-pyrazol-4-yl)pyrazolo[1,5-a]pyrimidine-3-carboxamide To a solution of N-(5-(5-chloro-2-methoxyphenyl)-1-((2-(trimethylsilyl)ethoxy)methyl)-1H-pyrazol-4-yl)pyrazolo[1,5-a]pyrimidine-3-carboxamide (2.75 g, 5.51 mmol) in 105 mL ethanol was added HCl (8.0 mL of a 5 M solution in water, 40 mmol). The reaction mixture was then stirred at 70° C. for 2 hours. After cooling to room temperature, the product was filtered as a light yellow solid, rinsing with methanol and diethyl ether. The filtrate was reduced in volume, and more solid product filtered. The combined collected solids were dried under vacuum to yield 1.81 g (89%) of N-(5-(5-chloro-2-methoxyphenyl)-1H-pyrazol-4-yl)pyrazolo[1,5-a]pyrimidine-3-carboxamide. LCMS (ESI) m+H=369.2; ¹H NMR (400 MHz, DMSO-d₆) δ: 9.66 (s, 1H), 9.33 (dd, J=7.0, 1.6, 1H), 8.78 (dd, J=4.2, 1.6, 1H), 8.65 (s, 1H), 8.20 (s, 1H), 7.50 (dd, J=8.8, 2.7, 1H), 7.44 (d, J=2.7, 1H), 7.29 (dd, J=7.8, 4.8, 2H), 3.86 (s, 3H).

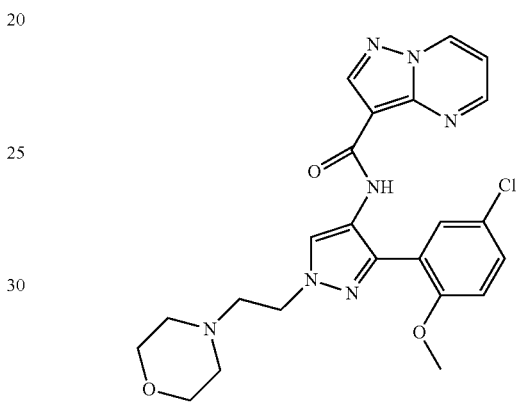

N-(3-(5-chloro-2-methoxyphenyl)-1-(2-morpholinoethyl)-1H-pyrazol-4-yl)pyrazolo[1,5-a]pyrimidine-3-carboxamide

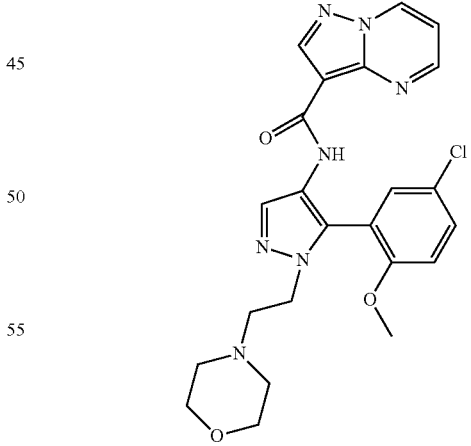

N-(5-(5-chloro-2-methoxyphenyl)-1-(2-morpholinoethyl)-1H-pyrazol-4-yl)pyrazolo[1,5-a]pyrimidine-3-carboxamide To a solution of N-(5-(5-chloro-2-methoxyphenyl)-1H-pyrazol-4-yl)pyrazolo[1,5-a]pyrimidine-3-carboxamide (39.1 mg, 0.106 mmol) in 3 mL DMF was added cesium carbonate (109.7 mg, 0.3367 mmol) and 4-(2-chloroethyl)morpholine HCl. The reaction mixture was stirred at 50° C. for 5 hours. The reaction mixture was partitioned between ethyl acetate and water, and the organic portion washed with brine, dried over magnesium sulfate, and concentrated. The mixture of regioisomer products was separated and purified by reverse phase HPLC and lyophilized to give 19.4 mg (38%) N-(3-(5-chloro-2-methoxyphenyl)-1-(2-morpholinoethyl)-1H-pyrazol-4-yl)pyrazolo[1,5-a]pyrimidine-3-carboxamide; LCMS (ESI) m+H=482.1; $^1$H NMR (400 MHz, DMSO-$d_6$) δ: 9.50 (s, 1H), 9.31 (dd, 1H), 8.66 (d, 1H), 8.63 (s, 1H), 8.03 (s, 1H), 7.58 (dd, 1H), 7.54 (d, 1H), 7.32 (d, 1H), 7.27 (dd, 1H), 4.05 (m, 2H), 3.85 (s, 3H), 3.44 (m, 2H), 2.71 (m, 2H), 2.60 (m, 2H), 2.23 (m, 4H); and 9.3 mg (18%) of N-(5-(5-chloro-2-methoxyphenyl)-1-(2-morpholinoethyl)-1H-pyrazol-4-yl)pyrazolo[1,5-a]pyrimidine-3-carboxamide; LCMS (ESI) m+H=482.1; $^1$H NMR (400 MHz, DMSO-$d_6$) δ: 9.67 (s, 1H), 9.31 (dd, 1H), 8.76 (d, 1H), 8.65 (s, 1H), 8.34 (s, 1H), 7.48 (dd, 1H), 7.39 (d, 1H), 7.30 (d, 1H), 7.38 (t, 1H), 4.29 (t, 2H), 3.84 (s, 3H), 3.58 (t, 2H), 2.77 (t, 2H), 2.46 (m, 4H).

Example 16

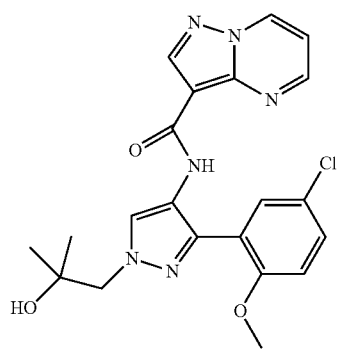 [SMILES: COc1ccc(Cl)cc1-c1nn(CC(C)(C)O)cc1NC(=O)c1cnn2cccnc12]

N-(3-(5-chloro-2-methoxyphenyl)-1-(2-hydroxy-2-methylpropyl)-1H-pyrazol-4-yl)pyrazolo[1,5-a]pyrimidine-3-carboxamide To a solution of N-(5-(5-chloro-2-methoxyphenyl)-1H-pyrazol-4-yl)pyrazolo[1,5-a]pyrimidine-3-carboxamide (102.7 mg, 0.279 mmol) in 3 mL, DMF was added isobutylene oxide (0.20 mL, 2.2 mmol) and cesium carbonate (180.0 mg, 0.5524 mmol). The reaction was stirred at 40° C. for 15 hours. The reaction mixture was partitioned between ethyl acetate and water, and the organic portion washed with brine, dried over magnesium sulfate, and concentrated. The crude product was purified by reverse phase HPLC and lyophilized to give 49.3 mg (40%) of N-(3-(5-chloro-2-methoxyphenyl)-1-(2-hydroxy-2-methylpropyl)-1H-pyrazol-4-yl)pyrazolo[1,5-a]pyrimidine-3-carboxamide. LCMS (ESI) m+H=441.1; $^1$H NMR (400 MHz, DMSO-$d_6$) δ: 9.68 (s, 1H), 9.32 (dd, 1H), 8.76 (d, 1H), 8.64 (s, 1H), 8.30 (s, 1H), 7.48 (dd, 1H), 7.39 (d, 1H), 7.31 (s, 1H), 7.28 (t, 1H), 4.72 (s, 1H), 4.07 (s, 2H), 3.84 (s, 3H), 1.12 (s, 6H).

Example 17

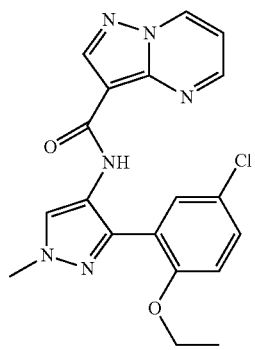 [SMILES: CCOc1ccc(Cl)cc1-c1nn(C)cc1NC(=O)c1cnn2cccnc12]

N-(3-(5-chloro-2-ethoxyphenyl)-1-methyl-1H-pyrazol-4-yl)pyrazolo[1,5-a]pyrimidine-3-carboxamide

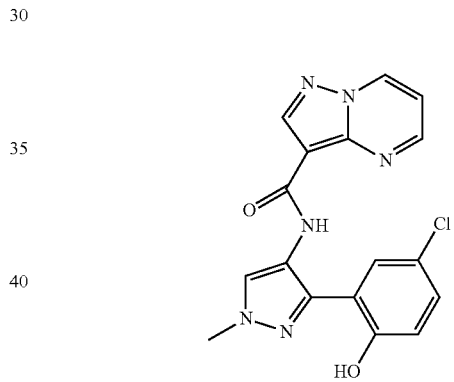

N-(3-(5-chloro-2-hydroxyphenyl)-1-methyl-1H-pyrazol-4-yl)pyrazolo[1,5-a]pyrimidine-3-carboxamide To a solution of N-(3-(5-chloro-2-methoxyphenyl)-1-methyl-1H-pyrazol-4-yl)pyrazolo[1,5-a]pyrimidine-3-carboxamide (synthesized following the procedures described for Example 14) (193.9 mg, 0.5065 mmol) in 8.0 mL dichloromethane was added boron tribromide (1.50 mL of a 1.0M solution in dichloromethane, 1.5 mmol). The reaction was stirred at room temperature for 1 hour. The reaction was then quenched with 1 mL methanol, diluted with ethyl acetate, and washed with saturated aqueous sodium bicarbonate and brine, dried over magnesium sulfate, and concentrated to give 191.5 mg (100%) of N-(3-(5-chloro-2-hydroxyphenyl)-1-methyl-1H-pyrazol-4-yl)pyrazolo[1,5-a]pyrimidine-3-carboxamide, which was carried forward without purification. LCMS (ESI) m+H=369.1.

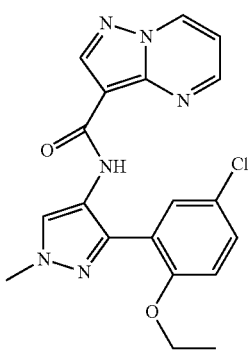 [SMILES: CCOc1ccc(Cl)cc1-c1nn(C)cc1NC(=O)c1cnn2cccnc12]

N-(3-(5-chloro-2-ethoxyphenyl)-1-methyl-1H-pyrazol-4-yl)pyrazolo[1,5-a]pyrimidine-3-carboxamide To a solution of N-(3-(5-chloro-2-hydroxyphenyl)-1-methyl-1H-pyrazol-4-yl)pyrazolo[1,5-a]pyrimidine-3-carboxamide (61.1 mg, 0.166 mmol) in 3.0 mL acetone was added iodoethane (26.0 µL, 0.325 mmol) and potassium carbonate (70.6 mg, 0.511 mmol) The reaction was stirred at 45° C. for 3 hours. The reaction mixture was partitioned between ethyl acetate and water, and the organic portion washed with brine, dried over magnesium sulfate, and concentrated. The crude product was purified by reverse phase HPLC and lyophilized to give 34.8 mg (54%) N-(3-(5-chloro-2-ethoxyphenyl)-1-methyl-1H-pyrazol-4-yl)pyrazolo[1,5-a]pyrimidine-3-carboxamide. LCMS (ESI) m+H=397.1; $^1$H NMR (400 MHz, DMSO-$d_6$) δ: 9.68 (s, 1H), 9.33 (dd, J=7.0, 1.6, 1H), 8.73 (dd, J=4.2, 1.6, 1H), 8.66 (s, 1H), 8.28 (s, 1H), 7.46 (dd, J=8.8, 2.7, 1H), 7.38 (d, J=2.7, 1H), 7.32-7.23 (m, 2H), 4.12 (q, J=6.9, 2H), 3.91 (s, 3H), 1.04 (t, J=6.9, 3H).

Example 18

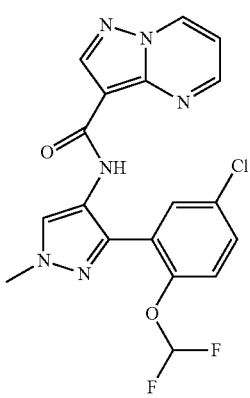 [SMILES: Cn1cc(NC(=O)c2cnn3cccnc23)c(-c2cc(Cl)ccc2OC(F)F)n1]

N-(3-(5-chloro-2-(difluoromethoxy)phenyl)-1-methyl-1H-pyrazol-4-yl)pyrazolo[1,5-a]pyrimidine-3-carboxamide

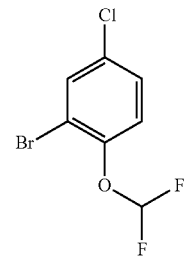

2-bromo-4-chloro-1-(difluoromethoxy)benzene

To a solution of 2-bromo-4-chlorophenol (4.98 g, 24.0 mmol) in 25 mL DMF was added sodium chlorodifluoroacetate (8.42 g, 55.2 mmol), cesium carbonate (10.97 g, 33.67 mmol) and 2.5 mL water. The reaction was stirred at 100° C. for 16 hours. The reaction mixture was partitioned between ethyl acetate and water, and the organic portion washed with brine, dried over magnesium sulfate, and concentrated. The crude product was purified by flash chromatography on silica gel (0 to 20% ethyl acetate in heptanes) to yield 2.98 g (48%) of 2-bromo-4-chloro-1-(difluoromethoxy)benzene as a clear, colorless oil. LCMS (ESI) no m/z signal; $^1$H NMR (400 MHz, DMSO-$d_6$) δ: 7.90 (d, 1H), 7.54 (dd, 1H), 7.38 (d, 1H), 7.28 (t, 1H).

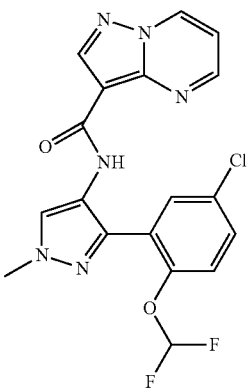 [SMILES: Cn1cc(NC(=O)c2cnn3cccnc23)c(-c2cc(Cl)ccc2OC(F)F)n1]

N-(3-(5-chloro-2-(difluoromethoxy)phenyl)-1-methyl-1H-pyrazol-4-yl)pyrazolo[1,5-a]pyrimidine-3-carboxamide Using 2-bromo-4-chloro-1-(difluoromethoxy)benzene, the title compound was synthesized following the synthetic procedures described for Example 14. LCMS (ESI) m+H=419.0; $^1$H NMR (400 MHz, DMSO-$d_6$) δ: 9.71 (s, 1H), 9.34 (dd, J=7.0, 1.6, 1H), 8.67 (dd, J=4.7, 2.0, 1H), 8.66 (s, 1H), 8.30 (s, 1H), 7.62 (dd, J=8.8, 2.7, 1H), 7.59 (d, J=2.6, 1H), 7.45 (d, J=8.7, 1H), 7.29 (dd, J=7.0, 4.2, 1H), 7.23 (t, 1H), 3.93 (s, 3H).

Example 19

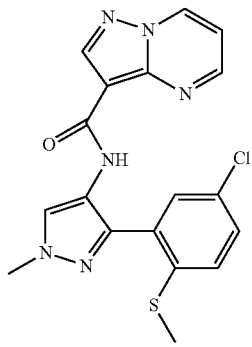 [SMILES: CSc1ccc(Cl)cc1-c1nn(C)cc1NC(=O)c1cnn2cccnc12]

N-(3-(5-chloro-2-(methylthio)phenyl)-1-methyl-1H-pyrazol-4-yl)pyrazolo[1,5-a]pyrimidine-3-carboxamide

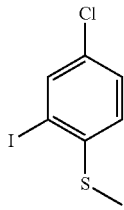

(4-chloro-2-iodophenyl)(methyl)sulfane

To a 0° C. solution of concentrated sulfuric acid (0.3 mL, 5.0 mmol) in 5.0 mL water and 5.0 mL acetonitrile was added 5-chloro-2-(methylthio)aniline (472 mg, 2.72 mmol), followed by slow addition of sodium nitrite (210 mg, 3.0 mmol) as a solution in 1 mL water. The reaction mixture was stirred at 0° C. for 30 minutes. This mixture was then slowly added to a 0° C. solution of potassium iodide (691.7 mg, 4.167 mmol) in 5 mL water. The reaction was stirred for 1 hour, allowing the ice bath to warm to room temperature. The reaction mixture was then partitioned between water and ethyl acetate. The organic layer was dried with brine and magnesium sulfate and concentrated. The crude product was purified by flash chromatography on silica gel (0 to 30% ethyl acetate in dichloromethane) to yield 598.4 mg (77%) of (4-chloro-2-iodophenyl)(methyl)sulfane. LCMS (ESI) no m/z signal; $^1$H NMR (400 MHz, DMSO-d$_6$) δ: 7.87 (d, 1H), 7.47 (dd, 1H), 7.20 (d, 1H), 2.47 (s, 3H).

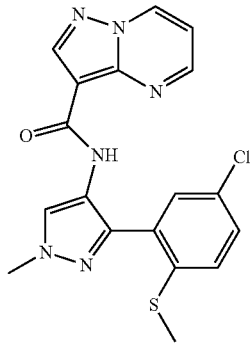 [SMILES: CSc1ccc(Cl)cc1-c1nn(C)cc1NC(=O)c1cnn2cccnc12]

N-(3-(5-chloro-2-(methylthio)phenyl)-1-methyl-1H-pyrazol-4-yl)pyrazolo[1,5-a]pyrimidine-3-carboxamide Using (4-chloro-2-iodophenyl)(methyl)sulfane, the title compound was prepared following the synthetic procedures described for Example 14. LCMS (ESI) m+H=399.0; $^1$H NMR (400 MHz, DMSO-d$_6$) δ: 9.69 (s, 1H), 9.32 (dd, J=7.0, 1.6, 1H), 8.65 (s, 1H), 8.57 (dd, J=4.2, 1.6, 1H), 8.27 (s, 1H), 7.55 (dd, J=8.6, 2.4, 1H), 7.45 (d, J=8.6, 1H), 7.40 (d, J=2.4, 1H), 7.25 (dd, J=7.0, 4.2, 1H), 3.91 (s, 3H), 2.38 (s, 3H).

Example 20

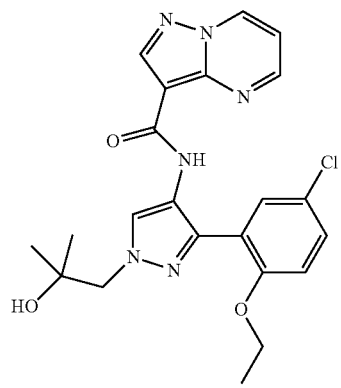 [SMILES: CCOc1ccc(Cl)cc1-c1nn(CC(C)(C)O)cc1NC(=O)c1cnn2cccnc12]

N-(3-(5-chloro-2-ethoxyphenyl)-1-(2-hydroxy-2-methylpropyl)-1H-pyrazol-4-yl)pyrazolo[1,5-a]pyrimidine-3-carboxamide

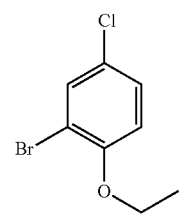

2-bromo-4-chloro-1-ethoxybenzene

To a solution of 2-Bromo-4-chlorophenol (2.12 g, 10.2 mmol) in 25 mL acetone was added iodoethane (0.850 mL, 10.6 mmol) and cesium carbonate (4.08 g, 12.5 mmol). The reaction mixture was stirred at 50° C. for 2 hours. The reaction mixture was partitioned between ethyl acetate and water, and the organic portion washed with brine, dried over magnesium sulfate, and concentrated to yield 2.37 g (98%) of 2-bromo-4-chloro-1-ethoxybenzene as a yellow oil, which was carried forward without further purification. LCMS (ESI) no m/z signal; $^1$H NMR (400 MHz, DMSO-d$_6$) δ: 7.67 (d, J=2.6, 1H), 7.39 (dd, J=8.8, 2.6, 1H), 7.12 (d, J=8.9, 1H), 4.11 (q, J=7.0, 2H), 1.35 (t, J=7.0, 3H).

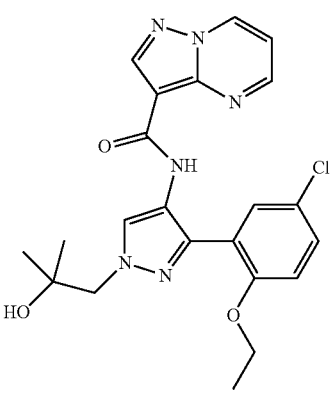 [SMILES: CCOc1ccc(Cl)cc1-c1nn(CC(C)(C)O)cc1NC(=O)c1cnn2cccnc12]

N-(3-(5-chloro-2-ethoxyphenyl)-1-(2-hydroxy-2-methylpropyl)-1H-pyrazol-4-yl)pyrazolo[1,5-a]pyrimidine-3-carboxamide Using 2-bromo-4-chloro-1-ethoxybenzene, the title compound was prepared using the synthetic procedures described for Examples 14 and 16. LCMS (ESI) m+H=455.1; $^1$H NMR (400 MHz, DMSO-d$_6$) δ: 9.71 (s, 1H), 9.33 (dd, J=7.0, 1.6, 1H), 8.73 (dd, J=4.2, 1.6, 1H), 8.66 (s, 1H), 8.33 (s, 1H), 7.47 (dd, J=8.8, 2.7, 1H), 7.38 (d, J=2.7, 1H), 7.28 (m, 2H), 4.73 (s, 1H), 4.12 (q, J=6.9, 2H), 4.07 (s, 2H), 1.13 (s, 6H), 1.03 (t, J=6.9, 3H).

Example 21

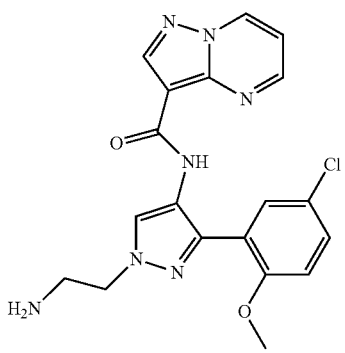 [SMILES: COc1ccc(Cl)cc1-c1nn(CCN)cc1NC(=O)c1cnn2cccnc12]

N-(1-(2-aminoethyl)-3-(5-chloro-2-methoxyphenyl)-1H-pyrazol-4-yl)pyrazolo[1,5-a]pyrimidine-3-carboxamide To a solution of N-(3-(5-chloro-2-methoxyphenyl)-1-(2-(1,3-dioxoisoindolin-2-yl)ethyl)-1H-pyrazol-4-yl)pyrazolo[1,5-a]pyrimidine-3-carboxamide (prepared following the synthetic procedures described for Example 14) (104.1 mg, 0.192 mmol) in 8 mL ethanol was added hydrazine (78 μL, 2.5 mmol). The reaction mixture was stirred at room temperature for 18 hours, and then concentrated. The crude product was purified by reverse phase HPLC and lyophilized to give 17.7 mg (15.4%) of N-(1-(2-aminoethyl)-3-(5-chloro-2-methoxyphenyl)-1H-pyrazol-4-yl)pyrazolo[1,5-a]pyrimidine-3-carboxamide. LCMS (ESI) m+H=412.1; $^1$H NMR (400 MHz, DMSO-d$_6$) δ: 9.68 (s, 1H), 9.33 (dd, J=7.0, 1.6, 1H), 8.77 (dd, J=4.2, 1.6, 1H), 8.65 (s, 1H), 8.30 (s, 1H), 7.49 (dd, J=8.8, 2.7, 1H), 7.42 (d, J=2.7, 1H), 7.29 (m, 2H), 4.14 (t, J=6.2, 2H), 3.85 (s, 3H), 2.99 (t, J=6.2, 2H).

Example 22 and Example 23

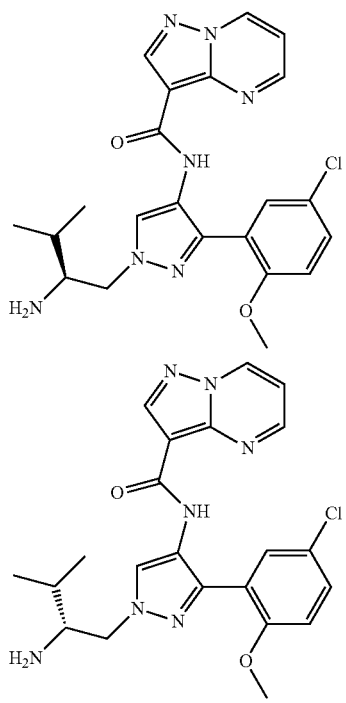

(S)—N-(3-(5-chloro-2-methoxyphenyl)-1-(2-hydroxy-3-methylbutyl)-1H-pyrazol-4-yl)pyrazolo[1,5-a]pyrimidine-3-carboxamide (R)—N-(3-(5-chloro-2-methoxyphenyl)-1-(2-hydroxy-3-methylbutyl)-1H-pyrazol-4-yl)pyrazolo[1,5-a]pyrimidine-3-carboxamide Racemic N-(3-(5-chloro-2-methoxyphenyl)-1-(2-hydroxy-3-methylbutyl)-1H-pyrazol-4-yl)pyrazolo[1,5-a]pyrimidine-3-carboxamide (prepared as described for example 16) was subjected to chiral SFC chromatography to yield the title compounds. LCMS (ESI) m+H=455.1; $^1$H NMR (400 MHz, DMSO-d$_6$) δ: 9.67 (s, 1H), 9.33 (dd, J=7.0, 1.6, 1H), 8.77 (dd, J=4.2, 1.6, 1H), 8.65 (s, 1H), 8.30 (s, 1H), 7.49 (dd, J=8.8, 2.8, 1H), 7.40 (d, J=2.7, 1H), 7.34-7.24 (m, 2H), 4.86

(d, J=5.8, 1H), 4.19 (dd, J=13.8, 3.7, 1H), 4.04 (dd, J=13.8, 8.1, 1H), 3.84 (s, 3H), 3.64 (m, 1H), 1.63 (m, 1H), 0.93 (t, J=7.2, 6H).

Example 24

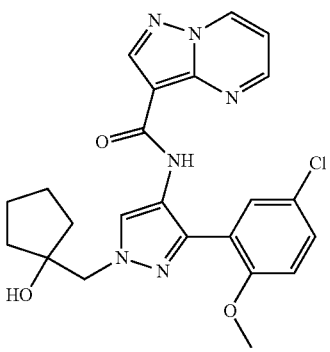 [SMILES: COc1ccc(Cl)cc1-c1nn(CC2(O)CCCC2)cc1NC(=O)c1cnn2cccnc12]

N-(3-(5-chloro-2-methoxyphenyl)-1-((1-hydroxycyclopentyl)methyl)-1H-pyrazol-4-yl)pyrazolo[1,5-a]pyrimidine-3-carboxamide

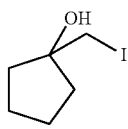

1-(iodomethyl)cyclopentanol

In a 100 mL flask was placed samarium powder (40 mesh, 3.07 g, 2.02 mmol), and this flask was cooled under nitrogen in an ice bath. An addition funnel was charged with a solution of cyclopentanone (0.90 mL, 10.1 mmol) and diiodomethane (2.40 mL, 29.8 mmol) in 50 mL tetrahydrofuran, and this solution was dropwise added to the stirring samarium powder over 1 hour. After addition was complete, the reaction was stirred for one additional hour at 0° C. The reaction was treated with 40 mL of 1N aqueous HCl and extracted with 100 mL diethyl ether. The ether layer was washed with 4% aqueous $Na_2S_2O_3$ and brine, dried over magnesium sulfate, and concentrated. The crude product was purified by flash chromatography on silica gel (0 to 30% ethyl acetate in heptane) to yield 1.17 g (51%) of 1-(iodomethyl)cyclopentanol as a yellow oil. $^1$H NMR (400 MHz, CDCl$_3$) δ: 3.47 (s, 2H), 1.70-1.92 (m, 8H).

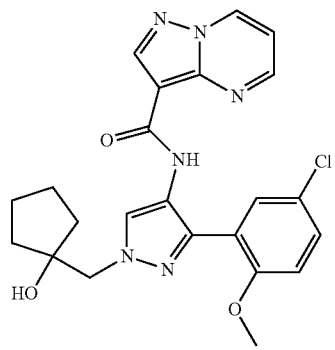 [SMILES: COc1ccc(Cl)cc1-c1nn(CC2(O)CCCC2)cc1NC(=O)c1cnn2cccnc12]

N-(3-(5-chloro-2-methoxyphenyl)-1-((1-hydroxycyclopentyl)methyl)-1H-pyrazol-4-yl)pyrazolo[1,5-a]pyrimidine-3-carboxamide To a solution of N-(5-(5-chloro-2-methoxyphenyl)-1H-pyrazol-4-yl)pyrazolo[1,5-a]pyrimidine-3-carboxamide (prepared as described for Example 14, 115.4 mg, 0.313 mmol) in 3 mL DMF is added 1-(iodomethyl)cyclopentanol (195.4 mg, 2.762 mmol) and cesium carbonate (339.2 mg, 3.327 mmol). The reaction was stirred in a sealed vessel at 140° C. for 18 hours. The reaction mixture was partitioned between ethyl acetate and water, and the organic portion washed with brine, dried over magnesium sulfate, and concentrated. The crude product was separated from the other regioisomeric product and purified by reverse phase HPLC and lyophilized to give 32.1 mg (22%) of N-(3-(5-chloro-2-methoxyphenyl)-1-((1-hydroxycyclopentyl)methyl)-1H-pyrazol-4-yl)pyrazolo[1,5-a]pyrimidine-3-carboxamide. LCMS (ESI) m+H=467.1; $^1$H NMR (400 MHz, DMSO-d$_6$) δ: 9.68 (s, 1H), 9.33 (dd, J=7.0, 1.6, 1H), 8.77 (dd, J=4.2, 1.6, 1H), 8.64 (s, 1H), 8.33 (s, 1H), 7.49 (dd, J=8.9, 2.7, 1H), 7.39 (d, J=2.7, 1H), 7.32-7.25 (m, 2H), 4.67 (s, 1H), 4.19 (s, 2H), 3.84 (s, 3H), 1.61 (m, 8H).

Example 25

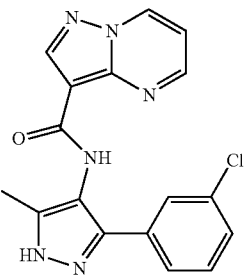 [SMILES: Cc1[nH]nc(-c2cccc(Cl)c2)c1NC(=O)c1cnn2cccnc12]

N-(3-(3-chlorophenyl)-5-methyl-1H-pyrazol-4-yl)pyrazolo[1,5-a]pyrimidine-3-carboxamide

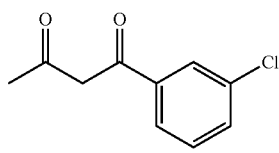

1-(3-chlorophenyl)butane-1,3-dione

To a solution of 3-chloroacetophenone (1.30 mL, 10.0 mmol) in 20 mL THF was added Potassium tert-butoxide (11.0 mL of a 1.0 M solution in THF, 11.0 mmol) and then anhydrous ethyl acetate (1.05 mL, 10.7 mmol). The reaction was stirred at room temperature for 2 hours and then at 50° C. for 15 hours. The reaction mixture was partitioned between ethyl acetate and water, and the organic portion washed with brine, dried over magnesium sulfate, and concentrated. The crude product was purified by flash chromatography on silica gel (0 to 50% ethyl acetate in heptanes) to yield 0.75 g (38%) of 1-(3-chlorophenyl)butane-1,3-dione. LCMS (ESI) m+H=197.2.

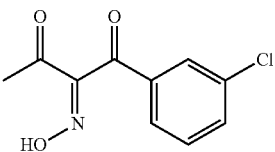

1-(3-chlorophenyl)-2-(hydroxyimino)butane-1,3-dione

To a 0° C. solution of 1-(3-chlorophenyl)butane-1,3-dione (0.75 g, 3.8 mmol) in 15 mL acetic acid was slowly added sodium nitrite (0.560 g, 8.11 mmol) as a solution in 1.5 mL water. The reaction was stirred at 0° C. for 30 minutes and then warmed to room temperature. After an additional 4 hours, the reaction was poured into aqueous saturated sodium bicarbonate and extracted three times with dichloromethane. The combined extracts were dried over magnesium sulfate and concentrated to yield 765.7 mg (89%) of 1-(3-chlorophenyl)-2-(hydroxyimino)butane-1,3-dione, which was carried forward without further purification. LCMS (ESI) m+H=226; $^1$H NMR (400 MHz, DMSO-d$_6$) δ: 7.81 (d, 1H), 7.80 (s, 1H), 7.75 (d, 1H), 7.62 (t, 1H), 2.60 (s, 1H), 2.48 (s, 3H).

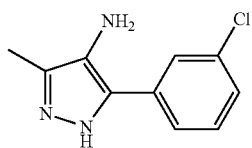

5-(3-chlorophenyl)-3-methyl-1H-pyrazol-4-amine

To a 0° C. solution of 1-(3-chlorophenyl)-2-(hydroxyimino)butane-1,3-dione (224.8 mg, 0.996 mmol) in 5 mL ethanol was dropwise added hydrazine (0.30 mL, 9.6 mmol). The reaction was warmed to room temperature and stirred for 15 hours. The crude reaction mixture was concentrated and purified by flash chromatography on silica gel (20 to 100% ethyl acetate in dichloromethane) to yield 113.3 mg (55%) of 5-(3-chlorophenyl)-3-methyl-1H-pyrazol-4-amine. LCMS (ESI) m+H=208.2; $^1$H NMR (400 MHz, DMSO-d$_6$) δ: 12.20 (s, 1H), 7.94-7.57 (m, 2H), 7.40 (s, 1H), 7.27 (d, J=9.1, 1H), 2.12 (s, 3H).

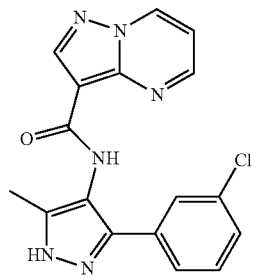 [SMILES: Cc1[nH]nc(-c2cccc(Cl)c2)c1NC(=O)c1cnn2cccnc12]

N-(3-(3-chlorophenyl)-5-methyl-1H-pyrazol-4-yl)pyrazolo[1,5-a]pyrimidine-3-carboxamide A mixture of 5-(3-chlorophenyl)-3-methyl-1H-pyrazol-4-amine (113.3 mg, 0.546 mmol), pyrazolo[1,5-a]pyrimidine-3-carboxylic acid (109.5 mg, 0.6712 mmol), 7-azabenzotriazol-1-yloxy-tris-(pyrrolidino)phosphonium hexafluorophosphate (338.2 mg, 0.652 mmol), N,N-diisopropylethylamine (0.30 mL, 1.7 mmol), and 4-dimethylaminopyridine (19.1 mg, 0.156 mmol) in 8.0 mL N,N-dimethylformamide was stirred at 50° C. for 15 hours. The reaction mixture was partitioned between ethyl acetate and water, and the organic portion washed with brine, dried over magnesium sulfate, and concentrated. The crude product was purified by reverse phase HPLC and lyophilized to give 86.9 mg (45%) of N-(3-(3-chlorophenyl)-5-methyl-1H-pyrazol-4-yl)pyrazolo[1,5-a]pyrimidine-3-carboxamide. LCMS (ESI) m+H=353.0; $^1$H NMR (400 MHz, DMSO-d$_6$) δ: 12.90 (s, 1H), 9.37 (d, J=7.0, 1H), 9.30 (s, 1H), 8.86 (dd, J=4.1, 1.3, 1H), 8.69 (s, 1H), 7.80 (d, J=12.1, 1H), 7.72 (d, J=7.6, 1H), 7.37 (t, J=7.8, 1H), 7.32 (dd, J=6.9, 4.4, 2H), 2.18 (s, 3H).

Example 26

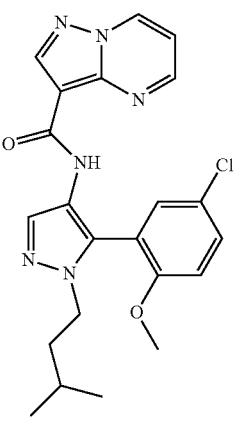 [SMILES: COc1ccc(Cl)cc1-c1c(NC(=O)c2cnn3cccnc23)cnn1CCC(C)C]

N-(5-(5-chloro-2-methoxyphenyl)-1-isopentyl-1H-pyrazol-4-yl)pyrazolo[1,5-a]pyrimidine-3-carboxamide

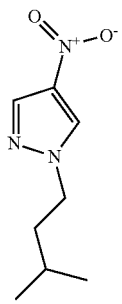

1-isopentyl-4-nitro-1H-pyrazole

A mixture of 4-Nitro-1H-pyrazole (234 mg, 2.06 mmol, 1.0 eq), 1-Bromo-3-methylbutane (0.30 ml, 2.48 mmol, 1.2 eq), and Cesium carbonate (1.01 g, 3.10 mmol, 1.5 eq) in 5.0 mL 1,2-Dimethoxyethane was stirred at 55° C. for 12 hours. The reaction mixture was cooled to room temperature and diluted with 25 mL ethyl acetate and filtered. The filtrate was then concentrated and the residue was dissolved in 5 mL dichloromethane and purified by flash column chromatography (silica, 0-80% ethyl acetate in heptane in 30 minutes) to yield 357.6 mg (94.32%) of Isopentyl-4-nitro-1H-pyrazole as a white solid. LCMS (ESI) m+H=184.1 $^1$H NMR (400 MHz, CDCl$_3$) δ 8.11 (s, 1H), 8.06 (s, 1H), 4.20-4.14 (m, 2H), 1.80 (dd, J=14.8, 7.1, 2H), 1.60 (dp, J=13.4, 6.7, 1H), 0.97 (d, J=6.6, 6H).

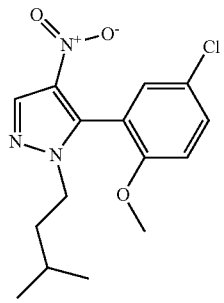 [SMILES: COc1ccc(Cl)cc1-c1c([N+](=O)[O-])cnn1CCC(C)C]

N-(5-(5-chloro-2-methoxyphenyl)-1-isopentyl-4-nitro-1H-pyrazole

A mixture of 1-Isopentyl-4-nitro-1H-pyrazole (356.9 mg, 1.95 mmol, 1.00 eq), 2-Bromo-4-chloroanisole (0.37 ml, 2.72 mmol, 1.40 eq), Palladium (II) acetate (88 mg, 0.39 mmol, 0.20 eq), Di(1-adanmtyl)-n-butylphosphine (209 mg, 0.58 mmol, 0.30 eq), potassium carbonate (807 mg, 5.84 mmol, 3.00 eq) and trimethylacetic acid (52 mg, 0.50 mmol, 0.26 eq) in 5.0 mL N,N-Dimethylacetamide was stirred at 120° C. for 12 hours. The reaction mixture was cooled to room temperature and diluted with 20 mL ethyl acetate and filtered. The filtrate was then concentrated and used as is for the next step. LCMS (ESI) m+H=324.3

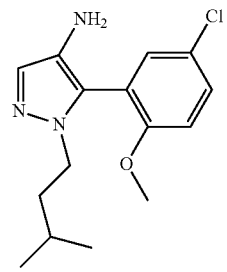 [SMILES: COc1ccc(Cl)cc1-c1c(N)cnn1CCC(C)C]

N-(5-(5-chloro-2-methoxyphenyl)-1-isopentyl-1H-pyrazole-4-amine

A mixture of 5-(5-Chloro-2-methoxyphenyl)-1-isopentyl-4-nitro-1H-pyrazole (632 mg, 1.95 mmol, 1.00 eq), iron (642.5 mg, 11.50 mmol, 5.90 eq), and ammonium chloride (500.7 mg, 9.36 mmol, 4.80 eq) in 5.0 mL ethanol and 10 mL water was stirred at 75° C. for 2 hours. The reaction mixture was concentrated, 10 mL of saturated bicarbonate solution was added, and the aqueous layer was extracted with dichloromethane (20 mL*3). The combined dichloromethane layers were dried with magnesium sulfate, filtered and concentrated. The reddish yellow oil was used as is for the next step LCMS (ESI) m+H=293.8.

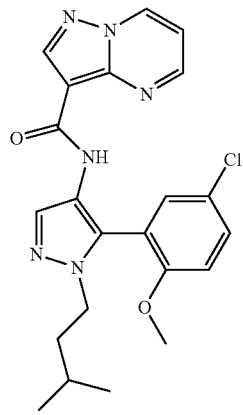 [SMILES: COc1ccc(Cl)cc1-c1c(NC(=O)c2cnn3cccnc23)cnn1CCC(C)C]

N-(5-(5-chloro-2-methoxyphenyl)-1-isopentyl-1H-pyrazol-4-yl)pyrazolo[1,5-a]pyrimidine-3-carboxamide A mixture of 5-(5-Chloro-2-methoxyphenyl)-1-isopentyl-1H-pyrazole-4-amine (573.0 mg, 1.95 mmol, 1.00 eq), pyrazolo[1,5-a]pyrimidine-3-carboxylic acid (349.9 mg, 2.145 mmol, 1.10 eq), 7-azabenzotriazol-1-yloxy-tris-(pyrrolidino) phosphonium hexafluorophosphate (1.25 g, 2.42 mmol, 1.24 eq), and N,N-diisopropylethylamine (0.95 mL, 5.5 mmol, 2.8 eq) in 5.0 mL N,N-dimethylformamide was stirred at room temperature for 12 hours. The reaction mixture was concentrated. The crude product was purified by reverse phase HPLC and lyophilized to give 105.2 mg (12.3%) of N-(5-(5-chloro-2-methoxyphenyl)-1-isopentyl-1H-pyrazol-4-yl) pyrazolo[1,5-a]pyrimidine-3-carboxamide. LCMS (ESI) m+H=439.1; $^1$H NMR (400 MHz, DMSO) δ 9.50 (s, 1H), 9.32 (dd, J=7.0, 1.6, 1H), 8.73-8.57 (m, 2H), 8.01 (s, 1H), 7.60 (dd, J=8.9, 2.7, 1H), 7.48 (d, J=2.7, 1H), 7.33 (d, J=9.0, 1H), 7.27 (dd, J=7.0, 4.2, 1H), 3.97 (dq, J=16.6, 6.8, 2H), 3.84 (s, 3H), 1.54 (q, J=7.1, 2H), 1.45-1.31 (m, 1H), 0.75 (dd, J=12.0, 6.6, 6H).

Example 27

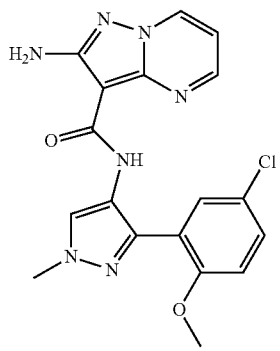 [SMILES: COc1ccc(Cl)cc1-c1nn(C)cc1NC(=O)c1c(N)nn2cccnc12]

2-amino-N-(3-(5-chloro-2-methoxyphenyl)-1-methyl-1H-pyrazol-4-yl)pyrazolo[1,5-a]pyrimidine-3-carboxamide

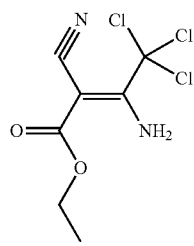

(Z)-ethyl 3-amino-4,4,4-trichloro-2-cyanobut-2-enoate

To a mixture of trichloroacetonitrile (38 mL, 0.38 mol) and cyanoacetic acid ethyl ester (20 mL, 0.2 mol) in ethanol (63 mL) was added triethylamine (1 mL, 7 mmol). The reaction mixture began to turn red and an exotherm occurred after ~1 minute. The reaction mixture was cooled to 0° C., then stirred for two hours while slowly warming to room temperature. The reaction mixture was concentrated in vacuo to a red oil, which was taken up in DCM, filtered through a plug of silica gel, and concentrated in vacuo to afford 44.95 g (90%) of (Z)-ethyl 3-amino-4,4,4-trichloro-2-cyanobut-2-enoate as a colorless oil that slowly solidified to a white solid. $^1$H NMR (400 MHz, CDCl$_3$) δ 10.19 (s, 1H), 6.85 (s, 1H), 4.31 (q, J=7.1, 1H), 1.37 (t, J=7.1, 3H).

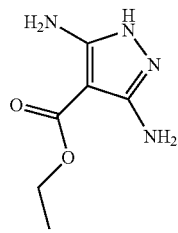

ethyl 3,5-diamino-1H-pyrazole-4-carboxylate

Hydrazine (2.19 mL, 70 mmol) was added to (Z)-ethyl 3-amino-4,4,4-trichloro-2-cyanobut-2-enoate (15.0 g, 58 mmol) in DMF (50 mL). The reaction mixture was heated to 100° C. for 1 hr, then cooled to room temperature. The DMF was removed in vacuo, then the residue was slurried in a 95:5 mixture of DCM:2M methanolic ammonia solution. The resulting precipitate was filtered off, washed with a 95:5 mixture of DCM:MeOH, and dried under vacuum to afford 5.72 g (58%) of ethyl 3,5-diamino-1H-pyrazole-4-carboxylate as a white solid. $^1$H NMR (400 MHz, DMSO) δ 10.53 (s, 1H), 5.28 (br, 4H), 4.14 (q, J=7.1, 2H), 1.33-1.15 (t, J=7.1, 3H).

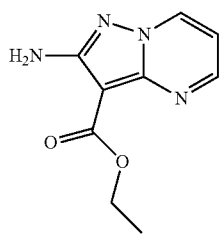

ethyl 2-aminopyrazolo[1,5-a]pyrimidine-3-carboxylate

A mixture of ethyl 3,5-diamino-1H-pyrazole-4-carboxylate (1.0 g, 5.9 mmol), 1,1,3,3-tetramethoxypropane (2.9 mL, 18 mmol), triethylamine (2 mL, 10 mmol), and DMF (15 mL) was heated at 100° C. for 14 hrs, then a further 2 mL of 1,1,3,3-tetramethoxypropane was added. After adding the additional 1,1,3,3-tetramethoxypropane, a significant by-product was noted and heating was stopped immediately. The reaction was cooled to room temperature and the DMF was removed in vacuo. The residue was partitioned between DCM and water, then the organic layer was concentrated and the residue purified by silica chromatography, eluting with 95:5 DCM: 2M methanolic ammonia solution to afford 420 mg (35%) of ethyl 2-aminopyrazolo[1,5-a]pyrimidine-3-carboxylate. $^1$H NMR (500 MHz, CDCl$_3$) δ 8.57 (dd, J=4.3, 1.6, 1H), 8.43 (dd, J=6.7, 1.6, 1H), 6.84 (dd, J=6.7, 4.4, 1H), 5.52 (s, 2H), 4.48 (q, J=7.1, 2H), 1.45 (t, J=7.1, 3H).

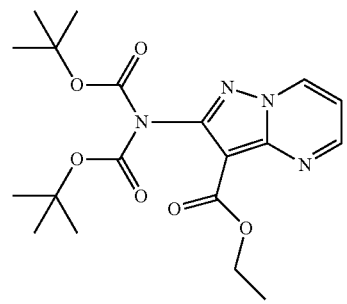 [SMILES: CCOC(=O)c1c(N(C(=O)OC(C)(C)C)C(=O)OC(C)(C)C)nn2cccnc12]

ethyl 2-(bis(tert-butoxycarbonyl)amino)pyrazolo[1,5-a]pyrimidine-3-carboxylate

Di-tert-butyldicarbonate (1.30 g, 5.9 mmol) was added to a solution of ethyl 2-aminopyrazolo[1,5-a]pyrimidine-3-carboxylate (810 mg, 3.9 mmol), 4-dimethylaminopyridine (96 mg, 0.78 mmol), and N,N-diisopropylethylamine (1.4 mL, 7.8 mmol) in acetonitrile (100 mL). The reaction was stirred at room temperature for 3 hours, then concentrated in vacuo. The residue was partitioned between EtOAc and water, then the layers were separated and the organic layer was washed with brine, then dried over Na$_2$SO$_4$, filtered and concentrated. The residue was purified by silica chromatography, eluting with a 97:3 mixture of DCM: 2M methanolic ammonia solution to afford 370 mg (31%) of ethyl 2-(bis(tert-butoxycarbonyl)amino)pyrazolo[1,5-a]pyrimidine-3-carboxylate. $^1$H NMR (500 MHz, CDCl$_3$) δ 8.79 (dd, J=4.2, 1.8, 1H), 8.69 (dd, J=7.0, 1.8, 1H), 7.05 (dd, J=7.0, 4.2, 1H), 4.40 (q, J=7.1, 2H), 1.43 (s, 18H), 1.38 (t, J=7.1, 3H).

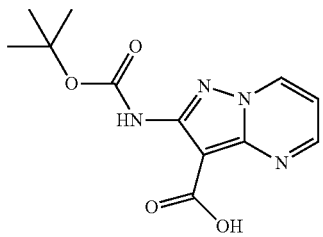 [SMILES: CC(C)(C)OC(=O)Nc1nn2cccnc2c1C(=O)O]

2-(tert-butoxycarbonylamino)pyrazolo[1,5-a]pyrimidine-3-carboxylic acid

To a solution of 2-(bis(tert-butoxycarbonyl)amino)pyrazolo[1,5-a]pyrimidine-3-carboxylate (220 mg, 0.54 mmol) in ethanol (15 mL) was added 4 mL of a 10% aqueous lithium hydroxide solution. The reaction mixture was heated to 70° C. for 18 hrs, then cooled to room temperature. 15 mL of a 10% aqueous solution of citric acid was added and the reaction mixture concentrated in vacuo. The residue was partitioned between EtOAc and a saturated aqueous solution of citric acid, then the organic layer was washed with water and brine, then dried over Na$_2$SO$_4$, filtered and concentrated in vacuo to afford 150 mg of 2-(tert-butoxycarbonylamino)pyrazolo[1,5-a]pyrimidine-3-carboxylic acid. $^1$H NMR (400 MHz, DMSO) δ 9.34 (s, 1H), 9.12 (dd, J=6.9, 1.7, 1H), 8.71 (dd, J=4.3, 1.7, 1H), 7.20 (dd, J=6.9, 4.3, 1H), 1.49 (s, 9H).

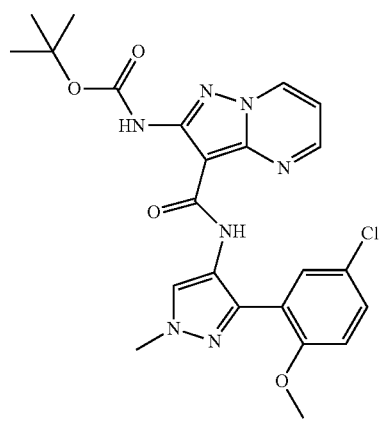 [SMILES: COc1ccc(Cl)cc1-c1nn(C)cc1NC(=O)c1c(NC(=O)OC(C)(C)C)nn2cccnc12]

tert-butyl 3-(3-(5-chloro-2-methoxyphenyl)-1-methyl-1H-pyrazol-4-ylcarbamoyl)pyrazolo[1,5-a]pyrimidin-2-ylcarbamate To a solution of 2-(tert-butoxycarbonylamino)pyrazolo[1,5-a]pyrimidine-3-carboxylic acid (88 mg, 0.32 mmol), 5-(5-chloro-2-methoxyphenyl)-1-methyl-1H-pyrazol-4-amine (75 mg, 0.32 mmol), 4-dimethylaminopyridine (7.7 mg, 0.063 mmol), and N,N-diisopropylethylamine (0.16 mL, 0.95 mmol) in DMF (3 mL) was added PyAOP (200 mg, 0.38 mmol). The reaction mixture was stirred for 14 hrs at 50° C., then diluted with EtOAc. The organic layer was washed twice with water, and once with brine, then dried over Na$_2$SO$_4$, filtered and concentrated. The residue was purified by silica gel chromatography, eluting with EtOAc to afford 98 mg (62%) of tert-butyl 3-(3-(5-chloro-2-methoxyphenyl)-1-methyl-1H-pyrazol-4-ylcarbamoyl)pyrazolo[1,5-a]pyrimidin-2-ylcarbamate. $^1$H NMR (400 MHz, CDCl$_3$) δ 9.85 (s, 1H), 9.65 (s, 1H), 8.76 (dd, J=6.8, 1.7, 1H), 8.44 (dd, J=4.3, 1.7, 1H), 8.20 (s, 1H), 7.56 (d, J=2.7, 1H), 7.36 (dd, J=8.8, 2.7, 1H), 6.97 (d, J=8.9, 1H), 6.90 (dd, J=6.9, 4.3, 1H), 3.97 (s, 3H), 3.87 (s, 3H), 1.56 (s, 9H).

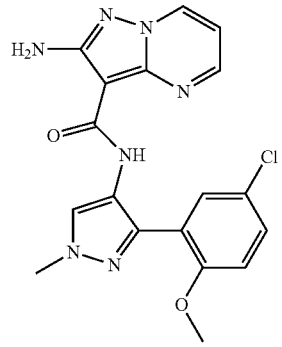 [SMILES: COc1ccc(Cl)cc1-c1nn(C)cc1NC(=O)c1c(N)nn2cccnc12]

2-amino-N-(3-(5-chloro-2-methoxyphenyl)-1-methyl-1H-pyrazol-4-yl)pyrazolo[1,5-a]pyrimidine-3-carboxamide TFA (0.5 mL) was added to a solution of tert-butyl 3-(3-(5-chloro-2-methoxyphenyl)-1-methyl-1H-pyrazol-4-ylcarbamoyl)pyrazolo[1,5-a]pyrimidin-2-ylcarbamate (80 mg, 0.2 mmol) in DCM (10 mL). The reaction mixture was stirred for 3 hrs at room temperature, then concentrated in vacuo. The residue was purified by silica gel chromatography to afford 55 mg (90%) of 2-amino-N-(3-(5-chloro-2-methoxyphenyl)-1-methyl-1H-pyrazol-4-yl)pyrazolo pyrimidine-3-carboxamide as a white solid. LCMS (ESI) m+H=398.1; $^1$H NMR (400 MHz, DMSO) δ 9.46 (s, 1H), 8.91 (dd, J=6.7, 1.6, 1H), 8.44 (dd, J=4.5, 1.6, 1H), 8.21 (s, 1H), 7.47 (dd, J=8.9, 2.7, 1H), 7.37 (d, J=2.7, 1H), 7.27 (d, J=8.9, 1H), 6.99 (dd, J=6.7, 4.5, 1H), 6.56 (s, 2H), 3.89 (s, 3H), 3.83 (s, 3H).

Examples 28-131 shown in Table 1 were prepared generally following the above-described Examples. For each compound shown in Table 1, the Example number followed is given in the Method column.

TABLE 1

| Ex | Structure | Name | Mthd | LCMS (ESI) m/z |
|---|---|---|---|---|
| 28 | 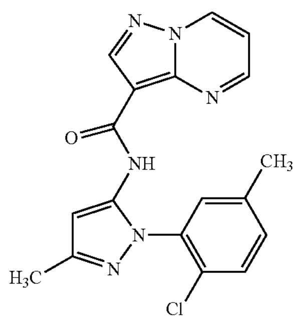 | N-(1-(2-chloro-5-methylphenyl)-3-methyl-1H-pyrazol-5-yl)pyrazolo[1,5-a]pyrimidine-3-carboxamide | 6 | 367.0 |
| 29 | 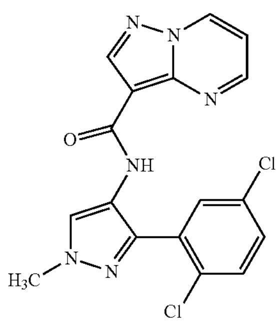 [SMILES: Cn1cc(NC(=O)c2cnn3cccnc23)c(-c2cc(Cl)ccc2Cl)n1] | N-(3-(2,5-dichlorophenyl)-1-methyl-1H-pyrazol-4-yl)pyrazolo[1,5-a]pyrimidine-3-carboxamide | 4 | 387.0 |
| 30 | 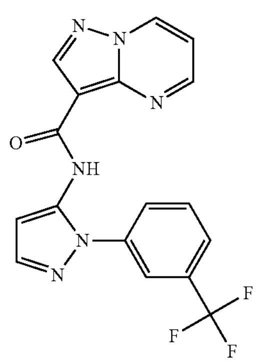 [SMILES: O=C(Nc1ccnn1-c1cccc(C(F)(F)F)c1)c1cnn2cccnc12] | N-(3-(2,5-dichlorophenyl)-1-methyl-1H-pyrazol-4-yl)pyrazolo[1,5-a]pyrimidine-3-carboxamide | 13 | 373.2 |
| 31 | 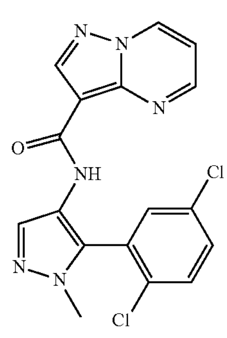 [SMILES: Cn1ncc(NC(=O)c2cnn3cccnc23)c1-c1cc(Cl)ccc1Cl] | N-(5-(2,5-dichlorophenyl)-1-methyl-1H-pyrazol-4-yl)pyrazolo[1,5-a]pyrimidine-3-carboxamide | 5 | 387.0 |

TABLE 1-continued

| Ex | Structure | Name | Mthd | LCMS (ESI) m/z |
|---|---|---|---|---|
| 32 | 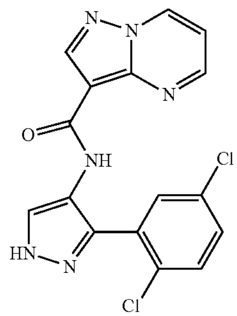 [SMILES: O=C(Nc1c[nH]nc1-c1cc(Cl)ccc1Cl)c1cnn2cccnc12] | N-(3-(2,5-dichlorophenyl)-1H-pyrazol-4-yl)pyrazolo[1,5-a]pyrimidine-3-carboxamide | 4 | 373.2 |
| 33 | 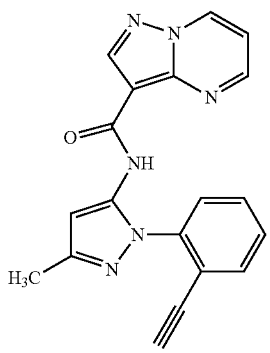 [SMILES: C#Cc1ccccc1-n1nc(C)cc1NC(=O)c1cnn2cccnc12] | N-(1-(2-ethynylphenyl)-3-methyl-1H-pyrazol-5-yl)pyrazolo[1,5-a]pyrimidine-3-carboxamide | 6 | 342.9 |
| 34 | 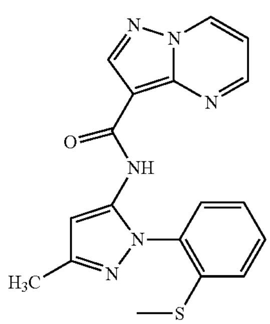 [SMILES: CSc1ccccc1-n1nc(C)cc1NC(=O)c1cnn2cccnc12] | N-(3-methyl-1-(2-(methylthio)phenyl)-1H-pyrazol-5-yl)pyrazolo[1,5-a]pyrimidine-3-carboxamide | 6 | 364.9 |
| 35 | 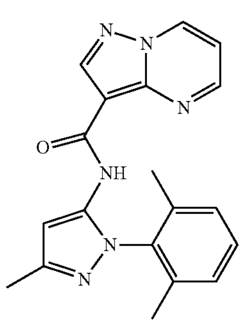 [SMILES: Cc1cc(NC(=O)c2cnn3cccnc23)n(-c2c(C)cccc2C)n1] | N-(1-(2,6-dimethylphenyl)-3-methyl-1H-pyrazol-5-yl)pyrazolo[1,5-a]pyrimidine-3-carboxamide | 6 | 346.9 |

| Ex | Structure | Name | Mthd | LCMS (ESI) m/z |
|---|---|---|---|---|
| 36 | 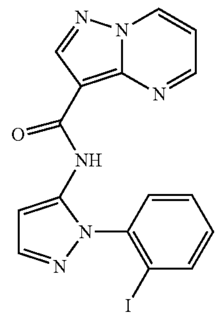 [SMILES: O=C(Nc1ccnn1-c1ccccc1I)c1cnn2cccnc12] | N-(1-(2-iodophenyl)-1H-pyrazol-5-yl)pyrazolo[1,5-a]pyrimidine-3-carboxamide | 13 | 430.8 |
| 37 | 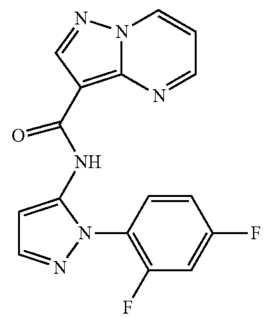 [SMILES: O=C(Nc1ccnn1-c1ccc(F)cc1F)c1cnn2cccnc12] | N-(1-(2,4-difluorophenyl)-1H-pyrazol-5-yl)pyrazolo[1,5-a]pyrimidine-3-carboxamide | 13 | 340.9 |
| 38 | 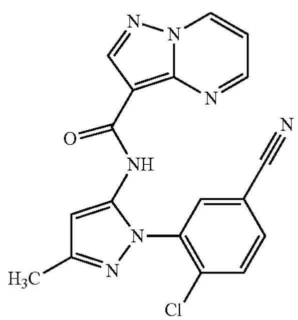 [SMILES: Cc1cc(NC(=O)c2cnn3cccnc23)n(-c2cc(C#N)ccc2Cl)n1] | N-(1-(2-chloro-5-cyanophenyl)-3-methyl-1H-pyrazol-5-yl)pyrazolo[1,5-a]pyrimidine-3-carboxamide | 6 | 377.8 |
| 39 | 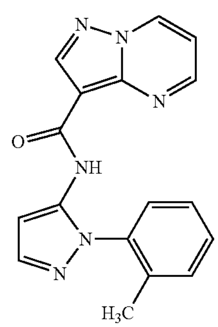 [SMILES: Cc1ccccc1-n1nccc1NC(=O)c1cnn2cccnc12] | N-(1-o-tolyl-1H-pyrazol-5-yl)pyrazolo[1,5-a]pyrimidine-3-carboxamide | 13 | 318.9 |
| 40 | 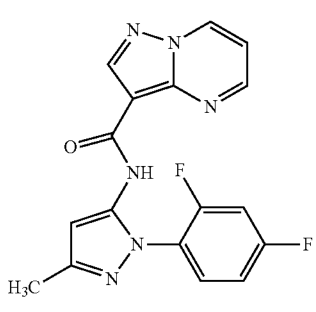 [SMILES: Cc1cc(NC(=O)c2cnn3cccnc23)n(-c2ccc(F)cc2F)n1] | N-(1-(2,4-difluorophenyl)-3-methyl-1H-pyrazol-5-yl)pyrazolo[1,5-a]pyrimidine-3-carboxamide | 6 | 355.2 |

TABLE 1-continued
| Ex | Structure | Name | Mthd | LCMS (ESI) m/z |
|---|---|---|---|---|
| 41 | 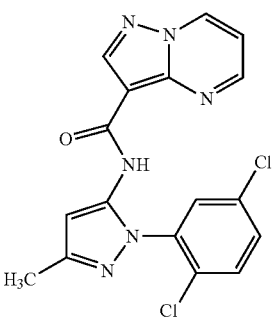 [SMILES: Cc1cc(NC(=O)c2cnn3cccnc23)n(-c2cc(Cl)ccc2Cl)n1] | N-(1-(2,5-dichlorophenyl)-3-methyl-1H-pyrazol-5-yl)pyrazolo[1,5-a]pyrimidine-3-carboxamide | 6 | 387.1 |
| 42 | 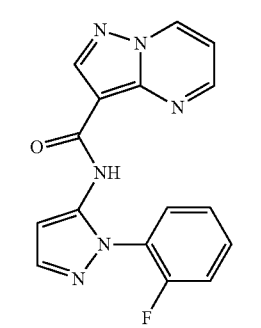 | N-(1-(2-fluorophenyl)-1H-pyrazol-5-yl)pyrazolo[1,5-a]pyrimidine-3-carboxamide | 13 | 323.2 |
| 43 | 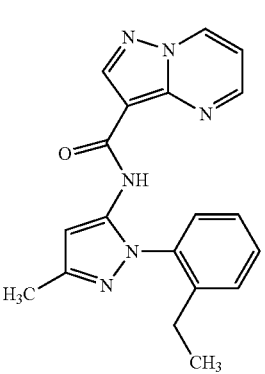 [SMILES: CCc1ccccc1-n1nc(C)cc1NC(=O)c1cnn2cccnc12] | N-(1-(2-ethylphenyl)-3-methyl-1H-pyrazol-5-yl)pyrazolo[1,5-a]pyrimidine-3-carboxamide | 6 | 347.2 |
| 44 | 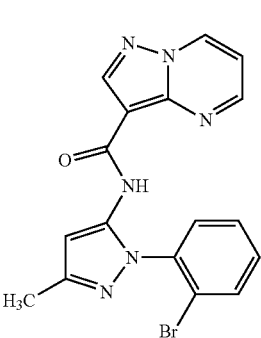 [SMILES: Cc1cc(NC(=O)c2cnn3cccnc23)n(-c2ccccc2Br)n1] | N-(1-(2-bromophenyl)-3-methyl-1H-pyrazol-5-yl)pyrazolo[1,5-a]pyrimidine-3-carboxamide | 6 | 397.2 |

TABLE 1-continued

| Ex | Structure | Name | Mthd | LCMS (ESI) m/z |
|---|---|---|---|---|
| 45 | 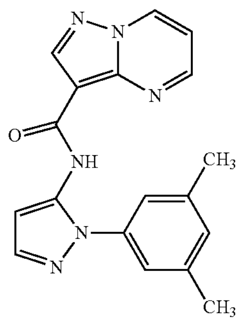 [SMILES: Cc1cc(C)cc(-n2nccc2NC(=O)c2cnn3cccnc23)c1] | N-(1-(3,5-dimethylphenyl)-1H-pyrazol-5-yl)pyrazolo[1,5-a]pyrimidine-3-carboxamide | 13 | 333.2 |
| 46 | 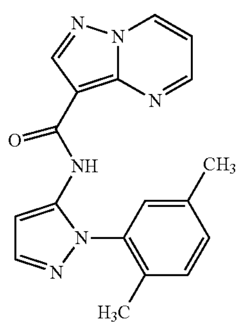 [SMILES: Cc1ccc(C)c(-n2nccc2NC(=O)c2cnn3cccnc23)c1] | N-(1-(2,5-dimethylphenyl)-1H-pyrazol-5-yl)pyrazolo[1,5-a]pyrimidine-3-carboxamide | 13 | 333.2 |
| 47 | 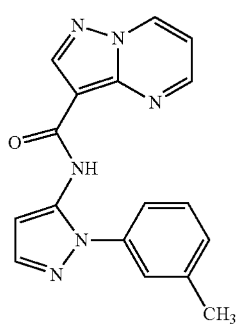 [SMILES: Cc1cccc(-n2nccc2NC(=O)c2cnn3cccnc23)c1] | N-(1-m-tolyl-1H-pyrazol-5-yl)pyrazolo[1,5-a]pyrimidine-3-carboxamide | 13 | 319.2 |
| 48 | 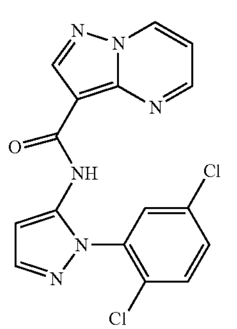 [SMILES: O=C(Nc1ccnn1-c1cc(Cl)ccc1Cl)c1cnn2cccnc12] | N-(1-(2,5-dichlorophenyl)-1H-pyrazol-5-yl)pyrazolo[1,5-a]pyrimidine-3-carboxamide | 13 | 373.0 |

TABLE 1-continued

| Ex | Structure | Name | Mthd | LCMS (ESI) m/z |
|---|---|---|---|---|
| 49 | 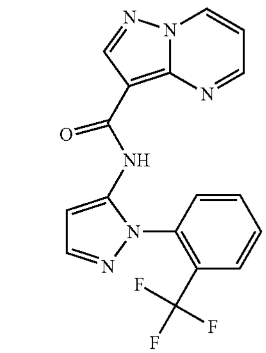 [SMILES: O=C(Nc1ccnn1-c1ccccc1C(F)(F)F)c1cnn2cccnc12] | N-(1-(2-(trifluoromethyl)phenyl)-1H-pyrazol-5-yl)pyrazolo[1,5-a]pyrimidine-3-carboxamide | 13 | 373.1 |
| 50 | 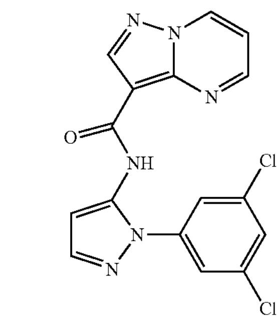 [SMILES: O=C(Nc1ccnn1-c1cc(Cl)cc(Cl)c1)c1cnn2cccnc12] | N-(1-(3,5-dichlorophenyl)-1H-pyrazol-5-yl)pyrazolo[1,5-a]pyrimidine-3-carboxamide | 13 | 373.0 |
| 51 | 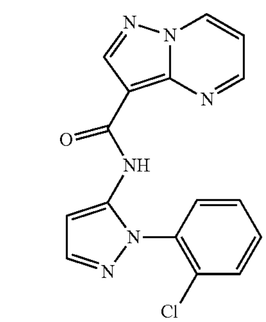 [SMILES: O=C(Nc1ccnn1-c1ccccc1Cl)c1cnn2cccnc12] | N-(1-(2-chlorophenyl)-1H-pyrazol-5-yl)pyrazolo[1,5-a]pyrimidine-3-carboxamide | 13 | 338.9 |
| 52 | 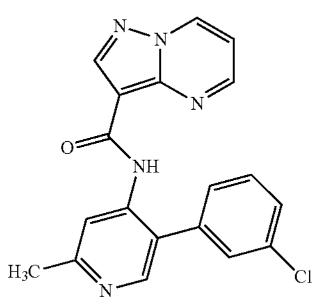 [SMILES: Cc1cc(NC(=O)c2cnn3cccnc23)c(-c2cccc(Cl)c2)cn1] | N-(5-(3-chlorophenyl)-2-methylpyridin-4-yl)pyrazolo[1,5-a]pyrimidine-3-carboxamide | 7 | 364.0 |
| 53 | 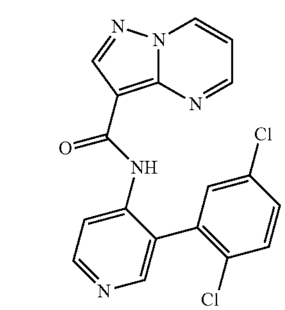 [SMILES: O=C(Nc1ccncc1-c1cc(Cl)ccc1Cl)c1cnn2cccnc12] | N-(3-(2,5-dichlorophenyl)pyridin-4-yl)pyrazolo[1,5-a]pyrimidine-3-carboxamide | 7 | 384.3 |

TABLE 1-continued

| Ex | Structure | Name | Mthd | LCMS (ESI) m/z |
|---|---|---|---|---|
| 54 | 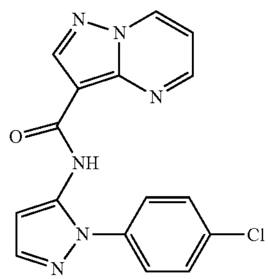 [SMILES: O=C(Nc1ccnn1-c1ccc(Cl)cc1)c1cnn2cccnc12] | N-(1-(4-chlorophenyl)-1H-pyrazol-5-yl)pyrazolo[1,5-a]pyrimidine-3-carboxamide | 13 | 338.9 |
| 55 | 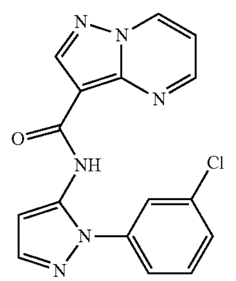 [SMILES: O=C(Nc1ccnn1-c1cccc(Cl)c1)c1cnn2cccnc12] | N-(1-(3-chlorophenyl)-1H-pyrazol-5-yl)pyrazolo[1,5-a]pyrimidine-3-carboxamide | 13 | 338.9 |
| 56 | 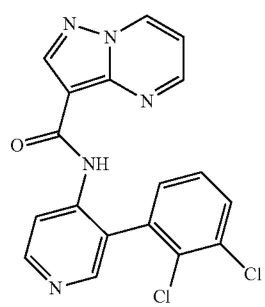 [SMILES: O=C(Nc1ccncc1-c1cccc(Cl)c1Cl)c1cnn2cccnc12] | N-(3-(2,3-dichlorophenyl)pyridin-4-yl)pyrazolo[1,5-a]pyrimidine-3-carboxamide | 7 | 384.0 |
| 57 | 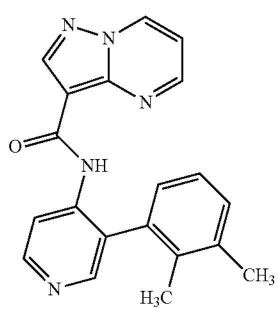 [SMILES: Cc1cccc(-c2cnccc2NC(=O)c2cnn3cccnc23)c1C] | N-(3-(2,3-dimethylphenyl)pyridin-4-yl)pyrazolo[1,5-a]pyrimidine-3-carboxamide | 7 | 344.1 |
| 58 | 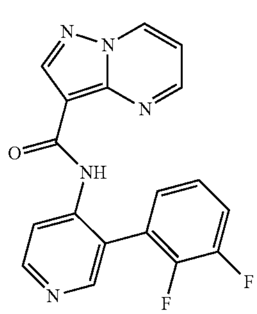 [SMILES: O=C(Nc1ccncc1-c1cccc(F)c1F)c1cnn2cccnc12] | N-(3-(2,3-difluorophenyl)pyridin-4-yl)pyrazolo[1,5-a]pyrimidine-3-carboxamide | 7 | 352.0 |

| Ex | Structure | Name | Mthd | LCMS (ESI) m/z |
|---|---|---|---|---|
| 59 | 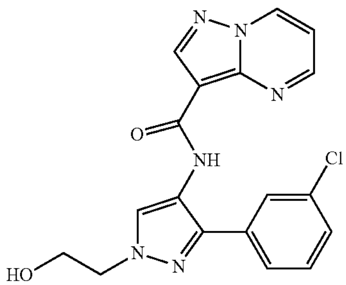 [SMILES: O=C(Nc1cn(CCO)nc1-c1cccc(Cl)c1)c1cnn2cccnc12] | N-(3-(3-chlorophenyl)-1-(2-hydroxyethyl)-1H-pyrazol-4-yl)pyrazolo[1,5-a]pyrimidine-3-carboxamide | 10 | 383.1 |
| 60 | 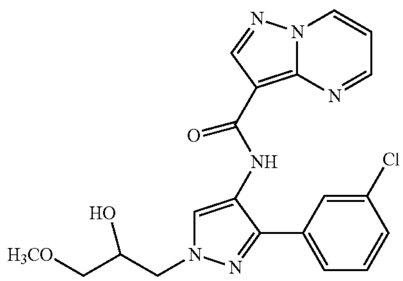 [SMILES: COCC(O)Cn1cc(NC(=O)c2cnn3cccnc23)c(-c2cccc(Cl)c2)n1] | N-(3-(3-chlorophenyl)-1-(2-hydroxy-3-methoxypropyl)-1H-pyrazol-4-yl)pyrazolo[1,5-a]pyrimidine-3-carboxamide | 10 | 427.1 |
| 61 | 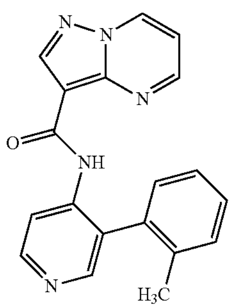 [SMILES: Cc1ccccc1-c1cnccc1NC(=O)c1cnn2cccnc12] | N-(3-o-tolylpyridin-4-yl)pyrazolo[1,5-a]pyrimidine-3-carboxamide | 7 | 330.0 |
| 62 | 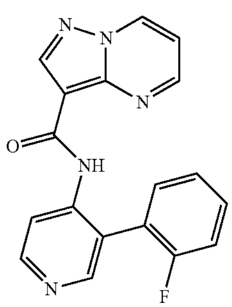 [SMILES: O=C(Nc1ccncc1-c1ccccc1F)c1cnn2cccnc12] | N-(3-(2-fluorophenyl)pyridin-4-yl)pyrazolo[1,5-a]pyrimidine-3-carboxamide | 7 | 334.1 |
| 63 | 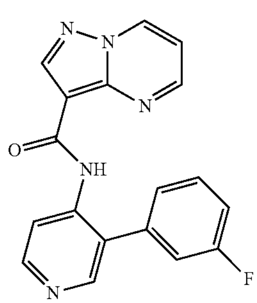 [SMILES: O=C(Nc1ccncc1-c1cccc(F)c1)c1cnn2cccnc12] | N-(3-(3-fluorophenyl)pyridin-4-yl)pyrazolo[1,5-a]pyrimidine-3-carboxamide | 7 | 334.1 |

TABLE 1-continued

| Ex | Structure | Name | Mthd | LCMS (ESI) m/z |
|---|---|---|---|---|
| 64 | 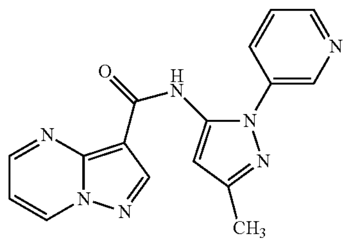 [SMILES: Cc1cc(NC(=O)c2cnn3cccnc23)n(-c2cccnc2)n1] | N-(3-methyl-1-(pyridin-3-yl)-1H-pyrazol-5-yl)pyrazolo[1,5-a]pyrimidine-3-carboxamide | 6 | 319.8 |
| 65 | 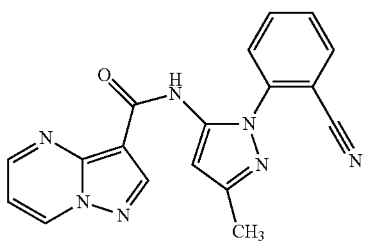 [SMILES: Cc1cc(NC(=O)c2cnn3cccnc23)n(-c2ccccc2C#N)n1] | N-(1-(2-cyanophenyl)-3-methyl-1H-pyrazol-5-yl)pyrazolo[1,5-a]pyrimidine-3-carboxamide | 6 | 344.1 |
| 66 | 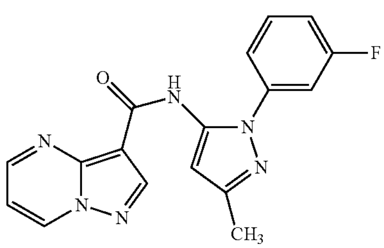 [SMILES: Cc1cc(NC(=O)c2cnn3cccnc23)n(-c2cccc(F)c2)n1] | N-(1-(3-fluorophenyl)-3-methyl-1H-pyrazol-5-yl)pyrazolo[1,5-a]pyrimidine-3-carboxamide | 6 | 336.9 |
| 67 | 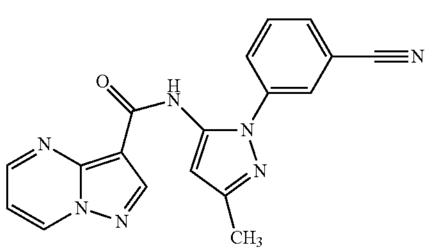 [SMILES: Cc1cc(NC(=O)c2cnn3cccnc23)n(-c2cccc(C#N)c2)n1] | N-(1-(3-cyanophenyl)-3-methyl-1H-pyrazol-5-yl)pyrazolo[1,5-a]pyrimidine-3-carboxamide | 6 | 344.0 |
| 68 | 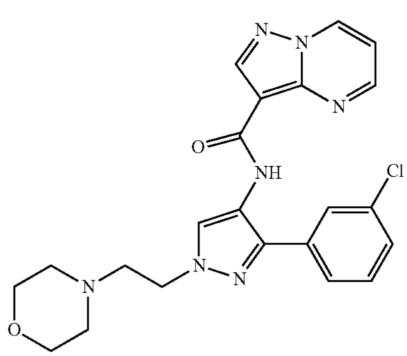 [SMILES: O=C(Nc1cn(CCN2CCOCC2)nc1-c1cccc(Cl)c1)c1cnn2cccnc12] | N-(3-(3-chlorophenyl)-1-(2-morpholinoethyl)-1H-pyrazol-4-yl)pyrazolo[1,5-a]pyrimidine-3-carboxamide | 10 | 452.1 |

TABLE 1-continued

| Ex | Structure | Name | Mthd | LCMS (ESI) m/z |
|---|---|---|---|---|
| 69 | 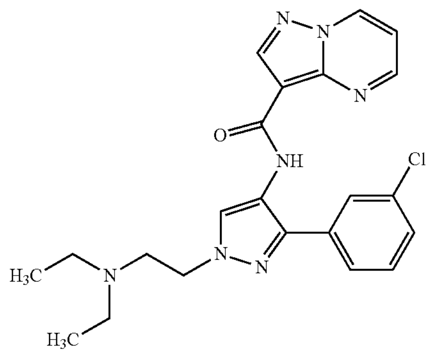 [SMILES: CCN(CC)CCn1cc(NC(=O)c2cnn3cccnc23)c(-c2cccc(Cl)c2)n1] | N-(3-(3-chlorophenyl)-1-(2-(diethylamino)ethyl)-1H-pyrazol-4-yl)pyrazolo[1,5-a]pyrimidine-3-carboxamide | 10 | 438.1 |
| 70 | 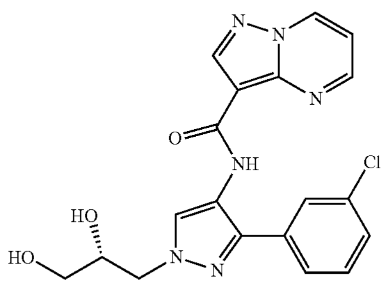 [SMILES: O=C(Nc1cn(C[C@@H](O)CO)nc1-c1cccc(Cl)c1)c1cnn2cccnc12] | (R)-N-(3-(3-chlorophenyl)-1-(2,3-dihydroxypropyl)-1H-pyrazol-4-yl)pyrazolo[1,5-a]pyrimidine-3-carboxamide | 10 | 413.1 |
| 71 | 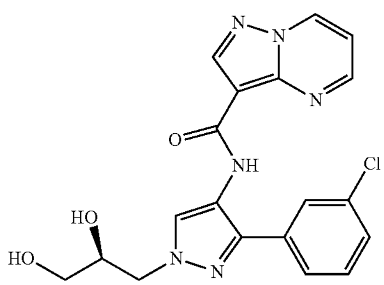 [SMILES: O=C(Nc1cn(C[C@H](O)CO)nc1-c1cccc(Cl)c1)c1cnn2cccnc12] | (S)-N-(3-(3-chlorophenyl)-1-(2,3-dihydroxypropyl)-1H-pyrazol-4-yl)pyrazolo[1,5-a]pyrimidine-3-carboxamide | 10 | 413.1 |
| 72 | 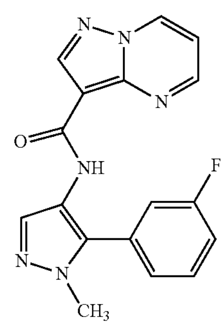 [SMILES: Cn1ncc(NC(=O)c2cnn3cccnc23)c1-c1cccc(F)c1] | N-(5-(3-fluorophenyl)-1-methyl-1H-pyrazol-4-yl)pyrazolo[1,5-a]pyrimidine-3-carboxamide | 8 | 337.3 |
| 73 | 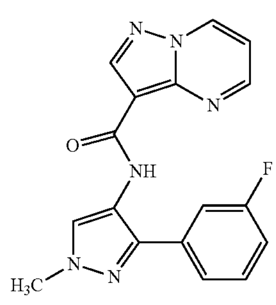 [SMILES: Cn1cc(NC(=O)c2cnn3cccnc23)c(-c2cccc(F)c2)n1] | N-(3-(3-fluorophenyl)-1-methyl-1H-pyrazol-4-yl)pyrazolo[1,5-pyrimidine-3-carboxamide | 8 | 337.3 |

TABLE 1-continued

| Ex | Structure | Name | Mthd | LCMS (ESI) m/z |
|---|---|---|---|---|
| 74 | 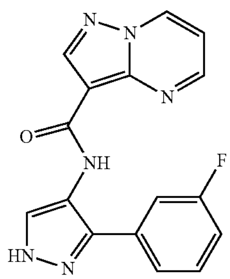 [SMILES: O=C(Nc1c[nH]nc1-c1cccc(F)c1)c1cnn2cccnc12] | N-(3-(3-fluorophenyl)-1H-pyrazol-4-yl)pyrazolo[1,5-a]pyrimidine-3-carboxamide | 9 | 323.0 |
| 75 | 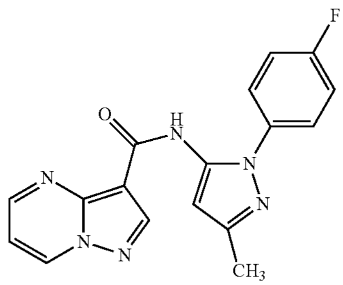 [SMILES: Cc1cc(NC(=O)c2cnn3cccnc23)n(-c2ccc(F)cc2)n1] | N-(1-(4-fluorophenyl)-3-methyl-1H-pyrazol-5-yl)pyrazolo[1,5-a]pyrimidine-3-carboxamide | 6 | 337.1 |
| 76 | 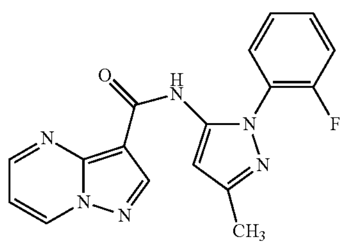 [SMILES: Cc1cc(NC(=O)c2cnn3cccnc23)n(-c2ccccc2F)n1] | N-(1-(2-fluorophenyl)-3-methyl-1H-pyrazol-5-yl)pyrazolo[1,5-a]pyrimidine-3-carboxamide | 6 | 337.0 |
| 77 | 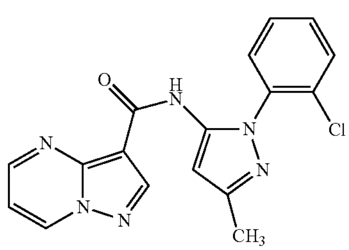 [SMILES: Cc1cc(NC(=O)c2cnn3cccnc23)n(-c2ccccc2Cl)n1] | N-(1-(2-chlorophenyl)-3-methyl-1H-pyrazol-5-yl)pyrazolo[1,5-a]pyrimidine-3-carboxamide | 6 | 353.1 |
| 78 | 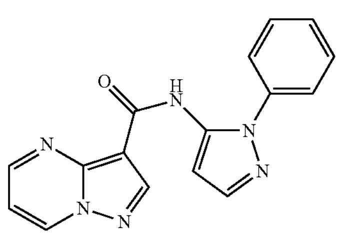 [SMILES: O=C(Nc1ccnn1-c1ccccc1)c1cnn2cccnc12] | N-(1-phenyl-1H-pyrazol-5-yl)pyrazolo[1,5-a]pyrimidine-3-carboxamide | 13 | 305.0 |

TABLE 1-continued

| Ex | Structure | Name | Mthd | LCMS (ESI) m/z |
|---|---|---|---|---|
| 79 | 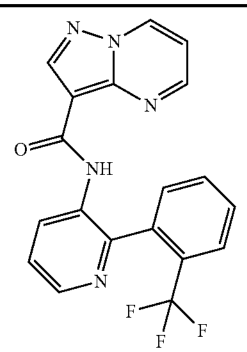 | N-(2-(2-(trifluoromethyl)phenyl)pyridin-3-yl)pyrazolo[1,5-a]pyrimidine-3-carboxamide | 7 | 384.1 |
| 80 | 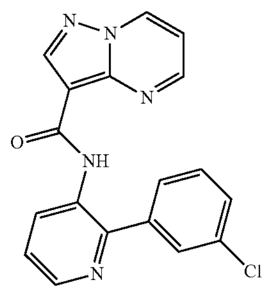 [SMILES: O=C(Nc1cccnc1-c1cccc(Cl)c1)c1cnn2cccnc12] | N-(2-(3-chlorophenyl)pyridin-3-yl)pyrazolo[1,5-a]pyrimidine-3-carboxamide | 7 | 350.0 |
| 81 | 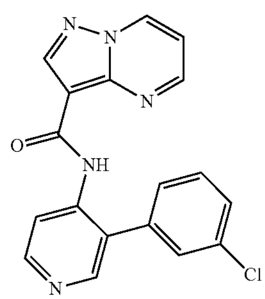 [SMILES: O=C(Nc1ccncc1-c1cccc(Cl)c1)c1cnn2cccnc12] | N-(3-(3-chlorophenyl)pyridin-4-yl)pyrazolo[1,5-a]pyrimidine-3-carboxamide | 7 | 350.0 |
| 82 | 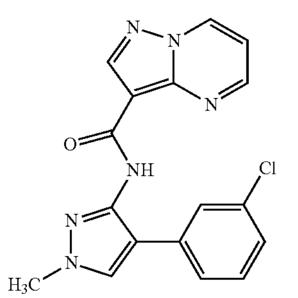 [SMILES: Cn1cc(-c2cccc(Cl)c2)c(NC(=O)c2cnn3cccnc23)n1] | N-(4-(3-chlorophenyl)-1-methyl-1H-pyrazol-3-yl)pyrazolo[1,5-a]pyrimidine-3-carboxamide | 12 | 353.0 |
| 83 | 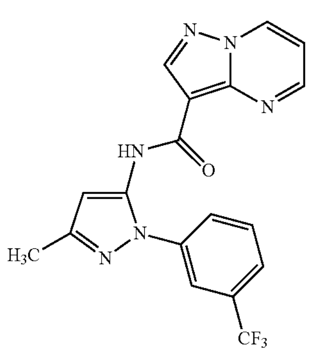 [SMILES: Cc1cc(NC(=O)c2cnn3cccnc23)n(-c2cccc(C(F)(F)F)c2)n1] | N-(3-methyl-1-(3-(trifluoromethyl)phenyl)-1H-pyrazol-5-yl)pyrazolo[1,5-a]pyrimidine-3-carboxamide | 6 | 386.8 |

TABLE 1-continued

| Ex | Structure | Name | Mthd | LCMS (ESI) m/z |
|---|---|---|---|---|
| 84 | 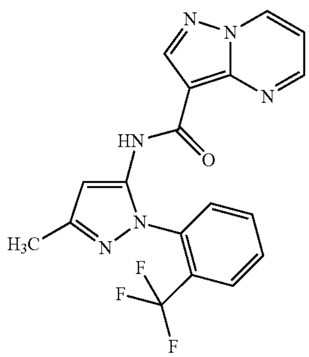 [SMILES: Cc1cc(NC(=O)c2cnn3cccnc23)n(-c2ccccc2C(F)(F)F)n1] | N-(3-methyl-1-(2-(trifluoromethyl)phenyl)-1H-pyrazol-5-yl)pyrazolo[1,5-a]pyrimidine-3-carboxamide | 6 | 387.2 |
| 85 | 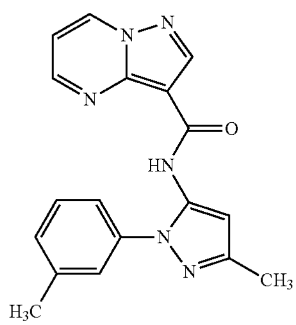 [SMILES: Cc1cccc(-n2nc(C)cc2NC(=O)c2cnn3cccnc23)c1] | N-(3-methyl-1-m-tolyl-1H-pyrazol-5-yl)pyrazolo[1,5-a]pyrimidine-3-carboxamide | 6 | 333.2 |
| 86 | 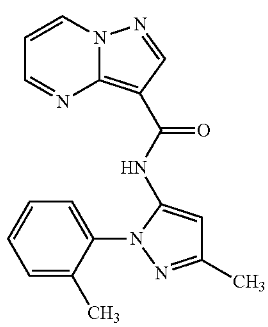 [SMILES: Cc1cc(NC(=O)c2cnn3cccnc23)n(-c2ccccc2C)n1] | N-(3-methyl-1-o-tolyl-1H-pyrazol-5-yl)pyrazolo[1,5-a]pyrimidine-3-carboxamide | 6 | 332.9 |
| 87 | 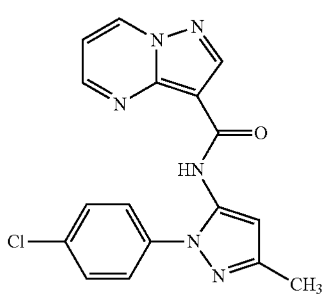 [SMILES: Cc1cc(NC(=O)c2cnn3cccnc23)n(-c2ccc(Cl)cc2)n1] | N-(1-(4-chlorophenyl)-3-methyl-1H-pyrazol-5-yl)pyrazolo[1,5-a]pyrimidine-3-carboxamide | 6 | 353.1 |

TABLE 1-continued

| Ex | Structure | Name | Mthd | LCMS (ESI) m/z |
|---|---|---|---|---|
| 88 | 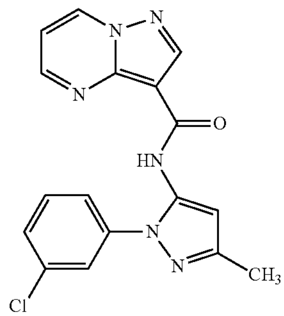 [SMILES: Cc1cc(NC(=O)c2cnn3cccnc23)n(-c2cccc(Cl)c2)n1] | N-(1-(3-chlorophenyl)-3-methyl-1H-pyrazol-5-yl)pyrazolo[1,5-a]pyrimidine-3-carboxamide | 6 | 353.1 |
| 89 | 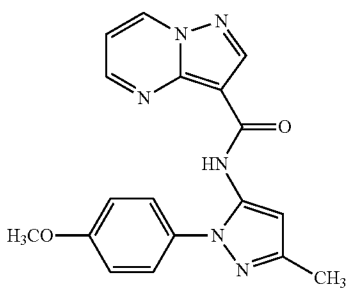 [SMILES: COc1ccc(-n2nc(C)cc2NC(=O)c2cnn3cccnc23)cc1] | N-(1-(4-methoxyphenyl)-3-methyl-1H-pyrazol-5-yl)pyrazolo[1,5-a]pyrimidine-3-carboxamide | 6 | 349.2 |
| 90 | 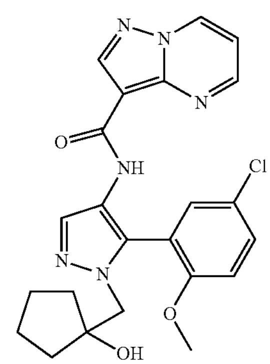 [SMILES: COc1ccc(Cl)cc1-c1c(NC(=O)c2cnn3cccnc23)cnn1CC1(O)CCCC1] | N-(5-(5-chloro-2-methoxyphenyl)-1-((1-hydroxycyclopentyl)methyl)-1H-pyrazol-4-yl)pyrazolo[1,5-a]pyrimidine-3-carboxamide | 24 | 467.1 |
| 91 | 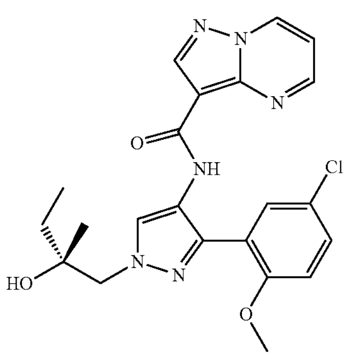 [SMILES: CC[C@@](C)(O)Cn1cc(NC(=O)c2cnn3cccnc23)c(-c2cc(Cl)ccc2OC)n1] | (R)-N-(3-(5-chloro-2-methoxyphenyl)-1-(2-hydroxy-2-methylbutyl)-1H-pyrazol-4-yl)pyrazolo[1,5-a]pyrimidine-3-carboxamide | 22 | 455.1 |

TABLE 1-continued

| Ex | Structure | Name | Mthd | LCMS (ESI) m/z |
|---|---|---|---|---|
| 92 | 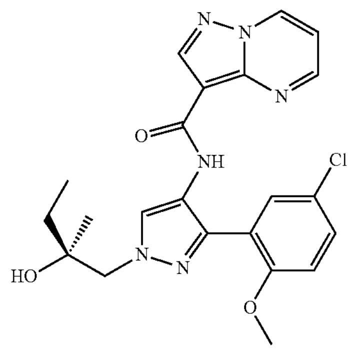 [SMILES: CC[C@](C)(O)Cn1cc(NC(=O)c2cnn3cccnc23)c(-c2cc(Cl)ccc2OC)n1] | (S)-N-(3-(5-chloro-2-methoxyphenyl)-1-(2-hydroxy-2-methylbutyl)-1H-pyrazol-4-yl)pyrazolo[1,5-a]pyrimidine-3-carboxamide | 22 | 455.1 |
| 93 | 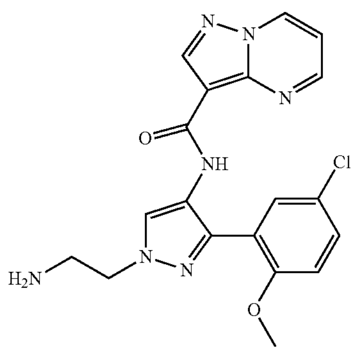 [SMILES: COc1ccc(Cl)cc1-c1nn(CCN)cc1NC(=O)c1cnn2cccnc12] | N-(1-(2-aminoethyl)-3-(5-chloro-2-ethoxyphenyl)-1H-pyrazol-4-yl)pyrazolo[1,5-a]pyrimidine-3-carboxamide | 20, 21 | 426.1 |
| 94 | 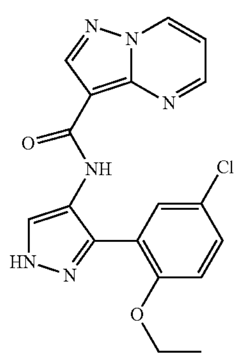 [SMILES: CCOc1ccc(Cl)cc1-c1n[nH]cc1NC(=O)c1cnn2cccnc12] | N-(3-(5-chloro-2-ethoxyphenyl)-1H-pyrazol-4-yl)pyrazolo[1,5-a]pyrimidine-3-carboxamide | 20 | 383.0 |
| 95 | 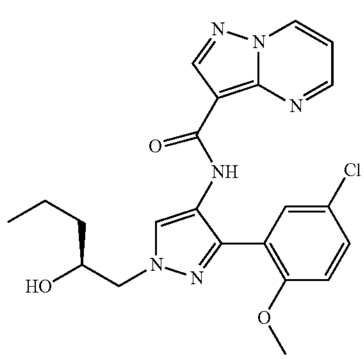 [SMILES: CCC[C@H](O)Cn1cc(NC(=O)c2cnn3cccnc23)c(-c2cc(Cl)ccc2OC)n1] | (S)-N-(3-(5-chloro-2-methoxyphenyl)-1-(2-hydroxypentyl)-1H-pyrazol-4-yl)pyrazolo[1,5-a]pyrimidine-3-carboxamide | 22 | 455.1 |

TABLE 1-continued

| Ex | Structure | Name | Mthd | LCMS (ESI) m/z |
|----|-----------|------|------|----------------|
| 96 | 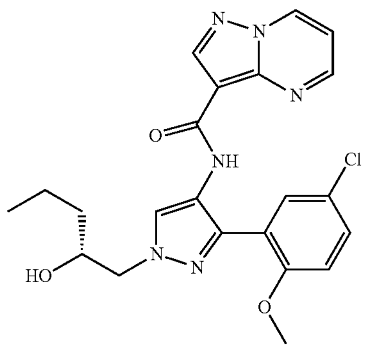 [SMILES: CCC[C@@H](O)Cn1cc(NC(=O)c2cnn3cccnc23)c(-c2cc(Cl)ccc2OC)n1] | (R)-N-(3-(5-chloro-2-methoxyphenyl)-1-(2-hydroxypentyl)-1H-pyrazol-4-yl)pyrazolo[1,5-a]pyrimidine-3-carboxamide | 22 | 455.1 |
| 97 | 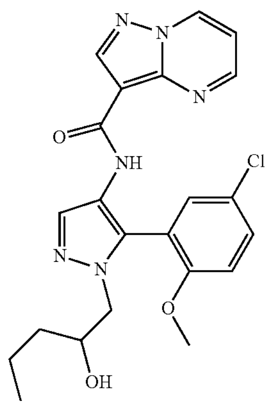 [SMILES: CCCC(O)Cn1ncc(NC(=O)c2cnn3cccnc23)c1-c1cc(Cl)ccc1OC] | N-(5-(5-chloro-2-methoxyphenyl)-1-(2-hydroxypentyl)-1H-pyrazol-4-yl)pyrazolo[1,5-a]pyrimidine-3-carboxamide | 16 | 455.1 |
| 98 | 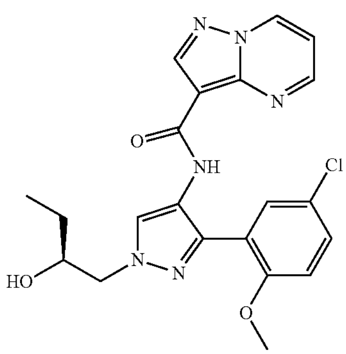 [SMILES: CC[C@H](O)Cn1cc(NC(=O)c2cnn3cccnc23)c(-c2cc(Cl)ccc2OC)n1] | (S)-N-(3-(5-chloro-2-methoxyphenyl)-1-(2-hydroxybutyl)-1H-pyrazol-4-yl)pyrazolo[1,5-a]pyrimidine-3-carboxamide | 22 | 441.1 |
| 99 | 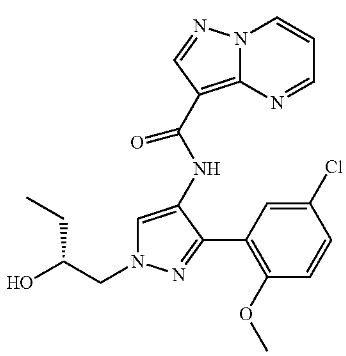 [SMILES: CC[C@@H](O)Cn1cc(NC(=O)c2cnn3cccnc23)c(-c2cc(Cl)ccc2OC)n1] | (R)-N-(3-(5-chloro-2-methoxyphenyl)-1-(2-hydroxybutyl)-1H-pyrazol-4-yl)pyrazolo[1,5-a]pyrimidine-3-carboxamide | 22 | 441.1 |

TABLE 1-continued

| Ex | Structure | Name | Mthd | LCMS (ESI) m/z |
|----|-----------|------|------|----------------|
| 100 | 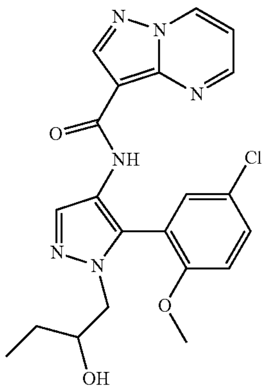 [SMILES: CCC(O)Cn1ncc(NC(=O)c2cnn3cccnc23)c1-c1cc(Cl)ccc1OC] | N-(5-(5-chloro-2-methoxyphenyl)-1-(2-hydroxybutyl)-1H-pyrazol-4-yl)pyrazolo[1,5-a]pyrimidine-3-carboxamide | 16 | 441.1 |
| 101 | | N-(3-(5-chloro-2-methoxyphenyl)-1-((1S,2S)-2-hydroxycyclohexyl)-1H-pyrazol-4-yl)pyrazolo[1,5-a]pyrimidine-3-carboxamide And | 16 | 467.1 |
| | | N-(3-(5-chloro-2-methoxyphenyl)-1-((1R,2R)-2-hydroxycyclohexyl)-1H-pyrazol-4-yl)pyrazolo[1,5-a]pyrimidine-3-carboxamide | | |
| 102 | 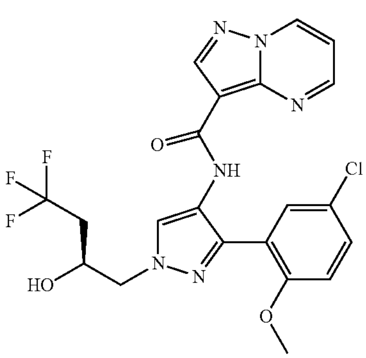 [SMILES: COc1ccc(Cl)cc1-c1nn(C[C@@H](O)CC(F)(F)F)cc1NC(=O)c1cnn2cccnc12] | (S)-N-(3-(5-chloro-2-methoxyphenyl)-1-(4,4,4-trifluoro-2-hydroxybutyl)-1H-pyrazol-4-yl)pyrazolo[1,5-a]pyrimidine-3-carboxamide | 22 | 495.1 |

TABLE 1-continued

| Ex | Structure | Name | Mthd | LCMS (ESI) m/z |
|---|---|---|---|---|
| 103 | 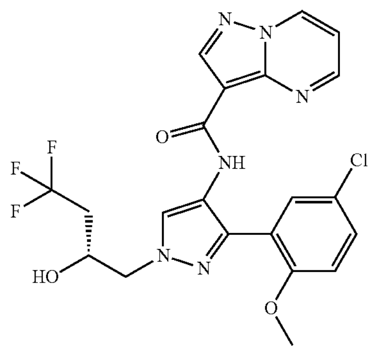 [SMILES: COc1ccc(Cl)cc1-c1nn(C[C@H](O)CC(F)(F)F)cc1NC(=O)c1cnn2cccnc12] | (R)-N-(3-(5-chloro-2-methoxyphenyl)-1-(4,4,4-trifluoro-2-hydroxybutyl)-1H-pyrazol-4-yl)pyrazolo[1,5-a]pyrimidine-3-carboxamide | 22 | 495.1 |
| 104 | 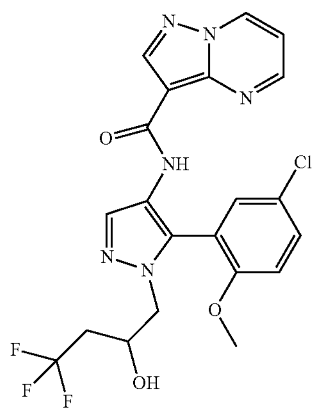 [SMILES: COc1ccc(Cl)cc1-c1c(NC(=O)c2cnn3cccnc23)cnn1CC(O)CC(F)(F)F] | N-(5-(5-chloro-2-methoxyphenyl)-1-(4,4,4-trifluoro-2-hydroxybutyl)-1H-pyrazol-4-yl)pyrazolo[1,5-a]pyrimidine-3-carboxamide | 16 | 495.1 |
| 105 | 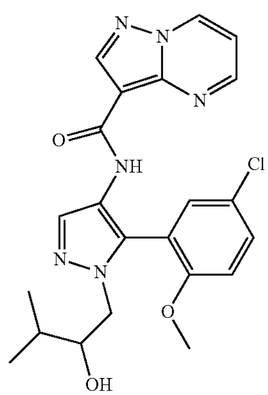 [SMILES: COc1ccc(Cl)cc1-c1c(NC(=O)c2cnn3cccnc23)cnn1CC(O)C(C)C] | N-(5-(5-chloro-2-methoxyphenyl)-1-(2-hydroxy-3-methylbutyl)-1H-pyrazol-4-yl)pyrazolo[1,5-a]pyrimidine-3-carboxamide | 16 | 455.1 |
| 106 | 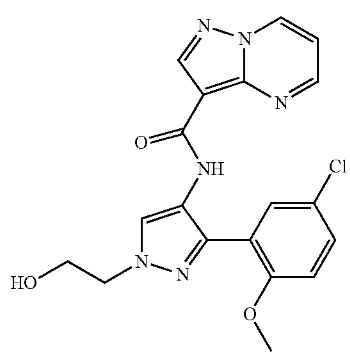 [SMILES: COc1ccc(Cl)cc1-c1nn(CCO)cc1NC(=O)c1cnn2cccnc12] | N-(3-(5-chloro-2-methoxyphenyl)-1-(2-hydroxyethyl)-1H-pyrazol-4-yl)pyrazolo[1,5-a]pyrimidine-3-carboxamide | 14 | 413.1 |

TABLE 1-continued

| Ex | Structure | Name | Mthd | LCMS (ESI) m/z |
|----|-----------|------|------|----------------|
| 107 | 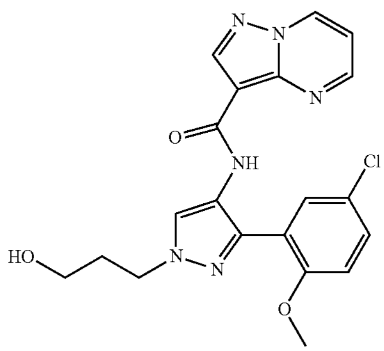 [SMILES: COc1ccc(Cl)cc1-c1nn(CCCO)cc1NC(=O)c1cnn2cccnc12] | N-(3-(5-chloro-2-methoxyphenyl)-1-(3-hydroxypropyl)-1H-pyrazol-4-yl)pyrazolo[1,5-a]pyrimidine-3-carboxamide | 14 | 427.1 |
| 108 | 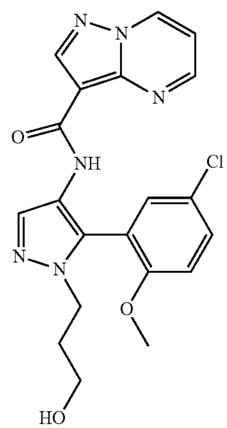 [SMILES: COc1ccc(Cl)cc1-c1c(NC(=O)c2cnn3cccnc23)cnn1CCCO] | N-(5-(5-chloro-2-methoxyphenyl)-1-(3-hydroxypropyl)-1H-pyrazol-4-yl)pyrazolo[1,5-a]pyrimidine-3-carboxamide | 15 | 427.1 |
| 109 | 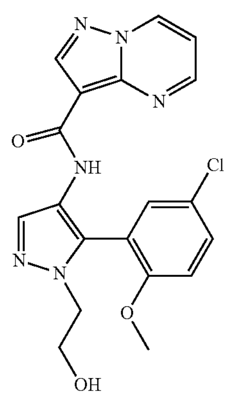 [SMILES: COc1ccc(Cl)cc1-c1c(NC(=O)c2cnn3cccnc23)cnn1CCO] | N-(5-(5-chloro-2-methoxyphenyl)-1-(2-hydroxyethyl)-1H-pyrazol-4-yl)pyrazolo[1,5-a]pyrimidine-3-carboxamide | 15 | 413.1 |
| 110 | 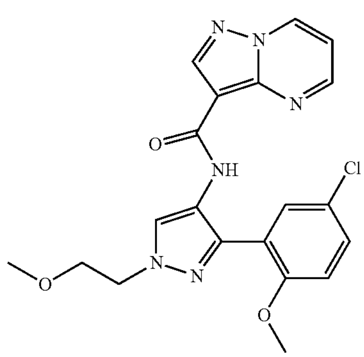 [SMILES: COCCn1cc(NC(=O)c2cnn3cccnc23)c(-c2cc(Cl)ccc2OC)n1] | N-(3-(5-chloro-2-methoxyphenyl)-1-(2-methoxyethyl)-1H-pyrazol-4-yl)pyrazolo[1,5-a]pyrimidine-3-carboxamide | 14 | 427.0 |

TABLE 1-continued

| Ex | Structure | Name | Mthd | LCMS (ESI) m/z |
|---|---|---|---|---|
| 111 | 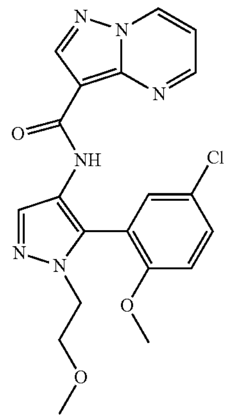 [SMILES: COCCn1ncc(NC(=O)c2cnn3cccnc23)c1-c1cc(Cl)ccc1OC] | N-(5-(5-chloro-2-methoxyphenyl)-1-(2-methoxyethyl)-1H-pyrazol-4-yl)pyrazolo[1,5-a]pyrimidine-3-carboxamide | 15 | 427.1 |
| 112 | 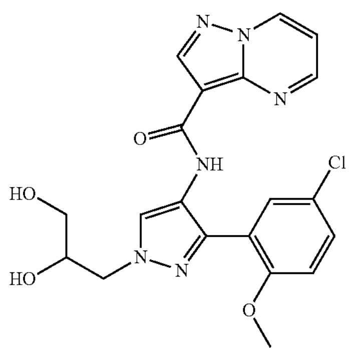 [SMILES: COc1ccc(Cl)cc1-c1nn(CC(O)CO)cc1NC(=O)c1cnn2cccnc12] | N-(3-(5-chloro-2-methoxyphenyl)-1-(2,3-dihydroxypropyl)-1H-pyrazol-4-yl)pyrazolo[1,5-a]pyrimidine-3-carboxamide | 16 | 443.1 |
| 113 | 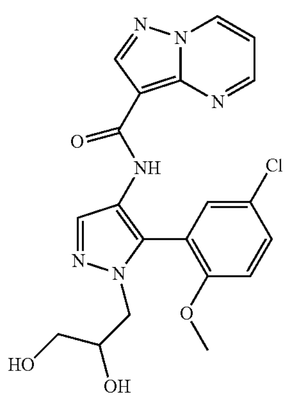 [SMILES: COc1ccc(Cl)cc1-c1c(NC(=O)c2cnn3cccnc23)cnn1CC(O)CO] | N-(5-(5-chloro-2-methoxyphenyl)-1-(2,3-dihydroxypropyl)-1H-pyrazol-4-yl)pyrazolo[1,5-a]pyrimidine-3-carboxamide | 16 | 443.1 |
| 114 | 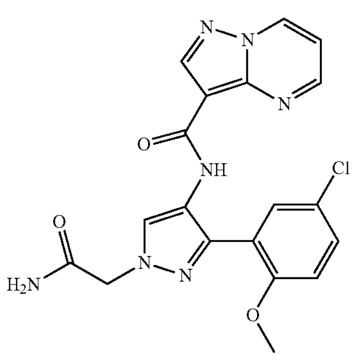 [SMILES: COc1ccc(Cl)cc1-c1nn(CC(N)=O)cc1NC(=O)c1cnn2cccnc12] | N-(1-(2-amino-2-oxoethyl)-3-(5-chloro-2-methoxyphenyl)-1H-pyrazol-4-yl)pyrazolo[1,5-a]pyrimidine-3-carboxamide | 14 | 426.1 |

TABLE 1-continued

| Ex | Structure | Name | Mthd | LCMS (ESI) m/z |
|---|---|---|---|---|
| 115 | 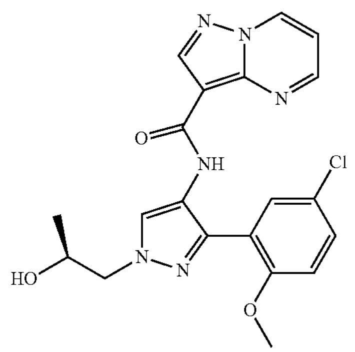 [SMILES: COc1ccc(Cl)cc1-c1nn(C[C@H](C)O)cc1NC(=O)c1cnn2cccnc12] | (S)-N-(3-(5-chloro-2-methoxyphenyl)-1-(2-hydroxypropyl)-1H-pyrazol-4-yl)pyrazolo[1,5-a]pyrimidine-3-carboxamide | 16 | 427.1 |
| 116 | 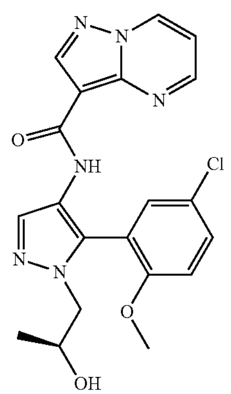 [SMILES: COc1ccc(Cl)cc1-c1c(NC(=O)c2cnn3cccnc23)cnn1C[C@H](C)O] | N-(5-(5-chloro-2-methoxyphenyl)-1-((S)-2-hydroxypropyl)-1H-pyrazol-4-yl)pyrazolo[1,5-a]pyrimidine-3-carboxamide | 16 | 427.1 |
| 117 | 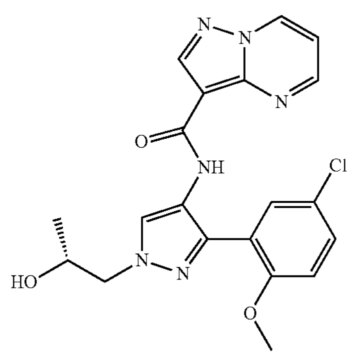 [SMILES: COc1ccc(Cl)cc1-c1nn(C[C@@H](C)O)cc1NC(=O)c1cnn2cccnc12] | (R)-N-(3-(5-chloro-2-methoxyphenyl)-1-(2-hydroxypropyl)-1H-pyrazol-4-yl)pyrazolo[1,5-a]pyrimidine-3-carboxamide | 16 | 427.1 |
| 118 | 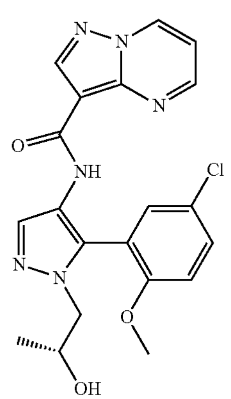 [SMILES: COc1ccc(Cl)cc1-c1c(NC(=O)c2cnn3cccnc23)cnn1C[C@@H](C)O] | N-(5-(5-chloro-2-methoxyphenyl)-1-((R)-2-hydroxypropyl)-1H-pyrazol-4-yl)pyrazolo[1,5-a]pyrimidine-3-carboxamide | 16 | 427.1 |

TABLE 1-continued

| Ex | Structure | Name | Mthd | LCMS (ESI) m/z |
|---|---|---|---|---|
| 119 | 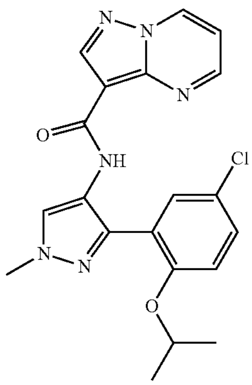 [SMILES: CC(C)Oc1ccc(Cl)cc1-c1nn(C)cc1NC(=O)c1cnn2cccnc12] | N-(3-(5-chloro-2-isopropoxyphenyl)-1-methyl-1H-pyrazol-4-yl)pyrazolo[1,5-a]pyrimidine-3-carboxamide | 17 | 411.1 |
| 120 | 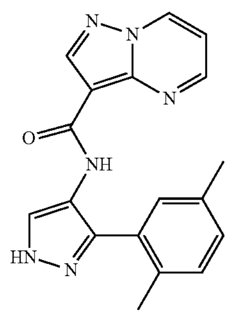 [SMILES: Cc1ccc(C)c(-c2n[nH]cc2NC(=O)c2cnn3cccnc23)c1] | N-(3-(2,5-dimethylphenyl)-1H-pyrazol-4-yl)pyrazolo[1,5-a]pyrimidine-3-carboxamide | 4 | 333.1 |
| 121 | 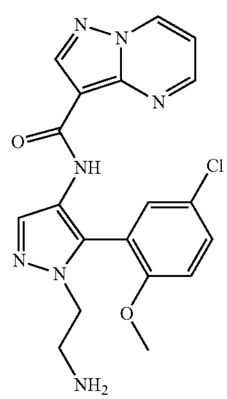 [SMILES: COc1ccc(Cl)cc1-c1c(NC(=O)c2cnn3cccnc23)cnn1CCN] | N-(1-(2-aminoethyl)-5-(5-chloro-2-methoxyphenyl)-1H-pyrazol-4-yl)pyrazolo[1,5-a]pyrimidine-3-carboxamide | 21 | 412.1 |
| 122 | 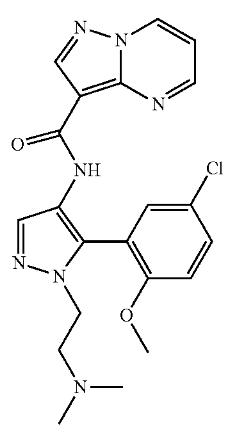 [SMILES: COc1ccc(Cl)cc1-c1c(NC(=O)c2cnn3cccnc23)cnn1CCN(C)C] | N-(5-(5-chloro-2-methoxyphenyl)-1-(2-(dimethylamino)ethyl)-1H-pyrazol-4-yl)pyrazolo[1,5-a]pyrimidine-3-carboxamide | 15 | 440.1 |

TABLE 1-continued

| Ex | Structure | Name | Mthd | LCMS (ESI) m/z |
|---|---|---|---|---|
| 123 | 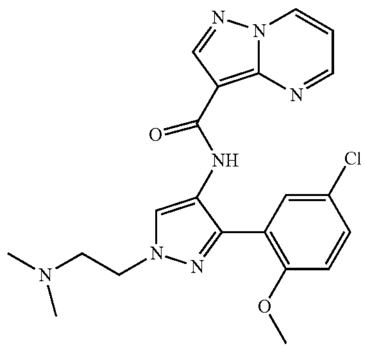 [SMILES: COc1ccc(Cl)cc1-c1nn(CCN(C)C)cc1NC(=O)c1cnn2cccnc12] | N-(3-(5-chloro-2-methoxyphenyl)-1-(2-(dimethylamino)ethyl)-1H-pyrazol-4-yl)pyrazolo[1,5-a]pyrimidine-3-carboxamide | 14 | 440.1 |
| 124 | 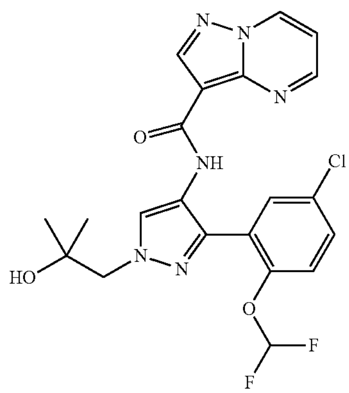 [SMILES: CC(C)(O)Cn1cc(NC(=O)c2cnn3cccnc23)c(-c2cc(Cl)ccc2OC(F)F)n1] | N-(3-(5-chloro-2-(difluoromethoxy)phenyl)-1-(2-hydroxy-2-methylpropyl)-1H-pyrazol-4-yl)pyrazolo[1,5-a]pyrimidine-3-carboxamide | 16 and 18 | 477.1 |
| 125 | 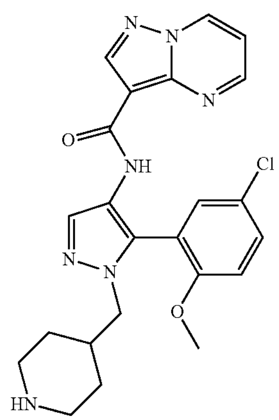 [SMILES: COc1ccc(Cl)cc1-c1c(NC(=O)c2cnn3cccnc23)cnn1CC1CCNCC1] | N-(5-(5-chloro-2-methoxyphenyl)-1-(piperidin-4-ylmethy;)methyl)-1H-pyrazol-4-yl)pyrazolo[1,5-a]pyrimidine-3-carboxamide | 26 | 466.1 |
| 126 | 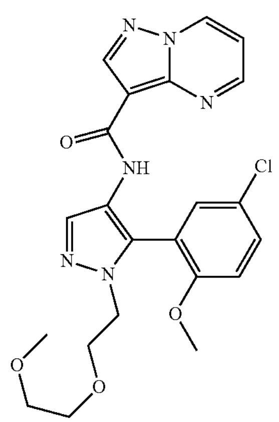 [SMILES: COCCOCCn1ncc(NC(=O)c2cnn3cccnc23)c1-c1cc(Cl)ccc1OC] | N-(5-(5-chloro-2-methoxyphenyl)-2-(2-methoxyethoxy)ethyl)-1H-pyrazol-4-yl)pyrazolo[1,5-a]pyrimidine-3-carboxamide | 26 | 471.1 |

TABLE 1-continued

| Ex | Structure | Name | Mthd | LCMS (ESI) m/z |
|----|-----------|------|------|----------------|
| 127 | 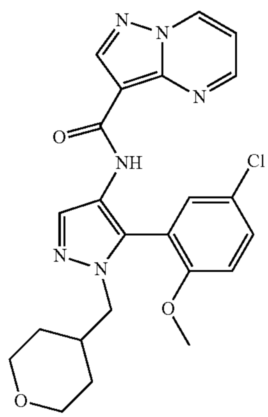 [SMILES: COc1ccc(Cl)cc1-c1c(NC(=O)c2cnn3cccnc23)cnn1CC1CCOCC1] | N-(5-(5-chloro-2-methoxyphenyl)-1-((tetrahydro-2H-pyran-4-yl)methyl)-1H-pyrazol-4-yl)pyrazolo[1,5-a]pyrimidine-3-carboxamide | 26 | 467.1 |
| 128 | 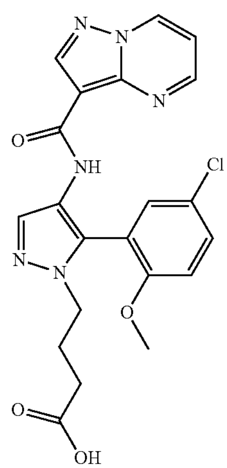 [SMILES: COc1ccc(Cl)cc1-c1c(NC(=O)c2cnn3cccnc23)cnn1CCCC(=O)O] | 4-(5-(5-chloro-2-methoxyphenyl)-4-(pyrazolo-4-yl)pyrazolo[1,5-a]pyrimidine-3-carboxamido)-1H-pyrazol-1-yl)butanoic acid | 26 | 455.1 |
| 129 | 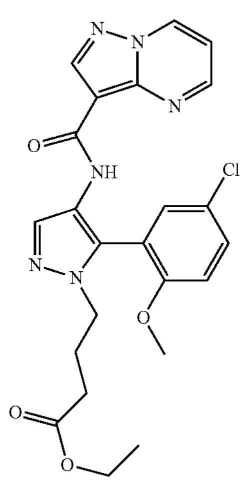 [SMILES: CCOC(=O)CCCn1ncc(NC(=O)c2cnn3cccnc23)c1-c1cc(Cl)ccc1OC] | Ethyl-4-(5-(5-chloro-2-methoxyphenyl)-4-(pyrazolo-4-yl)pyrazolo[1,5-a]pyrimidine-3-carboxamido)-1H-pyrazol-1-yl)butanoate | 26 | 483.1 |

TABLE 1-continued
| Ex | Structure | Name | Mthd | LCMS (ESI) m/z |
|---|---|---|---|---|
| 130 | 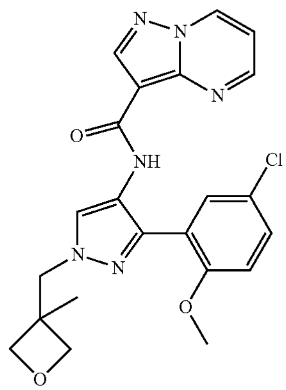 [SMILES: COc1ccc(Cl)cc1-c1nn(CC2(C)COC2)cc1NC(=O)c1cnn2cccnc12] | N-(3-(5-chloro-2-methoxyphenyl)-1-(3-methyloxetan-3-yl)methyl)-1H-pyrazol-4-yl)pyrazolo[1,5-a]pyrimidine-3-carboxamide | 26 | 453.1 |
| 131 | 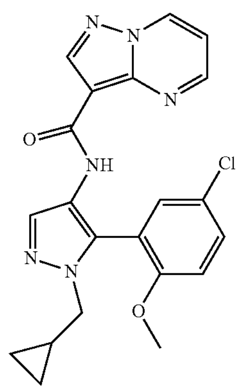 [SMILES: COc1ccc(Cl)cc1-c1c(NC(=O)c2cnn3cccnc23)cnn1CC1CC1] | N-(5-(5-chloro-2-methoxyphenyl)-1-(cyclopropylmethyl)-1H-pyrazol-4-yl)pyrazolo[1,5-a]pyrimidine-3-carboxamide | 26 | 423.1 |
Example 132
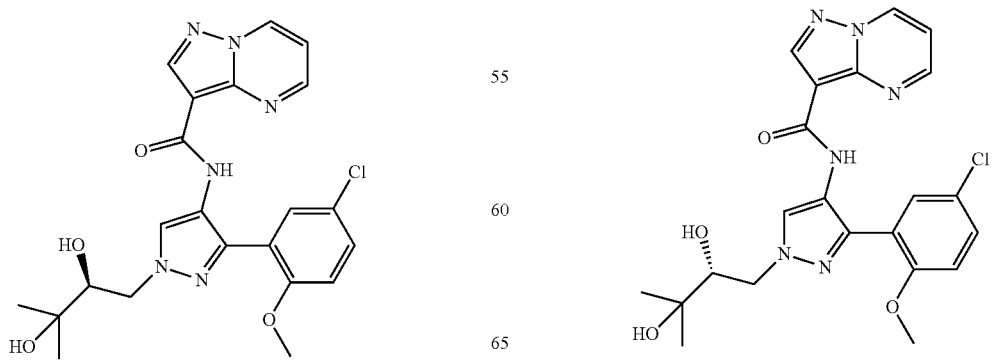
-continued (S)—N-(3-(5-chloro-2-methoxyphenyl)-1-(2,3-dihydroxy-3-methylbutyl)-1H-pyrazol-4-yl)pyrazolo[1,5-a]pyrimidine-3-carboxamide (R)—N-(3-(5-chloro-2-methoxyphenyl)-1-(2,3-dihydroxy-3-methylbutyl)-1H-pyrazol-4-yl)pyrazolo[1,5-a]pyrimidine-3-carboxamide To a suspension of N-(5-(5-chloro-2-methoxyphenyl)-1H-pyrazol-4-yl)pyrazolo[1,5-a]pyrimidine-3-carboxamide (114.0 mg, 0.31 mmol) and cesium carbonate (201.4 mg, 0.62 mmol) in N,N-dimethylformamide (2 mL), was added 4-bromo-2-methyl-2-butene (53 µL, 0.46 mmol). The reaction mixture was stirred for 3 hours at room temperature, then EtOAc was added. The organic layer was washed 1× each with water and saturated brine solution. The organic layer was separated, then dried over Na$_2$SO$_4$ and concentrated in vacuo. The residue was purified by silica gel chromatography (20-100% EtOAc:Hex) to afford N-(3-(5-chloro-2-methoxyphenyl)-1-(3-methylbut-2-enyl)-1H-pyrazol-4-yl)pyrazolo[1,5-a]pyrimidine-3-carboxamide as a light yellow foam (67 mg, 0.15 mmol). Acetone and water (1 mL each) were then added, followed by osmium tetraoxide (1.89 mg, 0.0074 mmol), and N-methylmorpholine-N-oxide in water (1:1, N-methylmorpholine-N-oxide:Water, 37 mg). The reaction mixture was stirred for 3 hours at room temperature. Celite was added and the mixture was concentrated in vacuo. The residue was purified by silica gel chromatography (50-100% EtOAc*:Hex, *EtOAc also contained 10% MeOH), and then by chiral SFC to separate enantiomers to give 11.2 mg and 15.8 mg of the title compounds as white solids. LCMS (ESI) m+H=471.1; $^1$H NMR (500 MHz, DMSO) δ 9.69 (s, 1H), 9.34 (d, J=6.9, 1H), 8.78 (d, J=4.0, 1H), 8.66 (s, 1H), 8.30 (s, 1H), 7.49 (dd, J=8.8, 2.6, 1H), 7.42 (d, J=2.6, 1H), 7.29 (dd, J=10.0, 4.6, 2H), 5.05 (d, J=6.3, 1H), 4.53 (s, 1H), 4.43 (d, J=13.5, 1H), 3.95 (dd, J=13.5, 10.1, 1H), 3.85 (s, 3H), 3.60 (s, 1H), 1.16 (s, 3H), 1.10 (s, 3H).

Example 133

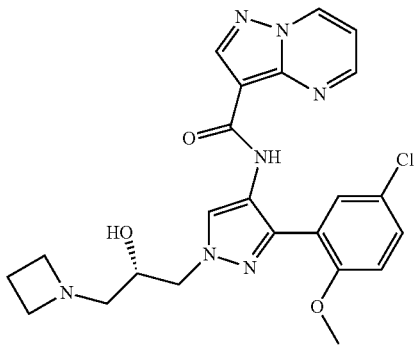 [SMILES: COc1ccc(Cl)cc1-c1nn(C[C@@H](O)CN2CCC2)cc1NC(=O)c1cnn2cccnc12]

(S)—N-(1-(3-(azetidin-1-yl)-2-hydroxypropyl)-3-(5-chloro-2-methoxyphenyl)-1H-pyrazol-4-yl)pyrazolo pyrimidine-3-carboxamide To a suspension of N-(5-(5-chloro-2-methoxyphenyl)-1H-pyrazol-4-yl)pyrazolo[1,5-a]pyrimidine-3-carboxamide (60 mg, 0.16 mmol) and cesium carbonate (212 mg, 0.65 mmol) in N,N-Dimethylformamide (1 mL) was added (S)-2-(chloromethyl)oxirane (26.3 mg, 0.28 mmol). The reaction mixture was stirred for 8 hours at room temperature, at which time LCMS analysis showed complete consumption of starting material. Azetidine (44 uL, 0.65 mmol) was added and the reaction mixture was stirred for an additional 16 hours at room temperature. The reaction mixture was filtered and purified by reverse phase HPLC to afford the title compound as a white solid (7.8 mg). LCMS (ESI) m+H=482.2; $^1$H NMR (400 MHz, DMSO) δ 9.69 (s, 1H), 9.34 (dd, J=7.0, 1.6, 1H), 8.78 (dd, J=4.2, 1.6, 1H), 8.66 (s, 1H), 8.27 (s, 1H), 7.50 (dd, J=8.9, 2.7, 1H), 7.40 (d, J=2.7, 1H), 7.33-7.26 (m, 2H), 4.94 (d, J=5.4, 1H), 4.21 (dd, J=13.7, 3.8, 1H), 3.99 (dd, J=13.8, 7.8, 1H), 3.84 (s, 3H), 3.77 (s, 1H), 3.17 (t, J=6.9, 4H), 2.39 (qd, J=12.0, 5.9, 2H), 2.02-1.93 (m, 2H).

Example 134

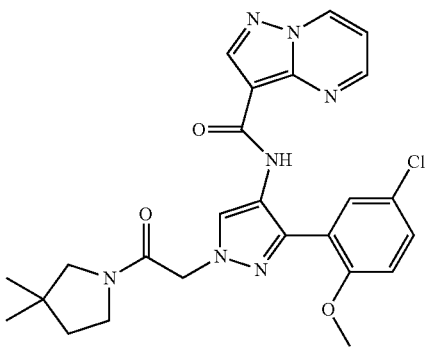 [SMILES: COc1ccc(Cl)cc1-c1nn(CC(=O)N2CCC(C)(C)C2)cc1NC(=O)c1cnn2cccnc12]

N-(3-(5-chloro-2-methoxyphenyl)-1-(2-(3,3-dimethylpyrrolidin-1-yl)-2-oxoethyl)-1H-pyrazol-4-yl)pyrazolo[1,5-a]pyrimidine-3-carboxamide

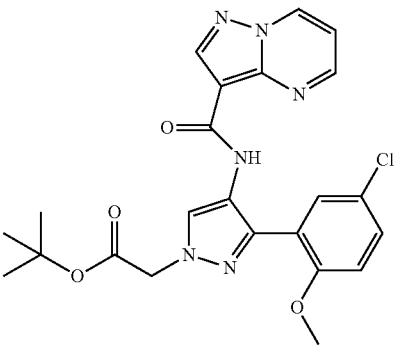 [SMILES: COc1ccc(Cl)cc1-c1nn(CC(=O)OC(C)(C)C)cc1NC(=O)c1cnn2cccnc12]

tert-butyl 2-(3-(5-chloro-2-methoxyphenyl)-4-(pyrazolo[1,5-a]pyrimidine-3-carboxamido)-1H-pyrazol-1-yl)acetate N-(3-(5-chloro-2-methoxyphenyl)-1H-pyrazol-4-yl)pyrazolo pyrimidine-3-carboxamide (2.0 g, 5.4 mmol), t-butylbromoacetate (0.88 mL, 6.0 mmol), and cesium carbonate (2.1 g, 6.5 mmol) were combined and stirred at 30° C. overnight. The mixture was warmed to 65° C. at which time additional carbonate and t-butylbromoacetate was added and stirred 8 hrs. The mixture was cooled to ambient temperature and stirred overnight, then partitioned EtOAc/water. The organic phase was separated, washed with brine, dried (Na₂SO₄), filtered through silica gel, and concentrated to a solid. The solid was washed with 1:1 EtOAc/hexanes to yield 1.85 g (71%) of tert-butyl 2-(3-(5-chloro-2-methoxyphenyl)-4-(pyrazolo[1,5-a]pyrimidine-3-carboxamido)-1H-pyrazol-1-yl)acetate as yellow crystals. LCMS (ESI) m+H=483.0. ¹H NMR (400 MHz, CDCl₃) δ 9.74 (s, 1H), 8.77 (m, 1H), 8.73 (s, 1H), 8.51 (m, 1H0, 8.38 (s, 1H), 8.02 (s, 1H), 7.58 (s, 1H), 7.31 (m, 1H), 6.97 (m, 2H), 4.85 (s, 2H), 3.83 (s, 3H), 1.49 (s, 9H).

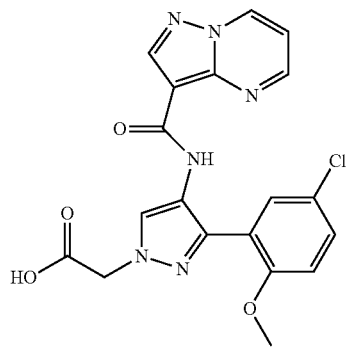 [SMILES: COc1ccc(Cl)cc1-c1nn(CC(=O)O)cc1NC(=O)c1cnn2cccnc12]

2-(3-(5-chloro-2-methoxyphenyl)-4-(pyrazolo[1,5-a]pyrimidine-3-carboxamido)-1H-pyrazol-1-yl)acetic acid To tert-butyl 2-(3-(5-chloro-2-methoxyphenyl)-4-(pyrazolo[1,5-a]pyrimidine-3-carboxamido)-1H-pyrazol-1-yl)acetate (1.85 g, 3.83 mmol) in 50 mL dichloromethane was added 30 ml of TFA. The mixture was stirred 2 h at ambient temperature, then concentrated and recrystallized from EtOAc to furnish 1.4 g (86%) of 2-(3-(5-chloro-2-methoxyphenyl)-4-(pyrazolo[1,5-a]pyrimidine-3-carboxamido)-1H-pyrazol-1-yl)acetic acid as a colorless solid. LCMS (ESI) m+H=427.1. ¹H NMR (400 MHz, CD₃OD) δ 9.95 (s, 1H), 9.08 (m, 1H), 8.69 (m, 1H), 8.63 (s, 1H), 8.34 (s, 1H), 7.47 (m, 2H), 7.21 (m, 2H), 5.03 (s, 2H), 3.86 (s, 3H).

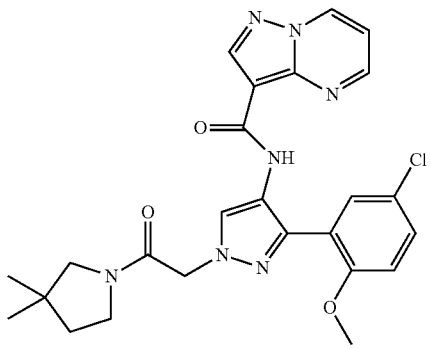 [SMILES: COc1ccc(Cl)cc1-c1nn(CC(=O)N2CCC(C)(C)C2)cc1NC(=O)c1cnn2cccnc12]

N-(3-(5-chloro-2-methoxyphenyl)-1-(2-(3,3-dimethylpyrrolidin-1-yl)-2-oxoethyl)-1H-pyrazol-4-yl)pyrazolo[1,5-a]pyrimidine-3-carboxamide To 2-(3-(5-chloro-2-methoxyphenyl)-4-(pyrazolo[1,5-a]pyrimidine-3-carboxamido)-1H-pyrazol-1-yl)acetic acid (31.9 mg, 0.075 mmol) in 1 mL DMF was added 3,3-dimethylpyrrolidine HCl (15 mg, 0.11 mmol) followed by N,N,N',N'-tetramethyl-O-(7-azabenzotriazol-1-yl)uronium hexafluorophosphate (43 mg, 0.11 mmol), then triethylamine (42 uL, 0.30 mmol) and the whole stirred 30 min. The crude mixture was purified by reverse phase HPLC and lyophilized to afford 28.9 mg (76%) as a colorless solid. LCMS (ESI) m+H=508.1. ¹H NMR (400 MHz, DMSO) δ 9.72 (s, 1H), 9.34 (d, J=6.9 Hz, 1H), 8.77 (s, 1H), 8.67 (s, 1H), 8.28 (s, 1H), 7.50 (d, J=8.9 Hz, 1H), 7.37 (s, 1H), 7.30 (t, J=9.3 Hz, 2H), 5.09 (d, J=17.8 Hz, 2H), 3.85 (s, 3H), 3.62 (t, J=6.7 Hz, 1H), 3.43 (t, J=7.1 Hz, 1H), 3.29 (s, 1H), 3.12 (s, 1H), 1.74 (t, J=7.0 Hz, 1H), 1.63 (t, J=6.9 Hz, 1H), 1.08 (d, J=9.9 Hz, 6H).

Example 135

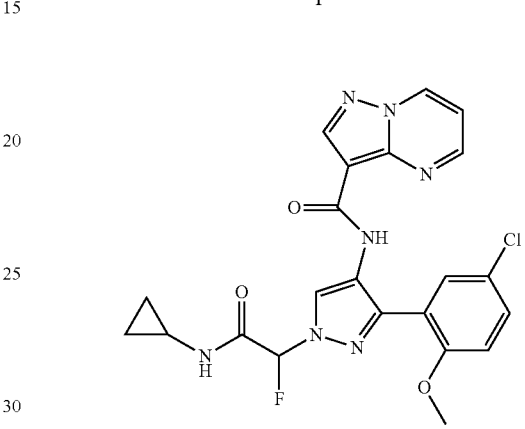

N-(3-(5-chloro-2-methoxyphenyl)-1-(2-(cyclopropylamino)-1-fluoro-2-oxoethyl)-1H-pyrazol-4-yl)pyrazolo pyrimidine-3-carboxamide

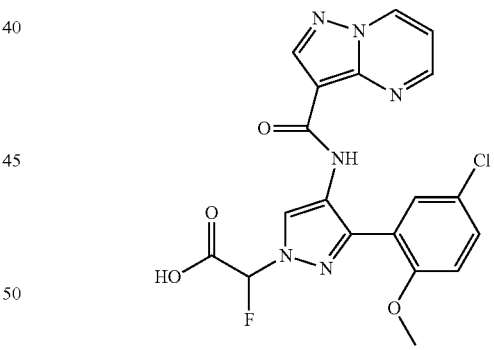

2-(3-(5-chloro-2-methoxyphenyl)-4-(pyrazolo pyrimidine-3-carboxamido)-1H-pyrazol-1-yl)-2-fluoroacetic acid To N-(3-(5-chloro-2-methoxyphenyl)-1H-pyrazol-4-yl)pyrazolo pyrimidine-3-carboxamide (37.1 mg, 0.10 mmol) in 1.5 DMF was added sodium hydride (10 mg, 0.40 mmol) and the mixture stirred for 5 min at which time ethyl bromofluoroacetate (37 mg, 0.20 mmol) was added. The mixture was stirred overnight, then purified by reverse phase HPLC and lyophilized to afford 13.3 mg (30%) of 2-(3-(5-chloro-2-methoxyphenyl)-(pyrazolo[1,5-a]pyrimidine-3-carboxamido)-1H-pyrazol-1-yl)-2-fluoroacetic acid as a colorless solid. LCMS (ESI) m+H=445.1. ¹H NMR (400 MHz, DMSO) δ 9.71 (s, 1H), 9.33 (d, J=7.0 Hz, 1H), 8.76-8.71 (m, 1H), 8.66 (d, J=8.3 Hz, 1H), 8.38 (s, 1H), 7.58-7.20 (m, 5H), 5.98 (d, J=56.5 Hz, 1H), 3.84 (s, 3H).

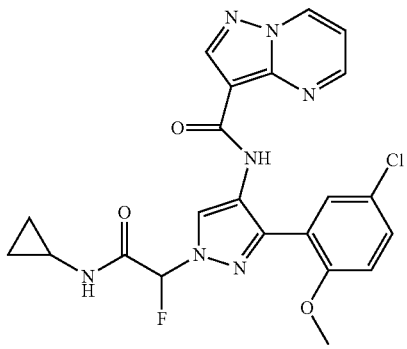 [SMILES: COc1ccc(Cl)cc1-c1nn(C(F)C(=O)NC2CC2)cc1NC(=O)c1cnn2cccnc12]

N-(3-(5-chloro-2-methoxyphenyl)-1-(2-(cyclopropylamino)-1-fluoro-2-oxoethyl)-1H-pyrazol-4-yl)pyrazolo pyrimidine-3-carboxamide To 2-(3-(5-chloro-2-methoxyphenyl)-4-(pyrazolo[1,5-a]pyrimidine-3-carboxamido)-1H-pyrazol-1-yl)-2-fluoroacetic acid (39.1 mg, 0.088 mmol) and cyclopropylamine (10 mg, 0.18 mmol) in 1.0 mL DMF was added (7-azabenzotriazol-1-yloxy)tripyrrolidinophosphonium hexafluorophosphate (91 mg, 0.18 mmol) and the mixture stirred for 1 h. The crude mixture was purified by reverse phase HPLC and lyophilized to give 9.1 mg (21%) of N-(3-(5-chloro-2-methoxyphenyl)-1-(2-(cyclopropylamino)-1-fluoro-2-oxoethyl)-1H-pyrazol-4-yl)pyrazolo[1,5-a]pyrimidine-3-carboxamide as a colorless solid. LCMS (ESI) m+H=484.1. ¹H NMR (400 MHz, DMSO) δ 9.77 (s, 1H), 9.34 (dd, J=7.0, 1.4 Hz, 1H), 8.83 (d, J=4.4 Hz, 1H), 8.76 (dd, J=4.2, 1.5 Hz, 1H), 8.68 (s, 1H), 8.55 (s, 1H), 7.58 (dd, J=8.9, 2.7 Hz, 1H), 7.37 (t, J=5.7 Hz, 2H), 7.29 (dd, J=7.0, 4.2 Hz, 1H), 6.80 (d, J=50.7 Hz, 1H), 3.85 (s, 3H), 2.82 (dd, J=7.3, 3.3 Hz, 1H), 0.70 (t, J=7.0 Hz, 2H), 0.64-0.57 (m, 2H).

Example 136

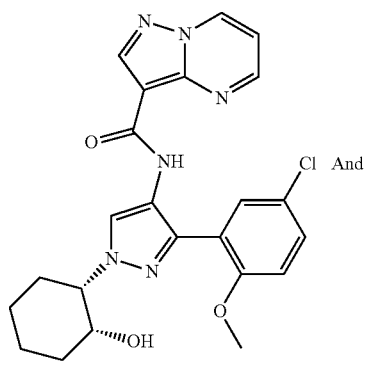

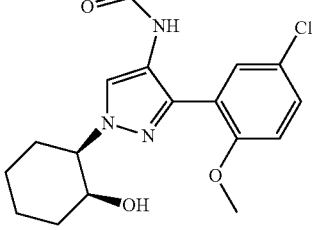

N-(3-(5-chloro-2-methoxyphenyl)-1-((1S,2R)-2-hydroxycyclohexyl)-1H-pyrazol-4-yl)pyrazolo pyrimidine-3-carboxamide And N-(3-(5-chloro-2-methoxyphenyl)-1-((1R,2S)-2-hydroxycyclohexyl)-1H-pyrazol-4-yl)pyrazolo pyrimidine-3-carboxamide To a stirring solution of N-(3-(5-chloro-2-methoxyphenyl)-1-((1S,2S)-2-hydroxycyclohexyl)-1H-pyrazol-1-yl)pyrazolo[1,5-a]pyrimidine-3-carboxamide and N-(3-(5-chloro-2-methoxyphenyl)-1-((1R,2R)-2-hydroxycyclohexyl)-1H-pyrazol-4-yl)pyrazolo pyrimidine-3-carboxamide (mixture of trans enantiomers; 107 mg, 0.229 mmol), 4-nitrobenzoic acid (50.6 mg, 0.303 mmol) and triphenylphosphine (81.8 mg, 0.312 mmol) in 3.0 mL tetrahydrofuran was dropwise added diethylazodicarboxylate (47.0 µL, 0.298 mmol). The reaction mixture was stirred at room temperature for one hour and then heated at 50° C. for 2.5 hours. 4-Nitrobenzoic acid (51 mg), triphenylphosphine (86 mg), and diethylazodicarboxylate (53 µL) were then added and the reaction mixture heated 50° C. overnight. The reaction mixture was partitioned between ethyl acetate and water, and the organic portion washed with brine, dried over magnesium sulfate, and evaporated in vacuo. The crude product was subjected to flash chromatography on silica gel (0 to 100% ethyl acetate in dichloromethane) to yield the mixture of enantiomers (1R,2S)- and (1S,2R)-2-(3-(5-chloro-2-methoxyphenyl)-4-(pyrazolo[1,5-a]pyrimidine-3-carboxamido)-1H-pyrazol-1-yl)cyclohexyl 4-nitrobenzoate as a mixture with triphenyl phosphine oxide. This material was carried forward without further purification.

The crude material from the previous step was dissolved in 3 mL tetrahydrofuran with 5.0 M sodium hydroxide in water (1.0 mL). The reaction mixture was stirred at room temperature for 18 hours. The reaction mixture was poured into ethyl acetate and washed twice with 2M aqueous sodium hydroxide. The organic layer was dried over magnesium sulfate and evaporated in vacuo. The crude product was purified by reverse phase HPLC and lyophilized to give 8.5 mg of the mixture of enantiomers N-(3-(5-chloro-2-methoxyphenyl)-1-((1S,2R)-2-hydroxycyclohexyl)-1H-pyrazol-4-yl)pyrazolo[1,5-a]pyrimidine-3-carboxamide and N-(3-(5-chloro-2-methoxyphenyl)-1-((1R,2S)-2-hydroxycyclohexyl)-1H-pyrazol-4-yl)pyrazolo pyrimidine-3-carboxamide. LCMS (ESI) m+H=467.1; ¹H NMR (400 MHz, DMSO-d6) δ: 9.68 (s, 1H), 9.33 (dd, J=7.0, 1.6 Hz, 1H), 8.78 (dd, J=4.2, 1.6 Hz, 1H), 8.65 (s, 1H), 8.33 (s, 1H), 7.49 (dd, J=8.8, 2.7 Hz, 1H), 7.42 (d, J=2.7 Hz, 1H), 7.33-7.25 (m, 2H), 4.84 (d, J=4.3 Hz, 1H), 4.24 (d, J=12.1 Hz, 1H), 4.11 (s, 1H), 3.84 (s, 3H), 2.16 (td, J=12.4, 8.6 Hz, 1H), 1.81 (m, 3H), 1.62 (dt, J=26.0, 13.0 Hz, 2H), 1.43 (d, J=6.1 Hz, 2H).

Example 137

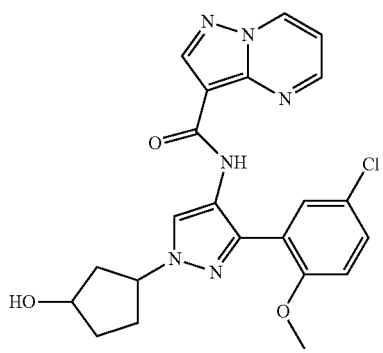 [SMILES: COc1ccc(Cl)cc1-c1nn(C2CCC(O)C2)cc1NC(=O)c1cnn2cccnc12]

N-(3-(5-chloro-2-methoxyphenyl)-1-(3-hydroxycyclopentyl)-1H-pyrazol-4-yl)pyrazolo[1,5-a]pyrimidine-3-carboxamide To a solution of N-(3-(5-chloro-2-methoxyphenyl)-1-(3-hydroxycyclopentyl)-1H-pyrazol-4-yl)pyrazolo[1,5-a]pyrimidine-3-carboxamide (171.1 mg, 0.3795 mmol) in 5.0 mL tetrahydrofuran at −78° C. was added 1.0 M lithium tri-tert-butoxyaluminum hydride in tetrahydrofuran (0.6 mL, 0.6 mmol). The reaction mixture was kept at −60° C. for 4 hours, and then 1.0 M lithium tri-tert-butoxyaluminum hydride in tetrahydrofuran (0.6 mL, 0.6 mmol) was added. The reaction mixture was kept at −25° C. for 8 hours. 1.0 M lithium tri-tert-butoxyaluminum hydride in tetrahydrofuran (0.9 mL, 0.9 mmol) was added and the reaction mixture was kept at −25° C. for an additional 6 hours until reduction of the ketone is judged complete by LCMS. The reaction mixture was then cooled at −40° C. and quenched with 3 mL saturated aqueous ammonium chloride. After warming to room temperature, this mixture was extracted with dichloromethane, and the organic extract was dried over magnesium sulfate and evaporated in vacuo. The crude product was purified by reverse phase HPLC and lyophilized to give 34 mg (20%) of N-(3-(5-chloro-2-methoxyphenyl)-1-(3-hydroxycyclopentyl)-1H-pyrazol-4-yl)pyrazolo[1,5-a]pyrimidine-3-carboxamide. LCMS (ESI) m+H=453.1; $^1$H NMR (400 MHz, DMSO-d6) δ: 9.67 (s, 1H), 9.34 (dd, J=7.0, 1.6 Hz, 1H), 8.78 (dd, J=4.2, 1.6 Hz, 1H), 8.64 (s, 1H), 8.38 (s, 1H), 7.50 (dd, J=8.8, 2.7 Hz, 1H), 7.40 (d, J=2.7 Hz, 1H), 7.34-7.25 (m, 2H), 4.90 (d, J=4.6 Hz, 1H), 4.83-4.69 (m, 1H), 4.21 (dd, J=10.2, 5.5 Hz, 1H), 3.85 (s, 3H), 2.42 (ddd, J=14.6, 8.7, 6.2 Hz, 1H), 2.21-2.04 (m, 2H), 2.00-1.87 (m, 1H), 1.86-1.70 (m, 2H).

Example 138

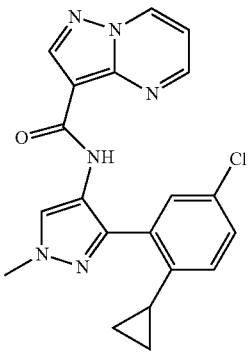 [SMILES: Cn1cc(NC(=O)c2cnn3cccnc23)c(-c2cc(Cl)ccc2C2CC2)n1]

N-(3-(5-chloro-2-cyclopropylphenyl)-1-methyl-1H-pyrazol-4-yl)pyrazolo[1,5-a]pyrimidine-3-carboxamide

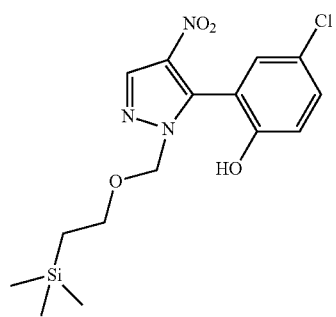 [SMILES: C[Si](C)(C)CCOCn1ncc([N+](=O)[O-])c1-c1cc(Cl)ccc1O]

4-chloro-2-(4-nitro-1-((2-(trimethylsilyl)ethoxy)methyl)-1H-pyrazol-5-yl)phenol

To a solution of 5-(5-chloro-2-(4-methoxybenzyloxy)phenyl)-4-nitro-1-((2-(trimethylsilyl)ethoxy)methyl)-1H-pyrazole (prepared according to the procedure described for Example 14) (1.193 g, 2.434 mmol) in 17 mL dichloromethane was added 3 mL water followed by dichlorodicyanoquinone (1.2208 g). The reaction was stirred at room temperature for 48 hours, and then additional Dichlorodicyanoquinone (0.4946 g) was added. After an additional 24 hours, the reaction was poured into saturated aqueous sodium bicarbonate and extracted with dichloromethane. The organic portion was dried over magnesium sulfate and evaporated in vacuo. The crude product was purified via flash chromatography on silica gel (0 to 35% ethyl acetate in heptanes) to yield 745.2 mg (83%) of 4-chloro-2-(4-nitro-1-((2-(trimethylsilyl)ethoxy)methyl)-1H-pyrazol-5-yl)phenol. LCMS (ESI) m+H=270.2; $^1$H NMR (400 MHz, DMSO-d6) δ: 10.47 (s, 1H), 8.44 (s, 1H), 7.47 (d, J=2.6 Hz, 1H), 7.43 (dd, J=8.8, 2.7, 1H), 7.00 (d, J=8.8 Hz, 1H), 5.30 (dd, J=65.1, 10.8, 2H), 3.42 (t, J=8.1, 2H), 0.74 (t, 2H), −0.08 (s, 9H).

181

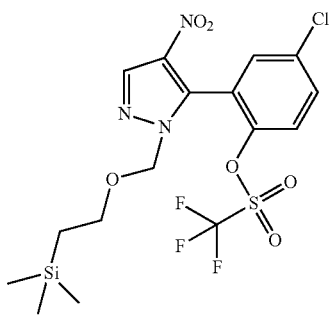 [SMILES: C[Si](C)(C)CCOCn1ncc([N+](=O)[O-])c1-c1cc(Cl)ccc1OS(=O)(=O)C(F)(F)F]

4-chloro-2-(4-nitro-1-((2-(trimethylsilyl)ethoxy)
methyl)-1H-pyrazol-5-yl)phenyl trifluoromethane-
sulfonate To a solution of 4-chloro-2-(4-nitro-1-((2-(trimethylsilyl)
ethoxy)methyl)-1H-pyrazol-5-3-yl)phenol (190.4 mg, 0.5148 mmol) in 8 mL dichloromethane at −40° C. was added triethylamine (0.30 mL, 2.2 mmol) followed by trifluoromethanesulfonic anhydride (0.15 mL, 0.89 mmol). After 30 minutes at this temperature the reaction mixture was warmed to room temperature. After 3 hours, the reaction mixture was poured into water and extracted twice with dichloromethane. The combined organic portions were dried over magnesium sulfate and evaporated in vacuo. The crude product was purified via flash chromatography on silica gel (0 to 30% ethyl acetate in heptanes) to yield 239.8 mg (93%) of 4-chloro-2-(4-nitro-1-((2-(trimethylsilyl)ethoxy)methyl)-1H-pyrazol-5-yl)phenyl trifluoromethanesulfonate. LCMS (ESI) m+Na=524.0.

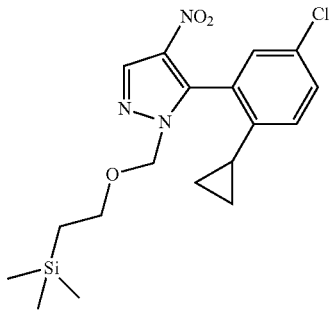 [SMILES: C[Si](C)(C)CCOCn1ncc([N+](=O)[O-])c1-c1cc(Cl)ccc1C1CC1]

5-(5-chloro-2-cyclopropylphenyl)-4-nitro-1-((2-(tri-
methylsilyl)ethoxy)methyl)-1H-pyrazole To a mixture of 4-chloro-2-(4-nitro-1-((2-(trimethylsilyl)
ethoxy)methyl)-1H-pyrazol-5-yl)phenyl trifluoromethane-
sulfonate (72.4 mg, 0.144 mmol), cyclopropylboronic acid (55.0 mg, 0.640 mmol), tetrakis(triphenylphosphine)palladium(0) (79.2 mg, 0.685 mmol), potassium phosphate (152.7 mg, 0.7194 mmol), and sodium bromide (149.2 mg, 1.450 mmol) was added water (13.0 µL, 0.722 mmol) and toluene (3.0 mL). The reaction mixture was heated at 90° C. for 72 hours. The reaction mixture was partitioned between ethyl acetate and water, and the organic layer washed with brine, dried over magnesium sulfate, and evaporated in vacuo. The crude product was purified via flash chromatography on silica gel (0 to 30% ethyl acetate in heptanes) to yield 30.1 mg (53%) of 5-(5-chloro-2-cyclopropylphenyl)-4-nitro-1-((2-(trimethylsilyl)ethoxy)methyl)-1H-pyrazole. LCMS (ESI) m+Na=416.2.

182

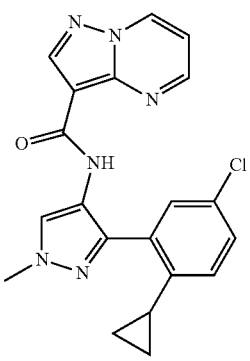 [SMILES: Cn1cc(NC(=O)c2cnn3cccnc23)c(-c2cc(Cl)ccc2C2CC2)n1]

N-(3-(5-chloro-2-cyclopropylphenyl)-1-methyl-1H-
pyrazol-4-yl)pyrazolo pyrimidine-3-carboxamide The title compound was synthesized from 5-(5-chloro-2-cyclopropylphenyl)-4-nitro-1-((2-(trimethylsilyl)ethoxy)methyl)-1H-pyrazole following the procedures described for Example 14. LCMS (ESI) m+H=393.1; $^1$H NMR (400 MHz, DMSO-d6) δ: 9.66 (s, 1H), 9.31 (dd, J=7.0, 1.5 Hz, 1H), 8.65 (s, 1H), 8.54-8.50 (m, 1H), 8.29 (s, 1H), 7.43 (dd, J=8.5, 2.3 Hz, 1H), 7.35 (d, J=2.3 Hz, 1H), 7.24 (dd, J=7.0, 4.2 Hz, 1H), 7.00 (d, J=8.6 Hz, 1H), 3.92 (s, 3H), 1.98 (s, 1H), 0.79 (dt, J=6.2, 4.3 Hz, 2H), 0.66-0.59 (m, 2H).

Example 139

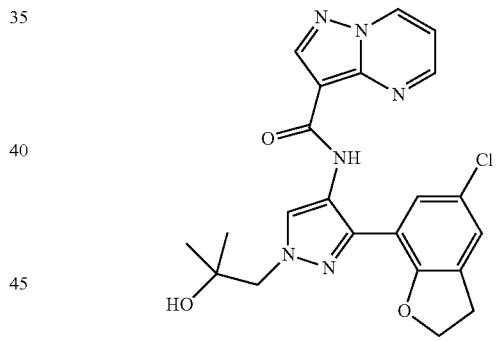

N-(3-(5-chloro-2,3-dihydrobenzofuran-7-yl)-1-(2-
hydroxy-2-methylpropyl)-1H-pyrazol-4-yl)pyrazolo
[1,5-a]pyrimidine-3-carboxamide

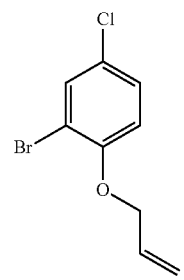

1-(allyloxy)-2-bromo-4-chlorobenzene

To a solution of 2-Bromo-4-chlorophenol (7.7897 g, 37.549 mmol) in 20 mL DMF was added potassium carbonate (5.784 g, 41.85 mmol) and allyl bromide (3.30 mL, 38.1 mmol). The reaction mixture was stirred at 50° C. for 15 hours. The reaction mixture was partitioned between ethyl acetate and water, and the organic layer washed with brine, dried over magnesium sulfate, and evaporated in vacuo to yield 9.4 g (100%) of 1-(allyloxy)-2-bromo-4-chlorobenzene, which was carried forward without further purification. $^1$H NMR (400 MHz, CDCl$_3$) δ: 7.54 (d, J=2.5, 1H), 7.21 (dd, J=8.8, 2.5, 1H), 6.81 (d, J=8.8, 1H), 6.10-5.98 (m, 1H), 5.46 (dd, J=17.3, 1.4, 1H), 5.31 (dd, J=10.6, 1.3, 1H), 4.59 (d, J=5.0, 2H).

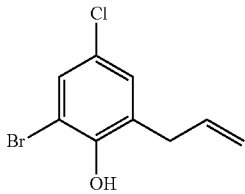

2-allyl-6-bromo-4-chlorophenol

A solution of 1-(allyloxy)-2-bromo-4-chlorobenzene (4.122 g, 16.65 mmol) in N,N-diethylaniline (20 mL, 100 mmol) was heated at 200° C. for 15 hours. After cooling to room temperature, the reaction mixture was partitioned between ethyl acetate and 1M aqueous HCl, and the organic layer washed with an additional portion of 1M aqueous HCl and then brine. The organic layer was dried over magnesium sulfate and evaporated in vacuo. The crude product was purified via flash chromatography on silica gel (0 to 20% ethyl acetate in heptanes) to yield 3.1761 g (77%) of 2-allyl-6-bromo-4-chlorophenol as a clear, colorless oil. 1H NMR (400 MHz, CDCl3) δ: 7.33 (d, J=2.4, 1H), 7.07 (d, J=2.3, 1H), 5.94 (ddt, J=16.8, 10.3, 6.6, 1H), 5.53 (s, 1H), 5.18-5.06 (m, 2H) 3.40 (d J=6.6, 2H).

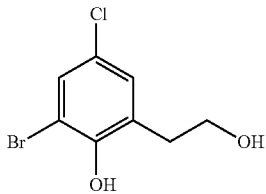 [SMILES: OCCc1cc(Cl)cc(Br)c1O]

2-bromo-4-chloro-6-(2-hydroxyethyl)phenol

A solution of 2-allyl-6-bromo-4-chlorophenol (1.378 g, 5.567 mmol) in 20 mL dichloromethane was cooled at −78° C. While stirring at this temperature, ozone was bubbled through the reaction solution for 6.5 hours. After flushing the reaction vessel with oxygen, while still at −78° C., the reaction was quenched with sodium tetrahydroborate (1.064 g, 28.12 mmol). The reaction was then warmed to room temperature and stirred overnight. The reaction mixture was partitioned between ethyl acetate and water, and the organic layer washed with brine, dried over magnesium sulfate, and evaporated in vacuo. The crude product was purified via flash chromatography on silica gel (10 to 60% ethyl acetate in heptanes) to yield 0.5911 g (42%) of 2-bromo-4-chloro-6-(2-hydroxyethyl)phenol. 1H NMR (400 MHz, CDCl3) δ: 7.38 (d, J=2.5, 1H), 7.27 (s, 1H), 7.06 (d, J=2.4, 1H), 3.96 (br s, 2H), 2.91 (t, J=5.7, 2H), 1.98 (s, 1H).

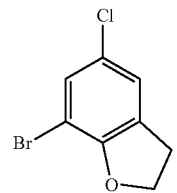

7-bromo-5-chloro-2,3-dihydrobenzofuran

To a mixture of 2-bromo-4-chloro-6-(2-hydroxyethyl)phenol (99.8 mg, 0.397 mmol), triethylamine (0.40 mL, 2.9 mmol), and dichloromethane (4 mL) at 0° C. was added methanesulfonyl chloride (56.0 µL, 0.724 mmol). The reaction was stirred at 0° C. for 1.5 hours, at which point additional methane sulfonyl chloride (10 µL) was added and the reaction mixture warmed to room temperature. After stirring overnight, the reaction mixture was re-cooled to 0° C. and triethylamine (0.2 mL) and methanesulfonyl chloride (15 µL) were added. After two hours the reaction mixture was partitioned between ethyl acetate and water, and the organic layer washed with brine, dried over magnesium sulfate, and evaporated in vacuo. The crude product was purified via flash chromatography on silica gel (0 to 30% ethyl acetate in heptanes) to yield 40.0 mg (40%) of 7-bromo-5-chloro-2,3-dihydrobenzofuran. $^1$H NMR (400 MHz, CDCl$_3$) δ: 7.26 (d, 1H), 7.09 (d, 1H), 4.67 (t, J=8.8, 2H), 3.30 (t, J=8.8, 2H).

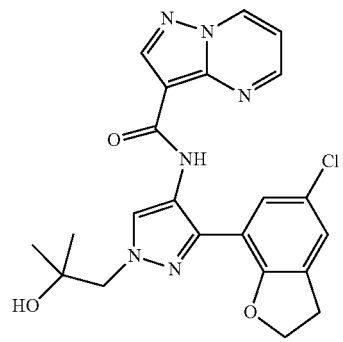 [SMILES: CC(C)(O)Cn1cc(NC(=O)c2cnn3cccnc23)c(-c2cc(Cl)cc3c2OCC3)n1]

N-(3-(5-chloro-2,3-dihydrobenzofuran-7-yl)-1-(2-hydroxy-2-methylpropyl)-1H-pyrazol-4-yl)pyrazolo[1,5-a]pyrimidine-3-carboxamide The title compound was prepared using 7-bromo-5-chloro-2,3-dihydrobenzofuran and following the procedures described for examples 14 and 16. LCMS (ESI) m+H=453.1; $^1$H NMR (400 MHz, DMSO-d6) δ: 9.72 (s, 1H), 9.33 (d, J=7.0, 1H), 8.82 (dd, J=4.2, 1.5, 1H), 8.65 (s, 1H), 8.35 (s, 1H), 7.36 (s, 1H), 7.33-7.23 (m, 2H), 4.70 (s, 1H), 4.62 (t, J=8.8, 2H), 4.07 (s, 2H), 3.37 (t, J=8.8, 2H), 1.12 (s, 6H).

Example 140

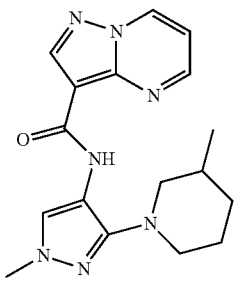 [SMILES: CC1CCCN(c2nn(C)cc2NC(=O)c2cnn3cccnc23)C1]

N-(1-methyl-3-(3-methylpiperidin-1-yl)-1H-pyrazol-4-yl)pyrazolo[1,5-a]pyrimidine-3-carboxamide

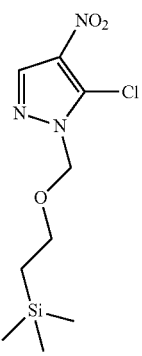 [SMILES: C[Si](C)(C)CCOCn1ncc([N+](=O)[O-])c1Cl]

5-chloro-4-nitro-1-((2-(trimethylsilyl)ethoxy)methyl)-1H-pyrazole

In an oven-dried flask, 4-nitro-1-((2-(trimethylsilyl)ethoxy)methyl)-1H-pyrazole (412.4 mg, 1.695 mmol) was dissolved in 5 mL THF and cooled at −78° C. To this solution was slowly added 1.0M Lithium hexamethyldisilazide in tetrahydrofuran (2.0 mL, 2.0 mmol). After stirring for 30 minutes at −78° C., a solution of hexachloroethane (455.2 mg, 1.923 mmol) in 3 mL THF was slowly added. The reaction mixture was kept at −78° C. for an additional hour, and then quenched with saturated aqueous ammonium chloride and warmed to room temperature. The reaction mixture was partitioned between ethyl acetate and water, and the organic layer dried over magnesium sulfate and evaporated in vacuo to yield 0.4592 g (98%) of 5-chloro-4-nitro-1-((2-(trimethylsilyl)ethoxy)methyl)-1H-pyrazole, which was carried forward without further purification. LCMS (ESI) m+H=220.2; $^1$H NMR (400 MHz, DMSO-d6) δ: 8.52 (s, 1H), 5.56 (s, 2H), 3.67-3.57 (m, 2H), 0.91-0.83 (m, 2H), −0.04 (s, 9H).

3-methyl-1-(4-nitro-1-((2-(trimethylsilyl)ethoxy)methyl)-1H-pyrazol-5-yl)piperidine To a solution of 5-chloro-4-nitro-1-((2-(trimethylsilyl)ethoxy)methyl)-1H-pyrazole (348.3 mg, 1.254 mmol) in 1 mL n-butanol was added 3-methyl-piperidine (0.20 mL, 1.7 mmol). The reaction mixture was subjected to microwave irradiation at a temperature of 120° C. for 30 minutes. The solvent was evaporated in vacuo and the crude product purified via flash chromatography on silica gel (0 to 40% ethyl acetate in heptanes) to yield 486.5 mg of 3-methyl-1-(4-nitro-1-((2-(trimethylsilyl)ethoxy)methyl)-1H-pyrazol-5-yl)piperidine. LCMS (ESI) m+H=341.4; $^1$H NMR (400 MHz, DMSO-d6) δ: 8.04 (s, 1H), 5.36 (s, 2H), 3.71-3.62 (m, 2H), 3.20 (m, 3H), 2.96-2.85 (m, 1H), 1.84-1.76 (m, 4H), 1.15 (m, 1H), 0.97-0.87 (m, 5H), 0.00 (s, 9H).

N-(1-methyl-3-(3-methylpiperidin-1-yl)-1H-pyrazol-4-yl)pyrazolo[1,5-a]pyrimidine-3-carboxamide The title compound was prepared using 3-methyl-1-(4-nitro-1-((2-(trimethylsilyl)ethoxy)methyl)-1H-pyrazol-5-yl) piperidine and following the procedures described for Example 14. LCMS (ESI) m+H=340.1; $^1$H NMR (400 MHz, DMSO-d6) δ: 9.59 (s, 1H), 9.36 (dd, J=7.0, 1.5, 1H), 8.83 (dd, J=4.2, 1.6, 1H), 8.66 (s, 1H), 7.98 (s, 1H), 7.32 (dd, J=7.0, 4.2, 1H), 3.71 (s, 3H), 3.25 (s, 1H), 2.64 (s, 1H), 2.41-2.29 (m, 1H), 1.96-1.70 (m, 4H), 1.04 (s, 1H), 0.91 (d, J=6.7, 3H).

Example 141

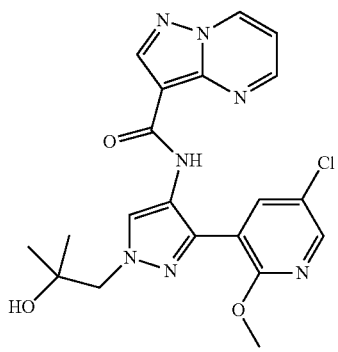 [SMILES: COc1ncc(Cl)cc1-c1nn(CC(C)(C)O)cc1NC(=O)c1cnn2cccnc12]

N-(3-(5-chloro-2-methoxypyridin-3-yl)-1-(2-hydroxy-2-methylpropyl)-1H-pyrazol-4-yl)pyrazolo[1,5-a]pyrimidine-3-carboxamide

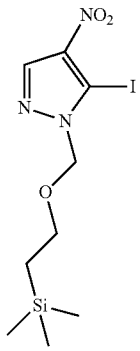 [SMILES: C[Si](C)(C)CCOCn1ncc([N+](=O)[O-])c1I]

5-iodo-4-nitro-1-((2-(trimethylsilyl)ethoxy)methyl)-1H-pyrazole

In an oven-dried flask, 4-nitro-1-((2-(trimethylsilyl)ethoxy)methyl)-1H-pyrazole (1.5192 g, 6.2432 mmol) was dissolved in 20 mL THF and cooled at −78° C. To this solution was slowly added 1.0M lithium hexamethyldisilazide in tetrahydrofuran (7.5 mL, 7.5 mmol). After stirring for 40 minutes at −78° C., a solution of iodine (1.7602 g, 6.9351 mmol) in 8 mL THF was slowly added. The reaction mixture was kept at −78° C. for an additional 1.5 hours, and then quenched with saturated aqueous ammonium chloride and warmed to room temperature. The reaction mixture was partitioned between ethyl acetate and half-saturated aqueous $Na_2S_2O_3$. The organic layer was dried with magnesium sulfate, filtered, and evaporated in vacuo. The crude product was purified via flash chromatography on silica gel (0 to 15% ethyl acetate in heptanes) to yield 2.2349 g (97%) of 5-iodo-4-nitro-1-((2-(trimethylsilyl)ethoxy)methyl)-1H-pyrazole. $^1$H NMR (400 MHz, DMSO-d6) δ: 8.48 (s, 1H), 5.59 (s, 2H), 3.61 (t, J=8.0, 2H), 0.86 (t, J=8.0, 2H), −0.04 (s, 9H).

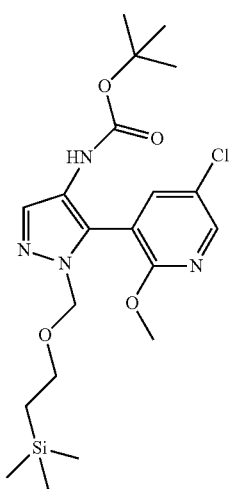 [SMILES: COc1ncc(Cl)cc1-c1c(NC(=O)OC(C)(C)C)cnn1COCC[Si](C)(C)C]

tert-butyl 5-iodo-1-((2-(trimethylsilyl)ethoxy)methyl)-1H-pyrazol-4-ylcarbamate

To a solution of 5-iodo-4-nitro-1-((2-(trimethylsilyl)ethoxy)methyl)-1H-pyrazole (2.234 g, 6.050 mmol) in ethanol (20 mL) was added ammonium chloride (1.303 g, 24.36 mmol), iron powder (1.695 g, 30.35 mmol), and water (30 mL). The reaction mixture was then stirred at 70° C. for 45 minutes and then cooled to room temperature, diluted with dichloromethane, and filtered through celite, rinsing with additional dichloromethane. Saturated aqueous sodium bicarbonate was added to the filtrate and the layers separated. The aqueous layer was extracted once more with dichloromethane, and the combined organic portions then dried over magnesium sulfate, filtered, and evaporated in vacuo. To the resulting residue was added dioxane (20 mL), triethylamine (2.0 mL, 14 mmol) and di-tert-butyldicarbonate (1.513 g, 6.932 mmol). This mixture was stirred at 60° C. for 4 hours. After cooling to room temperature, the reaction mixture was diluted in ethyl acetate, washed with water and brine, dried over magnesium sulfate, filtered, and evaporated in vacuo. The crude product was purified via flash chromatography on silica gel (0 to 40% ethyl acetate in heptanes) to yield 1.4353 g (54%) of tert-butyl 5-iodo-1-((2-(trimethylsilyl)ethoxy)methyl)-1H-pyrazol-4-ylcarbamate. 1H NMR (400 MHz, DMSO-d6) δ: 8.44 (s, 1H), 7.56 (s, 1H), 5.39 (s, 2H), 3.53 (t, J=8.0, 2H), 1.43 (s, 9H), 0.83 (t, J=8.0, 2H), −0.04 (s, 9H).

tert-butyl 5-(5-chloro-2-methoxypyridin-3-yl)-1-((2-(trimethylsilyl)ethoxy)methyl)-1H-pyrazol-4-ylcarbamate A mixture of tert-butyl 5-iodo-1-((2-(trimethylsilyl)ethoxy)methyl)-1H-pyrazol-4-ylcarbamate (390.7 mg, 0.8892 mmol), 5-chloro-2-methoxy-pyridine-3-boronic acid pinacol ester (364.0 mg, 1.350 mmol), tris(dibenzylideneacetone)dipalladium(0) chloroform adduct (48.5 mg, 0.0468 mmol), S-Phos (74.2 mg, 0.181 mmol), potassium phosphate (597.1 mg, 2.813 mmol), and 1-butanol (10 mL) was degassed with nitrogen and then stirred at 80° C. for 15 hours. The reaction mixture was diluted in ethyl acetate, washed with water and brine, dried over magnesium sulfate, filtered, and evaporated in vacuo. The crude product was purified via flash chromatography on silica gel (0 to 50% ethyl acetate in heptanes) to yield 212.3 mg (52%) of tert-butyl 5-(5-chloro-2-methoxypyridin-3-yl)-1-((2-(trimethylsilyl)ethoxy)methyl)-1H-pyrazol-4-ylcarbamate. LCMS (ESI) m+H=455.2; 1H NMR (400 MHz, DMSO-d6) δ: 8.53 (s, 1H), 8.33 (s, 1H), 7.79 (d, J=2.6, 1H), 5.22 (s, 2H), 3.85 (s, 3H), 3.35 (t, 2H), 1.38 (s, 9H), 0.70 (t, J=8.1, 2H), −0.10 (s, 9H).

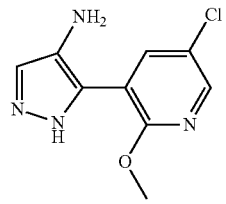

5-(5-chloro-2-methoxypyridin-3-yl)-1H-pyrazol-4-amine

To a solution of tert-butyl 5-(5-chloro-2-methoxypyridin-3-yl)-1-((2-(trimethylsilyl)ethoxy)methyl)-1H-pyrazol-4-ylcarbamate (211.7 mg, 0.4652 mmol) in 5 mL ethyl acetate was added tin tetrachloride (0.52 mL, 4.4 mmol). The reaction mixture was stirred at room temperature for 2 hours and then evaporated in vacuo. The residual oil was partitioned between ethyl acetate and saturated aqueous sodium bicarbonate, and the aqueous layer extracted twice more with ethyl acetate. The combined organic layers were dried over magnesium sulfate, filtered, and evaporated in vacuo. The crude product was purified via flash chromatography on silica gel (0 to 20% methanol in dichloromethane) to yield 32.4 mg (31%) of 5-(5-chloro-2-methoxypyridin-3-yl)-1H-pyrazol-4-amine LCMS (ESI) m+H=225.1.

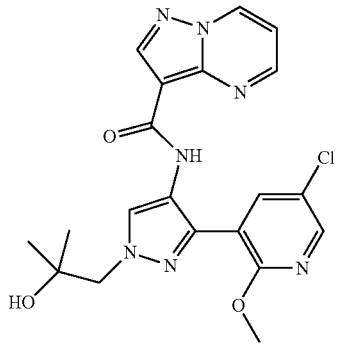 [SMILES: COc1ncc(Cl)cc1-c1nn(CC(C)(C)O)cc1NC(=O)c1cnn2cccnc12]

N-(3-(5-chloro-2-methoxypyridin-3-yl)-1-(2-hydroxy-2-methylpropyl)-1H-pyrazol-4-yl)pyrazolo[1,5-a]pyrimidine-3-carboxamide The title compound was prepared using 5-(5-chloro-2-methoxypyridin-3-yl)-1H-pyrazol-4-amine and following the procedures described for Examples 4 and 16. LCMS (ESI) m+H=442.1; 1H NMR (400 MHz, DMSO-d6) δ: 9.72 (s, 1H), 9.34 (d, J=6.8 Hz, 1H), 8.73 (s, 1H), 8.66 (s, 1H), 8.35 (s, 2H), 7.88 (s, 1H), 7.28 (s, 1H), 4.75 (s, 1H), 4.09 (s, 2H), 3.95 (s, 3H), 1.13 (s, 6H).

Example 142

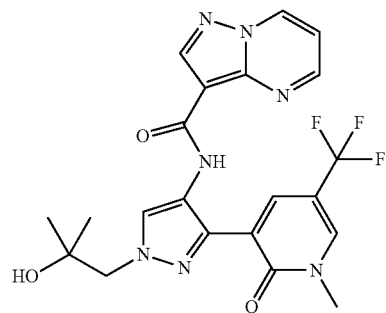 [SMILES: Cn1cc(C(F)(F)F)cc(-c2nn(CC(C)(C)O)cc2NC(=O)c2cnn3cccnc23)c1=O]

N-(1-(2-hydroxy-2-methylpropyl)-3-(1-methyl-2-oxo-5-(trifluoromethyl)-1,2-dihydropyridin-3-yl)-1H-pyrazol-4-yl)pyrazolo[1,5-a]pyrimidine-3-carboxamide

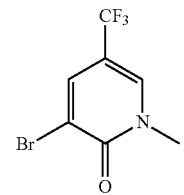

3-bromo-1-methyl-5-(trifluoromethyl)pyridin-2(1H)-one

To a solution of 3-bromo-2-hydroxy-5-(trifluoromethyl)pyridine (1.0097 g, 4.1724 mmol) in chloroform (20 mL) was added silver carbonate (1.1964 g, 4.3388 mmol) and methyl iodide (0.40 mL, 6.4 mmol). The reaction mixture was stirred at room temperature for two hours and then at 40° C. for 24 hours. Additional methyl iodide (0.40 mL, 6.4 mmol) was added and the reaction kept at 40° C. for an additional 15 hours. The reaction mixture was then diluted with dichloromethane, filtered through celite, and evaporated in vacuo. The crude product was purified via flash chromatography on silica gel (0 to 80% ethyl acetate in heptanes) to yield 0.5297 g (50%) of 3-bromo-1-methyl-5-(trifluoromethyl)pyridin-2 (1H)-one. 1H NMR (400 MHz, DMSO-d6) δ: 8.47 (d, J=0.9, 1H), 8.22 (d, J=2.5, 1H), 3.56 (s, 3H).

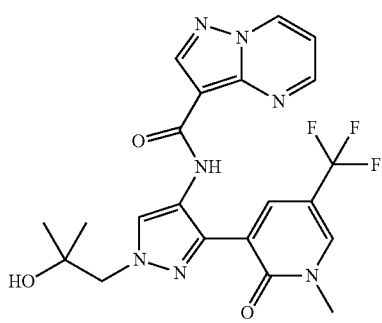 [SMILES: Cn1cc(C(F)(F)F)cc(-c2nn(CC(C)(C)O)cc2NC(=O)c2cnn3cccnc23)c1=O]

N-(1-(2-hydroxy-2-methylpropyl)-3-(1-methyl-2-oxo-5-(trifluoromethyl)-1,2-dihydropyridin-3-yl)-1H-pyrazol-4-yl)pyrazolo[1,5-a]pyrimidine-3-carboxamide The title compound was prepared using 3-bromo-1-methyl-5-(trifluoromethyl)pyridin-2(1H)-one and following the procedures as described for Examples 14 and 16. LCMS (ESI) m+H=476.1; 1H NMR (400 MHz, DMSO-d6) δ: 10.23 (s, 1H), 9.31 (dd, J=7.0, 1.5, 1H), 8.77 (dd, J=4.1, 1.6, 1H), 8.64 (s, 1H), 8.58 (s, 1H), 8.39 (s, 1H), 7.88 (d, J=2.7, 1H), 7.27 (dd, J=7.0, 4.2, 1H), 4.74 (s, 1H), 4.08 (s, 2H), 3.71 (s, 3H), 1.11 (s, 6H).

Example 143

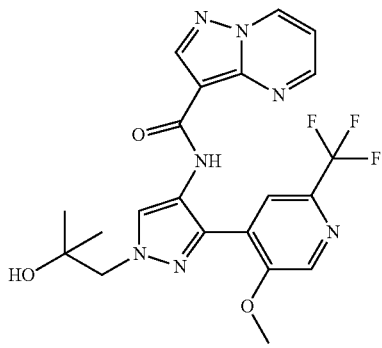 [SMILES: COc1cnc(C(F)(F)F)cc1-c1nn(CC(C)(C)O)cc1NC(=O)c1cnn2cccnc12]

N-(1-(2-hydroxy-2-methylpropyl)-3-(5-methoxy-2-(trifluoromethyl)pyridin-4-yl)-1H-pyrazol-4-yl)pyrazolo[1,5-a]pyrimidine-3-carboxamide

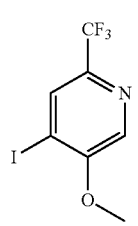

4-iodo-5-methoxy-2-(trifluoromethyl)pyridine

In an oven-dried flask, 5-methoxy-2-(trifluoromethyl)pyridine was dissolved in THF (20 mL). This mixture was cooled at −78° C., and then 2.5 M n-butyllithium in hexane (2.60 mL, 6.5 mmol) was added. After stirring at this same temperature for 40 minutes, 1-chloro-2-iodoethane (0.60 mL, 6.6 mmol) was added. The reaction was kept at −78° C. for an additional 30 minutes, and then quenched with saturated aqueous ammonium chloride. The mixture was warmed to room temperature, partitioned between ethyl acetate and water, and the organic layer dried with magnesium sulfate and evaporated in vacuo. The crude product was purified via flash chromatography on silica gel (0 to 40% ethyl acetate in heptanes) to yield 0.3128 g (16%) of 4-iodo-5-methoxy-2-(trifluoromethyl)pyridine. 1H NMR (400 MHz, DMSO-d6) δ: 8.38 (s, 1H), 8.29 (s, 1H), 4.05 (s, 3H).

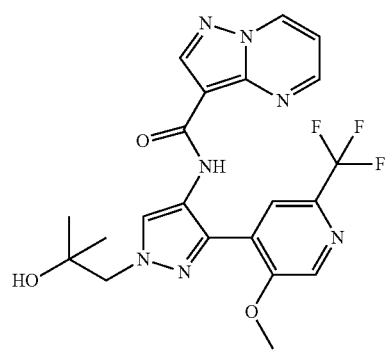 [SMILES: COc1cnc(C(F)(F)F)cc1-c1nn(CC(C)(C)O)cc1NC(=O)c1cnn2cccnc12]

N-(1-(2-hydroxy-2-methylpropyl)-3-(5-methoxy-2-(trifluoromethyl)pyridin-4-yl)-1H-pyrazol-4-yl)pyrazolo pyrimidine-3-carboxamide The title compound was prepared using 4-iodo-5-methoxy-2-(trifluoromethyl)pyridine and following the procedures as described for Examples 14 and 16. LCMS (ESI) m+H=476.1; 1H NMR (400 MHz, DMSO-d6) δ: 9.71 (s, 1H), 9.36 (d, J=6.9, 1H), 8.88 (d, J=3.8, 1H), 8.82 (s, 1H), 8.67 (s, 1H), 8.41 (s, 1H), 7.85 (s, 1H), 7.36-7.27 (m, 1H), 4.77 (s, 1H), 4.12 (s, 2H), 4.09 (s, 3H), 1.13 (s, 6H).

Example 144

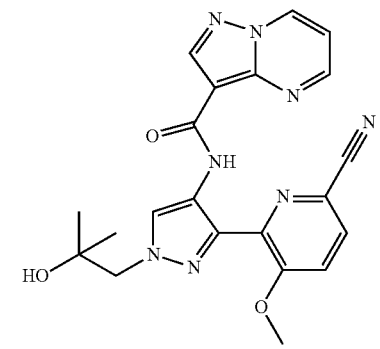

193

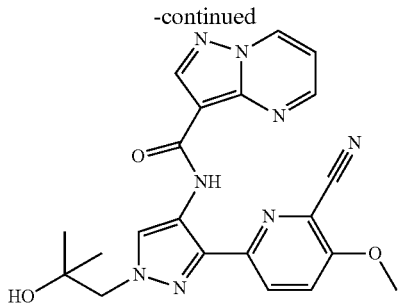

N-(3-(6-cyano-3-methoxypyridin-2-yl)-1-(2-hydroxy-2-methylpropyl)-1H-pyrazol-4-yl)pyrazolo[1,5-a]pyrimidine-3-carboxamide N-(3-(6-cyano-5-methoxypyridin-2-yl)-1-(2-hydroxy-2-methylpropyl)-1H-pyrazol-4-yl)pyrazolo[1,5-a]pyrimidine-3-carboxamide

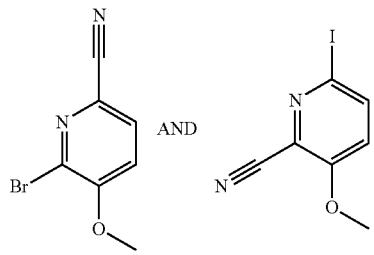

6-bromo-5-methoxypicolinonitrile 6-iodo-3-methoxypicolinonitrile

To a solution of 2-bromo-6-iodo-3-methoxypyridine (627.4 mg, 1.999 mmol) in N-methylpyrrolidinone (10 mL) was added copper cyanide (202.6 mg, 2.262 mmol). The reaction mixture was stirred at 130° C. for 3.5 hours and then cooled to room temperature. The crude reaction was partitioned between ethyl acetate and water, the organic layer washed with brine, dried with magnesium sulfate, filtered, and evaporated in vacuo. The crude product was purified via flash chromatography on silica gel (20 to 100% ethyl acetate in heptanes) to yield 157.8 mg (37%) of a mixture of the two regioisomeric products 6-bromo-5-methoxypicolinonitrile and 6-iodo-3-methoxypicolinonitrile. 1H NMR (400 MHz, DMSO) δ: 8.12 (d, J=8.3 Hz, 0.75H), 7.98 (d, J=9.0 Hz, 1H), 7.80 (d, J=9.1 Hz, 1H), 7.69 (d, J=8.5 Hz, 0.75H), 3.98 (overlapping s and s, 6H).

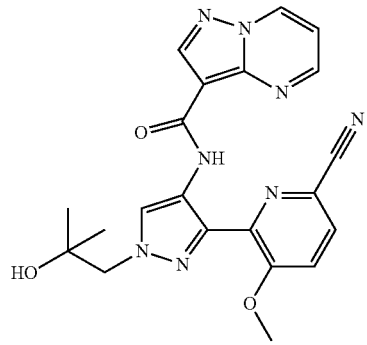 [SMILES: COc1ccc(C#N)nc1-c1nn(CC(C)(C)O)cc1NC(=O)c1cnn2cccnc12]

194

N-(3-(6-cyano-3-methoxypyridin-2-yl)-1-(2-hydroxy-2-methylpropyl)-1H-pyrazol-4-yl)pyrazolo[1,5-a]pyrimidine-3-carboxamide

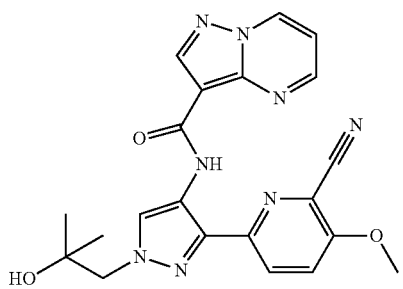 [SMILES: COc1ccc(-c2nn(CC(C)(C)O)cc2NC(=O)c2cnn3cccnc23)nc1C#N]

N-(3-(6-cyano-5-methoxypyridin-2-yl)-1-(2-hydroxy-2-methylpropyl)-1H-pyrazol-4-yl)pyrazolo[1,5-a]pyrimidine-3-carboxamide The title compounds were prepared using a mixture of 6-bromo-5-methoxypicolinonitrile and 6-iodo-3-methoxypicolinonitrile and following the procedures described for Examples 14 and 16, separating the two regioisomeric final products by reverse-phase HPLC to yield: N-(3-(6-cyano-3-methoxypyridin-2-yl)-1-(2-hydroxy-2-methylpropyl)-1H-pyrazol-4-yl)pyrazolo[1,5-a]pyrimidine-3-carboxamide; LCMS (ESI) m+H=433.1; 1H NMR (400 MHz, DMSO-d6) δ: 10.55 (s, 2H), 9.35 (d, J=6.9 Hz, 2H), 8.93 (s, 2H), 8.68 (s, 2H), 8.48 (s, 2H), 8.10 (d, J=8.6 Hz, 2H), 7.80 (d, J=8.4 Hz, 2H), 7.42-7.26 (m, 2H), 6.54 (s, 1H), 4.80 (s, 2H), 4.12 (s, 4H), 3.94 (s, 6H), 1.12 (s, 12H).

And N-(3-(6-cyano-5-methoxypyridin-2-yl)-1-(2-hydroxy-2-methylpropyl)-1H-pyrazol-4-yl)pyrazolo[1,5-a]pyrimidine-3-carboxamide; LCMS (ESI) m+H=433.1; 1H NMR (400 MHz, DMSO-d6) δ: 10.97 (s, 1H), 9.36 (d, J=6.8 Hz, 1H), 9.09 (s, 1H), 8.70 (s, 1H), 8.57 (s, 1H), 8.26 (d, J=9.4 Hz, 1H), 7.94 (d, J=9.1 Hz, 1H), 7.42-7.32 (m, 1H), 4.78 (s, 1H), 4.11 (s, 2H), 4.04 (s, 3H), 1.13 (s, 6H).

Example 145

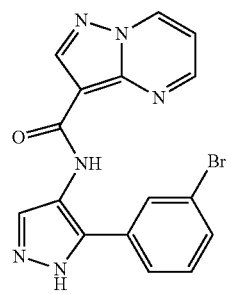 [SMILES: O=C(Nc1cn[nH]c1-c1cccc(Br)c1)c1cnn2cccnc12]

N-(5-(3-bromophenyl)-1H-pyrazol-4-yl)pyrazolo[1,5-a]pyrimidine-3-carboxamide

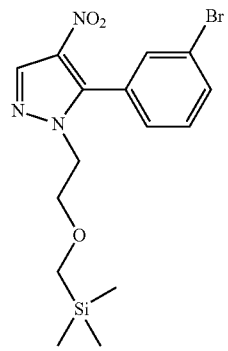 [SMILES: C[Si](C)(C)COCCn1ncc([N+](=O)[O-])c1-c1cccc(Br)c1]

5-(3-bromophenyl)-4-nitro-1-(2-((trimethylsilyl)methoxy)ethyl)-1H-pyrazole

To a solution of 4-nitro-1-((2-(trimethylsilyl)ethoxy)methyl)-1H-pyrazole (4 g, 16.4 mmol) in 40 mL of N,N-dimethylacetamide was added 1,3-dibromo-Benzene (4.6 g, 19.7 mmol), palladium (II) acetate (242 mg, 1.08 mmol), di(1-adamantyl)-n-butyl phosphine (565 mg, 1.58 mmol), potassium carbonate (8.28 g, 60 mmol), and trimethylacetic acid (552 mg, 5.2 mmol). While stirring at room temperature, nitrogen gas was bubbled through the reaction mixture for 10 minutes, and the reaction was then heated at 120° C. for 12 hours. The reaction was cooled to room temperature, diluted into ethyl acetate, and washed with water and brine, dried over magnesium sulfate and concentrated. The crude material was purified by flash chromatography on silica gel (0 to 25% ethyl acetate in hexanes) to obtain 800 mg (12%) of 5-(3-bromophenyl)-4-nitro-1-(2-((trimethylsilyl)methoxy)ethyl)-1H-pyrazole. LCMS (ESI) m+H=398.0; $^1$H NMR (400 MHz, CDCl$_3$) δ: 8.24 (d, 1H), 7.70 (m, 1H), 7.53 (s, 1H), 7.46 (d, 1H), 7.42 (d, 1H), 7.41 (d, 1H), 5.27 (s, 1H), 3.72 (m, 2H), 0.95 (m, 2H), 0.00 (s, 9H).

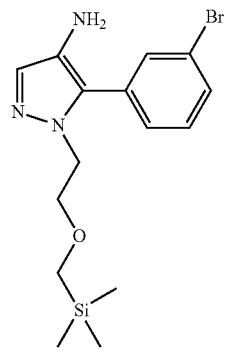 [SMILES: C[Si](C)(C)COCCn1ncc(N)c1-c1cccc(Br)c1]

5-(3-bromophenyl)-1-(2-((trimethylsilyl)methoxy)ethyl)-1H-pyrazol-4-amine

To a solution of 5-(3-bromophenyl)-4-nitro-1-(2-((trimethylsilyl)methoxy)ethyl)-1H-pyrazole (800 mg, 2.4 mmol) in 25 mL ethanol was added 50 mL of water, ammonium chloride (636 mg, 12 mmol), and iron powder (806 mg, 14 mmol). The reaction mixture was stirred at 75° C. for 6 hours. After cooling to room temperature, the reaction was diluted with dichloromethane and filtered through a celite pad, rinsing with more dichloromethane. The filtrate was added to 150 mL of saturated aqueous sodium bicarbonate and extracted twice with dichloromethane. The combined organic extracts were dried over magnesium sulfate and concentrated to yield 530 mg (71%) of 5-(3-bromophenyl)-1-(2-((trimethylsilyl)methoxy)ethyl)-1H-pyrazol-4-amine, which was carried forward without purification. LCMS (ESI) m+H=368.0.

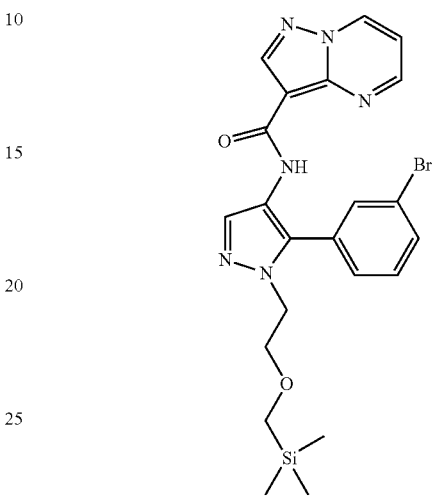

N-(5-(3-bromophenyl)-1-(2-((trimethylsilyl)methoxy)ethyl)-1H-pyrazol-4-yl)pyrazolo[1,5-a]pyrimidine-3-carboxamide A mixture of 5-(3-bromophenyl)-1-(2-((trimethylsilyl)methoxy)ethyl)-1H-pyrazol-4-amine (533 mg, 1.45 mmol), in tetrahydrofuran (5 mL) was added of pyrazolo[1,5-a]pyrimidine-3-carbonyl chloride (262 mg, 1.45 mmol) in tetrahydrofuran (5 mL) at 0° C. After addition, the mixture was warmed to room temperature, and then stirred overnight at this temperature. The mixture was concentrated to give 742 mg (99%) of N-(5-(3-bromophenyl)-1-(2-((trimethylsilyl)methoxy)ethyl)-1H-pyrazol-4-yl)pyrazolo[1,5-a]pyrimidine-3-carboxamide, which was carried forward without purification. LCMS (ESI) m+H=513.1.

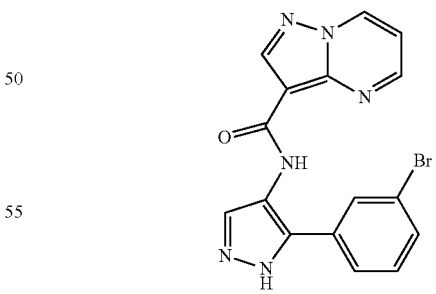

N-(5-(3-bromophenyl)-1H-pyrazol-4-yl)pyrazolo[1,5-a]pyrimidine-3-carboxamide

To a solution of N-(5-(3-bromophenyl)-1-(2-((trimethylsilyl)methoxy)ethyl)-1H-pyrazol-4-yl)pyrazolo[1,5-a]pyrimidine-3-carboxamide (742 mg, 1.45 mmol) in 20 mL of ethanol was added HCl (1.0 mL of a 6 M solution in water, 6 mmol). The reaction mixture was then stirred at 70° C. for 6 hours. After cooling to room temperature a light yellow precipitate formed, which was isolated by filtration and washed with methanol and diethyl ether. The filtrate was reduced in volume, and more solid product filtered. The combined collected solids were dried under vacuum to yield 320 mg (58%) of N-(5-(3-bromophenyl)-1H-pyrazol-4-yl)pyrazolo[1,5-a]pyrimidine-3-carboxamide. LCMS (ESI) m+H=383.0; $^1$H NMR (400 MHz, DMSO-$d_6$) δ13.01 (s, 1H), 9.93 (s, 1H), 9.33 (dd, 1H), 8.83 (dd, 1H), 8.66 (d, 1H), 8.26 (s, 1H), 7.57 (d, 1H), 7.47 (t, 1H), 7.28 (dd, 1H).

Example 146

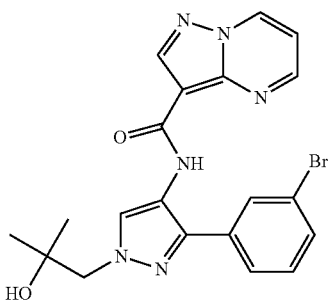 [SMILES: CC(C)(O)Cn1cc(NC(=O)c2cnn3cccnc23)c(-c2cccc(Br)c2)n1]

To a solution of N-(5-(3-bromophenyl)-1H-pyrazol-4-yl)pyrazolo[1,5-a]pyrimidine-3-carboxamide (200 mg, 0.523 mmol) in 20 mL DMF was added isobutylene oxide (0.20 mL, 2.2 mmol) and cesium carbonate (340 mg, 1.04 mmol). The reaction mixture was stirred at 80° C. for 6 hours, then cooled to room temperature, diluted with ethyl acetate, and filtered. The fitrate was washed with brine, dried over magnesium sulfate, and concentrated. The residue was purified by reverse phase HPLC and lyophilized to give 14.2 mg (6%) of desired compound. LCMS (ESI) m+H=456.8. $^1$H NMR (CDCl$_3$, 400 MHz): δ10.16 (d, J=1.2 Hz, 1H), 8.83-8.77 (m, 2H), 8.76 (t, J=5.2 Hz, 1H), 8.42 (s, 1H), 8.03 (s, 1H), 7.76 (d, J=8.4 Hz, 1H), 7.55 (d, J=8.4 Hz, 1H), 7.37 (t, J=8.0 Hz, 1H), 7.06 (dd, J=3.6, 6.8 Hz, 1H), 4.12 (s, 2H), 1.30 (s, 6H).

Example 147

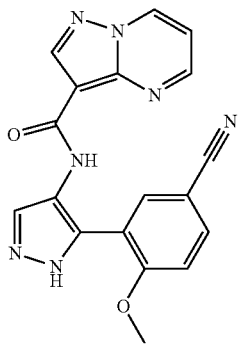 [SMILES: COc1ccc(C#N)cc1-c1[nH]ncc1NC(=O)c1cnn2cccnc12]

N-(5-(5-cyano-2-methoxyphenyl)-1H-pyrazol-4-yl)pyrazolo[1,5-a]pyrimidine-3-carboxamide

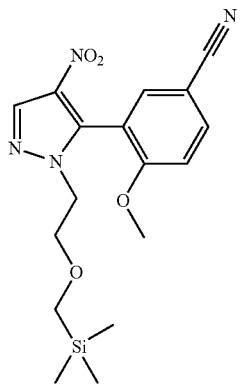

4-methoxy-3-(4-nitro-1-(2-((trimethylsilyl)methoxy)ethyl)-1H-pyrazol-5-yl)benzonitrile To a solution of 4-nitro-1-((2-(trimethylsilyl)ethoxy)methyl)-1H-pyrazole (2 g, 8.2 mmol) in 50 mL of N,N-dimethylacetamide was added 3-bromo-4-methoxybenzonitrile (2.1 g, 9.8 mmol), palladium (II) acetate (120 mg, 0.54 mmol), di(1-adamantyl)-n-butylphosphine (250 mg, 0.7 mmol), potassium carbonate (6.0 g, 43.3 mmol), and trimethylacetic acid (200 mg, 1.95 mmol). While stirring at room temperature, nitrogen gas was bubbled through the reaction mixture for 10 minutes, and the reaction mixture was then heated at 120° C. for 12 hours. The reaction was cooled to room temperature, diluted into ethyl acetate, and washed with water and brine, dried over magnesium sulfate and concentrated. The crude material was purified by flash chromatography on silica gel (0 to 25% ethyl acetate in heptanes) to obtain 730 mg (12%) of 4-methoxy-3-(4-nitro-1-(2-((trimethylsilyl)methoxy)ethyl)-1H-pyrazol-5-yl)benzonitrile. LCMS (ESI) m+H=375.1; $^1$H NMR (400 MHz, CDCl$_3$) δ: 8.24 (d, 1H), 7.86 (m, 1H), 7.72 (s, 1H), 7.12 (d, 1H), 5.27 (q, 2H), 3.86 (s, 3H), 3.68 (m, 2H), 0.89 (m, 2H), 0.00 (s, 9H).

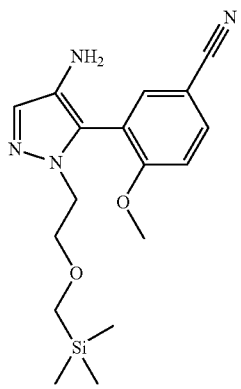 [SMILES: COc1ccc(C#N)cc1-c1c([N+](=O)[O-])cnn1CCOC[Si](C)(C)C]

3-(4-amino-1-(2-((trimethylsilyl)methoxy)ethyl)-1H-pyrazol-5-yl)-4-methoxybenzonitrile To a solution of 4-methoxy-3-(4-nitro-1-(2-((trimethylsilyl)methoxy)ethyl)-1H-pyrazol-5-yl)benzonitrile (900 mg, 2.4 mmol) in 25 mL ethanol was added 50 mL water, ammonium chloride (636 mg, 12 mmol), and iron powder (806 mg, 14 mmol). The reaction mixture was stirred at 75° C. for 6 hours. After cooling to room temperature, the reaction was diluted with dichloromethane and filtered through a celite pad, rinsing with more dichloromethane. The filtrate was added to 150 mL saturated aqueous sodium bicarbonate and extracted twice with dichloromethane. The combined organic extracts were dried over magnesium sulfate and concentrated to yield 717 mg (84%) of 3-(4-amino-1-(2-((trimethylsilyl)methoxy)ethyl)-1H-pyrazol-5-yl)-4-methoxybenzonitrile, which was carried forward without purification. LCMS (ESI) m+H=375.1.

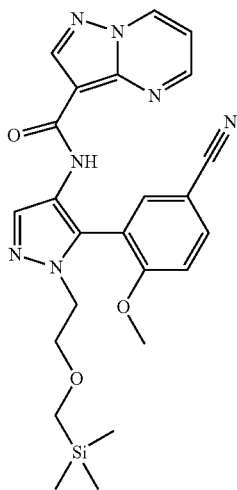 [SMILES: COc1ccc(C#N)cc1-c1c(NC(=O)c2cnn3cccnc23)cnn1CCOC[Si](C)(C)C]

N-(5-(5-cyano-2-methoxyphenyl)-1-(2-((trimethylsilyl)methoxy)ethyl)-1H-pyrazol-4-yl)pyrazolo[1,5-a]pyrimidine-3-carboxamide 3-(4-amino-1-(2-((trimethylsilyl)methoxy)ethyl)-1H-pyrazol-5-yl)-4-methoxybenzonitrile (717 mg, 2.08 mmol) in tetrahydrofuran (20 mL) was added to pyrazolo[1,5-a]pyrimidine-3-carbonyl chloride (262 mg, 1.45 mmol) in tetrahydrofuran (5 mL) at 0° C. After addition, the mixture was warmed to room temperature, and then stirred overnight at this temperature. The mixture was concentrated to give 1.0 g (98%) of N-(5-(5-cyano-2-methoxyphenyl)-1-(2-((trimethylsilyl)methoxy)ethyl)-1H-pyrazol-4-yl)pyrazolo[1,5-a]pyrimidine-3-carboxamide, which was carried forward without purification. LCMS (ESI) m+H=490.1.

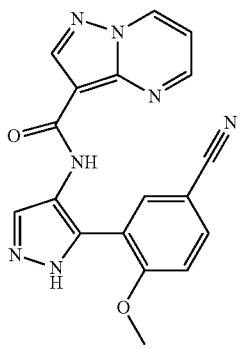 [SMILES: COc1ccc(C#N)cc1-c1[nH]ncc1NC(=O)c1cnn2cccnc12]

N-(5-(5-cyano-2-methoxyphenyl)-1H-pyrazol-4-yl) pyrazolo[1,5-a]pyrimidine-3-carboxamide To a solution of N-(5-(5-cyano-2-methoxyphenyl)-1-(2-((trimethylsilyl)methoxy)ethyl)-1H-pyrazol-4-yl)pyrazolo[1,5-a]pyrimidine-3-carboxamide (1.0 g, 2.04 mmol) in 20 mL ethanol was added HCl (2.0 mL of a 6 M solution in water, 12 mmol). The reaction mixture was then stirred at 70° C. for 4 hours. After cooling to room temperature, a light yellow precipitate formed, which was filtered off and rinsed with methanol and diethyl ether. The filtrate was reduced in volume to precipitate more solid product, which was filtered off. The combined collected solids were dried under vacuum to yield 530 mg (72%) of N-(5-(5-cyano-2-methoxyphenyl)-1H-pyrazol-4-yl)pyrazolo[1,5-a]pyrimidine-3-carboxamide. LCMS (ESI) m+H=360.1; $^1$H NMR (400 MHz, DMSO-$d_6$) δ12.98 (s, 1H), 9.59 (s, 1H), 9.30 (dd, 1H), 8.73 (d, 1H), 8.61 (s, 1H), 8.23 (s, 1H), 8.22 (s, 1H), 7.78 (s, 1H), 7.43 (d, 1H), 7.25 (s, 1H), 3.9 (s, 3H).

Example 148

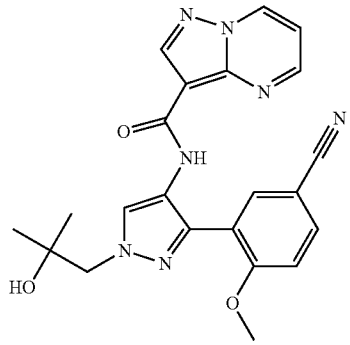 [SMILES: COc1ccc(C#N)cc1-c1nn(CC(C)(C)O)cc1NC(=O)c1cnn2cccnc12]

N-(3-(5-cyano-2-methoxyphenyl)-1-(2-hydroxy-2-methylpropyl)-1H-pyrazol-4-yl)pyrazolo[1,5-a]pyrimidine-3-carboxamide To a solution of N-(5-(5-cyano-2-methoxyphenyl)-1H-pyrazol-4-yl)pyrazolo[1,5-a]pyrimidine-3-carboxamide (200 mg, 0.557 mmol) in 20 mL DMF was added isobutylene oxide (0.20 mL, 2.2 mmol) and cesium carbonate (363 mg, 1.11 mmol). The reaction mixture was stirred at 80° C. for 6 hours, then diluted with ethyl acetate and filtered, and the organic portion washed with brine, dried over magnesium sulfate, and concentrated. The crude product was purified by reverse phase HPLC and lyophilized to give 27.2 mg (11%) of desired product. LCMS (ESI) m+H=431.9. $^1$H NMR (CDCl$_3$, 400 MHz): 69.68 (s, 1H), 8.78 (dd, J=2.0, 6.8 Hz, 1H), 8.71 (s, 1H), 8.56 (q, J=1.6 Hz, 1H), 8.37 (s, 1H), 7.87 (d, J=2.4 Hz, 1H), 7.72 (dd, J=2.0, 8.4 Hz, 1H), 7.1 (d, J=8.8 Hz, 1H), 7.01 (dd, J=4.4, 7.2 Hz, 1H), 4.11 (s, 2H), 3.91 (s, 3H), 1.23 (s, 6H).

Example 149

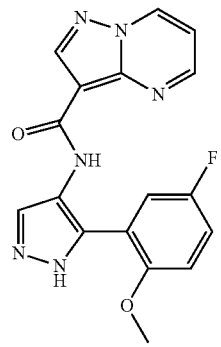 [SMILES: COc1ccc(F)cc1-c1[nH]ncc1NC(=O)c1cnn2cccnc12]

N-(5-(5-fluoro-2-methoxyphenyl)-1H-pyrazol-4-yl) pyrazolo pyrimidine-3-carboxamide

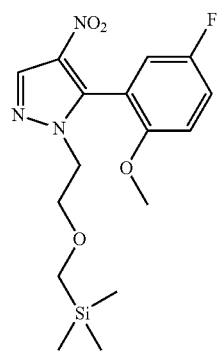 [SMILES: COc1ccc(F)cc1-c1c([N+](=O)[O-])cnn1CCOC[Si](C)(C)C]

5-(5-fluoro-2-methoxyphenyl)-4-nitro-1-(2-((trimethylsilyl)methoxy)ethyl)-1H-pyrazole To a solution of 4-nitro-1-((2-(trimethylsilyl)ethoxy)methyl)-1H-pyrazole (2.98 g, 12.28 mmol) in 25 mL N,N-dimethylacetamide was added 2-bromo-4-fluoro-1-methoxybenzene (3.54 g, 17.35 mmol), palladium (II) acetate (144 mg, 0.62 mmol), di(1-adamantyl)-n-butylphosphine (330 mg, 0.93 mmol), potassium carbonate (5.1 g, 37.1 mmol), and trimethylacetic acid (330 mg, 2.68 mmol). While stirring at room temperature, nitrogen gas was bubbled through the reaction mixture for 10 minutes, and the reaction mixture was then heated at 120° C. for 12 hours. The reaction was then cooled to room temperature, diluted into ethyl acetate, and washed with water and brine, dried over magnesium sulfate and concentrated. The crude material was purified by flash chromatography on silica gel (0 to 25% ethyl acetate in heptanes) to obtain 1.0 g (22%) of 5-(5-fluoro-2-methoxyphenyl)-4-nitro-1-(2-((trimethylsilyl)methoxy)ethyl)-1H-pyrazole. LCMS (ESI) m+H=368.1; $^1$H NMR (400 MHz, CDCl$_3$) δ: 8.25 (s, 1H), 7.29 (m, 1H), 7.18 (dd, 1H), 7.01 (dd, 1H), 5.31 (d, 2H), 3.77 (s, 3H), 3.65 (t, 2H), 2.03 (t, 2H), 0.92 (q, 2H), 0 (s, 9H).

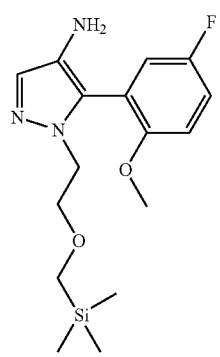

5-(5-fluoro-2-methoxyphenyl)-1-(2-((trimethylsilyl)methoxy)ethyl)-1H-pyrazol-4-amine To a solution of 5-(5-fluoro-2-methoxyphenyl)-4-nitro-1-(2-((trimethylsilyl)methoxy)ethyl)-1H-pyrazole (1.0 g, 2.7 mmol) in 8 mL ethanol was added 16 mL water, ammonium chloride (570 mg, 10.8 mmol), and iron powder (760 mg, 13.5 mmol). The reaction mixture was stirred at 75° C. for 6 hours. After cooling to room temperature, the reaction was diluted with dichloromethane and filtered through a celite pad, rinsing with more dichloromethane. The filtrate was added to 150 mL saturated aqueous sodium bicarbonate and extracted twice with dichloromethane. The combined organic extracts were dried over magnesium sulfate and concentrated to yield 640 mg (70%) of 5-(5-fluoro-2-methoxyphenyl)-1-(2-((trimethylsilyl)methoxy)ethyl)-1H-pyrazol-4-amine, which was carried forward without purification. LCMS (ESI) m+H=338.1. $^1$H NMR (400 MHz, CDCl$_3$) δ: 7.37 (m, 2H), 7.20 (t, 1H), 7.04 (dd, 1H), 5.42 (t, 2H), 3.90 (d, 3H), 3.65 (t, 2H), 0.96 (t, 2H), 0 (s, 9H).

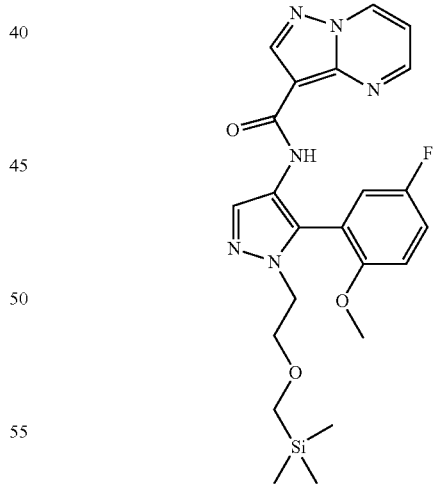

N-(5-(5-fluoro-2-methoxyphenyl)-1-(2-((trimethylsilyl)methoxy)ethyl)-1H-pyrazol-4-yl)pyrazolo pyrimidine-3-carboxamide 5-(5-fluoro-2-methoxyphenyl)-1-(2-((trimethylsilyl)methoxy)ethyl)-1H-pyrazol-4-amine (580 mg, 1.72 mmol) in tetrahydrofuran (40 mL) was added of pyrazolo[1,5-a]pyrimidine-3-carbonyl chloride (320 mg, 1.72 mmol) in THF (5 mL) at 0° C. After the addition, the mixture was warmed to room temperature, and then stirred overnight at this temperature. The mixture was concentrated to give 330 mg (40%) of N-(5-(5-fluoro-2-methoxyphenyl)-1-(2-((trimethylsilyl)methoxy)ethyl)-1H-pyrazol-4-yl)pyrazolo[1,5-a]pyrimidine-3-carboxamide, which was carried forward without purification. LCMS (ESI) m+H=483.1. $^1$H NMR (400 MHz, CDCl$_3$) δ: 9.63 (s, 1H), 8.82 (m, 1H), 8.76 (s, 1H), 8.52 (m, 1H), 8.42 (s, 1H), 7.38 (dd, 1H), 7.31 (d, 1H), 7.22 (m, 1H), 7.06 (m, 2H), 5.42 (d, 2H), 3.86 (s, 3H), 3.72 (m, 2H), 0.92 (q, 2H), 0 (s, 9H).

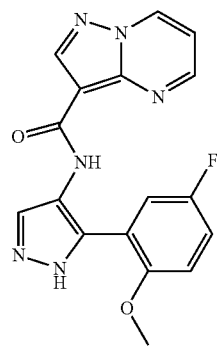 [SMILES: COc1ccc(F)cc1-c1[nH]ncc1NC(=O)c1cnn2cccnc12]

N-(5-(5-fluoro-2-methoxyphenyl)-1H-pyrazol-4-yl)pyrazolo[1,5-a]pyrimidine-3-carboxamide To a solution of N-(5-(5-fluoro-2-methoxyphenyl)-1-(2-((trimethylsilyl)methoxy)ethyl)-1H-pyrazol-4-yl)pyrazolo[1,5-a]pyrimidine-3-carboxamide (330 mg, 0.68 mmol) in 14 mL ethanol was added HCl (1.0 mL of a 6 M solution in water, 6.0 mmol). The reaction mixture was then stirred at 70° C. for 6 hours. After cooling to room temperature, a light yellow precipitate formed, which was filtered off and rinsed with methanol and diethyl ether. The filtrate was reduced in volume to precipitate more product, which was filtered off. The combined collected solids were dried under vacuum to yield 220 mg (92%) of N-(5-(5-fluoro-2-methoxyphenyl)-1H-pyrazol-4-yl)pyrazolo[1,5-a]pyrimidine-3-carboxamide. LCMS (ESI) m+H=353.1; $^1$H NMR (400 MHz, DMSO-d$_6$) δ: 9.68 (s, 1H), 9.32 (dd, 1H), 8.77 (dd, 1H), 8.63 (s, 1H), 8.19 (s, 1H), 7.30 (m, 4H), 3.82 (d, 3H).

Example 150

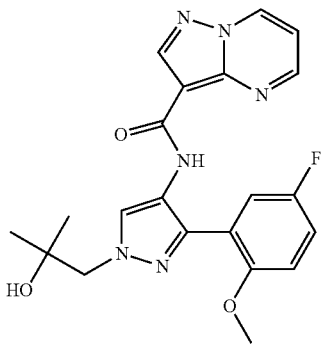 [SMILES: COc1ccc(F)cc1-c1nn(CC(C)(C)O)cc1NC(=O)c1cnn2cccnc12]

N-(3-(5-fluoro-2-methoxyphenyl)-1-(2-hydroxy-2-methylpropyl)-1H-pyrazol-4-yl)pyrazolo[1,5-a]pyrimidine-3-carboxamide To a solution of compound 8 (200 mg, 0.57 mmol) in 10 mL DMF is added isobutylene oxide (0.41 g, 5.7 mmol) and cesium carbonate (560 mg, 1.71 mmol). The reaction was stirred at 80° C. for 6 hours, then diluted with ethyl acetate and filtered, and the organic portion washed with brine, dried over magnesium sulfate, and concentrated. The crude product was purified by reverse phase HPLC and lyophilized to give 69.5 mg (29%) of desired compound. LCMS (ESI) m+Na=447.1. $^1$H NMR (CDCl$_3$, 400 MHz) δ: 9.83 (s, 1H), 8.80-8.78 (dd, J=2.0, 6.8 Hz, 1H), 8.73 (s, 1H), 8.56-8.54 (dd, J=1.6, 4.0 Hz, 1H), 8.36 (s, 1H), 7.33 (dd, J=3.2, 8.8 Hz, 1H), 7.11-7.08 (m, 1H), 7.02-6.97 (m, 2H), 4.12 (s, 1H), 3.85 (s, 3H), 1.24 (s, 6H).

Example 151

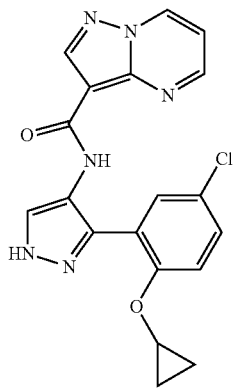 [SMILES: O=C(Nc1c[nH]nc1-c1cc(Cl)ccc1OC1CC1)c1cnn2cccnc12]

N-(3-(5-chloro-2-cyclopropoxyphenyl)-1H-pyrazol-4-yl)pyrazolo[1,5-a]pyrimidine-3-carboxamide

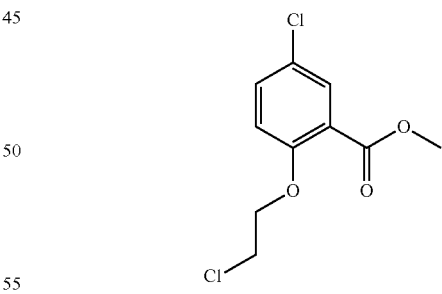

methyl 5-chloro-2-(2-chloroethoxy)benzoate

To a solution of methyl 5-chloro-2-hydroxybenzoate (54.06 g, 0.29 mol) in 300 mL of anhydrous DMF was added 2-chloroethyl 4-methylbenzenesulfonate (81.6 g, 0.35 mol) and Cs2CO3 (142 g, 0.44 mol). The mixture was stirred at 60-70° C. overnight, then water was added. A white solid precipitated from the solution, which was collected by filtration and coevaporated with toluene to afford 76.1 g (88%) of methyl 5-chloro-2-(2-chloroethoxy)benzoate. $^1$H NMR (400

MHz, CDCl₃) δ: 7.76 (d, 1H), 7.40 (dd, 1H), 6.91 (d, 1H), 4.27 (t, 2H), 3.87 (s, 3H), 3.83 (t, 2H).

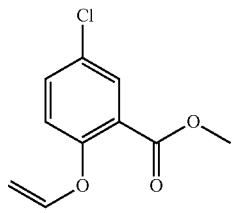

methyl 5-chloro-2-(vinyloxy)benzoate

Potassium tert-butoxide (40.4 g, 0.36 mol) was added portionwise to a solution of 5-chloro-2-(2-chloroethoxy)benzoate (76 g, 0.3 mol) in 600 mL of THF at 0° C. After stirring at that temperature for 1 hour, TLC showed complete consumption of starting material and the mixture was poured into ice water. The aqueous layer was extracted twice with EtOAc (200 mL), and the combined organics were evaporated to dryness. The residue was purified by silica gel column chromatography (Hexanes/EtOAc=50:1-30:1) to afford 22 g (34%) of methyl 5-chloro-2-(vinyloxy)benzoate. ¹H NMR (400 MHz, CDCl₃) δ: 7.76 (d, 1H), 7.38 (dd, 1H), 7.00 (d, 1H), 6.52 (dd, 1H), 4.67 (dd, 1H), 4.44 (dd, 1H), 3.83 (s, 3H).

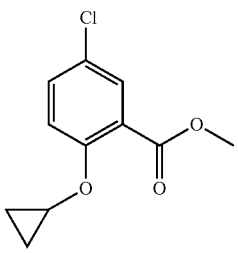

methyl 5-chloro-2-cyclopropoxybenzoate

To a solution of methyl 5-chloro-2-(vinyloxy)benzoate in 100 mL dichloromethane was added diethylzinc (1 M hexanes solution) (200 mL, 0.2 mol) under N₂ atmosphere. The solution was cooled in an ice bath and a solution of trifluoroacetic acid (16 mL) in dichloromethane (100 mL) was dropped very slowly into the mixture. After stirring for 20 minutes, a solution of CH2I2 (16.4 mL, 0.2 mol) in dichloromethane (100 mL) was added dropwise. After stirring an additional 20 minutes, a solution of methyl 5-chloro-2-(vinyloxy)benzoate (21.3 g, 0.1 mol) in dichloromethane (100 mL) was added and the ice bath was removed. 8 hours later, the mixture was quenched with saturated NH4Cl solution and extracted twice with dichloromethane. The combined organics were dried over Na2SO4, filtered and evaporated to dryness to afford 21 g (92%) of methyl 5-chloro-2-cyclopropoxybenzoate. ¹H NMR (400 MHz, CDCl₃) δ: 7.75 (d, 1H), 7.43 (q, 1H), 3.86 (s, 3H), 3.80 (m, 1H), 0.85 (m, 4H).

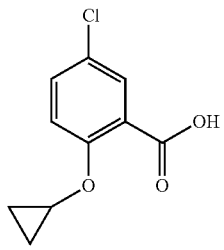 [SMILES: O=C(O)c1cc(Cl)ccc1OC1CC1]

5-chloro-2-cyclopropoxybenzoic acid

Methyl 5-chloro-2-cyclopropoxybenzoate was dissolved in THF/H2O (1:1, 400 mL), then sodium hydroxide (16 g, 0.4 mol) was added. The mixture was heated to 60° C. and stirred for 1 hour. The reaction mixture was cooled to room temperature, then the pH was adjusted to 4 using 4N aqueous HCl, resulting in precipitation of the product. The precipitate was collected by filtration and azeotroped with toluene to afford 19 g (96%) of 5-chloro-2-cyclopropoxybenzoic acid. ¹H NMR (400 MHz, CDCl₃) δ: 12.96 (br, 1H), 7.58 (m, 2H), 7.43 (q, 1H), 3.91 (m, 1H), 0.81 (m, 4H).

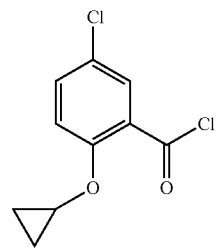 [SMILES: O=C(Cl)c1cc(Cl)ccc1OC1CC1]

5-chloro-2-cyclopropoxybenzoyl chloride 5-chloro-2-cyclopropoxybenzoic acid (18.5 g, 87 mmol) was dissolved in SOCl₂ and the solution was refluxed for 4 hours. The reaction mixture was concentrated in vacuo, then coevaporated with toluene to afford the desired acid chloride as a colorless oil that was used directly in the next step.

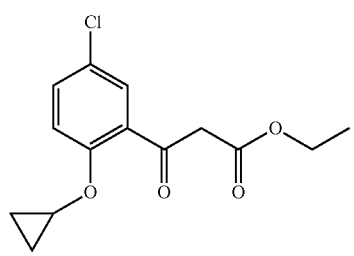 [SMILES: CCOC(=O)CC(=O)c1cc(Cl)ccc1OC1CC1]

ethyl 3-(5-chloro-2-cyclopropoxyphenyl)-3-oxopropanoate

Acetonitrile (200 mL) was added to potassium 3-ethoxy-3-oxopropanoate (31.1 g, 182.7 mmol), in a 1000 mL 3-necked flask under N₂ with stirring. The reaction mixture was cooled to 0° C., then triethylamine (38.8 mL, 278.4 mmol) was added, followed by MgCl₂ (20.71 g, 217.5 mmol).

The reaction mixture was warmed to room temperature and stirred for an additional 2.5 h. The resulting slurry was cooled to 0° C. and 5-chloro-2-cyclopropoxybenzoyl chloride (18.5 g, 87 mmol) was added dropwise followed by the addition of more triethylamine (3.9 mL, 28 mmol). The mixture was stirred at room temperature overnight, then concentrated in vacuo. 1 L of toluene was added, the mixture was cooled to 0° C., then 125 mL of HCl (13% aqueous solution) was added. The ice bath was removed, the mixture was stirred for 30 minutes, then the layers were separated and the organics washed with water and evaporated to dryness. The residue was purified by silica gel chromatography (Hexanes/EtOAc=3:1) to afford 21.8 g of ethyl 3-(5-chloro-2-cyclopropoxyphenyl)-3-oxopropanoate. LCMS (ESI) m+H=283.0; $^1$H NMR (400 MHz, CDCl$_3$) δ: 7.81 (t, 1H), 7.44 (dd, 1H), 7.29 (d, 1H), 4.24 (m, 2H), 3.87 (s, 2H), 3.78 (m, 1H), 1.23 (t, 2H), 0.85 (m, 4H).

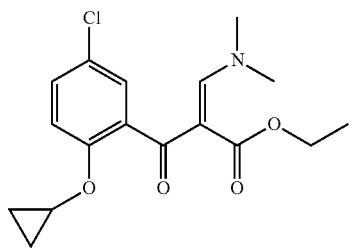 [SMILES: CCOC(=O)/C(=C\N(C)C)C(=O)c1cc(Cl)ccc1OC1CC1]

ethyl 2-(5-chloro-2-cyclopropoxybenzoyl)-3-(dimethylamino)acrylate

Ethyl 3-(5-chloro-2-cyclopropoxyphenyl)-3-oxopropanoate (21.8 g, 77 mmol) was dissolved in 150 mL of DMF-DMA. The mixture was heated to reflux for 2 hours. Evaporation gave a yellow solid which was used in the next step without further purification. $^1$H NMR (CDCl$_3$, 400 MHz) δ: 7.69 (s, 1H), 7.39 (s, 1H), 7.29 (dd, J=2.4, 8.8 Hz, 1H), 7.15 (d, J=8.8 Hz, 1H), 3.92 (q, J=6.8 Hz, 2H), 3.69-3.65 (m, 1H), 3.10 (br, 6H), 0.88 (t, J=6.8 Hz, 3H), 0.77-0.71 (m, 4H).

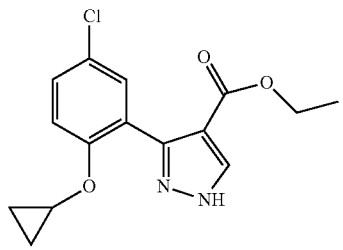 [SMILES: CCOC(=O)c1c[nH]nc1-c1cc(Cl)ccc1OC1CC1]

ethyl 3-(5-chloro-2-cyclopropoxyphenyl)-1H-pyrazole-4-carboxylate

Ethyl 2-(5-chloro-2-cyclopropoxybenzoyl)-3-(dimethylamino)acrylate (24 g, 71 mmol) was dissolved in 150 mL of HOAc. The reaction mixture was cooled to 0° C. then 85% hydrazine in water (25 mL) was added dropwise. The mixture was warmed to room temperature and stirred for 6 hours, then concentrated in vacuo. The residue was purified by EtOAc/Hexanes=1:2 to afford 24 g of the title compound as a syrup. $^1$H NMR (DMSO-d$_6$, 400 MHz) δ: 13.41 (s, 1H), 8.26 (s, 0.5H), 7.88 (s, 0.5H), 7.49-7.24 (m, 3H), 4.07-3.99 (m, 2H), 3.82-3.74 (m, 1H), 1.17-1.10 (m, 3H), 0.73-0.46 (m, 4H).

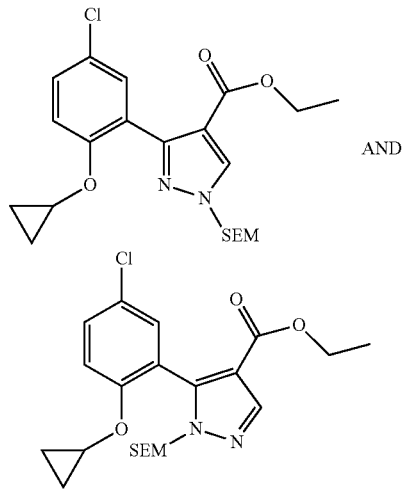

ethyl 3-(5-chloro-2-cyclopropoxyphenyl)-1-((2-(trimethylsilyl)ethoxy)methyl)-1H-pyrazole-4-carboxylate ethyl 5-(5-chloro-2-cyclopropoxyphenyl)-1-((2-(trimethylsilyl)ethoxy)methyl)-1H-pyrazole-4-carboxylate To a solution of ethyl 3-(5-chloro-2-cyclopropoxyphenyl)-1H-pyrazole-4-carboxylate (12 g, 39 mmol) in THF (200 mL) was added 60% sodium hydride in mineral oil (1.72 g, 43 mmol) and the reaction mixture was stirred for 10 min. SEMCl (7.2 g, 43 mmol) was added and the reaction mixture was stirred at room temperature overnight. The mixture was quenched with ice-water and extracted with EtOAc (300 mL×2). The combined organics were dried over sodium sulfate and concentrated in vacuo afford 16 g of the title compounds.

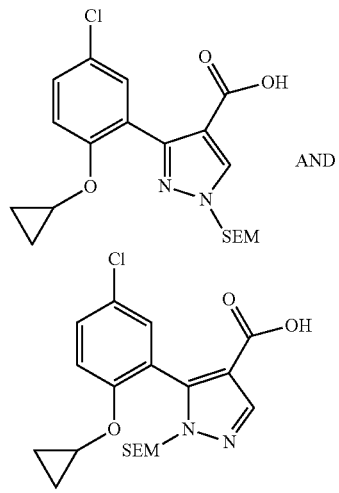

3-(5-chloro-2-cyclopropoxyphenyl)-1-((2-(trimethyl-silyl)ethoxy)methyl)-1H-pyrazole-4-carboxylic acid 5-(5-chloro-2-cyclopropoxyphenyl)-1-((2-(trimethyl-silyl)ethoxy)methyl)-1H-pyrazole-4-carboxylic acid The resulting crude ester from last step was dissolved in 200 mL of water. NaOH (7.32 g, 0.18 mmol) was added into the solution and the mixture was refluxed for 6 hours, then cooled to room temperature and neutralized with 4 N HCl to pH-7. The resulting precipitate was collected by filtration, then dissolved in MeOH. The remaining solids were filtered off and discarded and the filtrate evaporated to dryness to afford the title compounds (11.9 g) as a yellow solid.

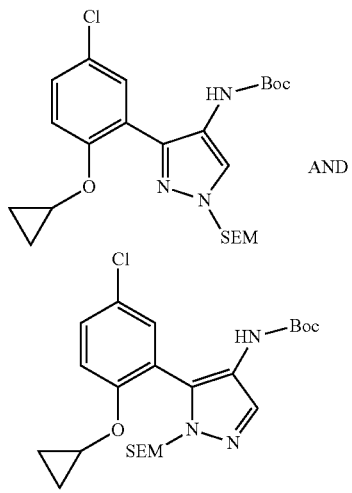

AND tert-butyl 3-(5-chloro-2-cyclopropoxyphenyl)-1-((2-(trimethylsilyl)ethoxy)methyl)-1H-pyrazol-4-ylcarbamate tert-butyl 5-(5-chloro-2-cyclopropoxyphenyl)-1-((2-(trimethylsilyl)ethoxy)methyl)-1H-pyrazol-4-ylcarbamate The product from the previous step (8.5 g, 20.8 mmol) was dissolved in toluene. DPPA (5.4 mL, 25 mmol) and TEA (3.5 mL, 25 mmol) were added and the mixture was stirred at room temperature for 1 hour. Tert-Butyl alcohol (5.3 mL, 50 mmol) was added. The mixture was heated to 90° C. and stirred overnight. The reaction mixture was concentrated in vacuo and the residue was purified by silica gel column chromatography eluting with Hexanes/EtOAc=10:1 to afford 2.5 g of the title compounds (not separated), which were used directly in the next step.

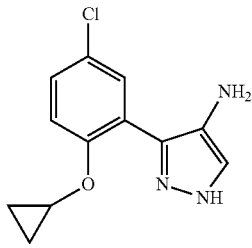 [SMILES: Nc1c[nH]nc1-c1cc(Cl)ccc1OC1CC1]

3-(5-chloro-2-cyclopropoxyphenyl)-1H-pyrazol-4-amine

Tert-butyl 3-(5-chloro-2-cyclopropoxyphenyl)-1-((2-(tri-methylsilyl)ethoxy)methyl)-1H-pyrazol-4-ylcarbamate and tert-butyl 5-(5-chloro-2-cyclopropoxyphenyl)-1-((2-(trim-ethylsilyl)ethoxy)methyl)-1H-pyrazol-4-ylcarbamate were dissolved in 50 mL of MeOH. 50 mL of 4 M HCl/MeOH was added dropwise. The mixture was stirred at room temperature overnight. The mixture was evaporated to dryness and purified by silica gel chromatography, eluting with EtOAc to afford 0.25 g of 3-(5-chloro-2-cyclopropoxyphenyl)-1H-pyrazol-4-amine. LCMS (ESI) m+H=249.8. $^1$H NMR (DMSO-$d_6$, 400 MHz) δ: 12.32-12.10 (br, 1H), 7.41-7.34 (m, 3H), 7.09 (s, 1H), 4.12 (q, J=5.2 Hz, 2H), 2.94-3.88 (m, 3H), 0.79-0.74 (m, 4H)

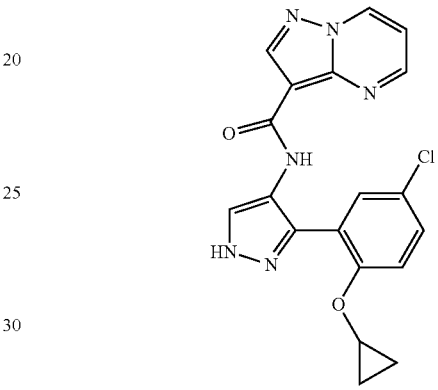

N-(3-(5-chloro-2-cyclopropoxyphenyl)-1H-pyrazol-4-yl)pyrazolo[1,5-a]pyrimidine-3-carboxamide 3-(5-chloro-2-cyclopropoxyphenyl)-1H-pyrazol-4-amine (0.2 g, 0.8 mmol) was dissolved in 15 mL of anhydrous THF. Pyrazolo[1,5-a]pyrimidine-3-carbonyl chloride (0.17 g, 0.96 mmol) was added followed by DIPEA (0.2 g, 1.6 mmol). The mixture was stirred at room temperature for 2 h, then evaporated to dryness. The residue was purified by silica gel chromatography (EtOAc as eluant) to afford 0.3 g of the title compound. Yield: 95%. $^1$H NMR (DMSO-$d_6$, 400 MHz) δ: 12.93 (d, 1H), 9.56 (d, J=5.2 Hz, 1H), 9.34 (d, J=7.2 Hz, 1H), 8.75-8.74 (m, 1H), 8.65 (s, 1H), 8.22 (s, 0.5H), 8.05 (s, 0.5H), 7.55-7.25 (m, 4H), 3.97-3.94 (m, 1H), 0.70-0.44 (m, 4H).

Example 152

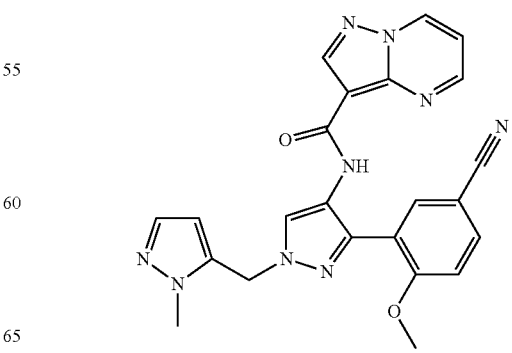

N-(3-(5-cyano-2-methoxyphenyl)-1-((1-methyl-1H-pyrazol-5-yl)methyl)-1H-pyrazol-4-yl)pyrazolo[1,5-a]pyrimidine-3-carboxamide

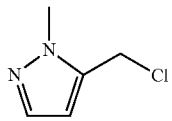

5-(chloromethyl)-1-methyl-1H-pyrazole

To a stirred solution of (1-methyl-1H-pyrazol-5-yl)methanol (200 mg, 1.8 mmol) in 20 mL of DCM was added SOCl$_2$ (262 mg, 2.2 mmol). The reaction mixture was refluxed for 2 hours, then the solvent was evaporated and the residue co-evaporated with DCM. The residue was partitioned between DCM and water. The organic phase was separated and washed with saturated aqueous NaHCO$_3$, water, and brine, then dried over magnesium sulfate, filtered, and concentrated to give 93 mg of 5-(chloromethyl)-1-methyl-1H-pyrazole. $^1$H NMR (400 MHz, CDCl$_3$) δ: 7.40 (s, 1H), 6.27 (s, 1H), 4.60 (s, 2H), 3.92 (s, 3H).

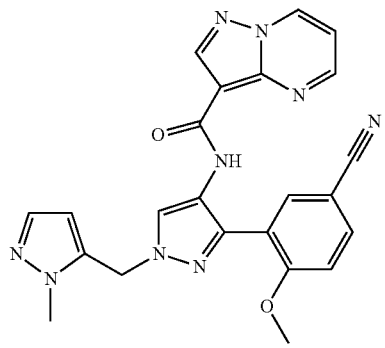 [SMILES: COc1ccc(C#N)cc1-c1nn(Cc2ccnn2C)cc1NC(=O)c1cnn2cccnc12]

N-(3-(5-cyano-2-methoxyphenyl)-1-((1-methyl-1H-pyrazol-5-yl)methyl)-1H-pyrazol-4-yl)pyrazolo[1,5-a]pyrimidine-3-carboxamide To a solution of N-(3-(5-cyano-2-methoxyphenyl)-1H-pyrazol-4-yl)pyrazolo[1,5-a]pyrimidine-3-carboxamide (144 mg, 0.40 mmol) in 3 mL of DMF was added 5-(chloromethyl)-1-methyl-1H-pyrazole (78 mg, 0.6 mmol) and cesium carbonate (391 mg, 1.20 mmol). The reaction mixture was stirred at 60° C. for 6 hours, then cooled to room temperature, diluted with ethyl acetate and filtered. The filtrate was washed with brine, dried over magnesium sulfate, and concentrated. The crude product was purified by reverse phase HPLC and lyophilized to give 58.3 mg (32%) of N-(3-(5-cyano-2-methoxyphenyl)-1-((1-methyl-1H-pyrazol-5-yl)methyl)-1H-pyrazol-4-yl)pyrazolo[1,5-a]pyrimidine-3-carboxamide. LCMS (ESI) m+H=454.1; $^1$H NMR (400 MHz, CDCl$_3$) δ: 9.58 (s, 1H), 8.74 (dd, 1H), 8.64 (s, 1H), 8.48 (dd, 1H), 8.21 (s, 1H), 7.81 (s, 1H), 7.69 (dd, 1H), 7.39 (s, 1H), 7.07 (d, 1H), 6.96 (dd, 1H), 6.31 (s, 2H), 5.33 (s, 2H), 3.86 (d, 6H).

Example 153

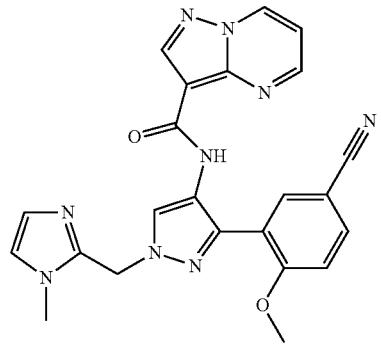 [SMILES: COc1ccc(C#N)cc1-c1nn(Cc2nccn2C)cc1NC(=O)c1cnn2cccnc12]

N-(3-(5-cyano-2-methoxyphenyl)-1-((1-methyl-1H-imidazol-2-yl)methyl)-1H-pyrazol-4-yl)pyrazolo pyrimidine-3-carboxamide To a solution of N-(3-(5-cyano-2-methoxyphenyl)-1H-pyrazol-4-yl)pyrazolo[1,5-a]pyrimidine-3-carboxamide (200 mg, 0.56 mmol) in 3 mL of DMF was added 2-(chloromethyl)-1-methyl-1H-imidazole (109 mg, 0.84 mmol) and cesium carbonate (547 mg, 1.68 mmol). The reaction mixture was stirred at room temperature for 3 hours, then diluted with ethyl acetate and filtered. The filtrate was washed with brine, dried over magnesium sulfate, and concentrated. The crude product was purified by reverse phase HPLC and lyophilized to give 82.2 mg (32%) of N-(3-(5-cyano-2-methoxyphenyl)-1-((1-methyl-1H-imidazol-2-yl)methyl)-1H-pyrazol-4-yl)pyrazolo[1,5-a]pyrimidine-3-carboxamide. LCMS (ESI) m+H=454.1; $^1$H NMR (400 MHz, CDCl$_3$) δ: 9.53 (s, 1H), 8.73 (dd, 1H), 8.64 (s, 1H), 8.48 (dd, 1H), 8.26 (s, 1H), 7.80 (d, 1H), 7.68 (dd, 1H), 7.06 (d, 1H), 6.97 (m, 2H), 6.83 (s, 1H), 5.42 (s, 2H), 3.85 (s, 3H), 3.63 (s, 3H).

Example 154

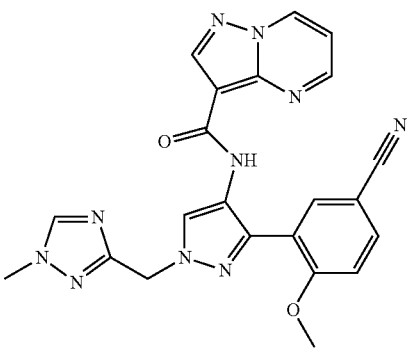 [SMILES: COc1ccc(C#N)cc1-c1nn(Cc2ncn(C)n2)cc1NC(=O)c1cnn2cccnc12]

213

N-(3-(5-cyano-2-methoxyphenyl)-1-((1-methyl-1H-1,2,4-triazol-3-yl)methyl)-1H-pyrazol-4-yl)pyrazolo[1,5-a]pyrimidine-3-carboxamide

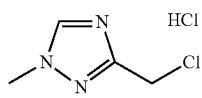

3-(chloromethyl)-1-methyl-1H-1,2,4-triazole hydrochloride (1-methyl-1H-1,2,4-triazol-3-yl)methanol (0.25 g, 2.2 mmol) was dissolved in 10 mL of SOCl₂ and refluxed for 2 hours. The mixture was evaporated to dryness and coevaporated with toluene. The resulting white solid (0.2 g) was used in the next step without further purification.

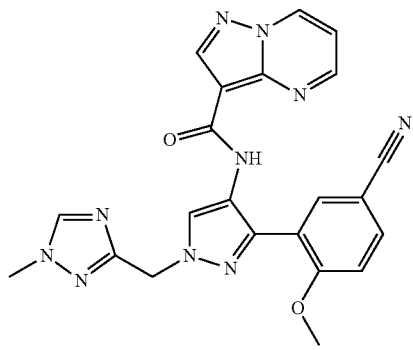 [SMILES: COc1ccc(C#N)cc1-c1nn(Cc2ncn(C)n2)cc1NC(=O)c1cnn2cccnc12]

N-(3-(5-cyano-2-methoxyphenyl)-1-((1-methyl-1H-1,2,4-triazol-3-yl)methyl)-1H-pyrazol-4-yl)pyrazolo[1,5-a]pyrimidine-3-carboxamide N-(3-(5-cyano-2-methoxyphenyl)-1H-pyrazol-4-yl)pyrazolo[1,5-a]pyrimidine-3-carboxamide (0.15 g, 0.42 mmol) was dissolved in 10 mL of DMF, then 3-(chloromethyl)-1-methyl-1H-1,2,4-triazole hydrochloride (82 mg, 0.63 mmol) and Cs₂CO₃ (0.41 g, 1.26 mmol) were added. The mixture was stirred at room temperature for 2 hours, then filtered through celite and purified by reverse phase HPLC to give 44.8 mg (23%) of N-(3-(5-cyano-2-methoxyphenyl)-1-((1-methyl-1H-1,2,4-triazol-3-yl)methyl)-1H-pyrazol-4-yl)pyrazolo[1,5-a]pyrimidine-3-carboxamide. LCMS (ESI) m+H=455.1; ¹H NMR (400 MHz, CDCl₃) δ: 9.64 (s, 1H), 9.34 (d, 1H), 8.75 (d, 1H), 8.64 (s, 1H), 8.44 (s, 1H), 8.35 (s, 1H), 7.95 (d, 1H), 7.73 (d, 1H), 7.47 (d, 1H), 7.28 (dd, 1H), 5.39 (s, 2H), 3.89 (s, 3H), 3.84 (s, 3H).

Example 155

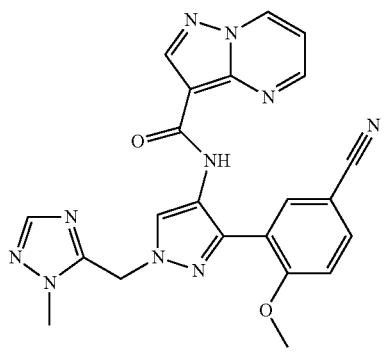 [SMILES: COc1ccc(C#N)cc1-c1nn(Cc2ncnn2C)cc1NC(=O)c1cnn2cccnc12]

214

N-(3-(5-cyano-2-methoxyphenyl)-1-(2-methyl-2H-1,2,4-triazol-3-yl)methyl)-1H-pyrazol-4-yl)pyrazolo[1,5-a]pyrimidine-3-carboxamide

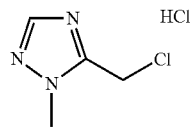

5-(chloromethyl)-1-methyl-1H-1,2,4-triazole hydrochloride (2-methyl-2H-1,2,4-triazol-3-yl)methanol (0.1 g, 0.88 mmol) was dissolved in 10 mL of SOCl₂ and refluxed for 2 hours. The mixture was evaporated to dryness and coevaporated with toluene. The resulting white solid (about 0.1 g) was used in the next step without further purification

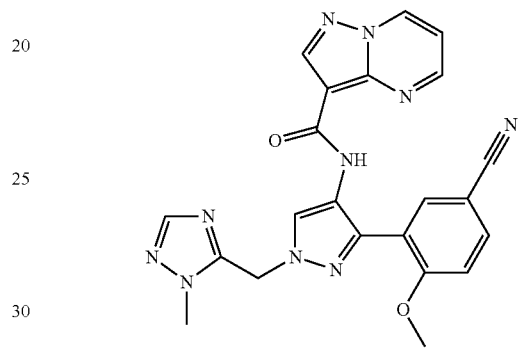

N-(3-(5-cyano-2-methoxyphenyl)-1-(2-methyl-2H-1,2,4-triazol-3-yl)methyl)-1H-pyrazol-4-yl)pyrazolo[1,5-a]pyrimidine-3-carboxamide N-(3-(5-cyano-2-methoxyphenyl)-1H-pyrazol-4-yl)pyrazolo[1,5-a]pyrimidine-3-carboxamide (0.21 g, 0.58 mmol) was dissolved in 10 mL of DMF. 5-(chloromethyl)-1-methyl-1H-1,2,4-triazole hydrochloride (about 0.1 g, 0.88 mmol) and Cs₂CO₃ (0.57 g, 1.75 mmol) were added and the mixture was stirred at room temperature overnight. The reaction mixture was filtered through Celite and purified by reverse phase HPLC to afford 60.8 mg (23%) of N-(3-(5-cyano-2-methoxyphenyl)-1-((2-methyl-2H-1,2,4-triazol-3-yl)methyl)-1H-pyrazol-4-yl)pyrazolo[1,5-a]pyramidine-3-carboxamide. LCMS (ESI) m+H=455.1; ¹H NMR (400 MHz, CDCl₃) δ: 9.64 (s, 1H), 9.64 (s, 1H), 9.33 (dd, 1H), 8.74 (dd, 1H), 8.64 (s, 1H), 8.42 (s, 1H), 7.95 (dd, 1H), 7.89 (s, 1H), 7.74 (d, 1H), 7.46 (d, 1H), 7.28 (dd, 1H), 5.65 (s, 2H), 3.90 (s, 3H), 3.88 (s, 3H).

Example 156

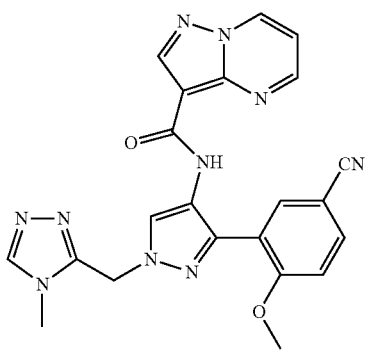 [SMILES: COc1ccc(C#N)cc1-c1nn(Cc2nncn2C)cc1NC(=O)c1cnn2cccnc12]

215

N-(3-(5-cyano-2-methoxyphenyl)-1-(4-methyl-4H-1,2,4-triazol-3-yl)methyl)-1H-pyrazol-4-yl)pyrazolo[1,5-a]pyrimidine-3-carboxamide

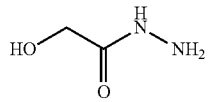

2-hydroxyacetohydrazide

Ethyl-2-hydroxyacetate (6 g, 0.12 mol) was added dropwise to a solution of hydrazine monohydrate (10.4 g, 0.1 mol) in EtOH (50 ml) at 0° C. The mixture was warmed to room temperature and stirred overnight. The mixture was concentrated in vacuo to give the desired product which was used in the next step without purification. Yield: 97%. $^1$H NMR (DMSO-d$_6$, 400 MHz) δ: 8.82 (s, 1H), 5.32-5.13 (m, 1H), 4.38-4.09 (m, 2H), 3.80 (s, 2H).

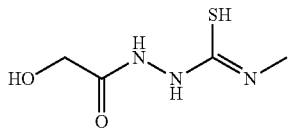

2-(2-hydroxyacetyl)-N-methylhydrazinecarbimidothioic acid

To a solution of 2-hydroxyacetohydrazide (4.5 g, 50 mmol) in EtOH was added dropwise methyl isothiocyanate (3.7 g, 50 mmol) under ice cooling. After addition was complete the reaction mixture was brought to room temperature and then stirred for 24 hr at 60° C. Ice water was then added and stirring was continued for 15 min. The reaction mixture was concentrated in vacuuo to give the title compound. Yield: 100%. LCMS (ESI) m+H=164.0.

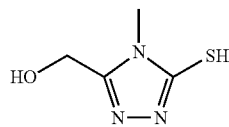

(5-mercapto-4-methyl-4H-1,2,4-triazol-3-yl)methanol

5N NaOH (50 mmol) was added to a solution of 2-(2-hydroxyacetyl)-N-methylhydrazinecarbimidothioic acid (8.15 g, 50 mmol) in EtOH, and then the mixture was stirred for 4 hr at 60° C. The mixture was cooled in an ice bath and the pH was adjusted to ~5-6 with concentrated HCl. The precipitated solid was filtered, washed with EtOH, and dried under vacuum to give the title compound. Yield: 83%. $^1$H NMR (DMSO-d$_6$, 400 MHz) δ: 5.64 (s, 1H), 4.46 (s, 2H), 3.44 (s, 3H).

216

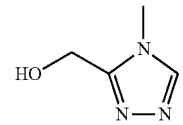

(4-methyl-4H-1,2,4-triazol-3-yl)methanol

NaNO$_2$ (70 mg, 1 mmol) was added to 5N HNO$_3$ (10 mL) at room temperature. The reaction mixture was cooled in an ice bath, then (5-mercapto-4-methyl-4H-1,2,4-triazol-3-yl)methanol (360 mg, 2.5 mmol) was added. The reaction mixture was then warmed to room temperature and stirred for one hour. Water (30 mL) was added, then the resulting mixture was neutralized using solid K$_2$CO$_3$ until the pH was ~7-8. The reaction mixture was concentrated in vacuo and the residue was dissolved in DCM/MeOH (5:1), filtered, and concentrated in vacuo to afford the title compound. Yield: 92%. $^1$H NMR (DMSO-d$_6$, 400 MHz) δ: 8.38 (s, 1H), 5.57 (s, 1H), 4.56 (d, J=10.8 Hz, 2H), 3.65 (s, 3H).

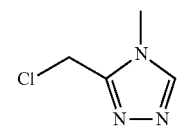

3-(chloromethyl)-4-methyl-4H-1,2,4-triazole

A solution of (4-methyl-4H-1,2,4-triazol-3-yl)methanol (260 mg, 2.3 mmol) in SOCl$_2$ (10 mL) was refluxed for 1 hour, and then concentrated in vacuo to give the desired compound. Yield: 100%. LCMS (ESI) m+H=132.1.

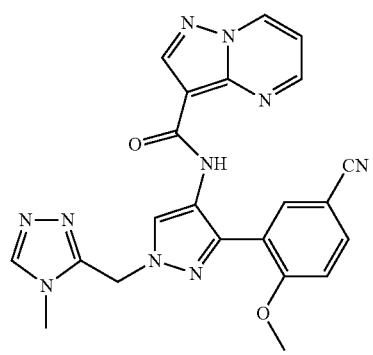 [SMILES: COc1ccc(C#N)cc1-c1nn(Cc2nncn2C)cc1NC(=O)c1cnn2cccnc12]

N-(3-(5-cyano-2-methoxyphenyl)-1-(4-methyl-4H-1,2,4-triazol-3-yl)methyl)-1H-pyrazol-4-yl)pyrazolo[1,5-a]pyrimidine-3-carboxamide N-(3-(5-cyano-2-methoxyphenyl)-1H-pyrazol-4-yl)pyrazolo[1,5-a]pyrimidine-3-carboxamide (120 mg, 0.334 mmol), 3-(chloromethyl)-4-methyl-4H-1,2,4-triazole (65 mg, 0.5 mmol) and Cs$_2$CO$_3$ (325 mg, 1 mmol) were suspended in DMF. The mixture was stirred overnight at room temperature, then filtered and concentrated in vacuo. The residue was purified by preparative HPLC to afford N-(3-(5-cyano-2-methoxyphenyl)-1-((4-methyl-4H-1,2,4-triazol-3- yl)methyl)-1H-pyrazol-4-yl)pyrazolo[1,5-a]pyrimidine-3-carboxamide (23.2 mg, yield: 15%). $^1$H NMR (CDCl$_3$, 400 MHz) δ: 9.59 (s, 1H), 8.77 (dd, J=2.0, 7.2 Hz, 1H), 8.70 (s, 1H), 8.51 (dd, J=2.0, 4.4 Hz, 1H), 8.39 (s, 1H), 8.11 (s, 1H), 7.82 (d, J=2.0 Hz, 1H), 7.73 (dd, J=2.0, 8.4 Hz, 1H), 7.10 (d, J=8.4 Hz, 1H), 6.99 (q, J=4.4, 6.8 Hz, 1H), 3.91 (s, 3H), 3.72 (s, 3H).

Example 157

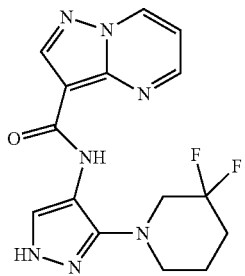 [SMILES: O=C(Nc1c[nH]nc1N1CCCC(F)(F)C1)c1cnn2cccnc12]

N-(3-(3,3-difluoropiperidin-1-yl)-1H-pyrazol-4-yl)pyrazolo[1,5-a]pyrimidine-3-carboxamide

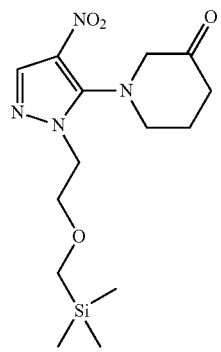

1-(4-nitro-1-(2-((trimethylsilyl)methoxy)ethyl)-1H-pyrazol-5-yl)piperidin-3-one

To a solution of oxalyl chloride (0.82 g, 6.44 mmol) and DMSO (1.07 g, 13.75 mmol) was added dropwise 1-(4-nitro-1-((2-(trimethylsilyl)ethoxy)methyl)-1H-pyrazol-5-yl)piperidin-3-ol (2.0 g, 5.85 mmol) at −78° C. the reaction mixture was stirred at that temperature for 15 min, then Et$_3$N (4.1 mL, 29.25 mmol) was added. The reaction mixture was warmed to room temperature and stirred for an additional 90 minutes. The reaction mixture was concentrated in vacuo and the residue was purified by silica gel column chromatography (hexanes/EtOAc=50:1) to afford 1.9 g (95%) of 1-(4-nitro-1-(2-((trimethylsilyl)methoxy)ethyl)-1H-pyrazol-5-yl)piperidin-3-one. $^1$H NMR (400 MHz, CDCl$_3$) δ: 8.09 (s, 1H), 5.30 (s, 2H), 3.68 (m, 2H), 3.69 (m, 2H), 3.48 (m, 2H), 2.63 (m, 2H), 2.14 (m, 2H), 0.93 (m, 2H), 0 (s, 9H).

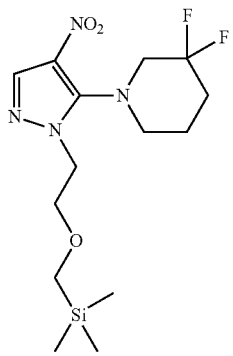 [SMILES: C[Si](C)(C)COCCn1ncc([N+](=O)[O-])c1N1CCCC(F)(F)C1]

3,3-difluoro-1-(4-nitro-1-(2-((trimethylsilyl)methoxy)ethyl)-1H-pyrazol-5-yl)piperidine To a solution of 1-(4-nitro-1-(2-((trimethylsilyl)methoxy)ethyl)-1H-pyrazol-5-yl)piperidin-3-one (1.8 g, 5.28 mmol) in 20 mL of ethanol was added DAST (1.3 g, 7.92 mmol). The reaction mixture was stirred at room temperature for 3 hours, then 100 mL of water was added to the mixture. The mixture was extracted twice with dichloromethane and the combined organic extracts were dried over magnesium sulfate and concentrated to afford 1.4 g (73%) of 3,3-difluoro-1-(4-nitro-1-(2-((trimethylsilyl)methoxy)ethyl)-1H-pyrazol-5-yl)piperidine. $^1$H NMR (400 MHz, CDCl$_3$) δ: 8.08 (s, 1H), 5.41 (m, 2H), 3.70 (m, 6H), 2.11 (m, 2H), 1.92 (s, 2H), 0.94 (m, 2H), 0 (s, 9H).

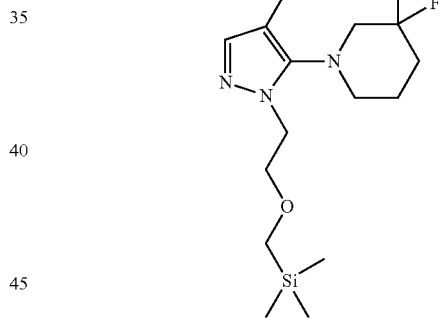

5-(3,3-difluoropiperidin-1-yl)-1-(2-((trimethylsilyl)methoxy)ethyl)-1H-pyrazol-4-amine To a solution of 3,3-difluoro-1-(4-nitro-1-(2-((trimethylsilyl)methoxy)ethyl)-1H-pyrazol-5-yl)piperidine (1.4 g, 3.86 mmol) in 20 mL of ethanol was added 40 mL of water, ammonium chloride (0.82 mg, 15.44 mmol), and iron powder (1.08 g, 19.3 mmol). The reaction mixture was stirred at 70° C. for 1 hour. After cooling to room temperature, the reaction mixture was diluted with dichloromethane and filtered through a celite pad, rinsing with more dichloromethane. The filtrate was extracted twice with dichloromethane, then the combined organic extracts were dried over magnesium sulfate and concentrated to afford 1.2 g (93%) of 5-(3,3-difluoropiperidin-1-yl)-1-(2-((trimethylsilyl)methoxy)ethyl)-1H-pyrazol-4-amine. LCMS (ESI) m+H=333.1; $^1$H NMR (400 MHz, CDCl$_3$) δ: 7.09 (s, 1H), 5.38 (m, 2H), 3.74 (m, 6H), 2.01 (s, 1H), 1.96 (s, 2H), 1.52 (m, 2H), 0.92 (m, 2H), 0 (s, 9H).

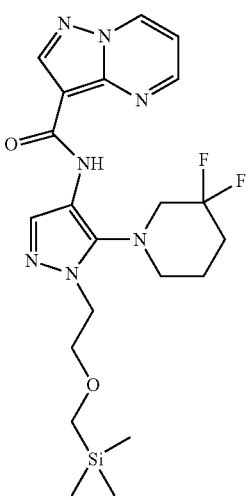 [SMILES: C[Si](C)(C)COCCn1ncc(NC(=O)c2cnn3cccnc23)c1N1CCCC(F)(F)C1]

N-(5-(3,3-difluoropiperidin-1-yl)-1-(2-((trimethylsilyl)methoxy)ethyl)-1H-pyrazol-4-yl)pyrazolo[1,5-a]pyrimidine-3-carboxamide To a solution of 5-(3,3-difluoropiperidin-1-yl)-1-(2-((trimethylsilyl)methoxy)ethyl)-1H-pyrazol-4-amine (1.2 g, 3.61 mmol) in 30 mL THF was added DIPEA (1.3 mL, 7.22 mmol) and pyrazolo[1,5-a]pyrimidine-3-carbonyl chloride (720 mg, 3.97 mmol) in THF (50 mL) at 0° C. After addition was complete, the mixture was warmed to room temperature, then stirred overnight. The mixture was concentrated in vacuo and the residue was purified by silica gel column chromatogaphy (hexanes:EtOAc=3:1 to 1:1) to afford 1.0 g (60%) of N-(5-(3,3-difluoropiperidin-1-yl)-1-(2-((trimethylsilyl)methoxy)ethyl)-1H-pyrazol-4-yl)pyrazolo[1,5-a]pyrimidine-3-carboxamide. LCMS (ESI) m+H=478.2; $^1$H NMR (400 MHz, CDCl$_3$) δ: 9.49 (s, 1H), 8.87 (dd, 1H), 8.75 (s, 1H), 8.71 (dd, 1H), 7.94 (s, 1H), 7.10 (dd, 1H), 5.40 (s, 2H), 3.67 (m, 6H), 2.06 (s, 2H), 1.93 (m, 2H), 0.95 (m, 2H), 0 (s, 9H).

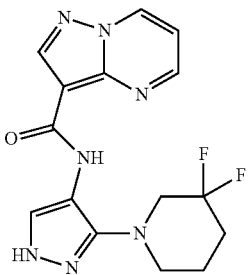 [SMILES: O=C(Nc1c[nH]nc1N1CCCC(F)(F)C1)c1cnn2cccnc12]

N-(3-(3,3-difluoropiperidin-1-yl)-1H-pyrazol-4-yl)pyrazolo[1,5-a]pyrimidine-3-carboxamide To a solution of N-(5-(3,3-difluoropiperidin-1-yl)-1-(2-((trimethylsilyl)methoxy)ethyl)-1H-pyrazol-4-yl)pyrazolo[1,5-a]pyrimidine-3-carboxamide (1.0 g, 2.1 mmol) in 50 mL of ethanol was added HCl (1.75 mL of a 6 M solution in water, 10.5 mmol). The reaction mixture was stirred at 70° C. for 1 hour. After cooling to room temperature, a light yellow precipitate formed, which was filtered off and rinsed with methanol and diethyl ether. The filtrate was then reduced in volume, and more solid product isolated by filteration. The combined collected solids were dried under vacuum to afford 0.77 g (94%) of N-(3-(3,3-difluoropiperidin-1-yl)-1H-pyrazol-4-yl)pyrazolo[1,5-a]pyrimidine-3-carboxamide. LCMS (ESI) m+H=348.1; $^1$H NMR (400 MHz, CDCl$_3$) δ: 9.59 (s, 1H), 9.37 (dd, 1H), 8.84 (m, 2H), 8.01 (s, 1H), 7.32 (dd, 1H), 3.74 (s, 1H), 3.33 (m, 2H), 3.12 (m, 2H), 2.10 (m, 2H), 2.00 (m, 2H).

Example 158

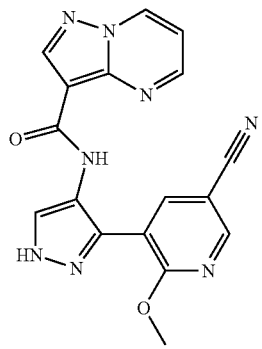 [SMILES: COc1ncc(C#N)cc1-c1n[nH]cc1NC(=O)c1cnn2cccnc12]

N-(3-(5-Cyano-2-methoxypyridin-3-yl)-1H-pyrazol-4-yl)pyrazolo[1,5-a]pyrimidine-3-carb oxamide

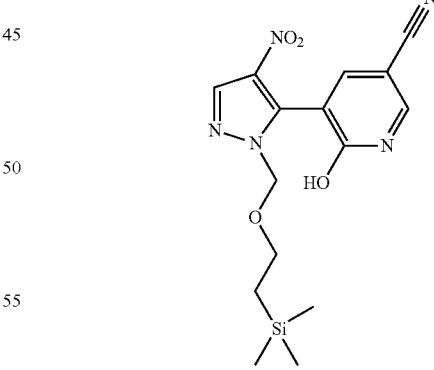

6-Hydroxy-5-(4-nitro-1-((2-(trimethylsilyl)ethoxy)methyl)-1H-pyrazol-5-yl)nicotinonitrile The title compound was prepared by following the procedures described for N-(5-(5-chloro-2-methoxyphenyl)-1-isopentyl-4-nitro-1H-pyrazole.

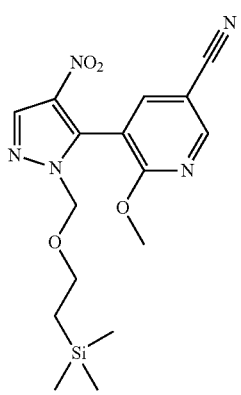 [SMILES: COc1ncc(C#N)cc1-c1c([N+](=O)[O-])cnn1COCC[Si](C)(C)C]

6-Methoxy-5-(4-nitro-1-((2-(trimethylsilyl)ethoxy)methyl)-1H-pyrazol-5-yl)nicotinonitrile To an ice-cooled solution of 6-methoxy-5-(4-nitro-1-((2-(trimethylsilyl)ethoxy)methyl)-1H-pyrazol-5-yl)nicotinonitrile (57 mg, 0.16 mmol, 1 equiv) in a 1:1 methanol/toluene solution (3 mL) was added trimethylsilyldiazomethane (0.8 mL, 1.6 mmol, 2.0 M solution in diethyl ether). The reaction mixture was warmed to 24° C. after 50 min and concentration in vacuo. Purification by flash column chromatography (1:1 heptane/ethyl acetate) provided product (3.3 mg, 5.6%). $^1$H NMR (400 MHz, CDCl$_3$), δ: 8.63 (d, J=2.2 Hz, 1H), 8.21 (s, 1H), 7.96 (d, J=2.2 Hz, 1H), 5.27 (m, 2H), 3.97 (s, 3H), 3.63 (m, 2H), 0.86 (m, 2H), −0.02 (s, 9H).

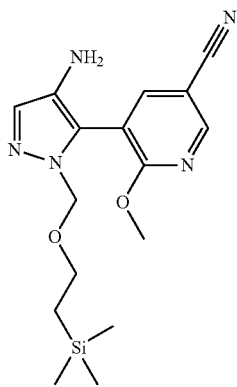

5-(4-Amino-1-((2-(trimethylsilyl)ethoxy)methyl)-1H-pyrazol-5-yl)-6-methoxynicotinonitrile A solution of 6-methoxy-5-(4-nitro-1-((2-(trimethylsilyl)ethoxy)methyl)-1H-pyrazol-5-yl)nicotinonitrile (11 mg, 0.029 mmol, 1 equiv) in methanol (4 mL) was circulated through a H-Cube® continuous-flow hydrogenation reactor (ThalesNano) fitted with a palladium on carbon catalyst cartridge at 30° C. The resulting solution was concentrated in vacuo to provide product (7.1 mg, 70% crude yield). $^1$H NMR (400 MHz, CDCl$_3$), δ: 8.52 (d, J=2.2 Hz, 1H), 8.09 (d, J=2.2 Hz, 1H), 5.21 (s, 2H), 4.06 (s, 3H), 3.58 (m, 2H), 0.85 (m, 2H), −0.04 (s, 9H).

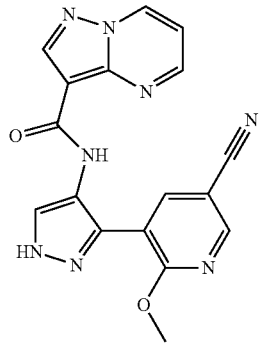 [SMILES: COc1ncc(C#N)cc1-c1n[nH]cc1NC(=O)c1cnn2cccnc12]

N-(3-(5-Cyano-2-methoxypyridin-3-yl)-1H-pyrazol-4-yl)pyrazolo[1,5-a]pyrimidine-3-carboxamide To a suspension of pyrazolo[1,5-a]pyrimidine-3-carboxylic acid (22.0 mg, 0.135 mmol, 6.56 equiv), 5-(4-amino-1-((2-(trimethylsilyl)ethoxy)methyl)-1H-pyrazol-5-yl)-6-methoxynicotinonitrile (7.1 mg, 0.020 mmol, 1 equiv), and 2-chloro-2,4-dimethoxy-1,3,5-triazine (23.7 mg, 0.135 equiv, 6.56 equiv) in acetonitrile (2 mL) was added 4-methylmorpholine (23 uL, 0.21 mmol, 10 equiv) at 24° C. After 2 days, the reaction mixture was partitioned between saturated aqueous sodium bicarbonate solution (2 mL), saturated aqueous sodium chloride solution (2 mL), and ethyl acetate (5 mL). The organic was separated, and the aqueous was extracted with ethyl acetate (2×5 mL). The combined organic was dried over anhydrous sodium sulfate, filtered, and concentrated. The crude material was dissolved in ethanol (3 mL) and 6 N aqueous hydrochloric acid (1 mL) and heated to 50° C. After 5 h, the reaction mixture was concentrated in vacuo and purified by preparative HPLC to afford a white solid (1.1 mg, 15% yield). $^1$H NMR (400 MHz, CDCl$_3$), δ: 9.72 (s, 1H), 8.80 (dd, J=7.0, 1.6 Hz, 1H), 8.74 (s, 1H), 8.66 (m, 1H), 8.54 (d, J=2.2 Hz, 1H), 8.47 (s, 1H), 8.22 (d, J=1.9 Hz, 1H), 7.04 (dd, J=7.0, 4.2 Hz, 1H), 4.11 (s, 3H). LCMS (ESI): M+H=361.1

Example 159

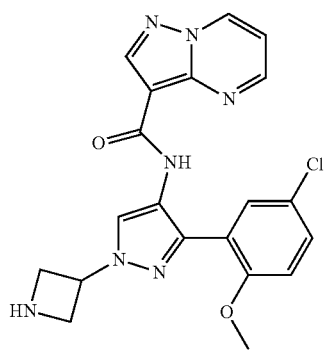 [SMILES: COc1ccc(Cl)cc1-c1nn(C2CNC2)cc1NC(=O)c1cnn2cccnc12]

N-(1-(Azetidin-3-yl)-3-(5-chloro-2-methoxyphenyl)-1H-pyrazol-4-yl)pyrazolo[1,5-a]pyrimidine-3-carboxamide A suspension of N-(3-(5-chloro-2-methoxyphenyl)-1H-pyrazol-4-yl)pyrazolo[1,5-a]pyrimidine-3-carboxamide (50.0 mg, 0.136 mmol, 1 equiv), tert-butyl 3-iodoazetidine-1-carboxylate (230.3 mg, 0.813 mmol, 6.00 equiv), and cesium carbonate (177 mg, 0.542 mmol, 4.00 equiv) in N,N-dimethylformamide (1 mL) was heated at 50° C. After 5 h, the reaction mixture was partitioned between saturated aqueous sodium chloride solution (5 mL) and ethyl acetate (5 mL). The aqueous layer was extracted with ethyl acetate (2×5 mL). The combined organic was dried over anhydrous sodium sulfate, filtered, and concentrated. The crude residue was dissolved in dichloromethane (2 mL) and trifluoroacetic acid (2 mL) at 24° C. After 5 h, the reaction mixture was concentrated in vacuo and purified by preparative HPLC to afford product (12.7 mg, 22% yield). $^1$H NMR (400 MHz, DMSO-$d_6$), δ: 9.75 (s, 1H), 9.36 (m, 1H), 8.79 (m, 1H), 8.67 (s, 1H), 8.46 (s, 1H), 7.53-7.56 (m, 2H), 7.29-7.34 (m, 2H), 5.45 (m, 1H), 4.33 (m, 2H), 4.23 (m, 2H), 3.86 (s, 3H). LCMS (ESI): M+H=424.1.

Example 160

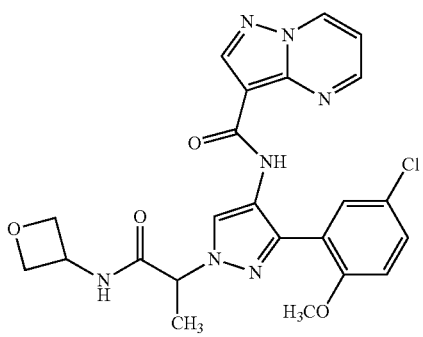 [SMILES: COc1ccc(Cl)cc1-c1nn(C(C)C(=O)NC2COC2)cc1NC(=O)c1cnn2cccnc12]

N-(3-(5-chloro-2-methoxyphenyl)-1-(1-(oxetan-3-ylamino)-1-oxopropan-2-yl)-1H-pyrazol-4-yl)pyrazolo pyrimidine-3-carboxamide

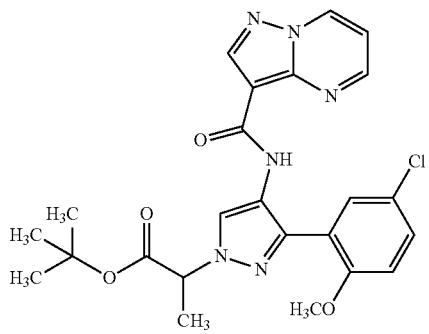 [SMILES: COc1ccc(Cl)cc1-c1nn(C(C)C(=O)OC(C)(C)C)cc1NC(=O)c1cnn2cccnc12]

tert-Butyl 2-(3-(5-chloro-2-methoxyphenyl)-4-(pyrazolo[1,5-a]pyrimidine-3-carboxamido)-1H-pyrazol-1-yl)propanoate A suspension of N-(3-(5-chloro-2-methoxyphenyl)-1H-pyrazol-4-yl)pyrazolo[1,5-a]pyrimidine-3-carboxamide (1.0 g, 2.7 mmol, 1 equiv), tert-butyl 2-bromopropanoate (0.54 mL, 3.2 mmol, 1.2 equiv), and cesium carbonate (1.1 g, 3.2 mmol, 1.2 equiv) in N,N-dimethylformamide (15 mL) was heated at 75° C. for 3 h. The reaction mixture was concentrated, and the resulting residue was partitioned between half-saturated aqueous sodium chloride solution (50 mL) and ethyl acetate (50 mL). The aqueous was extracted with ethyl acetate (2×50 mL). The collected organic was dried over anhydrous sodium sulfate, filtered, and concentrated. Purification by flash column chromatography (90% ethyl acetate in heptane) provided product (0.945 g, 70%). LCMS (ESI): M+H=497.2.

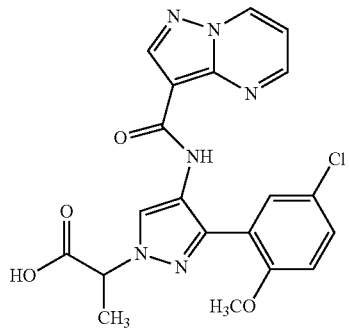 [SMILES: COc1ccc(Cl)cc1-c1nn(C(C)C(=O)O)cc1NC(=O)c1cnn2cccnc12]

2-(3-(5-Chloro-2-methoxyphenyl)-4-(pyrazolo pyrimidine-3-carboxamido)-1H-pyrazol-1-yl)propanoic acid Trifluoroacetic acid (10 mL) was added dropwise to a solution of tert-butyl 2-(3-(5-chloro-2-methoxyphenyl)-4-(pyrazolo pyrimidine-3-carboxamido)-1H-pyrazol-1-yl)propanoate (0.945 g, 1.90 mmol, 1 equiv) in dichloromethane (10 mL). After 2 h, the reaction mixture was concentrated in vacuo to afford crude product (quantitative) which was used without further purification. LCMS (ESI): M+H=441.1.

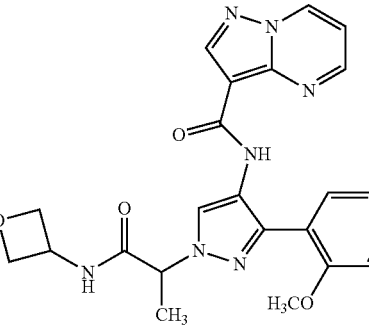

N-(3-(5-chloro-2-methoxyphenyl)-1-(1-(oxetan-3-ylamino)-1-oxopropan-2-yl)-1H-pyrazol-4-yl)pyrazolo pyrimidine-3-carboxamide A solution of 2-(3-(5-chloro-2-methoxyphenyl)-4-(pyrazolo pyrimidine-3-carboxamido)-1H-pyrazol-1-yl)propanoic acid (66.0 mg, 0.150 mmol, 1 equiv), oxetan-3-amine hydrochloride (41.0 mg, 0.374 mmol, 2.50 equiv), N,N,N',N'-tetramethyl-O-(7-azabenzotriazole-1-yl)uranium hexafluorophosphate (114 mg, 0.299 mmol, 2.00 equiv), and N,N-diisopropylethylamine (522 µL, 2.99 mmol, 20.0 equiv) in N,N-dimethylformamide (1.0 mL) was heated at 50° C. After 6 h, the reaction mixture was concentrated, and the resulting residue was partitioned between saturated aqueous sodium bicarbonate (10 mL) and ethyl acetate (10 mL). The aqueous was extracted with ethyl acetate (2×5 mL). The combined organic was dried over anhydrous sodium sulfate, filtered, and concentrated. Purification by preparative HPLC afforded product (39 mg, 51% yield). $^1$H NMR (400 MHz, DMSO-d$_6$), δ: 9.70 (s, 1H), 9.33 (m, 1H), 9.02 (d, J=6.5 Hz, 1H), 8.77 (dd, J=4.2, 1.5 Hz, 1H), 8.65 (s, 1H), 8.36 (s, 1H), 7.50 (dd, J=8.9, 2.7 Hz, 1H), 7.38 (d, J=2.6 Hz, 1H), 7.27-7.31 (m, 2H), 5.06 (q, J=7.1 Hz, 1H), 4.80 (m, 1H), 4.73 (m, 2H), 4.44 (m, 2H), 3.84 (s, 3H), 1.66 (d, J=7.1 Hz, 3H). LCMS (ESI): M+H=496.1.

Example 161

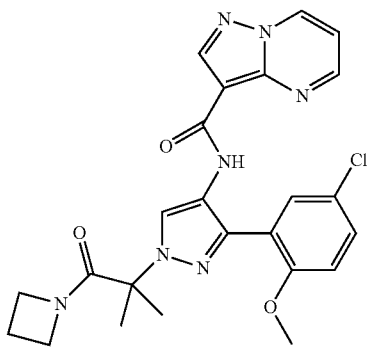 [SMILES: COc1ccc(Cl)cc1-c1nn(C(C)(C)C(=O)N2CCC2)cc1NC(=O)c1cnn2cccnc12]

N-(1-(1-(azetidin-1-yl)-2-methyl-1-oxopropan-2-yl)-3-(5-chloro-2-methoxyphenyl)-1H-pyrazol-4-yl)pyrazolo[1,5-a]pyrimidine-3-carboxamide

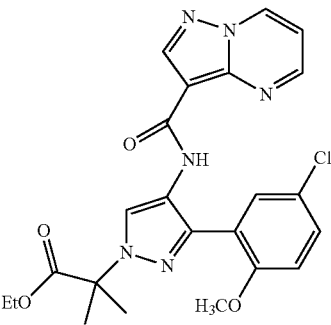 [SMILES: CCOC(=O)C(C)(C)n1cc(NC(=O)c2cnn3cccnc23)c(-c2cc(Cl)ccc2OC)n1]

Ethyl 2-(3-(5-chloro-2-methoxyphenyl)-4-(pyrazolo[1,5-a]pyrimidine-3-carboxamido)-1H-pyrazol-1-yl)-2-methylpropanoate A suspension of N-(3-(5-chloro-2-methoxyphenyl)-1H-pyrazol-4-yl)pyrazolo[1,5-a]pyrimidine-3-carboxamide (1.0 g, 2.7 mmol, 1 equiv), ethyl 2-bromoisobutyrate (0.597 mL, 4.07 mmol, 1.50 equiv), and cesium carbonate (1.77 g, 5.42 mmol, 2.00 equiv) in N,N-dimethylformamide (15 mL) was heated at 50° C. After 5 h, the reaction mixture was concentrated in vacuo, and the resulting residue was partitioned between saturate aqueous sodium chloride solution (30 mL) and ethyl acetate (20 mL). The aqueous was extracted with ethyl acetate (2×20 mL). The combined organic was dried over anhydrous sodium sulfate, filtered, and concentrated to provide crude product (1.13 g, 84% yield). LCMS (ESI): M+H=483.2.

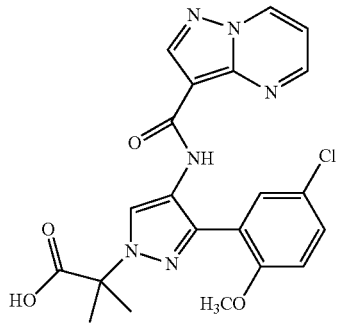 [SMILES: COc1ccc(Cl)cc1-c1nn(C(C)(C)C(=O)O)cc1NC(=O)c1cnn2cccnc12]

2-(3-(5-chloro-2-methoxyphenyl)-4-(pyrazolo[1,5-a]pyrimidine-3-carboxamido)-1H-pyrazol-1-yl)-2-methylpropanoic acid To a solution of ethyl 2-(3-(5-chloro-2-methoxyphenyl)-4-(pyrazolo[1,5-a]pyrimidine-3-carboxamido)-1H-pyrazol-1-yl)-2-methylpropanoate (0.918 g, 1.90 mmol, 1 equiv) was added 2 N aqueous sodium hydroxide solution (4 mL). After 18 h, additional 2 N aqueous sodium hydroxide solution (4 mL) was added. After 5 h, the reaction mixture was concentrated in vacuo, and the resulting residue was dissolved in water (15 mL). The aqueous solution was acidified with 6 N aqueous hydrochloric acid until pH=2. The resulting aqueous solution was extracted with ethyl acetate (3×30 mL). The combined organic was dried over anhydrous sodium sulfate, filtered, and concentrated to provide crude acid (quantitative). LCMS (ESI): M+H=455.1.

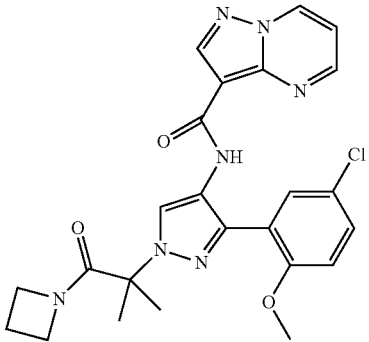 [SMILES: COc1ccc(Cl)cc1-c1nn(C(C)(C)C(=O)N2CCC2)cc1NC(=O)c1cnn2cccnc12]

N-(1-(1-(azetidin-1-yl)-2-methyl-1-oxopropan-2-yl)-3-(5-chloro-2-methoxyphenyl)-1H-pyrazol-4-yl)pyrazolo pyrimidine-3-carboxamide A solution of 2-(3-(5-chloro-2-methoxyphenyl)-4-(pyrazolo pyrimidine-3-carboxamido)-1H-pyrazol-1-yl)-2-methylpropanoic acid (0.050 g, 0.11 mmol, 1 equiv), azetidine (18.5 μL, 0.275 mmol, 2.50 equiv), N,N,N',N'-tetramethyl-O-(7-azabenzotriazole-1-yl)uranium hexafluorophosphate (84 mg, 0.20 mmol, 2.00 equiv), and N,N-diisopropylethylamine (380 μL, 2.2 mmol, 20 equiv) in N,N-dimethylformamide (1 mL) was heated at 50° C. After 6 h, the reaction mixture was concentrated, and the resulting residue was partitioned between saturated aqueous sodium bicarbonate (5 mL) and ethyl acetate (5 mL). The aqueous was extracted with ethyl acetate (2×5 mL). The combined organic was dried over anhydrous sodium sulfate, filtered, and concentrated. Purification by preparative HPLC afforded product (32 mg, 60% yield). $^1$H NMR (400 MHz, DMSO-d$_6$), δ: 9.70 (s, 1H), 9.34 (m, 1H), 8.77 (dd, J=4.2, 1.5 Hz, 1H), 8.64 (s, 1H), 8.36 (s, 1H), 7.52 (dd, J=8.9, 2.7 Hz, 1H), 7.41 (d, J=2.6 Hz, 1H), 7.28-7.32 (m, 2H), 3.88 (s, 2H), 3.86 (s, 3H), 3.41 (m, 2H), 2.04 (m, 2H), 1.72 (s, 6H). LCMS (ESI): M+H=494.1.

Example 162

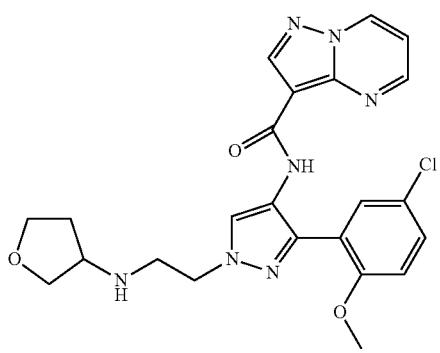 [SMILES: COc1ccc(Cl)cc1-c1nn(CCNC2CCOC2)cc1NC(=O)c1cnn2cccnc12]

N-(3-(5-Chloro-2-methoxyphenyl)-1-(2-(tetrahydrofuran-3-ylamino)ethyl)-1H-pyrazol-4-yl)pyrazolo pyrimidine-3-carboxamide

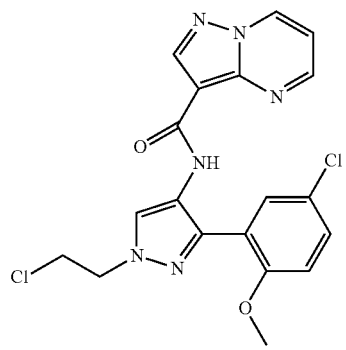 [SMILES: COc1ccc(Cl)cc1-c1nn(CCCl)cc1NC(=O)c1cnn2cccnc12]

N-(3-(5-Chloro-2-methoxyphenyl)-1-(2-chloroethyl)-1H-pyrazol-4-yl)pyrazolo[1,5-a]pyrimidine-3-carboxamide A suspension of N-(3-(5-chloro-2-methoxyphenyl)-1H-pyrazol-4-yl)pyrazolo[1,5-a]pyrimidine-3-carboxamide (1.0 g, 2.7 mmol, 1 equiv), 2-chloroethyl para-toluenesulfonate (745 μL, 4.11 mmol, 1.5 equiv), and cesium carbonate (2.16 g, 6.62 mmol, 2.4 equiv) in N,N-dimethylformamide (10 mL) was heated at 50° C. After 3 h, the reaction mixture was concentrated in vacuo, and the resulting residue was partitioned between ethyl acetate (30 mL) and half-saturated aqueous sodium chloride solution (30 mL). The aqueous was extracted with ethyl acetate (2×20 mL). The combined organic was dried over anhydrous sodium sulfate, filtered, and concentrated. Purification by flash column chromatography (ethyl acetate) provided product (950 mg, 77% yield). LCMS (ESI): M+H=432.1.

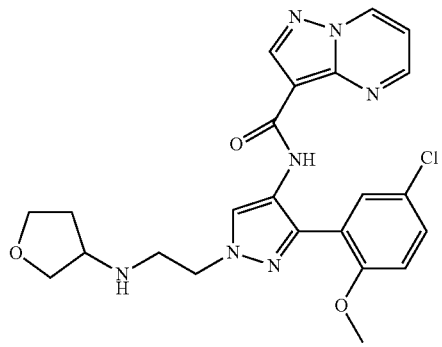 [SMILES: COc1ccc(Cl)cc1-c1nn(CCNC2CCOC2)cc1NC(=O)c1cnn2cccnc12]

N-(3-(5-Chloro-2-methoxyphenyl)-1-(2-(tetrahydrofuran-3-ylamino)ethyl)-1H-pyrazol-4-yl)pyrazolo[1,5-a]pyrimidine-3-carboxamide A solution of N-(3-(5-chloro-2-methoxyphenyl)-1-(2-chloroethyl)-1H-pyrazol-4-yl)pyrazolo[1,5-a]pyrimidine-3-carboxamide (0.040 g, 0.090 mmol, 1 equiv), 3-aminotetrahydrofuran hydrochloride (29 mg, 0.23 mmol, 2.50 equiv), and N,N-diisopropylethylamine (73 μL, 0.42 mmol, 4.5 equiv) in N-methylpyrrolidinone (1 mL) was heated at 100° C. After 18 h, the reaction mixture was partitioned between ethyl acetate (10 mL) and half-saturated aqueous sodium chloride solution (10 mL). The aqueous was extracted with ethyl acetate (2×10 mL). The combined organic was dried over anhydrous sodium sulfate, filtered, and concentrated. Purification by preparative HPLC provided product (13.3 mg, 30% yield). $^1$H NMR (400 MHz, DMSO-d$_6$), δ: 9.67 (s, 1H), 9.32 (dd, J=7.0, 1.5 Hz, 1H), 8.77 (dd, J=4.2, 1.6 Hz, 1H), 8.65 (s, 1H), 8.31 (s, 1H), 7.49 (dd, J=8.9, 2.7 Hz, 1H), 7.40 (d, J=2.7 Hz, 1H), 7.27-7.30 (m, 2H), 4.21 (t, J=6.4 Hz, 2H), 3.85 (s, 3H), 3.60-3.76 (m, 4H), 3.38 (m, 2H), 2.96 (m, 2H), 1.96 (m, 1H), 1.62 (m, 1H). LCMS (ESI): M+H=482.2.

Example 163

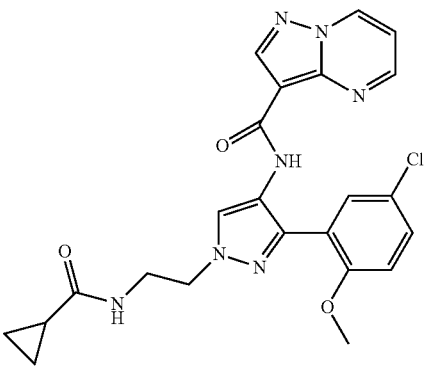 [SMILES: COc1ccc(Cl)cc1-c1nn(CCNC(=O)C2CC2)cc1NC(=O)c1cnn2cccnc12]

N-(3-(5-chloro-2-methoxyphenyl)-1-(2-(cyclopropanecarboxamido)ethyl)-1H-pyrazol-4-yl)pyrazolo[1,5-a]pyrimidine-3-carboxamide To a solution of N-(1-(2-aminoethyl)-3-(5-chloro-2-methoxyphenyl)-1H-pyrazol-4-yl)pyrazolo[1,5-a]pyrimidine-3-carboxamide (0.030 g, 0.073 mmol, 1 equiv) and N,N-diisopropylethylamine (51 µL, 0.29 mmol, 4.0 equiv) in dichloromethane (1 mL) was added dropwise cyclopropanecarbonyl chloride (0.020 mL, 0.22 mmol, 3.0 equiv) at 24° C. After 1 h, the reaction mixture was concentrated in vacuo. Purification by preparative HPLC provided product (16.5 mg, 47% yield). $^1$H NMR (400 MHz, DMSO-$d_6$), δ: 9.69 (s, 1H), 9.33 (dd, J=7.0, 1.6 Hz, 1H), 8.78 (dd, J=4.1, 1.5 Hz, 1H), 8.66 (s, 1H), 8.28 (s, 1H), 8.22 (t, J=5.5 Hz, 1H), 7.50 (dd, J=8.8, 2.8 Hz, 1H), 7.44 (d, J=2.7 Hz, 1H), 7.27-7.31 (m, 2H), 4.22 (t, J=6.1 Hz, 2H), 3.85 (s, 3H), 3.52 (q, J=6.0 Hz, 2H), 1.55 (m, 1H), 0.62-0.71 (m, 4H). LCMS (ESI): M+H=480.2.

Example 164

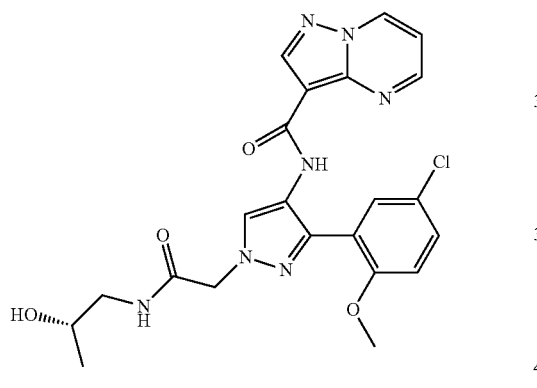

(S)—N-(3-chloro-2-methoxyphenyl)-1-(2-(2-hydroxypropylamino)-2-oxoethyl)-1H-pyrazol-4-yl)pyrazolo[1,5-a]pyrimidine-3-carboxamide A solution of 2-(3-(5-chloro-2-methoxyphenyl)-4-(pyrazolo[1,5-a]pyrimidine-3-carboxamido)-1H-pyrazol-1-yl) acetic acid (51 mg, 0.12 mmol, 1 equiv), (2S)-1-aminopropan-2-ol (24 µL, 0.30 mmol, 2.5 equiv), triethylamine (20 µL), and N,N,N',N'-tetramethyl-O-(7-azabenzotriazole-1-yl) uranium hexafluorophosphate (91 mg, 0.24 mmol, 2.0 equiv) in N,N-dimethylformamide (1.2 mL) was heated at 80° C. After 6 h, the reaction mixture was concentrated in vacuo, and the resulting residue was partitioned between saturated aqueous sodium bicarbonate (5 mL) and ethyl acetate (5 mL). The aqueous was extracted with ethyl acetate (2×5 mL). The combined organic was dried over anhydrous sodium sulfate, filtered, and concentrated. Purification by preparative HPLC afforded product (17 mg, 29% yield). $^1$H NMR (400 MHz, DMSO-$d_6$), δ: 9.70 (s, 1H), 9.35 (dd, J=7.0, 1.5 Hz, 1H), 8.70 (dd, J=4.2, 1.5 Hz, 1H), 8.66 (s, 1H), 8.32 (s, 1H), 8.11 (t, J=5.8 Hz, 1H), 7.50 (dd, J=8.9, 2.7 Hz, 1H), 7.38 (d, J=2.7 Hz, 1H), 7.27-7.32 (m, 2H), 4.88 (s, 2H), 4.74 (d, J=4.7 Hz, 1H), 3.85 (s, 3H), 3.68 (m, 1H), 3.06 (m, 2H), 1.04 (d, J=6.2 Hz, 3H). LCMS (ESI): M+H=484.2.

Example 165

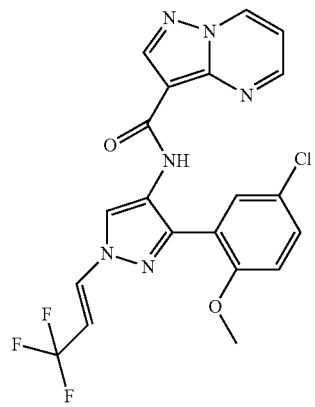 [SMILES: COc1ccc(Cl)cc1-c1nn(/C=C/C(F)(F)F)cc1NC(=O)c1cnn2cccnc12]

(E)-N-(3-(5-chloro-2-methoxyphenyl)-1-(3,3,3-trifluoroprop-1-enyl)-1H-pyrazol-4-yl)pyrazolo[1,5-a]pyrimidine-3-carboxamide

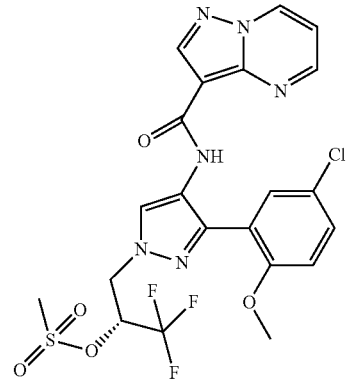 [SMILES: COc1ccc(Cl)cc1-c1nn(C[C@@H](OS(C)(=O)=O)C(F)(F)F)cc1NC(=O)c1cnn2cccnc12]

(R)-3-(3-(5-chloro-2-methoxyphenyl)-4-(pyrazolo[1,5-a]pyrimidine-3-carboxamido)-1H-pyrazol-1-yl)-1,1,1-trifluoropropan-2-yl methanesulfonate Under a nitrogen atmosphere, a solution of (R)—N-(3-(5-chloro-2-methoxyphenyl)-1-(3,3,3-trifluoro-2-hydroxypropyl)-1H-pyrazol-4-yl)pyrazolo[1,5-a]pyrimidine-3-carboxamide (188.7 mg, 0.3724 mmol, a 88:12 mixture of pyrazole regioisomers as determined by $^1$H NMR) in anhydrous dichloromethane (3.5 mL, 0.1 M) was charged with mesyl chloride (61 µL, 0.78 mmol), followed by degassed triethylamine (164 µL, 1.18 mmol). After stirring for 16.5 h, the reaction mixture was diluted with dichloromethane and washed with saturated aqueous ammonium chloride. The organic was dried over magnesium sulfate. Concentration in vacuo afforded a residue whose purification via flash column chromatography (dichloromethane/methanol, 100:0-96:4) afforded the target compound as a yellow solid (198.1 mg, 90%); $R_F$=0.28 (CH$_2$Cl$_2$:MeOH, 95:5); Major regioisomer: $^1$H NMR (400 MHz, CDCl$_3$) δ 9.75 (s, 1H), 8.79 (dd, J=7.1, 1.3 Hz, 1H), 8.72 (s, 1H), 8.54 (dd, J=4.0, 1.4 Hz, 1H), 8.41 (s, 1H), 7.55 (d, J=2.6 Hz, 1H), 7.41 (dd, J=8.7, 2.6 Hz, 1H), 7.03-6.98 (m, 2H), 5.56 (m, 1H), 4.67 (dd, J=14.7, 2.4 Hz, 1H), 4.43 (dd, J=14.6, 10.2 Hz, 1H), 3.84 (s, 3H), 2.76 (s, 3H).

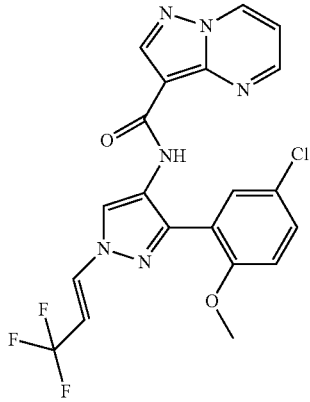 [SMILES: COc1ccc(Cl)cc1-c1nn(/C=C/C(F)(F)F)cc1NC(=O)c1cnn2cccnc12]

(E)-N-(3-(5-chloro-2-methoxyphenyl)-1-(3,3,3-trifluoroprop-1-enyl)-1H-pyrazol-4-yl)pyrazolo[1,5-a]pyrimidine-3-carboxamide A mixture of (R)-3-(3-(5-chloro-2-methoxyphenyl)-4-(pyrazolo[1,5-a]pyrimidine-3-carboxamido)-1H-pyrazol-1-yl)-1,1,1-trifluoropropan-2-yl methanesulfonate (35.4 mg, 0.0633 mmol), cesium carbonate (310 mg, 0.950 mmol), and dimethylamine hydrochloride (155 mg, 1.90 mmol) in N,N-dimethylformamide (1 mL, 0.06 M) was submitted to microwave irradiation (180° C.) for 45 min. After dilution with dichloromethane and filtration of solids, the organics were concentrated to dryness. Purification by flash column chromatography (dichloromethane:methanol, 100:0-95:5) afforded the target compound as a yellow solid (18.8 mg, 58%). The undesired regioisomer was removed by RP-HPLC, leaving 8.0 mg of product; $R_F$=0.36 (CH$_2$Cl$_2$:iPrOH, 90:10); LCMS (ESI) m+H=463.1; $^1$H NMR (400 MHz, CDCl$_3$) δ 9.82 (s, 1H), 8.80 (dd, J=7.0, 1.6 Hz, 1H), 8.74 (s, 1H), 8.56 (s, 1H), 8.52 (dd, J=4.1, 1.6 Hz, 1H), 7.58 (d, J=2.6 Hz, 1H), 7.52 (dd, J=14.0, 1.9 Hz, 1H), 7.45 (dd, J=8.8, 2.6 Hz, 1H), 7.07-6.95 (m, 2H), 6.24 (m, 1H), 3.85 (s, 3H).

Example 166

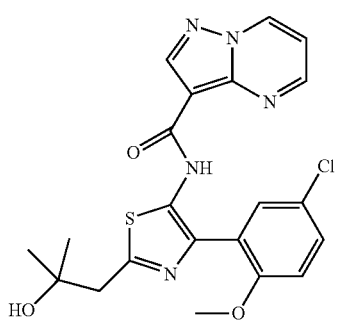 [SMILES: COc1ccc(Cl)cc1-c1nc(CC(C)(C)O)sc1NC(=O)c1cnn2cccnc12]

N-(4-(5-chloro-2-methoxyphenyl)-2-(2-hydroxy-2-methylpropyl)thiazol-5-yl)pyrazolo[1,5-a]pyrimidine-3-carboxamide

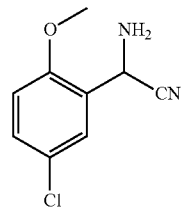

2-amino-2-(5-chloro-2-methoxyphenyl)acetonitrile

A solution of 5-chloro-2-methoxy-benzaldehyde (prepared according to U.S. Pat. No. 4,602,035) (2.04 g, 12.0 mmol) in methanol (80 mL) was added to a stirred solution of sodium cyanide (0.90 g) and ammonium chloride (1.50 g) in aqueous ammonium hydroxide (33% solution, 30 mL) at 0° C. then warmed to room temperature for 18 hours. The mixture was evaporated to dryness, the residues partitioned between DCM and water, the organics separated, washed with brine and evaporated under vacuum to afford 2.21 g (94%) of 2-amino-2-(5-chloro-2-methoxyphenyl)acetonitrile as an orange oil. LCMS (ESI) m+H=197.2.

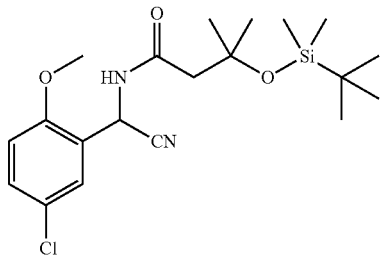 [SMILES: COc1ccc(Cl)cc1C(C#N)NC(=O)CC(C)(C)O[Si](C)(C)C(C)(C)C]

3-(tert-butyldimethylsilyloxy)-N-((5-chloro-2-methoxyphenyl)(cyano)methyl)-3-methylbutanamide 2-amino-2-(5-chloro-2-methoxyphenyl)acetonitrile (500 mg, 2.54 mmol) in DMF (2 mL) was added to a solution of 3-(tert-butyl-dimethyl-silanyloxy)-3-methyl-butyric acid (prepared according to patent EP2025667) (590 mg, 2.54 mmol), diisopropylethylamine (0.87 mL, 5.08 mmol) and HATU (966 mg, 2.54 mmol) in DMF (5 mL) and stirred for 18 hours. Ethyl acetate was added, the organics washed with sodium hydrogen carbonate (sat. aq.) and brine, then evaporated to dryness. The residues were purified by flash chromatography on silica gel (0 to 5% ethyl acetate in dichloromethane) to yield 740 mg (73%) of 3-(tert-butyldimethylsilyloxy)-N-((5-chloro-2-methoxyphenyl)(cyano)methyl)-3-methylbutanamide. LCMS (ESI) m+H=411.4.

233

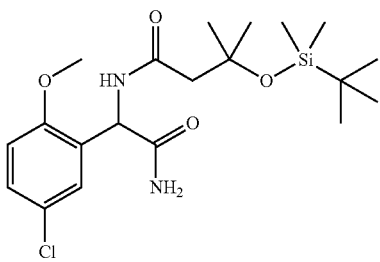 [SMILES: COc1ccc(Cl)cc1C(NC(=O)CC(C)(C)O[Si](C)(C)C(C)(C)C)C(N)=O]

N-(2-amino-1-(5-chloro-2-methoxyphenyl)-2-oxoethyl)-3-(tert-butyldimethylsilyloxy)-3-methylbutanamide Hydrogen peroxide (50% aq., 413 µL) was added to a solution of 3-(tert-butyldimethylsilyloxy)-N45-chloro-2-methoxyphenyl)(cyano)methyl)-3-methylbutanamide (740 mg, 1.80 mmol) and potassium carbonate (609 mg, 4.41 mmol) in DMSO (4 mL) and stirred for 18 hours. Ethyl acetate was added, the organics washed with water and brine, then evaporated to dryness to give 667 mg (86%) of N-(2-amino-1-(5-chloro-2-methoxyphenyl)-2-oxoethyl)-3-(tert-butyldimethylsilyloxy)-3-methylbutanamide as a white solid. LCMS (ESI) m+H=429.3.

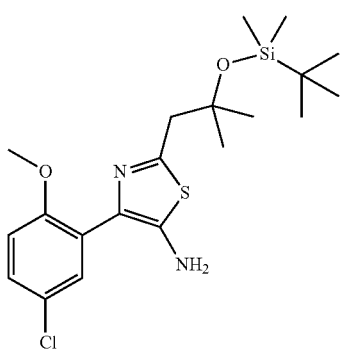 [SMILES: COc1ccc(Cl)cc1-c1nc(CC(C)(C)O[Si](C)(C)C(C)(C)C)sc1N]

2-(2-(tert-butyldimethylsilyloxy)-2-methylpropyl)-4-(5-chloro-2-methoxyphenyl)thiazol-5-amine A mixture of N-(2-amino-1-(5-chloro-2-methoxyphenyl)-2-oxoethyl)-3-(tert-butyldimethylsilyloxy)-3-methylbutanamide (327 mg, 0.76 mmol), Lawesson's reagent (308 mg, 0.76 mmol) and pyridine (2.5 mL) was heated to 95° C. for 18 hours. DCM was added, the organics washed with sodium hydrogen carbonate (sat. aq.) and brine, then evaporated to dryness. The residues were purified by flash chromatography on silica gel (DCM) to afford 107 mg (33%) of 2-(2-(tert-butyldimethylsilyloxy)-2-methylpropyl)-4-(5-chloro-2-methoxyphenyl)thiazol-5-amine LCMS (ESI) m+H=427.3.

234

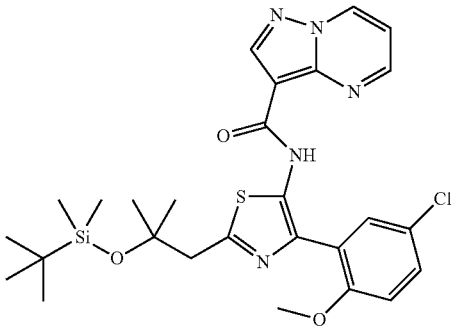 [SMILES: COc1ccc(Cl)cc1-c1nc(CC(C)(C)O[Si](C)(C)C(C)(C)C)sc1NC(=O)c1cnn2cccnc12]

N-(2-(2-(tert-butyldimethylsilyloxy)-2-methylpropyl)-4-(5-chloro-2-methoxyphenyl)thiazol-5-yl)pyrazolo[1,5-a]pyrimidine-3-carboxamide A solution of pyrazolo[1,5-a]pyrimidine-3-carbonyl chloride (52.0 mg, 0.29 mmol), 2-(2-(tert-butyldimethylsilyloxy)-2-methylpropyl)-4-(5-chloro-2-methoxyphenyl)thiazol-5-amine (103 mg, 0.24 mmol) and pyridine (2 mL) was stirred at 60° C. for 2 hours, then at room temperature for an additional 72 hours. DCM was added, the organics washed with water, sodium hydrogen carbonate (sat. aq.) and brine, then evaporated to dryness. The residues were purified by flash chromatography on silica gel (0 to 20% ethyl acetate in dichloromethane) to yield 90.6 mg (66%) of N-(2-(2-(tert-butyldimethylsilyloxy)-2-methylpropyl)-4-(5-chloro-2-methoxyphenyl)thiazol-5-yl)pyrazolo[1,5-a]pyrimidine-3-carboxamide as a yellow solid. LCMS (ESI) m+H=572.1; $^1$H NMR (400 MHz, DMSO-$d_6$): δ 10.45 (s, br, 1H); 9.38 (dd, 1H); 8.76 (s, 1H); 8.73-8.72 (m, 1H); 7.51 (dd, 1H); 7.45 (d, 1H); 7.35 (d, 1H); 7.31 (d, 1H); 3.79 (s, 3H); 3.06 (s, 2H); 1.32 (s, 6H); 0.90 (s, 9H); 0.11 (s, 6H).

N-(4-(5-chloro-2-methoxyphenyl)-2-(2-hydroxy-2-methylpropyl)thiazol-5-yl)pyrazolo[1,5-a]pyrimidine-3-carboxamide A solution of N-(2-(2-(tert-butyldimethylsilyloxy)-2-methylpropyl)-4-(5-chloro-2-methoxyphenyl)thiazol-5-yl) pyrazolo[1,5-a]pyrimidine-3-carboxamide (20 mg, 35.0 µmol) in trifluoroacetic acid (3 mL) was stirred for 7 days at room temperature. The reaction was evaporated under vacuum and the crude product purified by reverse phase HPLC then lyophilized to afford 11.3 mg (71%) of N-(4-(5-chloro-2-methoxyphenyl)-2-(2-hydroxy-2-methylpropyl) thiazol-5-yl)pyrazolo[1,5-a]pyrimidine-3-carboxamide as a white solid. LCMS (ESI) m+H=458.0; $^1$H NMR (400 MHz, DMSO-d$_6$): δ 10.43 (s, br, 1H); 9.38 (dd, 1H); 8.74 (dd, 1H); 8.73 (s, 1H); 7.51 (dd, 1H); 7.46 (d, 1H); 7.35 (s, 1H); 7.32-7.31 (m, 1H); 4.76 (s, 1H); 3.79 (s, 3H); 3.01 (s, 2H); 1.19 (s, 6H).

Example 167

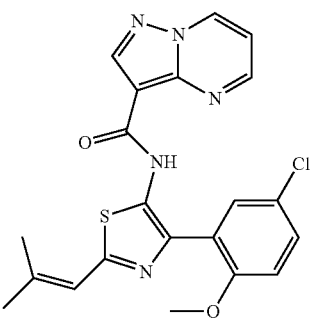 [SMILES: COc1ccc(Cl)cc1-c1nc(C=C(C)C)sc1NC(=O)c1cnn2cccnc12]

N-(4-(5-chloro-2-methoxyphenyl)-2-(2-methylprop-1-enyl)thiazol-5-yl)pyrazolo[1,5-a]pyrimidine-3-carboxamide

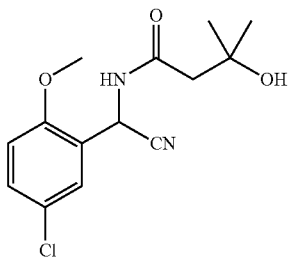 [SMILES: COc1ccc(Cl)cc1C(C#N)NC(=O)CC(C)(C)O]

N-((5-chloro-2-methoxyphenyl)(cyano)methyl)-3-hydroxy-3-methylbutanamide

Using amino-(5-chloro-2-methoxy-phenyl)-acetonitrile and 3-hydroxy-3-methyl-butyric acid, the title compound was synthesized following the synthetic procedures described for 3-(tert-butyldimethylsilyloxy)-N-((5-chloro-2-methoxyphenyl)(cyano)methyl)-3-methylbutanamide to give N-((5-chloro-2-methoxyphenyl)(cyano)methyl)-3-hydroxy-3-methylbutanamide. LCMS (ESI) m+H=297.1.

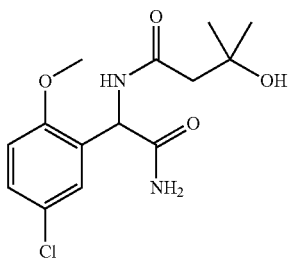 [SMILES: COc1ccc(Cl)cc1C(NC(=O)CC(C)(C)O)C(N)=O]

N-(2-amino-1-(5-chloro-2-methoxyphenyl)-2-oxoethyl)-3-hydroxy-3-methylbutanamide Using N-((5-chloro-2-methoxyphenyl)(cyano)methyl)-3-hydroxy-3-methylbutanamide the title compound was synthesized following the synthetic procedures described for N-(2-amino-1-(5-chloro-2-methoxyphenyl)-2-oxoethyl)-3-(tert-butyldimethylsilyloxy)-3-methylbutanamide to give N-(2-amino-1-(5-chloro-2-methoxyphenyl)-2-oxoethyl)-3-hydroxy-3-methylbutanamide as a yellow gum. LCMS (ESI) m+Na=337.4.

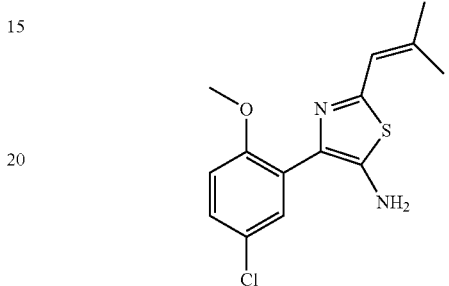

4-(5-chloro-2-methoxyphenyl)-2-(2-methylprop-1-enyl)thiazol-5-amine

A mixture of N-(2-amino-1-(5-chloro-2-methoxyphenyl)-2-oxoethyl)-3-hydroxy-3-methylbutanamide (240 mg, 0.762 mmol), Lawesson's reagent (308 mg, 0.76 mmol) and pyridine (2.5 mL) was heated to 100° C. for 18 hours. After cooling, DCM was added and the mixture washed with water, sodium hydrogen carbamate (sat. aq.) and brine, and concentrated to dryness. 4-(5-chloro-2-methoxyphenyl)-2-(2-methylprop-1-enyl)thiazol-5-amine (51.0 mg) was isolated as a pale yellow solid. LCMS (ESI) m+H=295.3; NMR (400 MHz, DMSO-d$_6$): δ 7.38 (d, 1H); 7.31 (dd, 1H); 7.09 (d, 1H); 6.24 (t, 1H); 5.50 (s, br, 2H); 3.83 (s, 3H); 2.02 (d, 3H); 1.89 (s, 3H).

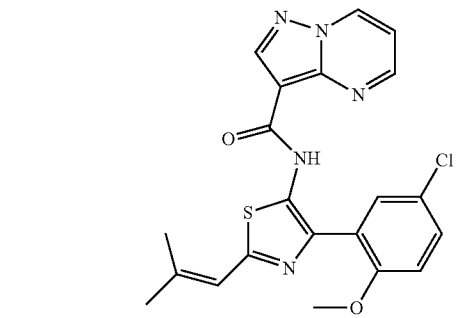 [SMILES: COc1ccc(Cl)cc1-c1nc(C=C(C)C)sc1NC(=O)c1cnn2cccnc12]

N-(4-(5-chloro-2-methoxyphenyl)-2-(2-methylprop-1-enyethiazol-5-yl)pyrazolo[1,5-a]pyrimidine-3-carboxamide Using 4-(5-chloro-2-methoxyphenyl)-2-(2-methylprop-1-enyl)thiazol-5-amine and pyrazolo[1,5-a]pyrimidine-3-carbonyl chloride the title compound was synthesized following the synthetic procedures described for N-(2-(2-(tert-butyldimethylsilyloxy)-2-methylpropyl)-4-(5-chloro-2-methoxyphenyl)thiazol-5-yl)pyrazolo[1,5-a]pyrimidine-3-carboxamide with further purification by reverse phase HPLC and lyophilized to give N-(4-(5-chloro-2-methoxyphenyl)-2-(2-methylprop-1-enyl)thiazol-5-yl)pyrazolo[1,5-a]pyrimidine-3-carboxamide. LCMS (ESI) m+H=440.0; $^1$H NMR (400 MHz, DMSO-d$_6$): δ 10.50 (s, br, 1H); 9.39 (dd, 1H); 8.74 (d, 1H); 8.73 (s, 1H); 7.54 (dd, 1H); 7.49 (d, 1H); 7.37 (d, 1H); 7.34 (dd, 1H); 6.47 (t, 1H); 3.80 (s, 3H); 2.16 (s, 3H); 1.97 (s, 3H).

Example 168

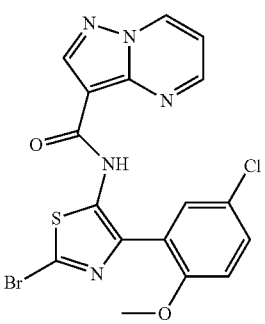 [SMILES: COc1ccc(Cl)cc1-c1nc(Br)sc1NC(=O)c1cnn2cccnc12]

N-(2-bromo-4-(5-chloro-2-methoxyphenyl)thiazol-5-yl)pyrazolo pyrimidine-3-carboxamide

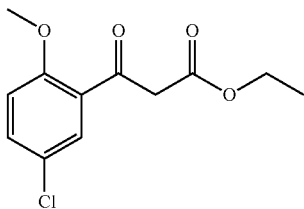 [SMILES: CCOC(=O)CC(=O)c1cc(Cl)ccc1OC]

ethyl 3-(5-chloro-2-methoxyphenyl)-3-oxopropanoate

Sodium hydride (60% dispersion in mineral oil, 2.17 g, 54.2 mmol) was added portionwise to a stirred solution of 1-(5-chloro-2-methoxy-phenyl)-ethanone (10.0 g, 54.2 mmol) in THF (100 mL) at 0° C. The mixture was then stirred for 10 minutes before addition of diethyl carbonate (7.68 g, 65.0 mmol) and then for an additional 1 hour. The mixture was warmed to room temperature for 2 hours and then heated to 65° C. for 2 hours. Diethyl ether was added, the organics washed with water and brine, then evaporated to dryness. The residues were purified by flash chromatography on silica gel (50 to 100% dichloromethane in cyclohexane) to yield 3.41 g of ethyl 3-(5-chloro-2-methoxyphenyl)-3-oxopropanoate. LCMS (ESI) m+H=257.2; NMR (400 MHz, CDCl$_3$): δ 7.59 (d, 1H); 7.38 (dd, 1H); 6.89 (d, 1H); 4.18 (q, 2H); 3.95 (s, 2H); 3.88 (s, 3H); 1.24 (t, 3H).

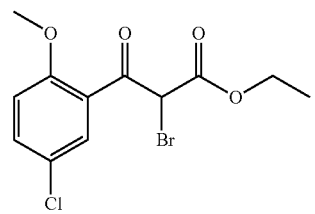 [SMILES: CCOC(=O)C(Br)C(=O)c1cc(Cl)ccc1OC]

ethyl 2-bromo-3-(5-chloro-2-methoxyphenyl)-3-oxopropanoate

Bromine (0.70 mL, 13.6 mmol) was added to a solution of ethyl 3-(5-chloro-2-methoxyphenyl)-3-oxopropanoate (3.39 g, 13.2 mmol) in dioxane (25 mL) and stirred for 1 hour. The reaction was poured onto ice water, extracted with ethyl acetate, the organics washed with water and brine and evaporated to dryness to give ethyl 2-bromo-3-(5-chloro-2-methoxyphenyl)-3-oxopropanoate. LCMS (ESI) m+H=337.2

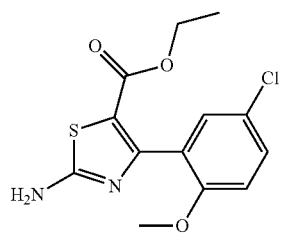 [SMILES: CCOC(=O)c1sc(N)nc1-c1cc(Cl)ccc1OC]

ethyl 2-amino-4-(5-chloro-2-methoxyphenyl)thiazole-5-carboxylate

A mixture of ethyl 2-bromo-3-(5-chloro-2-methoxyphenyl)-3-oxopropanoate (assumed to be 13.2 mmol) and thiourea (1.01 g, 13.3 mmol) in ethanol (25 mL) were heated to reflux for 3 hours, then cooled to room temperature for 18 hours. The resultant solid was removed by filtration and the filtrate evaporated under vacuum. DCM was added to the residue, the organics washed with sodium hydrogen carbonate (sat. aq.), water and brine, and evaporated to dryness. The residue was triturated (DCM) to give 1.30 g (31%) of ethyl 2-amino-4-(5-chloro-2-methoxyphenyl)thiazole-5-carboxylate as a yellow solid. LCMS (ESI) m+H=313.2. $^1$H NMR (400 MHz, DMSO-d$_6$): δ 7.77 (s, br, 2H); 7.39 (dd, 1H); 7.22 (d, 1H); 7.05 (d, 1H); 4.00 (q, 2H); 3.70 (s, 3H); 1.04 (t, 3H).

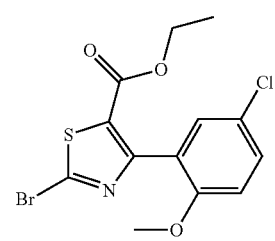 [SMILES: CCOC(=O)c1sc(Br)nc1-c1cc(Cl)ccc1OC]

ethyl 2-bromo-4-(5-chloro-2-methoxyphenyl)thiazole-5-carboxylate

Copper bromide (1.07 g, 4.79 mmol) in acetonitrile (20 mL) was degassed with nitrogen and cooled to 0° C. before addition of tert-butyl nitrite (0.80 mL, 6.00 mmol), then a suspension of ethyl 2-amino-4-(5-chloro-2-methoxyphenyl)thiazole-5-carboxylate (1.25 g, 3.99 mmol) in acetonitrile (20 mL) was added and stirred at room temperature for 18 hours. The reaction was concentrated under vacuum, ethyl acetate added, the organics washed with sodium hydrogen carbonate (sat. aq.) and brine, then evaporated to dryness to give 1.40 g (93%) of ethyl 2-bromo-4-(5-chloro-2-methoxyphenyl)thiazole-5-carboxylate. LCMS (ESI) m+H=378.1. $^1$H NMR (400 MHz, DMSO-$d_6$): δ 7.50 (dd, 1H); 7.42 (d, 1H); 7.14 (d, 1H) 4.16 (q, 2H); 3.73 (s, 3H); 1.12 (t, 3H).

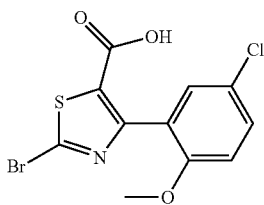 [SMILES: COc1ccc(Cl)cc1-c1nc(Br)sc1C(=O)O]

2-bromo-4-(5-chloro-2-methoxyphenyl)thiazole-5-carboxylic acid

A mixture of ethyl 2-bromo-4-(5-chloro-2-methoxyphenyl)thiazole-5-carboxylate (1.40 g, 3.72 mmol), potassium hydroxide (278 mg) in THF (40 mL) and water (10 mL) was stirred for 20 hours at ambient temperature. The mixture was treated with 1M HCl aq. (ca. 8 mL, 2 eq.), DCM was added, and the organics separated and evaporated to dryness to give 1.23 g (95%) of 2-bromo-4-(5-chloro-2-methoxyphenyl)thiazole-5-carboxylic acid as a yellow solid. LCMS (ESI) m+H=350.1. $^1$H NMR (400 MHz, DMSO-$d_6$): δ 7.47 (dd, 1H); 7.39 (d, 1H); 7.13 (d, 1H); 3.73 (s, 3H).

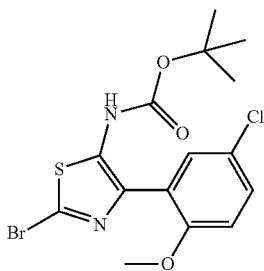 [SMILES: COc1ccc(Cl)cc1-c1nc(Br)sc1NC(=O)OC(C)(C)C]

tert-butyl 2-bromo-4-(5-chloro-2-methoxyphenyl)thiazol-5-ylcarbamate 2-bromo-4-(5-chloro-2-methoxyphenyl)thiazole-5-carboxylic acid (1.22 g, 3.50 mmol), diphenylphosphoryl azide (963 mg, 3.50 mmol) and triethylamine (354 mg, 3.50 mmol) in tert-butanol (30 mL) were stirred at 85° C. for 4 hours. After cooling, the reaction was partitioned between ethyl acetate and water, the organics separated then washed with brine, and evaporated to dryness. The resulting residues were purified by flash chromatography on silica gel (50 to 100% dichloromethane in cyclohexane) to yield 970 mg (66%) of tert-butyl 2-bromo-4-(5-chloro-2-methoxyphenyl)thiazol-5-ylcarbamate. LCMS (ESI) m+H=421.2; $^1$H NMR (400 MHz, DMSO-$d_6$): δ 7.43 (dd, 1H), 7.30 (d, 1H); 7.11 (d, 1H); 3.77 (s, 3H); 1.45 (s, 9H).

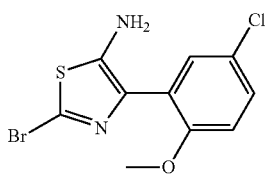 [SMILES: COc1ccc(Cl)cc1-c1nc(Br)sc1N]

2-bromo-4-(5-chloro-2-methoxyphenyl)thiazol-5-amine

TFA (4.0 mL) was added to a solution of tert-butyl 2-bromo-4-(5-chloro-2-methoxyphenyl)thiazol-5-ylcarbamate (360 mg, 0.86 mmol) in DCM (10 mL) and water (3 drops). The reaction mixture was stirred for 1.5 hours at room temperature and then evaporated to dryness. The residue was taken up into DCM and washed with sodium hydrogen carbonate (sat. aq.), water and brine, and concentrated under vacuum to give 2-bromo-4-(5-chloro-2-methoxyphenyl)thiazol-5-amine as an orange residue. LCMS (ESI) m+H=321.3. NMR (400 MHz, DMSO-$d_6$): δ 7.36 (d, 1H); 7.34-7.32 (m, 1H); 7.10 (d, 1H); 3.83 (s, 3H).

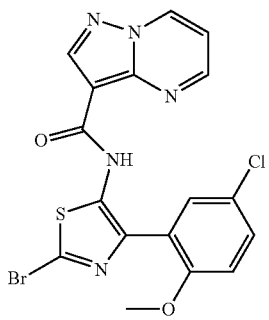 [SMILES: COc1ccc(Cl)cc1-c1nc(Br)sc1NC(=O)c1cnn2cccnc12]

N-(2-bromo-4-(5-chloro-2-methoxyphenyl)thiazol-5-yl)pyrazolo pyrimidine-3-carboxamide Using 2-bromo-4-(5-chloro-2-methoxyphenyl)thiazol-5-amine and pyrazolo[1,5-a]pyrimidine-3-carbonyl chloride the title compound was prepared following the synthetic procedures described for N-(2-(2-(tert-butyldimethylsilyloxy)-2-methylpropyl)-4-(5-chloro-2-methoxyphenyl)thiazol-5-yl)pyrazolo[1,5-a]pyrimidine-3-carboxamide with further purification by flash chromatography on silica gel (0 to 40% ethyl acetate in DCM) to give N-(2-bromo-4-(5-chloro-2-methoxyphenyl)thiazol-5-yl)pyrazolo[1,5-a]pyrimidine-3-carboxamide. LCMS (ESI) m+H=465.8. $^1$H NMR (400 MHz, DMSO-$d_6$): δ 10.68 (s, br, 1H); 9.41 (dd, 1H); 8.78 (s, 1H); 8.76 (dd, 1H); 7.57 (dd, 1H); 7.50 (d, 1H); 7.37-7.34 (m, 2H); 3.81 (s, 3H).

Example 169

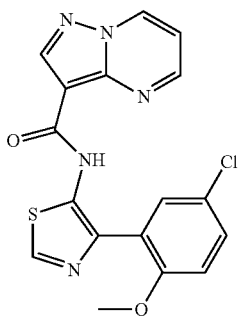 [SMILES: COc1ccc(Cl)cc1-c1ncsc1NC(=O)c1cnn2cccnc12]

N-(4-(5-chloro-2-methoxyphenyl)thiazol-5-yl)pyrazolo[1,5-a]pyrimidine-3-carboxamide N-(2-bromo-4-(5-chloro-2-methoxyphenyl)thiazol-5-yl) pyrazolo pyrimidine-3-carboxamide (50.0 mg, 0.11 mmol), Pd(PPh$_3$)$_4$ (6.20 mg, 5.35 μmol), sodium formate (10.9 mg, 0.16 mmol) and DMF (0.5 mL) were sealed, under nitrogen, in a microwave vial and heated to 130° C. for 10 minutes using microwave irradiation. The reaction was cooled, DCM was then added and the organics washed with sodium hydrogen carbonate (sat. aq.), water and brine, dried and evaporated to dryness. The residues were purified by flash chromatography on silica gel (0 to 40% ethyl acetate in DCM) then further purified by reverse phase HPLC and lyophilized to give 11.1 mg (27%) of N-(4-(5-chloro-2-methoxyphenyl)thiazol-5-yl) pyrazolo[1,5-a]pyrimidine-3-carboxamide as a beige solid. LCMS (ESI) m+H=386.0. $^1$H NMR (400 MHz, DMSO-d$_o$): δ 10.56 (s, 1H); 9.39 (dd, 1H); 8.74-8.73 (m, 3H); 7.55 (dd, 1H); 7.49 (d, 1H); 7.37 (d, 1H); 7.34 (dd, 1H); 3.80 (s, 3H).

Example 170

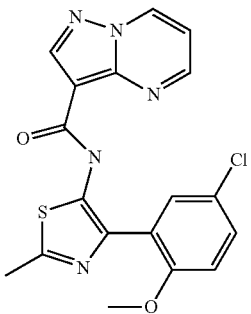 [SMILES: COc1ccc(Cl)cc1-c1nc(C)sc1NC(=O)c1cnn2cccnc12]

N-(4-(5-chloro-2-methoxyphenyl)-2-methylthiazol-5-yl)pyrazolo[1,5-a]pyrimidine-3-carboxamide

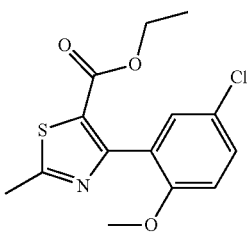 [SMILES: CCOC(=O)c1sc(C)nc1-c1cc(Cl)ccc1OC]

ethyl 4-(5-chloro-2-methoxyphenyl)-2-methylthiazole-5-carboxylate

Using 2-bromo-3-(5-chloro-2-methoxy-phenyl)-3-oxopropionic acid ethyl ester and thioacetamide, the title compound was prepared following the synthetic procedures described for ethyl 2-amino-4-(5-chloro-2-methoxyphenyl) thiazole-5-carboxylate with additional purification by flash chromatography on silica gel (50 to 100% DCM in cyclohexane) to give ethyl 4-(5-chloro-2-methoxyphenyl)-2-methylthiazole-5-carboxylate. LCMS (ESI) m+H=321.4; $^1$H NMR (400 MHz, CDCl$_3$): δ 7.38 (d, 1H); 7.33 (dd, 1H); 6.87 (d, 1H); 4.20 (q, 2H); 3.75 (s, 3H); 2.76 (s, 3H); 1.20 (t, 3H).

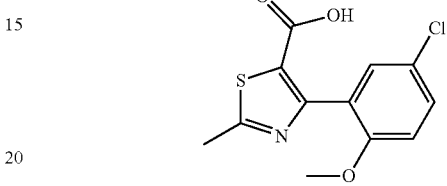

4-(5-chloro-2-methoxyphenyl)-2-methylthiazole-5-carboxylic acid

A mixture of ethyl 4-(5-chloro-2-methoxyphenyl)-2-methylthiazole-5-carboxylate (520 mg, 1.67 mmol) and potassium hydroxide (125 mg) in THF (18 mL) and water (4.5 mL) was stirred for 20 hours at room temperature and then at 75° C. for a further 8 hours. The solution was treated with 1M HCl aq. (pH 2) and extracted with DCM. The organics were evaporated to dryness to give 450 mg (95%) of 4-(5-chloro-2-methoxyphenyl)-2-methylthiazole-5-carboxylic acid as a white solid. LCMS (ESI) m+H=284.3; $^1$H NMR (400 MHz, DMSO-d$_6$): δ 7.43 (dd, 1H); 7.31 (d, 1H); 7.10 (d, 1H); 3.71 (s, 3H); 2.69 (s, 3H).

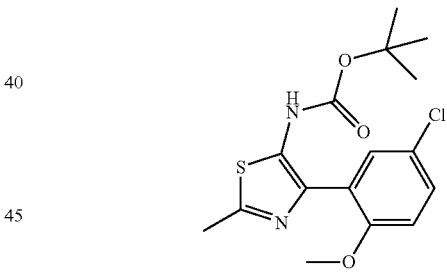

tert-butyl 4-(5-chloro-2-methoxyphenyl)-2-methylthiazol-5-ylcarbamate

Using 4-(5-chloro-2-methoxyphenyl)-2-methylthiazole-5-carboxylic acid, the title compound was prepared following the synthetic procedures described for tert-butyl 2-bromo-4-(5-chloro-2-methoxyphenyl)thiazol-5-ylcarbamate to give tert-butyl 4-(5-chloro-2-methoxyphenyl)-2-methylthiazol-5-ylcarbamate. LCMS (ESI) m+H=355.3; $^1$H NMR (400 MHz, DMSO-d$_6$): δ 7.40 (dd, 1H); 7.32 (d, 1H); 7.11 (d, 1H); 3.77 (s, 3H); 2.55 (s, 3H); 1.42 (s, 9H).

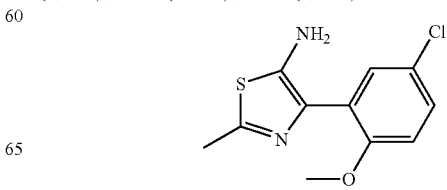

4-(5-chloro-2-methoxyphenyl)-2-methylthiazol-5-amine

TFA (4.0 mL) was added to a solution of tert-butyl 4-(5-chloro-2-methoxyphenyl)-2-methylthiazol-5-ylcarbamate (315 mg, 0.89 mmol) in DCM (10 mL) and water (3 drops). The reaction mixture was stirred for 1.5 hours at room temperature, then evaporated to dryness to give 215 mg (95%) of 4-(5-chloro-2-methoxyphenyl)-2-methylthiazol-5-amine as a yellow solid. LCMS (ESI) m+H=255.2.

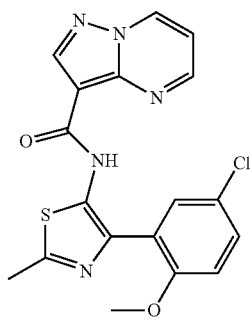 [SMILES: COc1ccc(Cl)cc1-c1nc(C)sc1NC(=O)c1cnn2cccnc12]

N-(4-(5-chloro-2-methoxyphenyl)-2-methylthiazol-5-yl)pyrazolo[1,5-a]pyrimidine-3-carboxamide Using 4-(5-chloro-2-methoxyphenyl)-2-methylthiazol-5-amine and pyrazolo[1,5-a]pyrimidine-3-carbonyl chloride the title compound was synthesized following the synthetic procedures described for N-(2-(2-(tert-butyldimethylsilyloxy)-2-methylpropyl)-4-(5-chloro-2-methoxyphenyl)thiazol-5-yl)pyrazolo[1,5-a]pyrimidine-3-carboxamide with further purification by flash chromatography on silica gel (0 to 100% ethyl aceate in DCM) to give N-(4-(5-chloro-2-methoxyphenyl)-2-methylthiazol-5-yl)pyrazolo[1,5-a]pyrimidine-3-carboxamide as an orange solid. LCMS (ESI) m+H=400.0; $^1$H NMR (400 MHz, DMSO-d$_6$): δ 10.43 (s, br, 1H); 9.38 (dd, 1H); 8.75-8.73 (m, 1H); 8.72 (s, 1H); 7.52 (dd, 1H); 7.47 (d, 1H); 7.34-7.32 (m, 2H); 3.79 (s, 3H); 2.62 (s, 3H).

Example 171

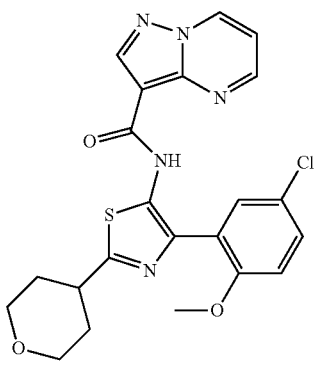 [SMILES: COc1ccc(Cl)cc1-c1nc(C2CCOCC2)sc1NC(=O)c1cnn2cccnc12]

N-(4-(5-chloro-2-methoxyphenyl)-2-(tetrahydro-2H-pyran-4-yl)thiazol-5-yl)pyrazolo[1,5-a]pyrimidine-3-carboxamide

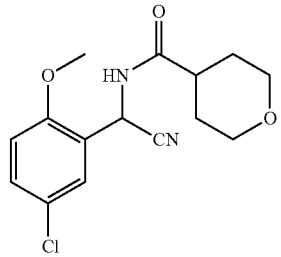 [SMILES: COc1ccc(Cl)cc1C(C#N)NC(=O)C1CCOCC1]

N-((5-chloro-2-methoxyphenyl)(cyano)methyl)tetrahydro-2H-pyran-4-carboxamide Using amino-(5-chloro-2-methoxy-phenyl)-acetonitrile and tetrahydro-2H-pyran-4-carboxylic acid, the title compound was prepared following the synthetic procedures described for 3-(tert-butyldimethylsilyloxy)-N-((5-chloro-2-methoxyphenyl)(cyano)methyl)-3-methylbutanamide to give N-((5-chloro-2-methoxyphenyl)(cyano)methyl)tetrahydro-2H-pyran-4-carboxamide as a white solid. LCMS (ESI) m+H=309.3.

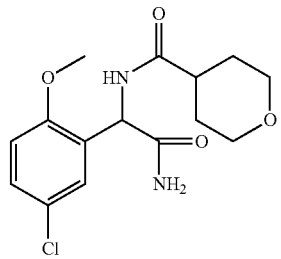 [SMILES: COc1ccc(Cl)cc1C(NC(=O)C1CCOCC1)C(N)=O]

N-(2-amino-1-(5-chloro-2-methoxyphenyl)-2-oxoethyl)tetrahydro-2H-pyran-4-carboxamide Using N-((5-chloro-2-methoxyphenyl)(cyano)methyl)tetrahydro-2H-pyran-4-carboxamide, the title compound was prepared following the synthetic procedures described for N-(2-amino-1-(5-chloro-2-methoxyphenyl)-2-oxoethyl)-3-(tert-butyldimethylsilyloxy)-3-methylbutanamide to give N-(2-amino-1-(5-chloro-2-methoxyphenyl)-2-oxoethyl)tetrahydro-2H-pyran-4-carboxamide as a white solid. LCMS (ESI) m+H=327.3; $^1$H NMR (400 MHz, DMSO-d$_6$): δ 8.30 (d, br, 1H); 7.31-7.31 (m, 2H); 7.24 (s, br, 1H); 7.13 (s, br, 1H); 7.05-7.01 (d, 1H); 5.62 (d, 1H); 3.91-3.81 (m, 2H); 3.79 (s, 3H); 3.30-3.24 (m, 2H); 2.55-2.54 (m, 1H); 1.56-1.55 (m, 4H).

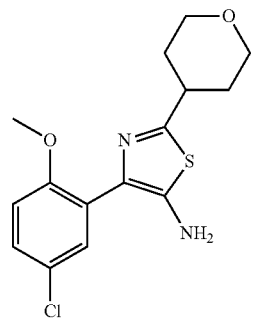 [SMILES: COc1ccc(Cl)cc1-c1nc(C2CCOCC2)sc1N]

4-(5-chloro-2-methoxyphenyl)-2-(tetrahydro-2H-pyran-4-yl)thiazol-5-amine

Using N-(2-amino-1-(5-chloro-2-methoxyphenyl)-2-oxoethyl)tetrahydro-2H-pyran-4-carboxamide, the title compound was prepared following the synthetic procedures described for 2-(2-(tert-butyldimethylsilyloxy)-2-methylpropyl)-4-(5-chloro-2-methoxyphenyl)thiazol-5-amine to give 4-(5-chloro-2-methoxyphenyl)-2-(tetrahydro-2H-pyran-4-yl)thiazol-5-amine as a white gum. LCMS (ESI) m+H=325.2; $^1$H NMR (400 MHz, DMSO-d$_6$): δ 7.38 (d, 1H); 7.31 (dd, 1H); 7.09 (d, 1H); 5.31 (s, br, 2H); 3.90 (d, 2H); 3.84 (s, 3H); 3.43 (m, 2H); 3.04-2.99 (m, 1H); 1.90 (d, 2H); 1.66-1.66 (m, 2H).

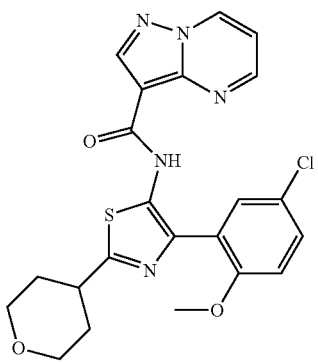 [SMILES: COc1ccc(Cl)cc1-c1nc(C2CCOCC2)sc1NC(=O)c1cnn2cccnc12]

N-(4-(5-chloro-2-methoxyphenyl)-2-(tetrahydro-2H-pyran-4-yl)thiazol-5-yl)pyrazolo[1,5-a]pyrimidine-3-carboxamide Using N-(2-amino-1-(5-chloro-2-methoxyphenyl)-2-oxoethyl)tetrahydro-2H-pyran-4-carboxamide, the title compound was prepared following the synthetic procedures described for N-(2-(2-(tert-butyldimethylsilyloxy)-2-methylpropyl)-4-(5-chloro-2-methoxyphenyl)thiazol-5-yl)pyrazolo[1,5-a]pyrimidine-3-carboxamide with additional purification by trituration in diethyl ether to give N-(4-(5-chloro-2-methoxyphenyl)-2-(tetrahydro-2H-pyran-4-yl)thiazol-5-yl)pyrazolo[1,5-a]pyrimidine-3-carboxamide. LCMS (ESI) m+H=470.0; $^1$H NMR (400 MHz, DMSO-d$_6$): δ 10.44 (s, br, 1H); 9.38 (dd, 1H); 8.75 (dd, 1H); 8.73 (s, 1H); 7.52 (dd, 1H); 7.46 (d, 1H); 7.35 (d, 1H); 7.32-7.31 (m, 1H); 3.95-3.94 (m, 2H); 3.80 (s, 3H); 3.47 (m, 2H); 3.23 (m, 1H); 2.00 (dd, 2H); 1.77 (m, 2H).

Examples 172-508 shown in Table 2 were prepared generally following the above-described Examples. For each compound shown in Table 2, the Example number followed is given in the Method column.

TABLE 2

| Ex | Structure | Name | Mthd | LCMS (ESI) m/z |
|---|---|---|---|---|
| 172 | *structure* | N-(3-(5-chloro-2-methoxyphenyl)-1-((2S,3R)-2,3-dihydroxybutyl)-1H-pyrazol-4-yl)pyrazolo[1,5-a]pyrimidine-3-carboxamide | 132 | 457.1 |
| 173 | *structure* | N-(3-(5-chloro-2-methoxyphenyl)-1-((2R,3R)-2,3-dihydroxybutyl)-1H-pyrazol-4-yl)pyrazolo[1,5-a]pyrimidine-3-carboxamide | 132 | 457.1 |

TABLE 2-continued

| Ex | Structure | Name | Mthd | LCMS (ESI) m/z |
|---|---|---|---|---|
| 174 | 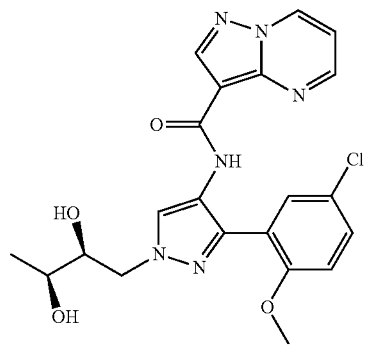 [SMILES: COc1ccc(Cl)cc1-c1nn(C[C@H](O)[C@H](C)O)cc1NC(=O)c1cnn2cccnc12] | N-(3-(5-chloro-2-methoxyphenyl)-1-((2S,3S)-2,3-dihydroxybutyl)-1H-pyrazol-4-yl)pyrazolo[1,5-a]pyrimidine-3-carboxamide | 132 | 457.1 |
| 175 | 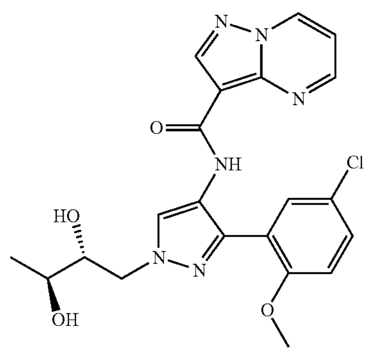 [SMILES: COc1ccc(Cl)cc1-c1nn(C[C@@H](O)[C@H](C)O)cc1NC(=O)c1cnn2cccnc12] | N-(3-(5-chloro-2-methoxyphenyl)-1-((2R,3S)-2,3-dihydroxybutyl)-1H-pyrazol-4-yl)pyrazolo[1,5-a]pyrimidine-3-carboxamide | 132 | 457.1 |
| 176 | 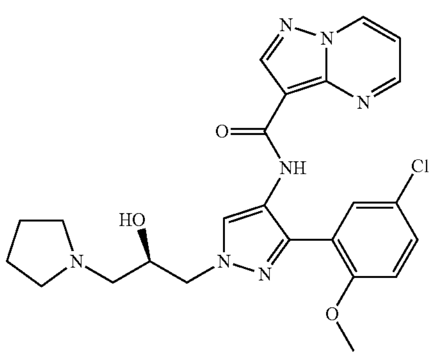 [SMILES: COc1ccc(Cl)cc1-c1nn(C[C@H](O)CN2CCCC2)cc1NC(=O)c1cnn2cccnc12] | (R)-N-(3-(5-chloro-2-methoxyphenyl)-1-(2-hydroxy-3-(pyrrolidin-1-yl)propyl)-1H-pyrazol-4-yl)pyrazolo[1,5-a]pyrimidine-3-carboxamide | 133 | 496.2 |
| 177 | 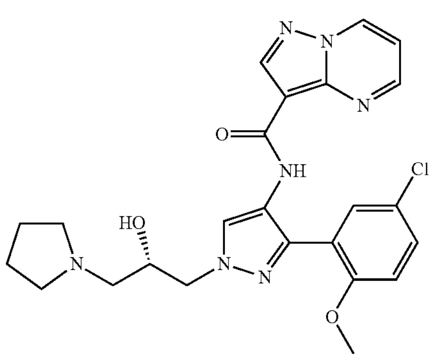 [SMILES: COc1ccc(Cl)cc1-c1nn(C[C@@H](O)CN2CCCC2)cc1NC(=O)c1cnn2cccnc12] | (S)-N-(3-(5-chloro-2-methoxyphenyl)-1-(2-hydroxy-3-(pyrrolidin-1-yl)propyl)-1H-pyrazol-4-yl)pyrazolo[1,5-a]pyrimidine-3-carboxamide | 133 | 496.2 |

TABLE 2-continued

| Ex | Structure | Name | Mthd | LCMS (ESI) m/z |
|---|---|---|---|---|
| 178 | 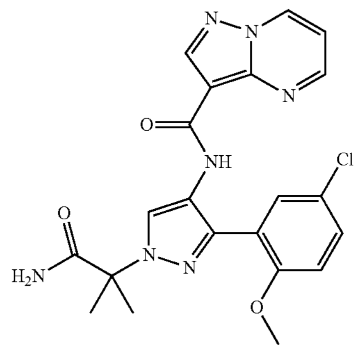 [SMILES: COc1ccc(Cl)cc1-c1nn(C(C)(C)C(N)=O)cc1NC(=O)c1cnn2cccnc12] | N-(1-(1-amino-2-methyl-1-oxopropan-2-yl)-3-(5-chloro-2-methoxyphenyl)-1H-pyrazol-4-yl)pyrazolo[1,5-a]pyrimidine-3-carboxamide | 14 | 454.1 |
| 179 | 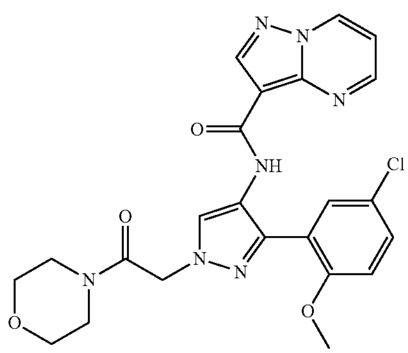 [SMILES: COc1ccc(Cl)cc1-c1nn(CC(=O)N2CCOCC2)cc1NC(=O)c1cnn2cccnc12] | N-(3-(5-chloro-2-methoxyphenyl)-1-(2-morpholino-2-oxoethyl)-1H-pyrazol-4-yl)pyrazolo[1,5-a]pyrimidine-3-carboxamide | 134 | 496.2 |
| 180 | 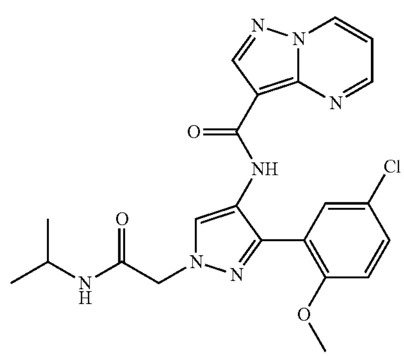 [SMILES: COc1ccc(Cl)cc1-c1nn(CC(=O)NC(C)C)cc1NC(=O)c1cnn2cccnc12] | N-(3-(5-chloro-2-methoxyphenyl)-1-(2-(isopropylamino)-2-oxoethyl)-1H-pyrazol-4-yl)pyrazolo[1,5-a]pyrimidine-3-carboxamide | 134 | 468.2 |
| 181 | 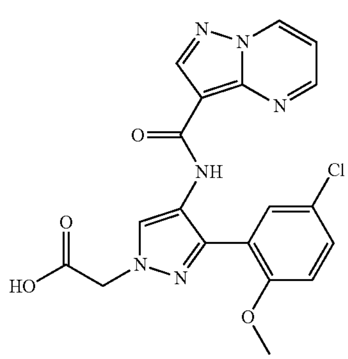 [SMILES: COc1ccc(Cl)cc1-c1nn(CC(=O)O)cc1NC(=O)c1cnn2cccnc12] | 2-(3-(5-chloro-2-methoxyphenyl)-4-(pyrazolo[1,5-a]pyrimidine-3-carboxamido)-1H-pyrazol-1-yl)acetic acid | 134 | 427.1 |

TABLE 2-continued

| Ex | Structure | Name | Mthd | LCMS (ESI) m/z |
|---|---|---|---|---|
| 182 | 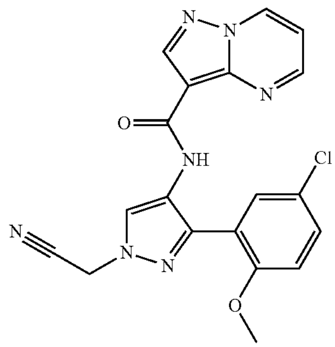 [SMILES: COc1ccc(Cl)cc1-c1nn(CC#N)cc1NC(=O)c1cnn2cccnc12] | N-(3-(5-chloro-2-methoxyphenyl)-1-(cyanomethyl)-1H-pyrazol-4-yl)pyrazolo[1,5-a]pyrimidine-3-carboxamide | 14 | 408.0 |
| 183 | 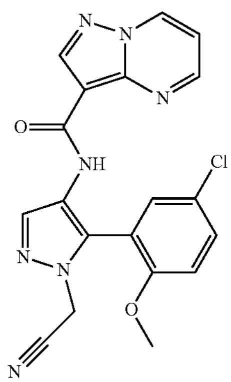 [SMILES: COc1ccc(Cl)cc1-c1c(NC(=O)c2cnn3cccnc23)cnn1CC#N] | N-(5-(5-chloro-2-methoxyphenyl)-1-(cyanomethyl)-1H-pyrazol-4-yl)pyrazolo[1,5-a]pyrimidine-3-carboxamide | 15 | 408.1 |
| 184 | 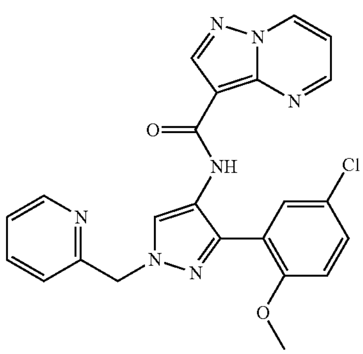 [SMILES: COc1ccc(Cl)cc1-c1nn(Cc2ccccn2)cc1NC(=O)c1cnn2cccnc12] | N-(3-(5-chloro-2-methoxyphenyl)-1-(pyridin-2-ylmethyl)-1H-pyrazol-4-yl)pyrazolo[1,5-a]pyrimidine-3-carboxamide | 14 | 460.1 |
| 185 | 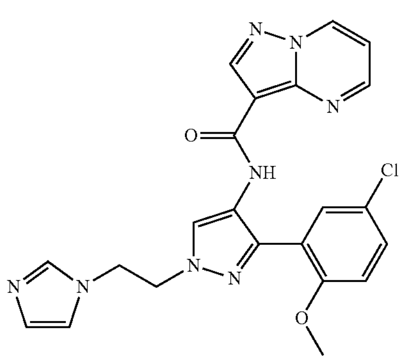 [SMILES: COc1ccc(Cl)cc1-c1nn(CCn2ccnc2)cc1NC(=O)c1cnn2cccnc12] | N-(1-(2-(1H-imidazol-1-yl)ethyl)-3-(5-chloro-2-methoxyphenyl)-1H-pyrazol-4-yl)pyrazolo[1,5-a]pyrimidine-3-carboxamide | 14 | 463.2 |

TABLE 2-continued

| Ex | Structure | Name | Mthd | LCMS (ESI) m/z |
|---|---|---|---|---|
| 186 | 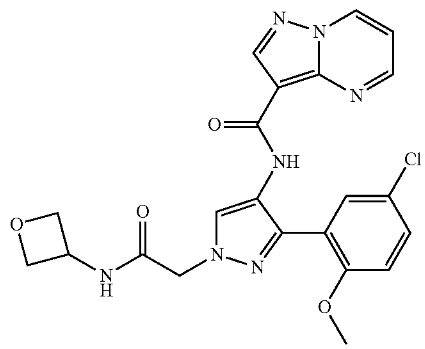 [SMILES: COc1ccc(Cl)cc1-c1nn(CC(=O)NC2COC2)cc1NC(=O)c1cnn2cccnc12] | N-(3-(5-chloro-2-methoxyphenyl)-1-(2-(oxetan-3-ylamino)-2-oxoethyl)-1H-pyrazol-4-yl)pyrazolo[1,5-a]pyrimidine-3-carboxamide | 134 | 482.1 |
| 187 | 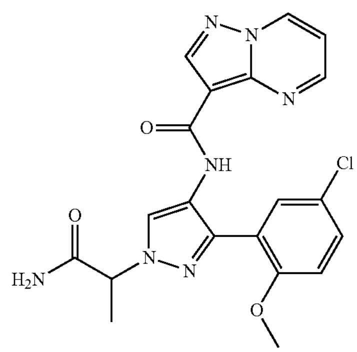 [SMILES: COc1ccc(Cl)cc1-c1nn(C(C)C(N)=O)cc1NC(=O)c1cnn2cccnc12] | N-(1-(1-amino-1-oxopropan-2-yl)-3-(5-chloro-2-methoxyphenyl)-1H-pyrazol-4-yl)pyrazolo[1,5-a]pyrimidine-3-carboxamide | 14 | 440.1 |
| 188 | 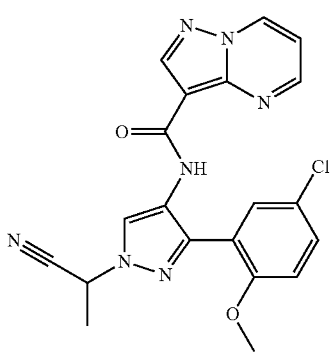 [SMILES: COc1ccc(Cl)cc1-c1nn(C(C)C#N)cc1NC(=O)c1cnn2cccnc12] | N-(3-(5-chloro-2-methoxyphenyl)-1-(1-cyanoethyl)-1H-pyrazol-4-yl)pyrazolo[1,5-a]pyrimidine-3-carboxamide | 14 | 422.1 |
| 189 | 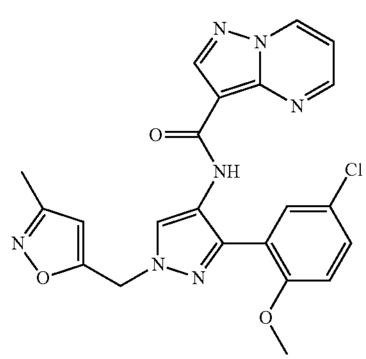 [SMILES: COc1ccc(Cl)cc1-c1nn(Cc2cc(C)no2)cc1NC(=O)c1cnn2cccnc12] | N-(3-(5-chloro-2-methoxyphenyl)-1-((3-methylisoxazol-5-yl)methyl)-1H-pyrazol-4-yl)pyrazolo[1,5-a]pyrimidine-3-carboxamide | 14 | 464.1 |

TABLE 2-continued

| Ex | Structure | Name | Mthd | LCMS (ESI) m/z |
|---|---|---|---|---|
| 190 | 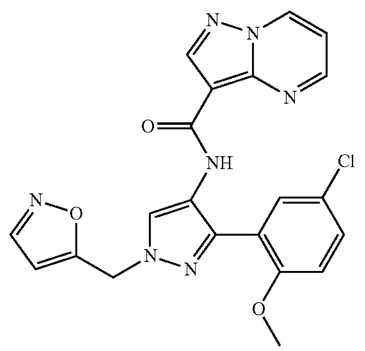 [SMILES: COc1ccc(Cl)cc1-c1nn(Cc2ccno2)cc1NC(=O)c1cnn2cccnc12] | N-(3-(5-chloro-2-methoxyphenyl)-1-(isoxazol-5-ylmethyl)-1H-pyrazol-4-yl)pyrazolo[1,5-a]pyrimidine-3-carboxamide | 14 | 450.1 |
| 191 | 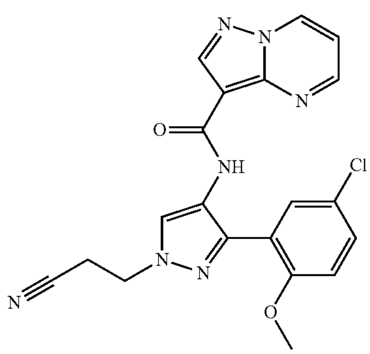 [SMILES: COc1ccc(Cl)cc1-c1nn(CCC#N)cc1NC(=O)c1cnn2cccnc12] | N-(3-(5-chloro-2-methoxyphenyl)-1-(2-cyanoethyl)-1H-pyrazol-4-yl)pyrazolo[1,5-a]pyrimidine-3-carboxamide | 14 | 422.1 |
| 192 | 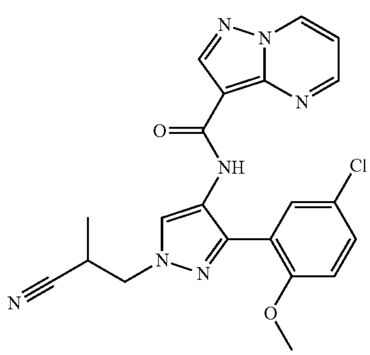 [SMILES: COc1ccc(Cl)cc1-c1nn(CC(C)C#N)cc1NC(=O)c1cnn2cccnc12] | N-(3-(5-chloro-2-methoxyphenyl)-1-(2-cyanopropyl)-1H-pyrazol-4-yl)pyrazolo[1,5-a]pyrimidine-3-carboxamide | 14 | 436.1 |
| 193 | 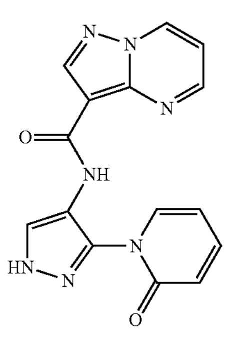 [SMILES: O=C(Nc1c[nH]nc1-n1ccccc1=O)c1cnn2cccnc12] | N-(3-(2-oxopyridin-1(2H)-yl)-1H-pyrazol-4-yl)pyrazolo[1,5-a]pyrimidine-3-carboxamide | 140 | 322.0 |

TABLE 2-continued

| Ex | Structure | Name | Mthd | LCMS (ESI) m/z |
|---|---|---|---|---|
| 194 | 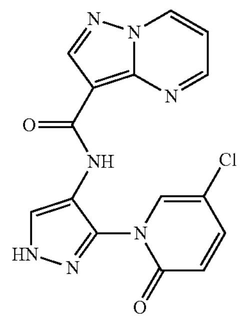 [SMILES: O=C(Nc1c[nH]nc1-n1cc(Cl)ccc1=O)c1cnn2cccnc12] | N-(3-(5-chloro-2-oxopyridin-1(2H)-yl)-1H-pyrazol-4-yl)pyrazolo[1,5-a]pyrimidine-3-carboxamide | 140 | 356.0 |
| 195 | 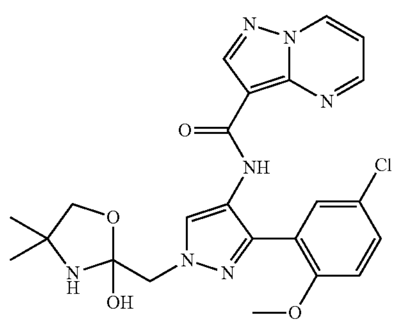 [SMILES: COc1ccc(Cl)cc1-c1nn(CC2(O)NC(C)(C)CO2)cc1NC(=O)c1cnn2cccnc12] | N-(3-(5-chloro-2-methoxyphenyl)-1-((2-hydroxy-4,4-dimethyloxazolidin-2-yl)methyl)-1H-pyrazol-4-yl)pyrazolo[1,5-a]pyrimidine-3-carboxamide | 14 | 498.1 |
| 196 | 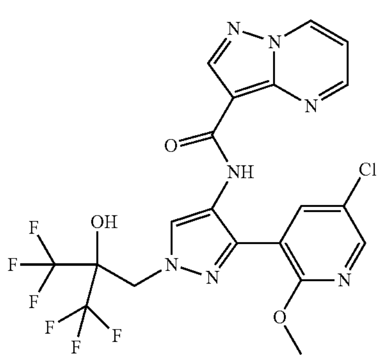 [SMILES: COc1ncc(Cl)cc1-c1nn(CC(O)(C(F)(F)F)C(F)(F)F)cc1NC(=O)c1cnn2cccnc12] | N-(3-(5-chloro-2-methoxypyridin-3-yl)-1-(3,3,3-trifluoro-2-hydroxy-2-(trifluoromethyl)propyl)-1H-pyrazol-4-yl)pyrazolo[1,5-a]pyrimidine-3-carboxamide | 141, 16 | 550.1 |
| 197 | 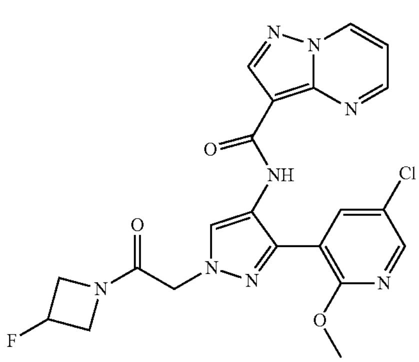 [SMILES: COc1ncc(Cl)cc1-c1nn(CC(=O)N2CC(F)C2)cc1NC(=O)c1cnn2cccnc12] | N-(3-(5-chloro-2-methoxypyridin-3-yl)-1-(2-(3-fluoroazetidin-1-yl)-2-oxoethyl)-1H-pyrazol-4-yl)pyrazolo[1,5-a]pyrimidine-3-carboxamide | 141, 134 | 485.1 |

| Ex | Structure | Name | Mthd | LCMS (ESI) m/z |
|---|---|---|---|---|
| 198 | 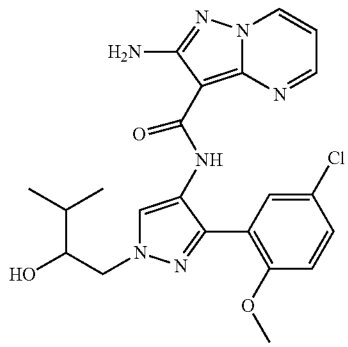 [SMILES: COc1ccc(Cl)cc1-c1nn(CC(O)C(C)C)cc1NC(=O)c1c(N)nn2cccnc12] | 2-amino-N-(3-(5-chloro-2-methoxyphenyl)-1-(2-hydroxy-3-methylbutyl)-1H-pyrazol-4-yl)pyrazolo[1,5-a]pyrimidine-3-carboxamide | 27, 16 | 470.2 |
| 199 | 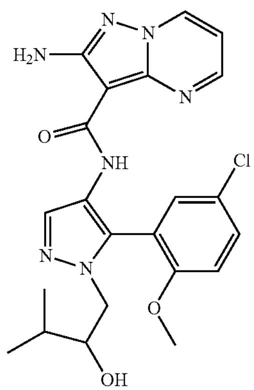 [SMILES: COc1ccc(Cl)cc1-c1c(NC(=O)c2c(N)nn3cccnc23)cnn1CC(O)C(C)C] | 2-amino-N-(5-(5-chloro-2-methoxyphenyl)-1-(2-hydroxy-3-methylbutyl)-1H-pyrazol-4-yl)pyrazolo[1,5-a]pyrimidine-3-carboxamide | 27, 16 | 470.2 |
| 200 | 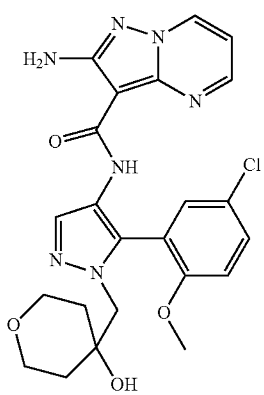 [SMILES: COc1ccc(Cl)cc1-c1c(NC(=O)c2c(N)nn3cccnc23)cnn1CC1(O)CCOCC1] | 2-amino-N-(5-(5-chloro-2-methoxyphenyl)-1-((4-hydroxytetrahydro-2H-pyran-4-yl)methyl)-1H-pyrazol-4-yl)pyrazolo[1,5-a]pyrimidine-3-carboxamide | 27, 16 | 498.2 |
| 201 | 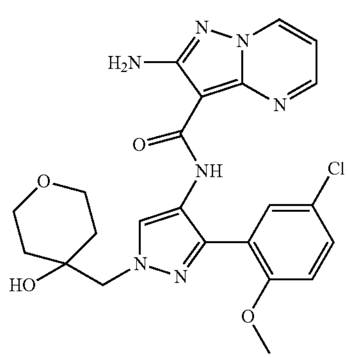 [SMILES: COc1ccc(Cl)cc1-c1nn(CC2(O)CCOCC2)cc1NC(=O)c1c(N)nn2cccnc12] | 2-amino-N-(3-(5-chloro-2-methoxyphenyl)-1-((4-hydroxytetrahydro-2H-pyran-4-yl)methyl)-1H-pyrazol-4-yl)pyrazolo[1,5-a]pyrimidine-3-carboxamide | 27, 16 | 498.2 |

TABLE 2-continued

| Ex | Name | Mthd | LCMS (ESI) m/z |
|---|---|---|---|
| 202 | 2-amino-N-(3-(5-chloro-2-methoxyphenyl)-1-((1-hydroxycyclohexyl)methyl)-1H-pyrazol-4-yl)pyrazolo[1,5-a]pyrimidine-3-carboxamide | 27, 16 | 496.2 |
| 203 | 2-amino-N-(3-(5-chloro-2-methoxyphenyl)-1-(2-hydroxy-2-methylbutyl)-1H-pyrazol-4-yl)pyrazolo[1,5-a]pyrimidine-3-carboxamide | 27, 16 | 470.1 |
| 204 | 2-amino-N-(5-(5-chloro-2-methoxyphenyl)-1-(2-hydroxy-2-methylbutyl)-1H-pyrazol-4-yl)pyrazolo[1,5-a]pyrimidine-3-carboxamide | 27, 16 | 470.2 |
| 205 | 2-amino-N-(3-(5-chloro-2-methoxyphenyl)-1-(pyrrolidin-2-ylmethyl)-1H-pyrazol-4-yl)pyrazolo[1,5-a]pyrimidine-3-carboxamide | 27, 14 | 467.1 |

| Ex | Structure | Name | Mthd | LCMS (ESI) m/z |
|---|---|---|---|---|
| 206 | 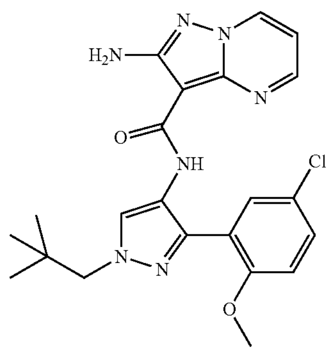 [SMILES: COc1ccc(Cl)cc1-c1nn(CC(C)(C)C)cc1NC(=O)c1c(N)nn2cccnc12] | 2-amino-N-(3-(5-chloro-2-methoxyphenyl)-1-neopentyl-1H-pyrazol-4-yl)pyrazolo[1,5-a]pyrimidine-3-carboxamide | 27, 14 | 454.2 |
| 207 | 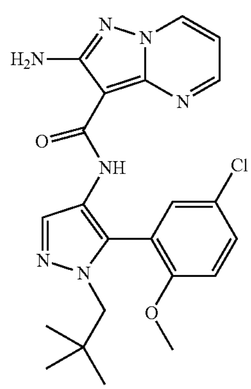 [SMILES: COc1ccc(Cl)cc1-c1c(NC(=O)c2c(N)nn3cccnc23)cnn1CC(C)(C)C] | 2-amino-N-(5-(5-chloro-2-methoxyphenyl)-1-neopentyl-1H-pyrazol-4-yl)pyrazolo[1,5-a]pyrimidine-3-carboxamide | 27, 15 | 454.2 |
| 208 | 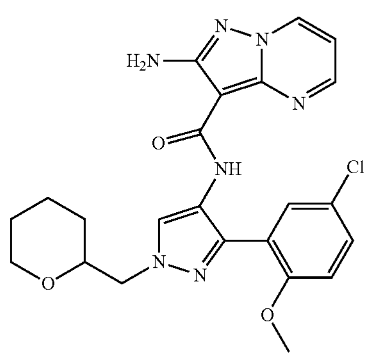 [SMILES: COc1ccc(Cl)cc1-c1nn(CC2CCCCO2)cc1NC(=O)c1c(N)nn2cccnc12] | 2-amino-N-(3-(5-chloro-2-methoxyphenyl)-1-((tetrahydro-2H-pyran-2-yl)methyl)-1H-pyrazol-4-yl)pyrazolo[1,5-a]pyrimidine-3-carboxamide | 27, 14 | 482.2 |
| 209 | 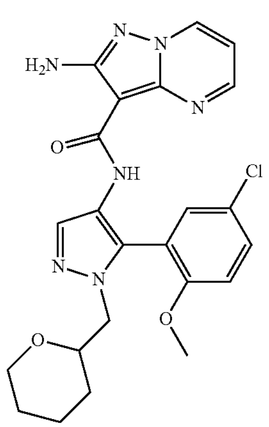 [SMILES: COc1ccc(Cl)cc1-c1c(NC(=O)c2c(N)nn3cccnc23)cnn1CC1CCCCO1] | 2-amino-N-(5-(5-chloro-2-methoxyphenyl)-1-((tetrahydro-2H-pyran-2-yl)methyl)-1H-pyrazol-4-yl)pyrazolo[1,5-a]pyrimidine-3-carboxamide | 27, 15 | 482.2 |

TABLE 2-continued

| Ex | Structure | Name | Mthd | LCMS (ESI) m/z |
|---|---|---|---|---|
| 210 | 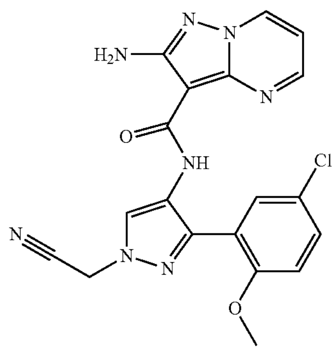 [SMILES: COc1ccc(Cl)cc1-c1nn(CC#N)cc1NC(=O)c1c(N)nn2cccnc12] | 2-amino-N-(3-(5-chloro-2-methoxyphenyl)-1-(cyanomethyl)-1H-pyrazol-4-yl)pyrazolo[1,5-a]pyrimidine-3-carboxamide | 27, 14 | 423.0 |
| 211 | 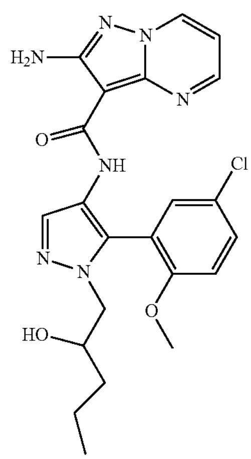 [SMILES: CCCC(O)Cn1ncc(NC(=O)c2c(N)nn3cccnc23)c1-c1cc(Cl)ccc1OC] | 2-amino-N-(5-(5-chloro-2-methoxyphenyl)-1-(2-hydroxypentyl)-1H-pyrazol-4-yl)pyrazolo[1,5-a]pyrimidine-3-carboxamide | 27, 16 | 470.1 |
| 212 | 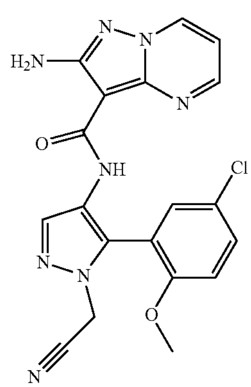 [SMILES: COc1ccc(Cl)cc1-c1c(NC(=O)c2c(N)nn3cccnc23)cnn1CC#N] | 2-amino-N-(5-(5-chloro-2-methoxyphenyl)-1-(cyanomethyl)-1H-pyrazol-4-yl)pyrazolo[1,5-a]pyrimidine-3-carboxamide | 27, 15 | 423.1 |
| 213 | 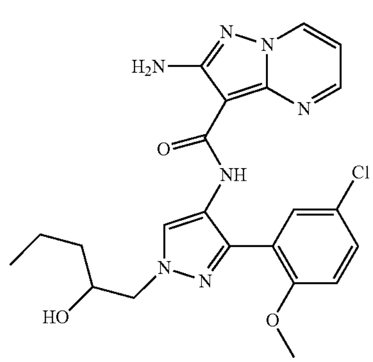 [SMILES: CCCC(O)Cn1cc(NC(=O)c2c(N)nn3cccnc23)c(-c2cc(Cl)ccc2OC)n1] | 2-amino-N-(3-(5-chloro-2-methoxyphenyl)-1-(2-hydroxypentyl)-1H-pyrazol-4-yl)pyrazolo[1,5-a]pyrimidine-3-carboxamide | 27, 16 | 470.1 |

TABLE 2-continued

| Ex | Structure | Name | Mthd | LCMS (ESI) m/z |
|---|---|---|---|---|
| 214 | 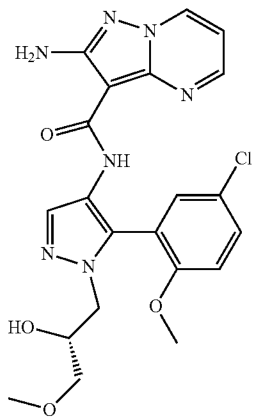 [SMILES: COC[C@H](O)Cn1ncc(NC(=O)c2c(N)nn3cccnc23)c1-c1cc(Cl)ccc1OC] | 2-amino-N-(5-(5-chloro-2-methoxyphenyl)-1-((R)-2-hydroxy-3-methoxypropyl)-1H-pyrazol-4-yl)pyrazolo[1,5-a]pyrimidine-3-carboxamide | 27, 16 | 472.1 |
| 215 | 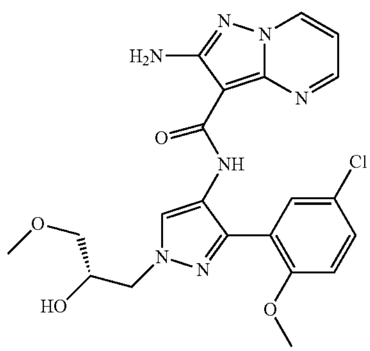 [SMILES: COC[C@@H](O)Cn1cc(NC(=O)c2c(N)nn3cccnc23)c(-c2cc(Cl)ccc2OC)n1] | (S)-2-amino-N-(3-(5-chloro-2-methoxyphenyl)-1-(2-hydroxy-3-methoxypropyl)-1H-pyrazol-4-yl)pyrazolo[1,5-a]pyrimidine-3-carboxamide | 27, 16 | 472.2 |
| 216 | 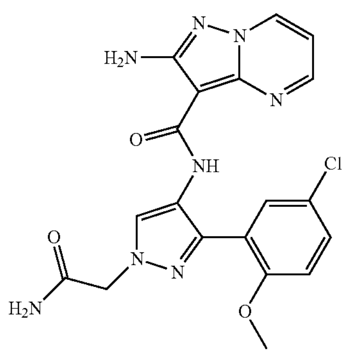 [SMILES: COc1ccc(Cl)cc1-c1nn(CC(N)=O)cc1NC(=O)c1c(N)nn2cccnc12] | 2-amino-N-(1-(2-amino-2-oxoethyl)-3-(5-chloro-2-methoxyphenyl)-1H-pyrazol-4-yl)pyrazolo[1,5-a]pyrimidine-3-carboxamide | 27, 14 | 441.1 |
| 217 | 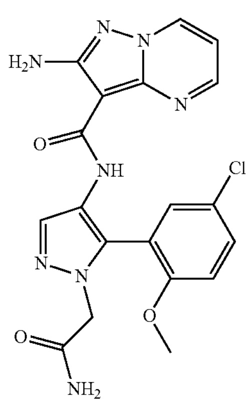 [SMILES: COc1ccc(Cl)cc1-c1c(NC(=O)c2c(N)nn3cccnc23)cnn1CC(N)=O] | 2-amino-N-(1-(2-amino-2-oxoethyl)-5-(5-chloro-2-methoxyphenyl)-1H-pyrazol-4-yl)pyrazolo[1,5-a]pyrimidine-3-carboxamide | 27, 15 | 441.1 |

TABLE 2-continued

| Ex | Structure | Name | Mthd | LCMS (ESI) m/z |
|---|---|---|---|---|
| 218 | 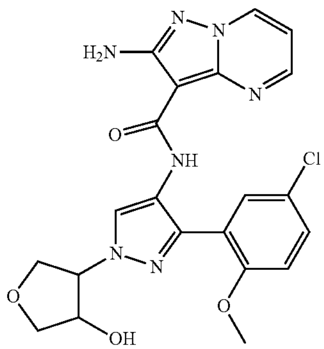 [SMILES: COc1ccc(Cl)cc1-c1nn(C2COCC2O)cc1NC(=O)c1c(N)nn2cccnc12] | 2-amino-N-(3-(5-chloro-2-methoxyphenyl)-1-(4-hydroxytetrahydrofuran-3-yl)-1H-pyrazol-4-yl)pyrazolo[1,5-a]pyrimidine-3-carboxamide | 27, 16 | 470.1 |
| 219 | 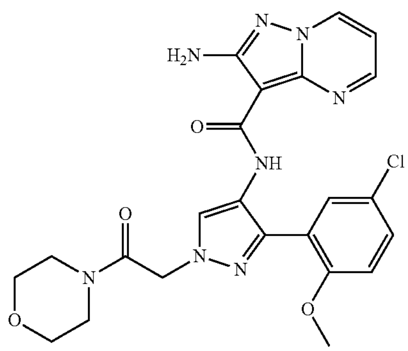 [SMILES: COc1ccc(Cl)cc1-c1nn(CC(=O)N2CCOCC2)cc1NC(=O)c1c(N)nn2cccnc12] | 2-amino-N-(3-(5-chloro-2-methoxyphenyl)-1-(2-morpholino-2-oxoethyl)-1H-pyrazol-4-yl)pyrazolo[1,5-a]pyrimidine-3-carboxamide | 27, 14 | 511.2 |
| 220 | 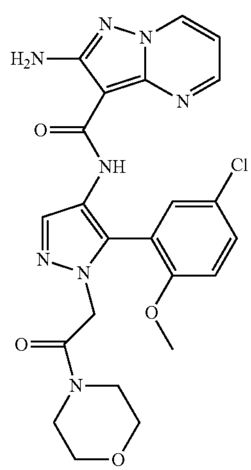 [SMILES: COc1ccc(Cl)cc1-c1c(NC(=O)c2c(N)nn3cccnc23)cnn1CC(=O)N1CCOCC1] | 2-amino-N-(5-(5-chloro-2-methoxyphenyl)-1-(2-morpholino-2-oxoethyl)-1H-pyrazol-4-yl)pyrazolo[1,5-a]pyrimidine-3-carboxamide | 27, 15 | 511.2 |
| 221 | 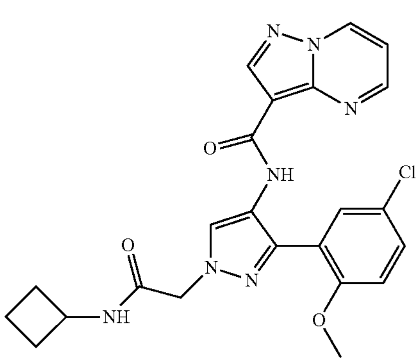 [SMILES: COc1ccc(Cl)cc1-c1nn(CC(=O)NC2CCC2)cc1NC(=O)c1cnn2cccnc12] | N-(3-(5-chloro-2-methoxyphenyl)-1-(2-(cyclobutylamino)-2-oxoethyl)-1H-pyrazol-4-yl)pyrazolo[1,5-a]pyrimidine-3-carboxamide | 134 | 480.1 |

TABLE 2-continued

| Ex | Structure | Name | Mthd | LCMS (ESI) m/z |
|---|---|---|---|---|
| 222 | 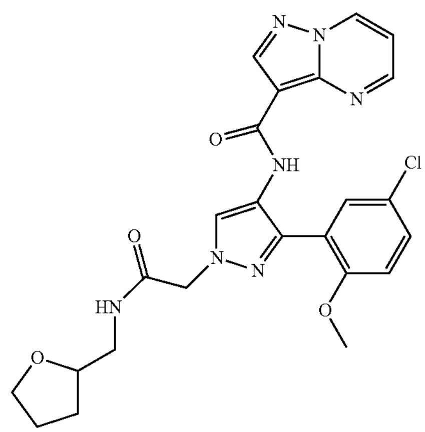 [SMILES: COc1ccc(Cl)cc1-c1nn(CC(=O)NCC2CCCO2)cc1NC(=O)c1cnn2cccnc12] | N-(3-(5-chloro-2-methoxyphenyl)-1-(2-oxo-2-((tetrahydrofuran-2-yl)methylamino)ethyl)-1H-pyrazol-4-yl)pyrazolo[1,5-a]pyrimidine-3-carboxamide | 134 | 510.1 |
| 223 | 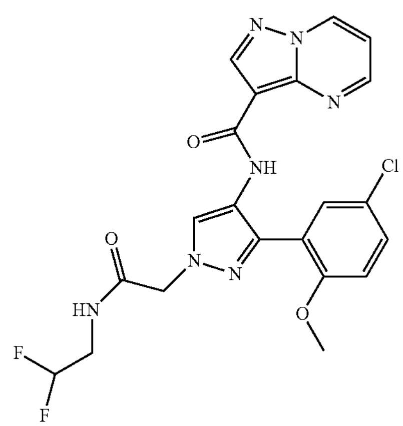 [SMILES: COc1ccc(Cl)cc1-c1nn(CC(=O)NCC(F)F)cc1NC(=O)c1cnn2cccnc12] | N-(3-(5-chloro-2-methoxyphenyl)-1-(2-(2,2-difluoroethylamino)-2-oxoethyl)-1H-pyrazol-4-yl)pyrazolo[1,5-a]pyrimidine-3-carboxamide | 134 | 490.1 |
| 224 | 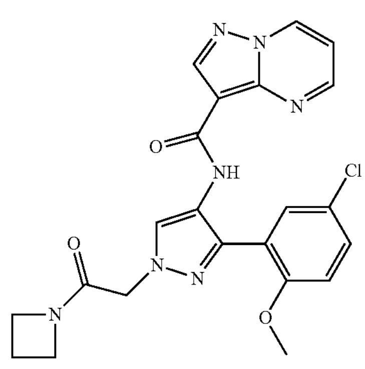 [SMILES: COc1ccc(Cl)cc1-c1nn(CC(=O)N2CCC2)cc1NC(=O)c1cnn2cccnc12] | N-(1-(2-(azetidin-1-yl)-2-oxoethyl)-3-(5-chloro-2-methoxyphenyl)-1H-pyrazol-4-yl)pyrazolo[1,5-a]pyrimidine-3-carboxamide | 134 | 466.1 |

TABLE 2-continued

| Ex | Structure | Name | Mthd | LCMS (ESI) m/z |
|---|---|---|---|---|
| 225 | 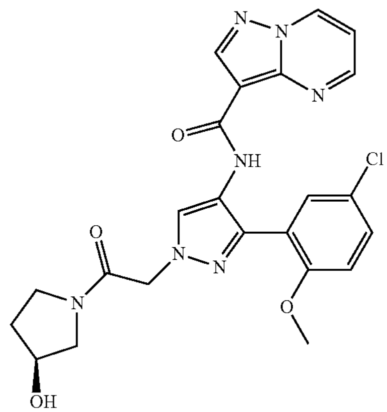 [SMILES: COc1ccc(Cl)cc1-c1nn(CC(=O)N2CC[C@H](O)C2)cc1NC(=O)c1cnn2cccnc12] | (S)-N-(3-(5-chloro-2-methoxyphenyl)-1-(2-(3-hydroxypyrrolidin-1-yl)-2-oxoethyl)-1H-pyrazol-4-yl)pyrazolo[1,5-a]pyrimidine-3-carboxamide | 134 | 496.1 |
| 226 | 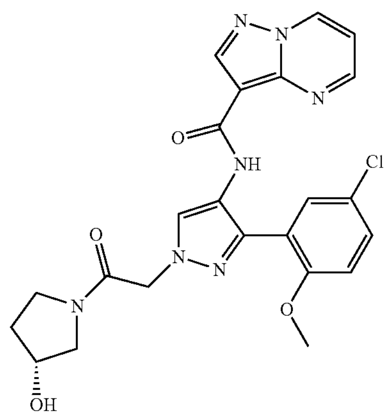 [SMILES: COc1ccc(Cl)cc1-c1nn(CC(=O)N2CC[C@@H](O)C2)cc1NC(=O)c1cnn2cccnc12] | (R)-N-(3-(5-chloro-2-methoxyphenyl)-1-(2-(3-hydroxypyrrolidin-1-yl)-2-oxoethyl)-1H-pyrazol-4-yl)pyrazolo[1,5-a]pyrimidine-3-carboxamide | 134 | 496.1 |
| 227 | 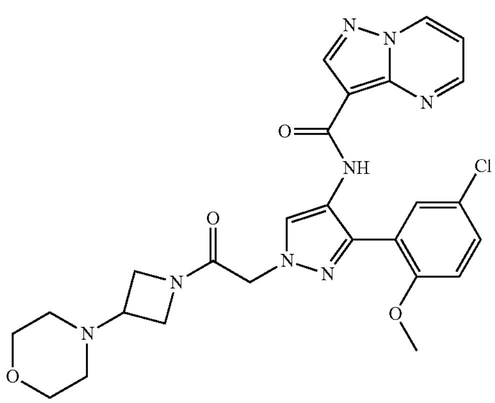 [SMILES: COc1ccc(Cl)cc1-c1nn(CC(=O)N2CC(N3CCOCC3)C2)cc1NC(=O)c1cnn2cccnc12] | N-(3-(5-chloro-2-methoxyphenyl)-1-(2-(3-morpholinoazetidin-1-yl)-2-oxoethyl)-1H-pyrazol-4-yl)pyrazolo[1,5-a]pyrimidine-3-carboxamide | 134 | 551.2 |
| 228 | 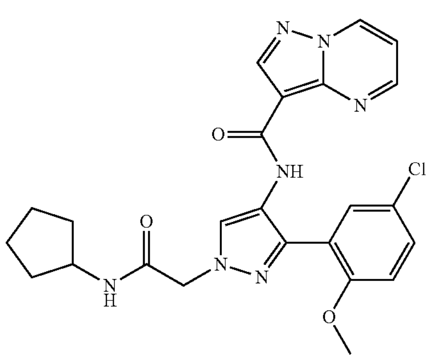 [SMILES: COc1ccc(Cl)cc1-c1nn(CC(=O)NC2CCCC2)cc1NC(=O)c1cnn2cccnc12] | N-(3-(5-chloro-2-methoxyphenyl)-1-(2-(cyclopentylamino)-2-oxoethyl)-1H-pyrazol-4-yl)pyrazolo[1,5-a]pyrimidine-3-carboxamide | 134 | 494.2 |

TABLE 2-continued

| Ex | Structure | Name | Mthd | LCMS (ESI) m/z |
|---|---|---|---|---|
| 229 | 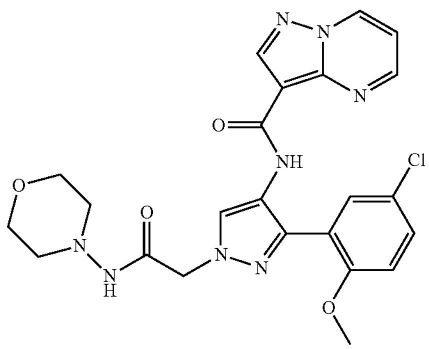 [SMILES: COc1ccc(Cl)cc1-c1nn(CC(=O)NN2CCOCC2)cc1NC(=O)c1cnn2cccnc12] | N-(3-(5-chloro-2-methoxyphenyl)-1-(2-(morpholinoamino)-2-oxoethyl)-1H-pyrazol-4-yl)pyrazolo[1,5-a]pyrimidine-3-carboxamide | 134 | 511.2 |
| 230 | 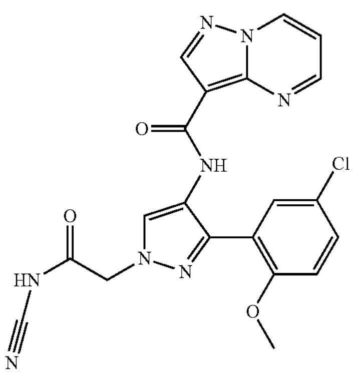 [SMILES: COc1ccc(Cl)cc1-c1nn(CC(=O)NC#N)cc1NC(=O)c1cnn2cccnc12] | N-(3-(5-chloro-2-methoxyphenyl)-1-(2-cyanamido-2-oxoethyl)-1H-pyrazol-4-yl)pyrazolo[1,5-a]pyrimidine-3-carboxamide | 134 | 451.2 |
| 231 | 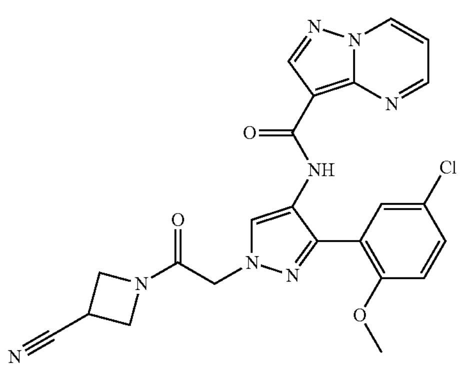 [SMILES: COc1ccc(Cl)cc1-c1nn(CC(=O)N2CC(C#N)C2)cc1NC(=O)c1cnn2cccnc12] | N-(3-(5-chloro-2-methoxyphenyl)-1-(2-(3-cyanoazetidin-1-yl)-2-oxoethyl)-1H-pyrazol-4-yl)pyrazolo[1,5-a]pyrimidine-3-carboxamide | 134 | 491.2 |
| 232 | 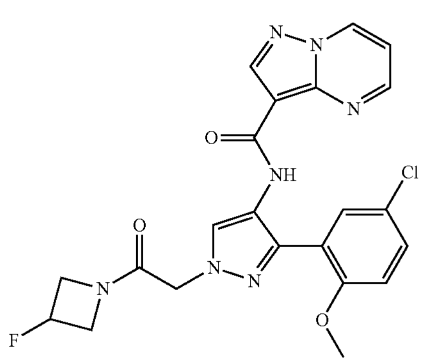 [SMILES: COc1ccc(Cl)cc1-c1nn(CC(=O)N2CC(F)C2)cc1NC(=O)c1cnn2cccnc12] | N-(3-(5-chloro-2-methoxyphenyl)-1-(2-(3-fluoroazetidin-1-yl)-2-oxoethyl)-1H-pyrazol-4-yl)pyrazolo[1,5-a]pyrimidine-3-carboxamide | 134 | 484.1 |

TABLE 2-continued

| Ex | Structure | Name | Mthd | LCMS (ESI) m/z |
|---|---|---|---|---|
| 233 | 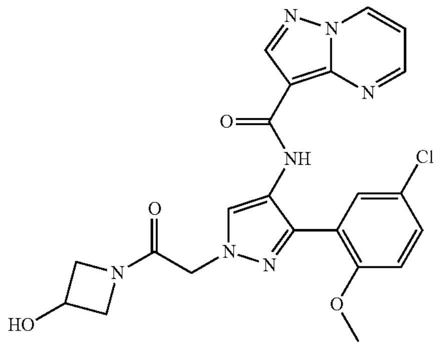 [SMILES: COc1ccc(Cl)cc1-c1nn(CC(=O)N2CC(O)C2)cc1NC(=O)c1cnn2cccnc12] | N-(3-(5-chloro-2-methoxyphenyl)-1-(2-(3-hydroxyazetidin-1-yl)-2-oxoethyl)-1H-pyrazol-4-yl)pyrazolo[1,5-a]pyrimidine-3-carboxamide | 134 | 482.2 |
| 234 | 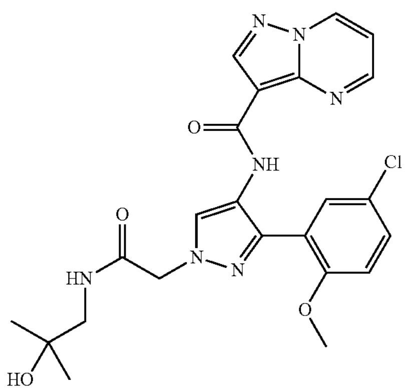 [SMILES: COc1ccc(Cl)cc1-c1nn(CC(=O)NCC(C)(C)O)cc1NC(=O)c1cnn2cccnc12] | N-(3-(5-chloro-2-methoxyphenyl)-1-(2-(2-hydroxy-2-methylpropylamino)-2-oxoethyl)-1H-pyrazol-4-yl)pyrazolo[1,5-a]pyrimidine-3-carboxamide | 134 | 498.2 |
| 235 | 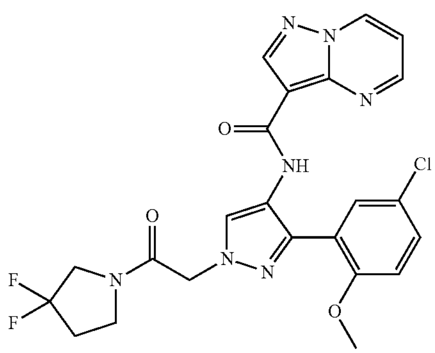 [SMILES: COc1ccc(Cl)cc1-c1nn(CC(=O)N2CCC(F)(F)C2)cc1NC(=O)c1cnn2cccnc12] | N-(3-(5-chloro-2-methoxyphenyl)-1-(2-(3,3-difluoropyrrolidin-1-yl)-2-oxoethyl)-1H-pyrazol-4-yl)pyrazolo[1,5-a]pyrimidine-3-carboxamide | 134 | 516.2 |
| 236 | 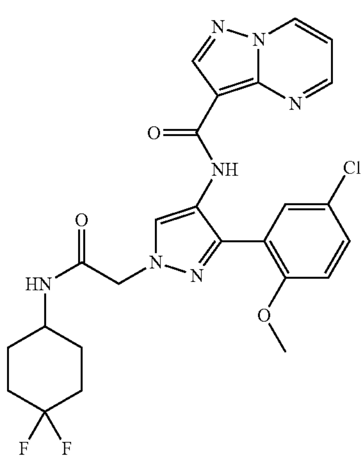 [SMILES: COc1ccc(Cl)cc1-c1nn(CC(=O)NC2CCC(F)(F)CC2)cc1NC(=O)c1cnn2cccnc12] | N-(3-(5-chloro-2-methoxyphenyl)-1-(2-(4,4-difluorocyclohexylamino)-2-oxoethyl)-1H-pyrazol-4-yl)pyrazolo[1,5-a]pyrimidine-3-carboxamide | 134 | 544.2 |

TABLE 2-continued

| Ex | Structure | Name | Mthd | LCMS (ESI) m/z |
|---|---|---|---|---|
| 237 | 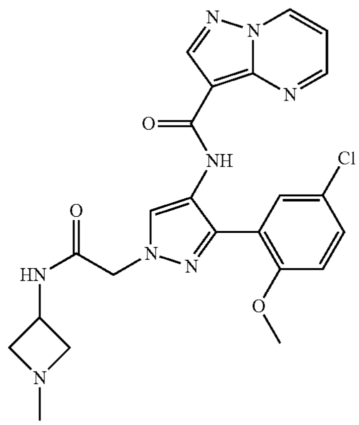 [SMILES: COc1ccc(Cl)cc1-c1nn(CC(=O)NC2CN(C)C2)cc1NC(=O)c1cnn2cccnc12] | N-(3-(5-chloro-2-methoxyphenyl)-1-(2-(1-methylazetidin-3-ylamino)-2-oxoethyl)-1H-pyrazol-4-yl)pyrazolo[1,5-a]pyrimidine-3-carboxamide | 134 | 495.0 |
| 238 | 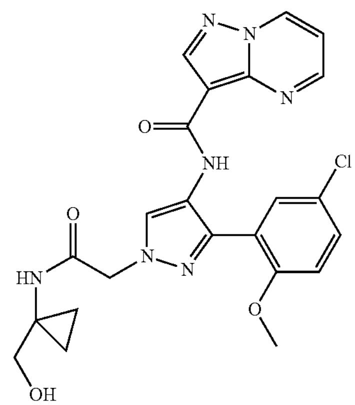 [SMILES: COc1ccc(Cl)cc1-c1nn(CC(=O)NC2(CO)CC2)cc1NC(=O)c1cnn2cccnc12] | N-(3-(5-chloro-2-methoxyphenyl)-1-(2-(1-(hydroxymethyl)cyclopropyl-amino)-2-oxoethyl)-1H-pyrazol-4-yl)pyrazolo[1,5-a]pyrimidine-3-carboxamide | 134 | 496.1 |
| 239 | 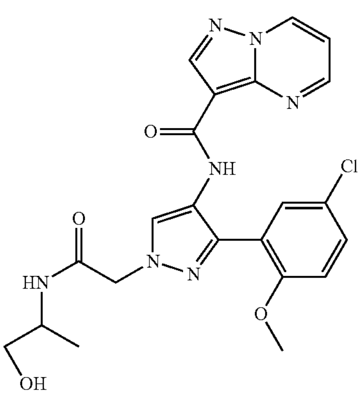 [SMILES: COc1ccc(Cl)cc1-c1nn(CC(=O)NC(C)CO)cc1NC(=O)c1cnn2cccnc12] | N-(3-(5-chloro-2-methoxyphenyl)-1-(2-(1-hydroxypropan-2-ylamino)-2-oxoethyl)-1H-pyrazol-4-yl)pyrazolo[1,5-a]pyrimidine-3-carboxamide | 134 | 484.1 |
| 240 | 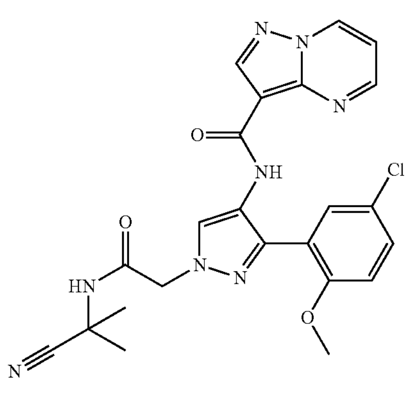 [SMILES: COc1ccc(Cl)cc1-c1nn(CC(=O)NC(C)(C)C#N)cc1NC(=O)c1cnn2cccnc12] | N-(3-(5-chloro-2-methoxyphenyl)-1-(2-(2-cyanopropan-2-ylamino)-2-oxoethyl)-1H-pyrazol-4-yl)pyrazolo[1,5-a]pyrimidine-3-carboxamide | 134 | 493.1 |

| Ex | Structure | Name | Mthd | LCMS (ESI) m/z |
|---|---|---|---|---|
| 241 | 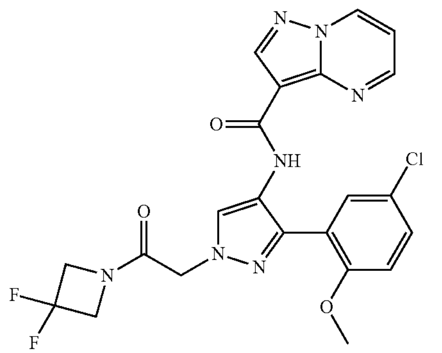 [SMILES: COc1ccc(Cl)cc1-c1nn(CC(=O)N2CC(F)(F)C2)cc1NC(=O)c1cnn2cccnc12] | N-(3-(5-chloro-2-methoxyphenyl)-1-(2-(3,3-difluoroazetidin-1-yl)-2-oxoethyl)-1H-pyrazol-4-yl)pyrazolo[1,5-a]pyrimidine-3-carboxamide | 134 | 502.1 |
| 242 | 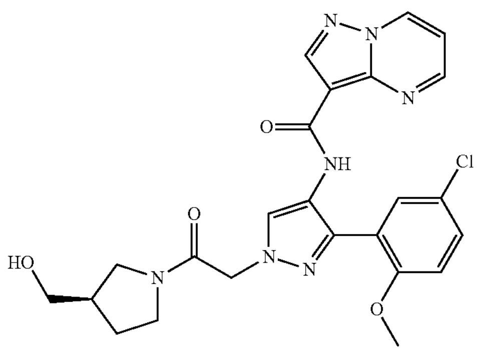 [SMILES: COc1ccc(Cl)cc1-c1nn(CC(=O)N2CC[C@@H](CO)C2)cc1NC(=O)c1cnn2cccnc12] | (R)-N-(3-(5-chloro-2-methoxyphenyl)-1-(2-(3-(hydroxymethyl)pyrrolidin-1-yl)-2-oxoethyl)-1H-pyrazol-4-yl)pyrazolo[1,5-a]pyrimidine-3-carboxamide | 134 | 510.1 |
| 243 | 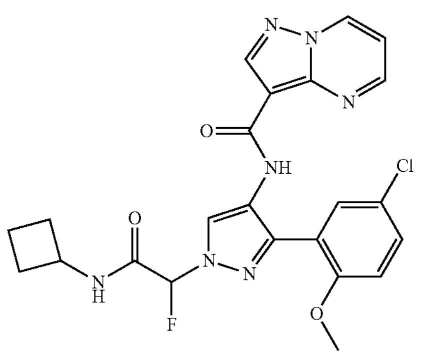 [SMILES: COc1ccc(Cl)cc1-c1nn(C(F)C(=O)NC2CCC2)cc1NC(=O)c1cnn2cccnc12] | N-(3-(5-chloro-2-methoxyphenyl)-1-(2-(cyclobutylamino)-1-fluoro-2-oxoethyl)-1H-pyrazol-4-yl)pyrazolo[1,5-a]pyrimidine-3-carboxamide | 135 | 498.1 |
| 244 | 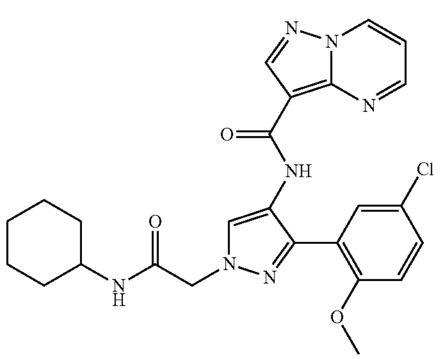 [SMILES: COc1ccc(Cl)cc1-c1nn(CC(=O)NC2CCCCC2)cc1NC(=O)c1cnn2cccnc12] | N-(3-(5-chloro-2-methoxyphenyl)-1-(2-(cyclohexylamino)-2-oxoethyl)-1H-pyrazol-4-yl)pyrazolo[1,5-a]pyrimidine-3-carboxamide | 134 | 508.2 |

TABLE 2-continued

| Ex | Structure | Name | Mthd | LCMS (ESI) m/z |
|---|---|---|---|---|
| 245 | 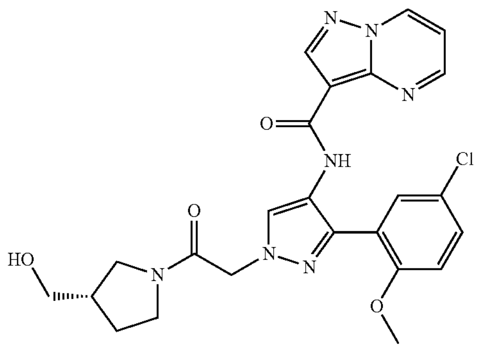 [SMILES: COc1ccc(Cl)cc1-c1nn(CC(=O)N2CC[C@H](CO)C2)cc1NC(=O)c1cnn2cccnc12] | (S)-N-(3-(5-chloro-2-methoxyphenyl)-1-(2-(3-(hydroxymethyl)pyrrolidin-1-yl)-2-oxoethyl)-1H-pyrazol-4-yl)pyrazolo[1,5-a]pyrimidine-3-carboxamide | 134 | 510.1 |
| 246 | 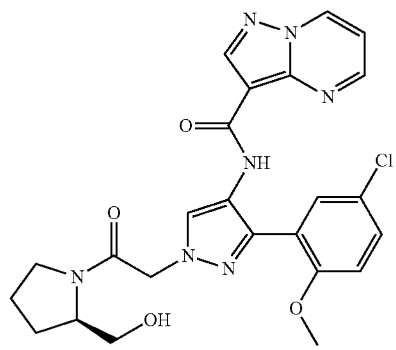 [SMILES: COc1ccc(Cl)cc1-c1nn(CC(=O)N2CCC[C@@H]2CO)cc1NC(=O)c1cnn2cccnc12] | (R)-N-(3-(5-chloro-2-methoxyphenyl)-1-(2-(2-(hydroxymethyl)pyrrolidin-1-yl)-2-oxoethyl)-1H-pyrazol-4-yl)pyrazolo[1,5-a]pyrimidine-3-carboxamide | 134 | 510.2 |
| 247 | 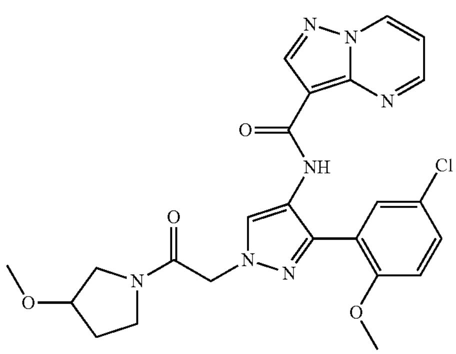 [SMILES: COc1ccc(Cl)cc1-c1nn(CC(=O)N2CCC(OC)C2)cc1NC(=O)c1cnn2cccnc12] | N-(3-(5-chloro-2-methoxyphenyl)-1-(2-(3-methoxypyrrolidin-1-yl)-2-oxoethyl)-1H-pyrazol-4-yl)pyrazolo[1,5-a]pyrimidine-3-carboxamide | 134 | 510.2 |
| 248 | 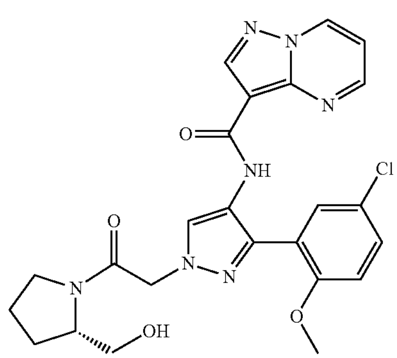 [SMILES: COc1ccc(Cl)cc1-c1nn(CC(=O)N2CCC[C@H]2CO)cc1NC(=O)c1cnn2cccnc12] | (S)-N-(3-(5-chloro-2-methoxyphenyl)-1-(2-(2-(hydroxymethyl)pyrrolidin-1-yl)-2-oxoethyl)-1H-pyrazol-4-yl)pyrazolo[1,5-a]pyrimidine-3-carboxamide | 134 | 510.0 |

TABLE 2-continued

| Ex | Structure | Name | Mthd | LCMS (ESI) m/z |
|---|---|---|---|---|
| 249 | 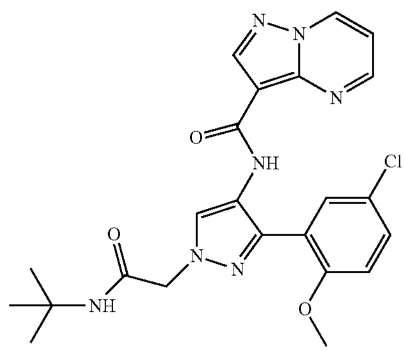 [SMILES: COc1ccc(Cl)cc1-c1nn(CC(=O)NC(C)(C)C)cc1NC(=O)c1cnn2cccnc12] | N-(1-(2-(tert-butylamino)-2-oxoethyl)-3-(5-chloro-2-methoxyphenyl)-1H-pyrazol-4-yl)pyrazolo[1,5-a]pyrimidine-3-carboxamide | 134 | 482.2 |
| 250 | 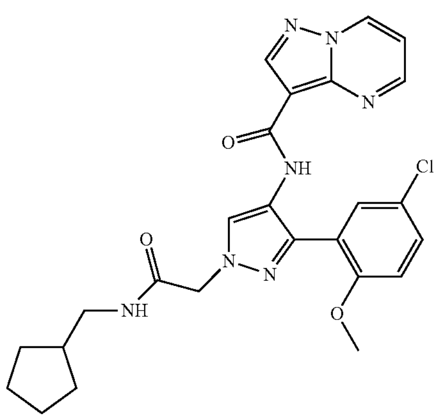 [SMILES: COc1ccc(Cl)cc1-c1nn(CC(=O)NCC2CCCC2)cc1NC(=O)c1cnn2cccnc12] | N-(3-(5-chloro-2-methoxyphenyl)-1-(2-(cyclopentylmethylamino)-2-oxoethyl)-1H-pyrazol-4-yl)pyrazolo[1,5-a]pyrimidine-3-carboxamide | 134 | 508.2 |
| 251 | 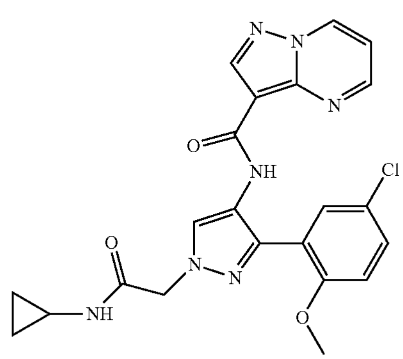 [SMILES: COc1ccc(Cl)cc1-c1nn(CC(=O)NC2CC2)cc1NC(=O)c1cnn2cccnc12] | N-(3-(5-chloro-2-methoxyphenyl)-1-(2-(cyclopropylamino)-2-oxoethyl)-1H-pyrazol-4-yl)pyrazolo[1,5-a]pyrimidine-3-carboxamide | 134 | 466.1 |
| 252 | 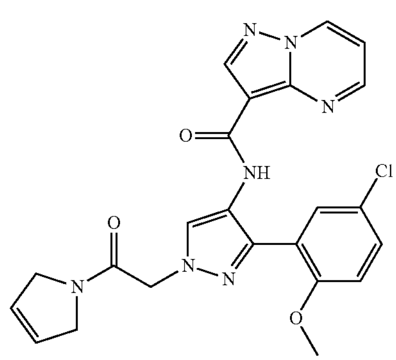 [SMILES: COc1ccc(Cl)cc1-c1nn(CC(=O)N2CC=CC2)cc1NC(=O)c1cnn2cccnc12] | N-(3-(5-chloro-2-methoxyphenyl)-1-(2-(2,5-dihydro-1H-pyrrol-1-yl)-2-oxoethyl)-1H-pyrazol-4-yl)pyrazolo[1,5-a]pyrimidine-3-carboxamide | 134 | 478.1 |

TABLE 2-continued

| Ex | Structure | Name | Mthd | LCMS (ESI) m/z |
|---|---|---|---|---|
| 253 | 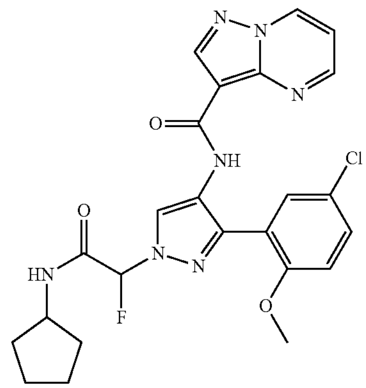 [SMILES: COc1ccc(Cl)cc1-c1nn(C(F)C(=O)NC2CCCC2)cc1NC(=O)c1cnn2cccnc12] | N-(3-(5-chloro-2-methoxyphenyl)-1-(2-(cyclopentylamino)-1-fluoro-2-oxoethyl)-1H-pyrazol-4-yl)pyrazolo[1,5-a]pyrimidine-3-carboxamide | 135 | 512.2 |
| 254 | 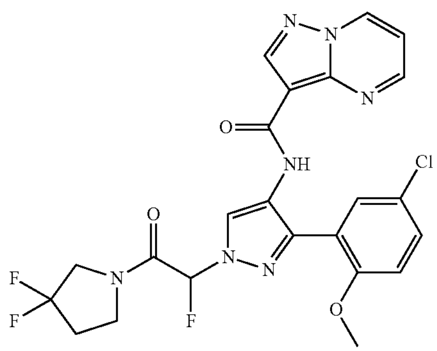 [SMILES: COc1ccc(Cl)cc1-c1nn(C(F)C(=O)N2CCC(F)(F)C2)cc1NC(=O)c1cnn2cccnc12] | N-(3-(5-chloro-2-methoxyphenyl)-1-(2-(3,3-difluoropyrrolidin-1-yl)-1-fluoro-2-oxoethyl)-1H-pyrazol-4-yl)pyrazolo[1,5-a]pyrimidine-3-carboxamide | 135 | 534.2 |
| 255 | 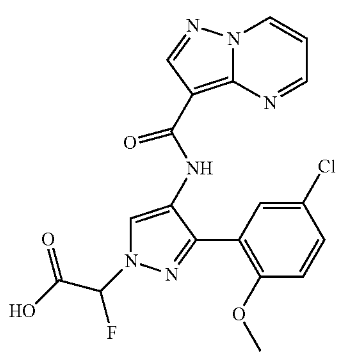 [SMILES: COc1ccc(Cl)cc1-c1nn(C(F)C(=O)O)cc1NC(=O)c1cnn2cccnc12] | 2-(3-(5-chloro-2-methoxyphenyl)-4-(pyrazolo[1,5-a]pyrimidine-3-carboxamido)-1H-pyrazol-1-yl)-2-fluoroacetic acid | 135 | 445.1 |
| 256 | 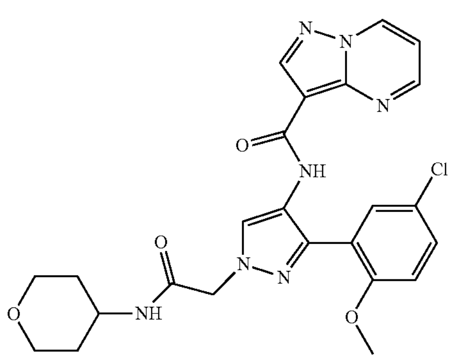 [SMILES: COc1ccc(Cl)cc1-c1nn(CC(=O)NC2CCOCC2)cc1NC(=O)c1cnn2cccnc12] | N-(3-(5-chloro-2-methoxyphenyl)-1-(2-oxo-2-(tetrahydro-2H-pyran-4-ylamino)ethyl)-1H-pyrazol-4-yl)pyrazolo[1,5-a]pyrimidine-3-carboxamide | 134 | 510.2 |

TABLE 2-continued

| Ex | Structure | Name | Mthd | LCMS (ESI) m/z |
|---|---|---|---|---|
| 257 | 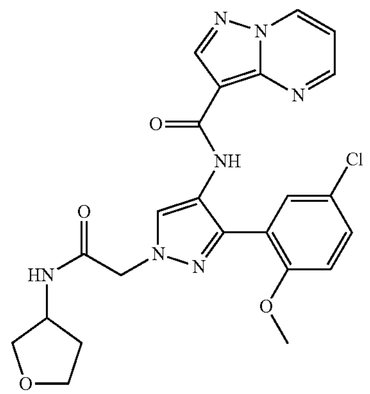 [SMILES: COc1ccc(Cl)cc1-c1nn(CC(=O)NC2CCOC2)cc1NC(=O)c1cnn2cccnc12] | N-(3-(5-chloro-2-methoxyphenyl)-1-(2-oxo-2-(tetrahydrofuran-3-ylamino)ethyl)-1H-pyrazol-4-yl)pyrazolo[1,5-a]pyrimidine-3-carboxamide | 134 | 496.1 |
| 258 | 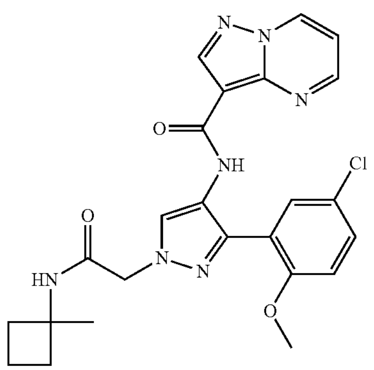 [SMILES: COc1ccc(Cl)cc1-c1nn(CC(=O)NC2(C)CCC2)cc1NC(=O)c1cnn2cccnc12] | N-(3-(5-chloro-2-methoxyphenyl)-1-(2-(1-methylcyclobutylamino)-2-oxoethyl)-1H-pyrazol-4-yl)pyrazolo[1,5-a]pyrimidine-3-carboxamide | 134 | 494.1 |
| 259 | 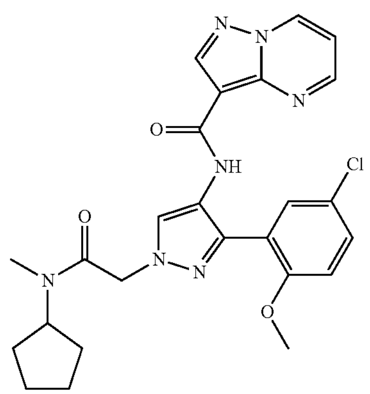 [SMILES: COc1ccc(Cl)cc1-c1nn(CC(=O)N(C)C2CCCC2)cc1NC(=O)c1cnn2cccnc12] | N-(3-(5-chloro-2-methoxyphenyl)-1-(2-(cyclopentyl(methyl)amino)-2-oxoethyl)-1H-pyrazol-4-yl)pyrazolo[1,5-a]pyrimidine-3-carboxamide | 134 | 508.1 |
| 260 | 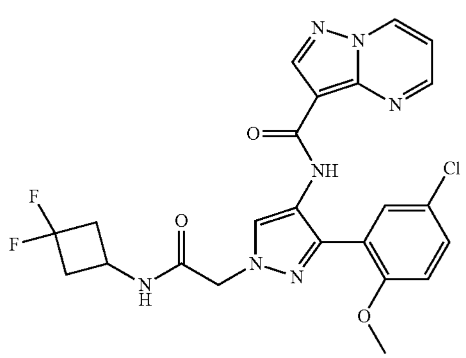 [SMILES: COc1ccc(Cl)cc1-c1nn(CC(=O)NC2CC(F)(F)C2)cc1NC(=O)c1cnn2cccnc12] | N-(3-(5-chloro-2-methoxyphenyl)-1-(2-(3,3-difluorocyclobutylamino)-2-oxoethyl)-1H-pyrazol-4-yl)pyrazolo[1,5-a]pyrimidine-3-carboxamide | 134 | 516.1 |

TABLE 2-continued

| Ex | Structure | Name | Mthd | LCMS (ESI) m/z |
|---|---|---|---|---|
| 261 | 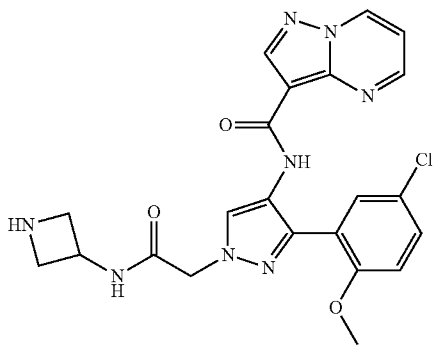 [SMILES: COc1ccc(Cl)cc1-c1nn(CC(=O)NC2CNC2)cc1NC(=O)c1cnn2cccnc12] | N-(1-(2-(azetidin-3-ylamino)-2-oxoethyl)-3-(5-chloro-2-methoxyphenyl)-1H-pyrazol-4-yl)pyrazolo[1,5-a]pyrimidine-3-carboxamide | 134 | 481.2 |
| 262 | 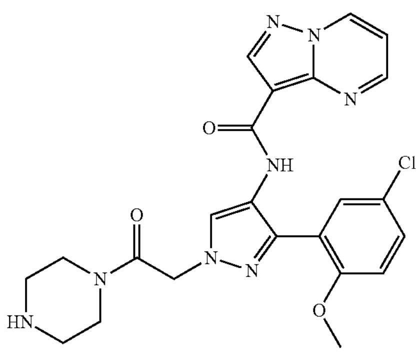 [SMILES: COc1ccc(Cl)cc1-c1nn(CC(=O)N2CCNCC2)cc1NC(=O)c1cnn2cccnc12] | N-(3-(5-chloro-2-methoxyphenyl)-1-(2-oxo-2-(piperazin-1-yl)ethyl)-1H-pyrazol-4-yl)pyrazolo[1,5-a]pyrimidine-3-carboxamide | 134 | 495.1 |
| 263 | 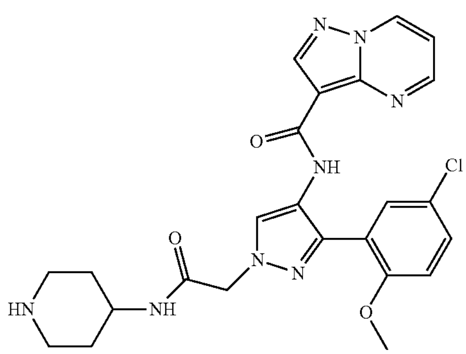 [SMILES: COc1ccc(Cl)cc1-c1nn(CC(=O)NC2CCNCC2)cc1NC(=O)c1cnn2cccnc12] | N-(3-(5-chloro-2-methoxyphenyl)-1-(2-oxo-2-(piperidin-4-ylamino)ethyl)-1H-pyrazol-4-yl)pyrazolo[1,5-a]pyrimidine-3-carboxamide | 134 | 509.1 |
| 264 | 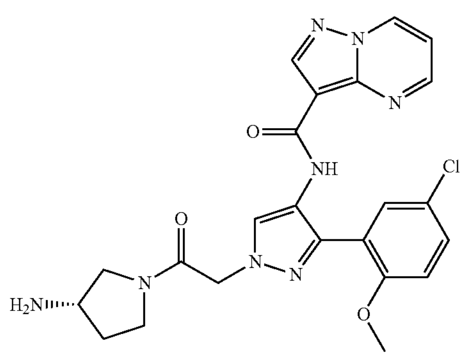 [SMILES: COc1ccc(Cl)cc1-c1nn(CC(=O)N2CC[C@H](N)C2)cc1NC(=O)c1cnn2cccnc12] | (S)-N-(1-(2-(3-aminopyrrolidin-1-yl)-2-oxoethyl)-3-(5-chloro-2-methoxyphenyl)-1H-pyrazol-4-yl)pyrazolo[1,5-a]pyrimidine-3-carboxamide | 134 | 495.1 |

TABLE 2-continued

| Ex | Structure | Name | Mthd | LCMS (ESI) m/z |
|---|---|---|---|---|
| 265 | 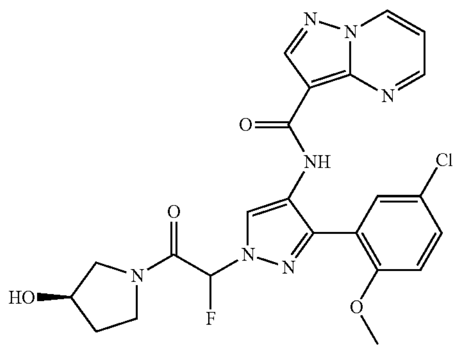 [SMILES: COc1ccc(Cl)cc1-c1nn(C(F)C(=O)N2CC[C@@H](O)C2)cc1NC(=O)c1cnn2cccnc12] | N-(3-(5-chloro-2-methoxyphenyl)-1-(1-fluoro-2-(3-hydroxypyrrolidin-1-yl)-2-oxoethyl)-1H-pyrazol-4-yl)pyrazolo[1,5-a]pyrimidine-3-carboxamide | 135 | 514.2 |
| 266 | 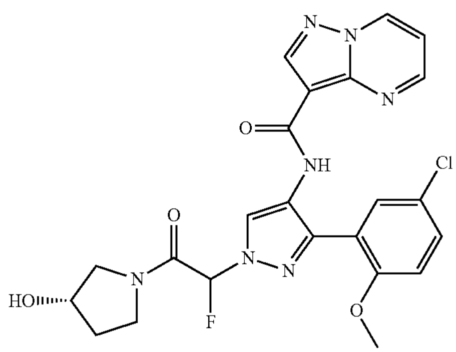 [SMILES: COc1ccc(Cl)cc1-c1nn(C(F)C(=O)N2CC[C@H](O)C2)cc1NC(=O)c1cnn2cccnc12] | N-(3-(5-chloro-2-methoxyphenyl)-1-(1-fluoro-2-(3-hydroxypyrrolidin-1-yl)-2-oxoethyl)-1H-pyrazol-4-yl)pyrazolo[1,5-a]pyrimidine-3-carboxamide | 135 | 514.2 |
| 267 | 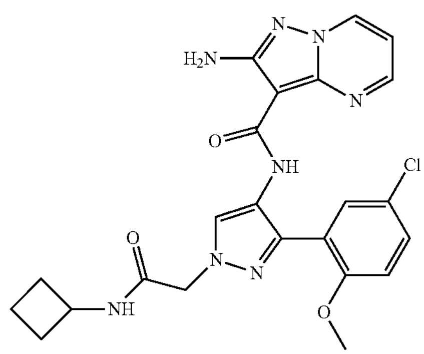 [SMILES: COc1ccc(Cl)cc1-c1nn(CC(=O)NC2CCC2)cc1NC(=O)c1c(N)nn2cccnc12] | 2-amino-N-(3-(5-chloro-2-methoxyphenyl)-1-(2-(cyclobutylamino)-2-oxoethyl)-1H-pyrazol-4-yl)pyrazolo[1,5-a]pyrimidine-3-carboxamide | 134 | 495.1 |
| 268 | 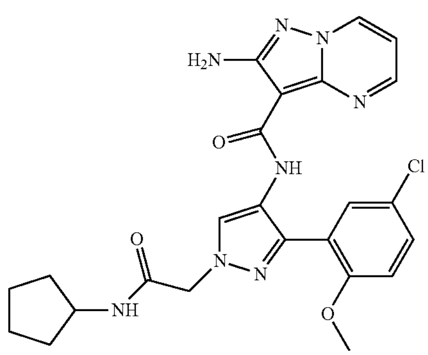 [SMILES: COc1ccc(Cl)cc1-c1nn(CC(=O)NC2CCCC2)cc1NC(=O)c1c(N)nn2cccnc12] | 2-amino-N-(3-(5-chloro-2-methoxyphenyl)-1-(2-(cyclopentylamino)-2-oxoethyl)-1H-pyrazol-4-yl)pyrazolo[1,5-a]pyrimidine-3-carboxamide | 134 | 509.2 |

TABLE 2-continued

| Ex | Structure | Name | Mthd | LCMS (ESI) m/z |
|---|---|---|---|---|
| 269 | 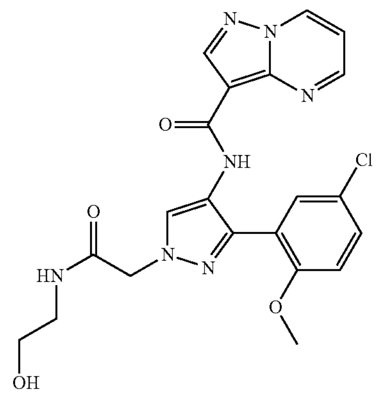 [SMILES: COc1ccc(Cl)cc1-c1nn(CC(=O)NCCO)cc1NC(=O)c1cnn2cccnc12] | N-(3-(5-chloro-2-methoxyphenyl)-1-(2-(2-hydroxyethylamino)-2-oxoethyl)-1H-pyrazol-4-yl)pyrazolo[1,5-a]pyrimidine-3-carboxamide | 134 | 470.1 |
| 270 | 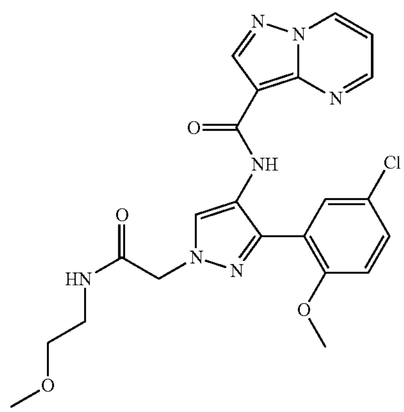 [SMILES: COCCNC(=O)Cn1cc(NC(=O)c2cnn3cccnc23)c(-c2cc(Cl)ccc2OC)n1] | N-(3-(5-chloro-2-methoxyphenyl)-1-(2-(2-methoxyethylamino)-2-oxoethyl)-1H-pyrazol-4-yl)pyrazolo[1,5-a]pyrimidine-3-carboxamide | 134 | 484.1 |
| 271 | 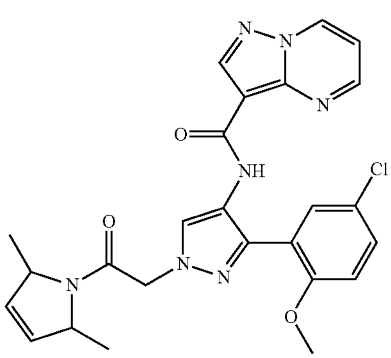 [SMILES: COc1ccc(Cl)cc1-c1nn(CC(=O)N2C(C)C=CC2C)cc1NC(=O)c1cnn2cccnc12] | N-(3-(5-chloro-2-methoxyphenyl)-1-(2-(2,5-dimethyl-2,5-dihydro-1H-pyrrol-1-yl)-2-oxoethyl)-1H-pyrazol-4-yl)pyrazolo[1,5-a]pyrimidine-3-carboxamide | 134 | 506.1 |
| 272 | 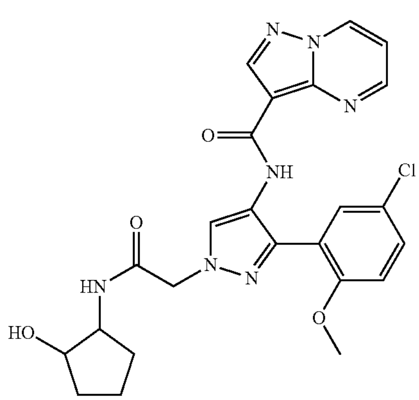 [SMILES: COc1ccc(Cl)cc1-c1nn(CC(=O)NC2CCCC2O)cc1NC(=O)c1cnn2cccnc12] | N-(3-(5-chloro-2-methoxyphenyl)-1-(2-(2-hydroxycyclopentylamino)-2-oxoethyl)-1H-pyrazol-4-yl)pyrazolo[1,5-a]pyrimidine-3-carboxamide | 134 | 510.1 |

TABLE 2-continued

| Ex | Structure | Name | Mthd | LCMS (ESI) m/z |
|---|---|---|---|---|
| 273 | 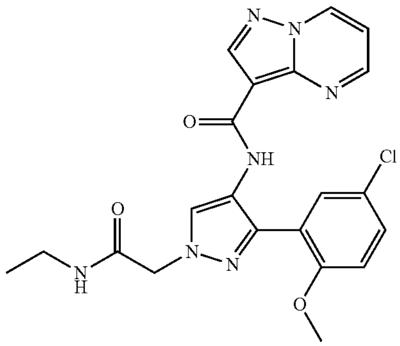 [SMILES: CCNC(=O)Cn1cc(NC(=O)c2cnn3cccnc23)c(-c2cc(Cl)ccc2OC)n1] | N-(3-(5-chloro-2-methoxyphenyl)-1-(2-(ethylamino)-2-oxoethyl)-1H-pyrazol-4-yl)pyrazolo[1,5-a]pyrimidine-3-carboxamide | 134 | 454.1 |
| 274 | 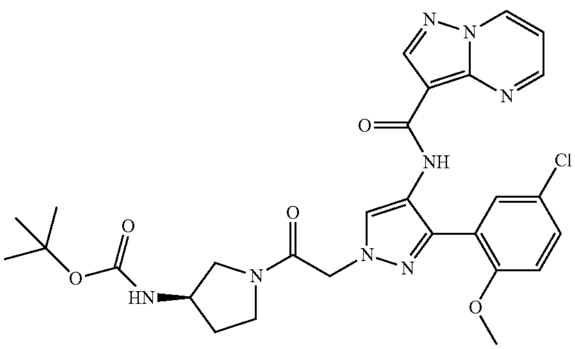 [SMILES: COc1ccc(Cl)cc1-c1nn(CC(=O)N2CC[C@@H](NC(=O)OC(C)(C)C)C2)cc1NC(=O)c1cnn2cccnc12] | (R)-tert-butyl 1-(2-(3-(5-chloro-2-methoxyphenyl)-4-(pyrazolo[1,5-a]pyrimidine-3-carboxamido)-1H-pyrazol-1-yl)acetyl)pyrrolidin-3-ylcarbamate | 134 | 595.2 |
| 275 | 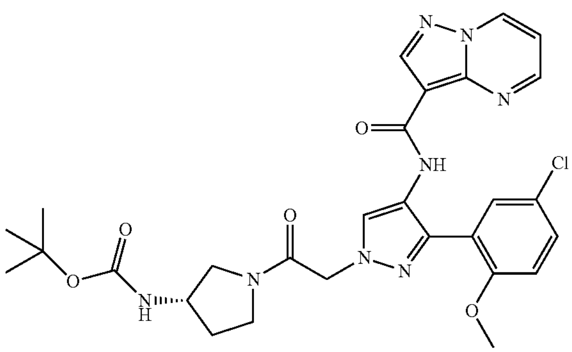 [SMILES: COc1ccc(Cl)cc1-c1nn(CC(=O)N2CC[C@H](NC(=O)OC(C)(C)C)C2)cc1NC(=O)c1cnn2cccnc12] | (S)-tert-butyl 1-(2-(3-(5-chloro-2-methoxyphenyl)-4-(pyrazolo[1,5-a]pyrimidine-3-carboxamido)-1H-pyrazol-1-yl)acetyl)pyrrolidin-3-ylcarbamate | 134 | 595.2 |
| 276 | 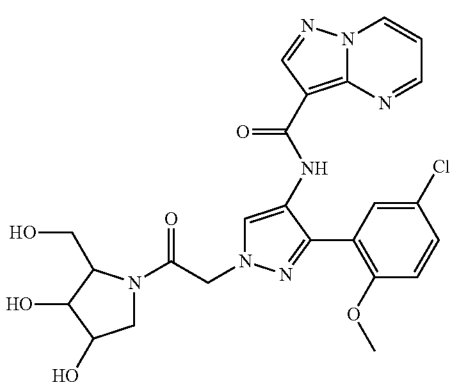 [SMILES: COc1ccc(Cl)cc1-c1nn(CC(=O)N2CC(O)C(O)C2CO)cc1NC(=O)c1cnn2cccnc12] | N-(3-(5-chloro-2-methoxyphenyl)-1-(2-(3,4-dihydroxy-2-(hydroxymethyl)pyrrolidin-1-yl)-2-oxoethyl)-1H-pyrazol-4-yl)pyrazolo[1,5-a]pyrimidine-3-carboxamide | 134 | 542.1 |

TABLE 2-continued

| Ex | Structure | Name | Mthd | LCMS (ESI) m/z |
|---|---|---|---|---|
| 277 | 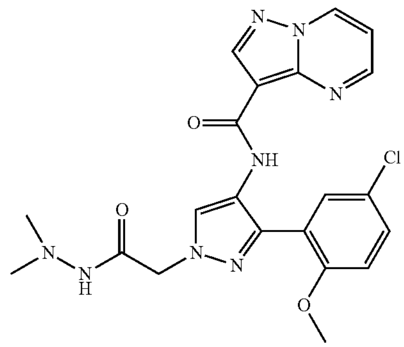 [SMILES: COc1ccc(Cl)cc1-c1nn(CC(=O)NN(C)C)cc1NC(=O)c1cnn2cccnc12] | N-(3-(5-chloro-2-methoxyphenyl)-1-(2-(2,2-dimethylhydrazinyl)-2-oxoethyl)-1H-pyrazol-4-yl)pyrazolo[1,5-a]pyrimidine-3-carboxamide | 134 | 469.1 |
| 278 | 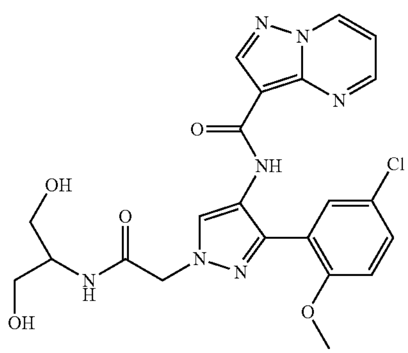 [SMILES: COc1ccc(Cl)cc1-c1nn(CC(=O)NC(CO)CO)cc1NC(=O)c1cnn2cccnc12] | N-(3-(5-chloro-2-methoxyphenyl)-1-(2-(1,3-dihydroxypropan-2-ylamino)-2-oxoethyl)-1H-pyrazol-4-yl)pyrazolo[1,5-a]pyrimidine-3-carboxamide | 134 | 500.1 |
| 279 | 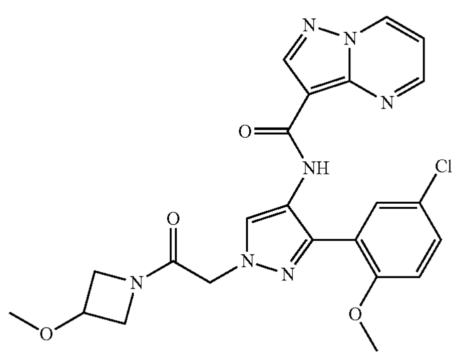 [SMILES: COc1ccc(Cl)cc1-c1nn(CC(=O)N2CC(OC)C2)cc1NC(=O)c1cnn2cccnc12] | N-(3-(5-chloro-2-methoxyphenyl)-1-(2-(3-methoxyazetidin-1-yl)-2-oxoethyl)-1H-pyrazol-4-yl)pyrazolo[1,5-a]pyrimidine-3-carboxamide | 134 | 496.2 |
| 280 | 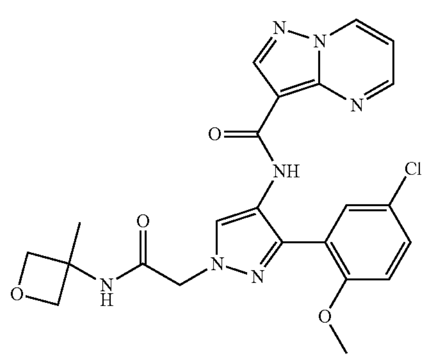 [SMILES: COc1ccc(Cl)cc1-c1nn(CC(=O)NC2(C)COC2)cc1NC(=O)c1cnn2cccnc12] | N-(3-(5-chloro-2-methoxyphenyl)-1-(2-(3-methyloxetan-3-ylamino)-2-oxoethyl)-1H-pyrazol-4-yl)pyrazolo[1,5-a]pyrimidine-3-carboxamide | 134 | 496.2 |

TABLE 2-continued

| Ex | Structure | Name | Mthd | LCMS (ESI) m/z |
|---|---|---|---|---|
| 281 | 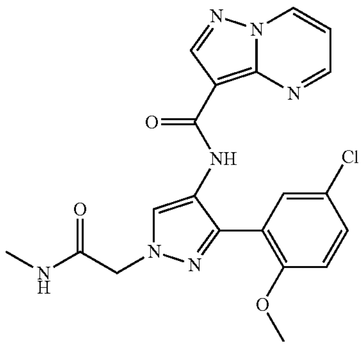 [SMILES: CNC(=O)Cn1cc(NC(=O)c2cnn3cccnc23)c(-c2cc(Cl)ccc2OC)n1] | N-(3-(5-chloro-2-methoxyphenyl)-1-(2-(methylamino)-2-oxoethyl)-1H-pyrazol-4-yl)pyrazolo[1,5-a]pyrimidine-3-carboxamide | 134 | 440.0 |
| 282 | 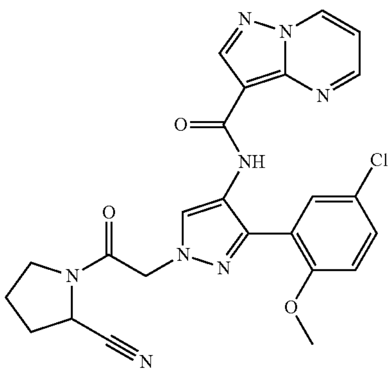 [SMILES: COc1ccc(Cl)cc1-c1nn(CC(=O)N2CCCC2C#N)cc1NC(=O)c1cnn2cccnc12] | N-(3-(5-chloro-2-methoxyphenyl)-1-(2-(2-cyanopyrrolidin-1-yl)-2-oxoethyl)-1H-pyrazol-4-yl)pyrazolo[1,5-a]pyrimidine-3-carboxamide | 134 | 505.1 |
| 283 | 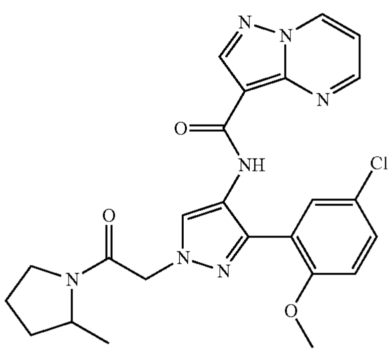 [SMILES: COc1ccc(Cl)cc1-c1nn(CC(=O)N2CCCC2C)cc1NC(=O)c1cnn2cccnc12] | N-(3-(5-chloro-2-methoxyphenyl)-1-(2-(2-methylpyrrolidin-1-yl)-2-oxoethyl)-1H-pyrazol-4-yl)pyrazolo[1,5-a]pyrimidine-3-carboxamide | 134 | 494.1 |
| 284 | 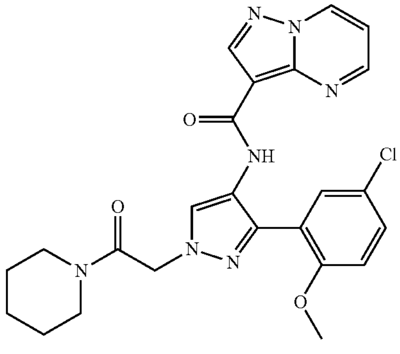 [SMILES: COc1ccc(Cl)cc1-c1nn(CC(=O)N2CCCCC2)cc1NC(=O)c1cnn2cccnc12] | N-(3-(5-chloro-2-methoxyphenyl)-1-(2-oxo-2-(piperidin-1-yl)ethyl)-1H-pyrazol-4-yl)pyrazolo[1,5-a]pyrimidine-3-carboxamide | 134 | 494.1 |

TABLE 2-continued

| Ex | Structure | Name | Mthd | LCMS (ESI) m/z |
|---|---|---|---|---|
| 285 | 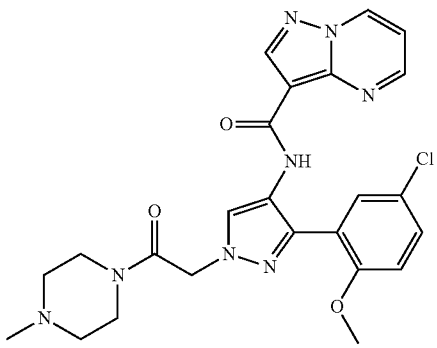 [SMILES: COc1ccc(Cl)cc1-c1nn(CC(=O)N2CCN(C)CC2)cc1NC(=O)c1cnn2cccnc12] | N-(3-(5-chloro-2-methoxyphenyl)-1-(2-(4-methylpiperazin-1-yl)-2-oxoethyl)-1H-pyrazol-4-yl)pyrazolo[1,5-a]pyrimidine-3-carboxamide | 134 | 509.2 |
| 286 | 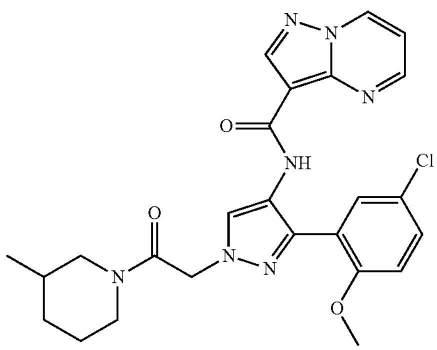 [SMILES: COc1ccc(Cl)cc1-c1nn(CC(=O)N2CCCC(C)C2)cc1NC(=O)c1cnn2cccnc12] | N-(3-(5-chloro-2-methoxyphenyl)-1-(2-(3-methylpiperidin-1-yl)-2-oxoethyl)-1H-pyrazol-4-yl)pyrazolo[1,5-a]pyrimidine-3-carboxamide | 134 | 508.1 |
| 287 | 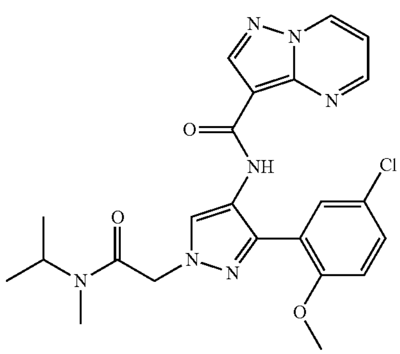 [SMILES: COc1ccc(Cl)cc1-c1nn(CC(=O)N(C)C(C)C)cc1NC(=O)c1cnn2cccnc12] | N-(3-(5-chloro-2-methoxyphenyl)-1-(2-(isopropyl(methyl)amino)-2-oxoethyl)-1H-pyrazol-4-yl)pyrazolo[1,5-a]pyrimidine-3-carboxamide | 134 | 482.1 |
| 288 | 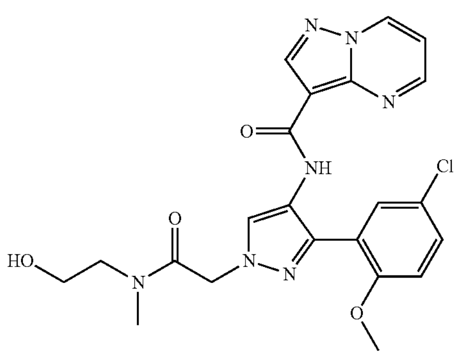 [SMILES: COc1ccc(Cl)cc1-c1nn(CC(=O)N(C)CCO)cc1NC(=O)c1cnn2cccnc12] | N-(3-(5-chloro-2-methoxyphenyl)-1-(2-((2-hydroxyethyl)(methyl)amino)-2-oxoethyl)-1H-pyrazol-4-yl)pyrazolo[1,5-a]pyrimidine-3-carboxamide | 134 | 484.1 |

TABLE 2-continued

| Ex | Structure | Name | Mthd | LCMS (ESI) m/z |
|---|---|---|---|---|
| 289 | 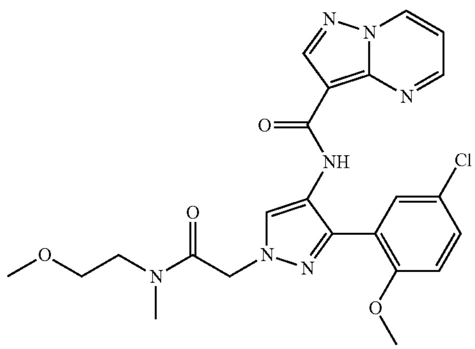 [SMILES: COCCN(C)C(=O)Cn1cc(NC(=O)c2cnn3cccnc23)c(-c2cc(Cl)ccc2OC)n1] | N-(3-(5-chloro-2-methoxyphenyl)-1-(2-((2-methoxyethyl)(methyl)amino)-2-oxoethyl)-1H-pyrazol-4-yl)pyrazolo[1,5-a]pyrimidine-3-carboxamide | 134 | 498.1 |
| 290 | 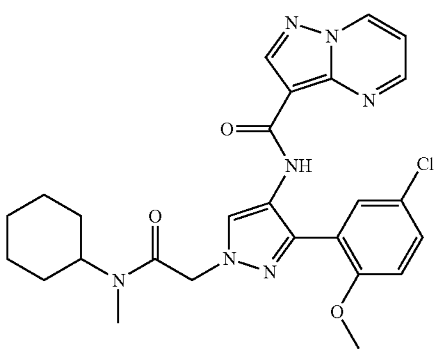 | N-(3-(5-chloro-2-methoxyphenyl)-1-(2-(cyclohexyl(methyl)amino)-2-oxoethyl)-1H-pyrazol-4-yl)pyrazolo[1,5-a]pyrimidine-3-carboxamide | 134 | 522.2 |
| 291 | 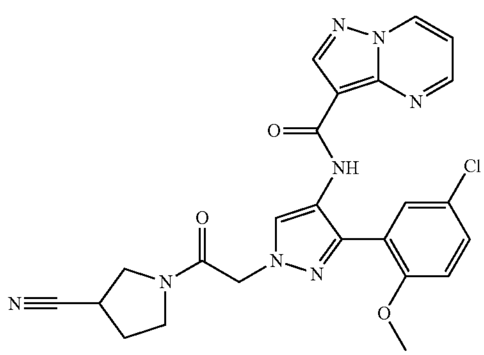 [SMILES: COc1ccc(Cl)cc1-c1nn(CC(=O)N2CCC(C#N)C2)cc1NC(=O)c1cnn2cccnc12] | N-(3-(5-chloro-2-methoxyphenyl)-1-(2-(3-cyanopyrrolidin-1-yl)-2-oxoethyl)-1H-pyrazol-4-yl)pyrazolo[1,5-a]pyrimidine-3-carboxamide | 134 | 505.1 |
| 292 | 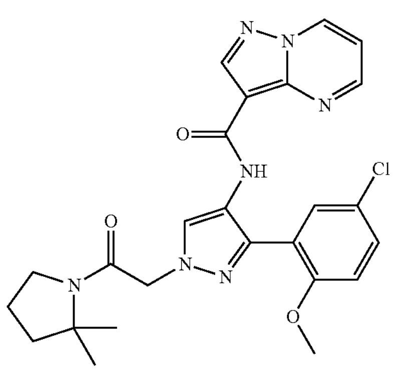 [SMILES: COc1ccc(Cl)cc1-c1nn(CC(=O)N2CCCC2(C)C)cc1NC(=O)c1cnn2cccnc12] | N-(3-(5-chloro-2-methoxyphenyl)-1-(2-(2,2-dimethylpyrrolidin-1-yl)-2-oxoethyl)-1H-pyrazol-4-yl)pyrazolo[1,5-a]pyrimidine-3-carboxamide | 134 | 508.1 |

TABLE 2-continued

| Ex | Structure | Name | Mthd | LCMS (ESI) m/z |
|---|---|---|---|---|
| 293 | 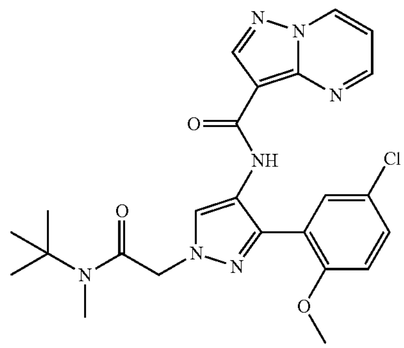 [SMILES: COc1ccc(Cl)cc1-c1nn(CC(=O)N(C)C(C)(C)C)cc1NC(=O)c1cnn2cccnc12] | N-(1-(2-(tert-butyl(methyl) amino)-2-oxoethyl)-3-(5-chloro-2-methoxyphenyl)-1H-pyrazol-4-yl)pyrazolo[1,5-a] pyrimidine-3-carboxamide | 134 | 496.1 |
| 294 | 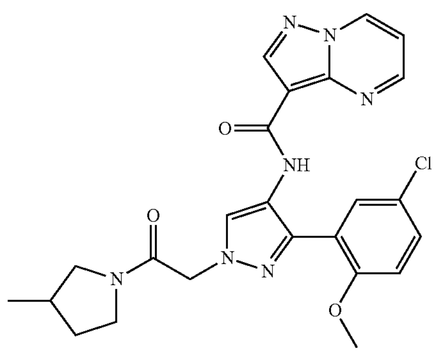 [SMILES: COc1ccc(Cl)cc1-c1nn(CC(=O)N2CCC(C)C2)cc1NC(=O)c1cnn2cccnc12] | N-(3-(5-chloro-2-methoxyphenyl)-1-(2-(3-methylpyrrolidin-1-yl)-2-oxoethyl)-1H-pyrazol-4-yl)pyrazolo[1,5-a]pyrimidine-3-carboxamide | 134 | 494.1 |
| 295 | 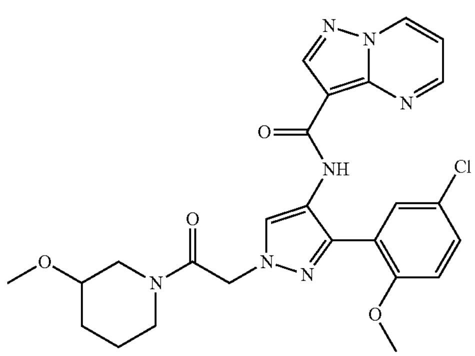 [SMILES: COc1ccc(Cl)cc1-c1nn(CC(=O)N2CCCC(OC)C2)cc1NC(=O)c1cnn2cccnc12] | N-(3-(5-chloro-2-methoxyphenyl)-1-(2-(3-methoxypiperidin-1-yl)-2-oxoethyl)-1H-pyrazol-4-yl)pyrazolo[1,5-a]pyrimidine-3-carboxamide | 134 | 524.1 |
| 296 | 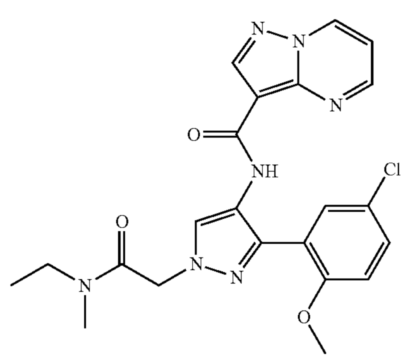 [SMILES: CCN(C)C(=O)Cn1cc(NC(=O)c2cnn3cccnc23)c(-c2cc(Cl)ccc2OC)n1] | N-(3-(5-chloro-2-methoxyphenyl)-1-(2-(ethyl(methyl)amino)-2-oxoethyl)-1H-pyrazol-4-yl)pyrazolo[1,5-a]pyrimidine-3-carboxamide | 134 | 468.1 |

TABLE 2-continued

| Ex | Structure | Name | Mthd | LCMS (ESI) m/z |
|---|---|---|---|---|
| 297 | 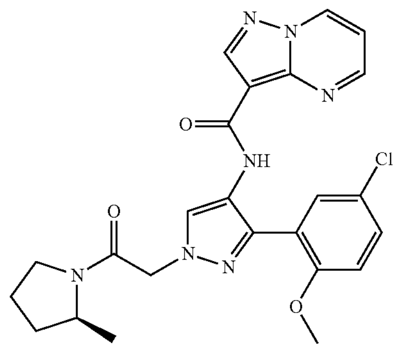 [SMILES: COc1ccc(Cl)cc1-c1nn(CC(=O)N2CCC[C@@H]2C)cc1NC(=O)c1cnn2cccnc12] | (S)-N-(3-(5-chloro-2-methoxyphenyl)-1-(2-(2-methylpyrrolidin-1-yl)-2-oxoethyl)-1H-pyrazol-4-yl)pyrazolo[1,5-a]pyrimidine-3-carboxamide | 134 | 494.1 |
| 298 | 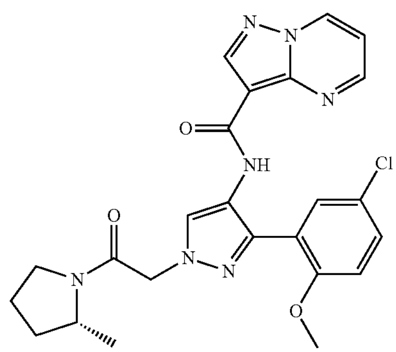 [SMILES: COc1ccc(Cl)cc1-c1nn(CC(=O)N2CCC[C@H]2C)cc1NC(=O)c1cnn2cccnc12] | (R)-N-(3-(5-chloro-2-methoxyphenyl)-1-(2-(2-methylpyrrolidin-1-yl)-2-oxoethyl)-1H-pyrazol-4-yl)pyrazolo[1,5-a]pyrimidine-3-carboxamide | 134 | 494.1 |
| 299 | 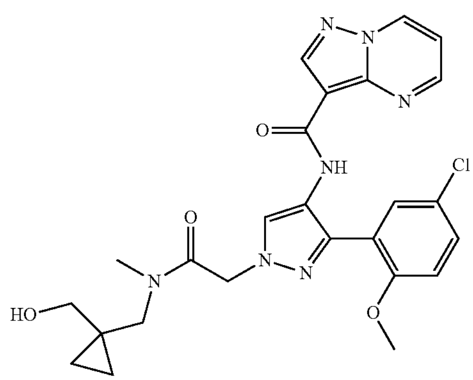 [SMILES: COc1ccc(Cl)cc1-c1nn(CC(=O)N(C)CC2(CO)CC2)cc1NC(=O)c1cnn2cccnc12] | N-(3-(5-chloro-2-methoxyphenyl)-1-(2-(((1-(hydroxymethyl)cyclopropyl)methyl)(methyl)amino)-2-oxoethyl)-1H-pyrazol-4-yl)pyrazolo[1,5-a]pyrimidine-3-carboxamide | 134 | 524.2 |
| 300 | 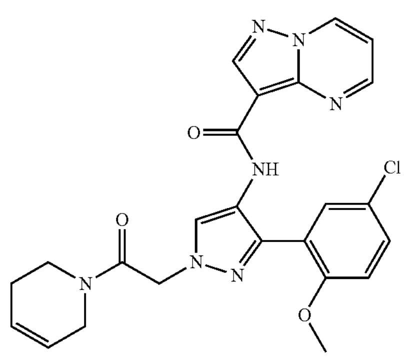 [SMILES: COc1ccc(Cl)cc1-c1nn(CC(=O)N2CC=CCC2)cc1NC(=O)c1cnn2cccnc12] | N-(3-(5-chloro-2-methoxyphenyl)-1-(2-(5,6-dihydropyridin-1(2H)-yl)-2-oxoethyl)-1H-pyrazol-4-yl)pyrazolo[1,5-a]pyrimidine-3-carboxamide | 134 | 492.1 |

TABLE 2-continued

| Ex | Structure | Name | Mthd | LCMS (ESI) m/z |
|---|---|---|---|---|
| 301 | 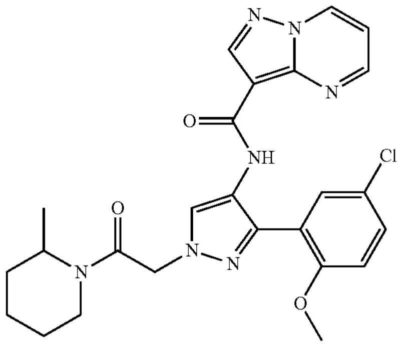 [SMILES: COc1ccc(Cl)cc1-c1nn(CC(=O)N2CCCCC2C)cc1NC(=O)c1cnn2cccnc12] | N-(3-(5-chloro-2-methoxyphenyl)-1-(2-(2-methylpiperidin-1-yl)-2-oxoethyl)-1H-pyrazol-4-yl)pyrazolo[1,5-a]pyrimidine-3-carboxamide | 134 | 508.1 |
| 302 | 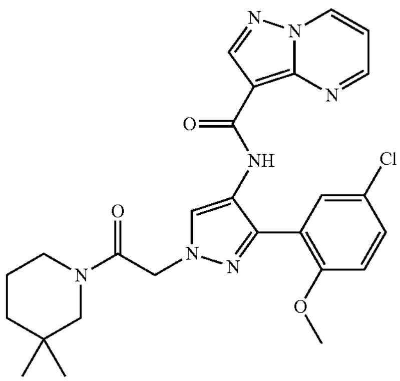 [SMILES: COc1ccc(Cl)cc1-c1nn(CC(=O)N2CCCC(C)(C)C2)cc1NC(=O)c1cnn2cccnc12] | N-(3-(5-chloro-2-methoxyphenyl)-1-(2-(3,3-dimethylpiperidin-1-yl)-2-oxoethyl)-1H-pyrazol-4-yl)pyrazolo[1,5-a]pyrimidine-3-carboxamide | 134 | 522.2 |
| 303 | 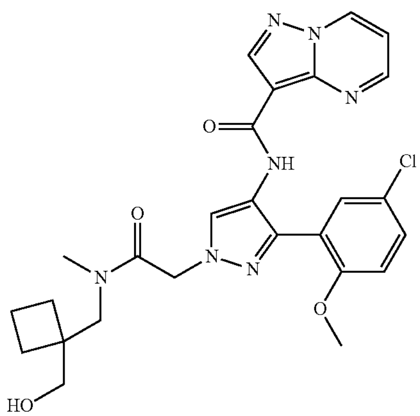 [SMILES: COc1ccc(Cl)cc1-c1nn(CC(=O)N(C)CC2(CO)CCC2)cc1NC(=O)c1cnn2cccnc12] | N-(3-(5-chloro-2-methoxyphenyl)-1-(2-(((1-(hydroxymethyl)cyclobutyl)methyl)(methyl)amino)-2-oxoethyl)-1H-pyrazol-4-yl)pyrazolo[1,5-a]pyrimidine-3-carboxamide | 134 | 538.2 |
| 304 | 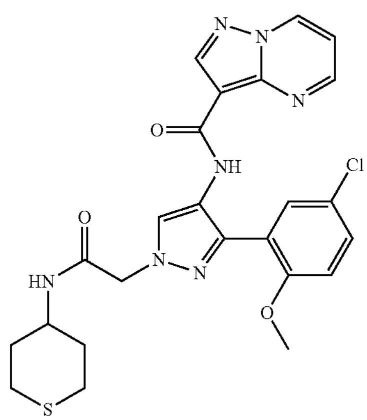 [SMILES: COc1ccc(Cl)cc1-c1nn(CC(=O)NC2CCSCC2)cc1NC(=O)c1cnn2cccnc12] | N-(3-(5-chloro-2-methoxyphenyl)-1-(2-oxo-2-(tetrahydro-2H-thiopyran-4-ylamino)ethyl)-1H-pyrazol-4-yl)pyrazolo[1,5-a]pyrimidine-3-carboxamide | 134 | 526.1 |

TABLE 2-continued

| Ex | Structure | Name | Mthd | LCMS (ESI) m/z |
|---|---|---|---|---|
| 305 | 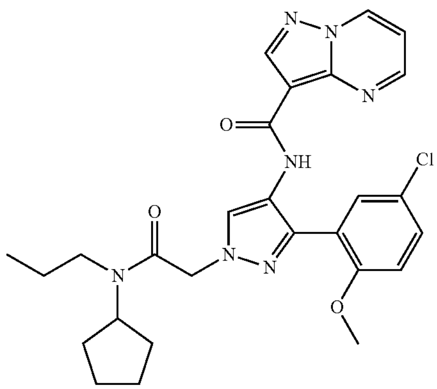 [SMILES: CCCN(C(=O)Cn1cc(NC(=O)c2cnn3cccnc23)c(-c2cc(Cl)ccc2OC)n1)C1CCCC1] | N-(3-(5-chloro-2-methoxyphenyl)-1-(2-(cyclopentyl(propyl)amino)-2-oxoethyl)-1H-pyrazol-4-yl)pyrazolo[1,5-a]pyrimidine-3-carboxamide | 134 | 536.2 |
| 306 | 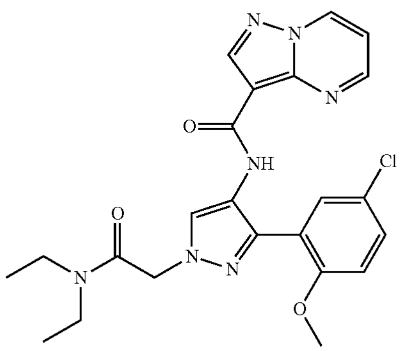 [SMILES: CCN(CC)C(=O)Cn1cc(NC(=O)c2cnn3cccnc23)c(-c2cc(Cl)ccc2OC)n1] | N-(3-(5-chloro-2-methoxyphenyl)-1-(2-(diethylamino)-2-oxoethyl)-1H-pyrazol-4-yl)pyrazolo[1,5-a]pyrimidine-3-carboxamide | 134 | 482.1 |
| 307 | 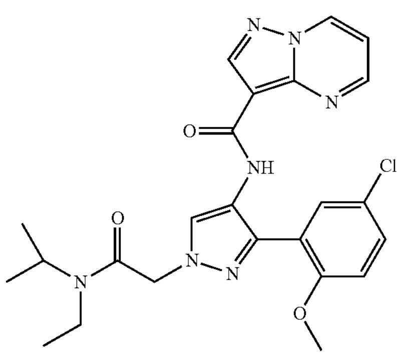 [SMILES: CCN(C(=O)Cn1cc(NC(=O)c2cnn3cccnc23)c(-c2cc(Cl)ccc2OC)n1)C(C)C] | N-(3-(5-chloro-2-methoxyphenyl)-1-(2-(ethyl(isopropyl)amino)-2-oxoethyl)-1H-pyrazol-4-yl)pyrazolo[1,5-a]pyrimidine-3-carboxamide | 134 | 496.2 |
| 308 | 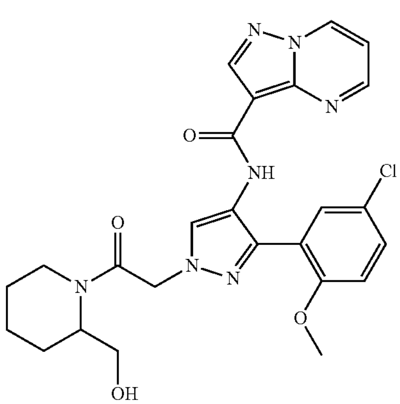 [SMILES: COc1ccc(Cl)cc1-c1nn(CC(=O)N2CCCCC2CO)cc1NC(=O)c1cnn2cccnc12] | N-(3-(5-chloro-2-methoxyphenyl)-1-(2-(2-(hydroxymethyl)piperidin-1-yl)-2-oxoethyl)-1H-pyrazol-4-yl)pyrazolo[1,5-a]pyrimidine-3-carboxamide | 134 | 524.2 |

TABLE 2-continued

| Ex | Structure | Name | Mthd | LCMS (ESI) m/z |
|---|---|---|---|---|
| 309 | 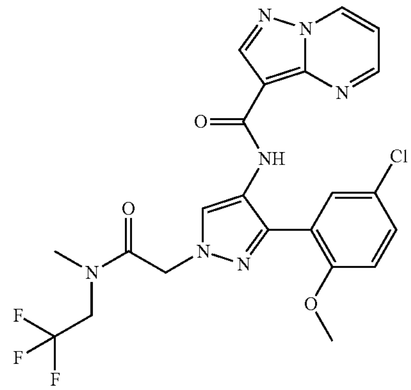 [SMILES: COc1ccc(Cl)cc1-c1nn(CC(=O)N(C)CC(F)(F)F)cc1NC(=O)c1cnn2cccnc12] | N-(3-(5-chloro-2-methoxyphenyl)-1-(2-(methyl(2,2-trifluoroethyl)amino)-2-oxoethyl)-1H-pyrazol-4-yl)pyrazolo[1,5-a]pyrimidine-3-carboxamide | 134 | 522.1 |
| 310 | 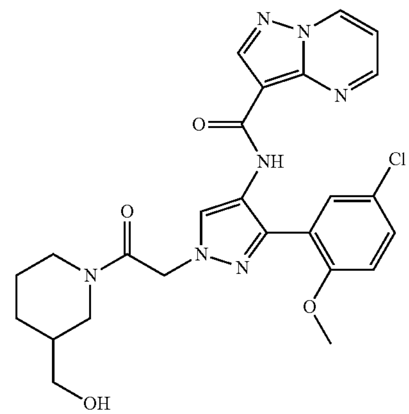 [SMILES: COc1ccc(Cl)cc1-c1nn(CC(=O)N2CCCC(CO)C2)cc1NC(=O)c1cnn2cccnc12] | N-(3-(5-chloro-2-methoxyphenyl)-1-(2-(3-(hydroxymethyl)piperidin-1-yl)-2-oxoethyl)-1H-pyrazol-4-yl)pyrazolo[1,5-a]pyrimidine-3-carboxamide | 134 | 524.2 |
| 311 | 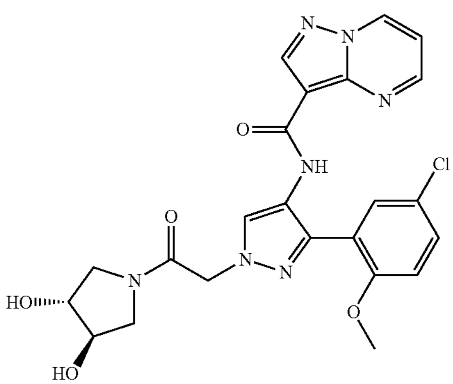 [SMILES: COc1ccc(Cl)cc1-c1nn(CC(=O)N2C[C@@H](O)[C@H](O)C2)cc1NC(=O)c1cnn2cccnc12] | N-(3-(5-chloro-2-methoxyphenyl)-1-(2-((3R,4R)-3,4-dihydroxypyrrolidin-1-yl)-2-oxoethyl)-1H-pyrazol-4-yl)pyrazolo[1,5-a]pyrimidine-3-carboxamide | 134 | 512.2 |
| 312 | 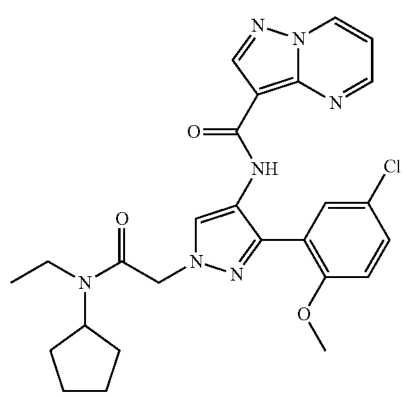 [SMILES: CCN(C(=O)Cn1cc(NC(=O)c2cnn3cccnc23)c(-c2cc(Cl)ccc2OC)n1)C1CCCC1] | N-(3-(5-chloro-2-methoxyphenyl)-1-(2-(cyclopentyl(ethyl)amino)-2-oxoethyl)-1H-pyrazol-4-yl)pyrazolo[1,5-a]pyrimidine-3-carboxamide | 134 | 522.2 |

TABLE 2-continued

| Ex | Structure | Name | Mthd | LCMS (ESI) m/z |
|---|---|---|---|---|
| 313 | 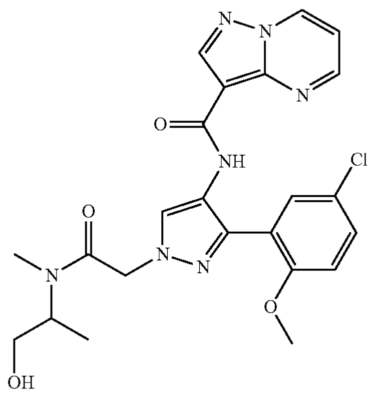 [SMILES: COc1ccc(Cl)cc1-c1nn(CC(=O)N(C)C(C)CO)cc1NC(=O)c1cnn2cccnc12] | N-(3-(5-chloro-2-methoxyphenyl)-1-(2-((1-hydroxypropan-2-yl)(methyl)amino)-2-oxoethyl)-1H-pyrazol-4-yl)pyrazolo[1,5-a]pyrimidine-3-carboxamide | 134 | 498.2 |
| 314 | 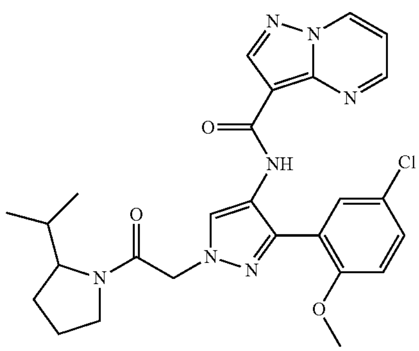 [SMILES: COc1ccc(Cl)cc1-c1nn(CC(=O)N2CCCC2C(C)C)cc1NC(=O)c1cnn2cccnc12] | N-(3-(5-chloro-2-methoxyphenyl)-1-(2-(2-isopropylpyrrolidin-1-yl)-2-oxoethyl)-1H-pyrazol-4-yl)pyrazolo[1,5-a]pyrimidine-3-carboxamide | 134 | 522.2 |
| 315 | 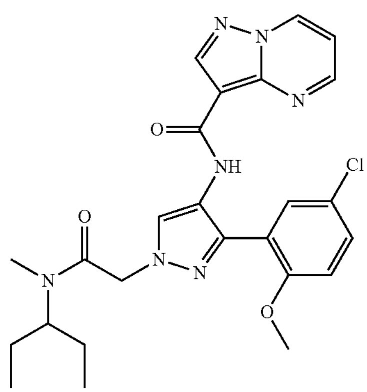 [SMILES: CCC(CC)N(C)C(=O)Cn1cc(NC(=O)c2cnn3cccnc23)c(-c2cc(Cl)ccc2OC)n1] | N-(3-(5-chloro-2-methoxyphenyl)-1-(2-(methyl(pentan-3-yl)amino)-2-oxoethyl)-1H-pyrazol-4-yl)pyrazolo[1,5-a]pyrimidine-3-carboxamide | 134 | 510.2 |
| 316 | 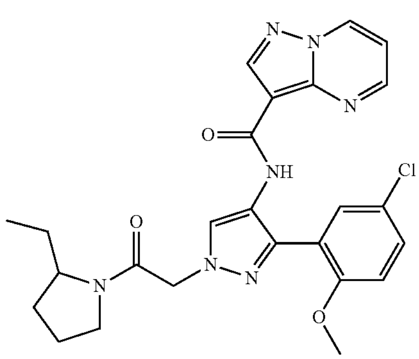 [SMILES: CCC1CCCN1C(=O)Cn1cc(NC(=O)c2cnn3cccnc23)c(-c2cc(Cl)ccc2OC)n1] | N-(3-(5-chloro-2-methoxyphenyl)-1-(2-(2-ethylpyrrolidin-1-yl)-2-oxoethyl)-1H-pyrazol-4-yl)pyrazolo[1,5-a]pyrimidine-3-carboxamide | 134 | 508.2 |

TABLE 2-continued

| Ex | Structure | Name | Mthd | LCMS (ESI) m/z |
|---|---|---|---|---|
| 317 | 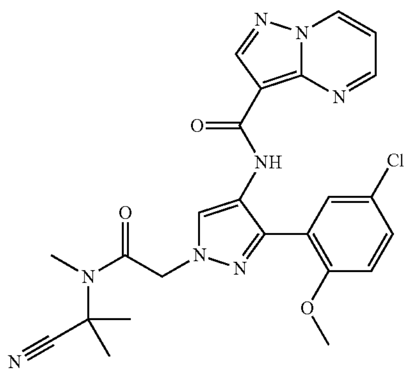 [SMILES: COc1ccc(Cl)cc1-c1nn(CC(=O)N(C)C(C)(C)C#N)cc1NC(=O)c1cnn2cccnc12] | N-(3-(5-chloro-2-methoxy-phenyl)-1-(2-((2-cyanopropan-2-yl)(methyl)amino)-2-oxoethyl)-1H-pyrazol-4-yl)pyrazolo[1,5-a]pyrimidine-3-carboxamide | 134 | 508.3 |
| 318 | 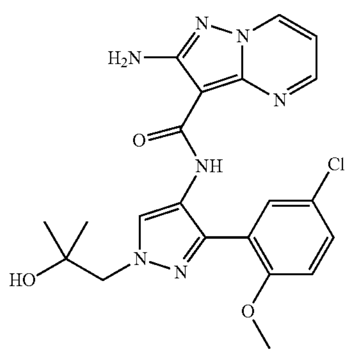 [SMILES: COc1ccc(Cl)cc1-c1nn(CC(C)(C)O)cc1NC(=O)c1c(N)nn2cccnc12] | 2-amino-N-(3-(5-chloro-2-methoxyphenyl)-1-(2-hydroxy-2-methylpropyl)-1H-pyrazol-4-yl)pyrazolo[1,5-a]pyrimidine-3-carboxamide | 27, 16 | 456.2 |
| 319 | 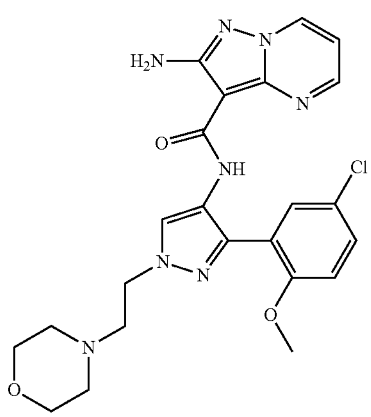 [SMILES: COc1ccc(Cl)cc1-c1nn(CCN2CCOCC2)cc1NC(=O)c1c(N)nn2cccnc12] | 2-amino-N-(3-(5-chloro-2-methoxyphenyl)-1-(2-morpholinoethyl)-1H-pyrazol-4-yl)pyrazolo[1,5-a]pyrimidine-3-carboxamide | 27, 14 | 497.2 |
| 320 | 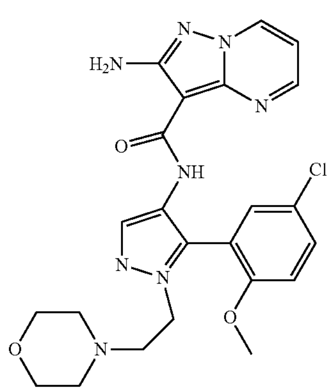 | 2-amino-N-(5-(5-chloro-2-methoxyphenyl)-1-(2-morpholinoethyl)-1H-pyrazol-4-yl)pyrazolo[1,5-a]pyrimidine-3-carboxamide | 27, 15 | 497.2 |

TABLE 2-continued

| Ex | Structure | Name | Mthd | LCMS (ESI) m/z |
|---|---|---|---|---|
| 321 | 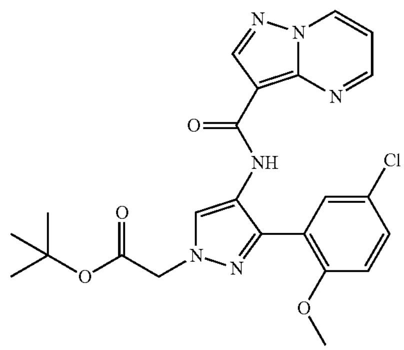 [SMILES: COc1ccc(Cl)cc1-c1nn(CC(=O)OC(C)(C)C)cc1NC(=O)c1cnn2cccnc12] | tert-butyl 2-(3-(5-chloro-2-methoxyphenyl)-4-(pyrazolo[1,5-a]pyrimidine-3-carboxamido)-1H-pyrazol-1-yl)acetate | 134 | 483.0 |
| 322 | 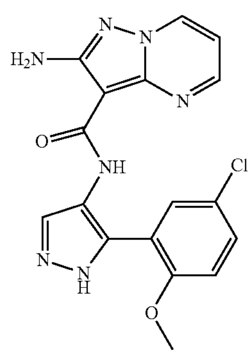 [SMILES: COc1ccc(Cl)cc1-c1[nH]ncc1NC(=O)c1c(N)nn2cccnc12] | 2-amino-N-(5-(5-chloro-2-methoxyphenyl)-1H-pyrazol-4-yl)pyrazolo[1,5-a]pyrimidine-3-carboxamide | 27 | 384.1 |
| 323 | 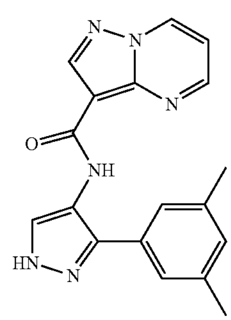 [SMILES: Cc1cc(C)cc(-c2n[nH]cc2NC(=O)c2cnn3cccnc23)c1] | N-(3-(3,5-dimethylphenyl)-1H-pyrazol-4-yl)pyrazolo[1,5-a]pyrimidine-3-carboxamide | 14 | 333.1 |
| 324 | 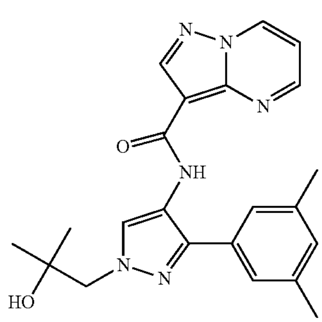 [SMILES: Cc1cc(C)cc(-c2nn(CC(C)(C)O)cc2NC(=O)c2cnn3cccnc23)c1] | N-(3-(3,5-dimethylphenyl)-1-(2-hydroxy-2-methylpropyl)-1H-pyrazol-4-yl)pyrazolo[1,5-a]pyrimidine-3-carboxamide | 14, 16 | 405.1 |

TABLE 2-continued

| Ex | Structure | Name | Mthd | LCMS (ESI) m/z |
|---|---|---|---|---|
| 325 | 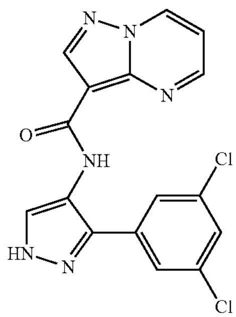 [SMILES: O=C(Nc1c[nH]nc1-c1cc(Cl)cc(Cl)c1)c1cnn2cccnc12] | N-(3-(3,5-dichlorophenyl)-1H-pyrazol-4-yl)pyrazolo[1,5-a]pyrimidine-3-carboxamide | 14 | 373.1 |
| 326 | 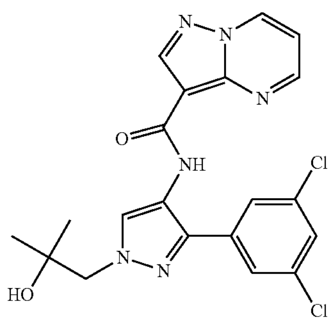 [SMILES: CC(C)(O)Cn1cc(NC(=O)c2cnn3cccnc23)c(-c2cc(Cl)cc(Cl)c2)n1] | N-(3-(3,5-dichlorophenyl)-1-(2-hydroxy-2-methylpropyl)-1H-pyrazol-4-yl)pyrazolo[1,5-a]pyrimidine-3-carboxamide | 14, 16 | 445.1 |
| 327 | 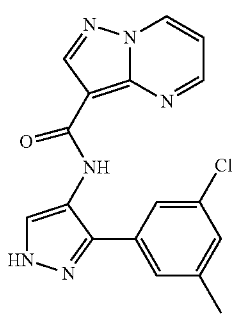 [SMILES: Cc1cc(Cl)cc(-c2n[nH]cc2NC(=O)c2cnn3cccnc23)c1] | N-(3-(3-chloro-5-methylphenyl)-1H-pyrazol-4-yl)pyrazolo[1,5-a]pyrimidine-3-carboxamide | 14 | 353.1 |
| 328 | 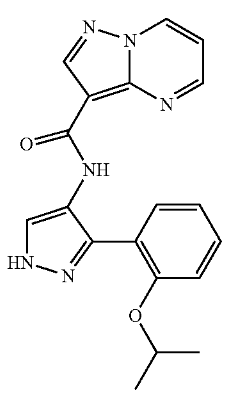 [SMILES: CC(C)Oc1ccccc1-c1n[nH]cc1NC(=O)c1cnn2cccnc12] | N-(3-(2-isopropoxyphenyl)-1H-pyrazol-4-yl)pyrazolo[1,5-a]pyrimidine-3-carboxamide | 14 | 363.1 |

TABLE 2-continued

| Ex | Structure | Name | Mthd | LCMS (ESI) m/z |
|---|---|---|---|---|
| 329 | 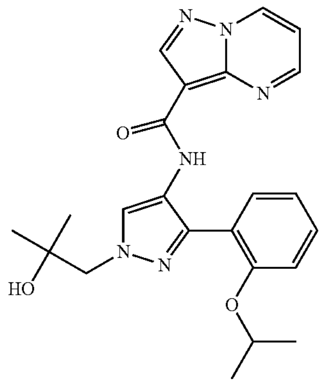 [SMILES: CC(C)Oc1ccccc1-c1nn(CC(C)(C)O)cc1NC(=O)c1cnn2cccnc12] | N-(1-(2-hydroxy-2-methylpropyl)-3-(2-isopropoxyphenyl)-1H-pyrazol-4-yl)pyrazolo[1,5-a]pyrimidine-3-carboxamide | 14, 16 | 435.1 |
| 330 | 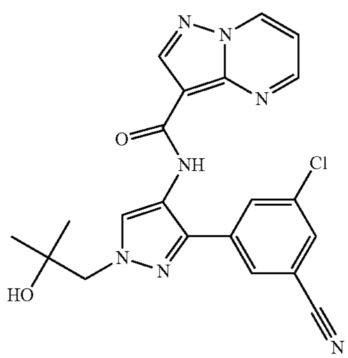 [SMILES: CC(C)(O)Cn1cc(NC(=O)c2cnn3cccnc23)c(-c2cc(Cl)cc(C#N)c2)n1] | N-(3-(3-chloro-5-cyanophenyl)-1-(2-hydroxy-2-methylpropyl)-1H-pyrazol-4-yl)pyrazolo[1,5-a]pyrimidine-3-carboxamide | 14, 16 | 436.1 |
| 331 | 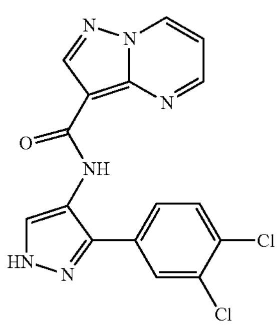 [SMILES: O=C(Nc1c[nH]nc1-c1ccc(Cl)c(Cl)c1)c1cnn2cccnc12] | N-(3-(3,4-dichlorophenyl)-1H-pyrazol-4-yl)pyrazolo[1,5-a]pyrimidine-3-carboxamide | 14 | 373.1 |
| 332 | 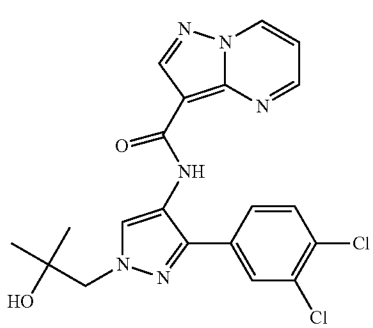 [SMILES: CC(C)(O)Cn1cc(NC(=O)c2cnn3cccnc23)c(-c2ccc(Cl)c(Cl)c2)n1] | N-(3-(3,4-dichlorophenyl)-1-(2-hydroxy-2-methylpropyl)-1H-pyrazol-4-yl)pyrazolo[1,5-a]pyrimidine-3-carboxamide | 14, 16 | 445.1 |

TABLE 2-continued

| Ex | Structure | Name | Mthd | LCMS (ESI) m/z |
|---|---|---|---|---|
| 333 | 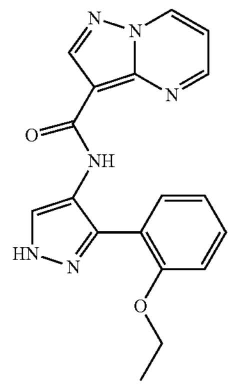 [SMILES: CCOc1ccccc1-c1n[nH]cc1NC(=O)c1cnn2cccnc12] | N-(3-(2-ethoxyphenyl)-1H-pyrazol-4-yl)pyrazolo[1,5-a]pyrimidine-3-carboxamide | 14 | 349.1 |
| 334 | 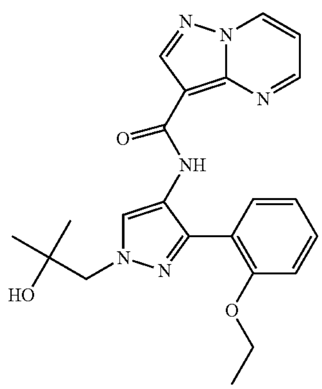 [SMILES: CCOc1ccccc1-c1nn(CC(C)(C)O)cc1NC(=O)c1cnn2cccnc12] | N-(3-(2-ethoxyphenyl)-1-(2-hydroxy-2-methylpropyl)-1H-pyrazol-4-yl)pyrazolo[1,5-a]pyrimidine-3-carboxamide | 14, 16 | 421.1 |
| 335 | 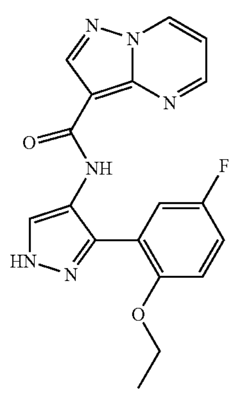 [SMILES: CCOc1ccc(F)cc1-c1n[nH]cc1NC(=O)c1cnn2cccnc12] | N-(3-(2-ethoxy-5-fluorophenyl)-1H-pyrazol-4-yl)pyrazolo[1,5-a]pyrimidine-3-carboxamide | 14 | 367.1 |
| 336 | 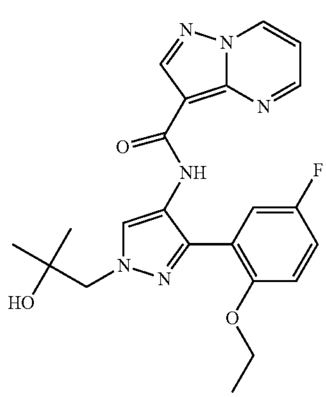 [SMILES: CCOc1ccc(F)cc1-c1nn(CC(C)(C)O)cc1NC(=O)c1cnn2cccnc12] | N-(3-(2-ethoxy-5-fluorophenyl)-1-(2-hydroxy-2-methylpropyl)-1H-pyrazol-4-yl)pyrazolo[1,5-a]pyrimidine-3-carboxamide | 14, 16 | 439.1 |

TABLE 2-continued

| Ex | Structure | Name | Mthd | LCMS (ESI) m/z |
|---|---|---|---|---|
| 337 | 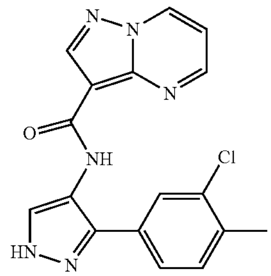 [SMILES: Cc1ccc(-c2n[nH]cc2NC(=O)c2cnn3cccnc23)cc1Cl] | N-(3-(3-chloro-4-methylphenyl)-1H-pyrazol-4-yl)pyrazolo[1,5-a]pyrimidine-3-carboxamide | 14 | 353.1 |
| 338 | 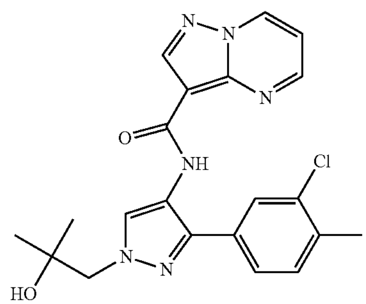 [SMILES: Cc1ccc(-c2nn(CC(C)(C)O)cc2NC(=O)c2cnn3cccnc23)cc1Cl] | N-(3-(3-chloro-4-methylphenyl)-1-(2-hydroxy-2-methylpropyl)-1H-pyrazol-4-yl)pyrazolo[1,5-a]pyrimidine-3-carboxamide | 14, 16 | 425.1 |
| 339 | 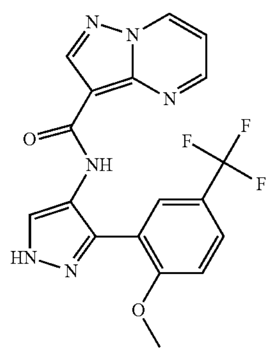 [SMILES: COc1ccc(C(F)(F)F)cc1-c1n[nH]cc1NC(=O)c1cnn2cccnc12] | N-(3-(2-methoxy-5-(trifluoromethyl)phenyl)-1H-pyrazol-4-yl)pyrazolo[1,5-a]pyrimidine-3-carboxamide | 14 | 403.1 |
| 340 | 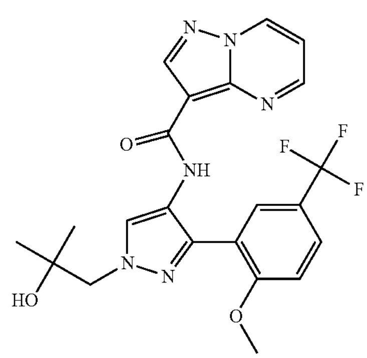 [SMILES: COc1ccc(C(F)(F)F)cc1-c1nn(CC(C)(C)O)cc1NC(=O)c1cnn2cccnc12] | N-(1-(2-hydroxy-2-methylpropyl)-3-(2-methoxy-5-(trifluoromethyl)phenyl)-1H-pyrazol-4-yl)pyrazolo[1,5-a]pyrimidine-3-carboxamide | 14, 16 | 475.1 |

TABLE 2-continued

| Ex | Structure | Name | Mthd | LCMS (ESI) m/z |
|---|---|---|---|---|
| 341 | 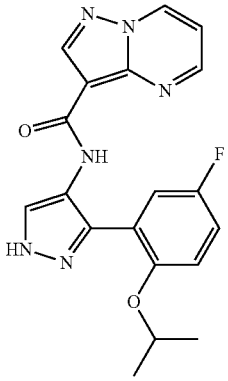 [SMILES: CC(C)Oc1ccc(F)cc1-c1n[nH]cc1NC(=O)c1cnn2cccnc12] | N-(3-(5-fluoro-2-isopropoxyphenyl)-1H-pyrazol-4-yl)pyrazolo[1,5-a]pyrimidine-3-carboxamide | 14 | 381.1 |
| 342 | 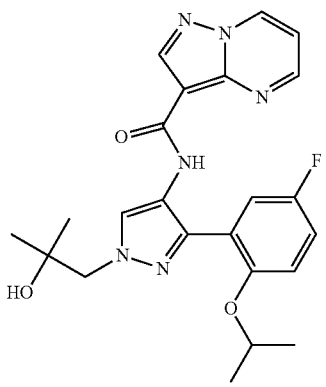 [SMILES: CC(C)Oc1ccc(F)cc1-c1nn(CC(C)(C)O)cc1NC(=O)c1cnn2cccnc12] | N-(3-(5-fluoro-2-isopropoxyphenyl)-1-(2-hydroxy-2-methylpropyl)-1H-pyrazol-4-yl)pyrazolo[1,5-a]pyrimidine-3-carboxamide | 14, 16 | 453.1 |
| 343 | 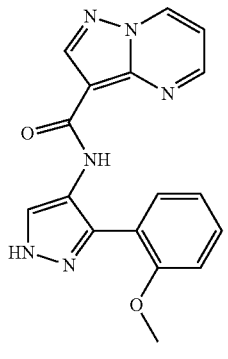 [SMILES: COc1ccccc1-c1n[nH]cc1NC(=O)c1cnn2cccnc12] | N-(3-(2-methoxyphenyl)-1H-pyrazol-4-yl)pyrazolo[1,5-a]pyrimidine-3-carboxamide | 14 | 335.1 |
| 344 | 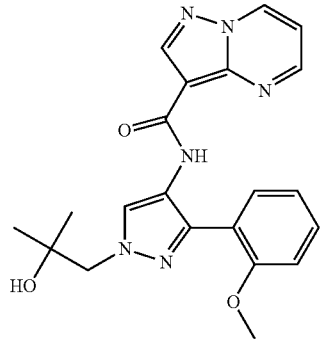 [SMILES: COc1ccccc1-c1nn(CC(C)(C)O)cc1NC(=O)c1cnn2cccnc12] | N-(1-(2-hydroxy-2-methyl-propyl)-3-(2-methoxyphenyl)-1H-pyrazol-4-yl)pyrazolo[1,5-a]pyrimidine-3-carboxamide | 14, 16 | 407.1 |

TABLE 2-continued

| Ex | Name | Mthd | LCMS (ESI) m/z |
|---|---|---|---|
| 345 | N-(3-(4-fluoro-2-methoxyphenyl)-1H-pyrazol-4-yl)pyrazolo[1,5-a]pyrimidine-3-carboxamide | 14 | 353.1 |
| 346 | N-(3-(4-fluoro-2-methoxy-phenyl)-1-(2-hydroxy-2-methyl-propyl)-1H-pyrazol-4-yl)pyrazolo[1,5-a]pyrimidine-3-carboxamide | 14, 16 | 425.1 |
| 347 | N-(3-(5-cyano-2-methoxyphenyl)-1-(cyanomethyl)-1H-pyrazol-4-yl)pyrazolo[1,5-a]pyrimidine-3-carboxamide | 147, 14 | 399.1 |
| 348 | N-(3-(2-(difluoromethoxy)phenyl)-1H-pyrazol-4-yl)pyrazolo[1,5-a]pyrimidine-3-carboxamide | 14 | 371.1 |

TABLE 2-continued

| Ex | Structure | Name | Mthd | LCMS (ESI) m/z |
|---|---|---|---|---|
| 349 | 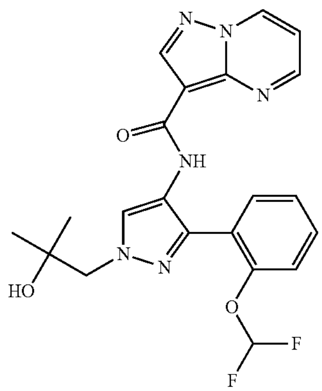 [SMILES: CC(C)(O)Cn1cc(NC(=O)c2cnn3cccnc23)c(-c2ccccc2OC(F)F)n1] | N-(3-(2-(difluoromethoxy) phenyl)-1-(2-hydroxy-2-methylpropyl)-1H-pyrazol-4-yl)pyrazolo[1,5-a]pyrimidine-3-carboxamide | 18, 16 | 443.1 |
| 350 | 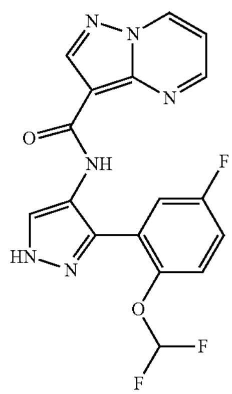 [SMILES: O=C(Nc1c[nH]nc1-c1cc(F)ccc1OC(F)F)c1cnn2cccnc12] | N-(3-(2-(difluoromethoxy)-5-fluorophenyl)-1H-pyrazol-4-yl)pyrazolo[1,5-a]pyrimidine-3-carboxamide | 18 | 389.1 |
| 351 | 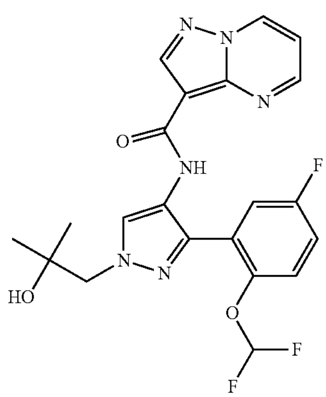 [SMILES: CC(C)(O)Cn1cc(NC(=O)c2cnn3cccnc23)c(-c2cc(F)ccc2OC(F)F)n1] | N-(3-(2-(difluoromethoxy)-5-fluorophenyl)-1-(2-hydroxy-2-methylpropyl)-1H-pyrazol-4-yl)pyrazolo[1,5-a]pyrimidine-3-carboxamide | 18, 26 | 461.1 |
| 352 | 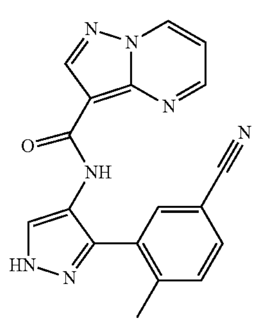 [SMILES: Cc1ccc(C#N)cc1-c1n[nH]cc1NC(=O)c1cnn2cccnc12] | N-(3-(5-cyano-2-methylphenyl)-1H-pyrazol-4-yl)pyrazolo[1,5-a]pyrimidine-3-carboxamide | 147 | 344.1 |

TABLE 2-continued

| Ex | Structure | Name | Mthd | LCMS (ESI) m/z |
|---|---|---|---|---|
| 353 | 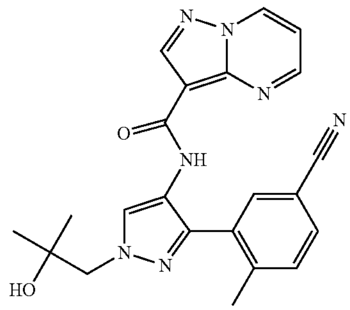 [SMILES: Cc1ccc(C#N)cc1-c1nn(CC(C)(C)O)cc1NC(=O)c1cnn2cccnc12] | N-(3-(5-cyano-2-methylphenyl)-1-(2-hydroxy-2-methylpropyl)-1H-pyrazol-4-yl)pyrazolo[1,5-a]pyrimidine-3-carboxamide | 147, 16 | 416.1 |
| 354 | 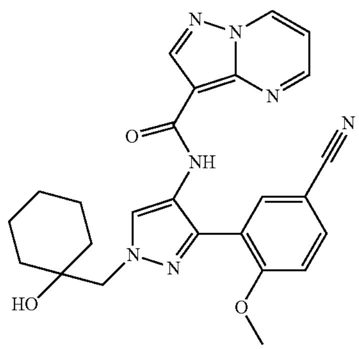 [SMILES: COc1ccc(C#N)cc1-c1nn(CC2(O)CCCCC2)cc1NC(=O)c1cnn2cccnc12] | N-(3-(5-cyano-2-methoxyphenyl)-1-((1-hydroxycyclohexyl)methyl)-1H-pyrazol-4-yl)pyrazolo[1,5-a]pyrimidine-3-carboxamide | 147, 16 | 472.1 |
| 355 | 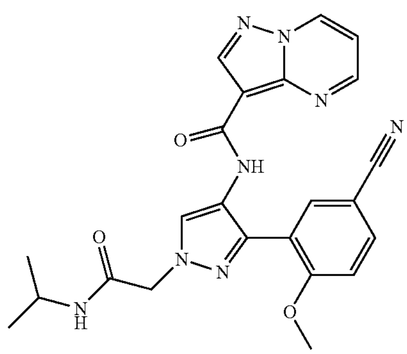 [SMILES: COc1ccc(C#N)cc1-c1nn(CC(=O)NC(C)C)cc1NC(=O)c1cnn2cccnc12] | N-(3-(5-cyano-2-methoxyphenyl)-1-(2-(isopropylamino)-2-oxoethyl)-1H-pyrazol-4-yl)pyrazolo[1,5-a]pyrimidine-3-carboxamide | 147, 134 | 459.1 |
| 356 | 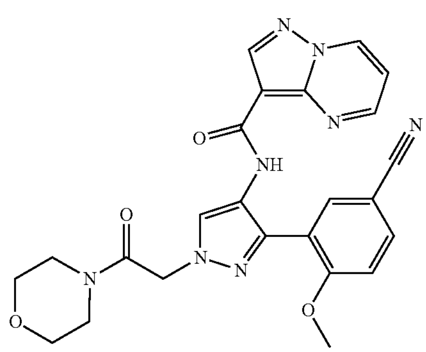 [SMILES: COc1ccc(C#N)cc1-c1nn(CC(=O)N2CCOCC2)cc1NC(=O)c1cnn2cccnc12] | N-(3-(5-cyano-2-methoxyphenyl)-1-(2-morpholino-2-oxoethyl)-1H-pyrazol-4-yl)pyrazolo[1,5-a]pyrimidine-3-carboxamide | 147, 134 | 487 |

TABLE 2-continued

| Ex | Structure | Name | Mthd | LCMS (ESI) m/z |
|---|---|---|---|---|
| 357 | 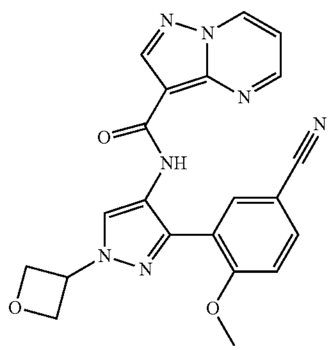 [SMILES: COc1ccc(C#N)cc1-c1nn(C2COC2)cc1NC(=O)c1cnn2cccnc12] | N-(3-(5-cyano-2-methoxyphenyl)-1-(oxetan-3-yl)-1H-pyrazol-4-yl)pyrazolo[1,5-a]pyrimidine-3-carboxamide | 147, 14 | 416.1 |
| 358 | 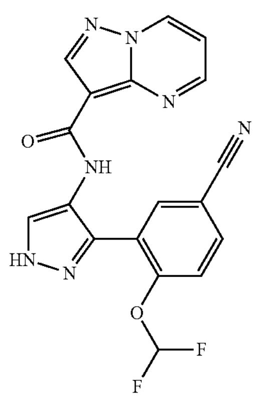 [SMILES: N#Cc1ccc(OC(F)F)c(-c2n[nH]cc2NC(=O)c2cnn3cccnc23)c1] | N-(3-(5-cyano-2-(difluoromethoxy)phenyl)-1H-pyrazol-4-yl)pyrazolo[1,5-a]pyrimidine-3-carboxamide | 147, 18 | 396.1 |
| 359 | 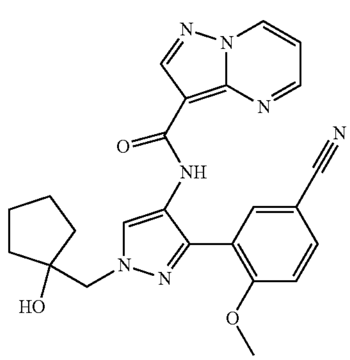 [SMILES: COc1ccc(C#N)cc1-c1nn(CC2(O)CCCC2)cc1NC(=O)c1cnn2cccnc12] | N-(3-(5-cyano-2-methoxyphenyl)-1-((1-hydroxycyclopentyl)methyl)-1H-pyrazol-4-yl)pyrazolo[1,5-a]pyrimidine-3-carboxamide | 147, 24 | 458.1 |
| 360 | 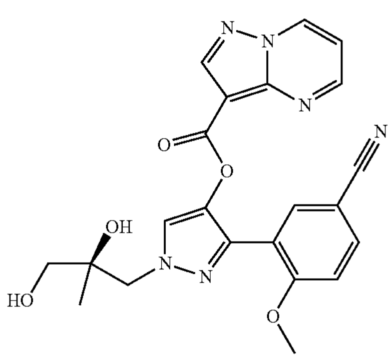 [SMILES: COc1ccc(C#N)cc1-c1nn(C[C@@](C)(O)CO)cc1OC(=O)c1cnn2cccnc12] | (R)-3-(5-cyano-2-methoxyphenyl)-1-(2,3-dihydroxy-2-methylpropyl)-1H-pyrazol-4-yl pyrazolo[1,5-a]pyrimidine-3-carboxylate | 147, 16, 22 | 449.1 |

TABLE 2-continued

| Ex | Structure | Name | Mthd | LCMS (ESI) m/z |
|---|---|---|---|---|
| 361 | 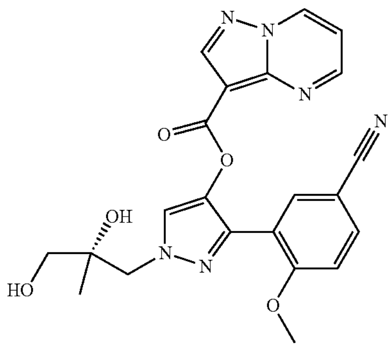 [SMILES: COc1ccc(C#N)cc1-c1nn(C[C@](C)(O)CO)cc1OC(=O)c1cnn2cccnc12] | (S)-3-(5-cyano-2-methoxyphenyl)-1-(2,3-dihydroxy-2-methylpropyl)-1H-pyrazol-4-yl pyrazolo[1,5-a]pyrimidine-3-carboxylate | 147, 16, 22 | 449.1 |
| 362 | 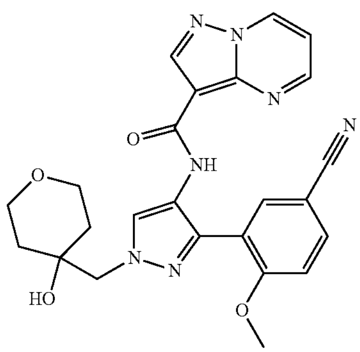 [SMILES: COc1ccc(C#N)cc1-c1nn(CC2(O)CCOCC2)cc1NC(=O)c1cnn2cccnc12] | N-(3-(5-cyano-2-methoxyphenyl)-1-((4-hydroxytetrahydro-2H-pyran-4-yl)methyl)-1H-pyrazol-4-yl)pyrazolo[1,5-a]pyrimidine-3-carboxamide | 147, 16 | 474.1 |
| 363 | 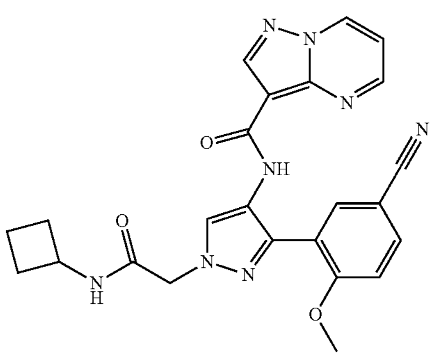 [SMILES: COc1ccc(C#N)cc1-c1nn(CC(=O)NC2CCC2)cc1NC(=O)c1cnn2cccnc12] | N-(3-(5-cyano-2-methoxyphenyl)-1-(2-(cyclobutylamino)-2-oxoethyl)-1H-pyrazol-4-yl)pyrazolo[1,5-a]pyrimidine-3-carboxamide | 147, 134 | 471.1 |
| 364 | 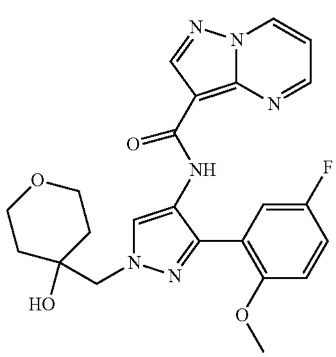 [SMILES: COc1ccc(F)cc1-c1nn(CC2(O)CCOCC2)cc1NC(=O)c1cnn2cccnc12] | N-(3-(5-fluoro-2-methoxyphenyl)-1-((4-hydroxytetrahydro-2H-pyran-4-yl)methyl)-1H-pyrazol-4-yl)pyrazolo[1,5-a]pyrimidine-3-carboxamide | 149, 16 | 467.1 |

TABLE 2-continued

| Ex | Structure | Name | Mthd | LCMS (ESI) m/z |
|---|---|---|---|---|
| 365 | 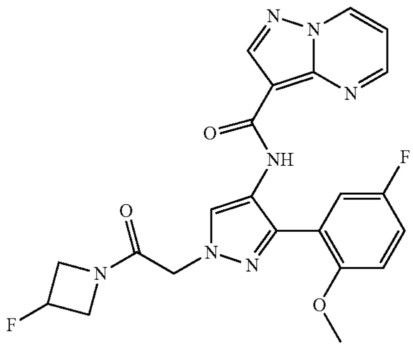 [SMILES: COc1ccc(F)cc1-c1nn(CC(=O)N2CC(F)C2)cc1NC(=O)c1cnn2cccnc12] | N-(3-(5-fluoro-2-methoxyphenyl)-1-(2-(3-fluoroazetidin-1-yl)-2-oxoethyl)-1H-pyrazol-4-yl)pyrazolo[1,5-a]pyrimidine-3-carboxamide | 149, 134 | 468.1 |
| 366 | 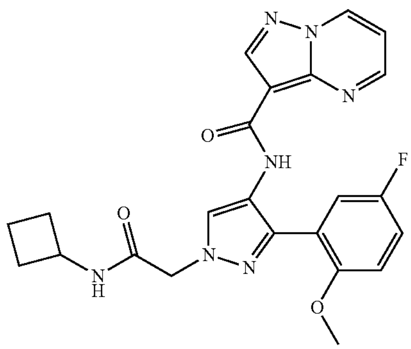 [SMILES: COc1ccc(F)cc1-c1nn(CC(=O)NC2CCC2)cc1NC(=O)c1cnn2cccnc12] | N-(1-(2-(cyclobutylamino)-2-oxoethyl)-3-(5-fluoro-2-methoxyphenyl)-1H-pyrazol-4-yl)pyrazolo[1,5-a]pyrimidine-3-carboxamide | 149, 134 | 464.1 |
| 367 | 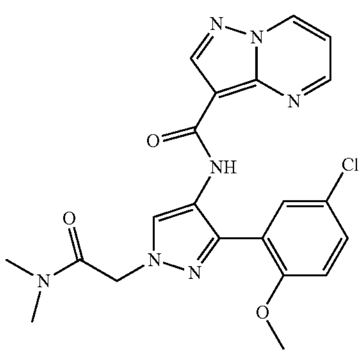 [SMILES: COc1ccc(Cl)cc1-c1nn(CC(=O)N(C)C)cc1NC(=O)c1cnn2cccnc12] | N-(3-(5-chloro-2-methoxyphenyl)-1-(2-(dimethylamino)-2-oxoethyl)-1H-pyrazol-4-yl)pyrazolo[1,5-a]pyrimidine-3-carboxamide | 14, 134 | 454.1 |
| 368 | 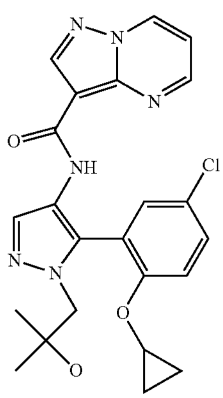 [SMILES: CC(C)(O)Cn1ncc(NC(=O)c2cnn3cccnc23)c1-c1cc(Cl)ccc1OC1CC1] | N-(5-(5-chloro-2-cyclopropoxyphenyl)-1-(2-hydroxy-2-methylpropyl)-1H-pyrazol-4-yl)pyrazolo[1,5-a]pyrimidine-3-carboxamide | 151, 15 | 467.1 |

TABLE 2-continued

| Ex | Structure | Name | Mthd | LCMS (ESI) m/z |
|---|---|---|---|---|
| 369 | 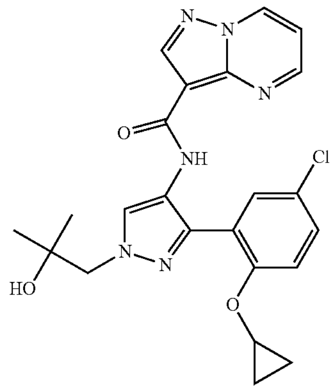 [SMILES: CC(C)(O)Cn1cc(NC(=O)c2cnn3cccnc23)c(-c2cc(Cl)ccc2OC2CC2)n1] | N-(3-(5-chloro-2-cyclopropoxyphenyl)-1-(2-hydroxy-2-methylpropyl)-1H-pyrazol-4-yl)pyrazolo[1,5-a]pyrimidine-3-carboxamide | 151, 16 | 467.1 |
| 370 | 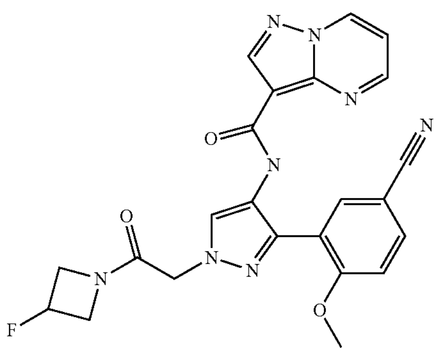 [SMILES: COc1ccc(C#N)cc1-c1nn(CC(=O)N2CC(F)C2)cc1NC(=O)c1cnn2cccnc12] | N-(3-(5-cyano-2-methoxyphenyl)-1-(2-(3-fluoroazetidin-1-yl)-2-oxoethyl)-1H-pyrazol-4-yl)pyrazolo[1,5-a]pyrimidine-3-carboxamide | 147, 134 | 475.1 |
| 371 | 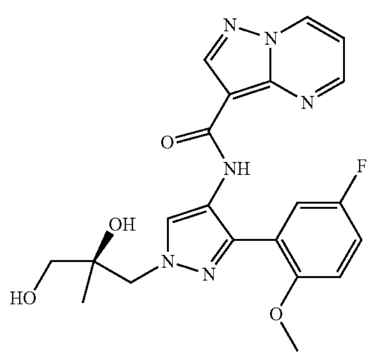 [SMILES: COc1ccc(F)cc1-c1nn(C[C@@](C)(O)CO)cc1NC(=O)c1cnn2cccnc12] | (R)-N-(1-(2,3-dihydroxy-2-methylpropyl)-3-(5-fluoro-2-methoxyphenyl)-1H-pyrazol-4-yl)pyrazolo[1,5-a]pyrimidine-3-carboxamide | 149, 16, 22 | 441.1 |
| 372 | 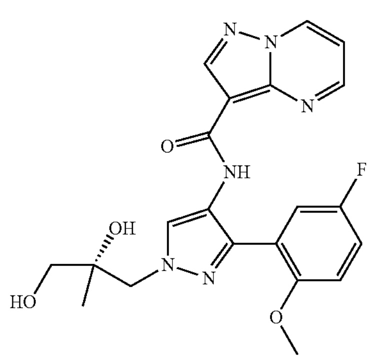 [SMILES: COc1ccc(F)cc1-c1nn(C[C@](C)(O)CO)cc1NC(=O)c1cnn2cccnc12] | (S)-N-(1-(2,3-dihydroxy-2-methylpropyl)-3-(5-fluoro-2-methoxyphenyl)-1H-pyrazol-4-yl)pyrazolo[1,5-a]pyrimidine-3-carboxamide | 149, 16, 22 | 441.1 |

TABLE 2-continued

| Ex | Structure | Name | Mthd | LCMS (ESI) m/z |
|---|---|---|---|---|
| 373 | 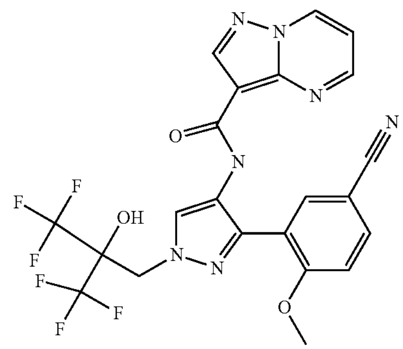 [SMILES: COc1ccc(C#N)cc1-c1nn(CC(O)(C(F)(F)F)C(F)(F)F)cc1NC(=O)c1cnn2cccnc12] | N-(3-(5-cyano-2-methoxyphenyl)-1-(3,3,3-trifluoro-2-hydroxy-2-(trifluoromethyl)propyl)-1H-pyrazol-4-yl)pyrazolo[1,5-a]pyrimidine-3-carboxamide | 147, 16 | 540.1 |
| 374 | 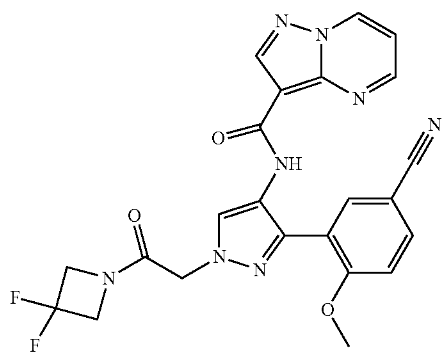 [SMILES: COc1ccc(C#N)cc1-c1nn(CC(=O)N2CC(F)(F)C2)cc1NC(=O)c1cnn2cccnc12] | N-(3-(5-cyano-2-methoxyphenyl)-1-(2-(3,3-difluoroazetidin-1-yl)-2-oxoethyl)-1H-pyrazol-4-yl)pyrazolo[1,5-a]pyrimidine-3-carboxamide | 147, 134 | 493.1 |
| 375 | 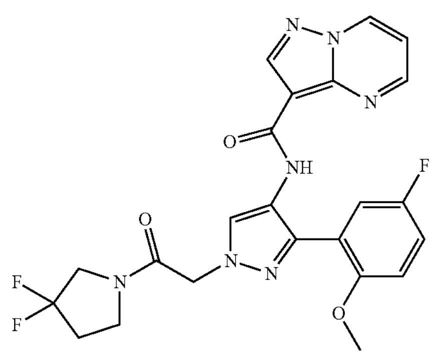 [SMILES: COc1ccc(F)cc1-c1nn(CC(=O)N2CCC(F)(F)C2)cc1NC(=O)c1cnn2cccnc12] | N-(1-(2-(3,3-difluoropyrrolidin-1-yl)-2-oxoethyl)-3-(5-fluoro-2-methoxyphenyl)-1H-pyrazol-4-yl)pyrazolo[1,5-a]pyrimidine-3-carboxamide | 14, 134 | 500.1 |
| 376 | 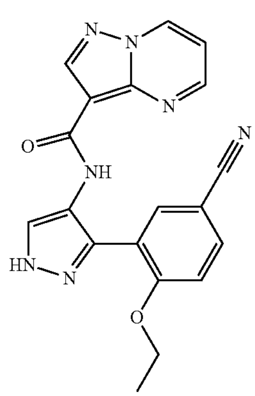 [SMILES: CCOc1ccc(C#N)cc1-c1n[nH]cc1NC(=O)c1cnn2cccnc12] | N-(3-(5-cyano-2-ethoxyphenyl)-1H-pyrazol-4-yl)pyrazolo[1,5-a]pyrimidine-3-carboxamide | 147 | 374.1 |

TABLE 2-continued

| Ex | Structure | Name | Mthd | LCMS (ESI) m/z |
|---|---|---|---|---|
| 377 | 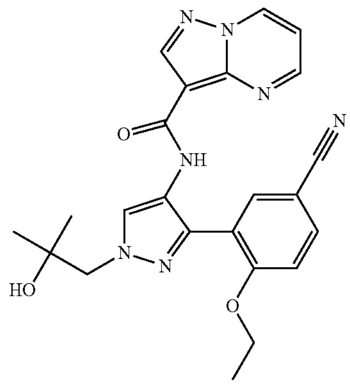 [SMILES: CCOc1ccc(C#N)cc1-c1nn(CC(C)(C)O)cc1NC(=O)c1cnn2cccnc12] | N-(3-(5-cyano-2-(ethylamino)phenyl)-1-(2-hydroxy-2-methylpropyl)-1H-pyrazol-4-yl)pyrazolo[1,5-a]pyrimidine-3-carboxamide | 147, 16 | 445.1 |
| 378 | 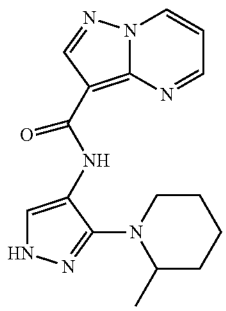 [SMILES: CC1CCCCN1c1n[nH]cc1NC(=O)c1cnn2cccnc12] | N-(3-(2-methylpiperidin-1-yl)-1H-pyrazol-4-yl)pyrazolo[1,5-a]pyrimidine-3-carboxamide | 140 | 326.1 |
| 379 | 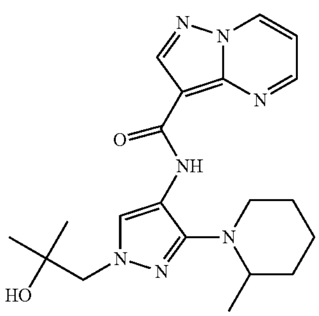 [SMILES: CC1CCCCN1c1nn(CC(C)(C)O)cc1NC(=O)c1cnn2cccnc12] | N-(1-(2-hydroxy-2-methylpropyl)-3-(2-methylpiperidin-1-yl)-1H-pyrazol-4-yl)pyrazolo[1,5-a]pyrimidine-3-carboxamide | 140, 16 | 398.1 |
| 380 | 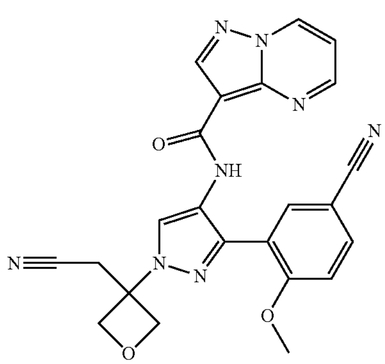 [SMILES: COc1ccc(C#N)cc1-c1nn(C2(CC#N)COC2)cc1NC(=O)c1cnn2cccnc12] | N-(3-(5-cyano-2-methoxyphenyl)-1-(3-(cyanomethyl)oxetan-3-yl)-1H-pyrazol-4-yl)pyrazolo[1,5-a]pyrimidine-3-carboxamide | 147, 14 | 455.1 |

TABLE 2-continued

| Ex | Structure | Name | Mthd | LCMS (ESI) m/z |
|---|---|---|---|---|
| 381 | 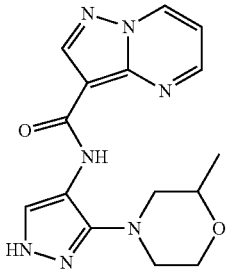 [SMILES: CC1CN(c2n[nH]cc2NC(=O)c2cnn3cccnc23)CCO1] | N-(3-(2-methylmorpholino)-1H-pyrazol-4-yl)pyrazolo[1,5-a]pyrimidine-3-carboxamide | 140 | 328.1 |
| 382 | 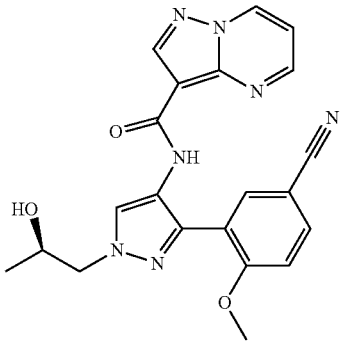 [SMILES: COc1ccc(C#N)cc1-c1nn(C[C@@H](C)O)cc1NC(=O)c1cnn2cccnc12] | (R)-N-(3-(5-cyano-2-methoxyphenyl)-1-(2-hydroxypropyl)-1H-pyrazol-4-yl)pyrazolo[1,5-a]pyrimidine-3-carboxamide | 147, 16 | 418.1 |
| 383 | 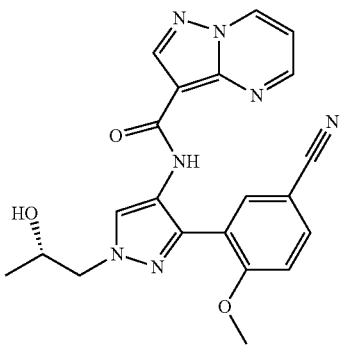 [SMILES: COc1ccc(C#N)cc1-c1nn(C[C@H](C)O)cc1NC(=O)c1cnn2cccnc12] | (S)-N-(3-(5-cyano-2-methoxyphenyl)-1-(2-hydroxypropyl)-1H-pyrazol-4-yl)pyrazolo[1,5-a]pyrimidine-3-carboxamide | 147, 16 | 418.1 |
| 384 | 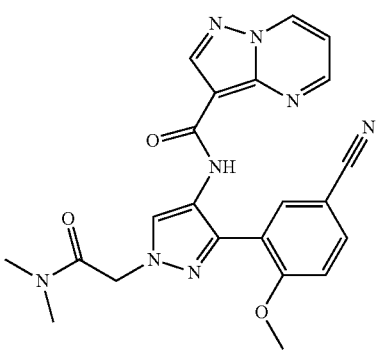 [SMILES: COc1ccc(C#N)cc1-c1nn(CC(=O)N(C)C)cc1NC(=O)c1cnn2cccnc12] | N-(3-(5-cyano-2-methoxyphenyl)-1-(2-(dimethylamino)-2-oxoethyl)-1H-pyrazol-4-yl)pyrazolo[1,5-a]pyrimidine-3-carboxamide | 147, 134 | 445.1 |

TABLE 2-continued

| Ex | Name | Mthd | LCMS (ESI) m/z |
|---|---|---|---|
| 385 | N-(3-(5-fluoro-2-methylphenyl)-1H-pyrazol-4-yl)pyrazolo[1,5-a]pyrimidine-3-carboxamide | 14 | 337.1 |
| 386 | N-(3-(5-fluoro-2-methylphenyl)-1-(2-hydroxy-2-methylpropyl)-1H-pyrazol-4-yl)pyrazolo[1,5-a]pyrimidine-3-carboxamide | 14, 16 | 409.1 |
| 387 | N-(3-(5-cyano-2-methoxyphenyl)-1-(2-(3,3-difluoropyrrolidin-1-yl)-2-oxoethyl)-1H-pyrazol-4-yl)pyrazolo[1,5-a]pyrimidine-3-carboxamide | 147, 134 | 507.1 |
| 388 | N-(3-(3-(trifluoromethyl)piperidin-1-yl)-1H-pyrazol-4-yl)pyrazolo[1,5-a]pyrimidine-3-carboxamide | 140 | 380.1 |
| 389 | N-(1-(2-hydroxy-2-methylpropyl)-3-(3-(trifluoromethyl)piperidin-1-yl)-1H-pyrazol-4-yl)pyrazolo[1,5-a]pyrimidine-3-carboxamide | 140, 16 | 452.1 |

TABLE 2-continued

| Ex | Structure | Name | Mthd | LCMS (ESI) m/z |
|---|---|---|---|---|
| 390 | 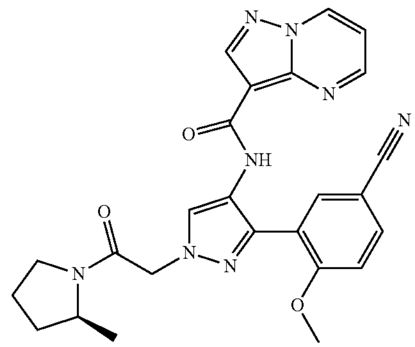 [SMILES: COc1ccc(C#N)cc1-c1nn(CC(=O)N2CCC[C@@H]2C)cc1NC(=O)c1cnn2cccnc12] | (S)-N-(3-(5-cyano-2-methoxyphenyl)-1-(2-(2-methylpyrrolidin-1-yl)-2-oxoethyl)-1H-pyrazol-4-yl)pyrazolo[1,5-a]pyrimidine-3-carboxamide | 147, 134 | 485.1 |
| 391 | 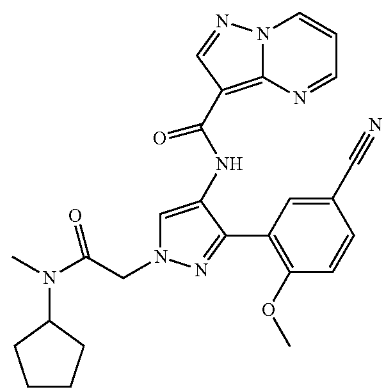 [SMILES: COc1ccc(C#N)cc1-c1nn(CC(=O)N(C)C2CCCC2)cc1NC(=O)c1cnn2cccnc12] | N-(3-(5-cyano-2-methoxyphenyl)-1-(2-(cyclopentyl(methyl)amino)-2-oxoethyl)-1H-pyrazol-4-yl)pyrazolo[1,5-a]pyrimidine-3-carboxamide | 147, 134 | 499.1 |
| 392 | 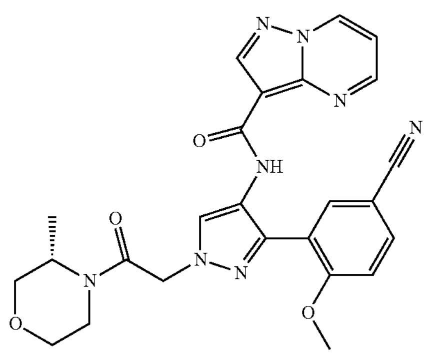 [SMILES: COc1ccc(C#N)cc1-c1nn(CC(=O)N2CCOC[C@@H]2C)cc1NC(=O)c1cnn2cccnc12] | (S)-N-(3-(5-cyano-2-methoxyphenyl)-1-(2-(3-methylmorpholino)-2-oxoethyl)-1H-pyrazol-4-yl)pyrazolo[1,5-a]pyrimidine-3-carboxamide | 147, 134 | 501.1 |
| 393 | 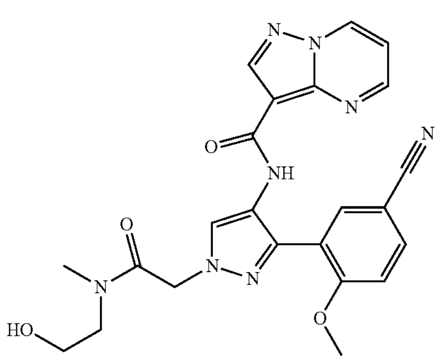 [SMILES: COc1ccc(C#N)cc1-c1nn(CC(=O)N(C)CCO)cc1NC(=O)c1cnn2cccnc12] | N-(3-(5-cyano-2-methoxyphenyl)-1-(2-((2-hydroxyethyl)(methyl)amino)-2-oxoethyl)-1H-pyrazol-4-yl)pyrazolo[1,5-a]pyrimidine-3-carboxamide | 147, 134 | 475.1 |

TABLE 2-continued

| Ex | Structure | Name | Mthd | LCMS (ESI) m/z |
|---|---|---|---|---|
| 394 | 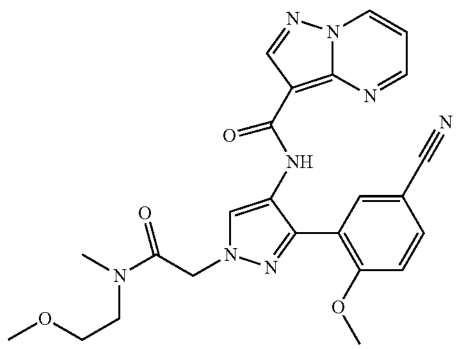 [SMILES: COCCN(C)C(=O)Cn1cc(NC(=O)c2cnn3cccnc23)c(-c2cc(C#N)ccc2OC)n1] | N-(3-(5-cyano-2-methoxyphenyl)-1-(2-((2-methoxyethyl)(methyl)amino)-2-oxoethyl)-1H-pyrazol-4-yl)pyrazolo[1,5-a]pyrimidine-3-carboxamide | 147, 134 | 489.1 |
| 395 | 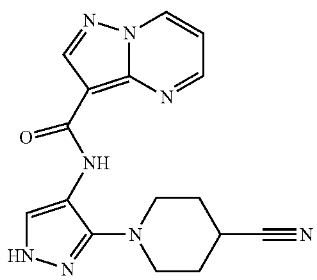 [SMILES: N#CC1CCN(c2n[nH]cc2NC(=O)c2cnn3cccnc23)CC1] | N-(3-(4-cyanopiperidin-1-yl)-1H-pyrazol-4-yl)pyrazolo[1,5-a]pyrimidine-3-carboxamide | 140 | 337.1 |
| 396 | 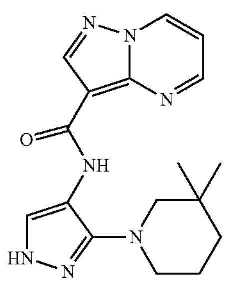 [SMILES: CC1(C)CCCN(c2n[nH]cc2NC(=O)c2cnn3cccnc23)C1] | N-(3-(3,3-dimethylpiperidin-1-yl)-1H-pyrazol-4-yl)pyrazolo[1,5-a]pyrimidine-3-carboxamide | 140 | 340.1 |
| 397 | 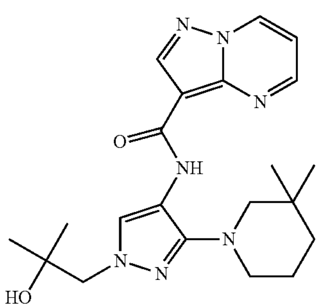 [SMILES: CC(C)(O)Cn1cc(NC(=O)c2cnn3cccnc23)c(N2CCCC(C)(C)C2)n1] | N-(3-(3,3-dimethylpiperidin-1-yl)-1-(2-hydroxy-2-methylpropyl)-1H-pyrazol-4-yl)pyrazolo[1,5-a]pyrimidine-3-carboxamide | 140, 16 | 412.1 |
| 398 | 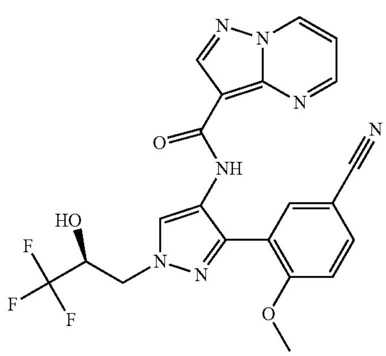 [SMILES: COc1ccc(C#N)cc1-c1nn(C[C@H](O)C(F)(F)F)cc1NC(=O)c1cnn2cccnc12] | (S)-N-(3-(5-cyano-2-methoxyphenyl)-1-(3,3,3-trifluoro-2-hydroxypropyl)-1H-pyrazol-4-yl)pyrazolo[1,5-a]pyrimidine-3-carboxamide | 147, 16 | 472.1 |

TABLE 2-continued

| Ex | Structure | Name | Mthd | LCMS (ESI) m/z |
|---|---|---|---|---|
| 399 | 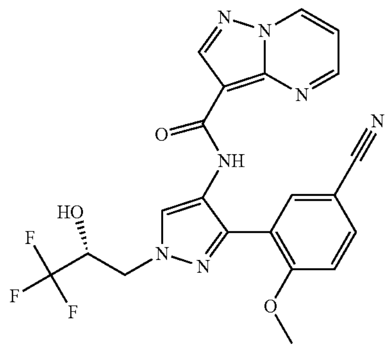 [SMILES: COc1ccc(C#N)cc1-c1nn(C[C@@H](O)C(F)(F)F)cc1NC(=O)c1cnn2cccnc12] | (R)-N-(3-(5-cyano-2-methoxyphenyl)-1-(3,3,3-trifluoro-2-hydroxypropyl)-1H-pyrazol-4-yl)pyrazolo[1,5-a]pyrimidine-3-carboxamide | 147, 16 | 472.1 |
| 400 | 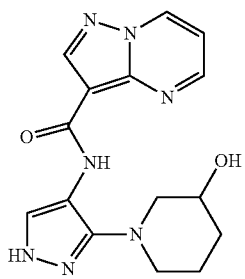 [SMILES: O=C(Nc1c[nH]nc1N1CCCC(O)C1)c1cnn2cccnc12] | N-(3-(3-hydroxypiperidin-1-yl)-1H-pyrazol-4-yl)pyrazolo[1,5-a]pyrimidine-3-carboxamide | 140 | 328.1 |
| 401 | 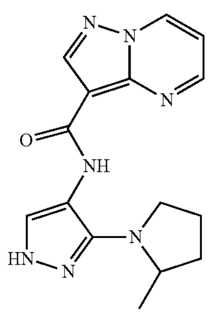 [SMILES: CC1CCCN1c1n[nH]cc1NC(=O)c1cnn2cccnc12] | N-(3-(2-methylpyrrolidin-1-yl)-1H-pyrazol-4-yl)pyrazolo[1,5-a]pyrimidine-3-carboxamide | 140 | 312.1 |
| 402 | 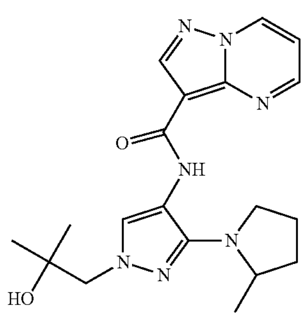 [SMILES: CC1CCCN1c1nn(CC(C)(C)O)cc1NC(=O)c1cnn2cccnc12] | N-(1-(2-hydroxy-2-methylpropyl)-3-(2-methylpyrrolidin-1-yl)-1H-pyrazol-4-yl)pyrazolo[1,5-a]pyrimidine-3-carboxamide | 140, 16 | 384.1 |
| 403 | 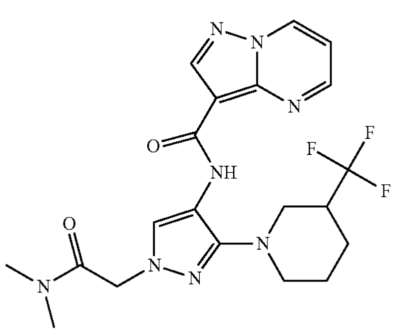 [SMILES: CN(C)C(=O)Cn1cc(NC(=O)c2cnn3cccnc23)c(N2CCCC(C(F)(F)F)C2)n1] | N-(1-(2-(dimethylamino)-2-oxoethyl)-3-(3-(trifluoromethyl)piperidin-1-yl)-1H-pyrazol-4-yl)pyrazolo[1,5-a]pyrimidine-3-carboxamide | 140, 134 | 465.1 |

TABLE 2-continued

| Ex | Structure | Name | Mthd | LCMS (ESI) m/z |
|---|---|---|---|---|
| 404 | 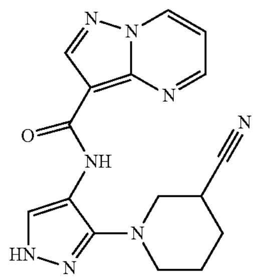 [SMILES: N#CC1CCCN(c2n[nH]cc2NC(=O)c2cnn3cccnc23)C1] | N-(3-(3-cyanopiperidin-1-yl)-1H-pyrazol-4-yl)pyrazolo[1,5-a]pyrimidine-3-carboxamide | 140 | 337.1 |
| 405 | 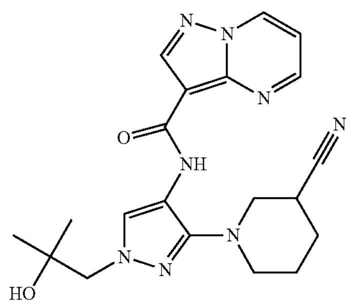 [SMILES: CC(C)(O)Cn1cc(NC(=O)c2cnn3cccnc23)c(N2CCCC(C#N)C2)n1] | N-(3-(3-cyanopiperidin-1-yl)-1-(2-hydroxy-2-methylpropyl)-1H-pyrazol-4-yl)pyrazolo[1,5-a]pyrimidine-3-carboxamide | 140, 16 | 409.1 |
| 406 | 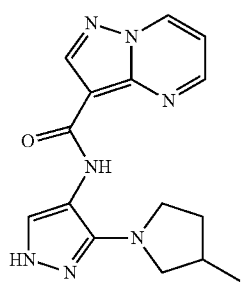 [SMILES: CC1CCN(c2n[nH]cc2NC(=O)c2cnn3cccnc23)C1] | N-(3-(3-methylpyrrolidin-1-yl)-1H-pyrazol-4-yl)pyrazolo[1,5-a]pyrimidine-3-carboxamide | 140 | 312.1 |
| 407 | 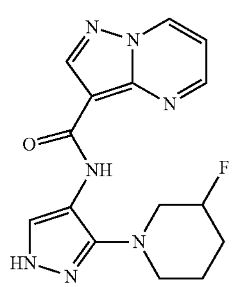 [SMILES: O=C(Nc1c[nH]nc1N1CCCC(F)C1)c1cnn2cccnc12] | N-(3-(3-fluoropiperidin-1-yl)-1H-pyrazol-4-yl)pyrazolo[1,5-a]pyrimidine-3-carboxamide | 140 | 330.1 |
| 408 | 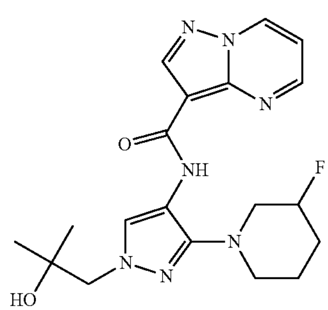 [SMILES: CC(C)(O)Cn1cc(NC(=O)c2cnn3cccnc23)c(N2CCCC(F)C2)n1] | N-(3-(3-fluoropiperidin-1-yl)-1-(2-hydroxy-2-methylpropyl)-1H-pyrazol-4-yl)pyrazolo[1,5-a]pyrimidine-3-carboxamide | 140, 16 | 402.1 |

TABLE 2-continued

| Ex | Structure | Name | Mthd | LCMS (ESI) m/z |
|---|---|---|---|---|
| 409 | 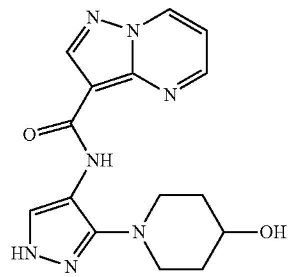 [SMILES: O=C(Nc1c[nH]nc1N1CCC(O)CC1)c1cnn2cccnc12] | N-(3-(4-hydroxypiperidin-1-yl)-1H-pyrazol-4-yl)pyrazolo[1,5-a]pyrimidine-3-carboxamide | 140 | 328.1 |
| 410 | 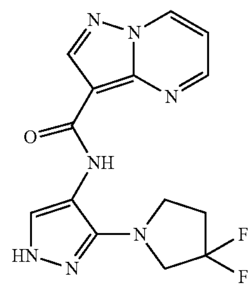 [SMILES: O=C(Nc1c[nH]nc1N1CCC(F)(F)C1)c1cnn2cccnc12] | N-(3-(3,3-difluoropyrrolidin-1-yl)-1H-pyrazol-4-yl)pyrazolo[1,5-a]pyrimidine-3-carboxamide | 140 | 334.1 |
| 411 | 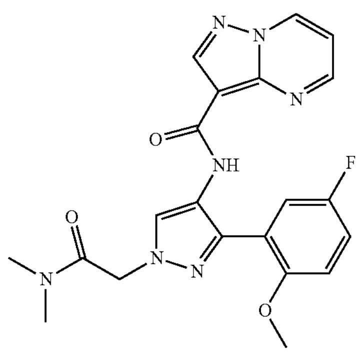 [SMILES: COc1ccc(F)cc1-c1nn(CC(=O)N(C)C)cc1NC(=O)c1cnn2cccnc12] | N-(1-(2-(dimethylamino)-2-oxoethyl)-3-(5-fluoro-2-methoxyphenyl)-1H-pyrazol-4-yl)pyrazolo[1,5-a]pyrimidine-3-carboxamide | 149, 134 | 438.1 |
| 412 | 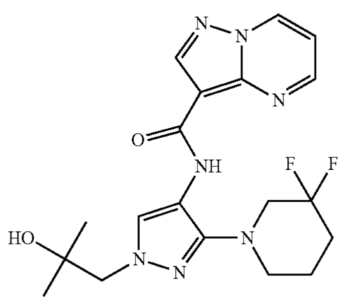 [SMILES: CC(C)(O)Cn1cc(NC(=O)c2cnn3cccnc23)c(N2CCCC(F)(F)C2)n1] | N-(3-(3,3-difluoropiperidin-1-yl)-1-(2-hydroxy-2-methylpropyl)-1H-pyrazol-4-yl)pyrazolo[1,5-a]pyrimidine-3-carboxamide | 157, 16 | 420.1 |
| 413 | 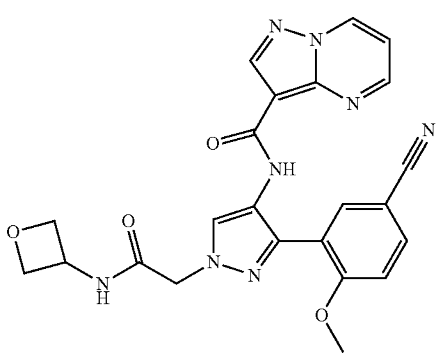 [SMILES: COc1ccc(C#N)cc1-c1nn(CC(=O)NC2COC2)cc1NC(=O)c1cnn2cccnc12] | N-(3-(5-cyano-2-methoxyphenyl)-1-(2-(oxetan-3-ylamino)-2-oxoethyl)-1H-pyrazol-4-yl)pyrazolo[1,5-a]pyrimidine-3-carboxamide | 147, 134 | 473.1 |

TABLE 2-continued

| Ex | Structure | Name | Mthd | LCMS (ESI) m/z |
|---|---|---|---|---|
| 414 | 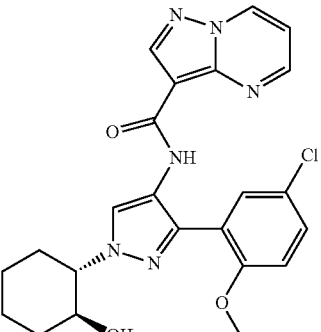 And 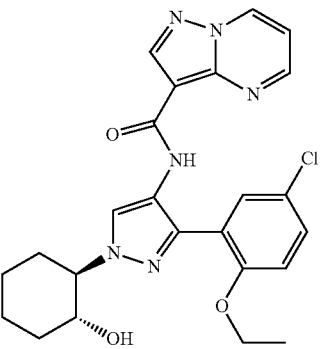 [SMILES: CCOc1ccc(Cl)cc1-c1nn([C@@H]2CCCC[C@H]2O)cc1NC(=O)c1cnn2cccnc12] | N-(3-(5-chloro-2-ethoxyphenyl)-1-((1S,2S)-2-hydroxycyclohexyl)-1H-pyrazol-4-yl)pyrazolo[1,5-a]pyrimidine-3-carboxamide And<br><br>N-(3-(5-chloro-2-ethoxyphenyl)-1-((1R,2R)-2-hydroxycyclohexyl)-1H-pyrazol-4-yl)pyrazolo[1,5-a]pyrimidine-3-carboxamide | 16 | 481.1 |
| 415 | 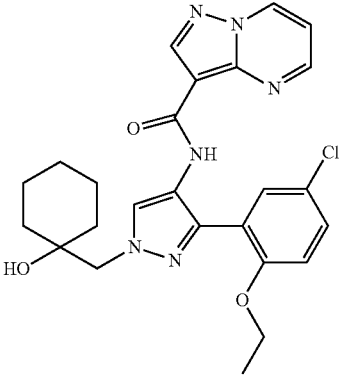 [SMILES: CCOc1ccc(Cl)cc1-c1nn(CC2(O)CCCCC2)cc1NC(=O)c1cnn2cccnc12] | N-(3-(5-chloro-2-ethoxyphenyl)-1-((1-hydroxycyclohexyl)methyl)-1H-pyrazol-4-yl)pyrazolo[1,5-a]pyrimidine-3-carboxamide | 20, 16 | 495.1 |
| 416 | 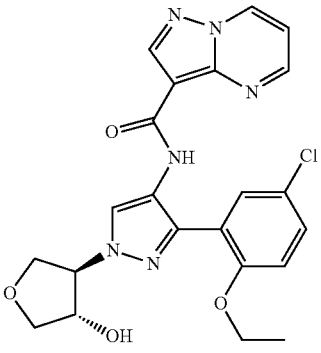 And | N-(3-(5-chloro-2-ethoxyphenyl)-1-((3R,4S)-4-hydroxytetrahydrofuran-3-yl)-1H-pyrazol-4-yl)pyrazolo[1,5-a]pyrimidine-3-carboxamide And | 20, 16 | 469.2 |

TABLE 2-continued

| Ex | Structure | Name | Mthd | LCMS (ESI) m/z |
|---|---|---|---|---|
| | | N-(3-(5-chloro-2-ethoxyphenyl)-1-((3S,4R)-4-hydroxytetrahydrofuran-3-yl)-1H-pyrazol-4-yl)pyrazolo[1,5-a]pyrimidine-3-carboxamide | | |
| 417 | 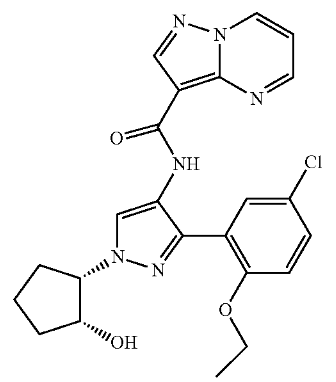 [SMILES: CCOc1ccc(Cl)cc1-c1nn([C@H]2CCC[C@H]2O)cc1NC(=O)c1cnn2cccnc12] | N-(3-(5-chloro-2-ethoxyphenyl)-1-((1S,2R)-2-hydroxycyclopentyl)-1H-pyrazol-4-yl)pyrazolo[1,5-a]pyrimidine-3-carboxamide | 20, 16, 136 | 467.2 |
| 418 | 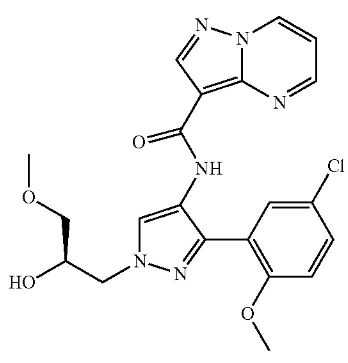 [SMILES: COC[C@H](O)Cn1cc(NC(=O)c2cnn3cccnc23)c(-c2cc(Cl)ccc2OC)n1] | (R)-N-(3-(5-chloro-2-methoxyphenyl)-1-(2-hydroxy-3-methoxypropyl)-1H-pyrazol-4-yl)pyrazolo[1,5-a]pyrimidine-3-carboxamide | 16 | 457.2 |
| 419 | 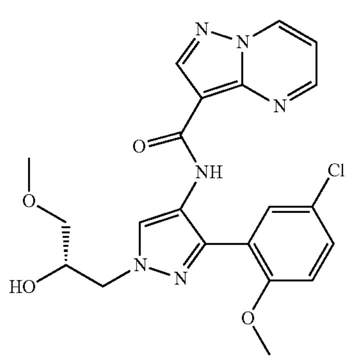 [SMILES: COC[C@@H](O)Cn1cc(NC(=O)c2cnn3cccnc23)c(-c2cc(Cl)ccc2OC)n1] | (S)-N-(3-(5-chloro-2-methoxyphenyl)-1-(2-hydroxy-3-methoxypropyl)-1H-pyrazol-4-yl)pyrazolo[1,5-a]pyrimidine-3-carboxamide | 16 | 457.2 |

TABLE 2-continued

| Ex | Structure | Name | Mthd | LCMS (ESI) m/z |
|---|---|---|---|---|
| 420 | 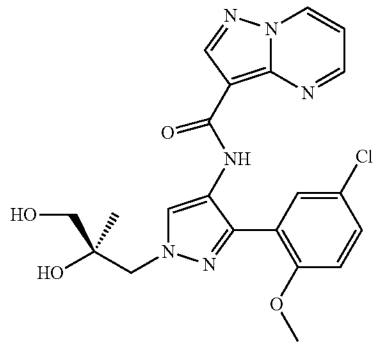 [SMILES: COc1ccc(Cl)cc1-c1nn(C[C@@](C)(O)CO)cc1NC(=O)c1cnn2cccnc12] | (R)-N-(3-(5-chloro-2-methoxyphenyl)-1-(2,3-dihydroxy-2-methylpropyl)-1H-pyrazol-4-yl)pyrazolo[1,5-a]pyrimidine-3-carboxamide | 16 | 457.2 |
| 421 | 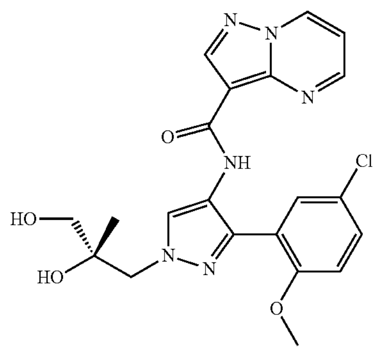 [SMILES: COc1ccc(Cl)cc1-c1nn(C[C@](C)(O)CO)cc1NC(=O)c1cnn2cccnc12] | (S)-N-(3-(5-chloro-2-methoxyphenyl)-1-(2,3-dihydroxy-2-methylpropyl)-1H-pyrazol-4-yl)pyrazolo[1,5-a]pyrimidine-3-carboxamide | 16 | 457.2 |
| 422 | 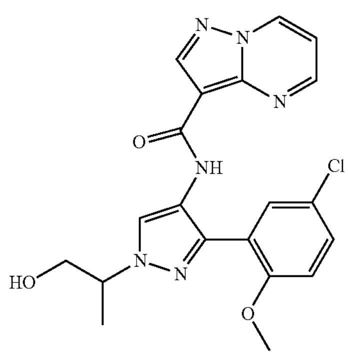 [SMILES: COc1ccc(Cl)cc1-c1nn(C(C)CO)cc1NC(=O)c1cnn2cccnc12] | N-(3-(5-chloro-2-methoxyphenyl)-1-(1-hydroxypropan-2-yl)-1H-pyrazol-4-yl)pyrazolo[1,5-]pyrimidine-3-carboxamide | 14 | 427.1 |
| 423 | 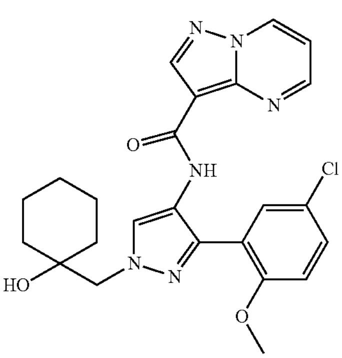 [SMILES: COc1ccc(Cl)cc1-c1nn(CC2(O)CCCCC2)cc1NC(=O)c1cnn2cccnc12] | N-(3-(5-chloro-2-methoxyphenyl)-1-((1-hydroxycyclohexyl)methyl)-1H-pyrazol-4-yl)pyrazolo[1,5-a]pyrimidine-3-carboxamide | 16 | 481.2 |

TABLE 2-continued

| Ex | Structure | Name | Mthd | LCMS (ESI) m/z |
|---|---|---|---|---|
| 424 | 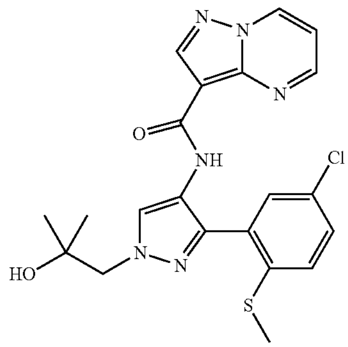 [SMILES: CSc1ccc(Cl)cc1-c1nn(CC(C)(C)O)cc1NC(=O)c1cnn2cccnc12] | N-(3-(5-chloro-2-(methylthio)phenyl)-1-(2-hydroxy-2-methylpropyl)-1H-pyrazol-4-yl)pyrazolo[1,5-a]pyrimidine-3-carboxamide | 16, 19 | 457.1 |
| 425 | | N-(3-(5-chloro-2-methoxyphenyl)-1-((3R,4S)-4-hydroxytetrahydrofuran-3-yl)-1H-pyrazol-4-yl)pyrazolo[1,5-a]pyrimidine-3-carboxamide And | 16 | 455.1 |
| | | N-(3-(5-chloro-2-methoxyphenyl)-1-((3S,4R)-4-hydroxytetrahydrofuran-3-yl)-1H-pyrazol-4-yl)pyrazolo[1,5-a]pyrimidine-3-carboxamide | | |
| 426 | 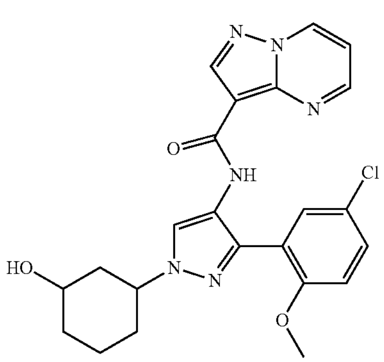 [SMILES: COc1ccc(Cl)cc1-c1nn(C2CCCC(O)C2)cc1NC(=O)c1cnn2cccnc12] | N-(3-(5-chloro-2-methoxyphenyl)-1-(3-hydroxycyclohexyl)-1H-pyrazol-4-yl)pyrazolo[1,5-a]pyrimidine-3-carboxamide | 137 | 467.2 |

TABLE 2-continued

| Ex | Structure | Name | Mthd | LCMS (ESI) m/z |
|---|---|---|---|---|
| 427 | 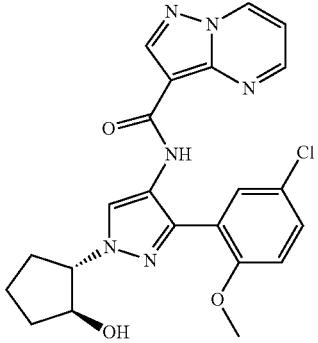 [SMILES: COc1ccc(Cl)cc1-c1nn([C@@H]2CCC[C@H]2O)cc1NC(=O)c1cnn2cccnc12] | N-(3-(5-chloro-2-methoxyphenyl)-1-((1S,2S)-2-hydroxycyclopentyl)-1H-pyrazol-4-yl)pyrazolo[1,5-a]pyrimidine-3-carboxamide And<br><br>N-(3-(5-chloro-2-methoxyphenyl)-1-((1R,2R)-2-hydroxycyclopentyl)-1H-pyrazol-4-yl)pyrazolo[1,5-a]pyrimidine-3-carboxamide | 16 | 453.1 |
| 428 | 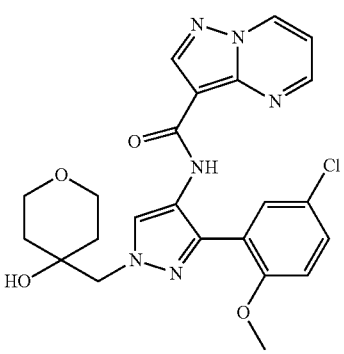 [SMILES: COc1ccc(Cl)cc1-c1nn(CC2(O)CCOCC2)cc1NC(=O)c1cnn2cccnc12] | N-(3-(5-chloro-2-methoxyphenyl)-1-((4-hydroxytetrahydro-2H-pyran-4-yl)methyl)-1H-pyrazol-4-yl)pyrazolo[1,5-a]pyrimidine-3-carboxamide | 16 | 483.2 |
| 429 | 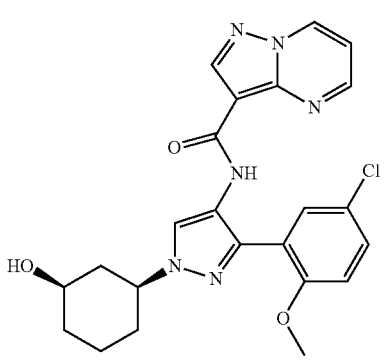 [SMILES: COc1ccc(Cl)cc1-c1nn([C@H]2CCC[C@@H](O)C2)cc1NC(=O)c1cnn2cccnc12] | N-(3-(5-chloro-2-methoxyphenyl)-1-((1S,3R)-3-hydroxycyclohexyl)-1H-pyrazol-4-yl)pyrazolo[1,5-a]pyrimidine-3-carboxamide | 137 And 136 | 467.2 |

TABLE 2-continued

| Ex | Structure | Name | Mthd | LCMS (ESI) m/z |
|---|---|---|---|---|
| 430 | 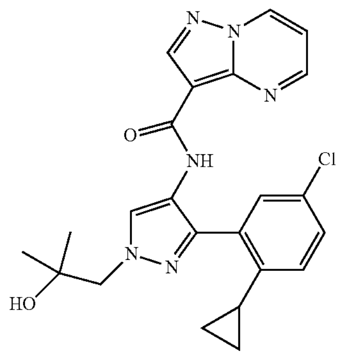 [SMILES: CC(C)(O)Cn1cc(NC(=O)c2cnn3cccnc23)c(-c2cc(Cl)ccc2C2CC2)n1] | N-(3-(5-chloro-2-cyclopropylphenyl)-1-(2-hydroxy-2-methylpropyl)-1H-pyrazol-4-yl)pyrazolo[1,5-a]pyrimidine-3-carboxamide | 138 And 16 | 451.1 |
| 431 | 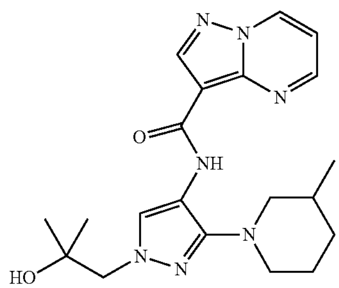 [SMILES: CC1CCCN(c2nn(CC(C)(C)O)cc2NC(=O)c2cnn3cccnc23)C1] | N-(1-(2-hydroxy-2-methylpropyl)-3-(3-methylpiperidin-1-yl)-1H-pyrazol-4-yl)pyrazolo[1,5-a]pyrimidine-3-carboxamide | 140, 16 | 398.2 |
| 432 | 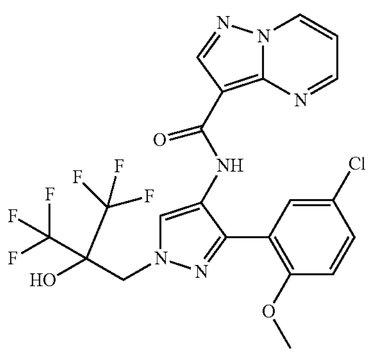 [SMILES: COc1ccc(Cl)cc1-c1nn(CC(O)(C(F)(F)F)C(F)(F)F)cc1NC(=O)c1cnn2cccnc12] | N-(3-(5-chloro-2-methoxyphenyl)-1-(3,3,3-trifluoro-2-hydroxy-2-(trifluoromethyl)propyl)-1H-pyrazol-4-yl)pyrazolo[1,5-a]pyrimidine-3-carboxamide | 16 | 549.1 |
| 433 | 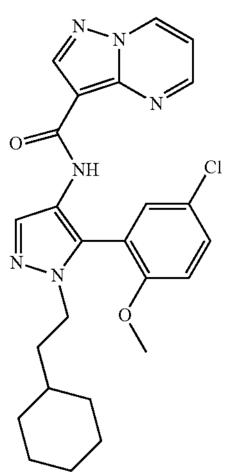 [SMILES: COc1ccc(Cl)cc1-c1c(NC(=O)c2cnn3cccnc23)cnn1CCC1CCCCC1] | N-(5-(5-chloro-2-methoxyphenyl)-1-(2-cyclohexylethyl)-1H-pyrazol-4-yl)pyrazolo[1,5-a]pyrimidine-3-carboxamide | 26 | 479.2 |

| Ex | Structure | Name | Mthd | LCMS (ESI) m/z |
|---|---|---|---|---|
| 434 | 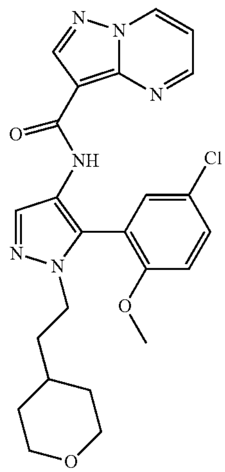 [SMILES: COc1ccc(Cl)cc1-c1c(NC(=O)c2cnn3cccnc23)cnn1CCC1CCOCC1] | N-(5-(5-chloro-2-methoxyphenyl)-1-(2-(tetrahydro-2H-pyran-4-yl)ethyl)-1H-pyrazol-4-yl)pyrazolo[1,5-a]pyrimidine-3-carboxamide | 26 | 481.1 |
| 435 | 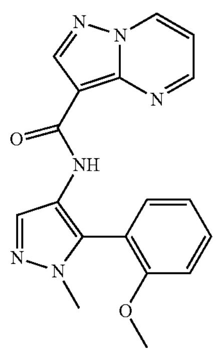 [SMILES: COc1ccccc1-c1c(NC(=O)c2cnn3cccnc23)cnn1C] | N-(5-(2-methoxyphenyl)-1-methyl-1H-pyrazol-4-yl)pyrazolo[1,5-a]pyrimidine-3-carboxamide | 26 | 249.1 |
| 436 | 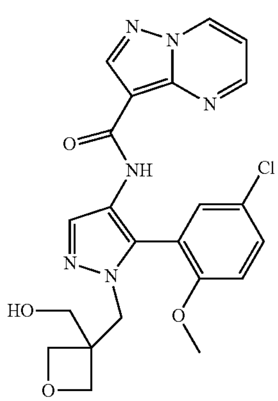 [SMILES: COc1ccc(Cl)cc1-c1c(NC(=O)c2cnn3cccnc23)cnn1CC1(CO)COC1] | N-(5-(5-chloro-2-methoxyphenyl)-1-((3-(hydroxymethyl)oxetan-3-yl)methyl)-1H-pyrazol-4-yl)pyrazolo[1,5-a]pyrimidine-3-carboxamide | 26 | 469.2 |

| Ex | Structure | Name | Mthd | LCMS (ESI) m/z |
|---|---|---|---|---|
| 437 | 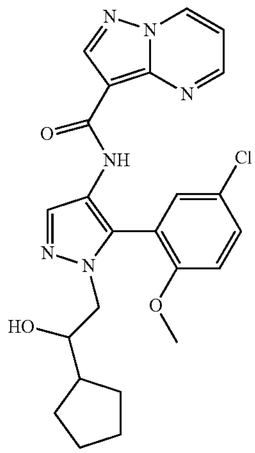 [SMILES: COc1ccc(Cl)cc1-c1c(NC(=O)c2cnn3cccnc23)cnn1CC(O)C1CCCC1] | N-(5-(5-chloro-2-methoxyphenyl)-1-(2-cyclopentyl-2-hydroxyethyl)-1H-pyrazol-4-yl)pyrazolo[1,5-a]pyrimidine-3-carboxamide | 26 | 481.2 |
| 438 | 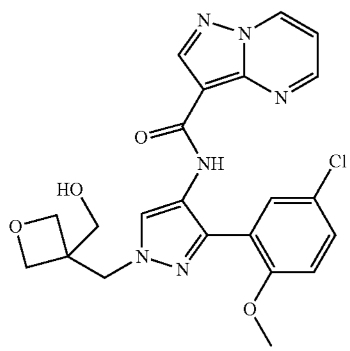 [SMILES: COc1ccc(Cl)cc1-c1nn(CC2(CO)COC2)cc1NC(=O)c1cnn2cccnc12] | N-(3-(5-chloro-2-methoxyphenyl)-1-((3-(hydroxymethyl)oxetan-3-yl)methyl)-1H-pyrazol-4-yl)pyrazolo[1,5-a]pyrimidine-3-carboxamide | 14 | 469.2 |
| 439 | 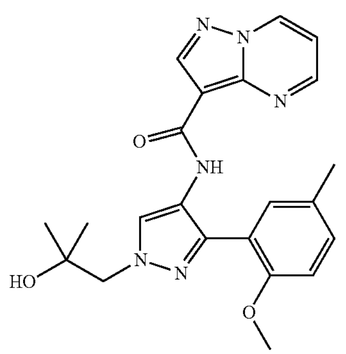 [SMILES: COc1ccc(C)cc1-c1nn(CC(C)(C)O)cc1NC(=O)c1cnn2cccnc12] | N-(1-(2-hydroxy-2-methylpropyl)-3-(2-methoxy-5-methylphenyl)-1H-pyrazol-4-yl)pyrazolo[1,5-a]pyrimidine-3-carboxamide | 16 | 421.2 |
| 440 | 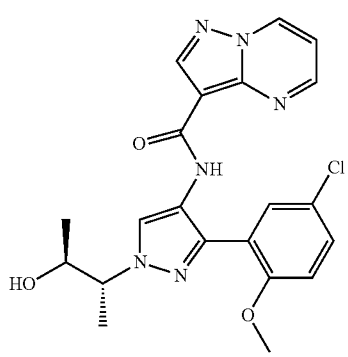 [SMILES: COc1ccc(Cl)cc1-c1nn([C@H](C)[C@H](C)O)cc1NC(=O)c1cnn2cccnc12] | N-(3-(5-chloro-2-methoxyphenyl)-1-((2R,3S)-3-hydroxybutan-2-yl)-1H-pyrazol-4-yl)pyrazolo[1,5-a]pyrimidine-3-carboxamide | 16 | 441.2 |

| Ex | Structure | Name | Mthd | LCMS (ESI) m/z |
|---|---|---|---|---|
| 441 | 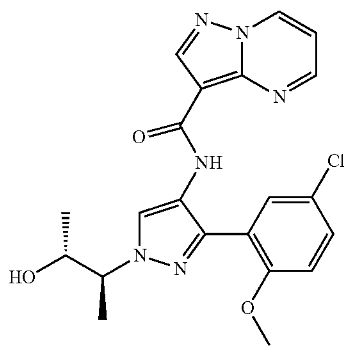 [SMILES: COc1ccc(Cl)cc1-c1nn([C@@H](C)[C@@H](C)O)cc1NC(=O)c1cnn2cccnc12] | N-(3-(5-chloro-2-methoxyphenyl)-1-((2S,3R)-3-hydroxybutan-2-yl)-1H-pyrazol-4-yl)pyrazolo[1,5-a]pyrimidine-3-carboxamide | 16 | 441.2 |
| 442 | 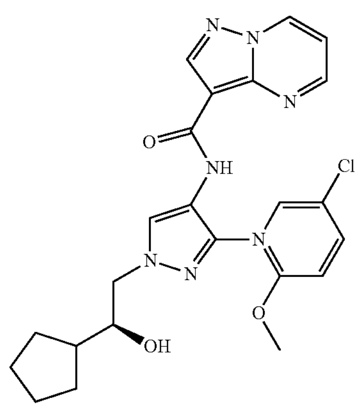 | (S)-N-(3-(5-chloro-2-methoxyphenyl)-1-(2-cyclopentyl-2-hydroxyethyl)-1H-pyrazol-4-yl)pyrazolo[1,5-a]pyrimidine-3-carboxamide | 16 | 481.2 |
| 443 | 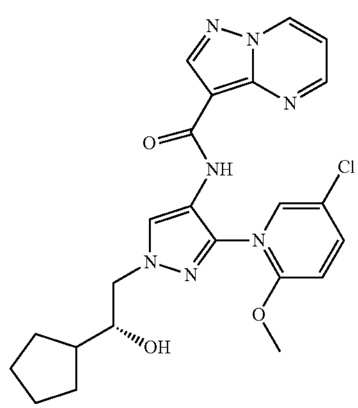 | (R)-N-(3-(5-chloro-2-methoxyphenyl)-1-(2-cyclopentyl-2-hydroxyethyl)-1H-pyrazol-4-yl)pyrazolo[1,5-a]pyrimidine-3-carboxamide | 16 | 481.2 |
| 444 | 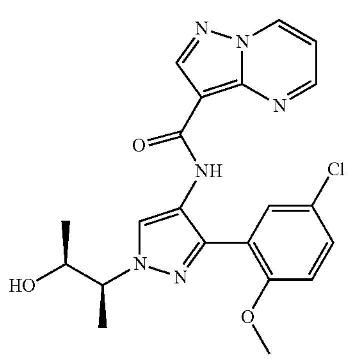 [SMILES: COc1ccc(Cl)cc1-c1nn([C@@H](C)[C@H](C)O)cc1NC(=O)c1cnn2cccnc12] | N-(3-(5-chloro-2-methoxyphenyl)-1-((2S,3S)-3-hydroxybutan-2-yl)-1H-pyrazol-4-yl)pyrazolo[1,5-a]pyrimidine-3-carboxamide | 16 | 441.2 |

TABLE 2-continued

| Ex | Name | Mthd | LCMS (ESI) m/z |
|---|---|---|---|
| 445 | N-(3-(5-chloro-2-methoxyphenyl)-1-((2R,3R)-3-hydroxybutan-2-yl)-1H-pyrazol-4-yl)pyrazolo[1,5-a]pyrimidine-3-carboxamide | 16 | 441.2 |
| 446 | N-(3-(5-chloro-2-methoxyphenyl)-1-(4-hydroxypyrrolidin-3-yl)-1H-pyrazol-4-yl)pyrazolo[1,5-a]pyrimidine-3-carboxamide | 16 | 454.1 |
| 447 | N-(3-(5-chloro-2-methoxyphenyl)-1-(2-cyclopropyl-2-oxoethyl)-1H-pyrazol-4-yl)pyrazolo[1,5-a]pyrimidine-3-carboxamide | 14 | 451.1 |
| 448 | (R)-N-(3-(5-chloro-2-methoxyphenyl)-1-(2-cyclopropyl-2-hydroxyethyl)-1H-pyrazol-4-yl)pyrazolo[1,5-a]pyrimidine-3-carboxamide | 16 | 453.0 |

TABLE 2-continued

| Ex | Structure | Name | Mthd | LCMS (ESI) m/z |
| --- | --- | --- | --- | --- |
| 449 | 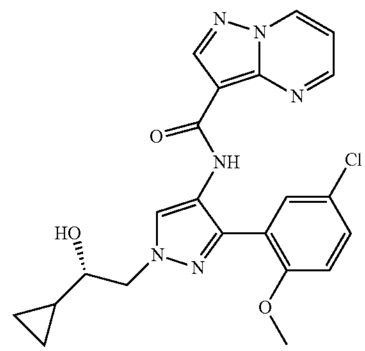 [SMILES: COc1ccc(Cl)cc1-c1nn(C[C@@H](O)C2CC2)cc1NC(=O)c1cnn2cccnc12] | (S)-N-(3-(5-chloro-2-methoxyphenyl)-1-(2-cyclopropyl-2-hydroxyethyl)-1H-pyrazol-4-yl)pyrazolo[1,5-a]pyrimidine-3-carboxamide | 16 | 453.0 |
| 450 | 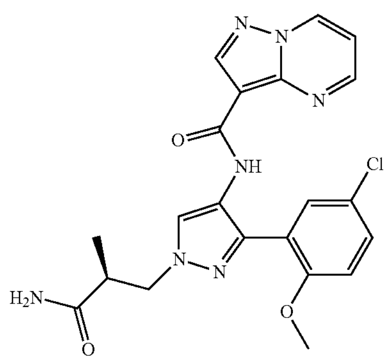 [SMILES: COc1ccc(Cl)cc1-c1nn(C[C@H](C)C(N)=O)cc1NC(=O)c1cnn2cccnc12] | (S)-N-(1-(3-amino-2-methyl-3-oxopropyl)-3-(5-chloro-2-methoxyphenyl)-1H-pyrazol-4-yl)pyrazolo[1,5-a]pyrimidine-3-carboxamide | 14 | 454.1 |
| 451 | 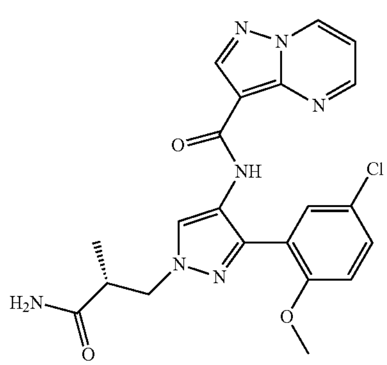 [SMILES: COc1ccc(Cl)cc1-c1nn(C[C@@H](C)C(N)=O)cc1NC(=O)c1cnn2cccnc12] | (R)-N-(1-(3-amino-2-methyl-3-oxopropyl)-3-(5-chloro-2-methoxyphenyl)-1H-pyrazol-4-yl)pyrazolo[1,5-a]pyrimidine-3-carboxamide | 14 | 454.1 |
| 452 | 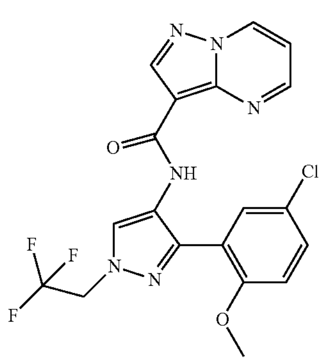 [SMILES: COc1ccc(Cl)cc1-c1nn(CC(F)(F)F)cc1NC(=O)c1cnn2cccnc12] | N-(3-(5-chloro-2-methoxyphenyl)-1-(2,2,2-trifluoroethyl)-1H-pyrazol-4-yl)pyrazolo[1,5-a]pyrimidine-3-carboxamide | 14 | 451.1 |

TABLE 2-continued

| Ex | Structure | Name | Mthd | LCMS (ESI) m/z |
|---|---|---|---|---|
| 453 | 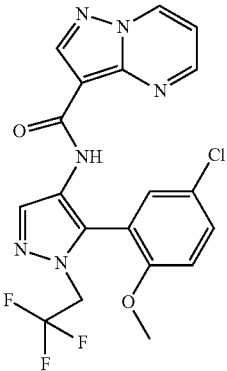 [SMILES: COc1ccc(Cl)cc1-c1c(NC(=O)c2cnn3cccnc23)cnn1CC(F)(F)F] | N-(5-(5-chloro-2-methoxyphenyl)-1-(2,2,2-trifluoroethyl)-1H-pyrazol-4-yl)pyrazolo[1,5-a]pyrimidine-3-carboxamide | 14 | 451.1 |
| 454 | 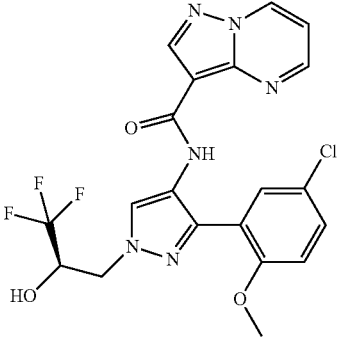 [SMILES: COc1ccc(Cl)cc1-c1nn(C[C@@H](O)C(F)(F)F)cc1NC(=O)c1cnn2cccnc12] | (R)-N-(3-(5-chloro-2-methoxyphenyl)-1-(3,3,3-trifluoro-2-hydroxypropyl)-1H-pyrazol-4-yl)pyrazolo[1,5-a]pyrimidine-3-carboxamide | 16 | 481.0 |
| 455 | 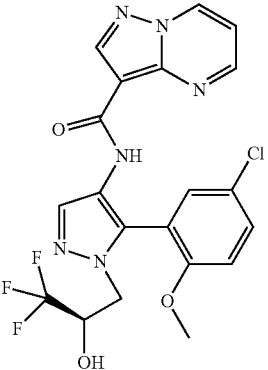 [SMILES: COc1ccc(Cl)cc1-c1c(NC(=O)c2cnn3cccnc23)cnn1C[C@@H](O)C(F)(F)F] | N-(5-(5-chloro-2-methoxyphenyl)-1-((R)-3,3,3-trifluoro-2-hydroxypropyl)-1H-pyrazol-4-yl)pyrazolo[1,5-a]pyrimidine-3-carboxamide | 16 | 481.1 |
| 456 | 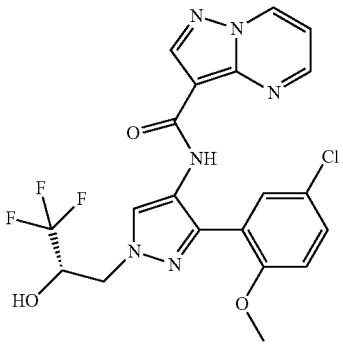 [SMILES: COc1ccc(Cl)cc1-c1nn(C[C@H](O)C(F)(F)F)cc1NC(=O)c1cnn2cccnc12] | (S)-N-(3-(5-chloro-2-methoxyphenyl)-1-(3,3,3-trifluoro-2-hydroxypropyl)-1H-pyrazol-4-yl)pyrazolo[1,5-a]pyrimidine-3-carboxamide | 16 | 481.1 |

| Ex | Structure | Name | Mthd | LCMS (ESI) m/z |
|---|---|---|---|---|
| 457 | 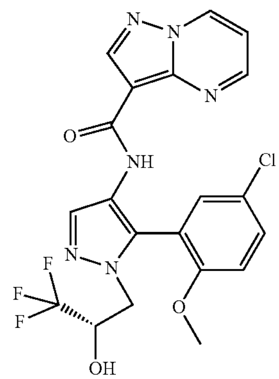 [SMILES: COc1ccc(Cl)cc1-c1c(NC(=O)c2cnn3cccnc23)cnn1C[C@H](O)C(F)(F)F] | N-(5-(5-chloro-2-methoxyphenyl)-1-((S)-3,3,3-trifluoro-2-hydroxypropyl)-1H-pyrazol-4-yl)pyrazolo[1,5-a]pyrimidine-3-carboxamide | 16 | 481.1 |
| 458 | 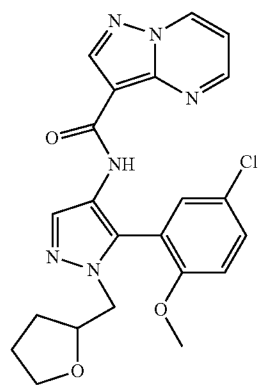 [SMILES: COc1ccc(Cl)cc1-c1c(NC(=O)c2cnn3cccnc23)cnn1CC1CCCO1] | N-(5-(5-chloro-2-methoxyphenyl)-1-((tetrahydrofuran-2-yl)methyl)-1H-pyrazol-4-yl)pyrazolo[1,5-a]pyrimidine-3-carboxamide | 26 | 453.1 |
| 459 | 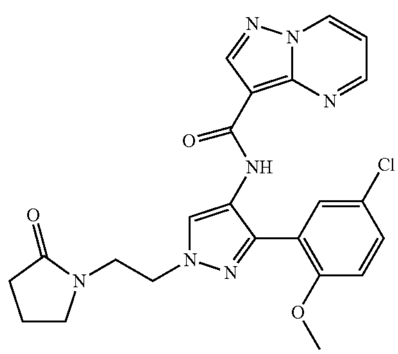 [SMILES: COc1ccc(Cl)cc1-c1nn(CCN2CCCC2=O)cc1NC(=O)c1cnn2cccnc12] | N-(3-(5-chloro-2-methoxyphenyl)-1-(2-(2-oxopyrrolidin-1-yl)ethyl)-1H-pyrazol-4-yl)pyrazolo[1,5-a]pyrimidine-3-carboxamide | 14 | 480.1 |
| 460 | 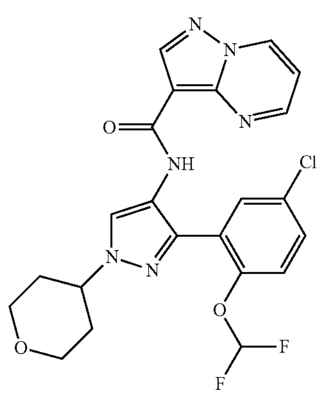 [SMILES: O=C(Nc1cn(C2CCOCC2)nc1-c1cc(Cl)ccc1OC(F)F)c1cnn2cccnc12] | N-(3-(5-chloro-2-(difluoromethoxy)phenyl)-1-(tetrahydro-2H-pyran-4-yl)-1H-pyrazol-4-yl)pyrazolo[1,5-a]pyrimidine-3-carboxamide | 18, 14 | 489.2 |

TABLE 2-continued

| Ex | Structure | Name | Mthd | LCMS (ESI) m/z |
|---|---|---|---|---|
| 461 | 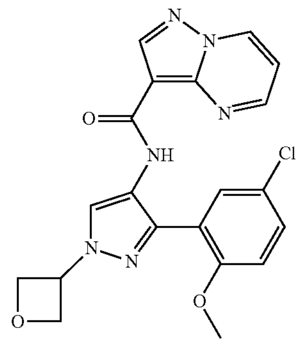 [SMILES: COc1ccc(Cl)cc1-c1nn(C2COC2)cc1NC(=O)c1cnn2cccnc12] | N-(3-(5-chloro-2-methoxyphenyl)-1-(oxetan-3-yl)-1H-pyrazol-4-yl)pyrazolo[1,5-a]pyrimidine-3-carboxamide | 14 | 425.1 |
| 462 | 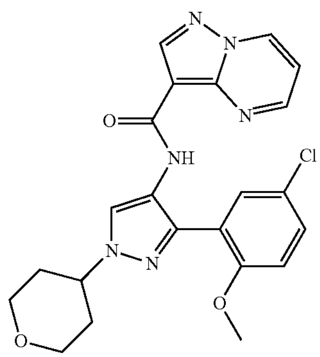 [SMILES: COc1ccc(Cl)cc1-c1nn(C2CCOCC2)cc1NC(=O)c1cnn2cccnc12] | N-(3-(5-chloro-2-methoxyphenyl)-1-(tetrahydro-2H-pyran-4-yl)-1H-pyrazol-4-yl)pyrazolo[1,5-a]pyrimidine-3-carboxamide | 14 | 453.1 |
| 463 | 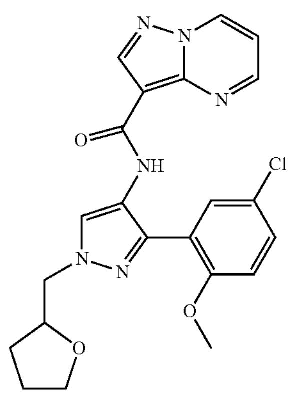 [SMILES: COc1ccc(Cl)cc1-c1nn(CC2CCCO2)cc1NC(=O)c1cnn2cccnc12] | N-(3-(5-chloro-2-methoxyphenyl)-1-((tetrahydrofuran-2-yl)methyl)-1H-pyrazol-4-yl)pyrazolo[1,5-a]pyrimidine-3-carboxamide | 14 | 453.2 |
| 464 | 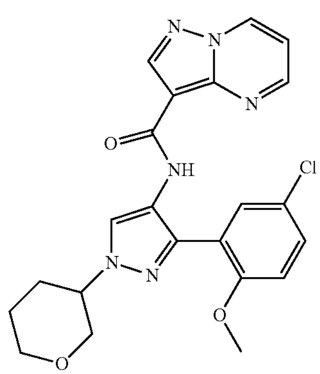 [SMILES: COc1ccc(Cl)cc1-c1nn(C2CCCOC2)cc1NC(=O)c1cnn2cccnc12] | N-(3-(5-chloro-2-methoxyphenyl)-1-(tetrahydro-2H-pyran-3-yl)-1H-pyrazol-4-yl)pyrazolo[1,5-a]pyrimidine-3-carboxamide | 14 | 453.1 |

TABLE 2-continued

| Ex | Structure | Name | Mthd | LCMS (ESI) m/z |
|---|---|---|---|---|
| 465 | 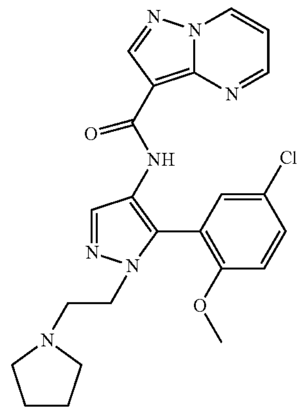 [SMILES: COc1ccc(Cl)cc1-c1c(NC(=O)c2cnn3cccnc23)cnn1CCN1CCCC1] | N-(5-(5-chloro-2-methoxyphenyl)-1-(2-(pyrrolidin-1-yl)ethyl)-1H-pyrazol-4-yl)pyrazolo[1,5-a]pyrimidine-3-carboxamide | 15 | 466.2 |
| 466 | 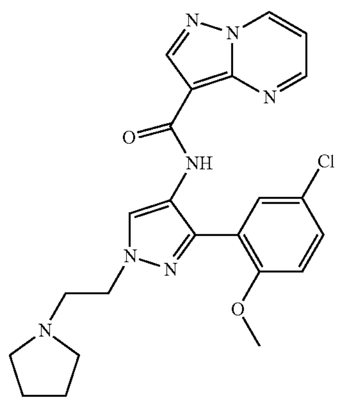 [SMILES: COc1ccc(Cl)cc1-c1nn(CCN2CCCC2)cc1NC(=O)c1cnn2cccnc12] | N-(3-(5-chloro-2-methoxyphenyl)-1-(2-(pyrrolidin-1-yl)ethyl)-1H-pyrazol-4-yl)pyrazolo[1,5-a]pyrimidine-3-carboxamide | 14 | 466.2 |
| 467 | 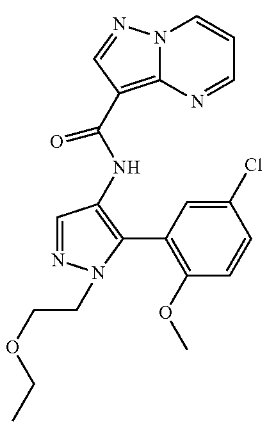 [SMILES: CCOCCn1ncc(NC(=O)c2cnn3cccnc23)c1-c1cc(Cl)ccc1OC] | N-(5-(5-chloro-2-methoxyphenyl)-1-(2-ethoxyethyl)-1H-pyrazol-4-yl)pyrazolo[1,5-a]pyrimidine-3-carboxamide | 15 | 441.2. |
| 468 | 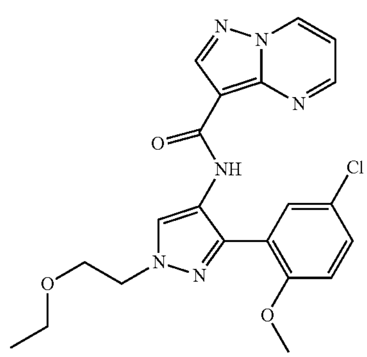 [SMILES: CCOCCn1cc(NC(=O)c2cnn3cccnc23)c(-c2cc(Cl)ccc2OC)n1] | N-(3-(5-chloro-2-methoxyphenyl)-1-(2-ethoxyethyl)-1H-pyrazol-4-yl)pyrazolo[1,5-a]pyrimidine-3-carboxamide | 14 | 441.2 |

TABLE 2-continued

| Ex | Structure | Name | Mthd | LCMS (ESI) m/z |
|---|---|---|---|---|
| 469 | 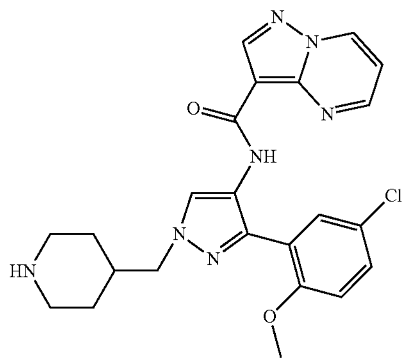 [SMILES: COc1ccc(Cl)cc1-c1nn(CC2CCNCC2)cc1NC(=O)c1cnn2cccnc12] | N-(3-(5-chloro-2-methoxyphenyl)-1-(piperidin-4-ylmethyl)-1H-pyrazol-4-yl)pyrazolo[1,5-a]pyrimidine-3-carboxamide | 159 | 466.2 |
| 470 | 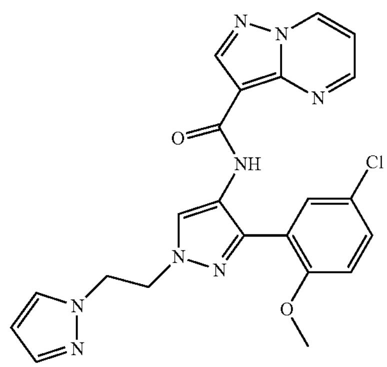 [SMILES: COc1ccc(Cl)cc1-c1nn(CCn2cccn2)cc1NC(=O)c1cnn2cccnc12] | N-(1-(2-(1H-pyrazol-1-yl)ethyl)-3-(5-chloro-2-methoxyphenyl)-1H-pyrazol-4-yl)pyrazolo[1,5-a]pyrimidine-3-carboxamide | 14 | 463.2 |
| 471 | 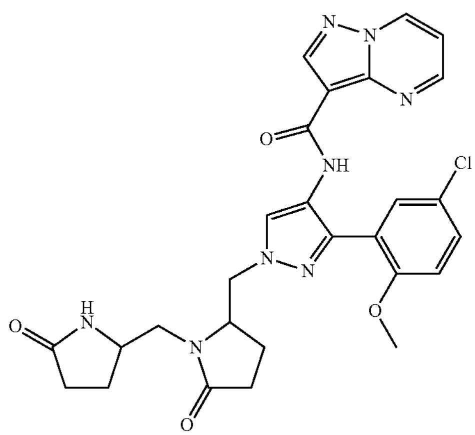 [SMILES: COc1ccc(Cl)cc1-c1nn(CC2CCC(=O)N2CC2CCC(=O)N2)cc1NC(=O)c1cnn2cccnc12] | N-(3-(5-chloro-2-methoxyphenyl)-1-((5-oxo-1-((5-oxopyrrolidin-2-yl)methyl)pyrrolidin-2-yl)methyl)-1H-pyrazol-4-yl)pyrazolo[1,5-a]pyrimidine-3-carboxamide | 14 | 563.2 |
| 472 | 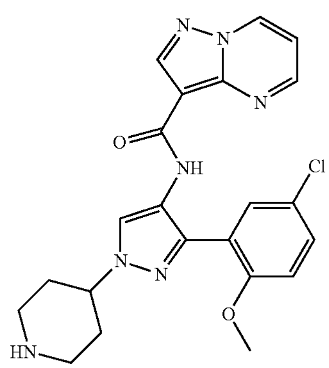 [SMILES: COc1ccc(Cl)cc1-c1nn(C2CCNCC2)cc1NC(=O)c1cnn2cccnc12] | N-(3-(5-chloro-2-methoxyphenyl)-1-(piperidin-4-yl)-1H-pyrazol-4-yl)pyrazolo[1,5-a]pyrimidine-3-carboxamide | 159 | 452.2 |

TABLE 2-continued

| Ex | Structure | Name | Mthd | LCMS (ESI) m/z |
|---|---|---|---|---|
| 473 | 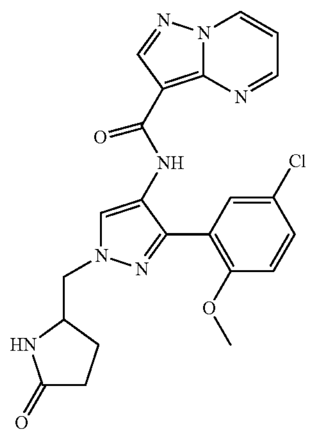 [SMILES: COc1ccc(Cl)cc1-c1nn(CC2CCC(=O)N2)cc1NC(=O)c1cnn2cccnc12] | N-(3-(5-chloro-2-methoxyphenyl)-1-((5-oxopyrrolidin-2-yl)methyl)-1H-pyrazol-4-yl)pyrazolo[1,5-a]pyrimidine-3-carboxamide | 14 | 466.1 |
| 474 | 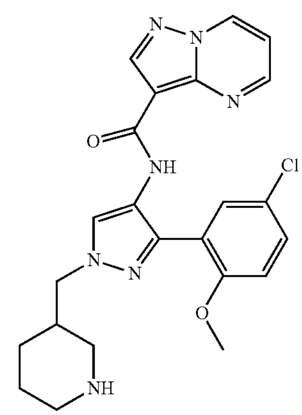 [SMILES: COc1ccc(Cl)cc1-c1nn(CC2CCCNC2)cc1NC(=O)c1cnn2cccnc12] | N-(3-(5-chloro-2-methoxyphenyl)-1-(piperidin-3-ylmethyl)-1H-pyrazol-4-yl)pyrazolo[1,5-a]pyrimidine-3-carboxamide | 159 | 466.2 |
| 475 | 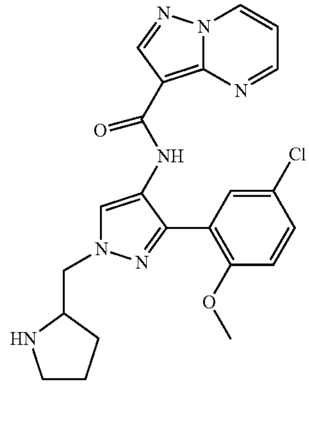 [SMILES: COc1ccc(Cl)cc1-c1nn(CC2CCCN2)cc1NC(=O)c1cnn2cccnc12] | N-(3-(5-chloro-2-methoxyphenyl)-1-(pyrrolidin-2-ylmethyl)-1H-pyrazol-4-yl)pyrazolo[1,5-a]pyrimidine-3-carboxamide | 159 | 452.2 |

TABLE 2-continued

| Ex | Structure | Name | Mthd | LCMS (ESI) m/z |
|---|---|---|---|---|
| 476 | 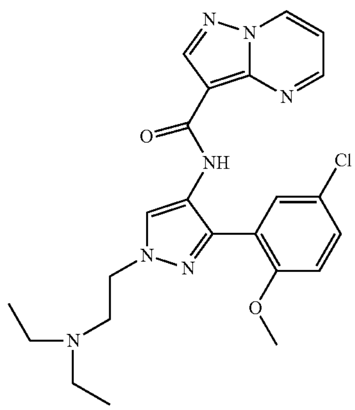 [SMILES: CCN(CC)CCn1cc(NC(=O)c2cnn3cccnc23)c(-c2cc(Cl)ccc2OC)n1] | N-(3-(5-chloro-2-methoxyphenyl)-1-(2-(diethylamino)ethyl)-1H-pyrazol-4-yl)pyrazolo[1,5-a]pyrimidine-3-carboxamide | 14 | 468.2 |
| 477 | 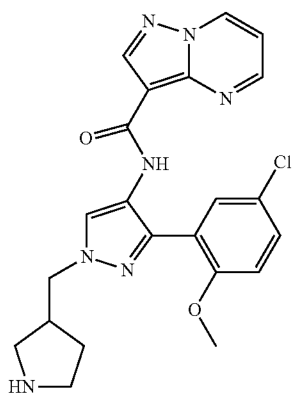 [SMILES: COc1ccc(Cl)cc1-c1nn(CC2CCNC2)cc1NC(=O)c1cnn2cccnc12] | N-(3-(5-chloro-2-methoxyphenyl)-1-(pyrrolidin-3-ylmethyl)-1H-pyrazol-4-yl)pyrazolo[1,5-a]pyrimidine-3-carboxamide | 159 | 452.2 |
| 478 | 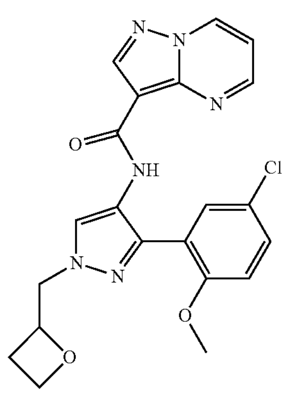 [SMILES: COc1ccc(Cl)cc1-c1nn(CC2CCO2)cc1NC(=O)c1cnn2cccnc12] | N-(3-(5-chloro-2-methoxyphenyl)-1-(oxetan-2-ylmethyl)-1H-pyrazol-4-yl)pyrazolo[1,5-a]pyrimidine-3-carboxamide | 14 | 439.1 |
| 479 | 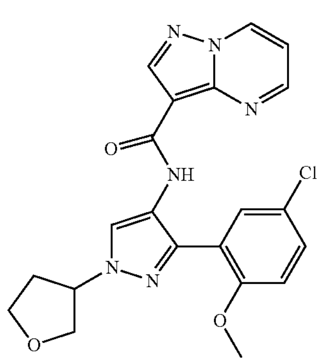 [SMILES: COc1ccc(Cl)cc1-c1nn(C2CCOC2)cc1NC(=O)c1cnn2cccnc12] | N-(3-(5-chloro-2-methoxyphenyl)-1-(tetrahydrofuran-3-yl)-1H-pyrazol-4-yl)pyrazolo[1,5-a]pyrimidine-3-carboxamide | 14 | 439.1 |

TABLE 2-continued

| Ex | Structure | Name | Mthd | LCMS (ESI) m/z |
|---|---|---|---|---|
| 480 | 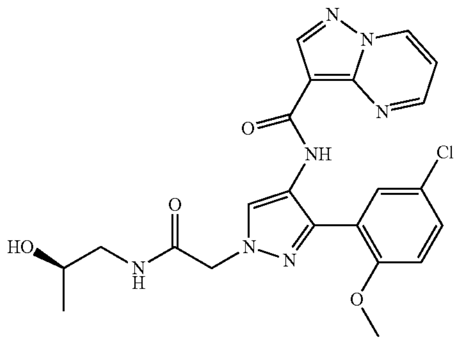 [SMILES: COc1ccc(Cl)cc1-c1nn(CC(=O)NC[C@@H](C)O)cc1NC(=O)c1cnn2cccnc12] | (R)-N-(3-(5-chloro-2-methoxyphenyl)-1-(2-(2-hydroxypropylamino)-2-oxoethyl)-1H-pyrazol-4-yl)pyrazolo[1,5-a]pyrimidine-3-carboxamide | 164 | 484.1 |
| 481 | 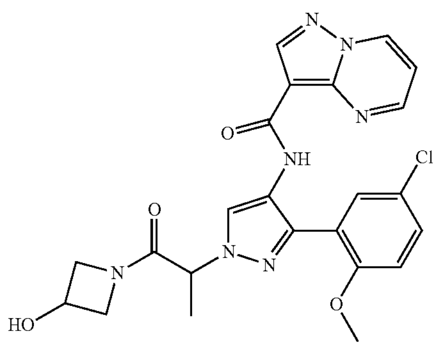 [SMILES: COc1ccc(Cl)cc1-c1nn(C(C)C(=O)N2CC(O)C2)cc1NC(=O)c1cnn2cccnc12] | N-(3-(5-chloro-2-methoxyphenyl)-1-(1-(3-hydroxyazetidin-1-yl)-1-oxopropan-2-yl)-1H-pyrazol-4-yl)pyrazolo[1,5-a]pyrimidine-3-carboxamide | 160 | 496.1 |
| 482 | 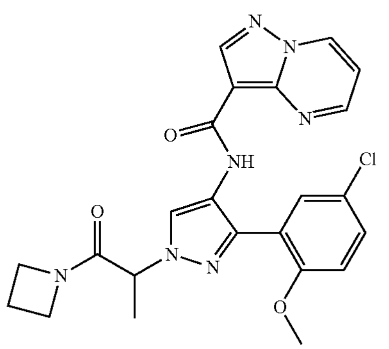 [SMILES: COc1ccc(Cl)cc1-c1nn(C(C)C(=O)N2CCC2)cc1NC(=O)c1cnn2cccnc12] | N-(1-(1-(azetidin-1-yl)-1-oxopropan-2-yl)-3-(5-chloro-2-methoxyphenyl)-1H-pyrazol-4-yl)pyrazolo[1,5-a]pyrimidine-3-carboxamide | 160 | 480.1 |
| 483 | 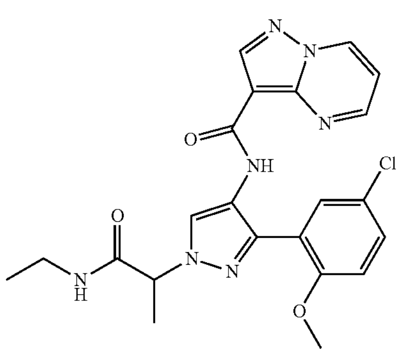 [SMILES: CCNC(=O)C(C)n1cc(NC(=O)c2cnn3cccnc23)c(-c2cc(Cl)ccc2OC)n1] | N-(3-(5-chloro-2-methoxyphenyl)-1-(1-(ethylamino)-1-oxopropan-2-yl)-1H-pyrazol-4-yl)pyrazolo[1,5-a]pyrimidine-3-carboxamide | 160 | 468.1 |

TABLE 2-continued

| Ex | Structure | Name | Mthd | LCMS (ESI) m/z |
|---|---|---|---|---|
| 484 | 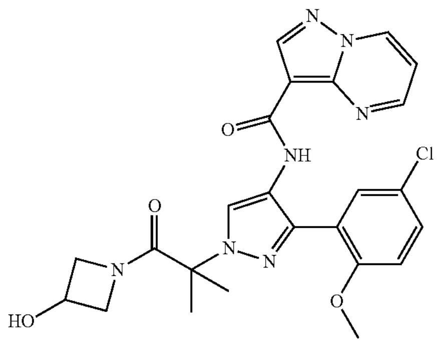 [SMILES: COc1ccc(Cl)cc1-c1nn(C(C)(C)C(=O)N2CC(O)C2)cc1NC(=O)c1cnn2cccnc12] | N-(3-(5-chloro-2-methoxyphenyl)-1-(1-(3-hydroxyazetidin-1-yl)-2-methyl-1-oxopropan-2-yl)-1H-pyrazol-4-yl)pyrazolo[1,5-a]pyrimidine-3-carboxamide | 161 | 510.2 |
| 485 | 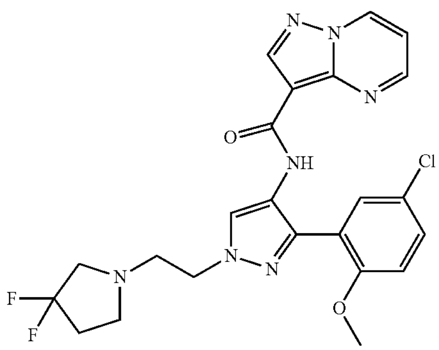 [SMILES: COc1ccc(Cl)cc1-c1nn(CCN2CCC(F)(F)C2)cc1NC(=O)c1cnn2cccnc12] | N-(3-(5-chloro-2-methoxyphenyl)-1-(2-(3,3-difluoropyrrolidin-1-yl)ethyl)-1H-pyrazol-4-yl)pyrazolo[1,5-a]pyrimidine-3-carboxamide | 162 | 502.2 |
| 486 | 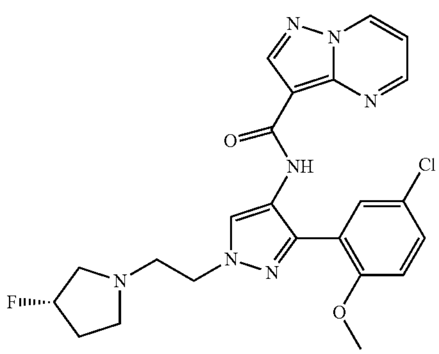 [SMILES: COc1ccc(Cl)cc1-c1nn(CCN2CC[C@H](F)C2)cc1NC(=O)c1cnn2cccnc12] | (S)-N-(3-(5-chloro-2-methoxyphenyl)-1-(2-(3-fluoropyrrolidin-1-yl)ethyl)-1H-pyrazol-4-yl)pyrazolo[1,5-a]pyrimidine-3-carboxamide | 162 | 484.2 |
| 487 | 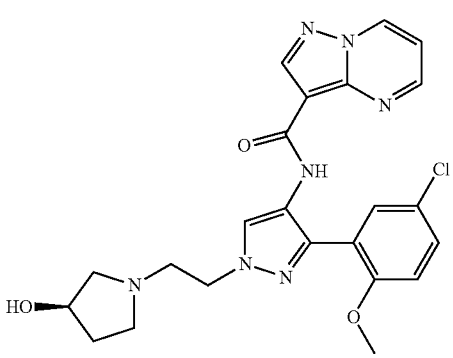 [SMILES: COc1ccc(Cl)cc1-c1nn(CCN2CC[C@@H](O)C2)cc1NC(=O)c1cnn2cccnc12] | (R)-N-(3-(5-chloro-2-methoxyphenyl)-1-(2-(3-hydroxypyrrolidin-1-yl)ethyl)-1H-pyrazol-4-yl)pyrazolo[1,5-a]pyrimidine-3-carboxamide | 162 | 482.2 |

TABLE 2-continued

| Ex | Structure | Name | Mthd | LCMS (ESI) m/z |
|---|---|---|---|---|
| 488 | 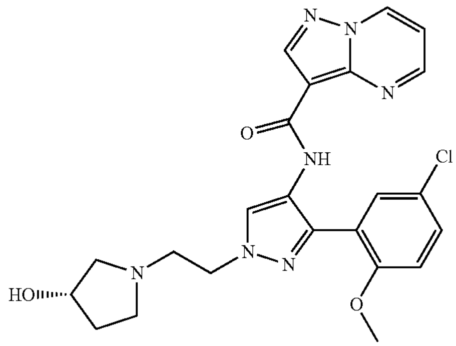 [SMILES: COc1ccc(Cl)cc1-c1nn(CCN2CC[C@H](O)C2)cc1NC(=O)c1cnn2cccnc12] | (S)-N-(3-(5-chloro-2-methoxyphenyl)-1-(2-(3-hydroxypyrrolidin-1-yl)ethyl)-1H-pyrazol-4-yl)pyrazolo[1,5-a]pyrimidine-3-carboxamide | 162 | 482.2 |
| 489 | 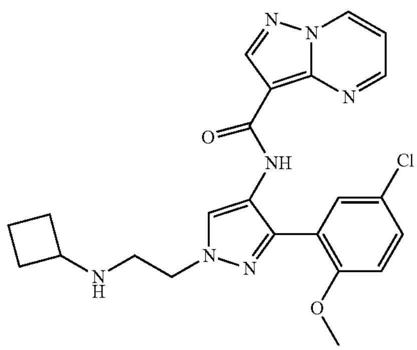 [SMILES: COc1ccc(Cl)cc1-c1nn(CCNC2CCC2)cc1NC(=O)c1cnn2cccnc12] | N-(3-(5-chloro-2-methoxyphenyl)-1-(2-(cyclobutylamino)ethyl)-1H-pyrazol-4-yl)pyrazolo[1,5-a]pyrimidine-3-carboxamide | 162 | 466.2 |
| 490 | 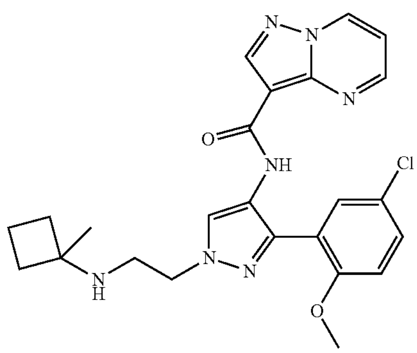 [SMILES: COc1ccc(Cl)cc1-c1nn(CCNC2(C)CCC2)cc1NC(=O)c1cnn2cccnc12] | N-(3-(5-chloro-2-methoxyphenyl)-1-(2-(1-methylcyclobutylamino)ethyl)-1H-pyrazol-4-yl)pyrazolo[1,5-a]pyrimidine-3-carboxamide | 162 | 480.1 |
| 491 | 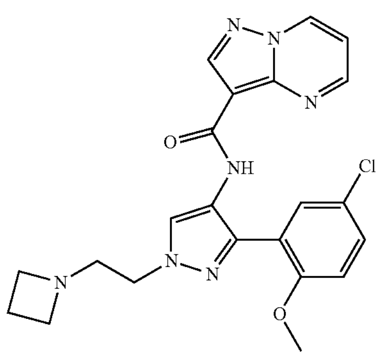 [SMILES: COc1ccc(Cl)cc1-c1nn(CCN2CCC2)cc1NC(=O)c1cnn2cccnc12] | N-(1-(2-(azetidin-1-yl)ethyl)-3-(5-chloro-2-methoxyphenyl)-1H-pyrazol-4-yl)pyrazolo[1,5-a]pyrimidine-3-carboxamide | 162 | 452.2 |

TABLE 2-continued

| Ex | Structure | Name | Mthd | LCMS (ESI) m/z |
|---|---|---|---|---|
| 492 | 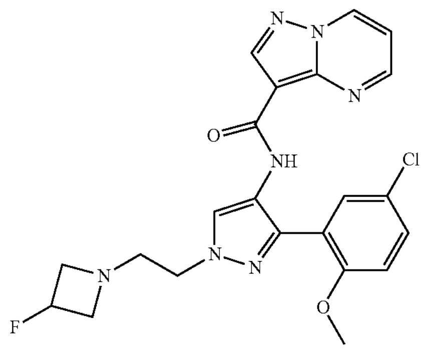 [SMILES: COc1ccc(Cl)cc1-c1nn(CCN2CC(F)C2)cc1NC(=O)c1cnn2cccnc12] | N-(3-(5-chloro-2-methoxyphenyl)-1-(2-(3-fluoroazetidin-1-yl)ethyl)-1H-pyrazol-4-yl)pyrazolo[1,5-a]pyrimidine-3-carboxamide | 162 | 470.1 |
| 493 | 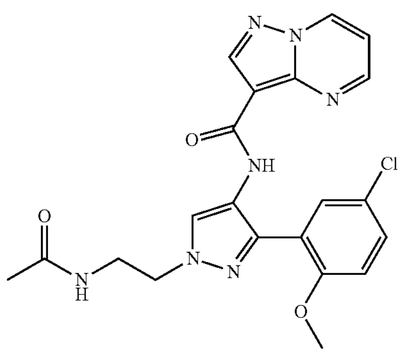 [SMILES: COc1ccc(Cl)cc1-c1nn(CCNC(C)=O)cc1NC(=O)c1cnn2cccnc12] | N-(1-(2-acetamidoethyl)-3-(5-chloro-2-methoxyphenyl)-1H-pyrazol-4-yl)pyrazolo[1,5-a]pyrimidine-3-carboxamide | 163 | 454.1 |
| 494 | 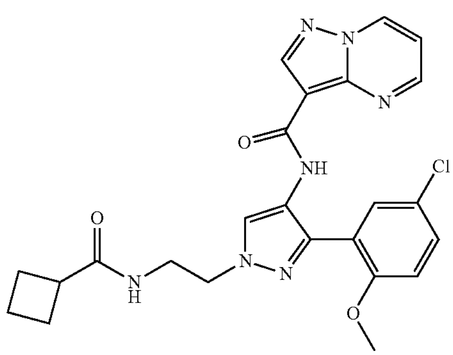 [SMILES: COc1ccc(Cl)cc1-c1nn(CCNC(=O)C2CCC2)cc1NC(=O)c1cnn2cccnc12] | N-(3-(5-chloro-2-methoxyphenyl)-1-(2-(cyclobutanecarboxamido)ethyl)-1H-pyrazol-4-yl)pyrazolo[1,5-a]pyrimidine-3-carboxamide | 163 | 494.2 |
| 495 | 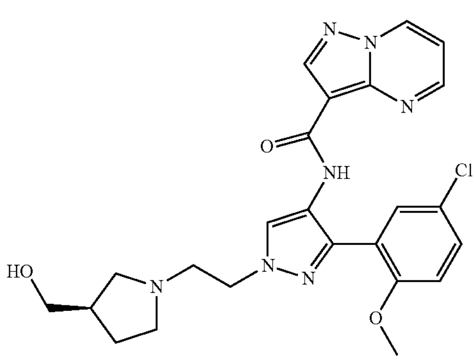 [SMILES: COc1ccc(Cl)cc1-c1nn(CCN2CC[C@@H](CO)C2)cc1NC(=O)c1cnn2cccnc12] | (R)-N-(3-(5-chloro-2-methoxyphenyl)-1-(2-(3-(hydroxymethyl)pyrrolidin-1-yl)ethyl)-1H-pyrazol-4-yl)pyrazolo[1,5-a]pyrimidine-3-carboxamide | 162 | 496.1 |

TABLE 2-continued

| Ex | Structure | Name | Mthd | LCMS (ESI) m/z |
|---|---|---|---|---|
| 496 | 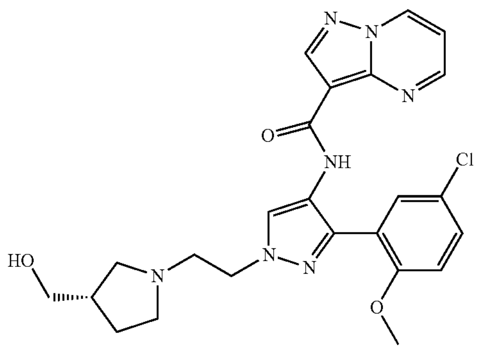 [SMILES: COc1ccc(Cl)cc1-c1nn(CCN2CC[C@H](CO)C2)cc1NC(=O)c1cnn2cccnc12] | (S)-N-(3-(5-chloro-2-methoxyphenyl)-1-(2-(3-(hydroxymethyl)pyrrolidin-1-yl)ethyl)-1H-pyrazol-4-yl)pyrazolo[1,5-a]pyrimidine-3-carboxamide | 162 | 496.2 |
| 497 | 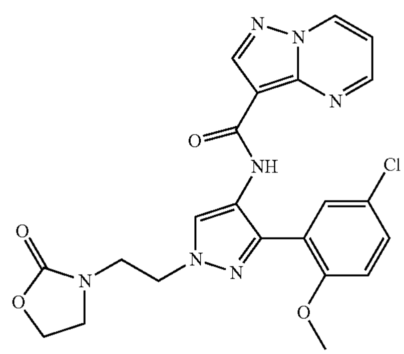 [SMILES: COc1ccc(Cl)cc1-c1nn(CCN2CCOC2=O)cc1NC(=O)c1cnn2cccnc12] | N-(3-(5-chloro-2-methoxyphenyl)-1-(2-(2-oxooxazolidin-3-yl)ethyl)-1H-pyrazol-4-yl)pyrazolo[1,5-a]pyrimidine-3-carboxamide | 14 | 482.1 |
| 498 | 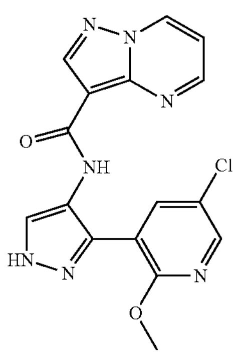 [SMILES: COc1ncc(Cl)cc1-c1n[nH]cc1NC(=O)c1cnn2cccnc12] | N-(3-(5-chloro-2-methoxypyridin-3-yl)-1H-pyrazol-4-yl)pyrazolo[1,5-a]pyrimidine-3-carboxamide | 141 | 370.0 |
| 499 | 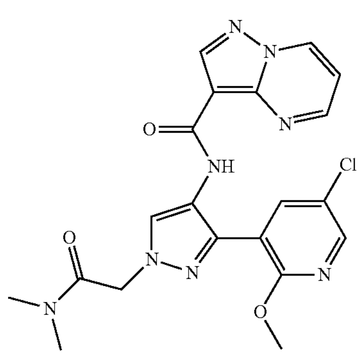 [SMILES: COc1ncc(Cl)cc1-c1nn(CC(=O)N(C)C)cc1NC(=O)c1cnn2cccnc12] | N-(3-(5-chloro-2-methoxypyridin-3-yl)-1-(2-(dimethylamino)-2-oxoethyl)-1H-pyrazol-4-yl)pyrazolo[1,5-a]pyrimidine-3-carboxamide | 141, 14 | 455.1 |

TABLE 2-continued

| Ex | Structure | Name | Mthd | LCMS (ESI) m/z |
|---|---|---|---|---|
| 500 | 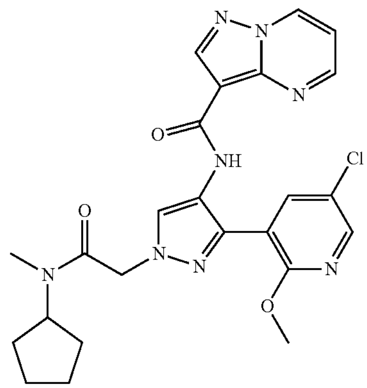 [SMILES: COc1ncc(Cl)cc1-c1nn(CC(=O)N(C)C2CCCC2)cc1NC(=O)c1cnn2cccnc12] | N-(3-(5-chloro-2-methoxypyridin-3-yl)-1-(2-(cyclopentyl(methyl)amino)-2-oxoethyl)-1H-pyrazol-4-yl)pyrazolo[1,5-a]pyrimidine-3-carboxamide | 141, 164 | 509.2 |
| 501 | 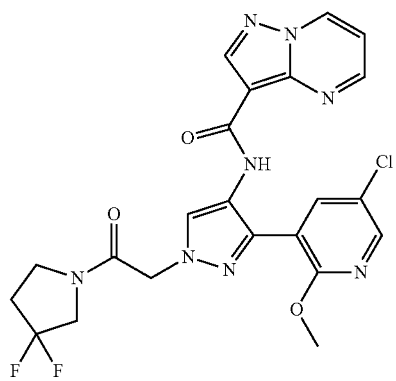 [SMILES: COc1ncc(Cl)cc1-c1nn(CC(=O)N2CCC(F)(F)C2)cc1NC(=O)c1cnn2cccnc12] | N-(3-(5-chloro-2-methoxypyridin-3-yl)-1-(2-(3,3-difluoropyrrolidin-1-yl)-2-oxoethyl)-1H-pyrazol-4-yl)pyrazolo[1,5-a]pyrimidine-3-carboxamide | 141, 164 | 517.1 |
| 502 | 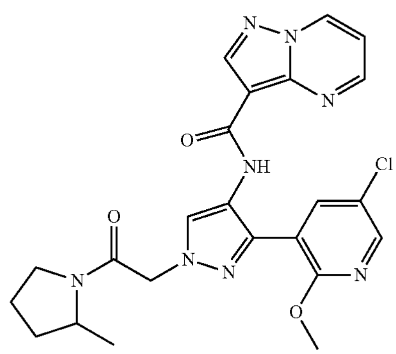 [SMILES: COc1ncc(Cl)cc1-c1nn(CC(=O)N2CCCC2C)cc1NC(=O)c1cnn2cccnc12] | N-(3-(5-chloro-2-methoxypyridin-3-yl)-1-(2-(2-methylpyrrolidin-1-yl)-2-oxoethyl)-1H-pyrazol-4-yl)pyrazolo[1,5-a]pyrimidine-3-carboxamide | 141, 164 | 495.1 |
| 503 | 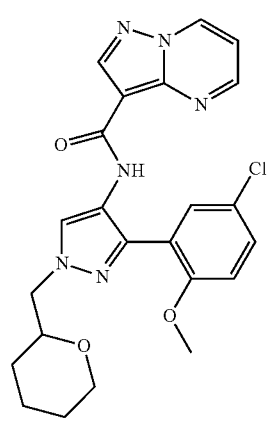 [SMILES: COc1ccc(Cl)cc1-c1nn(CC2CCCCO2)cc1NC(=O)c1cnn2cccnc12] | N-(3-(5-chloro-2-methoxyphenyl)-1-((tetrahydro-2H-pyran-2-yl)methyl)-1H-pyrazol-4-yl)pyrazolo[1,5-a]pyrimidine-3-carboxamide | 14 | 467.2 |

TABLE 2-continued

| Ex | Structure | Name | Mthd | LCMS (ESI) m/z |
|---|---|---|---|---|
| 504 | 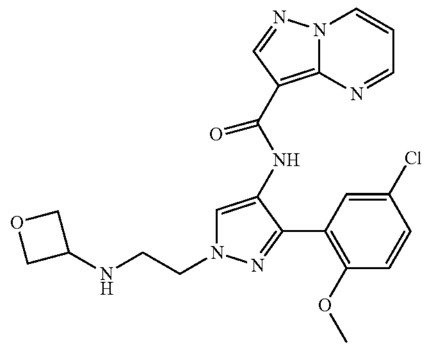 [SMILES: COc1ccc(Cl)cc1-c1nn(CCNC2COC2)cc1NC(=O)c1cnn2cccnc12] | N-(3-(5-chloro-2-methoxyphenyl)-1-(2-(oxetan-3-ylamino)ethyl)-1H-pyrazol-4-yl)pyrazolo[1,5-a]pyrimidine-3-carboxamide | 162 | 468.2 |
| 505 | 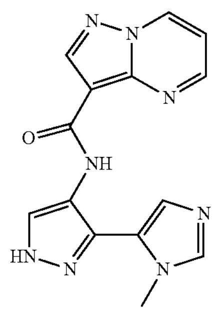 [SMILES: Cn1cncc1-c1n[nH]cc1NC(=O)c1cnn2cccnc12] | N-(3-(1-methyl-1H-imidazol-5-yl)-1H-pyrazol-4-yl)pyrazolo[1,5-a]pyrimidine-3-carboxamide | 14 | 309.1 |
| 506 | 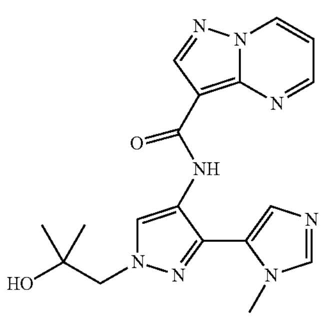 [SMILES: Cn1cncc1-c1nn(CC(C)(C)O)cc1NC(=O)c1cnn2cccnc12] | N-(1-(2-hydroxy-2-methylpropyl)-3-(1-methyl-1H-imidazol-5-yl)-1H-pyrazol-4-yl)pyrazolo[1,5-a]pyrimidine-3-carboxamide | 16 | 381.1 |
| 507 | 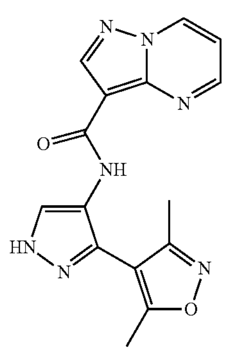 [SMILES: Cc1noc(C)c1-c1n[nH]cc1NC(=O)c1cnn2cccnc12] | N-(3-(3,5-dimethylisoxazol-4-yl)-1H-pyrazol-4-yl)pyrazolo[1,5-a]pyrimidine-3-carboxamide | 14 | 324.1 |

TABLE 2-continued

| Ex | Structure | Name | Mthd | LCMS (ESI) m/z |
|---|---|---|---|---|
| 508 | 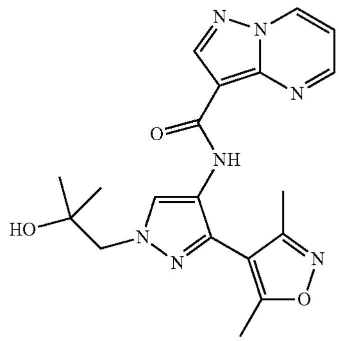 [SMILES: Cc1noc(C)c1-c1nn(CC(C)(C)O)cc1NC(=O)c1cnn2cccnc12] | N-(3-(3,5-dimethylisoxazol-4-yl)-1-(2-hydroxy-2-methylpropyl)-1H-pyrazol-4-yl)pyrazolo[1,5-a]pyrimidine-3-carboxamide | 16 | 396.1 |

The compounds of Examples 1-508 were tested in the above assays (Examples A-C) and found to have $K_i$ values of less than about 1 µM for inhibiting one or both of JAK1 and JAK2 kinases. The compounds of Examples 1-132 were tested in the above assays (Examples A-C) and found to have $K_i$ values of less than about 1 µM for inhibiting JAK2 kinase. The compounds of Examples 132-508 were tested in the above assays (Examples A-C) and found to have $K_i$ values of less than about 1 µM for inhibiting JAK1 kinase.

Table 3 below shows enzymatic activity data ($K_i$, µM) for certain compounds of the present invention run in the above assays (Examples A-C).

TABLE 3

| Example | JAK1 | JAK2 | JAK3 | TYK2$_i$ |
|---|---|---|---|---|
| 63 | 0.153 | 0.023 | 0.200 | 0.140 |
| 6 | 0.0462 | 0.0049 | 0.152 | 0.0996 |
| 194 | 0.775 | 0.110 | 4.10 | 0.980 |
| 44 | 0.131 | 0.018 | 0.140 | 0.480 |
| 217 | 0.0021 | 0.0005 | 0.0055 | 0.0023 |
| 379 | 0.0859 | 0.0263 | 0.2400 | 0.4100 |
| 158 | 0.0048 | 0.0015 | 0.0530 | 0.0066 |
| 155 | 0.0042 | 0.0026 | 0.2100 | 0.0650 |
| 364 | 0.0023 | 0.0062 | 0.7100 | 0.0470 |
| 283 | 0.0007 | 0.0031 | 0.2700 | 0.0091 |
| 359 | 0.0010 | 0.0042 | 0.6900 | 0.0460 |
| 432 | 0.0015 | 0.0057 | 0.5700 | 0.0310 |
| 300 | 0.0005 | 0.0025 | 0.1700 | 0.0100 |
| 170 | 0.0007 | 0.0004 | 0.0130 | 0.0021 |
| 499 | 0.0016 | 0.0058 | 0.7800 | 0.0140 |
| 414 | 0.0038 | 0.0125 | 0.2100 | 0.0760 |
| 143 | 0.0120 | 0.0385 | 1.500 | 0.3500 |
| 41 | 0.0351 | 0.0033 | 0.0739 | 0.1040 |
| 38 | 0.0403 | 0.0057 | 0.1020 | 0.1310 |
| 28 | 0.1100 | 0.0137 | 0.1350 | 0.4590 |
| 51 | 0.0837 | 0.0152 | 0.1500 | 0.0980 |
| 54 | 1.20 | 0.159 | | 0.850 |
| 109 | 0.0044 | 0.0010 | 0.0180 | 0.0056 |
| 395 | 0.1760 | 0.0313 | 0.3900 | 0.2300 |
| | 0.762 | 0.104 | 2.80 | 1.70 |

Reference is made to U.S. Provisional Application Ser. No. 61/222,918, filed Jul. 2, 2009, which is incorporated by reference herein in its entirety for all purposes.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

What is claimed is:

1. The compound selected from
   N-(4-(5-chloro-2-methoxyphenyl)-2-(2-hydroxy-2-methylpropyl)thiazol-5-yl)pyrazolo[1,5-a]pyrimidine-3-carboxamide;
   N-(4-(5-chloro-2-methoxyphenyl)-2-(2-methylprop-1-enyl)thiazol-5-yl)pyrazolo[1,5-a]pyrimidine-3-carboxamide;
   N-(2-bromo-4-(5-chloro-2-methoxyphenyl)thiazol-5-yl)pyrazolo[1,5-a]pyrimidine-3-carboxamide;
   N-(4-(5-chloro-2-methoxyphenyl)thiazol-5-yl)pyrazolo[1,5-a]pyrimidine-3-carboxamide;
   N-(4-(5-chloro-2-methoxyphenyl)-2-methylthiazol-5-yl)pyrazolo[1,5-a]pyrimidine-3-carboxamide; and
   N-(4-(5-chloro-2-methoxyphenyl)-2-(tetrahydro-2H-pyran-4-yl)thiazol-5-yl)pyrazolo[1,5-a]pyrimidine-3-carboxamide.

* * * * *